US009550000B2

(12) United States Patent
Robinson et al.

(10) Patent No.: US 9,550,000 B2
(45) Date of Patent: Jan. 24, 2017

(54) COMPOSITIONS, METHODS, AND SYSTEMS FOR THE SYNTHESIS AND USE OF IMAGING AGENTS

(75) Inventors: Simon P. Robinson, Stow, MA (US); Ming Yu, Chelmsford, MA (US)

(73) Assignee: Lantheus Medical Imaging, Inc., North Billerica, MA (US)

( * ) Notice: Subject to any disclaimer, the term of this patent is extended or adjusted under 35 U.S.C. 154(b) by 223 days.

(21) Appl. No.: 14/343,627

(22) PCT Filed: Sep. 7, 2012

(86) PCT No.: PCT/US2012/054309
§ 371 (c)(1),
(2), (4) Date: Jun. 30, 2014

(87) PCT Pub. No.: WO2013/036869
PCT Pub. Date: Mar. 14, 2013

(65) Prior Publication Data
US 2014/0328756 A1    Nov. 6, 2014

Related U.S. Application Data

(60) Provisional application No. 61/656,489, filed on Jun. 6, 2012, provisional application No. 61/656,492, filed on Jun. 6, 2012, provisional application No. 61/533,133, filed on Sep. 9, 2011.

(51) Int. Cl.
| A61K 51/00 | (2006.01) |
| A61M 36/14 | (2006.01) |
| A61K 51/04 | (2006.01) |
| C07C 279/04 | (2006.01) |
| C07D 233/46 | (2006.01) |
| C07D 209/14 | (2006.01) |
| C07C 257/14 | (2006.01) |
| C07C 279/06 | (2006.01) |
| C07C 279/08 | (2006.01) |
| C07C 279/12 | (2006.01) |
| C07C 279/14 | (2006.01) |
| C07C 281/18 | (2006.01) |
| C07C 217/70 | (2006.01) |

(52) U.S. Cl.
CPC .......... *A61K 51/0459* (2013.01); *A61K 51/04* (2013.01); *A61K 51/0453* (2013.01); *A61K 51/0497* (2013.01); *C07C 217/70* (2013.01); *C07C 257/14* (2013.01); *C07C 279/04* (2013.01); *C07C 279/06* (2013.01); *C07C 279/08* (2013.01); *C07C 279/12* (2013.01); *C07C 279/14* (2013.01); *C07C 281/18* (2013.01); *C07D 209/14* (2013.01); *C07D 233/46* (2013.01); *A61K 51/041* (2013.01); *C07B 2200/05* (2013.01)

(58) Field of Classification Search
CPC .................................................. A61K 51/041
See application file for complete search history.

(56) References Cited

U.S. PATENT DOCUMENTS

| 5,417,959 A | 5/1995 | Wallace |
| 7,344,702 B2 | 3/2008 | Casebier et al. |
| 8,226,929 B2 | 7/2012 | Casebier et al. |
| 8,491,868 B2 | 7/2013 | Purohit et al. |
| 8,936,777 B2 | 1/2015 | Cesati et al. |
| 9,161,997 B2 | 10/2015 | Casebier et al. |
| 2004/0018162 A1 | 1/2004 | Bimczok et al. |
| 2005/0191238 A1 | 9/2005 | Casebier et al. |
| 2006/0127309 A1 | 6/2006 | Raffel et al. |
| 2007/0036716 A1 | 2/2007 | Casebier et al. |
| 2007/0258887 A1 | 11/2007 | Tamagnan et al. |
| 2010/0322855 A1 | 12/2010 | Chong et al. |
| 2011/0091374 A1 | 4/2011 | Robinson et al. |
| 2012/0276006 A1 | 11/2012 | Casebier et al. |
| 2013/0064769 A1 | 3/2013 | Cesati et al. |
| 2013/0149244 A1 | 6/2013 | Purohit et al. |
| 2014/0030189 A1 | 1/2014 | Purohit et al. |
| 2015/0165074 A1 | 6/2015 | Lazewatsky et al. |
| 2015/0196672 A1 | 7/2015 | Cesati et al. |

FOREIGN PATENT DOCUMENTS

| CN | 101555232 A | 10/2009 |
| CN | 101585816 A | 11/2009 |
| GB | 672 048 A | 5/1952 |
| GB | 1 215 255 A | 12/1970 |

(Continued)

OTHER PUBLICATIONS

Bax et al. (Circ. Cardiovasc. Imaging 2008, 1, 131-140).*
Raffel et al., Radiolabeled phenethylguanidines: novel imaging agents for cardiac sympathetic neurons and adrenergic tumors. J Med Chem. May 3, 2007;50(9):2078-88. Epub Apr. 10, 2007.
Office Action for CN201180016758.9, mailed Jun. 26, 2014.
Extended European Search Report for EP11740546.4, mailed Jun. 25, 2013.
International Search Report and Written Opinion for PCT/US2011/024109 mailed Oct. 24, 2011.
International Preliminary Report on Patentability for PCT/US2011/024109 mailed Aug. 23, 2012.

(Continued)

*Primary Examiner* — Michael G Hartley
*Assistant Examiner* — Melissa Perreira
(74) *Attorney, Agent, or Firm* — Wolf, Greenfield & Sacks, P.C.

(57) ABSTRACT

The present invention relates to systems, compositions, and methods for the synthesis and use of imaging agents, or precursors thereof. An imaging agent precursor may be converted to an imaging agent using the methods described herein. In some cases, the imaging agent is enriched in $^{18}F$. In some cases, an imaging agent may be used to image an area of interest in a subject, including, but not limited to, the heart, cardiovascular system, cardiac vessels, brain, and other organs. In some embodiments, methods and compositions for assessing perfusion and innervation mismatch in a portion of a subject are provided.

29 Claims, 17 Drawing Sheets

(56) References Cited

FOREIGN PATENT DOCUMENTS

| | | |
|---|---|---|
| JP | S61-260018 A | 11/1986 |
| JP | H07-252236 A | 10/1995 |
| JP | 2007-112725 A | 5/2007 |
| WO | WO 95/11901 A1 | 5/1995 |
| WO | WO 00/09115 A1 | 2/2000 |
| WO | WO 2004/037166 A2 | 5/2004 |
| WO | WO 2005/053615 A2 | 6/2005 |
| WO | WO 2005/079391 A2 | 9/2005 |
| WO | WO 2005/082425 A1 | 9/2005 |
| WO | WO 2005/095345 A2 | 10/2005 |
| WO | WO 2005/115971 A1 | 12/2005 |
| WO | WO 2006/032705 A2 | 3/2006 |
| WO | WO 2006/136846 A1 | 12/2006 |
| WO | WO 2008/022979 A1 | 2/2008 |
| WO | WO 2008/075040 A2 | 6/2008 |
| WO | WO 2008/083056 A2 | 7/2008 |
| WO | WO 2008/115593 A1 | 9/2008 |
| WO | WO 2008/124651 A2 | 10/2008 |
| WO | WO 2009/054653 A2 | 4/2009 |
| WO | WO 2009/103478 A1 | 8/2009 |
| WO | WO 2009/108376 A2 | 9/2009 |
| WO | WO 2009/110984 A2 | 9/2009 |
| WO | WO 2010/015387 A1 | 2/2010 |
| WO | WO 2010/104818 A1 | 9/2010 |
| WO | WO 2010/115881 A1 | 10/2010 |
| WO | WO 2010/120368 A2 | 10/2010 |
| WO | WO 2011/097649 A2 | 8/2011 |
| WO | WO 2011/143360 A2 | 11/2011 |
| WO | WO 2014/026079 A2 | 2/2014 |

OTHER PUBLICATIONS

Partial Supplementary European Search Report for EP 11781241.2 mailed Jul. 1, 2015.

Extended European Search Report for EP11781241.2 mailed Nov. 2, 2015.

International Search Report and Written Opinion for PCT/US2011/036142 mailed Dec. 22, 2011.

International Preliminary Report on Patentability for PCT/US2011/036142 mailed Nov. 22, 2012.

Extended European Search Report for EP 12829763.7 mailed Jun. 22, 2015.

International Search Report and Written Opinion for PCT/US2012/054309 mailed Feb. 27, 2013.

International Preliminary Report on Patentability for PCT/US2012/054309 mailed Mar. 20, 2014.

Partial Supplementary European Search Report for EP13828042.5 mailed Dec. 16, 2015.

International Search Report and Written Opinion for PCT/US2013/054268, mailed Apr. 1, 2014.

International Preliminary Report on Patentability for PCT/US2013/054268 mailed Feb. 19, 2015.

[No Author Listed] "Pharmaceutical Salts." May 1, 1958. p. 334-45. Retrieved on Aug. 26, 2014 from http://phoenix.tuwien.ac.at/pdf/pharmaceutical_salts/Pharmaceutical_salts.pdf.

Breidenbach, No-carrier-added labelled 6-aminopurine derivatives as potential adensine A2A-receptorligands for positron-emission-tomography. Berichte des Forschungszentrums Juelich. 2004;4132:134 pages.

Chu et al., Synthesis and biodistribution of (99m)Tc-carbonyltechnetium-labeled fatty acids. Appl Radiat Isot. Jun. 2004;60(6):845-50.

Haas et al., Preoperative positron emission tomographic viability assessment and perioperative and postoperative risk in patients with advanced ischemic heart disease. J Am Coll Cardiol. Dec. 1997;30(7):1693-700.

Hattori et al., Global and regional functional measurements with gated FDG PET in comparison with left ventriculography. Eur J Nucl Med. Feb. 2001;28(2):221-9.

Ibrahim et al., Assessment of coronary flow reserve: comparison between contrast-enhanced magnetic resonance imaging and positron emission tomography. J Am Coll Cardiol. Mar. 6, 2002;39(5):864-70.

Klein et al., Assessment of myocardial viability with contrast-enhanced magnetic resonance imaging: comparison with positron emission tomography. Circulation. Jan. 15, 2002;105(2):162-7.

Koehler et al., Radiosynthesis and radiopharmacological evaluation of cyclin-dependent kinase 4 (Cdk4) inhibitors. Eur J Med Chem. Feb. 2010;45(2):727-37. doi: 10.1016/j.ejmech.2009.11.020. Epub Nov. 24, 2009.

Lee et al., Potential and practical adrenomedullary PET radiopharmaceuticals as an alternative to m-iodobenzylguanidine: m-(omega-[18F]fluoroalkyl)benzylguanidines. Bioconjug Chem. Jan.-Feb. 2004;15(1):104-11.

Mou et al., Preparation and biodistribution of [18F]FP2OP as myocardial perfusion imaging agent for positron emission tomography. Bioorg Med Chem. Feb. 2010;18(3):1312-20. Epub Dec. 26, 2009.

Nekolla et al., Reproducibility of polar map generation and assessment of defect severity and extent assessment in myocardial perfusion imaging using positron emission tomography. Eur J Nucl Med. Sep. 1998;25(9):1313-21.

Paixao et al., 1,3-Diphenylguanidinium Trifluoroacetate. Acta Cryst. 1998;C54:1484-6.

Purohit et al., Synthesis and biological evaluation of pyridazinone analogues as potential cardiac positron emission tomography tracers. J Med Chem. May 22, 2008;51(10):2954-70.

Robins et al., Synthesis and in vitro evaluation of (18)F-labelled S-fluoroalkyl diarylguanidines: Novel high-affinity NMDA receptor antagonists for imaging with PET. Bioorg Med Chem Lett. Mar. 1, 2010;20(5):1749-51. doi: 10.1016/j.bmcl.2010.01.052. Epub Jan. 20, 2010.

Sirion et al., An efficient F-18 labeling method for PET study: Huisgen 1,3-dipolar cycloaddition of bioactive substances and F-18-labeled compounds. Tetrahedron Letters. Jun. 4, 2007;48(23):3953-7.

Volkov et al., Interaction of Acetals and Ortho-Ethers With Triisobutylaluminum. Zhurnal Organicheskoi KHIMII. Dec. 31, 1986; 22(8):1787-1788.

Wang et al., Synthesis and preliminary biological evaluation of O6-[4-(2-[18F]fluoroethoxymethyl)benzyl]guanine as a novel potential PET probe for the DNA repair protein O6-alkylguanine-DNA alkyltransferase in cancer chemotherapy. Bioorg Med Chem. Oct. 15, 2005;13(20):5779-86.

Wu et al., Studies on Synthesis of the new Precursors of 18F Labelled Amino Acids Radiopharmaceuticals for Positron Emission Tomography. Chinese Doctoral Dissertations Full-text Database (Medicine and Health Sciences). 2009;7:E79-12, pp. 7-10.

Kagan et al., LMI1195 and Flurpiridaz F 18 PET Imaging in Evaluation of Time-Course Changes in Mismatch of Cardiac Denervated and Perfusion Defect Areas Following Acute Myocardial Infarction. J Nuc Med (Society of Nuclear Medicine Annual Meeting Abstracts). 2012;53(S1):84.

Maddahi et al., Phase I, First-in-Human Study of BMS747158, a Novel 18F-Labeled Tracer for Myocardial Perfusion PET: Dosimetry, Biodistribution, Safety, and Imaging Characteristics After a Single Injection at Rest. J Nucl Med. 2011;52: 1490-9.

Nekolla et al., Evaluation of the novel myocardial perfusion positron-emission tomography tracer 18F-BMS-747158-02: comparison to 13N-ammonia and validation with microspheres in a pig model. Circulation. May 5, 2009;119(17):2333-42. Epub Apr. 20, 2009.

Pauwels et al., Fluorine-18-radiolabeled pharmaceuticals for imaging with positron emission tomography, excluding [18F]-fluorodeoxyglucose. Drugs of the Future. 2002;27:655-67.

Sherif et al., Evaluation of a novel (18)F-labeled positron-emission tomography perfusion tracer for the assessment of myocardial infarct size in rats. Circ Cardiovasc Imaging. Mar. 2009;2(2):77-84. Epub Jan. 26, 2009.

Yu et al., BMS-747158-02: a novel PET myocardial perfusion imaging agent. J Nucl Cardiol. Nov.-Dec. 2007;14(6):789-98. Epub Oct. 22, 2007.

(56) References Cited

OTHER PUBLICATIONS

Yu et al., Cardiac imaging and safety evaluation of BMS747158, a novel PET myocardial perfusion imaging agent, in chronic myocardial compromised rabbits. J Nucl Cardiol. Aug. 2010;17(4):631-6. Epub Mar. 26, 2010.

Yu et al., Evaluation of LMI1195, a novel 18F-labeled cardiac neuronal PET imaging agent, in cells and animal models. Circ Cardiovasc Imaging. Jul. 2011;4(4):435-43. Epub May 9, 2011.

Yu et al., LMI1195 PET imaging in evaluation of regional cardiac sympathetic denervation and its potential role in antiarrhythmic drug treatment. Eur J Nucl Med Mol Imaging. Dec. 2012;39(12):1910-9. doi: 10.1007/s00259-012-2204-y. Epub Aug. 4, 2012.

Yu et al., The next generation of cardiac positron emission tomography imaging agents: discovery of flurpiridaz F-18 for detection of coronary disease. Semin Nucl Med. Jul. 2011;41(4):305-13. doi: 10.1053/j.semnuclmed.2011.02.004.

* cited by examiner

Example 1

Example 2

Example 8

Example 11

Example 12

Control
(same rabbit)

Global denervation
(same rabbit)

Short-axis  Long-axis  Polar map

Short-axis  Long-axis  Polar map

COMPOSITIONS, METHODS, AND SYSTEMS FOR THE SYNTHESIS AND USE OF IMAGING AGENTS

RELATED APPLICATIONS

The present application is a U.S. National Stage application of International Patent Application Serial No. PCT/US2012/054309, filed Sep. 7, 2012, entitled "COMPOSITIONS, METHODS, AND SYSTEMS FOR THE SYNTHESIS AND USE OF IMAGING AGENTS" which claims priority under 35 U.S.C. §119(e) to U.S. Provisional Application Ser. No. 61/533,133, filed Sep. 9, 2011, entitled "COMPOSITIONS, METHODS, AND SYSTEMS FOR THE SYNTHESIS AND USE OF IMAGING AGENTS"; U.S. Provisional Application Ser. No. 61/656,489, filed Jun. 6, 2012, entitled "COMPOSITIONS, METHODS, AND SYSTEMS FOR THE SYNTHESIS AND USE OF IMAGING AGENTS"; and U.S. Provisional Application Ser. No. 61/656,492, filed Jun. 6, 2012, entitled "METHODS AND COMPOSITIONS FOR ASSESSING PERFUSION AND INNERVATION MISMATCH", the entire contents of each of which are incorporated herein by reference.

FIELD OF THE INVENTION

The present invention relates to compounds useful as imaging agents, compositions thereof, methods for the synthesis and use thereof, and precursors thereto. In some embodiments, the compounds may be used to image perfusion (e.g., cardiac perfusion). In other embodiments, the compounds may be used to image innervation. The present invention also provides methods and compositions for assessing perfusion and innervation mismatch in a subject, for example, a human subject.

BACKGROUND OF THE INVENTION

Heart failure (HF) is defined as the inability of the heart to supply peripheral organs with sufficient blood flow. It may be characterized by a hyperadrenergic state whereby increased systemic levels of norepinephrine (NE) and increased local spillover of catecholamines occur. The condition afflicts increasingly more people each year and is a common end-stage of many cardiac diseases and conditions including myocardial infarction, pressure/volume overload, viral myocarditis, toxic cardiomyopathy, valve failure, and other abnormalities. The resultant myocardial damage, in conjunction with neurohormonal and cytokine activation, stimulates chamber remodeling which is the initial phase of heart failure. This remodeling process results in decreased overall myocardial efficiency and eventual progression to clinical HF. To date, however, no cure for the condition exists, thus early diagnosis is a key factor in its management and long-term prognosis. An imaging agent that identifies subjects in early HF would thus enable treatment and life-style improvements for patients living with the condition.

Myocardial damage may also occur following tissue insult (e.g., a myocardial infarction), whereby innervation and perfusion defects may form in a portion of the subject (i.e. a portion of the heart). In certain cases, the size of the defect areas, as detected by imaging, could be different (e.g., regional mismatch) and may be associated with an increased probability for cardiac arrhythmia as well as other conditions.

Accordingly, improved compositions, methods, systems, and apparatuses are needed for the synthesis and administration of imaging agents (e.g., for imaging the heart).

SUMMARY OF THE INVENTION

The present invention provides, in a broad sense, compounds and compositions thereof (including salt forms) that are useful as imaging agents or imaging agent precursors, methods of use thereof, and methods for synthesizing provided compounds. In some embodiments, the imaging agents may be used for imaging perfusion. In some embodiments, the imaging agents may be used for imaging a portion of the subject, for example, a portion of the heart. In some embodiments, method of imaging are provided. In some embodiments, methods and compositions for assessing perfusion and innervation mismatch in a portion of a subject are provided.

In some embodiments, a compound is provided having formula:

wherein

Ar is substituted or unsubstituted, monocyclic or bicyclic aryl; or substituted or unsubstituted, monocyclic or bicyclic heteroaryl;

L is a bond; substituted or unsubstituted, cyclic or acyclic alkylene; substituted or unsubstituted, cyclic or acyclic alkenylene; substituted or unsubstituted, cyclic or acyclic alkynylene; or substituted or unsubstituted, cyclic or acyclic heteroaliphatic;

$R^1$ is a substituted or unsubstituted nitrogen-containing moiety; and $R^0$ is halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, —$OR^{41}$, —$N(R^{42})_2$, —$SR^{41}$, —$C(=O)R^{41}$, —$C(=O)OR^{41}$, —$C(=O)SR^{41}$, —$C(=O)N(R^{42})_2$, —$OC(=O)R^{41}$, —$OC(=O)OR^{41}$, —$OC(=O)SR^{41}$, —$OC(=O)N(R^{42})_2$, —$NR^{42}C(=O)R^{42}$, —$NR^{42}C(=O)OR^{41}$, —$NR^{42}C(=O)SR^{41}$, —$NR^{42}C(=O)N(R^{42})_2$, —$SC(=O)R^{41}$, —$SC(=O)OR^{41}$, —$SC(=O)SR^{41}$, —$SC(=O)N(R^{42})_2$, —$C(=NR^{42})R^{41}$, —$C(=NR)OR^{41}$, —$C(=NR^{42})SR^{41}$, —$C(=NR^{42})N(R^{42})_2$, —$OC(=NR^{42})R^{41}$, —$OC(=NR^{42})OR^{41}$, —$OC(=NR^{42})SR^{41}$, —$OC(=NR^{42})N(R^{42})_2$, —$NR^{42}C(=NR^{42})R^{42}$, —$NR^{42}C(=NR)OR^{41}$, —$NR^{42}C(=NR^{42})SR^{41}$, —$NR^{42}C(=NR^{42})N(R^{42})_2$, —$SC(=NR^{42})R^{41}$, —$SC(=NR^{41})OR^{41}$, —$SC(=NR^{42})SR^{41}$, —$SC(=NR^{42})N(R^{42})_2$, —$C(=S)R^{41}$, —$C(=S)OR^{41}$, —$C(=S)SR^{41}$, —$C(=S)N(R^{42})_2$, —$OC(=S)R^{41}$, —$OC(=S)OR^{41}$, —$OC(=S)SR^{41}$, —$OC(=S)N(R^{42})_2$, —$NR^{42}C(=S)R^{42}$, —$NR^{42}C(=S)OR^{41}$, —$NR^{42}C(=S)SR^{41}$, —$NR^{42}C(=S)N(R^{42})_2$, —$SC(=S)R^{41}$, —$SC(=S)OR^{41}$, —$SC(=S)SR^{41}$, —$SC(=S)N(R^{42})_2$, —$S(=O)R^{41}$, —$SO_2R^{41}$, —$NR^{42}SO_2R^{41}$, —$SO_2N(R^{42})_2$, —CN, —SCN, or —$NO_2$;

each occurrence of $R^{41}$ is independently hydrogen, optionally substituted alkyl, optionally substituted alkenyl, optionally substituted alkynyl, optionally substituted carbocyclyl, optionally substituted heterocyclyl, optionally substituted aryl, or optionally substituted heteroaryl; and each occurrence of $R^{42}$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, or an amino protecting group, or two $R^{A2}$ groups are joined to form an optionally substituted heterocyclic ring; and $R^0$ or $R^1$ is substituted with an imaging moiety selected from the group consisting of $^{18}F$, $^{76}Br$, $^{124}I$, and $^{131}I$, or is associated with an imaging moiety selected from the group consisting of $^{64}Cu$, $^{89}Zr$, $^{99m}Tc$, and $^{111}In$ through a chelator, or is an imaging moiety selected from the group consisting of $^{18}F$, $^{76}Br$, $^{124}I$, and $^{131}I$; or a salt thereof.

In some embodiments, a compound is provided having formula:

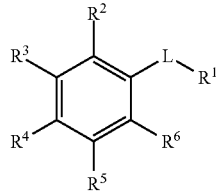

wherein

L is a bond; substituted or unsubstituted, cyclic or acyclic alkylene; substituted or unsubstituted, cyclic or acyclic alkenylene; substituted or unsubstituted, cyclic or acyclic alkynylene; or substituted or unsubstituted, cyclic or acyclic heteroaliphatic;

$R^1$ is selected from the group consisting of:

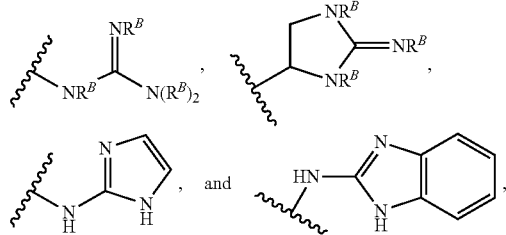

wherein each occurrence of $R^B$ is independently hydrogen, substituted or unsubstituted alkyl, or a nitrogen-protecting group, provided at least two $R^B$ are hydrogen;

$R^2$ and $R^6$ are hydrogen;

each of $R^3$, $R^4$ and $R^5$ is independently hydrogen, halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, —$OR^{A1}$, —$N(R^{A2})_2$, —$SR^{A1}$, —$C(=O)R^{A1}$, —$C(=O)OR^{A1}$, —$C(=O)SR^{A1}$, —$C(=O)N(R^{A2})_2$, —$OC(=O)R^{A1}$, —$OC(=O)OR^{A1}$, —$OC(=O)SR^{A1}$, —$OC(=O)N(R^{A2})_2$, —$NR^{A2}C(=O)R^{A2}$, —$NR^{A2}C(=O)OR^{A1}$, —$NR^{A2}C(=O)SR^{A1}$, —$NR^{A2}C(=O)N(R^{A2})_2$, —$SC(=O)R^{A1}$, —$SC(=O)OR^{A1}$, —$SC(=O)SR^{A1}$, —$SC(=O)N(R^{A2})_2$, —$C(=NR^{A2})R^{A1}$, —$C(=NR^{A2})OR^{A1}$, —$C(=NR^{A2})SR^{A1}$, —$C(=NR^{A2})N(R^{A2})_2$, —$OC(=NR^{A2})R^{A1}$, —$OC(=NR^{A2})OR^{A1}$, —$OC(=NR^{A2})SR^{A1}$, —$OC(=NR^{A2})N(R^{A2})_2$, —$NR^{A2}C(=NR^{A2})R^{A2}$, —$NR^{A2}C(=NR^{A2})OR^{A1}$, —$NR^{A2}C(=NR^{A2})SR^{A1}$, —$NR^{A2}C(=NR^{A2})N(R^{A2})_2$, —$SC(=NR^{A2})R^{A1}$, —$SC(=NR)OR^{A1}$, —$SC(=NR^{A2})SR^{A1}$, —$SC(=NR^{A2})N(R^{A2})_2$, —$C(=S)R^{A1}$, —$C(=S)OR^{A1}$, —$C(=S)SR^{A1}$, —$C(=S)N(R^{A2})_2$, —$OC(=S)R^{A1}$, —$OC(=S)OR^{A1}$, —$OC(=S)SR^{A1}$, —$OC(=S)N(R^{A2})_2$, —$NR^{A2}C(=S)R^{A2}$, —$NR^{A2}C(=S)OR^{A1}$, —$NR^{A2}C(=S)SR^{A1}$, —$NR^{A2}C(=S)N(R^{A2})_2$, —$SC(=S)R^{A1}$, —$SC(=S)OR^{A1}$, —$SC(=S)SR^{A1}$, —$SC(=S)N(R^{A2})_2$, —$S(=O)R^{A1}$, —$SO_2R^{A1}$, —$NR^{A2}SO_2R^{A1}$, —$SO_2N(R^{A2})_2$, —CN, —SCN, or —$NO_2$; or any two adjacent $R^3$, $R^4$ and $R^5$ are joined to form an optionally substituted or unsubstituted carbocyclic, heterocyclic, aryl, or heteroaryl ring;

each occurrence of $R^{A1}$ is independently hydrogen, optionally substituted alkyl, optionally substituted alkenyl, optionally substituted alkynyl, optionally substituted carbocyclyl, optionally substituted heterocyclyl, optionally substituted aryl, or optionally substituted heteroaryl; and each occurrence of $R^{A2}$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, or an amino protecting group, or two $R^{A2}$ groups are joined to form an optionally substituted heterocyclic ring; and wherein $R^4$ is substituted with an imaging moiety selected from the group consisting of $^{18}F$, $^{76}Br$, and $^{124}I$; or is associated with an imaging moiety selected from the group consisting of $^{64}Cu$, $^{89}Zr$, $^{99m}Tc$, and $^{111}In$ through a chelator; or is $^{124}I$;

or a salt thereof with the proviso that if one of $R^3$ or $R^5$ is Cl, Br, or $CF_3$, then the other of $R^3$ or $R^5$ is not H.

In some embodiments, a compound is provided having formula:

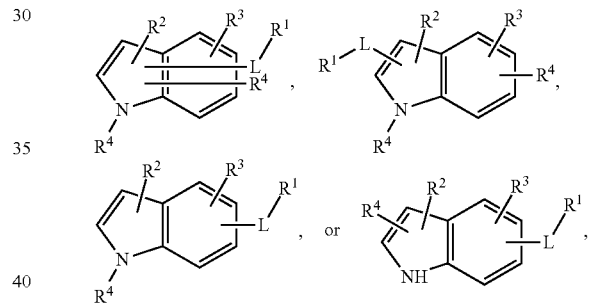

wherein

L is a bond; substituted or unsubstituted, cyclic or acyclic alkylene; substituted or unsubstituted, cyclic or acyclic alkenylene; substituted or unsubstituted, cyclic or acyclic alkynylene; or substituted or unsubstituted, cyclic or acyclic heteroaliphatic;

$R^1$ is a substituted or unsubstituted nitrogen-containing moiety;

$R^2$ is hydrogen, halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, —$OR^{A1}$, —$N(R^{A2})_2$, —$SR^{A1}$, —$C(=O)R^{A1}$, —$C(=O)OR^{A1}$, —$C(=O)SR^{A1}$, —$C(=O)N(R^{A2})_2$, —$OC(=O)R^{A1}$, —$OC(=O)OR^{A1}$, —$OC(=O)SR^{A1}$, —$OC(=O)N(R^{A2})_2$, —$NR^{A2}C(=O)R^{A2}$, —$NR^{A2}C(=O)OR^{A1}$, —$NR^{A2}C(=O)SR^{A1}$, —$NR^{A2}C(=O)N(R^{A2})_2$, —$SC(=O)R^{A1}$, —$SC(=O)OR^{A1}$, —$SC(=O)SR^{A1}$, —$SC(=O)N(R^{A2})_2$, —$C(=NR^{A2})R^{A1}$, —$C(=NR^{A2})OR^{A1}$, —$C(=NR^{A2})SR^{A1}$, —$C(=NR^{A2})N(R^{A2})_2$, —$OC(=NR^{A2})R^{A1}$, —$OC(=NR^{A2})OR^{A1}$, —$OC(=NR^{A2})SR^{A1}$, —$OC(=NR^{A2})N(R^{A2})_2$, —$NR^{A2}C(=NR^{A2})R^{A2}$, —$NR^{A2}C(=NR^{A2})OR^{A1}$, —$NR^{A2}C(=NR^{A2})SR^{A1}$, —$NR^{A2}C(=NR^{A2})N(R^{A2})_2$, —$SC(=NR^{A2})R^{A1}$, —$SC(=NR^{A2})OR^{A1}$, —$SC(=NR^{A2})SR^{A1}$, —$SC(=NR^{A2})N(R^{A2})_2$, —C(=S)R$^{A1}$, —C(=S)OR$^{A1}$, —C(=S)SR$^{A1}$, —C(=S)N(R$^{A2}$)$_2$, —OC(=S)R$^{A1}$, —OC(=S)OR$^{A1}$, —OC(=S)SR$^{A1}$, —OC(=S)N(R$^{A2}$)$_2$, —NR$^{A2}$C(=S)R$^{A2}$, —NR$^{A2}$C(=S)OR$^{A1}$, —NR$^{A2}$C(=S)SR$^{A1}$, —NR$^{A2}$C(=S)N(R$^{A2}$)$_2$, —SC(=S)R$^{A1}$, —SC(=S)OR$^{A1}$, —SC(=S)SR$^{A1}$, —SC(=S)N(R$^{A2}$)$_2$, —S(=O)R$^{A1}$, —SO$_2$R$^{A1}$, —NR$^{A2}$SO$_2$R$^{A1}$, —SO$_2$N(R$^{A2}$)$_2$, —CN, —SCN, or —NO$_2$;

R$^3$ is hydrogen, halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, —OR$^{A1}$, —N(R$^{A2}$)$_2$, —SR$^{A1}$, —C(=O)R$^{A1}$, —C(=O)OR$^{A1}$, —C(=O)SR$^{A1}$, —C(=O)N(R$^{A2}$)$_2$, —OC(=O)R$^{A1}$, —OC(=O)OR$^{A1}$, —OC(=O)SR$^{A1}$, —OC(=O)N(R$^{A2}$)$_2$, —NR$^{A2}$C(=O)R$^{A2}$, —NR$^{A2}$C(=O)OR$^{A1}$, —NR$^{A2}$C(=O)SR$^{A1}$, —NR$^{A2}$C(=O)N(R$^{A2}$)$_2$, —SC(=O)R$^{A1}$, —SC(=O)OR$^{A1}$, —SC(=O)SR$^{A1}$, —SC(=O)N(R$^{A2}$)$_2$, —C(=NR$^{A2}$)R$^{A1}$, —C(=NR$^{A2}$)OR$^{A1}$, —C(=NR$^{A2}$)SR$^{A1}$, —C(=NR$^{A2}$)N(R$^{A2}$)$_2$, —OC(=NR$^{A2}$)R$^{A1}$, —OC(=NR$^{A2}$)OR$^{A1}$, —OC(=NR$^{A2}$)SR$^{A1}$, —OC(=NR$^{A2}$)N(R$^{A2}$)$_2$, —NR$^{A2}$C(=NR$^{A2}$)R$^{A2}$, —NR$^{A2}$C(=NR$^{A2}$)OR$^{A1}$, —NR$^{A2}$C(=NR$^{A2}$)SR$^{A1}$, —NR$^{A2}$C(=NR$^{A2}$)N(R$^{A2}$)$_2$, —SC(=NR$^{A2}$)R$^{A1}$, —SC(=NR$^{A2}$)OR$^{A1}$, —SC(=NR$^{A2}$)SR$^{A1}$, —SC(=NR$^{A2}$)N(R$^{A2}$)$_2$, —C(=S)R$^{A1}$, —C(=S)OR$^{A1}$, —C(=S)SR$^{A1}$, —C(=S)N(R$^{A2}$)$_2$, —OC(=S)R$^{A1}$, —OC(=S)OR$^{A1}$, —OC(=S)SR$^{A1}$, —OC(=S)N(R$^{A2}$)$_2$, —NR$^{A2}$C(=S)R$^{A2}$, —NR$^{A2}$C(=S)OR$^{A1}$, —NR$^{A2}$C(=S)SR$^{A1}$, —NR$^{A2}$C(=S)N(R$^{A2}$)$_2$, —SC(=S)R$^{A1}$, —SC(=S)OR$^{A1}$, —SC(=S)SR$^{A1}$, —SC(=S)N(R$^{A2}$)$_2$, —S(=O)R$^{A1}$, —SO$_2$R$^{A1}$, —NR$^{A2}$SO$_2$R$^{A1}$, —SO$_2$N(R$^{A2}$)$_2$, —CN, —SCN, or —NO$_2$;

each occurrence of R$^4$ is independently hydrogen, halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, —OR$^{A1}$, —N(R$^{A2}$)$_2$, —SR$^{A1}$, —C(=O)R$^{A1}$, —C(=O)OR$^{A1}$, —C(=O)SR$^{A1}$, —C(=O)N(R$^{A2}$)$_2$, —OC(=O)R$^{A1}$, —OC(=O)OR$^{A1}$, —OC(=O)SR$^{A1}$, —OC(=O)N(R$^{A2}$)$_2$, —NR$^{A2}$C(=O)R$^{A2}$, —NR$^{A2}$C(=O)OR$^{A1}$, —NR$^{A2}$C(=O)SR$^{A1}$, —NR$^{A2}$C(=O)N(R$^{A2}$)$_2$, —SC(=O)R$^{A1}$, —SC(=O)OR$^{A1}$, —SC(=O)SR$^{A1}$, SC(=O)N(R$^{A2}$)$_2$, —C(=NR$^{A2}$)R$^{A1}$, —C(=NR$^{A2}$)OR$^{A1}$, —C(=NR$^{A2}$)SR$^{A1}$, —C(=NR$^{A2}$)N(R$^{A2}$)$_2$, —OC(=NR$^{A2}$)R$^{A1}$, —OC(=NR$^{A2}$)N(R$^{A2}$)$_2$, —NR$^{A2}$C(=NR$^{A2}$)R$^{A2}$, —NR$^{A2}$C(=NR$^{A2}$)OR$^{A1}$, —NR$^{A2}$C(=NR$^{A2}$)SR$^{A1}$, —NR$^{A2}$C(=NR$^{A2}$)N(R$^{A2}$)$_2$, —SC(=NR$^{A2}$)R$^{A1}$, —SC(=NR$^{A2}$)OR$^{A1}$, —SC(=NR$^{A2}$)SR$^{A1}$, —SC(=NR$^{A2}$)N(R$^{A2}$)$_2$, —C(=S)R$^{A1}$, —C(=S)OR$^{A1}$, —C(=S)SR$^{A1}$, —C(=S)N(R$^{A2}$)$_2$, —OC(=S)R$^{A1}$, —OC(=S)OR$^{A1}$, —OC(=S)SR$^{A1}$, —OC(=S)N(R$^{A2}$)$_2$, —NR$^{A2}$C(=S)R$^{A2}$, —NR$^{A2}$C(=S)OR$^{A1}$, —NR$^{A2}$C(=S)SR$^{A1}$, —NR$^{A2}$C(=S)N(R$^{A2}$)$_2$, —SC(=S)R$^{A1}$, —SC(=S)OR$^{A1}$, —SC(=S)SR$^{A1}$, —SC(=S)N(R$^{A2}$)$_2$, —S(=O)R$^{A1}$, —SO$_2$R$^{A1}$, —NR$^{A2}$SO$_2$R$^{A1}$, SO$_2$N(R$^{A2}$)$_2$, —CN, —SCN, or —NO$_2$;

each occurrence of R$^{A1}$ is independently hydrogen, optionally substituted alkyl, optionally substituted alkenyl, optionally substituted alkynyl, optionally substituted carbocyclyl, optionally substituted heterocyclyl, optionally substituted aryl, or optionally substituted heteroaryl; and each occurrence of R$^{A2}$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, or an amino protecting group, or two R$^{A2}$ groups are joined to form an optionally substituted heterocyclic ring;

at least one R$^4$ is substituted with an imaging moiety selected from the group consisting of $^{18}$F, $^{76}$Br, $^{124}$I, and $^{131}$I; or is associated with an imaging moiety selected from the group consisting of $^{64}$Cu, $^{89}$Zr, $^{99m}$Tc, and $^{111}$In through a chelator; or is an imaging moiety selected from the group consisting of $^{18}$F, 76Br, $^{124}$I, and $^{131}$I; or a salt thereof.

In some embodiments, a compound is provided having formula:

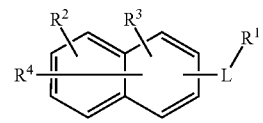

wherein

L is a bond; substituted or unsubstituted, cyclic or acyclic alkylene; substituted or unsubstituted, cyclic or acyclic alkenylene; substituted or unsubstituted, cyclic or acyclic alkynylene; or substituted or unsubstituted, cyclic or acyclic heteroaliphatic;

R$^1$ is a substituted or unsubstituted nitrogen-containing moiety;

R$^2$ is hydrogen, halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, —OR$^{A1}$, —N(R$^{A2}$)$_2$, —SR$^{A1}$, —C(=O)R$^{A1}$, —C(=O)OR$^{A1}$, —C(=O)SR$^{A1}$, —C(=O)N(R$^{A2}$)$_2$, —OC(=O)R$^{A1}$, —OC(=O)OR$^{A1}$, —OC(=O)SR$^{A1}$, —OC(=O)N(R$^{A2}$)$_2$, —NR$^{A2}$C(=O)R$^{A2}$, —NR$^{A2}$C(=O)OR$^{A1}$, —NR$^{A2}$C(=O)SR$^{A1}$, —NR$^{A2}$C(=O)N(R$^{A2}$)$_2$, —SC(=O)R$^{A1}$, —SC(=O)OR$^{A1}$, —SC(=O)SR$^{A1}$, —SC(=O)N(R$^{A2}$)$_2$, —C(=NR$^{A2}$)R$^{A1}$, —C(=NR$^{A2}$)OR$^{A1}$, —C(=NR$^{A2}$)SR$^{A1}$, —C(=NR$^{A2}$)N(R$^{A2}$)$_2$, —OC(=NR$^{A2}$)R$^{A1}$, —OC(=NR$^{A2}$)OR$^{A1}$, —OC(=NR$^{A2}$)SR$^{A1}$, —OC(=NR$^{A2}$)N(R$^{A2}$)$_2$, —NR$^{A2}$C(=NR$^{A2}$)R$^{A2}$, —NR$^{A2}$C(=NR$^{A2}$)OR$^{A1}$, —NR$^{A2}$C(=NR$^{A2}$)SR$^{A1}$, —NR$^{A2}$C(=NR$^{A2}$)N(R$^{A2}$)$_2$, —SC(=NR$^{A2}$)R$^{A1}$, —SC(=NR$^{A2}$)OR$^{A1}$, —SC(=NR$^{A2}$)SR$^{A1}$, —SC(=NR$^{A2}$)N(R$^{A2}$)$_2$, —C(=S)R$^{A1}$, —C(=S)OR$^{A1}$, —C(=S)SR$^{A1}$, —C(=S)N(R$^{A2}$)$_2$, —OC(=S)R$^{A1}$, —OC(=S)OR$^{A1}$, —OC(=S)SR$^{A1}$, —OC(=S)N(R$^{A2}$)$_2$, —NR$^{A2}$C(=S)R$^{A2}$, —NR$^{A2}$C(=S)OR$^{A1}$, —NR$^{A2}$C(=S)SR$^{A1}$, —NR$^{A2}$C(=S)N(R$^{A2}$)$_2$, —SC(=S)R$^{A1}$, —SC(=S)OR$^{A1}$, —SC(=S)SR$^{A1}$, —SC(=S)N(R$^{A2}$)$_2$, —S(=O)R$^{A1}$, —SO$_2$R$^{A1}$, —NR$^{A2}$SO$_2$R$^{A1}$, —SO$_2$N(R$^{A2}$)$_2$, —CN, —SCN, or —NO$_2$;

R$^3$ is hydrogen, halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, —OR$^{A1}$, —N(R$^{A2}$)$_2$, —SR$^{A1}$, —C(=O)R$^{A1}$, —C(=O)OR$^{A1}$, —C(=O)SR$^{A1}$, —C(=O)N(R$^{A2}$)$_2$, —OC(=O)R$^{A1}$, —OC(=O)OR$^{A1}$, —OC(=O)SR$^{A1}$, —OC(=O)N(R$^{A2}$)$_2$, —NR$^{A2}$C(=O)R$^{A2}$, —NR$^{A2}$C(=O)OR$^{A1}$, —NR$^{A2}$C(=O)SR$^{A1}$, —NR$^{A2}$C(=O)N(R$^{A2}$)$_2$, —SC(=O)R$^{A1}$, —SC(=O)OR$^{A1}$, —SC(=O)SR$^{A1}$, —SC(=O)N(R$^{A2}$)$_2$, —C(=NR$^{A2}$)R$^{A1}$, —C(=NR$^{A2}$)OR$^{A1}$, —C(=NR$^{A2}$)SR$^{A1}$, —C(=NR$^{A2}$)N(R$^{A2}$)$_2$, —OC(=NR$^{A2}$)R$^{A1}$, —OC(=NR$^{A2}$)OR$^{A1}$, —OC(=NR$^{A2}$)SR$^{A1}$, —OC(=NR$^{A2}$)N(R$^{A2}$)$_2$, —NR$^{A2}$C(=NR$^{A2}$)R$^{A2}$, —NR$^{A2}$C(=NR$^{A2}$)OR$^{A1}$, —NR$^{A2}$C(=NR$^{A2}$)SR$^{A1}$, —NR$^{A2}$C(=NR$^{A2}$)N(R$^{A2}$)$_2$, —SC(=NR$^{A2}$)R$^{A1}$, —SC(=NR$^{A2}$)OR$^{A1}$, —SC(=NR$^{A2}$)SR$^{A1}$, —SC(=NR$^{A2}$)N(R$^{A2}$)$_2$, —C(=S)R$^{A1}$, —C(=S)OR$^{A1}$, —C(=S)SR$^{A1}$, —C(=S)N(R$^{A2}$)$_2$, —OC(=S)R$^{A1}$, —OC(=S)OR$^{A1}$, —OC(=S)SR$^{A1}$, —OC(=S)N($R^{A2}$)$_2$, —$NR^{A2}$C(=S)$R^{A2}$, —$NR^{A2}$C(=S)$OR^{A1}$, —$NR^{A2}$C(=S)$SR^{A1}$, —$NR^{A2}$C(=S)N($R^{A2}$)$_2$, —SC(=S)$R^{A1}$, —SC(=S)$OR^{A1}$, —SC(=S)$SR^{A1}$, —SC(=S)N($R^{A2}$)$_2$, —S(=O)$R^{A1}$, —SO$_2$$R^{A1}$, —$NR^{A2}$SO$_2$$R^{A1}$, —SO$_2$N($R^{A2}$)$_2$, —CN, —SCN, or —NO$_2$;

$R^4$ is hydrogen, halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, —$OR^{A1}$, —N($R^{A2}$)$_2$, —$SR^{A1}$, —C(=O)$R^{A1}$, —C(=O)$OR^{A1}$, —C(=O)$SR^{A1}$, —C(=O)N($R^{A2}$)$_2$, —OC(=O)$R^{A1}$, —OC(=O)$OR^{A1}$, —OC(=O)$SR^{A1}$, —OC(=O)N($R^{A2}$)$_2$, —$NR^{A2}$C(=O)$R^{A2}$, —$NR^{A2}$C(=O)$OR^{A1}$, —$NR^{A2}$C(=O)$SR^{A1}$, —$NR^{A2}$C(=O)N($R^{A2}$)$_2$, —SC(=O)$R^{A1}$, —SC(=O)$OR^{A1}$, —SC(=O)$SR^{A1}$, —SC(=O)N($R^{A2}$)$_2$, —C(=$NR^{A2}$)$R^{A1}$, —C(=$NR^{A2}$)$OR^{A1}$, —C(=$NR^{A2}$)$SR^{A1}$, —C(=$NR^{A2}$)N($R^{A2}$)$_2$, —OC(=$NR^{A2}$)$R^{A1}$, —OC(=$NR^{A2}$)$OR^{A1}$, —OC(=$NR^{A2}$)$SR^{A1}$, —OC(=$NR^{A2}$)N($R^{A2}$)$_2$, —$NR^{A2}$C(=$NR^{A2}$)$R^{A2}$, —$NR^{A2}$C(=$NR^{A2}$)$OR^{A1}$, —$NR^{A2}$C(=$NR^{A2}$)$SR^{A1}$, —$NR^{A2}$C(=$NR^{A2}$)N($R^{A2}$)$_2$, —SC(=$NR^{A2}$)$R^{A1}$, —SC(=$NR^{A2}$)$OR^{A1}$, —SC(=$NR^{A2}$)$SR^{A1}$, —SC(=$NR^{A2}$)N($R^{A2}$)$_2$, —C(=S)$R^{A1}$, —C(=S)$OR^{A1}$, —C(=S)$SR^{A1}$, —C(=S)N($R^{A2}$)$_2$, —OC(=S)$R^{A1}$, —OC(=S)$OR^{A1}$, —OC(=S)$SR^{A1}$, —OC(=S)N($R^{A2}$)$_2$, —$NR^{A2}$C(=S)$R^{A2}$, —$NR^{A2}$C(=S)$OR^{A1}$, —$NR^{A2}$C(=S)$SR^{A1}$, —$NR^{A2}$C(=S)N($R^{A2}$)$_2$, —SC(=S)$R^{A1}$, —SC(=S)$OR^{A1}$, —SC(=S)$SR^{A1}$, —SC(=S)N($R^{A2}$)$_2$, —S(=O)$R^{A1}$, —SO$_2$$R^{A1}$, —$NR^{A2}$SO$_2$$R^{A1}$, —SO$_2$N($R^{A2}$)$_2$, —CN, —SCN, or —NO$_2$;

$R^4$ is substituted with an imaging moiety selected from the group consisting of $^{18}$F, $^{76}$Br, $^{124}$I, and $^{131}$I; or is associated with an imaging moiety selected from the group consisting of $^{64}$Cu, $^{89}$Zr, $^{99m}$Tc, and $^{111}$In through a chelator; or is an imaging moiety selected from the group consisting of $^{18}$F, $^{76}$Br, $^{124}$I, and $^{131}$I;

each occurrence of $R^{A1}$ is independently hydrogen, optionally substituted alkyl, optionally substituted alkenyl, optionally substituted alkynyl, optionally substituted carbocyclyl, optionally substituted heterocyclyl, optionally substituted aryl, or optionally substituted heteroaryl; and each occurrence of $R^{A2}$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, or an amino protecting group, or two $R^{A2}$ groups are joined to form an optionally substituted heterocyclic ring; or a salt thereof.

In some embodiments, a compound is provided having formula:

wherein

L is a bond; substituted or unsubstituted, cyclic or acyclic alkylene; substituted or unsubstituted, cyclic or acyclic alkenylene; substituted or unsubstituted, cyclic or acyclic alkynylene; or substituted or unsubstituted, cyclic or acyclic heteroaliphatic;

$R^1$ is a substituted or unsubstituted nitrogen-containing moiety;

$R^2$ is hydrogen, halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, —$OR^{A1}$, —N($R^{A2}$)$_2$, —$SR^{A1}$, —C(=O)$R^{A1}$, —C(=O)$OR^{A1}$, —C(=O)$SR^{A1}$, —C(=O)N($R^{A2}$)$_2$, —OC(=O)$R^{A1}$, —OC(=O)$OR^{A1}$, —OC(=O)$SR^{A1}$, —OC(=O)N($R^{A2}$)$_2$, —$NR^{A2}$C(=O)$R^{A2}$, —$NR^{A2}$C(=O)$OR^{A1}$, —$NR^{A2}$C(=O)$SR^{A1}$, —$NR^{A2}$C(=O)N($R^{A2}$)$_2$, —SC(=O)$R^{A1}$, —SC(=O)$OR^{A1}$, —SC(=O)$SR^{A1}$, —SC(=O)N($R^{A2}$)$_2$, —C(=$NR^{A2}$)$R^{A1}$, —C(=$NR^{A2}$)$OR^{A1}$, —C(=$NR^{A2}$)$SR^{A1}$, —C(=$NR^{A2}$)N($R^{A2}$)$_2$, —OC(=$NR^{A2}$)$R^{A1}$, —OC(=$NR^{A2}$)$OR^{A1}$, —OC(=$NR^{A2}$)$SR^{A1}$, —OC(=$NR^{A2}$)N($R^{A2}$)$_2$, —$NR^{A2}$C(=$NR^{A2}$)$R^{A2}$, —$NR^{A2}$C(=$NR^{A2}$)$OR^{A1}$, —$NR^{A2}$C(=$NR^{A2}$)$SR^{A1}$, —$NR^{A2}$C(=$NR^{A2}$)N($R^{A2}$)$_2$, —SC(=$NR^{A2}$)$R^{A1}$, —SC(=$NR^{A2}$)$OR^{A1}$, —SC(=$NR^{A2}$)$SR^{A1}$, —SC(=$NR^{A2}$)N($R^{A2}$)$_2$, —C(=S)$R^{A1}$, —C(=S)$OR^{A1}$, —C(=S)$SR^{A1}$, —C(=S)N($R^{A2}$)$_2$, —OC(=S)$R^{A1}$, —OC(=S)$OR^{A1}$, —OC(=S)$SR^{A1}$, —OC(=S)N($R^{A2}$)$_2$, —$NR^{A2}$C(=S)$R^{A2}$, —$NR^{A2}$C(=S)$OR^{A1}$, —$NR^{A2}$C(=S)$SR^{A1}$, —$NR^{A2}$C(=S)N($R^{A2}$)$_2$, —SC(=S)$R^{A1}$, —SC(=S)$OR^{A1}$, —SC(=S)$SR^{A1}$, —SC(=S)N($R^{A2}$)$_2$, —S(=O)$R^{A1}$, —SO$_2$$R^{A1}$, —$NR^{A2}$SO$_2$$R^{A1}$, —SO$_2$N($R^{A2}$)$_2$, —CN, —SCN, or —NO$_2$;

$R^3$ is hydrogen, halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, —$OR^{A1}$, —N($R^{A2}$)$_2$, —$SR^{A1}$, —C(=O)$R^{A1}$, —C(=O)$OR^{A1}$, —C(=O)$SR^{A1}$, —C(=O)N($R^{A2}$)$_2$, —OC(=O)$R^{A1}$, —OC(=O)$OR^{A1}$, —OC(=O)$SR^{A1}$, —OC(=O)N($R^{A2}$)$_2$, —$NR^{A2}$C(=O)$R^{A2}$, —$NR^{A2}$C(=O)$OR^{A1}$, —$NR^{A2}$C(=O)$SR^{A1}$, —$NR^{A2}$C(=O)N($R^{A2}$)$_2$, —SC(=O)$R^{A1}$, —SC(=O)$OR^{A1}$, —SC(=O)$SR^{A1}$, —SC(=O)N($R^{A2}$)$_2$, —C(=$NR^{A2}$)$R^{A1}$, —C(=$NR^{A2}$)$OR^{A1}$, —C(=$NR^{A2}$)$SR^{A1}$, —C(=$NR^{A2}$)N($R^{A2}$)$_2$, —OC(=$NR^{A2}$)$R^{A1}$, —OC(=$NR^{A2}$)$OR^{A1}$, —OC(=$NR^{A2}$)$SR^{A1}$, —OC(=$NR^{A2}$)N($R^{A2}$)$_2$, —$NR^{A2}$C(=$NR^{A2}$)$R^{A2}$, —$NR^{A2}$C(=$NR^{A2}$)$OR^{A1}$, —$NR^{A2}$C(=$NR^{A2}$)$SR^{A1}$, —$NR^{A2}$C(=$NR^{A2}$)N($R^{A2}$)$_2$, —SC(=$NR^{A2}$)$R^{A1}$, —SC(=$NR^{A2}$)$OR^{A1}$, —SC(=$NR^{A2}$)$SR^{A1}$, —SC(=$NR^{A2}$)N($R^{A2}$)$_2$, —C(=S)$R^{A1}$, —C(=S)$OR^{A1}$, —C(=S)$SR^{A1}$, —C(=S)N($R^{A2}$)$_2$, —OC(=S)$R^{A1}$, —OC(=S)$OR^{A1}$, —OC(=S)$SR^{A1}$, —OC(=S)N($R^{A2}$)$_2$, —$NR^{A2}$C(=S)$R^{A2}$, —$NR^{A2}$C(=S)$OR^{A1}$, —$NR^{A2}$C(=S)$SR^{A1}$, —$NR^{A2}$C(=S)N($R^{A2}$)$_2$, —SC(=S)$R^{A1}$, —SC(=S)$OR^{A1}$, —SC(=S)$SR^{A1}$, —SC(=S)N($R^{A2}$)$_2$, —S(=O)$R^{A1}$, —SO$_2$$R^{A1}$, —$NR^{A2}$SO$_2$$R^{A1}$, —SO$_2$N($R^{A2}$)$_2$, —CN, —SCN, or —NO$_2$;

$R^4$ is hydrogen, halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, —$OR^{A1}$, —N($R^{A2}$)$_2$, —$SR^{A1}$, —C(=O)$R^{A1}$, —C(=O)$OR^{A1}$, —C(=O)$SR^{A1}$, —C(=O)N($R^{A2}$)$_2$, —OC(=O)$R^{A1}$, —OC(=O)$OR^{A1}$, —OC(=O)$SR^{A1}$, —OC(=O)N($R^{A2}$)$_2$, —$NR^{A2}$C(=O)$R^{A2}$, —$NR^{A2}$C(=O)$OR^{A1}$, —$NR^{A2}$C(=O)$SR^{A1}$, —$NR^{A2}$C(=O)N($R^{A2}$)$_2$, —SC(=O)$R^{A1}$, —SC(=O)$OR^{A1}$, —SC(=O)$SR^{A1}$, —SC(=O)N($R^{A2}$)$_2$, —C(=$NR^{A2}$)$R^{A1}$, —C(=$NR^{A2}$)$OR^{A1}$, —C(=$NR^{A2}$)$SR^{A1}$, —C(=$NR^{A2}$)N($R^{A2}$)$_2$, —OC(=$NR^{A2}$)$R^{A1}$, —OC(=$NR^{A2}$)$OR^{A1}$, —OC(=$NR^{A2}$)$SR^{A1}$, —OC(=$NR^{A2}$)N($R^{A2}$)$_2$, —$NR^{A2}$C(=$NR^{A2}$)$R^{A2}$, —$NR^{A2}$C(=$NR^{A2}$)$OR^{A1}$, —$NR^{A2}$C(=$NR^{A2}$)$SR^{A1}$, —$NR^{A2}$C(=$NR^{A2}$)N($R^{A2}$)$_2$, —SC(=$NR^{A2}$)$R^{A1}$, —SC(=$NR^{A2}$)$OR^{A1}$, —SC(=$NR^{A2}$)$SR^{A1}$, —SC(=$NR^{A2}$)N($R^{A2}$)$_2$, —C(=S)$R^{A1}$, —C(=S)$OR^{A1}$, —C(=S)$SR^{A1}$, —C(=S)N($R^{A2}$)$_2$, —OC(=S)$R^{A1}$, —OC(=S)$OR^{A1}$, —OC(=S)$SR^{A1}$, —OC(=S)N($R^{A2}$)$_2$, —$NR^{A2}$C(=S)$R^{A2}$, —$NR^{A2}$C(=S)$OR^{A1}$, —$NR^{A2}$C(=S)$SR^{A1}$, —$NR^{A2}$C(=S)N($R^{A2}$)$_2$, —SC (=S)R$^{41}$, —SC(=S)OR$^{41}$, —SC(=S)SR$^{41}$, —SC(=S)N(R$^{42}$)$_2$, —S(=O)R$^{41}$, —SO$_2$R$^{41}$, —NR$^{42}$SO$_2$R$^{41}$, —SO$_2$N(R$^{42}$)$_2$, —CN, —SCN, or —NO$_2$;

R$^4$ is substituted with an imaging moiety selected from the group consisting of $^{18}$F, $^{76}$Br, $^{124}$I, and $^{131}$I; or is associated with an imaging moiety selected from the group consisting of $^{64}$Cu, $^{89}$Zr, $^{99m}$Tc, and $^{111}$In through a chelator; or is an imaging moiety selected from the group consisting of $^{18}$F, $^{76}$Br, $^{124}$I, and $^{131}$I;

each occurrence of R$^{41}$ is independently hydrogen, optionally substituted alkyl, optionally substituted alkenyl, optionally substituted alkynyl, optionally substituted carbocyclyl, optionally substituted heterocyclyl, optionally substituted aryl, or optionally substituted heteroaryl; and each occurrence of R$^{42}$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, or an amino protecting group, or two R$^{42}$ groups are joined to form an optionally substituted heterocyclic ring; or a salt thereof.

In some embodiments, a compound is provided having formula:

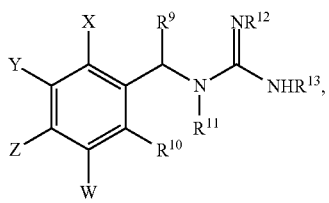

wherein

R$^9$ and R$^{10}$ are independently selected from the group consisting of H, —OR$^{11}$, F, Cl, Br, I, —CF$_3$, alkyl(C$_1$-C$_4$), and imaging moiety (I$_m$);

R$^{11}$, R$^{12}$ and R$^{13}$ are selected from the group consisting of H, alkyl, and aryl; and W and X are independently selected from the group consisting of H, —OR$^4$, —N(R$^{11}$)$_2$, F, Cl, Br, —CF$_3$, I$_m$, aryl, and heteroaryl;

wherein A) Y and Z are independently selected from the group consisting of —CH—, —CH$_2$—, —O—, —N—, —NR$^{11}$—, and —CH=CH— when a linking group Q between Y and Z is present or absent, wherein Q is selected from the group consisting of —CH—, —CH$_2$—, —CR$^{11}$—, —N—, —NH—, —NR$^{11}$—, —O—, and —S—; or B) Y and Z are independently selected from the group consisting of H, —OR$_4$, —N(R$^{11}$)$_2$, F, Cl, Br, —CF$_3$, I$_m$, aryl, and heteroaryl when linking group Q is absent;

wherein I$_m$ is selected from the group consisting of $^{18}$F, $^{76}$Br, $^{124}$I, and $^{131}$I, and is present in either W—Z or R$^9$-R$^{13}$, or a salt thereof.

In some embodiments, a compound is provided having formula:

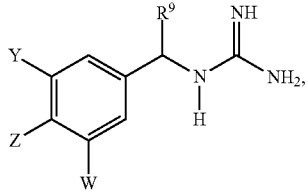

wherein R$^9$ is independently selected from the group consisting of H, —CF$_3$, and alkyl(C$_1$-C$_4$);

W, Y and Z are independently selected from the group consisting of H, —OR$^{11}$, —N(R$^{11}$)$_2$, F, Cl, Br, —CF$_3$, I$_m$, aryl and heteroaryl; and R$^{11}$ is selected from the group consisting of H, alkyl, and aryl;

wherein I$_m$ is selected from the group consisting of $^{18}$F, $^{76}$Br, $^{124}$I, and $^{131}$I, and is present in either W, Y, Z, R$^9$, or R$^{11}$; or a salt thereof.

In some embodiments, a compound is provided having formula:

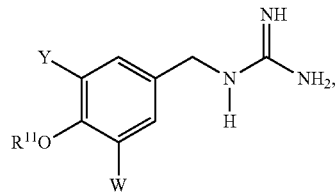

wherein W and Y are independently selected from the group consisting of H, —OR$^{11}$, F, Cl, Br, —CF$_3$, and I$_m$; and R$^{11}$ is alkyl, wherein I$_m$ is selected from the group consisting of $^{18}$F, $^{76}$Br, $^{124}$I, and $^{131}$I, and is present in either W, Y, or R$^{11}$; or a salt thereof.

In some embodiments, a compound is provided having formula:

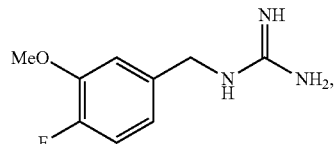

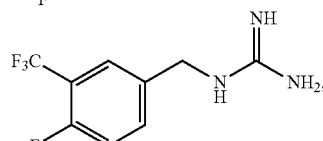

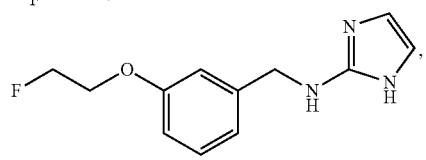

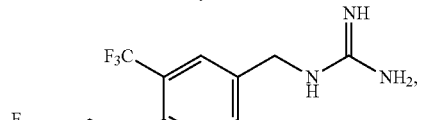

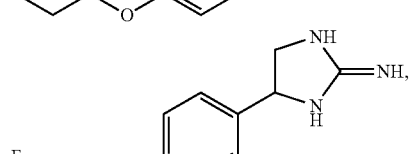

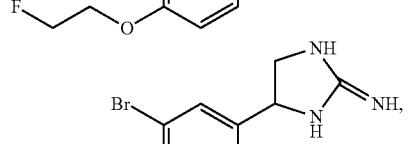

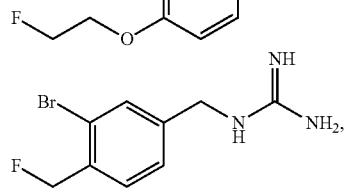

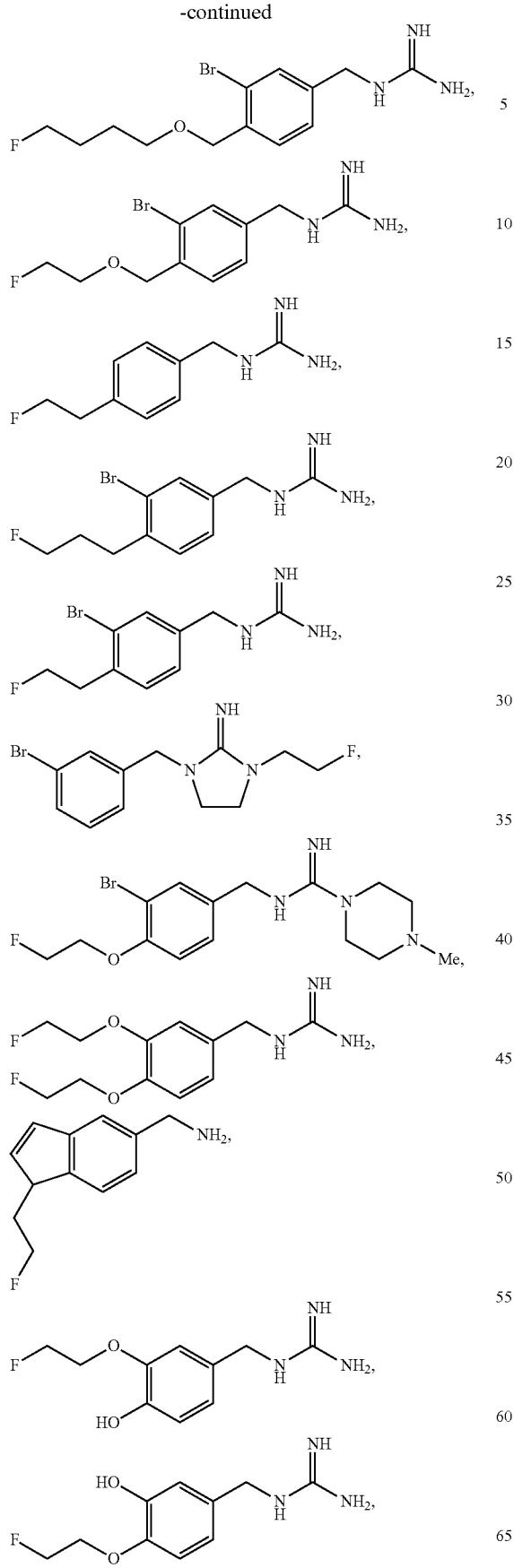
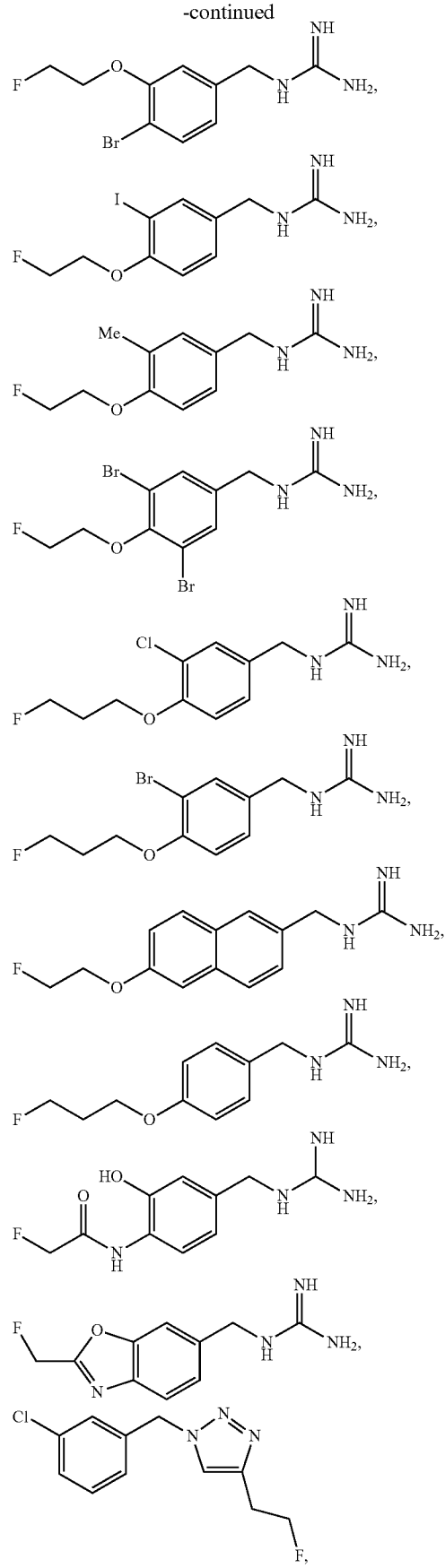

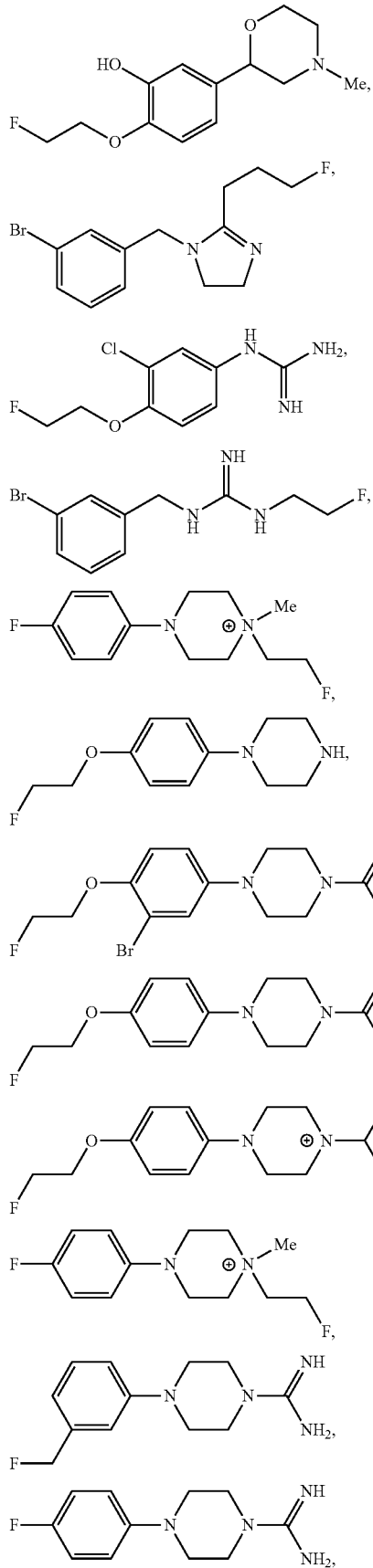
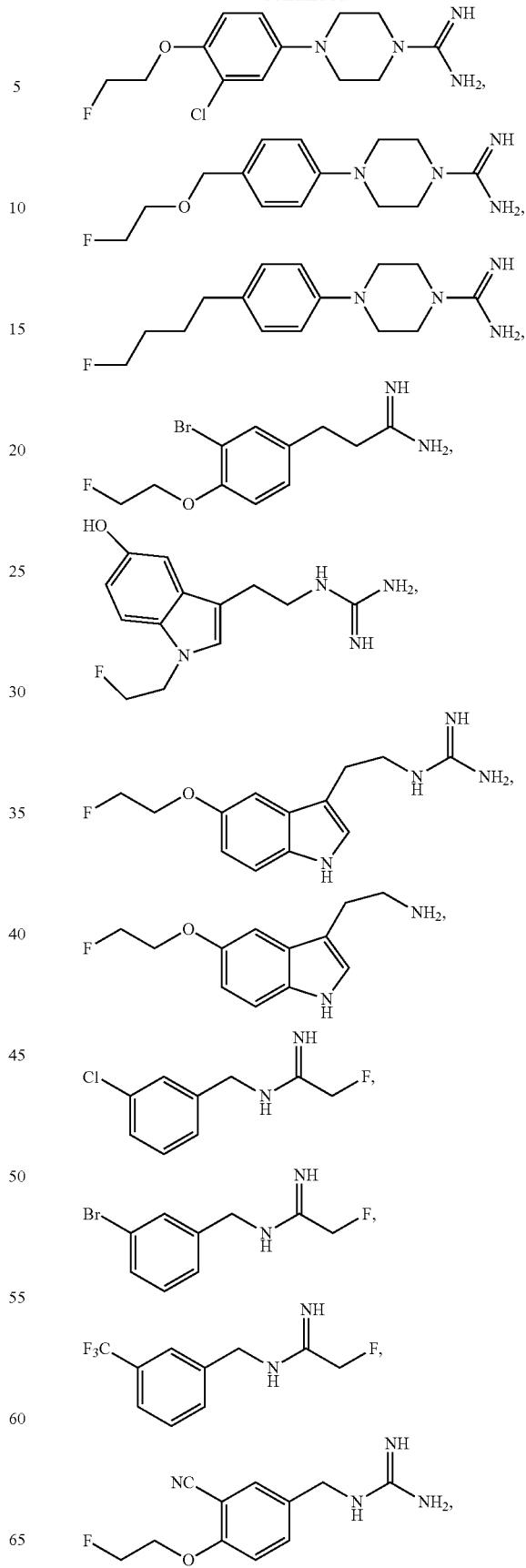

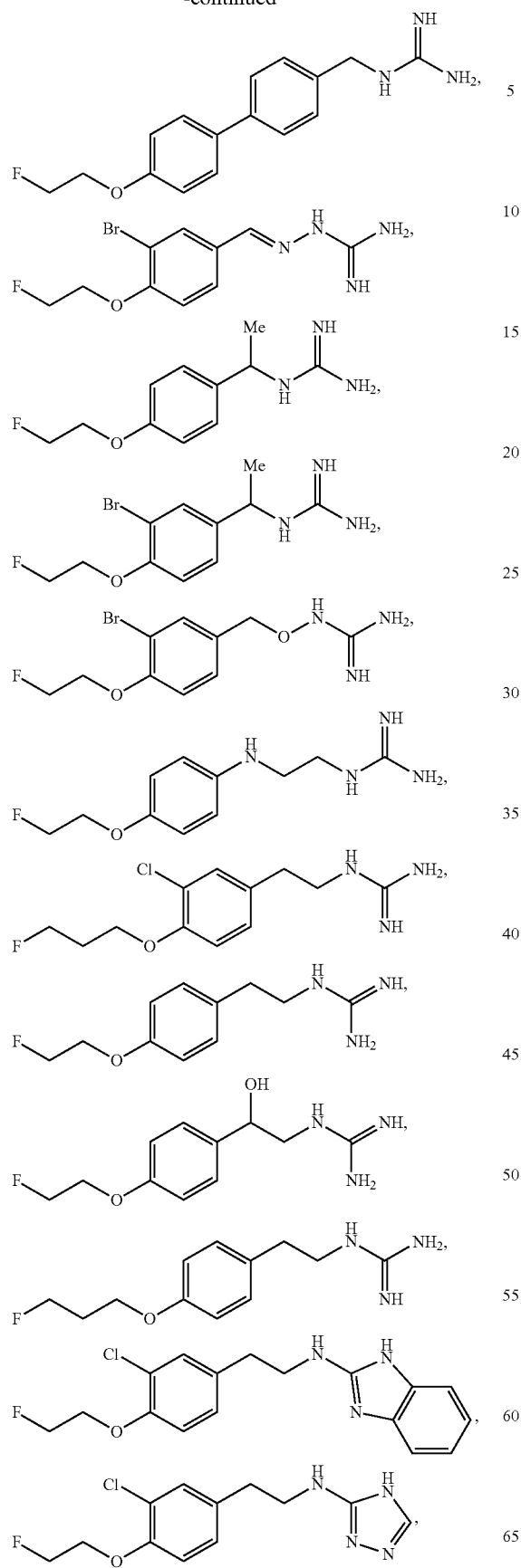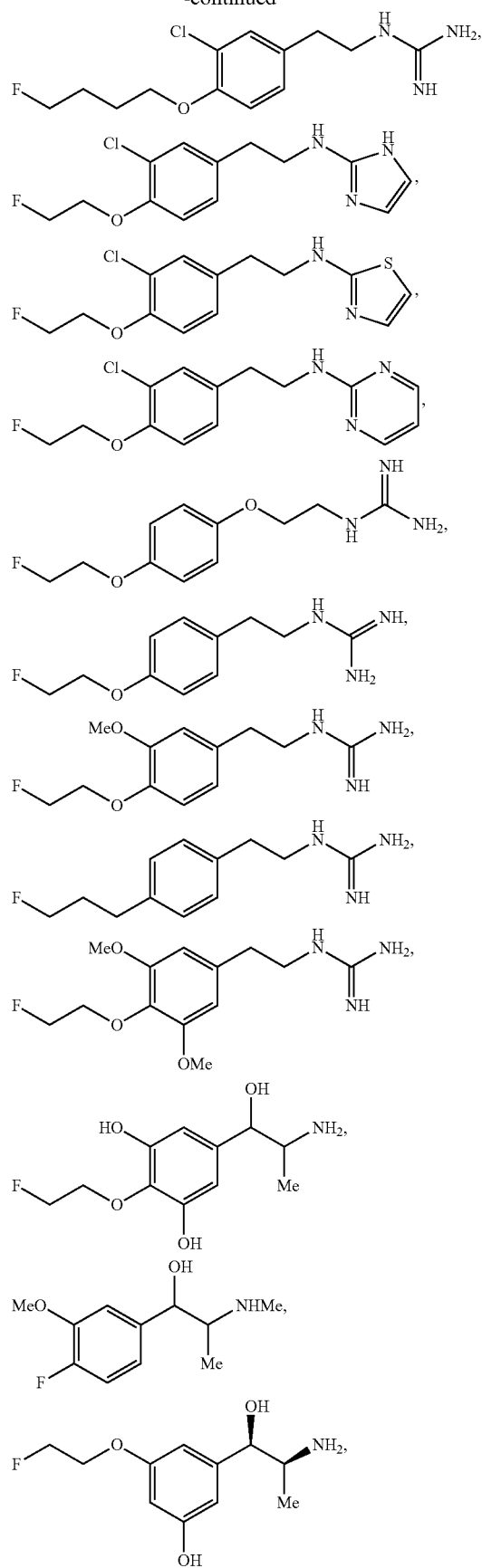

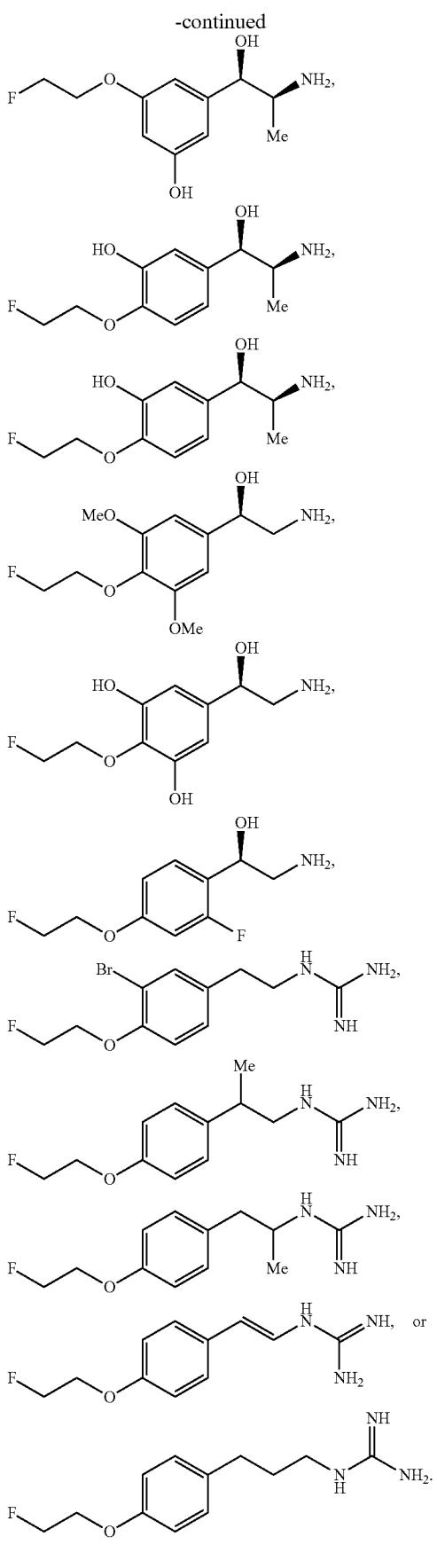

In one aspect, the present invention provides pharmaceutical compositions comprising an inventive compound. The pharmaceutical composition typically includes an amount of the inventive compound sufficient to image a subject or a portion of the subject. Pharmaceutical compositions of the present invention may optionally include a pharmaceutically acceptable excipient. Any mode of administration including oral and parenteral administration of an inventive compound or pharmaceutical composition thereof may be used.

In another aspect, the present invention provides methods of imaging a subject comprising administering an inventive compound to a subject; and acquiring an image of the subject or a portion of the subject. Compounds of the invention or pharmaceutical compositions thereof may be used to image an area of interest in a subject, including, but not limited to, the heart, a portion of the heart, the cardiovascular system, cardiac vessels, brain, and other organs. In certain embodiments, methods of the invention include a method of imaging cardiac innervation and a method of detecting norepinephrine transporter. In certain embodiments, the area of the subject being imaged is imaged by positron emission tomography (PET). A kit comprising an inventive compound or composition and instructions for use is also provided by the present invention.

In another aspect, the present invention provides methods for synthesizing an imaging agent by reacting an imaging agent precursor with an imaging moiety or source thereof to form an imaging agent. For example, in certain embodiments, fluorination of an imaging agent precursor comprising a leaving group (e.g., sulfonate leaving group) is performed with a fully deprotected form of the precursor eliminating the need for a subsequent deprotection step.

In another aspect, the present invention provides methods of selecting an antiarrhythmic agent and/or determining the dose of an antiarrhythmic agent for administration to a subject, the method comprising:

administering to the subject a compound as described herein or a salt thereof, or a compound of the formula:

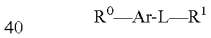

wherein

Ar is substituted or unsubstituted, monocyclic or bicyclic aryl; or substituted or unsubstituted, monocyclic or bicyclic heteroaryl;

L is a bond; substituted or unsubstituted, cyclic or acyclic alkylene; substituted or unsubstituted, cyclic or acyclic alkenylene; substituted or unsubstituted, cyclic or acyclic alkynylene; or substituted or unsubstituted, cyclic or acyclic heteroaliphatic;

$R^1$ is a substituted or unsubstituted nitrogen-containing moiety; and $R^0$ is halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, —$OR^{41}$, —$N(R^{42})_2$, —$SR^{41}$, —$C(=O)R^{41}$, —$C(=O)OR^{41}$, —$C(=O)SR^{41}$, —$C(=O)N(R^{42})_2$, —$OC(=O)R^{41}$, —$OC(=O)OR^{41}$, —$OC(=O)SR^{41}$, —$OC(=O)N(R^{42})_2$, —$NR^{42}C(=O)R^{42}$, —$NR^{42}C(=O)OR^{41}$, —$NR^{42}C(=O)SR^{41}$, —$NR^{42}C(=O)N(R^{42})_2$, —$SC(=O)R^{41}$, —$SC(=O)OR^{41}$, —$SC(=O)SR^{41}$, —$SC(=O)N(R^{42})_2$, —$C(=NR^{42})R^{41}$, —$C(=NR^{42})OR^{41}$, —$C(=NR^{42})SR^{41}$, —$C(=NR^{42})N(R^{42})_2$, —$OC(=NR^{42})R^{41}$, —$OC(=NR^{42})OR^{41}$, —$OC(=NR^{42})SR^{41}$, —$OC(=NR^{42})N(R^{42})_2$, —$NR^{42}C(=NR^{42})R^{42}$, —$NR^{42}C(=NR^{42})OR^{41}$, —$NR^{42}C(=NR^{42})SR^{41}$, —$NR^{42}C(=NR^{42})N(R^{42})_2$, —$SC(=NR^{42})R^{41}$, —$SC(=NR^{42})$ OR$^{A1}$, —SC(=NR$^{A2}$)SR$^{A1}$, —SC(=NR$^{A2}$)N(R$^{A2}$)$_2$, —C(=S)R$^{A1}$, —C(=S)OR$^{A1}$, —C(=S)SR$^{A1}$, —C(=S)N(R$^{A2}$)$_2$, —OC(=S)R$^{A1}$, —OC(=S)OR$^{A1}$, —OC(=S)SR$^{A1}$, —OC(=S)N(R$^{A2}$)$_2$, —NR$^{A2}$C(=S)R$^{A2}$, —NR$^{A2}$C(=S)OR$^{A1}$, —NR$^{A2}$C(=S)SR$^{A1}$, —NR$^{A2}$C(=S)N(R$^{A2}$)$_2$, —SC(=S)R$^{A1}$, —SC(=S)OR$^{A1}$, —SC(=S)SR$^{A1}$, —SC(=S)N(R$^{A2}$)$_2$, —S(=O)R$^{A1}$, —SO$_2$R$^{A1}$, —NR$^{A2}$SO$_2$R$^{A1}$, —SO$_2$N(R$^{A2}$)$_2$, —CN, —SCN, or —NO$_2$;

each occurrence of R$^{A1}$ is independently hydrogen, optionally substituted alkyl, optionally substituted alkenyl, optionally substituted alkynyl, optionally substituted carbocyclyl, optionally substituted heterocyclyl, optionally substituted aryl, or optionally substituted heteroaryl; and each occurrence of R$^{A2}$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, or an amino protecting group, or two R$^{A2}$ groups are joined to form an optionally substituted heterocyclic ring; and R$^0$ or R$^1$ is substituted with an imaging moiety selected from the group consisting of $^{18}$F, $^{76}$Br, $^{124}$I, and $^{131}$I, or is associated with an imaging moiety selected from the group consisting of $^{64}$Cu, $^{89}$Zr, $^{99m}$Tc, and $^{111}$In through a chelator, or is an imaging moiety selected from the group consisting of $^{18}$F, $^{76}$Br, $^{124}$I, and $^{131}$I; or a salt thereof;

acquiring at least one image of a portion of the subject;

selecting the antiarrhythmic agent and/or determining the dose of an antiarrhythmic agent for administration to a subject based on the image. In some embodiments, wherein the imaging agent is:

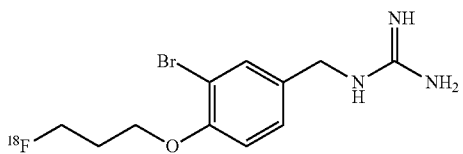 [SMILES: N=C(N)NCc1ccc(OCCC[18F])c(Br)c1]

or a pharmaceutically acceptable salt thereof. In some embodiments, the antiarrhythmic agent is an agent which is known to induce electrophysiological changes in a subject's heart. In some embodiments, the antiarrhythmic agent is an agent which does not induce electrophysiological changes in a subject's heart. In some embodiments, the electrophysiological changes comprise QT prolongation. In some embodiments, an antiarrhythmic agent that does not induce electrophysiological changes in a subject's heart is selected based on the image indicating the presence of cardiac denervation. In some embodiments, a reduced dose of an antiarrhythmic agent that induces electrophysiological changes in a subject's heart is prescribed based on the image indicating the presence of cardiac denervation.

In another aspect, the present invention provides methods comprising administering to the subject a compound described herein or a salt thereof, or a compound of the formula:

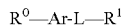

wherein

Ar is substituted or unsubstituted, monocyclic or bicyclic aryl or substituted or unsubstituted, monocyclic or bicyclic heteroaryl;

L is a bond; substituted or unsubstituted, cyclic or acyclic alkylene; substituted or unsubstituted, cyclic or acyclic alkenylene; substituted or unsubstituted, cyclic or acyclic alkynylene; or substituted or unsubstituted, cyclic or acyclic heteroaliphatic;

R$^1$ is a substituted or unsubstituted nitrogen-containing moiety; and

R$^0$ is halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, —OR$^{A1}$, —N(R$^{A2}$)$_2$, —SR$^{A1}$, —C(=O)R$^{A1}$, —C(=O)OR$^{A1}$, —C(=O)SR$^{A1}$, —C(=O)N(R$^{A2}$)$_2$, —OC(=O)R$^{A1}$, —OC(=O)OR$^{A1}$, —OC(=O)SR$^{A1}$, —OC(=O)N(R$^{A2}$)$_2$, —NR$^{A2}$C(=O)R$^{A2}$, —NR$^{A2}$C(=O)OR$^{A1}$, —NR$^{A2}$C(=O)SR$^{A1}$, —NR$^{A2}$C(=O)N(R$^{A2}$)$_2$, —SC(=O)R$^{A1}$, —SC(=O)OR$^{A1}$, —SC(=O)SR$^{A1}$, —SC(=O)N(R$^{A2}$)$_2$, —C(=NR$^{A2}$)R$^{A1}$, —C(=NR$^{A2}$)OR$^{A1}$, —C(=NR$^{A2}$)SR$^{A1}$, —C(=NR$^{A2}$)N(R$^{A2}$)$_2$, —OC(=NR$^{A2}$)R$^{A1}$, —OC(=NR$^{A2}$)OR$^{A1}$, —OC(=NR$^{A2}$)SR$^{A1}$, —OC(=NR$^{A2}$)N(R$^{A2}$)$_2$, —NR$^{A2}$C(=NR$^{A2}$)R$^{A2}$, —NR$^{A2}$C(=NR$^{A2}$)OR$^{A1}$, —NR$^{A2}$C(=NR$^{A2}$)SR$^{A1}$, —NR$^{A2}$C(=NR$^{A2}$)N(R$^{A2}$)$_2$, —SC(=NR$^{A2}$)R$^{A1}$, —SC(=NR$^{A2}$)OR$^{A1}$, —SC(=NR$^{A2}$)SR$^{A1}$, —SC(=NR$^{A2}$)N(R$^{A2}$)$_2$, —C(=S)R$^{A1}$, —C(=S)OR$^{A1}$, —C(=S)SR$^{A1}$, —C(=S)N(R$^{A2}$)$_2$, —OC(=S)R$^{A1}$, —OC(=S)OR$^{A1}$, —OC(=S)SR$^{A1}$, —OC(=S)N(R$^{A2}$)$_2$, —NR$^{A2}$C(=S)R$^{A2}$, —NR$^{A2}$C(=S)OR$^{A1}$, —NR$^{A2}$C(=S)SR$^{A1}$, —NR$^{A2}$C(=S)N(R$^{A2}$)$_2$, —SC(=S)R$^{A1}$, —SC(=S)OR$^{A1}$, —SC(=S)SR$^{A1}$, —SC(=S)N(R$^{A2}$)$_2$, —S(=O)R$^{A1}$, —SO$_2$R$^{A1}$, —NR$^{A2}$SO$_2$R$^{A1}$, —SO$_2$N(R$^{A2}$)$_2$, —CN, —SCN, or —NO$_2$;

each occurrence of R$^{A1}$ is independently hydrogen, optionally substituted alkyl, optionally substituted alkenyl, optionally substituted alkynyl, optionally substituted carbocyclyl, optionally substituted heterocyclyl, optionally substituted aryl, or optionally substituted heteroaryl; and each occurrence of R$^{A2}$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, or an amino protecting group, or two R$^{A2}$ groups are joined to form an optionally substituted heterocyclic ring; and R$^0$ or R$^1$ is substituted with an imaging moiety selected from the group consisting of $^{18}$F, $^{76}$Br, $^{124}$I, and $^{131}$I, or is associated with an imaging moiety selected from the group consisting of $^{64}$Cu, $^{89}$Zr, $^{99m}$Tc, and $^{111}$In through a chelator, or is an imaging moiety selected from the group consisting of $^{18}$F, $^{76}$Br, $^{124}$I, and $^{131}$I; or a salt thereof;

acquiring at least one image of a portion of the subject; and identifying:

(i) a subject to be treated with an antiarrhythmic agent that does not induce electrophysiological changes in the heart of the subject based on presence of cardiac denervation in the image, (ii) a subject to be treated with a reduced dose of an antiarrhythmic agent that induces electrophysiological changes in the heart of the subject based on presence of cardiac denervation in the image, and/or (iii) a subject in need of a dose reduction of an antiarrhythmic agent that induces electrophysiological changes in the heart of the subject based on presence of cardiac denervation in the image. In some embodiments, the antiarrhythmic agent that induces electrophysiological changes in the heart of the subject is a sodium channel blocker, a potassium channel blocker, or a calcium channel blocker. In some embodiments, the antiarrhythmic agent that induces electrophysiological changes in the heart of the subject is a calcium channel blocker. In some embodiments, the antiarrhythmic agent that induces electrophysiological changes in the heart of the subject is quinidine, procainamide, disopyramide, lidocaine, phenyloin, mexiletine, tocainade, amiodarone, sotalol, ibutilide, dofetilide, dronedarone, E-4031, verapamil, or ditiazem. In some embodiments, the antiarrhythmic agent that does not induce electrophysiological changes in the heart of the subject is a beta-blocker. In some embodiments, the antiarrhythmic agent that does not induce electrophysiological changes in the heart of the subject is propranolol, esmolol, timolol, metoprolol, atenolol, or bisoprolol.

In some embodiments, a compound (e.g., an imaging agent precursor) is provided having formula:

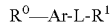

wherein

Ar is substituted or unsubstituted, monocyclic or bicyclic aryl; or substituted or unsubstituted, monocyclic or bicyclic heteroaryl;

L is a bond; substituted or unsubstituted, cyclic or acyclic alkylene; substituted or unsubstituted, cyclic or acyclic alkenylene; substituted or unsubstituted, cyclic or acyclic alkynylene; or substituted or unsubstituted, cyclic or acyclic heteroaliphatic;

$R^0$ is halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, $-OR^{41}$, $-N(R^{42})_2$, $-N(R^{42})_3{}^+$, $-SR^{41}$, $-C(=O)R^{41}$, $-C(=O)OR^{41}$, $-C(=O)SR^{41}$, $-C(=O)N(R^{42})_2$, $-OC(=O)R^{41}$, $-OC(=O)OR^{41}$, $-OC(=O)SR^{41}$, $-OC(=O)N(R^{42})_2$, $-NR^{42}C(=O)R^{42}$, $-NR^{42}C(=O)OR^{41}$, $-NR^{42}C(=O)SR^{41}$, $-NR^{42}C(=O)N(R^{42})_2$, $-SC(=O)R^{41}$, $-SC(=O)OR^{41}$, $-SC(=O)SR^{41}$, $-SC(=O)N(R^{42})_2$, $-C(=NR^{42})R^{41}$, $-C(=NR^{42})OR^{41}$, $-C(=NR^{42})SR^{41}$, $-C(=NR^{42})N(R^{42})_2$, $-OC(=NR^{42})R^{41}$, $-OC(=NR^{42})OR^{41}$, $-OC(=NR^{42})SR^{41}$, $-OC(=NR^{42})N(R^{42})_2$, $-NR^{42}C(=NR^{42})R^{42}$, $-NR^{42}C(=NR^{42})OR^{41}$, $-NR^{42}C(=NR^{42})SR^{41}$, $-NR^{42}C(=NR^{42})N(R^{42})_2$, $-SC(=NR^{42})R^{41}$, $-SC(=NR^{42})OR^{41}$, $-SC(=NR^{42})SR^{41}$, $-SC(=NR^{42})N(R^{42})_2$, $-C(=S)R^{41}$, $-C(=S)OR^{41}$, $-C(=S)SR^{41}$, $-C(=S)N(R^{42})_2$, $-OC(=S)R^{41}$, $-OC(=S)OR^{41}$, $-OC(=S)SR^{41}$, $-OC(=S)N(R^{42})_2$, $-NR^{42}C(=S)R^{42}$, $-NR^{42}C(=S)OR^{41}$, $-NR^{42}C(=S)SR^{41}$, $-NR^{42}C(=S)N(R^{42})_2$, $-SC(=S)R^{41}$, $-SC(=S)OR^{41}$, $-SC(=S)SR^{41}$, $-SC(=S)N(R^{42})_2$, $-S(=O)R^{41}$, $-SO_2R^{41}$, $-OSO_2R^{41}$, $-Si(R^{41})_3$, $-Sn(R^{41})_3$, $-B(OR^{41})_2$, $-NR^{42}SO_2R^{41}$, $-NO_2$, $-SO_2N(R^{42})_2$, $-CN$, $-SCN$, or $-NO_2{}^2$; and $R^0$ is substituted with a leaving group or is a leaving group; and $R^1$ is a substituted or unsubstituted nitrogen-containing moiety;

each occurrence of $R^{41}$ is independently hydrogen, optionally substituted alkyl, optionally substituted alkenyl, optionally substituted alkynyl, optionally substituted carbocyclyl, optionally substituted heterocyclyl, optionally substituted aryl, or optionally substituted heteroaryl; and each occurrence of $R^{42}$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, or an amino protecting group, or two $R^{42}$ groups are joined to form an optionally substituted heterocyclic ring; or a salt thereof.

In some embodiments, a method is provided comprising reacting a compound of formula:

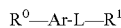

wherein

Ar is substituted or unsubstituted, monocyclic or bicyclic aryl; or substituted or unsubstituted, monocyclic or bicyclic heteroaryl;

L is a bond; substituted or unsubstituted, cyclic or acyclic alkylene; substituted or unsubstituted, cyclic or acyclic alkenylene; substituted or unsubstituted, cyclic or acyclic alkynylene; or substituted or unsubstituted, cyclic or acyclic heteroaliphatic;

$R^0$ is halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, $-OR^{41}$, $-N(R^{42})_2$, $-SR^{41}$, $-C(=O)R^{41}$, $-C(=O)OR^{41}$, $-C(=O)SR^{41}$, $-C(=O)N(R^{42})_2$, $-OC(=O)R^{41}$, $-OC(=O)OR^{41}$, $-OC(=O)SR^{41}$, $-OC(=O)N(R^{42})_2$, $-NR^{42}C(=O)R^{42}$, $-NR^{42}C(=O)OR^{41}$, $-NR^{42}C(=O)SR^{41}$, $-NR^{42}C(=O)N(R^{42})_2$, $-SC(=O)R^{41}$, $-SC(=O)OR^{41}$, $-SC(=O)SR^{41}$, $-SC(=O)N(R^{42})_2$, $-C(=NR^{42})R^{41}$, $-C(=NR^{42})OR^{41}$, $-C(=NR^{42})SR^{41}$, $-C(=NR^{42})N(R^{42})_2$, $-OC(=NR^{42})R^{41}$, $-OC(=NR^{42})OR^{41}$, $-OC(=NR^{42})SR^{41}$, $-OC(=NR^{42})N(R^{42})_2$, $-NR^{42}C(=NR^{42})R^{42}$, $-NR^{42}C(=NR^{42})OR^{41}$, $-NR^{42}C(=NR^{42})SR^{41}$, $-NR^{42}C(=NR^{42})N(R^{42})_2$, $-SC(=NR^{42})R^{41}$, $-SC(=NR^{42})OR^{41}$, $-SC(=NR^{42})SR^{41}$, $-SC(=NR^{42})N(R^{42})_2$, $-C(=S)R^{41}$, $-C(=S)OR^{41}$, $-C(=S)SR^{41}$, $-C(=S)N(R^{42})_2$, $-OC(=S)R^{41}$, $-OC(=S)OR^{41}$, $-OC(=S)SR^{41}$, $-OC(=S)N(R^{42})_2$, $-NR^{42}C(=S)R^{42}$, $-NR^{42}C(=S)OR^{41}$, $-NR^{42}C(=S)SR^{41}$, $-NR^{42}C(=S)N(R^{42})_2$, $-SC(=S)R^{41}$, $-SC(=S)OR^{41}$, $-SC(=S)SR^{41}$, $-SC(=S)N(R^{42})_2$, $-S(=O)R^{41}$, $-SO_2R^{41}$, $-NR^{42}SO_2R^{41}$, $-SO_2N(R^{42})_2$, $-CN$, $-SCN$, or $-NO_2$; and $R^0$ is substituted with a leaving group or is a leaving group;

$R^1$ is a substituted or unsubstituted nitrogen-containing moiety;

each occurrence of $R^{41}$ is independently hydrogen, optionally substituted alkyl, optionally substituted alkenyl, optionally substituted alkynyl, optionally substituted carbocyclyl, optionally substituted heterocyclyl, optionally substituted aryl, or optionally substituted heteroaryl; and each occurrence of $R^{42}$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, or an amino protecting group, or two $R^{42}$ groups are joined to form an optionally substituted heterocyclic ring;

or a salt, free base, or combination thereof;

with a fluorinating reagent under suitable conditions to form a compound of formula:

wherein $R^0$ is substituted with a fluorine.

In some embodiments, a method of determining perfusion and innervation mismatch in a portion of a human subject is provided comprising:

administering to the subject a first imaging agent and acquiring at least one first image of a portion of the subject, wherein the first imaging agent is employed to image perfusion;

administering to the subject a second imaging agent and acquiring at least one second image of the portion of the subject, wherein the second imaging agent is employed to image innervation; and determining regional mismatch of innervation and perfusion areas in the portion of the subject based at least in part on the at least one first image and the at least one second image, wherein the first imaging agent has the structure:

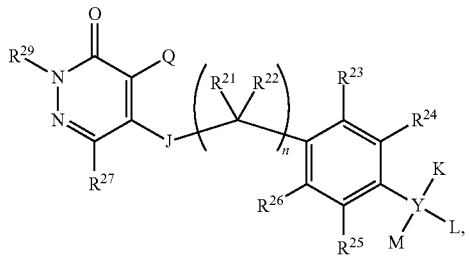

wherein

J is selected from the group consisting of $N(R^{28})$, S, O, C(=O), C(=O)O, $NHCH_2CH_2O$, a bond, and C(=O)N $(R^{27})$;

when present, K is selected from the group consisting of hydrogen, alkoxyalkyl optionally substituted with an imaging moiety, alkyloxy optionally substituted with an imaging moiety, aryl optionally substituted with an imaging moiety, $C_1$-$C_6$ alkyl optionally substituted with an imaging moiety, heteroaryl optionally substituted with an imaging moiety, and an imaging moiety;

when present, L is selected from the group consisting of hydrogen, alkoxyalkyl optionally substituted with an imaging moiety, alkyloxy optionally substituted with an imaging moiety, aryl optionally substituted with an imaging moiety, $C_1$-$C_6$ alkyl optionally substituted with an imaging moiety, heteroaryl optionally substituted with an imaging moiety, and an imaging moiety;

M is selected from the group consisting of hydrogen, alkoxyalkyl optionally substituted with an imaging moiety, alkyloxy optionally substituted with an imaging moiety, aryl optionally substituted with an imaging moiety, $C_1$-$C_6$ alkyl optionally substituted with an imaging moiety, heteroaryl optionally substituted with an imaging moiety, and an imaging moiety; or L and M, together with the atom to which they are attached, may form a three- or four-membered carbocyclic ring;

Q is halo or haloalkyl;

n is 0, 1, 2, or 3;

$R^{21}$, $R^{22}$, $R^{27}$, and $R^{28}$ are independently selected from hydrogen, $C_1$-$C_6$ alkyl optionally substituted with an imaging moiety, and an imaging moiety;

$R^{23}$, $R^{24}$, $R^{25}$, and $R^{26}$ are independently selected from hydrogen, halogen, hydroxyl, alkyloxy, $C_1$-$C_6$ alkyl optionally substituted with an imaging moiety, and an imaging moiety; $R^{29}$ is $C_1$-$C_6$ alkyl optionally substituted with an imaging moiety; and Y is selected from the group consisting of a bond, carbon, and oxygen; provided that when Y is a bond, K and L are absent, and M is selected from the group consisting of aryl optionally substituted with an imaging moiety and heteroaryl optionally substituted with an imaging moiety; and provided that when Y is oxygen, K and L are absent, and M is selected from hydrogen, alkoxyalkyl optionally substituted with an imaging moiety, aryl optionally substituted with an imaging moiety, $C_1$-$C_6$ alkyl optionally substituted with an imaging moiety, and heteroaryl optionally substituted with an imaging moiety; or a salt thereof, provided that at least one imaging moiety is present.

In some embodiments, a method of assessing perfusion and innervation mismatch in a portion of a human subject is provided comprising:

administering to a subject a first imaging agent and acquiring at least one first image of a portion of a subject, wherein the first imaging agent employed to image perfusion;

administering to a subject a second imaging agent and acquiring at least one second image of the portion of the subject, wherein the second imaging agent is employed to image innervation; and determining regional mismatch of innervation and perfusion areas in the portion of the subject based at least in part on the at least one first image and the at least one second image, wherein the second imaging agent has the structure:

$$R^0\text{—Ar-L—}R^1$$

wherein

Ar is substituted or unsubstituted, monocyclic or bicyclic aryl or substituted or unsubstituted, monocyclic or bicyclic heteroaryl;

L is a bond; substituted or unsubstituted, cyclic or acyclic alkylene; substituted or unsubstituted, cyclic or acyclic alkenylene; substituted or unsubstituted, cyclic or acyclic alkynylene; or substituted or unsubstituted, cyclic or acyclic heteroaliphatic;

$R^1$ is a substituted or unsubstituted nitrogen-containing moiety; and $R^0$ is halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, $-OR^{41}$, $-N(R^{42})_2$, $-SR^{41}$, $-C(=O)R^{41}$, $-C(=O)OR^{41}$, $-C(=O)SR^{41}$, $-C(=O)N(R^{42})_2$, $-OC(=O)R^{41}$, $-OC(=O)OR^{41}$, $-OC(=O)SR^{41}$, $-OC(=O)N(R^{42})_2$, $-NR^{42}C(=O)R^{42}$, $-NR^{42}C(=O)OR^{41}$, $-NR^{42}C(=O)SR^{41}$, $-NR^{42}C(=O)N(R^{42})_2$, $-SC(=O)R^{41}$, $-SC(=O)OR^{41}$, $-SC(=O)SR^{41}$, $-SC(=O)N(R^{42})_2$, $-C(=NR^{42})R^{41}$, $-C(=NR^{42})OR^{41}$, $-C(=NR^{42})SR^{41}$, $-C(=NR^{42})N(R^{42})_2$, $-OC(=NR^{42})R^{41}$, $-OC(=NR^{42})OR^{41}$, $-OC(=NR^{42})SR^{41}$, $-OC(=NR^{42})N(R^{42})_2$, $-NR^{42}C(=NR^{42})R^{42}$, $-NR^{42}C(=NR^{42})OR^{41}$, $-NR^{42}C(=NR^{42})SR^{41}$, $-NR^{42}C(=NR^{42})N(R^{42})_2$, $-SC(=NR^{42})R^{41}$, $-SC(=NR^{42})OR^{41}$, $-SC(=NR^{42})SR^{41}$, $-SC(=NR^{42})N(R^{42})_2$, $-C(=S)R^{41}$, $-C(=S)OR^{41}$, $-C(=S)SR^{41}$, $-C(=S)N(R^{42})_2$, $-OC(=S)R^{41}$, $-OC(=S)OR^{41}$, $-OC(=S)SR^{41}$, $-OC(=S)N(R^{42})_2$, $-NR^{42}C(=S)R^{42}$, $-NR^{42}C(=S)OR^{41}$, $-NR^{42}C(=S)SR^{41}$, $-NR^{42}C(=S)N(R^{42})_2$, $-SC(=S)R^{41}$, $-SC(=S)OR^{41}$, $-SC(=S)SR^{41}$, $-SC(=S)N(R^{42})_2$, $-S(=O)R^{41}$, $-SO_2R^{41}$, $-NR^{42}SO_2R^{41}$, $-SO_2N(R^{42})_2$, $-CN$, $-SCN$, or $-NO_2$;

each occurrence of $R^{41}$ is independently hydrogen, optionally substituted alkyl, optionally substituted alkenyl, optionally substituted alkynyl, optionally substituted carbocyclyl, optionally substituted heterocyclyl, optionally substituted aryl, or optionally substituted heteroaryl; and each occurrence of $R^{42}$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, or an amino protecting group, or two $R^{42}$ groups are joined to form an optionally substituted heterocyclic ring; and $R^0$ or $R^1$ is substituted with an imaging moiety selected from the group consisting of $^{18}F$, $^{76}Br$, $^{124}I$, and $^{131}I$, or is associated with an imaging moiety selected from the group consisting of $^{64}Cu$, $^{89}Zr$, $^{99m}Tc$, and $^{111}In$ through a chelator, or is an imaging moiety selected from the group consisting of $^{18}$F, $^{76}$Br, $^{124}$I, and $^{131}$I; or a salt thereof.

Figure 1:
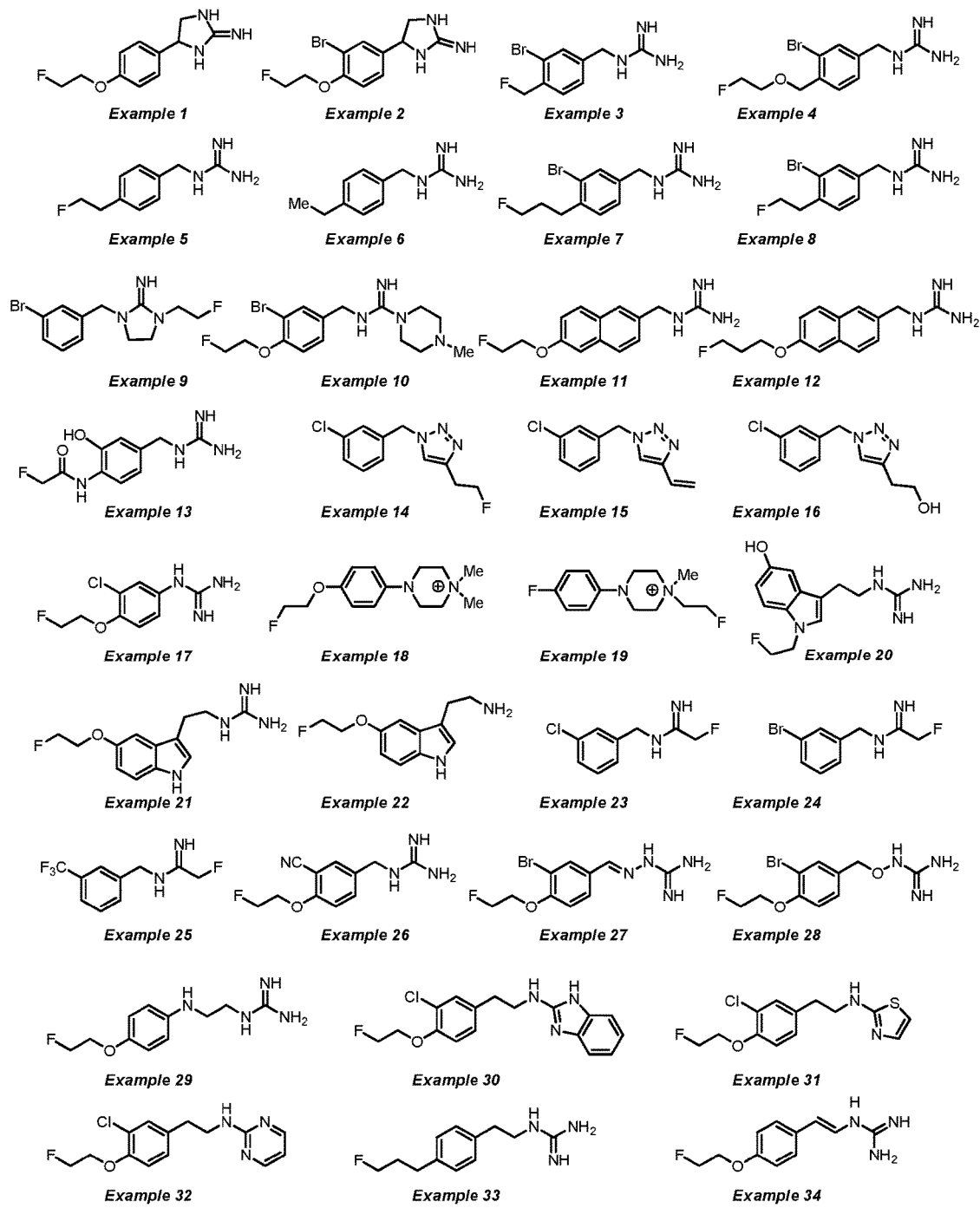
FIG. 1 depicts non-limiting examples of imaging agents.
Figure 2:
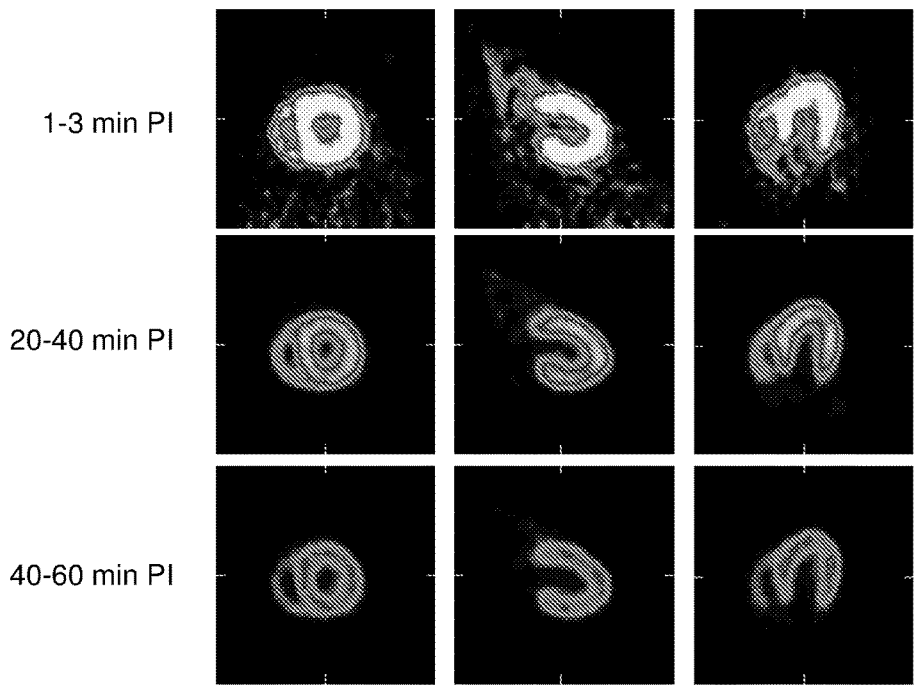
FIGS. 2 through 8 show images derived using non-limiting examples of imaging agents.
Figure 3:
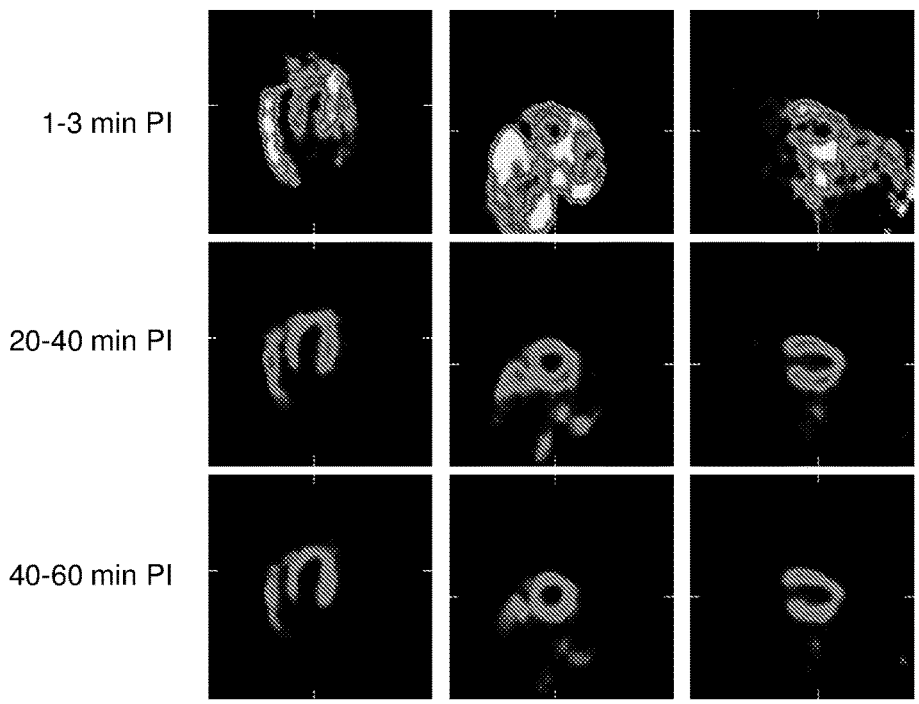
Figure 4:
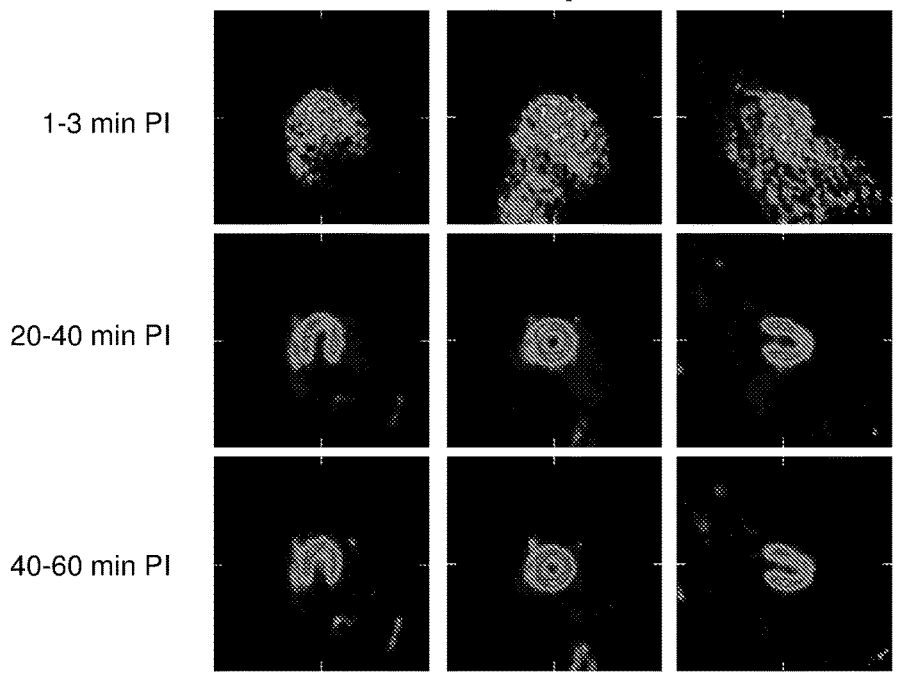
Figure 5:
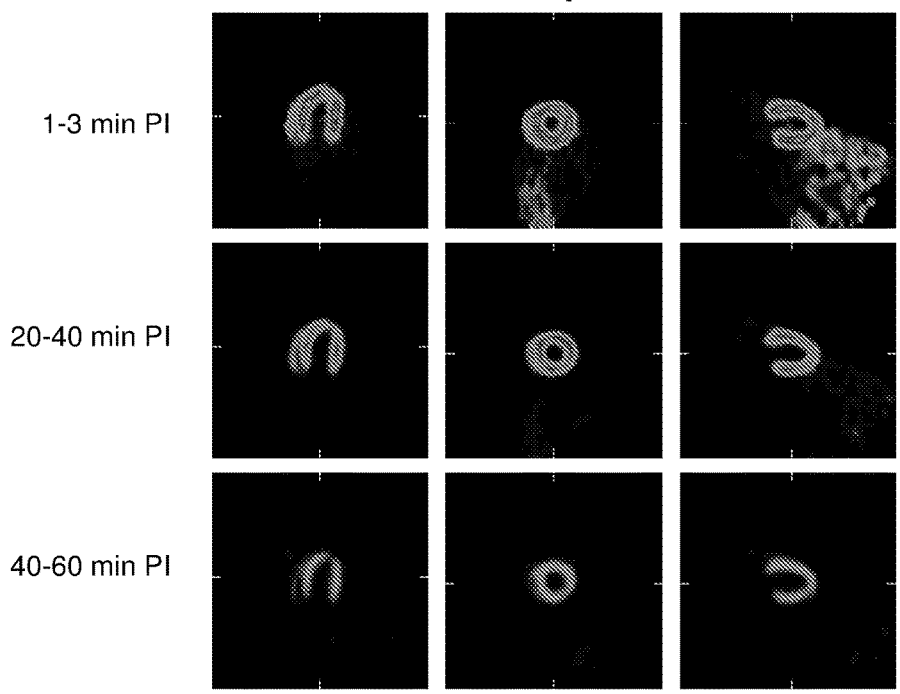
Figure 6:
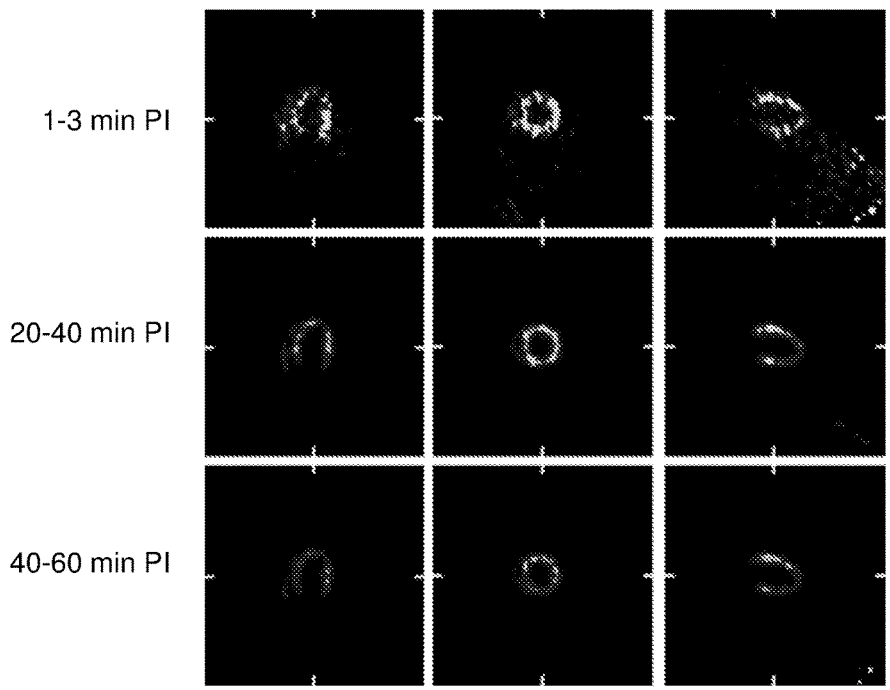
Figure 7:
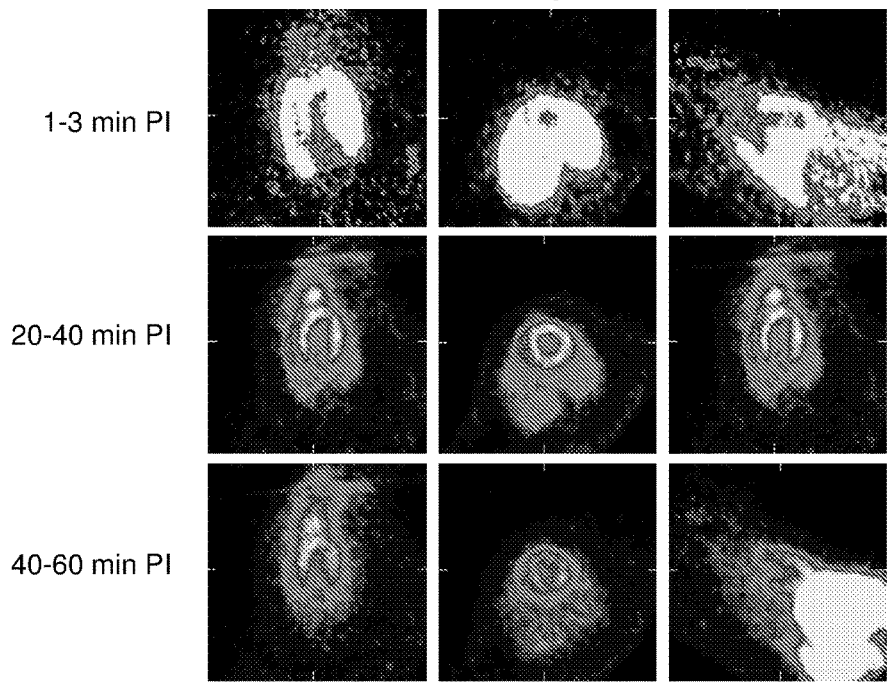
Figure 8:
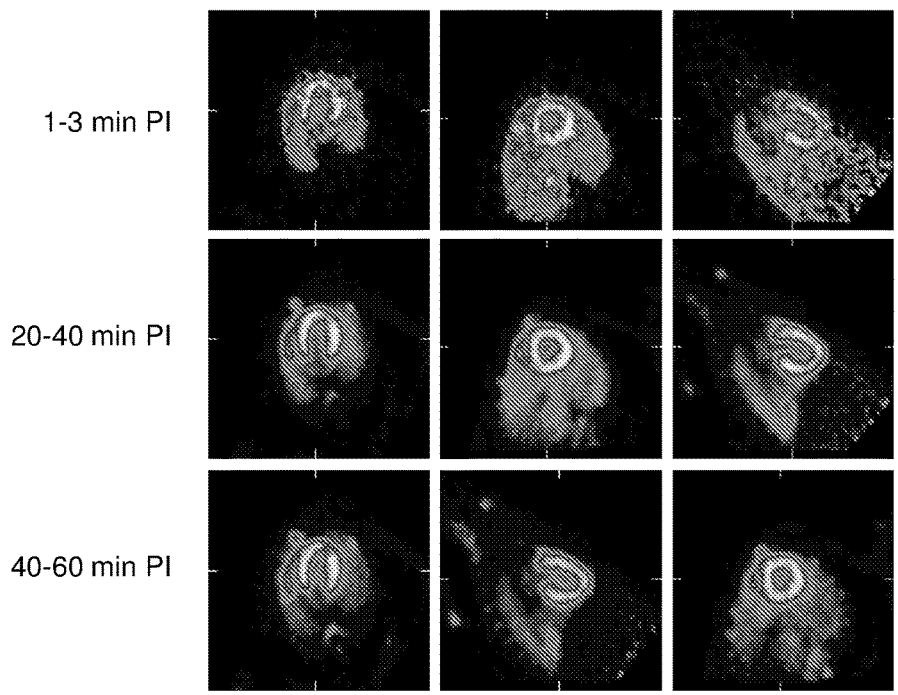

Other aspects, embodiments, and features of the invention will become apparent from the following detailed description when considered in conjunction with the accompanying drawings. The accompanying figures are schematic and are not intended to be drawn to scale. For purposes of clarity, not every component is labeled in every figure, nor is every component of each embodiment of the invention shown where illustration is not necessary to allow those of ordinary skill in the art to understand the invention. All patent applications and patents incorporated herein by reference are incorporated by reference in their entirety. In case of conflict, the present specification, including definitions, controls.

DETAILED DESCRIPTION OF THE INVENTION

The present invention provides compounds, compositions thereof, systems comprising such compounds, reagents, cassettes, methods, kits, and apparatuses for the synthesis and/or use of imaging agents and precursors thereof. In some aspects, the invention generally relates to an imaging agent of Formula (Ia)-(Id), (IIa)-(IIb), (III), (IV), (Va)-(Vd), (VI), or (VII). The imaging agents of the invention may be used to image an area of interest in a subject, including, but not limited to, the heart, a portion of the heart, the cardiovascular system, cardiac vessels, brain, and other organs. In certain embodiments, the area of the subject being imaged is imaged by positron emission tomography (PET). The present invention also provides methods for synthesizing an imaging agent by reacting an imaging agent precursor with an imaging moiety or source thereof to form an imaging agent.

In some embodiments, methods and compositions for assessing perfusion and innervation mismatch in a portion in a subject, for example, a human subject, are provided. In some embodiments, the methods and compositions may be employed for assessing perfusion and innervation mismatch in a subject following a tissue insult. In some embodiments, the tissue insult is a cardiac insult, for example, a myocardial infarction. In some embodiments, the portion of the subject is the heart or a portion of the heart.

A. Imaging Agents

In one aspect, the invention provides compounds useful as imaging agents for imaging a subject or an area of interest of a subject. In certain embodiments, the imaging agent is labeled with $^{18}$F and is useful in PET imaging.

In some embodiments, a compound is provided comprising Formula (Ia):

$$R^0\text{—Ar-L-}R^1 \tag{Ia}$$

wherein

Ar is substituted or unsubstituted, monocyclic or bicyclic aryl; or substituted or unsubstituted, monocyclic or bicyclic heteroaryl;

L is a bond; substituted or unsubstituted, cyclic or acyclic alkylene; substituted or unsubstituted, cyclic or acyclic alkenylene; substituted or unsubstituted, cyclic or acyclic alkynylene; or substituted or unsubstituted, cyclic or acyclic heteroaliphatic;

$R^1$ is a substituted or unsubstituted nitrogen-containing moiety; and $R^0$ is halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, —OR$^{41}$, —N(R$^{42}$)$_2$, —SR$^{41}$, —C(=O)R$^{41}$, —C(=O)OR$^{41}$, —C(=O)SR$^{41}$, —C(=O)N(R$^{42}$)$_2$, —OC(=O)R$^{41}$, —OC(=O)OR$^{41}$, —OC(=O)SR$^{41}$, —OC(=O)N(R$^{42}$)$_2$, —NR$^{42}$C(=O)R$^{42}$, —NR$^{42}$C(=O)OR$^{41}$, —NR$^{42}$C(=O)SR$^{41}$, —NR$^{42}$C(=O)N(R$^{42}$)$_2$, —SC(=O)R$^{41}$, —SC(=O)OR$^{41}$, —SC(=O)SR$^{41}$, —SC(=O)N(R$^{42}$)$_2$, —C(=NR$^{42}$)R$^{41}$, —C(=NR$^{42}$)OR$^{41}$, —C(=NR$^{42}$)SR$^{41}$, —C(=NR$^{42}$)N(R$^{42}$)$_2$, —OC(=NR$^{42}$)R$^{41}$, —OC(=NR$^{42}$)OR$^{41}$, —OC(=NR$^{42}$)SR$^{41}$, —OC(=NR$^{42}$)N(R$^{42}$)$_2$, —NR$^{42}$C(=NR$^{42}$)R$^{42}$, —NR$^{42}$C(=NR$^{42}$)OR$^{41}$, —NR$^{42}$C(=NR$^{42}$)SR$^{41}$, —NR$^{42}$C(=NR$^{42}$)N(R$^{42}$)$_2$, —SC(=NR$^{42}$)R$^{41}$, —SC(=NR$^{42}$)OR$^{41}$, —SC(=NR)SR$^{41}$, —SC(=NR$^{42}$)N(R$^{42}$)$_2$, —C(=S)R$^{41}$, —C(=S)OR$^{41}$, —C(=S)SR$^{41}$, —C(=S)N(R$^{42}$)$_2$, —OC(=S)R$^{41}$, —OC(=S)OR$^{41}$, —OC(=S)SR$^{41}$, —OC(=S)N(R$^{42}$)$_2$, —NR$^{42}$C(=S)R$^{42}$, —NR$^{42}$C(=S)OR$^{41}$, —NR$^{42}$C(=S)SR$^{41}$, —NR$^{42}$C(=S)N(R$^{42}$)$_2$, —SC(=S)R$^{41}$, —SC(=S)OR$^{41}$, —SC(=S)SR$^{41}$, —SC(=S)N(R$^{42}$)$_2$, —S(=O)R$^{41}$, —SO$_2$R$^{41}$, —NR$^{42}$SO$_2$R$^{41}$, —SO$_2$N(R$^{42}$)$_2$, —CN, —SCN, or —NO$_2$;

each occurrence of R$^{41}$ is independently hydrogen, optionally substituted alkyl, optionally substituted alkenyl, optionally substituted alkynyl, optionally substituted carbocyclyl, optionally substituted heterocyclyl, optionally substituted aryl, or optionally substituted heteroaryl; and each occurrence of R$^{42}$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, or an amino protecting group, or two $R^{A2}$ groups are joined to form an optionally substituted heterocyclic ring; and $R^0$ or $R^1$ is substituted with an imaging moiety selected from the group consisting of $^{18}F$, $^{76}Br$, $^{124}I$, and $^{131}I$, or is associated with an imaging moiety selected from the group consisting of $^{64}Cu$, $^{89}Zr$, $^{99m}Tc$, and $^{111}In$ through a chelator, or is an imaging moiety selected from the group consisting of $^{18}F$, $^{76}Br$, $^{124}I$, and $^{131}I$; or a salt thereof.

In certain embodiments, the compound of Formula (Ia) is not of the formula:

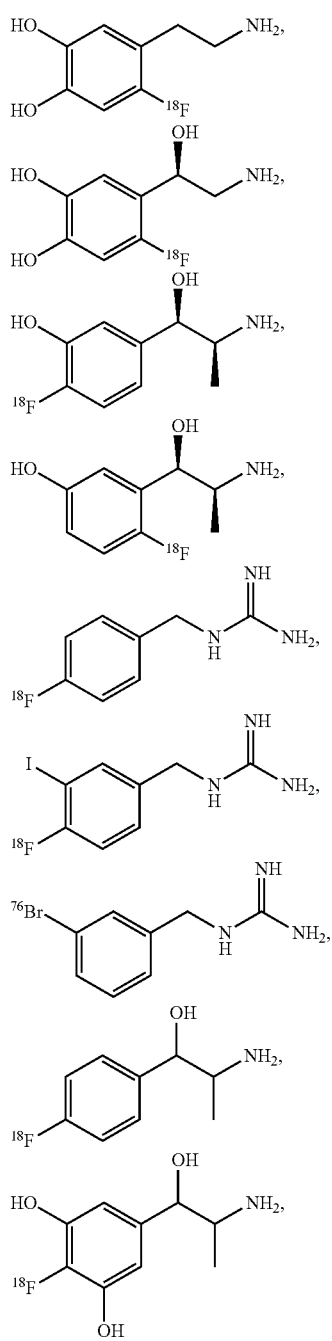

-continued

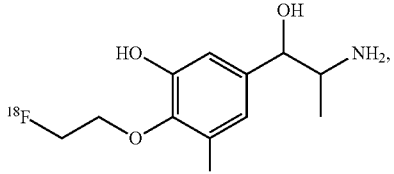

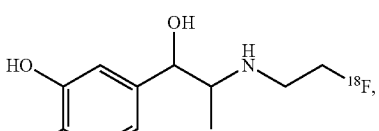

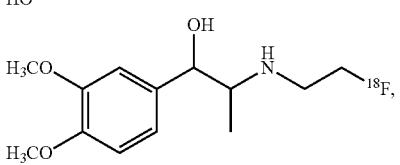

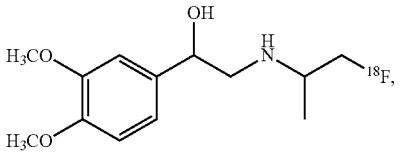

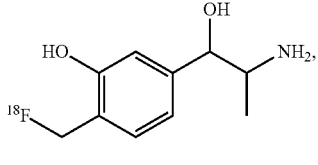

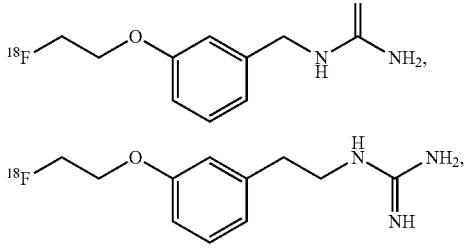

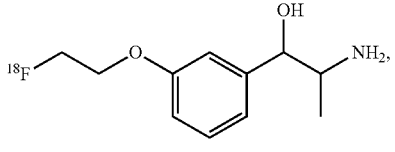

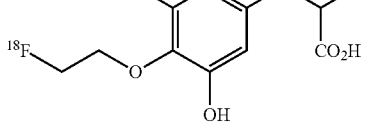

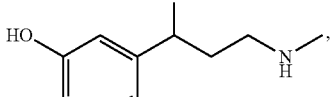

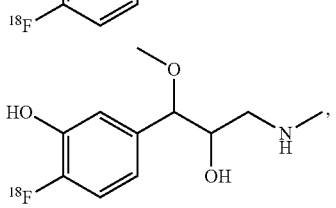

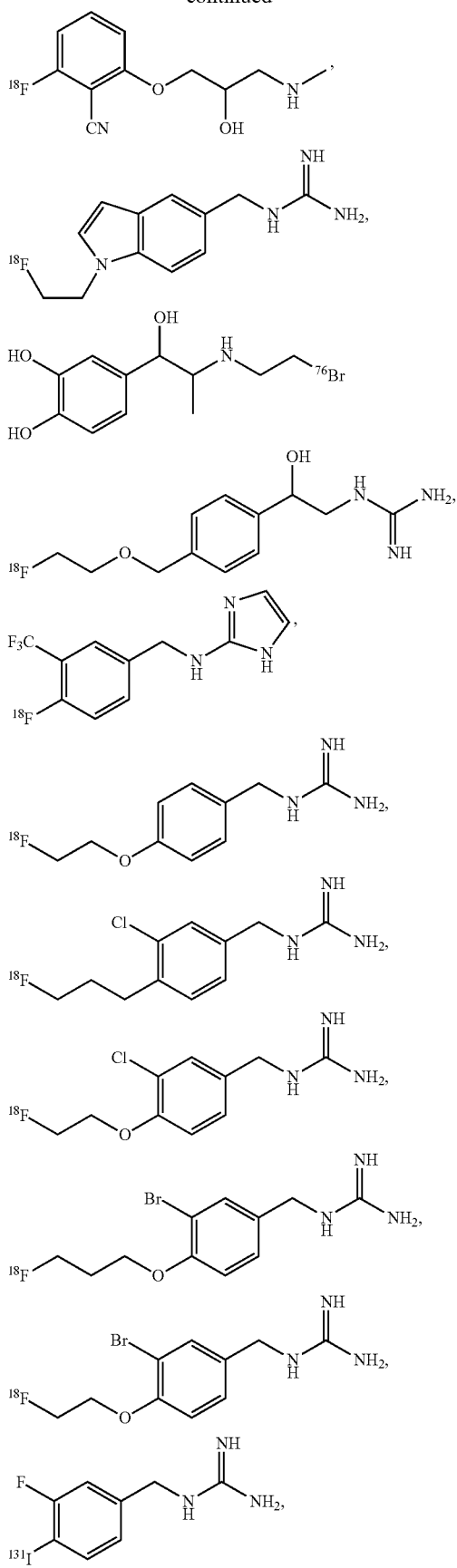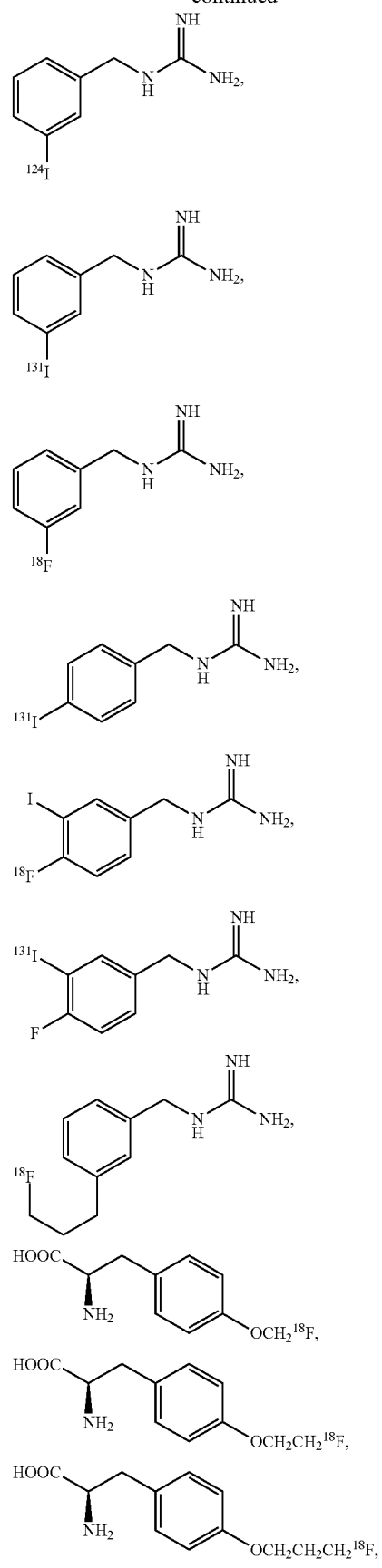

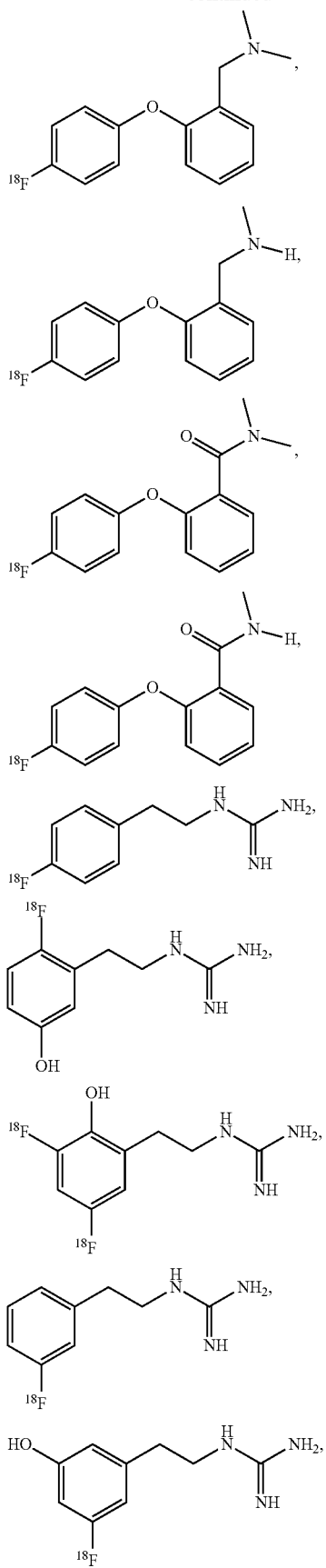
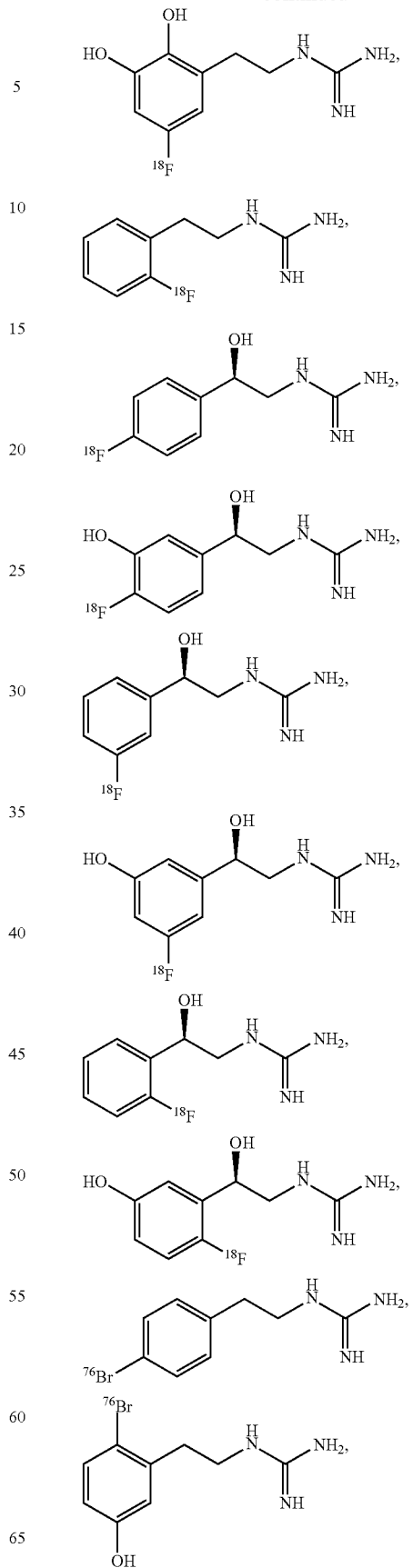

33
-continued
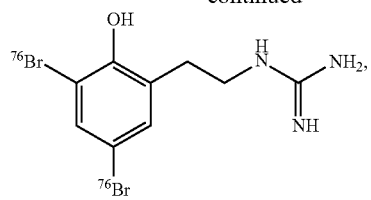
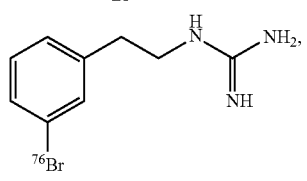
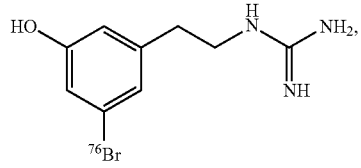
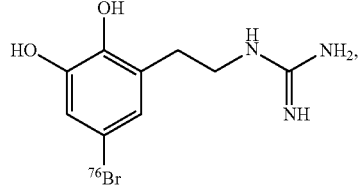
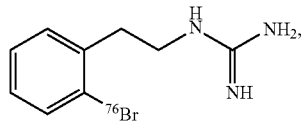
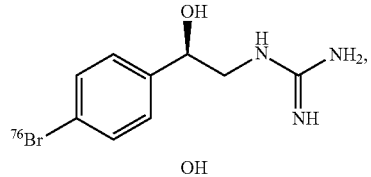
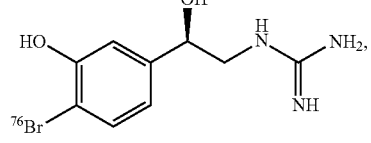
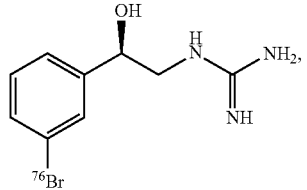
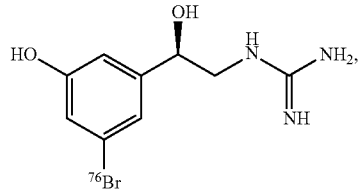
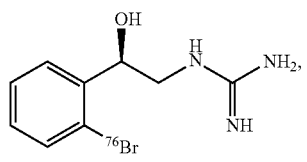 [SMILES: N=C(N)NC[C@H](O)c1ccccc1[76Br]]
34
-continued
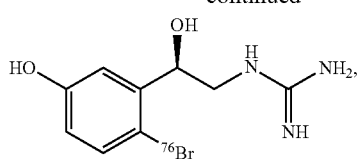
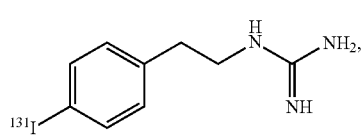
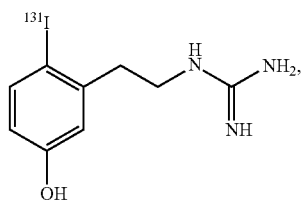
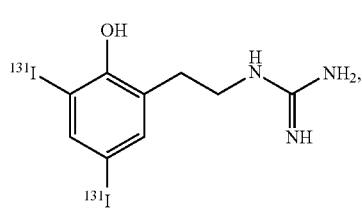
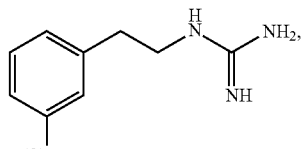
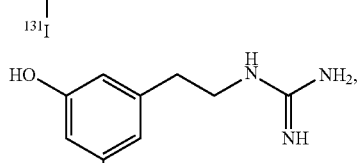
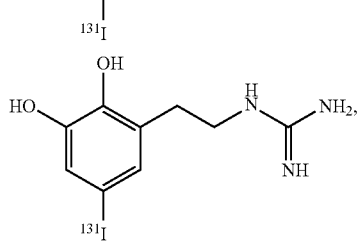
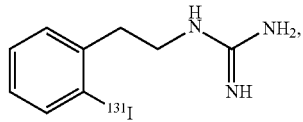
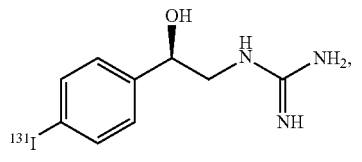
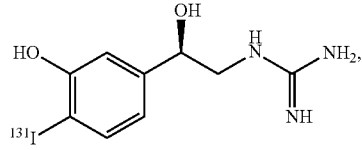

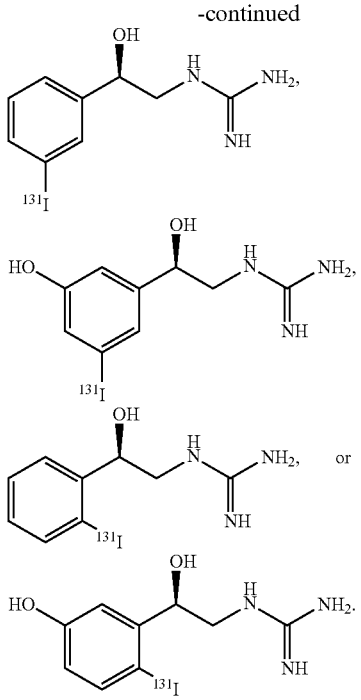

In some embodiments, a compound is provided comprising Formula (Ib):

R⁰—Ar-L-R¹    (Ib)

wherein

Ar is substituted or unsubstituted, monocyclic or bicyclic aryl; or substituted or unsubstituted, monocyclic or bicyclic heteroaryl;

L is a bond; substituted or unsubstituted, cyclic or acyclic alkylene; substituted or unsubstituted, cyclic or acyclic alkenylene; substituted or unsubstituted, cyclic or acyclic alkynylene; or substituted or unsubstituted, cyclic or acyclic heteroaliphatic;

R¹ is a substituted or unsubstituted nitrogen-containing moiety;

R⁰ is halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, —OR$^{A1}$, —N(R$^{A2}$)$_2$, —SR$^{A1}$, —C(=O)R$^{A1}$, —C(=O)OR$^{A1}$, —C(=O)SR$^{A1}$, —C(=O)N(R$^{A2}$)$_2$, —OC(=O)R$^{A1}$, —OC(=O)OR$^{A1}$, —OC(=O)SR$^{A1}$, —OC(=O)N(R$^{A2}$)$_2$, —NR$^{A2}$C(=O)R$^{A2}$, —NR$^{A2}$C(=O)OR$^{A1}$, —NR$^{A2}$C(=O)SR$^{A1}$, —NR$^{A2}$C(=O)N(R$^{A2}$)$_2$, —SC(=O)R$^{A1}$, —SC(=O)OR$^{A1}$, —SC(=O)SR$^{A1}$, —SC(=O)N(R$^{A2}$)$_2$, —C(=NR$^{A2}$)R$^{A1}$, —C(=NR$^{A2}$)OR$^{A1}$, —C(=NR$^{A2}$)SR$^{A1}$, —C(=NR$^{A2}$)N(R$^{A2}$)$_2$, —OC(=NR$^{A2}$)R$^{A1}$, —OC(=NR$^{A2}$)OR$^{A1}$, —OC(=NR$^{A2}$)SR$^{A1}$, —OC(=NR$^{A2}$)N(R$^{A2}$)$_2$, —NR$^{A2}$C(=NR$^{A2}$)R$^{A2}$, —NR$^{A2}$C(=NR$^{A2}$)OR$^{A1}$, —NR$^{A2}$C(=NR$^{A2}$)SR$^{A1}$, —NR$^{A2}$C(=NR$^{A2}$)N(R$^{A2}$)$_2$, —SC(=NR$^{A2}$)R$^{A1}$, —SC(=NR$^{A2}$)OR$^{A1}$, —SC(=NR$^{A2}$)SR$^{A1}$, —SC(=NR$^{A2}$)N(R$^{A2}$)$_2$, —C(=S)R$^{A1}$, —C(=S)OR$^{A1}$, —C(=S)SR$^{A1}$, —C(=S)N(R$^{A2}$)$_2$, —OC(=S)R$^{A1}$, —OC(=S)OR$^{A1}$, —OC(=S)SR$^{A1}$, —OC(=S)N(R$^{A2}$)$_2$, —NR$^{A2}$C(=S)R$^{A2}$, —NR$^{A2}$C(=S)OR$^{A1}$, —NR$^{A2}$C(=S)SR$^{A1}$, —NR$^{A2}$C(=S)N(R$^{A2}$)$_2$, —SC(=S)R$^{A1}$, —SC(=S)OR$^{A1}$, —SC(=S)SR$^{A1}$, —SC(=S)N(R$^{A2}$)$_2$, —S(=O)R$^{A1}$, —SO$_2$R$^{A1}$, —NR$^{A2}$SO$_2$R$^{A1}$, —SO$_2$N(R$^{A2}$)$_2$, —CN, —SCN, or —NO$_2$;

each occurrence of R$^{A1}$ is independently hydrogen, optionally substituted alkyl, optionally substituted alkenyl, optionally substituted alkynyl, optionally substituted carbocyclyl, optionally substituted heterocyclyl, optionally substituted aryl, or optionally substituted heteroaryl; and each occurrence of R$^{A2}$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, or an amino protecting group, or two R$^{A2}$ groups are joined to form an optionally substituted heterocyclic ring; and R⁰ or R¹ is substituted with an imaging moiety selected from the group consisting of ¹⁸F, ⁷⁶Br, and ¹²⁴I, or is associated with an imaging moiety selected from the group consisting of ⁶⁴Cu, ⁸⁹Zr, ⁹⁹ᵐTc, and ¹¹¹In through a chelator, or is an imaging moiety selected from the group consisting of ¹⁸F, ⁷⁶Br, and ¹²⁴I; or a salt thereof;

provided that when Ar is phenyl, when L is —CH$_2$—, when R¹ is

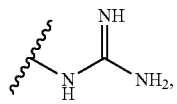

and when R⁰ is an imaging moiety selected from the group consisting of ¹⁸F, ⁷⁶Br, and ¹²⁴I, then Ar is substituted with substituents other than —R⁰ and -L-R¹.

In some embodiments, a compound of Formula (Ib) is not of the formula:

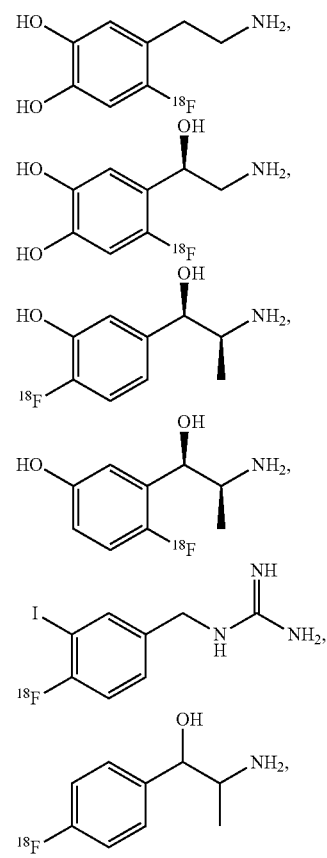

37
-continued
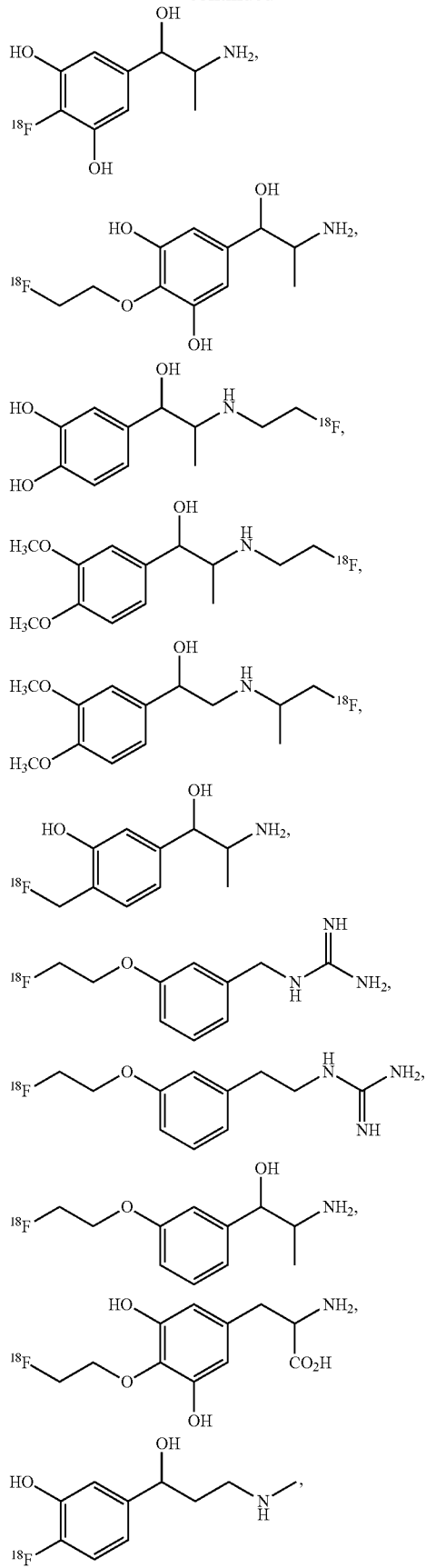
38
-continued
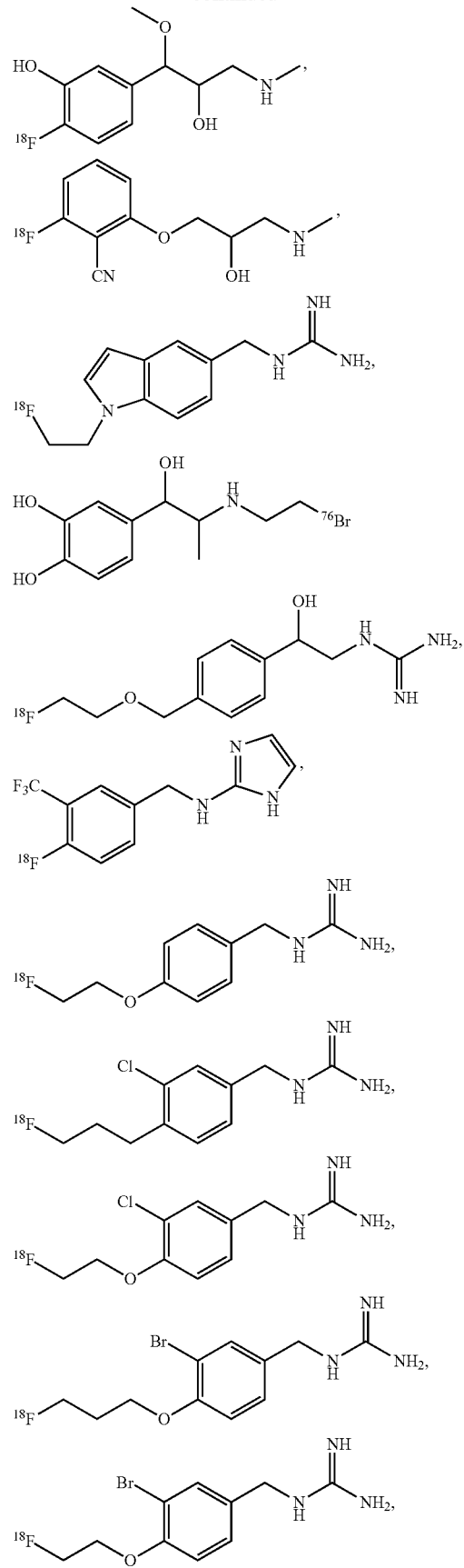

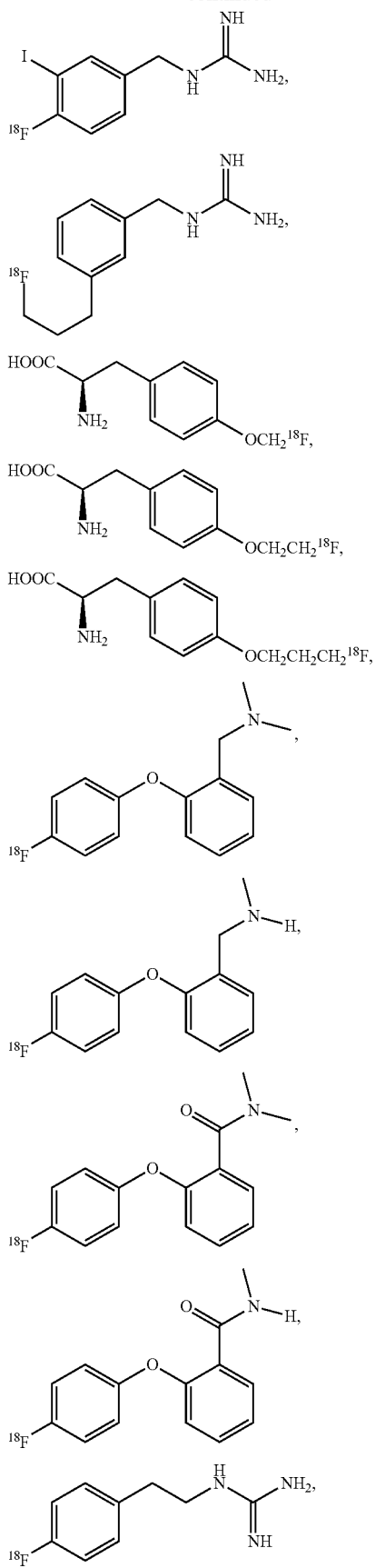
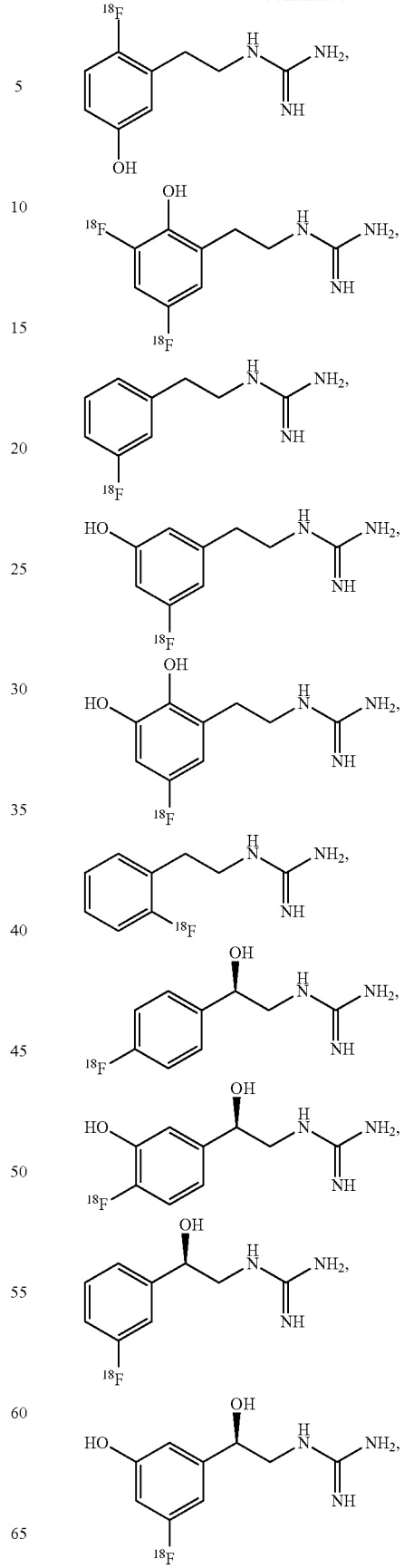

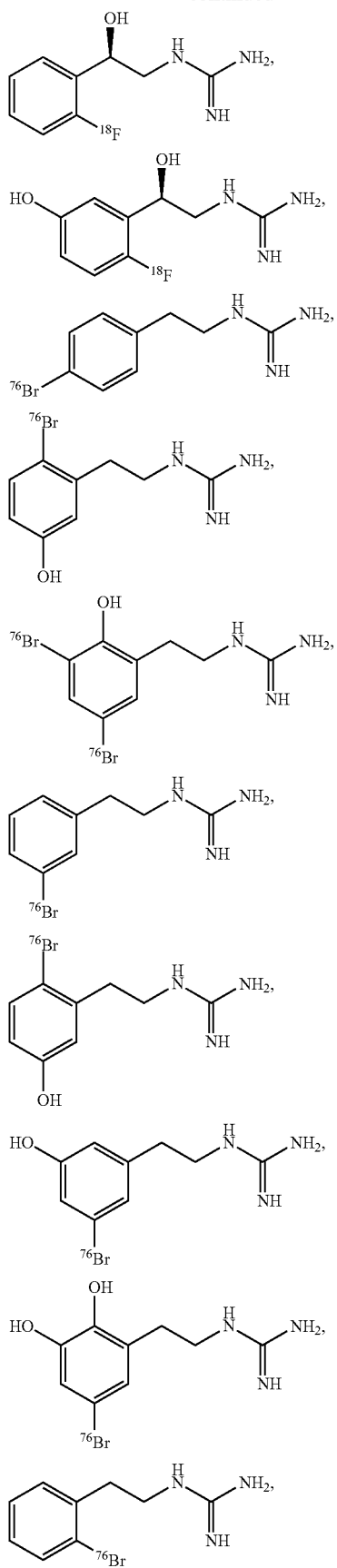
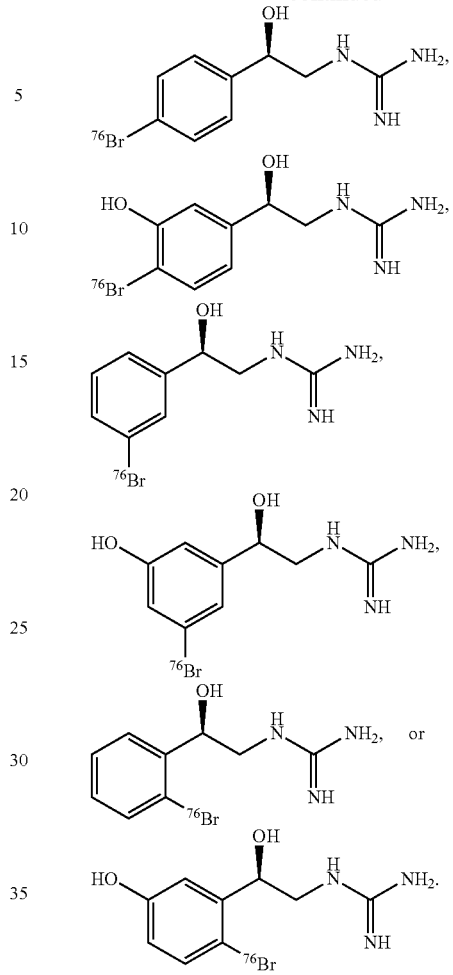

In some embodiments, a compound is provided comprising Formula (Ic):

$$R^0\text{—Ar-L-}R^1 \qquad (Ic)$$

wherein

Ar is substituted or unsubstituted, monocyclic or bicyclic aryl; or substituted or unsubstituted, monocyclic or bicyclic heteroaryl;

L is a bond; substituted or unsubstituted, cyclic or acyclic alkylene; substituted or unsubstituted, cyclic or acyclic alkenylene; substituted or unsubstituted, cyclic or acyclic alkynylene; or substituted or unsubstituted, cyclic or acyclic heteroaliphatic;

$R^1$ is a substituted or unsubstituted nitrogen-containing moiety;

$R^0$ is halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, —$OR^{A1}$, —$N(R^{A2})_2$, —$SR^{A1}$, —$C(=O)R^{A1}$, —$C(=O)OR^{A1}$, —$C(=O)SR^{A1}$, —$C(=O)N(R^{A2})_2$, —$OC(=O)R^{A1}$, —$OC(=O)OR^{A1}$, —$OC(=O)SR^{A1}$, —$OC(=O)N(R^{A2})_2$, —$NR^{A2}C(=O)R^{A2}$, —$NR^{A2}C(=O)OR^{A1}$, —$NR^{A2}C(=O)SR^{A1}$, —$NR^{A2}C(=O)N(R^{A2})_2$, —$SC(=O)R^{A1}$, —$SC(=O)OR^{A1}$, —$SC(=O)SR^{A1}$, —$SC(=O)N(R^{A2})_2$, —$C(=NR^{A2})R^{A1}$, —$C(=NR^{A2})OR^{A1}$, —$C(=NR^{A2})SR^{A1}$, —$C(=NR^{A2})N(R^{A2})_2$, —$OC(=NR^{A2})R^{A1}$, —$OC(=NR^{A2})OR^{A1}$, —$OC(=NR^{A2})SR^{A1}$, —OC (=NR$^{A2}$)N(R$^{A2}$)$_2$, —NR$^{A2}$C(=NR$^{A2}$)R$^{A2}$, —NR$^{A2}$C(=NR$^{A2}$)OR$^{A1}$, —NR$^{A2}$C(=NR$^{A2}$)SR$^{A1}$, —NR$^{A2}$C(=NR$^{A2}$)N(R$^{A2}$)$_2$, —SC(=NR$^{A2}$)R$^{A1}$, —SC(=NR$^{A2}$)OR$^{A1}$, —SC(=NR$^{A2}$)SR$^{A1}$, —SC(=NR$^{A2}$)N(R$^{A2}$)$_2$, —C(=S)R$^{A1}$, —C(=S)OR$^{A1}$, —C(=S)SR$^{A1}$, —C(=S)N(R$^{A2}$)$_2$, —OC(=S)R$^{A1}$, —OC(=S)OR$^{A1}$, —OC(=S)SR$^{A1}$, —OC(=S)N(R$^{A2}$)$_2$, —NR$^{A2}$C(=S)R$^{A2}$, —NR$^{A2}$C(=S)OR$^{A1}$, —NR$^{A2}$C(=S)SR$^{A1}$, —NR$^{A2}$C(=S)N(R$^{A2}$)$_2$, —SC(=S)R$^{A1}$, —SC(=S)OR$^{A1}$, —SC(=S)SR$^{A1}$, —SC(=S)N(R$^{A2}$)$_2$, —S(=O)R$^{A1}$, —SO$_2$R$^{A1}$, —NR$^{A2}$SO$_2$R$^{A1}$, —SO$_2$N(R$^{A2}$)$_2$, —CN, —SCN, or —NO$_2$;

each occurrence of R$^{A1}$ is independently hydrogen, optionally substituted alkyl, optionally substituted alkenyl, optionally substituted alkynyl, optionally substituted carbocyclyl, optionally substituted heterocyclyl, optionally substituted aryl, or optionally substituted heteroaryl; and each occurrence of R$^{A2}$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, or an amino protecting group, or two R$^{A2}$ groups are joined to form an optionally substituted heterocyclic ring; and R$^0$ or R$^1$ is substituted with an imaging moiety selected from the group consisting of $^{18}$F, $^{76}$Br, and $^{124}$I, or is associated with an imaging moiety selected from the group consisting of $^{64}$Cu, $^{89}$Zr, $^{99m}$Tc, and $^{111}$In through a chelator, or is an imaging moiety selected from the group consisting of $^{18}$F, $^{76}$Br, and $^{124}$I; or a salt thereof;

provided that when Ar is phenyl, then R$^0$ is not $^{18}$F; and further provided that when Ar is phenyl, when L is —CH$_2$—, when R$^1$ is

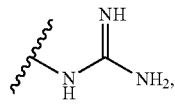

and when R$^0$ is an imaging moiety selected from the group consisting of $^{76}$Br and $^{124}$I, then Ar is substituted with substituents other than —R$^0$ and -L-R$^1$.

In some embodiments, a compound of Formula (Ic) is not of the formula:

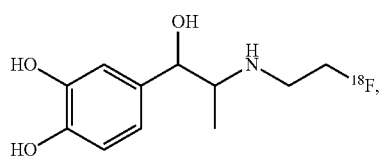

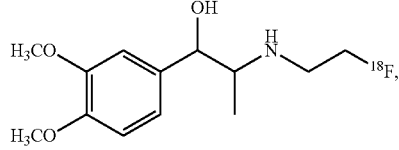

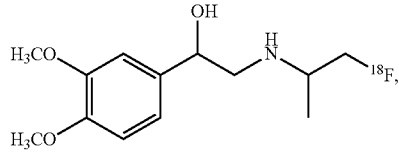

-continued

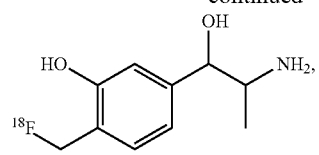

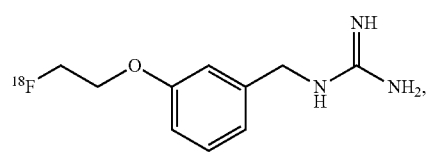

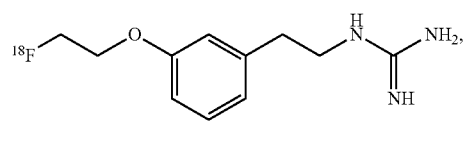

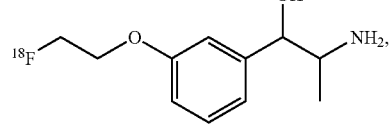

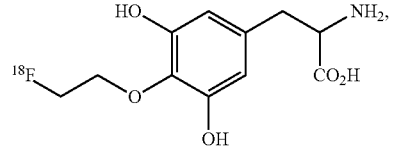

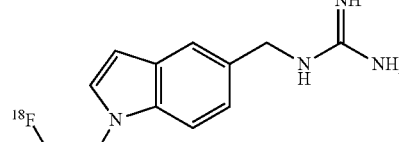

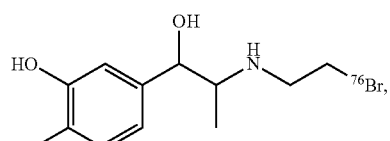

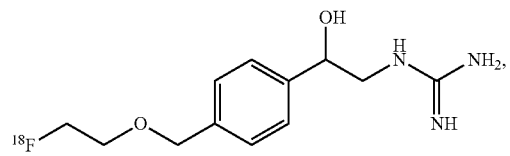

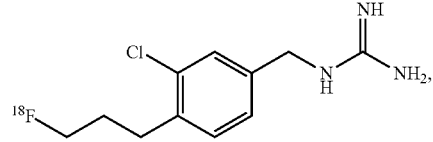

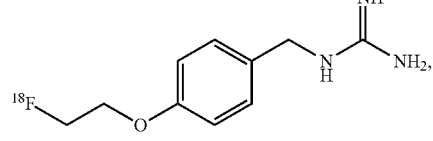

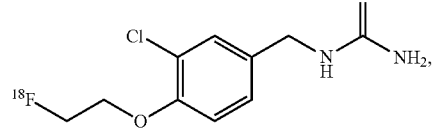

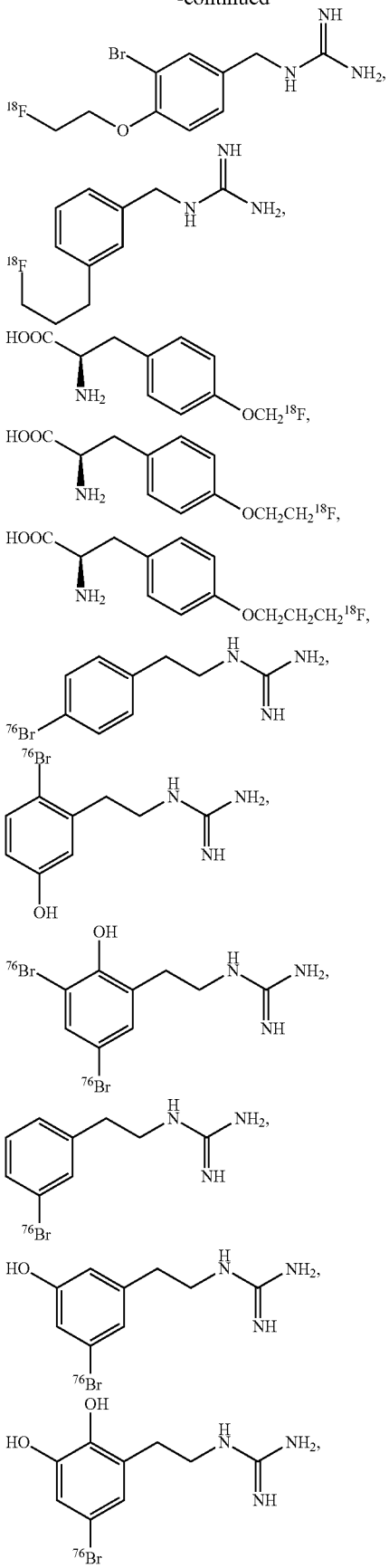
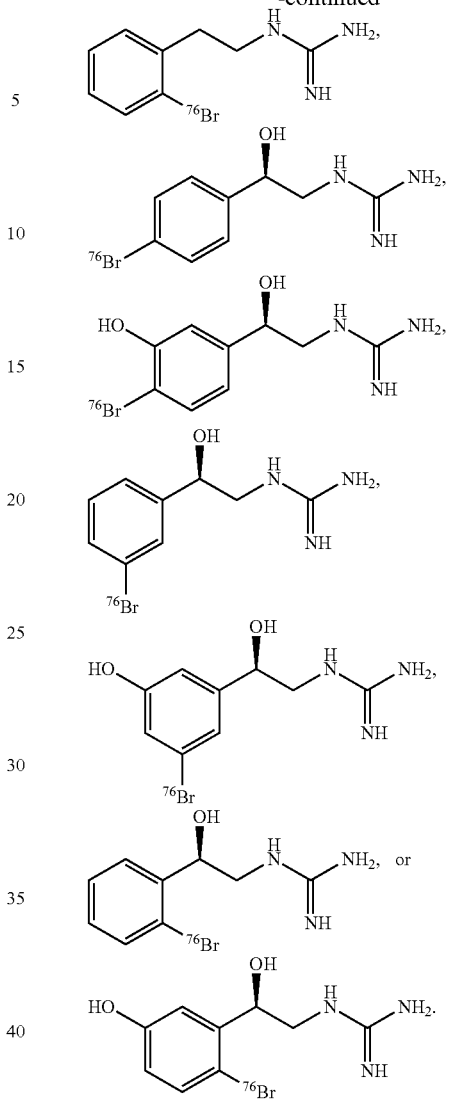

In some embodiments, a compound is provided comprising Formula (Id):

$$R^0-Ar-L-R^1 \quad (Id)$$

wherein

Ar is substituted or unsubstituted, monocyclic or bicyclic aryl; or substituted or unsubstituted, monocyclic or bicyclic heteroaryl;

L is a bond; substituted or unsubstituted, cyclic or acyclic alkylene; substituted or unsubstituted, cyclic or acyclic alkenylene; substituted or unsubstituted, cyclic or acyclic alkynylene; or substituted or unsubstituted, cyclic or acyclic heteroaliphatic;

$R^1$ is a substituted or unsubstituted nitrogen-containing moiety;

$R^0$ is halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, —$OR^{41}$, —$N(R^{42})_2$, —$SR^{41}$, —$C(=O)R^{41}$, —$C(=O)OR^{41}$, —$C(=O)SR^{41}$, —$C(=O)N(R^{42})_2$, —$OC(=O)R^{41}$, —$OC(=O)OR^{41}$, —$OC(=O)SR^{41}$, —$OC(=O)N(R^{42})_2$, —$NR^{42}C(=O)R^{42}$, —$NR^{42}C(=O)OR^{41}$, —NR$^{A2}$C(=O)SR$^{A1}$, —NR$^{A2}$C(=O)N(R$^{A2}$)$_2$, —SC(=O)R$^{A1}$, —SC(=O)OR$^{A1}$, —SC(=O)SR$^{A1}$, —SC(=O)N(R$^{A2}$)$_2$, —C(=NR$^{A2}$)R$^{A1}$, —C(=NR$^{A2}$)OR$^{A1}$, —C(=NR$^{A2}$)SR$^{A1}$, —C(=NR$^{A2}$)N(R$^{A2}$)$_2$, —OC(=NR$^{A2}$)R$^{A1}$, —OC(=NR$^{A2}$)OR$^{A1}$, —OC(=NR$^{A2}$)SR$^{A1}$, —OC(=NR$^{A2}$)N(R$^{A2}$)$_2$, —NR$^{A2}$C(=NR$^{A2}$)R$^{A2}$, —NR$^{A2}$C(=NR$^{A2}$)OR$^{A1}$, —NR$^{A2}$C(=NR$^{A2}$)SR$^{A1}$, —NR$^{A2}$C(=NR$^{A2}$)N(R$^{A2}$)$_2$, —SC(=NR$^{A2}$)R$^{A1}$, —SC(=NR$^{A2}$)OR$^{A1}$, —SC(=NR$^{A2}$)SR$^{A1}$, —SC(=NR$^{A2}$)N(R$^{A2}$)$_2$, —C(=S)R$^{A1}$, —C(=S)OR$^{A1}$, —C(=S)SR$^{A1}$, —C(=S)N(R$^{A2}$)$_2$, —OC(=S)R$^{A1}$, —OC(=S)OR$^{A1}$, —OC(=S)SR$^{A1}$, —OC(=S)N(R$^{A2}$)$_2$, —NR$^{A2}$C(=S)R$^{A2}$, —NR$^{A2}$C(=S)OR$^{A1}$, —NR$^{A2}$C(=S)SR$^{A1}$, —NR$^{A2}$C(=S)N(R$^{A2}$)$_2$, —SC(=S)R$^{A1}$, —SC(=S)OR$^{A1}$, —SC(=S)SR$^{A1}$, —SC(=S)N(R$^{A2}$)$_2$, —S(=O)R$^{A1}$, —SO$_2$R$^{A1}$, —NR$^{A2}$SO$_2$R$^{A1}$, —SO$_2$N(R$^{A2}$)$_2$, —CN, —SCN, or —NO$_2$;

each occurrence of R$^{A1}$ is independently hydrogen, optionally substituted alkyl, optionally substituted alkenyl, optionally substituted alkynyl, optionally substituted carbocyclyl, optionally substituted heterocyclyl, optionally substituted aryl, or optionally substituted heteroaryl; and each occurrence of R$^{A2}$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, or an amino protecting group, or two R$^{A2}$ groups are joined to form an optionally substituted heterocyclic ring; and R$^0$ or R$^1$ is substituted with an imaging moiety selected from the group consisting of $^{18}$F, $^{76}$Br, and $^{124}$I, or is associated with an imaging moiety selected from the group consisting of $^{64}$Cu, $^{89}$Zr, $^{99m}$Tc, and $^{111}$In through a chelator, or is an imaging moiety selected from the group consisting of $^{18}$F, $^{76}$Br, and $^{124}$I; or a salt thereof;

provided that when Ar is phenyl, then R$^0$ is not $^{18}$F;

further provided that when Ar is phenyl, when L is —CH$_2$—, when R$^1$ is

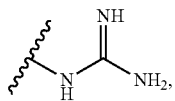

and when R$^0$ is an imaging moiety selected from the group consisting of $^{76}$Br and $^{124}$I, then Ar is substituted with substituents other than —R$^0$ and -L-R$^1$; and further provided that when Ar is phenyl, then Ar is not substituted with —OH.

In some embodiments, a compound of Formula (Id) is not of the formula:

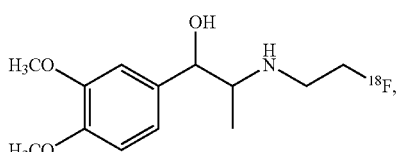

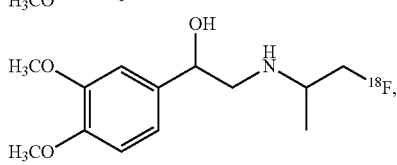

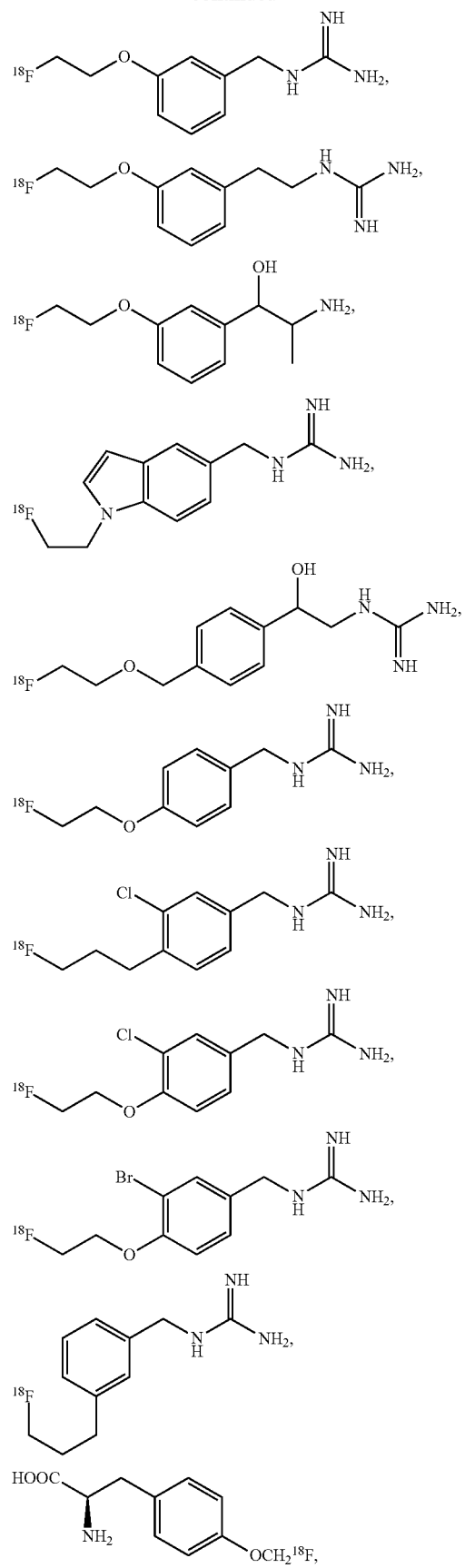

-continued

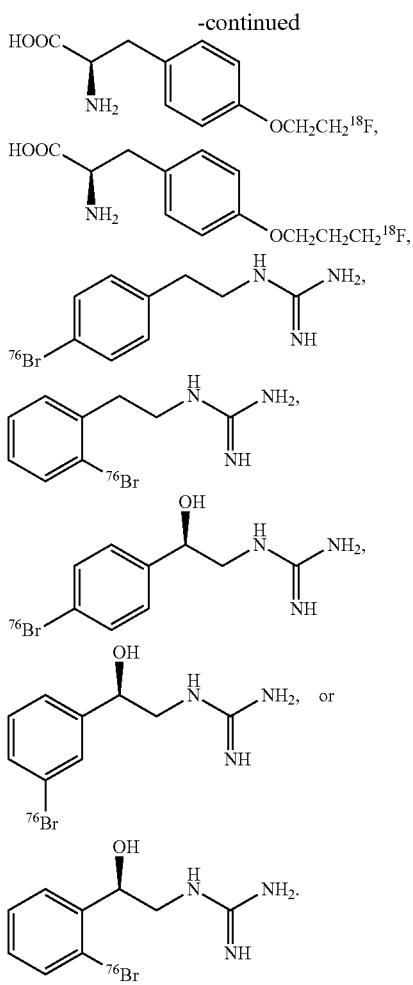

In certain embodiments, a compound of Formula (Ia), (Ib), (Ic), or (Id) is any suitable salt, as described herein. In certain embodiments, a compound of Formula (Ia), (Ib), (Ic), or (Id) is a pharmaceutically acceptable salt. Non-limiting examples of salts include mesylate (i.e., methanesulfonate), phosphate, sulfate, acetate, formate, benzoate, chloride, iodide, bromide, ascorbate, trifluoroacetate, or tosylate salt of a compound of Formula (Ia), (Ib), (Ic), or (Id).

As described above, in some embodiments for a compound of Formula (Ia), $R^0$ or $R^1$ is substituted with an imaging moiety selected from the group consisting of $^{18}F$, $^{76}Br$, $^{124}I$, and $^{131}I$, or is associated with an imaging moiety selected from the group consisting of $^{64}Cu$, $^{89}Zr$, $^{99m}Tc$, and $^{111}In$ through a chelator, or is an imaging moiety selected from the group consisting of $^{18}F$, $^{76}Br$, $^{124}I$, and $^{131}I$. In certain embodiments, the imaging moiety is $^{18}F$. In certain embodiments, the imaging moiety is $^{76}Br$. In certain embodiments, the imaging moiety is $^{124}I$. In certain embodiments, the imaging moiety is $^{131}I$. In some cases, the imaging moiety is not $^{131}I$. In some cases, the imaging moiety is $^{18}F$, $^{76}Br$, or $^{124}I$. In some cases, the imaging moiety is $^{18}F$ or $^{76}Br$. In some embodiments, the imaging moiety is not directly bound to Ar. In certain embodiments, $R^0$ is substituted with an imaging moiety selected from the group consisting of $^{18}F$, $^{76}Br$, $^{124}I$, and $^{131}I$; or is associated with an imaging moiety selected from the group consisting of $^{64}Cu$, $^{89}Zr$, $^{99m}Tc$, and $^{111}In$ through a chelator; or is an imaging moiety selected from the group consisting of $^{18}F$, $^{76}Br$, $^{124}I$, and $^{131}I$. In certain embodiments, $R^0$ is substituted with an imaging moiety selected from the group consisting of $^{18}F$, $^{76}Br$, $^{124}I$, and $^{131}I$. In certain embodiments, $R^0$ is associated with an imaging moiety selected from the group consisting of $^{64}Cu$, $^{89}Zr$, $^{99m}Tc$, and $^{111}In$ through a chelator. In certain embodiments, $R^0$ is an imaging moiety selected from the group consisting of $^{18}F$, $^{76}Br$, $^{124}I$, and $^{131}I$. In some embodiments, $R^1$ is substituted with an imaging moiety selected from the group consisting of $^{18}F$, $^{76}Br$, $^{124}I$, and $^{131}I$; or is associated with an imaging moiety selected from the group consisting of $^{64}Cu$, $^{89}Zr$, $^{99m}Tc$, and $^{111}In$ through a chelator; or is an imaging moiety selected from the group consisting of $^{18}F$, $^{76}Br$, $^{124}I$, and $^{131}I$. In some cases, $R^1$ is substituted with an imaging moiety selected from the group consisting of $^{18}F$, $^{76}Br$, $^{124}I$, and $^{131}I$. In some cases, $R^1$ is substituted with $^{18}F$.

As described above, in some embodiments for a compound of Formula (Ib), (Ic), or (Id), $R^0$ or $R^1$ is substituted with an imaging moiety selected from the group consisting of $^{18}F$, $^{76}Br$, and $^{124}I$, or is associated with an imaging moiety selected from the group consisting of $^{64}Cu$, $^{89}Zr$, $^{99m}Tc$, and $^{111}In$ through a chelator, or is an imaging moiety selected from the group consisting of $^{18}F$, $^{76}Br$, and $^{124}I$. In certain embodiments, the imaging moiety is $^{18}F$. In certain embodiments, the imaging moiety is $^{76}Br$. In certain embodiments, the imaging moiety is $^{124}I$. In certain embodiments, the imaging moiety is $^{131}I$. In certain embodiments, the imaging moiety is not $^{131}I$. In some cases, the imaging moiety is not $^{131}I$. In some cases, the imaging moiety is $^{18}F$, $^{76}Br$, or $^{124}I$. In some cases, the imaging moiety is $^{18}F$ or $^{76}Br$. In some embodiments, the imaging moiety is not directly bound to Ar. In certain embodiments, $R^0$ is substituted with an imaging moiety selected from the group consisting of $^{18}F$, $^{76}Br$, and $^{124}I$; or is associated with an imaging moiety selected from the group consisting of $^{64}Cu$, $^{89}Zr$, $^{99m}Tc$, and $^{111}In$ through a chelator; or is an imaging moiety selected from the group consisting of $^{18}F$, $^{76}Br$, and $^{124}I$. In certain embodiments, $R^0$ is substituted with an imaging moiety selected from the group consisting of $^{18}F$, $^{76}Br$, and $^{124}I$. In certain embodiments, $R^0$ is associated with an imaging moiety selected from the group consisting of $^{64}Cu$, $^{89}Zr$, $^{99m}Tc$, and $^{111}In$ through a chelator. In certain embodiments, $R^0$ is an imaging moiety selected from the group consisting of $^{18}F$, $^{76}Br$, and $^{124}I$. In certain embodiments, the imaging moiety is $^{18}F$. In some embodiments, $R^1$ is substituted with an imaging moiety selected from the group consisting of $^{18}F$, $^{76}Br$, and $^{124}I$; or is associated with an imaging moiety selected from the group consisting of $^{64}Cu$, $^{89}Zr$, $^{99m}Tc$, and $^{111}In$ through a chelator; or is an imaging moiety selected from the group consisting of $^{18}F$, $^{76}Br$, and $^{124}I$. In some cases, $R^1$ is substituted with an imaging moiety selected from the group consisting of $^{18}F$, $^{76}Br$, and $^{124}I$. In some cases, $R^1$ is substituted with $^{18}F$.

As described above, in some embodiments for a compound of Formula (Ia), (Ib), (Ic), or (Id), Ar may be substituted or unsubstituted, monocyclic or bicyclic aryl; or substituted or unsubstituted, monocyclic or bicyclic heteroaryl. As described above, in some embodiments, the imaging moiety is not directly bound to Ar. In certain embodiments, when $^{18}F$ is the imaging moiety, then $^{18}F$ is not bound directly to Ar. In certain embodiments, when $^{18}F$ is the imaging moiety and Ar is phenyl then $^{18}F$ is not bound directly to Ar. In other embodiments, when $^{76}Br$ is the imaging moiety, then $^{76}Br$ is not bound directly to Ar. In other embodiments, when $^{76}Br$ is the imaging moiety and Ar is phenyl then $^{76}Br$ is not bound directly to Ar. In other embodiments, when $^{124}I$ is the imaging moiety then $^{124}I$ is not bound directly to Ar. In other embodiments, when $^{124}$I is the imaging moiety and Ar is phenyl then $^{124}$I is not bound directly to Ar. In other embodiments, when $^{131}$I is the imaging moiety, then $^{131}$I is not bound directly to Ar. In other embodiments, when $^{131}$I is the imaging moiety and Ar is phenyl then $^{131}$I is not bound directly to Ar. However, in other embodiments, the imaging moiety is directly bound to Ar. In some embodiments, when Ar is phenyl then the imaging moiety is not present in $R^0$. In some embodiments, when Ar is phenyl then the imaging moiety is not present in $R^0$ when $R^0$ is $OR^{41}$ and $R^{41}$ is alkyl. In some embodiments, when Ar is phenyl then the imaging moiety is not present in $R^0$, when $R^0$ is alkyl.

In certain embodiments, for a compound of Formula (Ia), (Ib), (Ic), or (Id), Ar is selected from the group consisting of substituted or unsubstituted phenyl, substituted or unsubstituted naphthyl, substituted or unsubstituted biphenyl, substituted or unsubstituted heteroaryl, substituted or unsubstituted monocyclic heteroaryl, substituted or unsubstituted bicyclic heteroaryl, substituted or unsubstituted benzoxazolyl, substituted or unsubstituted benzimidazoly, substituted or unsubstituted benzthiazolyl, substituted or unsubstituted indolyl, substituted or unsubstituted quinolinyl, substituted or unsubstituted isoquinolinyl, substituted or unsubstituted chromanyl, substituted or unsubstituted chromenyl, substituted or unsubstituted benzofuranyl, or substituted or unsubstituted benzpyrazolyl. In certain embodiments, Ar is substituted or unsubstituted aryl. In some embodiments, Ar is substituted or unsubstituted phenyl. In other embodiments, Ar is not phenyl. In some embodiments, Ar is substituted or unsubstituted naphthyl. In some embodiments, Ar is substituted or unsubstituted biphenyl. In some embodiments, Ar is substituted or unsubstituted heteroaryl. In some embodiments, Ar is substituted or unsubstituted monocyclic heteroaryl. In some embodiments, Ar is substituted or unsubstituted bicyclic heteroaryl. In certain embodiments, Ar is substituted or unsubstituted, 10-membered heteroaryl. In certain, embodiments, Ar is substituted or unsubstituted, 9-membered heteroaryl. In certain embodiments, Ar is substituted or unsubstituted 8-membered heteroaryl. In some embodiments, Ar is substituted or unsubstituted benzoxazolyl. In some embodiments, Ar is substituted or unsubstituted benzimidazolyl. In some embodiments, Ar is substituted or unsubstituted benzthiazolyl. In some embodiments, Ar is substituted or unsubstituted indolyl. In some embodiments, Ar is substituted or unsubstituted quinolinyl. In some embodiments, Ar is substituted or unsubstituted isoquinolinyl. In some embodiments, Ar is substituted or unsubstituted chromanyl. In some embodiments, Ar is substituted or unsubstituted chromenyl. In some embodiments, Ar is substituted or unsubstituted benzofuranyl. In some embodiments, Ar is substituted or unsubstituted benzpyrazolyl. In some embodiments, Ar is substituted or unsubstituted indazolyl. In some embodiments, Ar is substituted or unsubstituted benztriazolyl.

As described above, in some embodiments for a compound of Formula (Ia), (Ib), (Ic), or (Id), L may be a bond; substituted or unsubstituted, cyclic or acyclic alkylene; substituted or unsubstituted, cyclic or acyclic alkenylene; substituted or unsubstituted, cyclic or acyclic alkynylene; or substituted or unsubstituted, cyclic or acyclic heteroaliphatic. L may be of any suitable length. In some cases, L ranges from 0 to 6 atoms in length, from 0 to 3 atoms in length, or from 0 to 2 atoms in length. In certain embodiments, L is 0, 1, 2, 3, 4, 5, or 6 atoms in length. The length of L may be determined by determining the number of atoms in the shortest distance from Ar to $R^1$, wherein $R^1$ begins at the first atom of $R^1$ or N. In some cases, when determining the length of L, the substituents are not considered.

In some embodiments, L is selected from the group consisting of a bond; substituted or unsubstituted, cyclic or acyclic $C_{1-6}$alkylene; unsubstituted, acyclic $C_{1-6}$alkylene; acyclic $C_{1-6}$alkylene; substituted or unsubstituted, cyclic or acyclic $C_{1-6}$alkenylene; or substituted or unsubstituted, and cyclic or acyclic heteroaliphatic.

In some embodiments, L is selected from the group consisting of CR'$_2$—, —CR'$_2$CR'$_2$—, —CR'$_2$CR'$_2$CR'$_2$—, —CR'=CR'—, —CR'=CR'CR'$_2$—, —CR'$_2$CR'=CR'—, —OCR'$_2$—, —CR'$_2$O—, —OCR'$_2$CR'$_2$—, —CR'$_2$CR'$_2$O—, —NR'CR'$_2$—, —CR'$_2$NR'—, —NR'CR'$_2$C R'$_2$—, —CR'$_2$CR'$_2$NR'—, —CR'=N—, —N=CR'—,

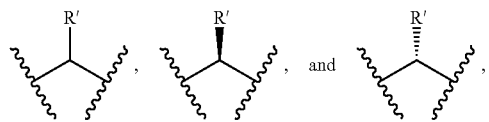

wherein R' is independently hydrogen, halogen, —OH, substituted or unsubstituted alkyl, substituted or unsubstituted alkenyl, substituted or unsubstituted alkynyl, substituted or unsubstituted carbocyclyl, substituted unsubstituted heterocyclyl, substituted or unsubstituted aryl, substituted or unsubstituted heteroaryl, substituted or unsubstituted alkoxy, or substituted or unsubstituted alkoxyalkyl.

In some embodiments, L is a bond. In some embodiments, L is selected from the group consisting of —CH$_2$—, —CH$_2$CH$_2$—, —CH$_2$CH$_2$CH$_2$—, —CH=CH—, —CH=CHCH$_2$—, —CH$_2$CH=CH—, —OCH$_2$—, —CH$_2$O—, —OCH$_2$CH$_2$—, —CH$_2$CH$_2$O—, —NHCH$_2$—, —CH$_2$NH—, —NHCH$_2$CH$_2$—, —CH$_2$CH$_2$NH—, —CH=N—, —N=CH—,

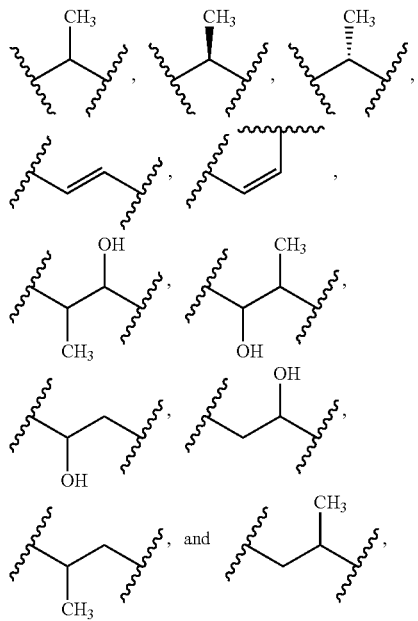

each optionally substituted.

In some embodiments, L is substituted or unsubstituted, cyclic or acyclic alkylene. In some embodiments, L is substituted or unsubstituted, cyclic or acyclic $C_{1-6}$alkylene.

In some embodiments, L is unsubstituted, acyclic $C_{1-6}$alkylene. In some embodiments, L is substituted, acyclic $C_{1-6}$alkylene. In some embodiments, L is —$CH_2$—. In some embodiments, L is —$CH_2CH_2$—. In some embodiments, L is —$CH_2CH_2CH_2$—. In some embodiments, L is —CH=CH—. In some embodiments, L is substituted or unsubstituted, cyclic or acyclic $C_{1-6}$alkenylene. In some embodiments, L is substituted or unsubstituted, cyclic or acyclic heteroaliphatic. In some embodiments, L is —$OCH_2$— or —$CH_2O$—. In some embodiments, L is —$OCH_2CH_2$— or —$CH_2CH_2O$—. In some embodiments, L is —$NHCH_2$— or —$CH_2NH$—. In some embodiments, L is $NHCH_2CH_2$— or —$CH_2CH_2NH$—. In some embodiments, L is —CH=N— or —N=CH—. In some embodiments, L is —$CH_2CH_2CH_2$—. In some embodiments, L is:

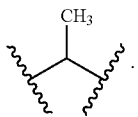

In some embodiments, L is:

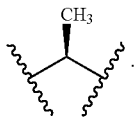

In some embodiments, L is:

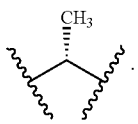

In some embodiments, L is:

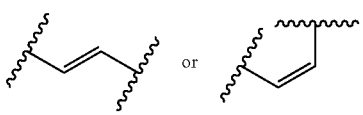

In some embodiments, L is:

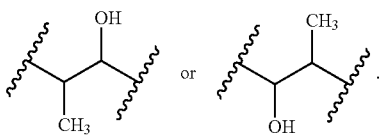

In some embodiments, L is:

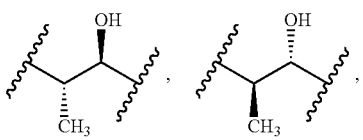

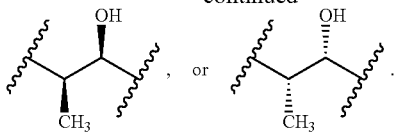

In some embodiments, L is:

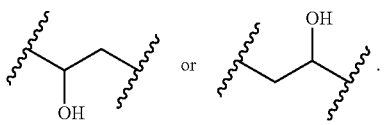 [SMILES: *CC(*)O ; *CC(*)O]

In some embodiments, L is:

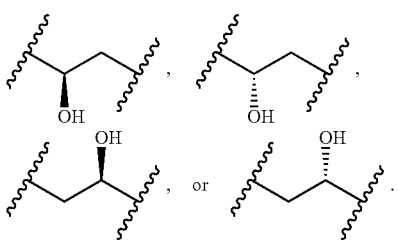

In some embodiments, L is:

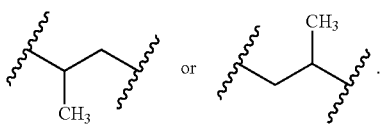

In some embodiments, L is:

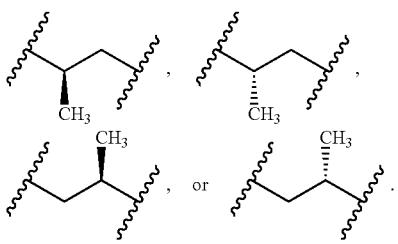

Each of the L groups described herein may be combined with any suitable Ar, $R^1$, and/or $R^0$ group, or combinations described herein.

As described above, in some embodiments for a compound of Formula (Ia), (Ib), (Ic), or (Id), $R^1$ is a substituted or unsubstituted nitrogen-containing moiety. In some embodiments, $R^1$ is —$N(R^A)_2$, heteroaryl, heterocyclic, —C(=NH)$NH_2$, —NHC(=NH)$NH_2$, —$NR^AC$(=$NR^A$)N($R^A$)$_2$, —NHC(=NH)$NHR^A$, or —NHC(=NH)N($R^A$)$_2$, wherein each occurrence of $R^A$ is independently hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl, or two $R^A$ groups may be joined to form an optionally substituted heterocyclic ring. In some embodiments, $R^1$ is a non-aromatic, cyclic, substituted or unsubstituted nitrogen-containing moiety. In some embodiments, $R^1$ is selected from the group consisting of —NHC(=NH)NH$_2$, —NH$_2$, —NHR$^A$ (wherein R$^A$ is as defined herein), —NHCH$_3$, —NHCH$_2$CH$_3$, —NHCH$_2$CH$_2$CH$_3$,

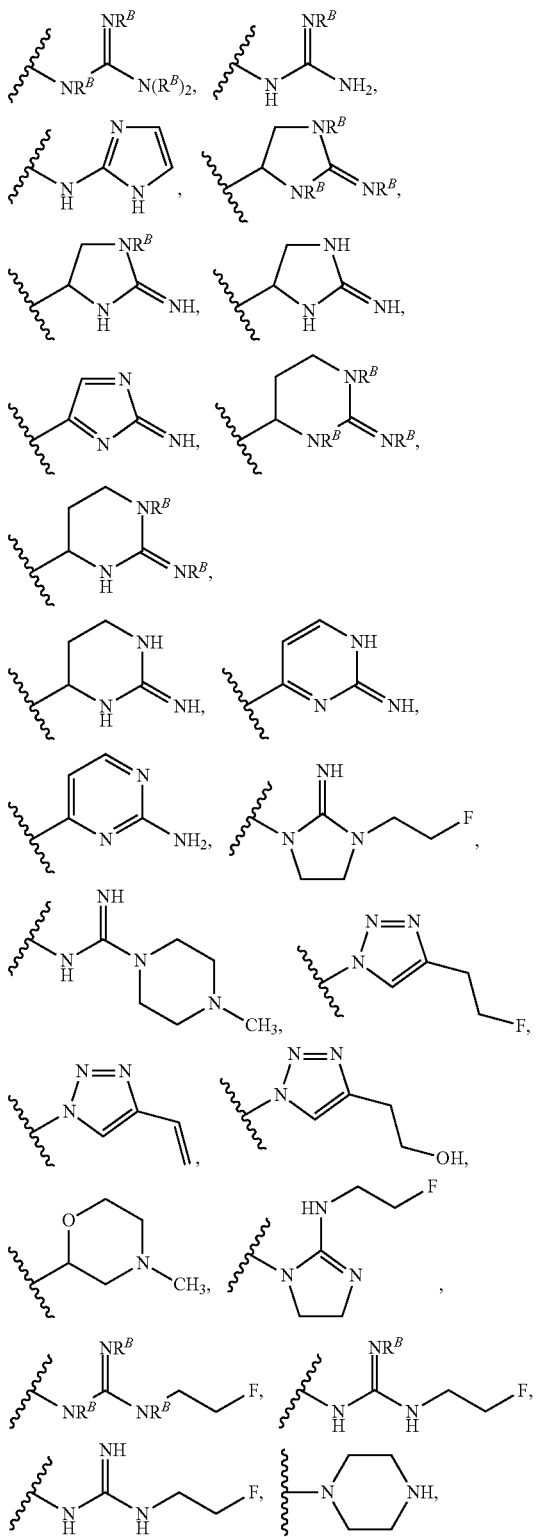

each optionally substituted, wherein each occurrence of $R^B$ is independently hydrogen, substituted or unsubstituted alkyl, or a nitrogen-protecting group. In some cases, at least two $R^B$ are hydrogen.

In some embodiments, $R^1$ is —NHC(=NH)NH$_2$. In some embodiments, $R^1$ is:

wherein each occurrence of $R^B$ is independently hydrogen, substituted or unsubstituted alkyl, or a nitrogen-protecting group, provided at least two $R^B$ are hydrogen. In some embodiments, $R^1$ is:

wherein $R^B$ is hydrogen, substituted or unsubstituted alkyl, or a nitrogen-protecting group.

However, in other embodiments, $R^1$ is not —NHC(=NH)NH$_2$. In some embodiments, $R^1$ is not:

wherein each occurrence of $R^B$ is independently hydrogen, substituted or unsubstituted alkyl, or a nitrogen-protecting group, provided at least two $R^B$ are hydrogen. In some embodiments, $R^1$ is not:

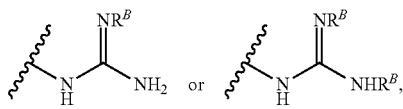

wherein $R^B$ is hydrogen, substituted or unsubstituted alkyl, or a nitrogen-protecting group. In certain embodiments, when L is —CH$_2$—, then $R^1$ is not —NHC(=NH)NH$_2$. In certain embodiment, when L is —CH$_2$—, and Ar is phenyl, then $R^1$ is not —NHC(=NH)NH$_2$.

In some embodiments, $R^1$ is —NH$_2$. In some embodiments, $R^1$ is —NHR$^A$. In some embodiments, $R^1$ is —NHCH$_3$, —NHCH$_2$CH$_3$, or —NHCH$_2$CH$_2$CH$_3$. In some embodiments, $R^1$ is:

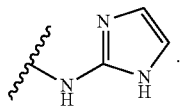

In some embodiments, $R^1$ is:

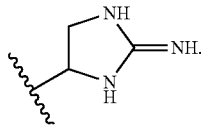 [SMILES: *C1CNC(=N)N1]

In some embodiments, $R^1$ is:

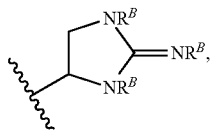

wherein each occurrence of $R^B$ is independently hydrogen, substituted or unsubstituted alkyl, or a nitrogen-protecting group, provided at least two $R^B$ are hydrogen. In some embodiments, $R^1$ is:

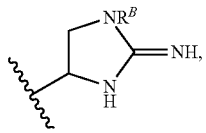

wherein $R^B$ is hydrogen, substituted or unsubstituted alkyl, or a nitrogen-protecting group. In some embodiments, $R^1$ is:

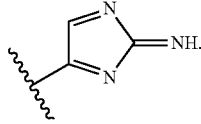 [SMILES: *C1=NC(=N)N=C1]

In some embodiments, $R^1$ is:

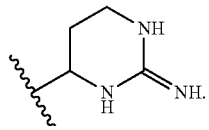 [SMILES: *C1CCNC(=N)N1]

In some embodiments, $R^1$ is:

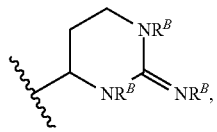

wherein each occurrence of $R^B$ is independently hydrogen, substituted or unsubstituted alkyl, or a nitrogen-protecting group, provided at least two $R^B$ are hydrogen. In some embodiments, $R^1$ is:

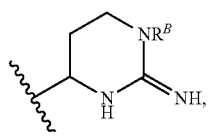

wherein $R^B$ is hydrogen, substituted or unsubstituted alkyl, or a nitrogen-protecting group. In some embodiments, $R^1$ is:

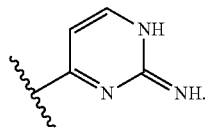 [SMILES: *c1cc[nH]c(=N)n1]

In some embodiments, $R^1$ is:

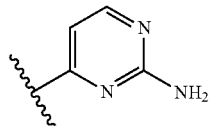 [SMILES: *c1ccnc(N)n1]

In some embodiments, $R^1$ is:

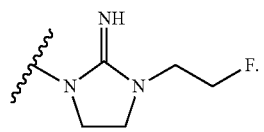 [SMILES: *N1CCN(CCF)C1=N]

In some embodiments, $R^1$ is:

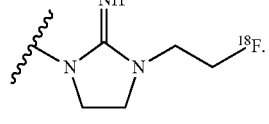

In some embodiments, R¹ is:

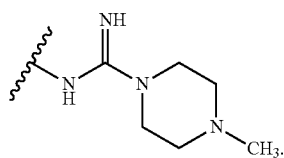

In some embodiments, R¹ is:

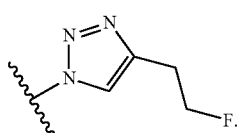 [SMILES: *n1cc(CCF)nn1]

In some embodiments, R¹ is:

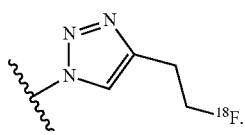

In some embodiments, R¹ is:

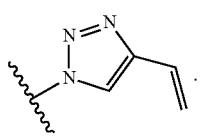 [SMILES: *n1cc(C=C)nn1]

In some embodiments, R¹ is:

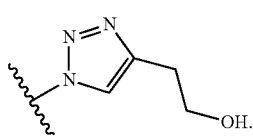 [SMILES: *n1cc(CCO)nn1]

In some embodiments, R¹ is:

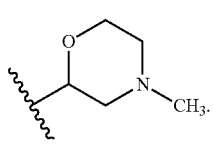 [SMILES: *C1CN(C)CCO1]

In some embodiments, R¹ is:

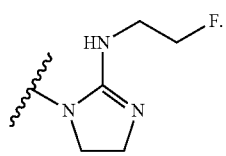 [SMILES: *N1CCN=C1NCCF]

In some embodiments, R¹ is:

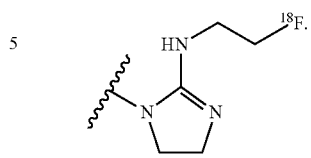

In some embodiments, R¹ is:

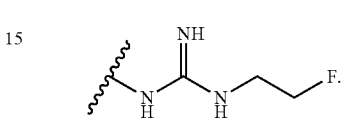

In some embodiments, R¹ is:

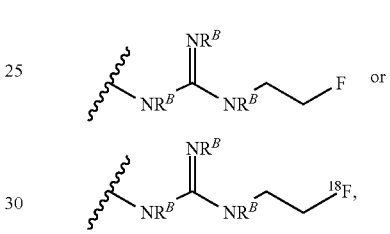

wherein each occurrence of $R^B$ is independently hydrogen, substituted or unsubstituted alkyl, or a nitrogen-protecting group, provided at least two $R^B$ are hydrogen. In some embodiments, R¹ is:

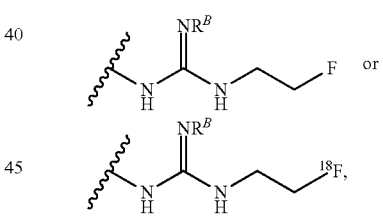

wherein $R^B$ is hydrogen, substituted or unsubstituted alkyl, or a nitrogen-protecting group. In some embodiments, R¹ is:

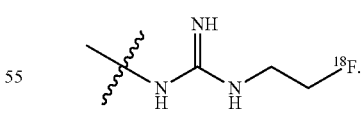

In some embodiments, R¹ is:

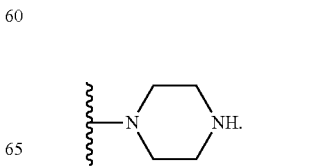

In some embodiments, $R^1$ is:

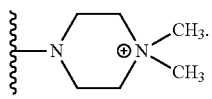

In some embodiments, $R^1$ is:

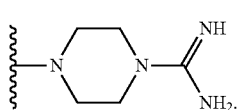

In some embodiments, $R^1$ is:

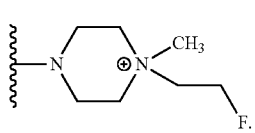

In some embodiments, $R^1$ is:

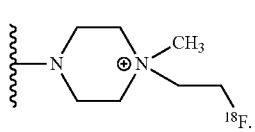

In some embodiments, $R^1$ is:

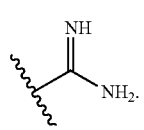

In some embodiments, $R^1$ is:

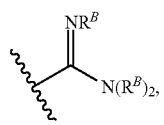

wherein each occurrence of $R^B$ is independently hydrogen, substituted or unsubstituted alkyl, or a nitrogen-protecting group, provided at least two $R^B$ are hydrogen. In some embodiments, $R^1$ is:

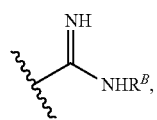

wherein $R^B$ is hydrogen, substituted or unsubstituted alkyl, or a nitrogen-protecting group.

In some embodiments, $R^1$ is:

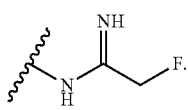

In some embodiments, $R^1$ is:

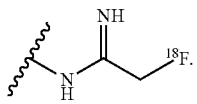

In some embodiments, $R^1$ is:

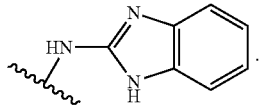 [SMILES: *Nc1nc2ccccc2[nH]1]

In some embodiments, $R^1$ is:

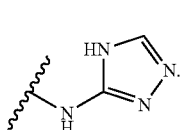

In some embodiments, $R^1$ is:

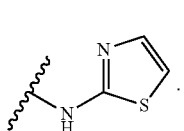

In some embodiments, $R^1$ is:

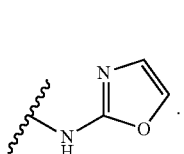

In some embodiments, $R^1$ is:

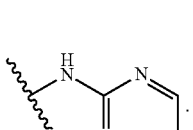

Each of the $R^1$ groups described herein may be combined with any suitable Ar, $R^O$, and/or L groups and combinations described herein, for example, as described in connection with a compound of Formula (Ia), (Ib), (Ic), or (Id). For example, in certain embodiments, when L is a bond; R¹ is:

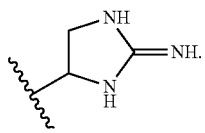 [SMILES: *C1CNC(=N)N1]

As another example, in certain embodiments, when L is a bond; Ar is phenyl; and R¹ is:

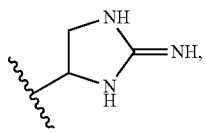 [SMILES: *C1CNC(=N)N1]

then Ar is substituted with at least one other group besides R⁰ and L-R¹. As another example, in certain embodiments, when L is a bond; Ar is not phenyl; and R¹ is:

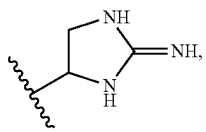 [SMILES: *C1CNC(=N)N1]

then Ar is substituted with at least one other group besides R⁰ and L-R¹.

As yet another example, in certain embodiments, when L is —CH₂—; then R¹ is —NHC(=NH)NH₂. In some embodiments, Ar is phenyl; L is —CH₂—; and R¹ is —NHC(=NH)NH₂. In some embodiments, Ar is not phenyl; L is —CH₂—; and R¹ is —NHC(=NH)NH₂.

In some embodiments, for a compound of Formula (Ia), (Ib), (Ic), or (Id), when Ar is phenyl, Ar is not substituted with a hydroxyl group. In some embodiments, when Ar is phenyl, Ar is not substituted with a hydroxyl group or a halogen. In some embodiments, when Ar is phenyl, and R⁰ is alkyl substituted with an imaging moiety, then Ar is not substituted with a hydroxyl group. In some embodiments, when Ar is phenyl, and R⁰ is alkoxy substituted with an imaging moiety, then Ar is not substituted with a hydroxyl group. In some embodiments, when Ar is phenyl, and the imaging moiety is attached directly to the phenyl ring, then the phenyl ring is not substituted with a hydroxyl group or unsubstituted except with R⁰ and -L-R¹.

In some embodiments, when Ar is phenyl, L is —CH₂—, R¹ is:

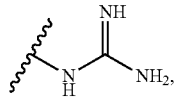

and R⁰ is alkoxy substituted with an imaging moiety, then Ar is not substituted with a halogen. In some embodiments, when Ar is phenyl, R⁰ is alkoxymethyl substituted with an imaging moiety, and R¹ is:

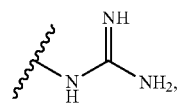

then L is —CH₂—. In some embodiments, when Ar is phenyl, L is —CH₂—, R¹ is:

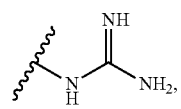

and R⁰ is alkoxy substituted with an imaging moiety or alkyl substituted with an imaging moiety, then Ar is not substituted with a halogen or unsubstituted except with R⁰ and -L-R¹. In some embodiments, when Ar is phenyl, R¹ is:

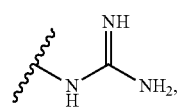

and R⁰ is alkoxy substituted with an imaging moiety, then L is not:

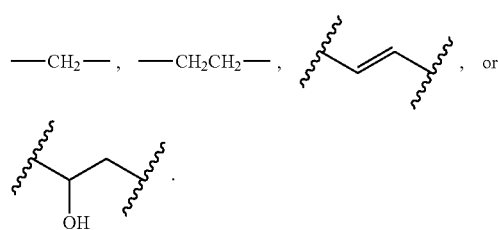

In some embodiments, when Ar is phenyl, and L is a bond, then R¹ is not:

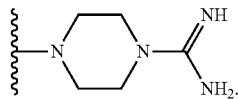

In some embodiments, when Ar is phenyl, L is a bond, and R¹ is:

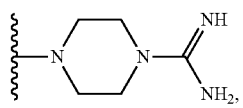 [SMILES: *N1CCN(C(=N)N)CC1]

then R⁰ is not an imaging moiety directly attached to the phenyl ring, alkyl substituted with an imaging moiety, alkoxyalkyl substituted with an imaging moiety, or alkoxy substituted with an imaging moiety.

In some embodiments, one, two, three, four, or five of the following a)-e) apply to a compound of Formula (Ia), (Ib), (Ic), or (Id), where suitable:
a) Ar is a substituted or unsubstituted group selected from the group consisting of phenyl, naphthyl, biphenyl, monocyclic heteroaryl, and bicyclic heteroaryl;
b) Ar is not phenyl;
c) L is selected from the group consisting of a bond; substituted or unsubstituted, cyclic or acyclic $C_{1-6}$alkylene; unsubstituted, acyclic $C_{1-6}$alkylene; acyclic $C_{1-6}$alkylene; substituted or unsubstituted, cyclic or acyclic $C_{1-6}$alkenylene; and substituted or unsubstituted, cyclic or acyclic heteroaliphatic;
d) $R^1$ is selected from the group consisting of —N($R^A$)$_2$, heteroaryl, heterocyclic, —C(=NH)NH$_2$, —NHC(=NH)NH$_2$, —NR$^A$C(=NR$^A$)N(R$^A$)$_2$; —NHC(=NH)NHR$^A$, and —NHC(=NH)N(R$^A$)$_2$, wherein $R^A$ is as described herein;
e) $R^O$ is substituted with an imaging moiety selected from the group consisting of $^{18}$F, $^{76}$Br, $^{124}$I, and $^{131}$I; or is associated with an imaging moiety selected from the group consisting of $^{64}$Cu, $^{89}$Zr, $^{99m}$Tc, and $^{111}$In through a chelator; or is an imaging moiety selected from the group consisting of $^{18}$F, $^{76}$Br, $^{124}$I and $^{131}$I.

In some embodiments, one, two, three, four, five, six, or seven of the following a)-g) apply to a compound of Formula (Ia), (Ib), (Ic), or (Id), where suitable:
a) Ar is a substituted or unsubstituted group selected from the group consisting of phenyl, naphthyl, biphenyl, benzothiazolyl, indolyl, quinolinyl, isoquinolinyl, chromanyl, chromenyl, benzofuranyl, and benzpyrazolyl;
b) Ar is not phenyl;
c) L is selected from the group consisting of a bond; —CH$_2$—, —CH$_2$CH$_2$—, —CH$_2$CH$_2$CH$_2$—, —CH=CH—, —OCH$_2$—, —CH$_2$O—, OCH$_2$CH$_2$—, —CH$_2$CH$_2$O—, —NHCH$_2$—, —CH$_2$NH—, —NHCH$_2$CH$_2$—, —CH$_2$CH$_2$NH—, —CH=N—, —N=CH—, —CH$_2$CH$_2$CH$_2$—,

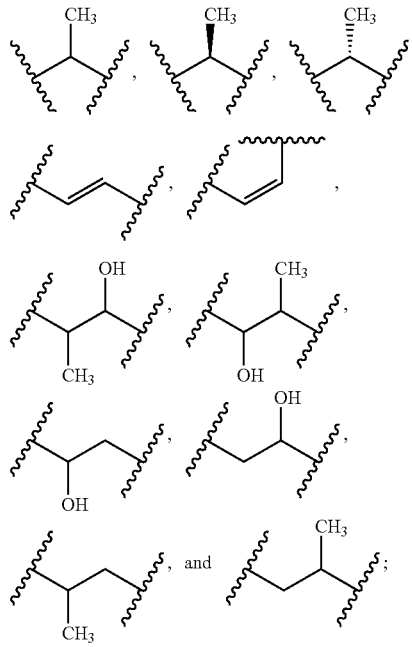

d) $R^1$ is selected from the group consisting of —NHC(=NH)NH$_2$, —NH$_2$, —NHR$^A$, —NHCH$_3$, —NHCH$_2$CH$_3$, —NHCH$_2$CH$_2$CH$_3$,

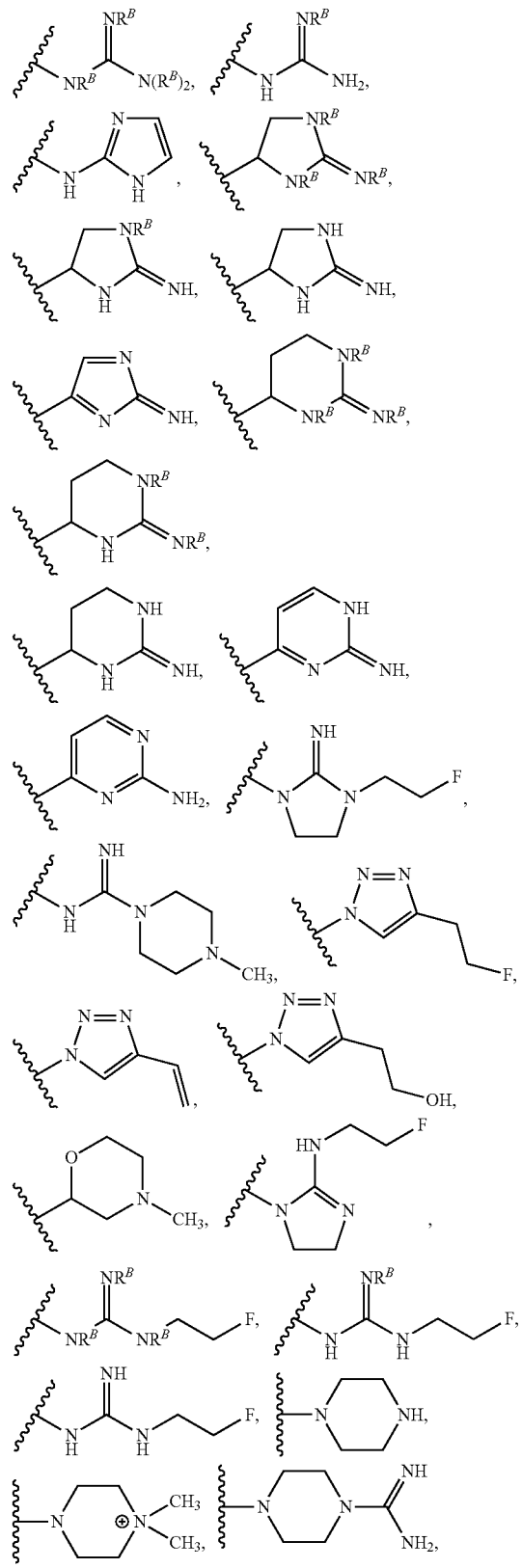

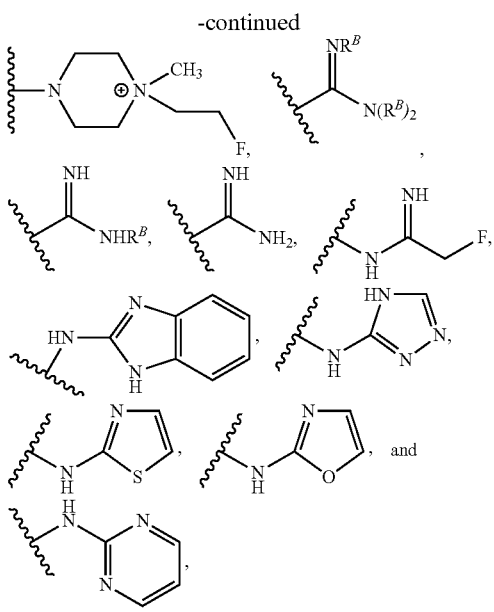

each optionally substituted, wherein each occurrence of $R^B$ is independently hydrogen, substituted or unsubstituted alkyl, or a nitrogen-protecting group, provided at least two $R^B$ are hydrogen;

e) $R^1$ is not —NHC(=NH)NH$_2$;

f) $R^1$ is substituted with an imaging moiety selected from the group consisting of $^{18}$F, $^{76}$Br, $^{124}$I, and $^{131}$I; or is an imaging moiety selected from the group consisting of $^{18}$F, $^{76}$Br, $^{124}$I, and $^{131}$I;

g) $R^0$ is substituted with an imaging moiety selected from the group consisting of $^{18}$F, $^{76}$Br, $^{124}$I, and $^{131}$I; or is an imaging moiety selected from the group consisting of $^{18}$F, $^{76}$Br, $^{124}$I, and $^{131}$I.

In certain embodiments, a compound of Formula (Ia) comprises Formula (IIa):

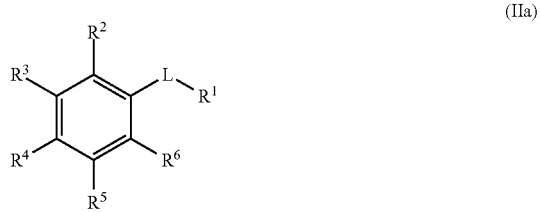

(IIa)

wherein

L is a bond; substituted or unsubstituted, cyclic or acyclic alkylene; substituted or unsubstituted, cyclic or acyclic alkenylene; substituted or unsubstituted, cyclic or acyclic alkynylene; or substituted or unsubstituted, cyclic or acyclic heteroaliphatic;

$R^1$ is a substituted or unsubstituted nitrogen-containing moiety;

each of $R^2$-$R^6$ is independently hydrogen, halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, —OR$^{41}$, —N(R$^{42}$)$_2$, —SR$^{41}$, —C(O)R$^{41}$, —C(=O)OR$^{41}$, —C(=O)SR$^{41}$, —C(=O)N(R$^{42}$)$_2$, —OC(=O)R$^{41}$, —OC(=O)OR$^{41}$, —OC(=O)SR$^{41}$, —OC(=O)N(R$^{42}$)$_2$, —NR$^{42}$C(=O)R$^{42}$, —NR$^{42}$C(=O)OR$^{41}$, —NR$^{42}$C(=O)SR$^{41}$, —NR$^{42}$C(=O)N(R$^{42}$)$_2$, —SC(=O)R$^{41}$, —SC(=O)OR$^{41}$, —SC(=O)SR$^{41}$, —SC(=O)N(R$^{42}$)$_2$, —C(=NR$^{42}$)R$^{41}$, C(=NR$^{42}$)OR$^{41}$, —C(=NR$^{42}$)SR$^{41}$, —C(=NR$^{42}$)N(R$^{42}$)$_2$, —OC(=NR$^{42}$)R$^{41}$, —OC(=NR$^{42}$)OR$^{41}$, —OC(=NR)SR$^{41}$, —OC(=NR$^{42}$)N(R$^{42}$)$_2$, —NR$^{42}$C(=NR$^{42}$)R$^{42}$, —NR$^{42}$C(=NR$^{42}$)OR$^{41}$, —NR$^{42}$C(=NR$^{42}$)SR$^{41}$, —NR$^{42}$C(=NR$^{42}$)N(R$^{42}$)$_2$, —SC(=NR$^{42}$)R$^{41}$, —SC(=NR$^{42}$)OR$^{41}$, —SC(=NR$^{42}$)SR$^{41}$, —SC(=NR$^{42}$)N(R$^{42}$)$_2$, —C(=S)R$^{41}$, —C(=S)OR$^{41}$, —C(=S)SR$^{41}$, —C(=S)N(R$^{42}$)$_2$, —OC(=S)R$^{41}$, —OC(=S)OR$^{41}$, —OC(=S)SR$^{41}$, —OC(=S)N(R$^{42}$)$_2$, —NR$^{42}$C(=S)R$^{42}$, —NR$^{42}$C(=S)OR$^{41}$, —NR$^{42}$C(=S)SR$^{41}$, —NR$^{42}$C(=S)N(R$^{42}$)$_2$, —SC(=S)R$^{41}$, —SC(=S)OR$^{41}$, —SC(=S)SR$^{41}$, —SC(=S)N(R$^{42}$)$_2$, —S(=O)R$^{41}$, —SO$_2$R$^{41}$, —NR$^{42}$SO$_2$R$^{41}$, —SO$_2$N(R$^{42}$)$_2$, —CN, —SCN, or —NO$_2$; or any two adjacent R$^2$-R$^6$ are joined to form an optionally substituted or unsubstituted carbocyclic, heterocyclic, aryl, or heteroaryl ring;

each occurrence of $R^{41}$ is independently hydrogen, optionally substituted alkyl, optionally substituted alkenyl, optionally substituted alkynyl, optionally substituted carbocyclyl, optionally substituted heterocyclyl, optionally substituted aryl, or optionally substituted heteroaryl; and each occurrence of $R^{42}$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, or an amino protecting group, or two $R^{42}$ groups are joined to form an optionally substituted heterocyclic ring; and one or more of $R^1$-$R^6$ is substituted with an imaging moiety selected from the group consisting of $^{18}$F, $^{76}$Br, $^{124}$I and $^{131}$I; or is associated with an imaging moiety selected from the group consisting of $^{64}$Cu, $^{89}$Zr, $^{99m}$Tc, and $^{111}$In through a chelator; or is an imaging moiety selected from the group consisting of $^{18}$F, $^{76}$Br, $^{124}$I, and $^{131}$I; or a salt thereof.

As described above for a compound of Formula (IIa), one or more of $R^1$-$R^6$ is substituted with an imaging moiety selected from the group consisting of $^{18}$F, $^{76}$Br, $^{124}$I, and $^{131}$I; or is associated with an imaging moiety selected from the group consisting of $^{64}$Cu, $^{89}$Zr, $^{99m}$Tc, and $^{111}$In through a chelator; or is an imaging moiety selected from the group consisting of $^{18}$F, $^{76}$Br, $^{124}$I, and $^{131}$I. In some embodiments, one of $R^1$-$R^6$ is substituted with an imaging moiety selected from the group consisting of $^{18}$F, $^{76}$Br, $^{124}$I, and $^{131}$I; or is associated with an imaging moiety selected from the group consisting of $^{64}$Cu, $^{89}$Zr, $^{99m}$Tc, and $^{111}$In through a chelator; or is an imaging moiety selected from the group consisting of $^{18}$F, $^{76}$Br, $^{124}$I, and $^{131}$I. In certain embodiments, the imaging moiety is $^{18}$F. In certain embodiments, the imaging moiety is $^{76}$Br. In certain embodiments, the imaging moiety is $^{124}$I. In certain embodiments, the imaging moiety is $^{131}$I. In some cases, the imaging moiety is not $^{131}$I. In some cases, the imaging moiety is $^{18}$F, $^{76}$Br, or $^{124}$I. In some cases, the imaging moiety is $^{18}$F or $^{76}$Br.

In some cases, $R^4$ is substituted with an imaging moiety selected from the group consisting of $^{18}$F, $^{76}$Br, $^{124}$I, and $^{131}$I; or is associated with an imaging moiety selected from the group consisting of $^{64}$Cu, $^{89}$Zr, $^{99m}$Tc, and $^{111}$In through a chelator; or is an imaging moiety selected from the group consisting of $^{18}$F, $^{76}$Br, $^{124}$I, and $^{131}$I. In some embodiments, $R^4$ is substituted with an imaging moiety selected from the group consisting of $^{18}$F, $^{76}$Br, $^{124}$I, and $^{131}$I. In some embodiments, $R^4$ is substituted with an imaging moiety selected from the group consisting of $^{18}$F.

In some embodiments, $R^4$ is selected from the group consisting of hydrogen, halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, —$OR^{41}$, —$N(R^{42})_2$, —$SR^{41}$, —$C(=O)R^{41}$, —$C(=O)OR^{41}$, —$C(=O)SR^{41}$, —$C(=O)N(R^{42})_2$, —$OC(=O)R^{41}$, —$OC(=O)OR^{41}$, —$OC(=O)SR^{41}$, —$OC(=O)N(R^{42})_2$, —$NR^{42}C(=O)R^{42}$, —$NR^{42}C(=O)OR^{41}$, —$NR^{42}C(=O)SR^{41}$, —$NR^{42}C(=O)N(R^{42})_2$, —$SC(=O)R^{41}$, —$SC(=O)OR^{41}$, —$SC(=O)SR^{41}$, —$SC(=O)N(R^{42})_2$, —$C(=NR^{42})R^{41}$, —$C(=NR^{42})OR^{41}$, —$C(=NR^{42})SR^{41}$—, —$C(=NR^{42})N(R^{42})_2$, —$OC(=NR^{42})R^{41}$, $OC(=NR^{42})OR^{41}$, —$OC(=NR^{42})SR^{41}$, —$OC(=NR^{42})N(R^{42})_2$, —$NR^{42}C(=NR^{42})R^{42}$, —$NR^{42}C(=NR^{42})OR^{41}$, —$NR^{42}C(=NR^{42})SR^{41}$, —$NR^{42}C(=NR^{42})N(R^{42})_2$, —$SC(=NR^{42})R^{41}$, —$SC(=NR^{42})OR^{41}$, —$SC(=NR^{42})SR^{41}$, —$SC(=NR^{42})N(R^{42})_2$, —$C(=S)R^{41}$, —$C(=S)OR^{41}$, —$C(=S)SR^{41}$, —$C(=S)N(R^{42})_2$, —$OC(=S)R^{41}$, —$OC(=S)OR^{41}$, —$OC(=S)SR^{41}$, —$OC(=S)N(R^{42})_2$, —$NR^{42}C(=S)R^{42}$, —$NR^{42}C(=S)OR^{41}$, —$NR^{42}C(=S)SR^{41}$, —$NR^{42}C(=S)N(R^{42})_2$, —$SC(=S)R^{41}$, —$SC(=S)OR^{41}$, —$SC(=S)SR^{41}$, —$SC(=S)N(R^{42})_2$, —$S(=O)R^{41}$, —$SO_2R^{41}$, —$NR^{42}SO_2R^{41}$, —$SO_2N(R^{42})_2$, —CN, —SCN, or —$NO_2$.

In some embodiments, for a compound of Formula (IIa), $R^4$ is selected from the group consisting of $C_{1-6}$alkyl, alkoxy, and alkoxyalkyl, each optionally substituted with an imaging moiety, or any combination of $R^4$ groups in this list. In some cases, $R^4$ is alkoxymethyl, optionally substituted with the imaging moiety. In some cases, $R^4$ is selected from the group consisting of —$CH_2F$, —$CH_2CH_2F$, —$CH_2CH_2CH_2F$, —$CH_2CH_2CH_2CH_2F$, —$OCH_2F$, —$OCH_2CH_2F$, —$OCH_2CH_2CH_2F$, —$OCH_2CH_2CH_2CH_2F$, —$CH_2OCH_2F$, —$CH_2OCH_2CH_2F$, —$CH_2OCH_2CH_2CH_2F$, and —$CH_2OCH_2CH_2CH_2CH_2F$. In some cases, the F is isotopically enriched with $^{18}F$.

In some embodiments, $R^4$ is $C_{1-6}$alkyl. In some embodiments, $R^4$ is alkyl substituted with an imaging moiety. In some embodiments, $R^4$ is —$CH_2F$, —$CH_2CH_2F$, —$CH_2CH_2CH_2F$, or —$CH_2CH_2CH_2CH_2F$. In some cases, the F is isotopically enriched with $^{18}F$. In some embodiments, $R^4$ is alkoxy substituted with an imaging moiety. In some embodiments, $R^4$ is —$OCH_2F$, —$OCH_2CH_2F$, —$OCH_2CH_2CH_2F$, or —$OCH_2CH_2CH_2CH_2F$. In some cases, the F is isotopically enriched with $^{18}F$. In some embodiments, $R^4$ is alkoxyalkyl substituted with an imaging moiety. In some embodiments, $R^4$ is of the formula:

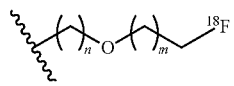

wherein n is an integer between 0 and 6, inclusive; and m is an integer between 0 and 6, inclusive. In some embodiments, $R^4$ is alkoxymethyl substituted with an imaging moiety. In some embodiments, $R^4$ is —$CH_2OCH_2F$, —$CH_2OCH_2CH_2F$, —$CH_2OCH_2CH_2CH_2F$, or —$CH_2OCH_2CH_2CH_2CH_2F$. In some cases, the F is isotopically enriched with $^{18}F$.

Additional examples of $R^4$ groups which may be used in connection with a compound of Formula (IIa) are described herein, for example, in connection with a compound of Formula (IV).

In some embodiments, $R^4$ is selected from the group consisting of halogen; alkoxy, optionally substituted; $C_{1-6}$alkyl, optionally substituted; —CN; and —OH. In some embodiments, $R^3$ is selected from the group consisting of fluorine, chlorine, bromine, iodine, —$CF_3$, $OCH_3$, —OH, —$CH_3$, and CN.

In some embodiments, $R^4$ is halogen. In some embodiments, $R^4$ is fluorine. In some embodiments, $R^4$ is isotopically enriched with $^{18}F$. In some embodiments, $R^4$ is chlorine. In some embodiments, $R^4$ is bromine. In some embodiments, $R^4$ is iodine. In some embodiments, $R^4$ is —$CF_3$. In some embodiments, $R^4$ is alkoxy. In some embodiments, $R^4$ is substituted alkoxy. In some embodiments, $R^3$ is —$OCH_3$. In some embodiments, $R^4$ is —OH. In some embodiments, $R^4$ is $C_{1-6}$alkyl. In some embodiments, $R^4$ is —$CH_3$. In some embodiments, $R^4$ is —CN. Additional examples of $R^4$ groups which may be used in connection with a compound of Formula (IIa) are described below in connection with a compound of Formula (IV).

Furthermore, each of the $R^4$ groups described herein in connection with a compound of Formula (IIa) may be combined with any suitable $R^1$ and/or L group as described herein, for example, in connection with a compound of Formula (Ia)-(Id).

In some cases, for a compound of Formula (IIa), $R^3$ is substituted with an imaging moiety selected from the group consisting of $^{18}F$, $^{76}Br$, $^{124}I$, and $^{131}I$; or is associated with an imaging moiety selected from the group consisting of $^{64}Cu$, $^{89}Zr$, $^{99m}Tc$, and $^{111}In$ through a chelator; or is an imaging moiety selected from the group consisting of $^{18}F$, $^{76}Br$, $^{124}I$, and $^{131}I$. In some embodiments, $R^3$ is substituted with an imaging moiety selected from the group consisting of $^{18}F$, $^{76}Br$, $^{124}I$, and $^{131}I$. In some embodiments, $R^3$ is substituted with an imaging moiety selected from the group consisting of $^{18}F$. In some embodiments, $R^3$ is halogen. In some embodiments, $R^3$ is fluorine. In some embodiments, $R^3$ is isotopically enriched with $^{18}F$.

In some embodiments, for a compound of Formula (IIa), $R^3$ is selected from the group consisting of hydrogen, halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, —$OR^{41}$, —$N(R^{42})_2$, —$SR^{41}$, —$C(=O)R^{41}$, —$C(=O)OR^{41}$, —$C(=O)SR^{41}$, —$C(=O)N(R^{42})_2$, —$OC(=O)R^{41}$, —$OC(=O)OR^{41}$, —$OC(=O)SR^{41}$, —$OC(=O)N(R^{42})_2$, —$NR^{42}C(=O)R^{42}$, —$NR^{42}C(=O)OR^{41}$, —$NR^{42}C(=O)SR^{41}$, —$NR^{42}C(=O)N(R^{42})_2$, —$SC(=O)R^{41}$, —$SC(=O)OR^{41}$, —$SC(=O)SR^{41}$, —$SC(=O)N(R^{42})_2$, —$C(=NR^{42})R^{41}$, —$C(=NR^{42})OR^{41}$, —$C(=NR^{42})SR^{41}$, —$C(=NR^{42})N(R^{42})_2$, —$OC(=NR^{42})R^{41}$, —$OC(=NR^{42})OR^{41}$, —$OC(=NR^{42})SR^{41}$, —$OC(=NR^{42})N(R^{42})_2$, —$NR^{42}C(=NR^{42})R^{42}$, —$NR^{42}C(=NR^{42})OR^{41}$, —$NR^{42}C(=NR^{42})SR^{41}$, —$NR^{42}C(=NR^{42})N(R^{42})_2$, —$SC(=NR^{42})R^{41}$, —$SC(=NR^{42})OR^{41}$, —$SC(=NR^{42})SR^{41}$, —$SC(=NR^{42})N(R^{42})_2$, —$C(=S)R^{41}$, —$C(=S)OR^{41}$, —$C(=S)SR^{41}$, —$C(=S)N(R^{42})_2$, —$OC(=S)R^{41}$, —$OC(=S)OR^{41}$, —$OC(=S)SR^{41}$, —$OC(=S)N(R^{42})_2$, —$NR^{42}C(=S)R^{42}$, —$NR^{42}C(=S)OR^{41}$, —$NR^{42}C(=S)SR^{41}$, —$NR^{42}C(=S)N(R^{42})_2$, —$SC(=S)R^{41}$, —$SC(=S)OR^{41}$, —$SC(=S)SR^{41}$, —$SC(=S)N(R^{42})_2$, —$S(=O)R^{41}$, —$SO_2R^{41}$, —$NR^{42}SO_2R^{41}$, —$SO_2N(R^{42})_2$, —CN, —SCN, or —$NO_2$.

In some embodiments, $R^3$ is selected from the group consisting of $C_{1-6}$alkyl, alkoxy, and alkoxyalkyl, each optionally substituted with an imaging moiety, or any combination of $R^3$ groups in this list. In some cases, $R^3$ is alkoxymethyl, optionally substituted with the imaging moiety. In some cases, $R^3$ is selected from the group consisting of —$CH_2F$, —$CH_2CH_2F$, —$CH_2CH_2CH_2F$, —$CH_2CH_2CH_2CH_2F$, —$OCH_2F$, —$OCH_2CH_2F$, —$OCH_2CH_2CH_2F$, —$OCH_2CH_2CH_2CH_2F$, —$CH_2OCH_2F$, —$CH_2OCH_2CH_2F$, —$CH_2OCH_2CH_2CH_2F$, and —$CH_2OCH_2CH_2CH_2CH_2F$. In some cases, the F is isotopically enriched in $^{18}F$.

In some embodiments, $R^3$ is $C_{1-6}$alkyl. In some embodiments, $R^3$ is alkyl substituted with an imaging moiety. In some embodiments, $R^3$ is —$CH_2F$, —$CH_2CH_2F$, —$CH_2CH_2CH_2F$, or —$CH_2CH_2CH_2CH_2F$. In some embodiments, $R^3$ is alkoxy substituted with an imaging moiety. In some embodiments, $R^3$ is —$OCH_2F$, —$OCH_2CH_2F$, —$OCH_2CH_2CH_2F$, or —$OCH_2CH_2CH_2CH_2F$. In some embodiments, $R^3$ is alkoxyalkyl substituted with an imaging moiety. In some embodiments, $R^3$ is of the formula:

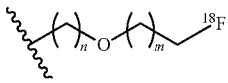

wherein n is an integer between 0 and 6, inclusive; and m is an integer between 0 and 6, inclusive. In some embodiments, $R^3$ is alkoxymethyl substituted with an imaging moiety. In some embodiments, $R^3$ is —$CH_2OCH_2F$, —$CH_2OCH_2CH_2F$, —$CH_2OCH_2CH_2CH_2F$, or —$CH_2OCH_2CH_2CH_2CH_2F$.

In some embodiments, $R^3$ is selected from the group consisting of halogen; alkoxy, optionally substituted; $C_{1-6}$alkyl, optionally substituted; —CN; and —OH. In some embodiments, $R^3$ is selected from the group consisting of fluorine, chlorine, bromine, iodine, —$CF_3$, $OCH_3$, —OH, —$CH_3$, and —CN.

In some embodiments, $R^3$ is halogen. In some embodiments, $R^3$ is fluorine. In some embodiments, $R^3$ is chlorine. In some embodiments, $R^3$ is bromine. In some embodiments, $R^3$ is iodine. In some embodiments, $R^3$ is —$CF_3$. In some embodiments, $R^3$ is alkoxy. In some embodiments, $R^3$ is substituted alkoxy. In some embodiments, $R^3$ is —$OCH_3$. In some embodiments, $R^3$ is —OH. In some embodiments, $R^3$ is $C_{1-6}$alkyl. In some embodiments, $R^3$ is —$CH_3$. In some embodiments, $R^3$ is —CN. Additional examples of $R^3$ groups which may be used in connection with a compound of Formula (IIa) are described below in connection with a compound of Formula (IV).

Each of the $R^3$ groups described herein in connection with a compound of Formula (IIa) may be combined with any $R^4$ group described herein, for example, in connection with a compound of Formula (IIa) or (IV), and/or any suitable $R^1$ and/or L group as described herein, for example, in connection with a compound of Formula (Ia)-(Id).

As described above, for a compound of Formula (IIa), each of $R^2$-$R^6$ is independently hydrogen, halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, —$OR^{41}$, —$N(R^{42})_2$, —$SR^{41}$, —$C(=O)R^{41}$, —$C(=O)OR^{41}$, —$C(=O)SR^{41}$, —$C(=O)N(R^{42})_2$, —$OC(=O)R^{41}$, —$OC(=O)OR^{41}$, —$OC(=O)SR^{41}$, —$OC(=O)N(R^{42})_2$, —$NR^{42}C(=O)R^{42}$, —$NR^{42}C(=O)OR^{41}$, —$NR^{42}C(=O)SR^{41}$, —$NR^{42}C(=O)N(R^{42})_2$, —$SC(=O)R^{41}$, —$SC(=O)OR^{41}$, —$SC(=O)SR^{41}$, —$SC(=O)N(R^{42})_2$, —$C(=NR^{42})R^{41}$, —$C(=NR^{42})OR^{41}$, —$C(=NR^{42})SR^{41}$, —$C(=NR^{42})N(R^{42})_2$, —$OC(=NR^{42})R^{41}$, —$OC(=NR^{42})OR^{41}$, —$OC(=NR^{42})SR^{41}$, —$OC(=NR^{42})N(R^{42})_2$, —$NR^{42}C(=NR^{42})R^{42}$, —$NR^{42}C(=NR^{42})OR^{41}$, —$NR^{42}C(=NR^{42})SR^{41}$, —$NR^{42}C(=NR^{42})N(R^{42})_2$, —$SC(=NR^{42})R^{41}$, —$SC(=NR^{42})OR^{41}$, —$SC(=NR^{42})SR^{41}$, —$SC(=NR^{42})N(R^{42})_2$, —$C(=S)R^{41}$, —$C(=S)OR^{41}$, —$C(=S)SR^{41}$, —$C(=S)N(R^{42})_2$, —$OC(=S)R^{41}$, —$OC(=S)OR^{41}$, —$OC(=S)SR^{41}$, —$OC(=S)N(R^{42})_2$, —$NR^{42}C(=S)R^{42}$, —$NR^{42}C(=S)OR^{41}$, —$NR^{42}C(=S)SR^{41}$, —$NR^{42}C(=S)N(R^{42})_2$, —$SC(=S)R^{41}$, —$SC(=S)OR^{41}$, —$SC(=S)SR^{41}$, —$SC(=S)N(R^{42})_2$, —$S(=O)R^{41}$, —$SO_2R^{41}$, —$NR^{42}SO_2R^{41}$, —$SO_2N(R^{42})_2$, —CN, —SCN, or —$NO_2$; or any two adjacent $R^2$-$R^6$ are joined to form an optionally substituted or unsubstituted carbocyclic, heterocyclic, aryl, or heteroaryl ring.

In some embodiments, each of $R^2$, $R^3$, $R^5$, and $R^6$ are hydrogen. In some embodiments, $R^2$, $R^5$, and $R^6$ are all hydrogen. In some embodiments, $R^2$ and $R^6$ are both hydrogen. In some embodiments, $R^3$ is hydrogen. In some embodiments, at least one, two, three, or four of $R^2$, $R^3$, $R^5$, and $R^6$ is not hydrogen. In some embodiments, at least one of $R^2$, $R^3$, $R^5$, and $R^6$ is not hydrogen. In some embodiments, at least two of $R^2$, $R^3$, $R^5$, and $R^6$ are not hydrogen. In some embodiments, $R^2$ and $R^6$ are hydrogen, and at least one of $R^3$, $R^4$, and $R^5$ is not hydrogen. In some embodiments, $R^2$, $R^5$ and $R^6$ are hydrogen, and $R^3$ and $R^4$ are not hydrogen. In some embodiments, $R^2$, $R^5$ and $R^6$ are hydrogen, $R^3$ and $R^4$ are not hydrogen, and at least one of $R^3$ and $R^4$ is substituted with an imaging moiety. In some embodiments, $R^2$, $R^5$ and $R^6$ are hydrogen, $R^3$ and $R^4$ are not hydrogen, and at least one of $R^3$ and $R^4$ is an imaging moiety.

In some embodiments, one, two, three, four, five, six, seven, or eight of the following a)-h) apply for a provided compound of Formula (IIa), where suitable:

a) $R^1$ is substituted with an imaging moiety selected from the group consisting of $^{18}F$, $^{76}Br$, $^{124}I$, and $^{131}I$; or is an imaging moiety selected from the group consisting of $^{18}F$, $^{76}Br$, $^{124}I$, and $^{131}I$;

b) $R^4$ is substituted with an imaging moiety selected from the group consisting of $^{18}F$, $^{76}Br$, $^{124}I$, and $^{131}I$; or is an imaging moiety selected from the group consisting of $^{18}F$, $^{76}Br$, $^{124}I$, and $^{131}I$;

c) L is selected from the group consisting of a bond; substituted or unsubstituted, cyclic or acyclic $C_{1-6}$alkylene; unsubstituted, acyclic $C_{1-6}$alkylene; acyclic $C_{1-6}$alkylene; substituted or unsubstituted, cyclic or acyclic $C_{1-6}$alkenylene; and substituted or unsubstituted, cyclic or acyclic heteroaliphatic;

d) $R^1$ is selected from the group consisting of —$N(R^4)_2$, heteroaryl, heterocyclic, —$C(=NH)NH_2$, —NHC(=NH)$NH_2$, —$NR^4C(=NR^4)N(R^4)_2$; —NHC(=NH)$NHR^4$, and —NHC(=NH)N($R^4$)$_2$, wherein $R^4$ is as described herein;

e) $R^4$ is selected from the group consisting of $C_{1-6}$alkyl, alkoxy, and alkoxyalkyl, each optionally substituted with an imaging moiety;

f) $R^3$ is selected from the group consisting of halogen; optionally substituted alkoxy; optionally substituted $C_{1-6}$alkyl; —CN; and —OH;

g) $R^2$ is hydrogen;

h) $R^6$ is hydrogen or halogen.

In some embodiments, a compound is provided comprising Formula (IIb):

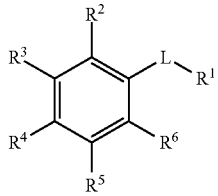

wherein

L is a bond; substituted or unsubstituted, cyclic or acyclic alkylene; substituted or unsubstituted, cyclic or acyclic alkenylene; substituted or unsubstituted, cyclic or acyclic alkynylene; or substituted or unsubstituted, cyclic or acyclic heteroaliphatic;

$R^1$ is selected from the group consisting of:

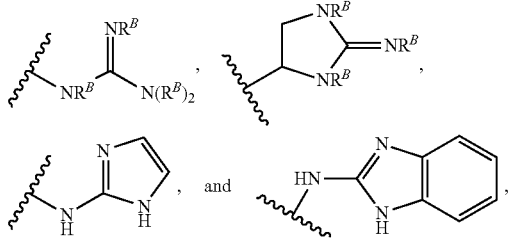

wherein each occurrence of $R^B$ is independently hydrogen, substituted or unsubstituted alkyl, or a nitrogen-protecting group, provided at least two $R^B$ are hydrogen;

$R^2$ and $R^6$ are hydrogen;

each of $R^3$, $R^4$ and $R^5$ is independently hydrogen, halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, $-OR^{41}$, $-N(R^{42})_2$, $-SR^{41}$, $-C(=O)R^{41}$, $-C(=O)OR^{41}$, $-C(=O)SR^{41}$, $-C(=O)N(R^{42})_2$, $-OC(=O)R^{41}$, $-OC(=O)OR^{41}$, $-OC(=O)SR^{41}$, $-OC(=O)N(R^{42})_2$, $-NR^{42}C(=O)R^{42}$, $-NR^{42}C(=O)OR^{41}$, $-NR^{42}C(=O)SR^{41}$, $-NR^{42}C(=O)N(R^{42})_2$, $-SC(=O)R^{41}$, $-SC(=O)OR^{41}$, $-SC(=O)SR^{41}$, $-SC(=O)N(R^{42})_2$, $-C(=NR^{42})R^{41}$, $-C(=NR^{42})OR^{41}$, $-C(=NR)SR^{41}$, $-C(=NR^{42})N(R^{42})_2$, $-OC(=NR^{42})R^{41}$, $-OC(=NR^{42})OR^{41}$, $-OC(=NR^{42})R^{41}$, $-OC(=NR^{42})N(R^{42})_2$, $-NR^{42}C(=NR^{42})R^{42}$, $-NR^{42}C(=NR^{42})OR^{41}$, $-NR^{42}C(=NR^{42})SR^{41}$, $-NR^{42}C(=NR^{42})N(R^{42})_2$, $-SC(=NR^{42})R^{41}$, $-SC(=NR^{42})OR^{41}$, $-SC(=NR^{42})SR^{41}$, $-SC(=NR^{42})N(R^{42})_2$, $-C(=S)R^{41}$, $-C(=S)OR^{41}$, $-C(=S)SR^{41}$, $-C(=S)N(R^{42})_2$, $-OC(=S)R^{41}$, $-OC(=S)OR^{41}$, $-OC(=S)SR^{41}$, $-OC(=S)N(R^{42})_2$, $-NR^{42}C(=S)R^{42}$, $-NR^{42}C(=S)OR^{41}$, $-NR^{42}C(=S)SR^{41}$, $-NR^{42}C(=S)N(R^{42})_2$, $-SC(=S)R^{41}$, $-SC(=S)OR^{41}$, $-SC(=S)SR^{41}$, $-SC(=S)N(R^{42})_2$, $-S(=O)R^{41}$, $-SO_2R^{41}$, $-NR^{42}SO_2R^{41}$, $-SO_2N(R^{42})_2$, $-CN$, $-SCN$, or $-NO_2$; or any two adjacent $R^3$, $R^4$ and $R^5$ are joined to form an optionally substituted or unsubstituted carbocyclic, heterocyclic, aryl, or heteroaryl ring;

each occurrence of $R^{41}$ is independently hydrogen, optionally substituted alkyl, optionally substituted alkenyl, optionally substituted alkynyl, optionally substituted carbocyclyl, optionally substituted heterocyclyl, optionally substituted aryl, or optionally substituted heteroaryl; and each occurrence of $R^{42}$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, or an amino protecting group, or two $R^{42}$ groups are joined to form an optionally substituted heterocyclic ring; and wherein $R^4$ is substituted with an imaging moiety selected from the group consisting of $^{18}F$, $^{76}Br$, and $^{124}I$; or is associated with an imaging moiety selected from the group consisting of $^{64}Cu$, $^{89}Zr$, $^{99m}Tc$, and $^{111}In$ through a chelator; or is $^{124}I$; or a salt thereof;

provided that if one of $R^3$ or $R^5$ is Cl, Br, or $CF_3$, then the other of $R^3$ or $R^5$ is not H. In some embodiments, the compound is not of the formula:

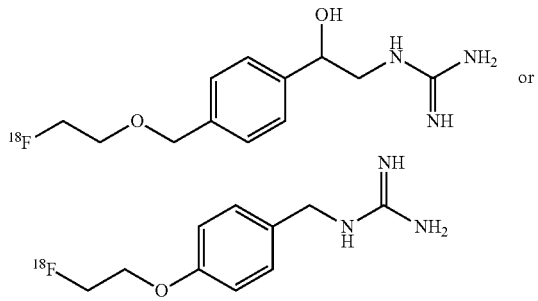

For a compound of Formula (IIb), any suitable $R^1$, $R^2$, $R^3$, $R^4$, $R^5$, $R^6$, and/or L groups as described herein, for example, in connection with a compound of Formula (IIa) may be employed. In some embodiments, for a compound of Formula (IIb), $R^1$ is:

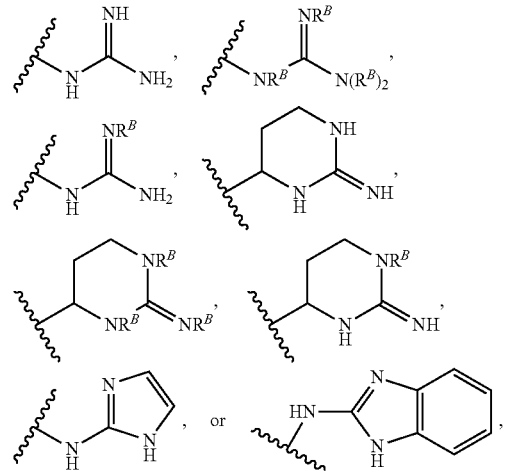

wherein each occurrence of $R^B$ is independently hydrogen, substituted or unsubstituted alkyl, or a nitrogen-protecting group, provided at least two $R^B$ are hydrogen. In some embodiments, for a compound of Formula (IIb), $R^4$ is:

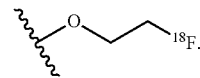

In some embodiments, a compound of Formula (IIa) comprises Formula (III):

(III)

wherein

L is a bond; substituted or unsubstituted alkylene; substituted or unsubstituted alkenylene; or substituted or unsubstituted heteroalkylene;

$R^1$ is a substituted or unsubstituted nitrogen-containing moiety;

$R^3$ is hydrogen, halogen, optionally substituted alkyl, —$OR^{41}$, —$N(R^{42})_2$, —$C(=O)R^{41}$, —$C(=O)N(R^{42})_2$, —$NR^{42}C(=O)R^{42}$, or —CN;

$R^4$ is hydrogen, halogen, optionally substituted alkyl, —$OR^{41}$, —$N(R^{42})_2$, —$C(=O)R^{41}$, —$C(=O)N(R^{42})_2$, —$NR^{42}C(=O)R^{42}$, or —CN;

each occurrence of $R^{41}$ is independently hydrogen, or optionally substituted alkyl; and each occurrence of $R^{42}$ is independently hydrogen or optionally substituted alkyl, or two $R^{42}$ groups are joined to form an optionally substituted heterocyclic ring; and one or more of $R^3$ and $R^4$ and is substituted with an imaging moiety selected from the group consisting of $^{18}F$, $^{76}Br$, $^{124}I$, and $^{131}I$; or is associated with an imaging moiety selected from the group consisting of $^{64}Cu$, $^{89}Zr$, $^{99m}Tc$, and $^{111}In$ through a chelator; or is $^{18}F$, $^{76}Br$, $^{124}I$ and $^{131}I$; or a salt thereof.

In some cases, $R^4$ is substituted with an imaging moiety selected from the group consisting of $^{18}F$, $^{76}Br$, $^{124}I$, and $^{131}I$; or is associated with an imaging moiety selected from the group consisting of $^{64}Cu$, $^{99m}Tc$, and $^{111}In$ through a chelator; or is $^{18}F$, $^{76}Br$, and $^{131}I$. In some cases, $R^3$ is substituted with an imaging moiety selected from the group consisting of $^{18}F$, $^{76}Br$, $^{124}I$, and $^{131}I$; or is associated with an imaging moiety selected from the group consisting of $^{64}Cu$, $^{89}Zr$, $^{99m}Tc$, and $^{111}In$ through a chelator; or is $^{18}F$, $^{76}Br$, $^{124}I$, and $^{131}I$.

The compound of Formula (III) may comprise any suitable $R^3$ and/or $R^4$ group(s) as described herein, for example, in connection with a compound of Formula (IIa) or (IV), and/or any L and/or $R^1$ group as described herein, for example, in connection with a compound of Formula (Ia)-(Id).

In some embodiments, a compound of Formula (III) comprises the structure:

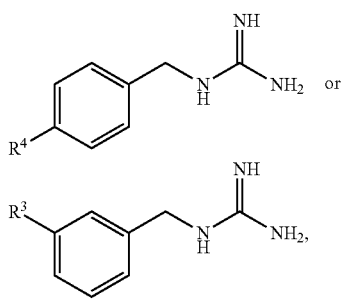

or salt thereof, wherein $R^4$ and $R^3$ may be any suitable $R^4$ and $R^3$ group as described herein, for example, in connection with a compound of Formula (IIa) or Formula (IV). In some embodiments, a compound of Formula (III) comprises the structure:

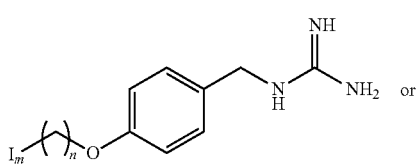

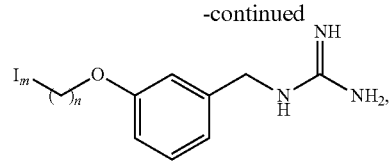

wherein n is an integer between 1 and 6, inclusive; and $I_m$ is an imaging moiety selected from the group consisting of $^{18}F$, $^{76}Br$, $^{124}I$, and $^{131}I$. In some embodiments, a compound of Formula (III) comprises the structure:

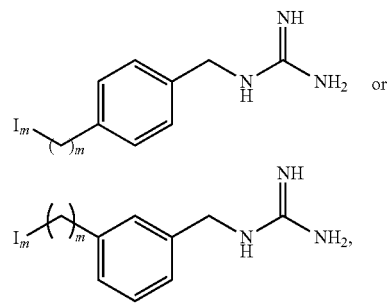

wherein m is an integer between 1 and 6, inclusive; and $I_m$ is an imaging moiety selected from the group consisting of $^{18}F$, $^{76}Br$, $^{124}I$, and $^{131}I$. In some embodiments, a compound of Formula (III) comprises the structure:

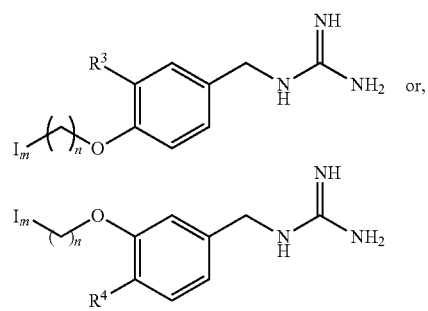

wherein n is an integer between 1 and 6, inclusive; and $I_m$ is an imaging moiety selected from the group consisting of $^{18}F$, $^{76}Br$, $^{124}I$, and $^{131}I$. $R^3$ and $R^4$ may be any suitable $R^3$ and $R^4$ as described herein, for example, in connection with a compound of Formula (IIa) or Formula (IV). In some embodiments, a compound of Formula (III) comprises the structure:

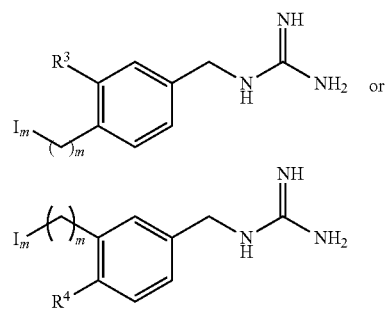

wherein m is an integer between 1 and 6, inclusive; and $I_m$ is an imaging moiety selected from the group consisting of $^{18}$F, $^{76}$Br, $^{124}$I, and $^{131}$I. $R^3$ and $R^4$ may be any suitable $R^3$ and $R^4$ as described herein, for example, in connection with a compound of Formula (IIa) or Formula (IV). In some embodiments, a compound of Formula (III) comprises the structure:

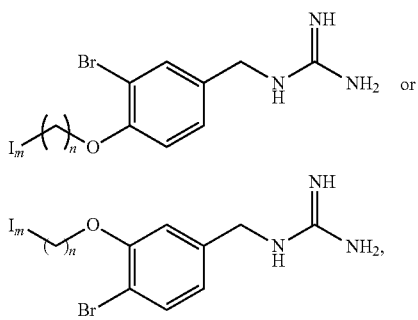

wherein n is an integer between 1 and 6, inclusive; and $I_m$ is an imaging moiety selected from the group consisting of $^{18}$F, $^{76}$Br, $^{124}$I, and $^{131}$I. In some embodiments, a compound of Formula (III) comprises the structure:

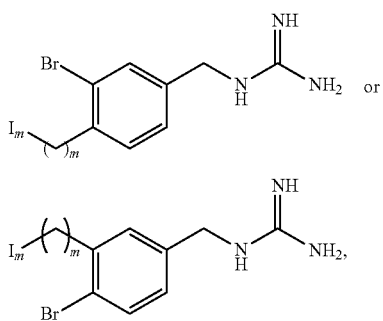

wherein m is an integer between 1 and 6, inclusive; and $I_m$ is an imaging moiety selected from the group consisting of $^{18}$F, $^{76}$Br, $^{124}$I, and $^{131}$I. In some embodiments, a compound of Formula (III) comprises the structure:

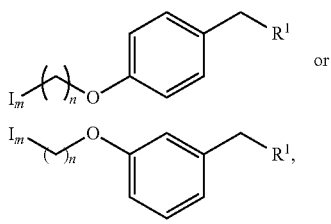

wherein n is an integer between 1 and 6, inclusive; and $I_m$ is an imaging moiety selected from the group consisting of $^{18}$F, $^{76}$Br, $^{124}$I, and $^{131}$I. $R^1$ may be any suitable $R^1$ as described herein, for example, in connection with a compound of Formula (Ia)-(Id). In some embodiments, a compound of Formula (III) comprises the structure:

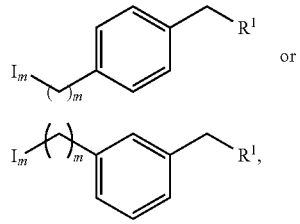

wherein m is an integer between 1 and 6, inclusive; and $I_m$ is an imaging moiety selected from the group consisting of $^{18}$F, $^{76}$Br, $^{124}$I, and $^{131}$I. $R^1$ may be any suitable $R^1$ as described herein, for example, in connection with a compound of Formula (Ia)-(Id). In some embodiments, a compound of Formula (III) comprises the structure:

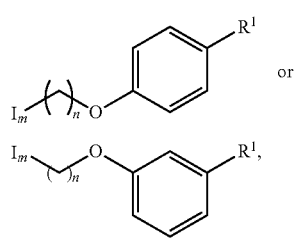

wherein n is an integer between 1 and 6, inclusive; and $I_m$ is an imaging moiety selected from the group consisting of $^{18}$F, $^{76}$Br, $^{124}$I, and $^{131}$I. $R^1$ may be any suitable $R^1$ as described herein, for example, in connection with a compound of Formula (Ia)-(Id). In some embodiments, a compound of Formula (III) comprises the structure:

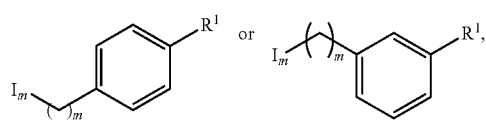

wherein m is an integer between 1 and 6, inclusive; and $I_m$ is an imaging moiety selected from the group consisting of $^{18}$F, $^{76}$Br, $^{124}$I, and $^{131}$I. $R^1$ may be any suitable $R^1$ as described herein, for example, in connection with a compound of Formula (Ia)-(Id). In some embodiments, a compound of Formula (III) comprises the structure:

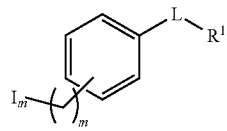

wherein m is an integer between 1 and 6, inclusive; and $I_m$ is an imaging moiety selected from the group consisting of $^{18}$F, $^{76}$Br, $^{124}$I, and $^{131}$I. L and/or $R^1$ may be any suitable L and/or $R^1$ as described herein, for example, in connection with a compound of Formula (Ia)-(Id). In some embodiments, a compound of Formula (III) comprises the structure:

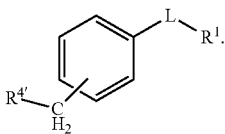

L and/or R¹ may be any suitable L and/or R¹ as described in connection with a compound of Formula (Ia)-(Id) and/or R⁴ may be any suitable R⁴ as described herein, for example, in connection with a compound of Formula (IIa) or Formula (IV). In some embodiments, a compound of Formula (III) comprises the structure:

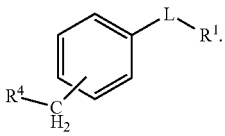

L and/or R¹ may be any suitable L and/or R¹ as described herein, for example, in connection with a compound of Formula (Ia)-(Id) and/or R⁴ may be any suitable R⁴ as described in connection with a compound of Formula (IIa) or Formula (IV). In some embodiments, a compound of Formula (III) comprises the structure:

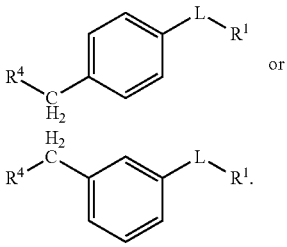

L and/or R¹ may be any suitable L and/or R¹ as described herein, for example, in connection with a compound of Formula (Ia)-(Id) and/or R⁴ may be any suitable R⁴ as described in connection with a compound of Formula (IIa) or Formula (IV).

In some embodiments, a compound of Formula (III) comprises Formula (IV):

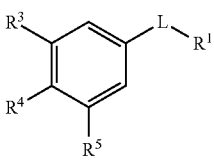

(IV)

wherein

L is a bond; substituted or unsubstituted alkylene; substituted or unsubstituted alkenylene; or substituted or unsubstituted heteroalkylene;

R¹ is a substituted or unsubstituted nitrogen-containing moiety;

R³ is halogen, optionally substituted alkyl, —OR$^{A1}$, —N(R$^{A2}$)₂, —C(═O)R$^{A1}$, —C(═O)N(R$^{A2}$)₂, —NR$^{A2}$C(═O)R$^{A2}$, or —CN;

R⁴ is hydrogen, halogen, optionally substituted alkyl, —OR$^{A1}$, —N(R$^{A2}$)₂, —C(═O)R$^{A1}$, —C(═O)N(R$^{A2}$)₂, —NR$^{A2}$C(═O)R$^{A2}$, or —CN;

R⁵ is halogen, optionally substituted alkyl, —OR$^{A1}$, —N(R$^{A2}$)₂, —C(═O)R$^{A1}$, —C(═O)N(R$^{A2}$)₂, —NR$^{A2}$C(═O)R$^{A2}$, or —CN;

each occurrence of R$^{A1}$ is independently hydrogen, or optionally substituted alkyl; and each occurrence of R$^{A2}$ is independently hydrogen or optionally substituted alkyl, or two R$^{A2}$ groups are joined to form an optionally substituted heterocyclic ring; and one or more of R³ and R⁴ is substituted with an imaging moiety selected from the group consisting of $^{18}$F, $^{76}$Br, $^{124}$I, and $^{131}$I; or is associated with an imaging moiety selected from the group consisting of $^{64}$Cu, $^{89}$Zr, $^{99m}$Tc, and $^{111}$In through a chelator; or is an imaging moiety selected from the group consisting of $^{18}$F, $^{76}$Br, $^{124}$I, and $^{131}$I; or a salt thereof.

The compound of Formula (IV) may comprise any suitable R³ and/or R⁴ as described herein, for example, in connection with a compound of Formula (IIa), and/or any L and/or R¹ group as described herein, for example, in connection with a compound of Formula (Ia)-(Id). In certain embodiments, the imaging moiety is $^{18}$F. In certain embodiments, the imaging moiety is $^{76}$Br. In certain embodiments, the imaging moiety is $^{124}$I. In certain embodiments, the imaging moiety is $^{131}$I. In some cases, the imaging moiety is not $^{131}$I. In some cases, the imaging moiety is $^{18}$F, $^{76}$Br, or $^{124}$I. In some cases, the imaging moiety is $^{18}$F or $^{76}$Br.

In some embodiments, in a compound of Formula (IV), both R³ and R⁵ are not —OH.

In some embodiments, L is a bond. In some embodiments, L is —CH₂—. In some embodiments, L is —CH═CH—. Other suitable L groups are described in connection with a compound of Formula (Ia)-(Id).

The following description of R³ groups may be used in connection with a compound of Formula (IV), or as noted herein. In some embodiments, R³ is halogen, optionally substituted alkyl, —OR$^{A1}$, —N(R$^{A2}$)₂, —C(═O)R$^{A1}$, —C(═O)N(R$^{A2}$)₂, —NR$^{A2}$C(═O)R$^{A2}$, or CN. In some embodiments, R³ is hydrogen, halogen, optionally substituted alkyl, —OR$^{A1}$, or CN. In some embodiments, R³ is hydrogen, fluoro, bromo, chloro, iodo, trifluoromethyl, methoxy, hydroxyl, or CN. In some embodiments, R³ is not hydroxyl. In some embodiments, R³ is not iodo, bromo, chloro, or fluoro. In some embodiments, R³ is fluoro. In some embodiments, R³ is $^{18}$F. In some embodiments, R³ is alkyl substituted with an imaging moiety. In some embodiments, R³ is alkoxyalkyl substituted with an imaging moiety. In some embodiments, R³ is alkoxymethyl substituted with an imaging moiety. In some embodiments, R³ is alkoxyethyl substituted with an imaging moiety. In some embodiments, R³ is alkoxypropyl substituted with an imaging moiety.

In some embodiments, R³ is selected from the group consisting of:

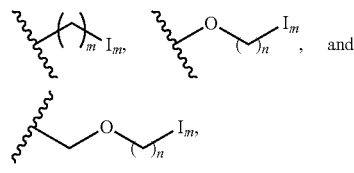

wherein m and n is an integer between 1 and 6, inclusive; and I$_m$ is an imaging moiety. In some embodiments, R³ is selected from the group consisting of:

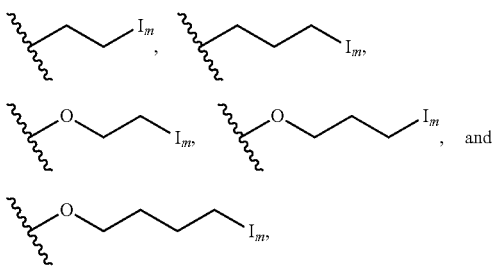

wherein $I_m$ is an imaging moiety. In some embodiments, $R^3$ is selected from the group consisting of:

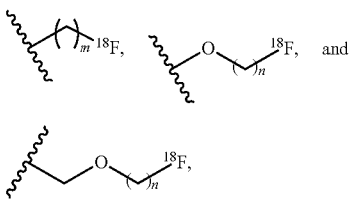

wherein m and n is an integer between 1 and 6, inclusive. In some embodiments, $R^3$ is selected from the group consisting of:

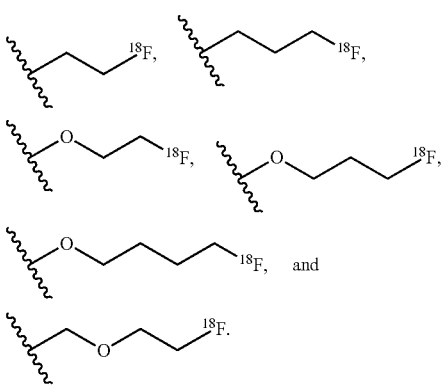

In some embodiments, $R^3$ is:

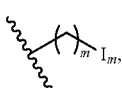

wherein m is an integer between 1 and 6, inclusive; and $I_m$ is an imaging moiety. In some embodiments, $R^3$ is:

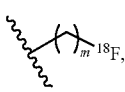

wherein m is an integer between 1 and 6, inclusive. In some embodiments, $R^3$ is:

wherein $I_m$ is an imaging moiety. In some embodiments, $R^3$ is:

In some embodiments, $R^3$ is:

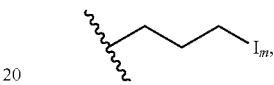

wherein $I_m$ is an imaging moiety. In some embodiments, $R^3$ is:

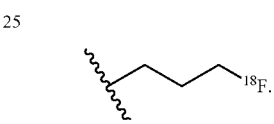

In some cases, $R^3$ is —$(CH_2)_4 I_m$, —$(CH_2)_5 I_m$, —$(CH_2)_6 I_m$, —$(CH_2)_7 I_m$, —$(CH_2)_8 I_m$, —$(CH_2)_9 I_m$, or —$(CH_2)_{10} I_m$. In some cases, $R^3$ is —$(CH_2)_4{}^{18}F_5$, —$(CH_2)_5{}^{18}F$, —$(CH_2)_6{}^{18}F$, —$(CH_2)_7{}^{18}F$, —$(CH_2)_8{}^{18}F$, —$(CH_2)_9{}^{18}F$, or —$(CH_2)_{10}{}^{18}F$. In some embodiments, $R^3$ is:

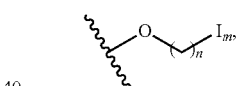

wherein n is an integer between 1 and 6, inclusive; and $I_m$ is an imaging moiety. In some embodiments, $R^3$ is:

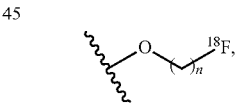

wherein n is an integer between 1 and 6, inclusive. In some embodiments, $R^3$ is:

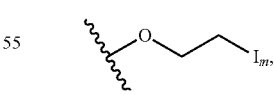

wherein $I_m$ is an imaging moiety. In some embodiments, $R^3$ is:

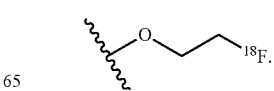

In some embodiments, $R^3$ is:

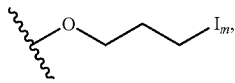

wherein $I_m$ is an imaging moiety. In some embodiments, $R^3$ is:

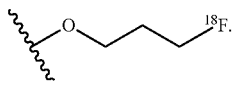

In some embodiments, $R^3$ is:

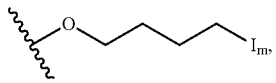

wherein $I_m$ is an imaging moiety. In some embodiments, $R^3$ is:

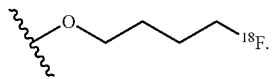

In some cases, $R^3$ is —O(CH$_2$)$_5$I$_m$, —O(CH$_2$)$_6$I$_m$, —O(CH$_2$)$_7$I$_m$, —O(CH$_2$)$_8$I$_m$, —O(CH$_2$)$_9$I$_m$, or —O(CH$_2$)$_{10}$I$_m$. In some cases, $R^3$ is —O(CH$_2$)$_5$$^{18}$F, —O(CH$_2$)$_6$$^{18}$F, —O(CH$_2$)$_7$$^{18}$F, —O(CH$_2$)$_8$$^{18}$F, —O(CH$_2$)$_9$$^{18}$F, or —O(CH$_2$)$_{10}$$^{18}$F. In some embodiments, $R^3$ is:

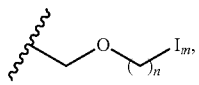

wherein n is an integer between 1 and 6, inclusive; and $I_m$ is an imaging moiety. In some embodiments, $R^3$ is:

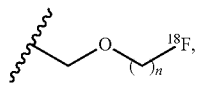

wherein n is an integer between 1 and 6, inclusive. In some embodiments, $R^3$ is:

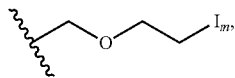

wherein $I_m$ is an imaging moiety. In some embodiments, $R^3$ is:

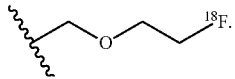

In some cases, $R^3$ is —CH$_2$O(CH$_2$)$_3$I$_m$, —CH$_2$O(CH$_2$)$_4$I$_m$, —CH$_2$O(CH$_2$)$_5$I$_m$, —CH$_2$O(CH$_2$)$_6$I$_m$, —CH$_2$O(CH$_2$)$_7$I$_m$, —CH$_2$O(CH$_2$)$_8$I$_m$, —CH$_2$O(CH$_2$)$_9$I$_m$, or —CH$_2$O(CH$_2$)$_{10}$I$_m$. In some cases, $R^3$ is —CH$_2$O(CH$_2$)$_3$$^{18}$F, —CH$_2$O(CH$_2$)$_4$$^{18}$F, —CH$_2$O(CH$_2$)$_5$$^{18}$F, —CH$_2$O(CH$_2$)$_6$$^{18}$F, —CH$_2$O(CH$_2$)$_7$$^{18}$F, —CH$_2$O(CH$_2$)$_8$$^{18}$F, —CH$_2$O(CH$_2$)$_9$$^{18}$F, or —CH$_2$O(CH$_2$)$_{10}$$^{18}$F.

In the above embodiments wherein $R^3$ is described in connection with a compound of Formula (IV), the compound of Formula (III) may comprise any suitable $R^4$ group as described in connection with a compound of Formula (IIa), and/or any L and/or $R^1$ group as described in connection with a compound of Formula (Ia)-(Id).

The following description of $R^4$ groups may be used in connection with a compound of Formula (IV), or as noted herein. In some embodiments, $R^4$ is hydrogen, halogen, optionally substituted alkyl, —OR$^{41}$, or —NR$^{42}$C(=O)R$^{42}$. In some embodiments, $R^4$ is fluoro. In some embodiments, $R^4$ is $^{18}$F. In some embodiments, $R^4$ is alkyl substituted with an imaging moiety. In some embodiments, $R^4$ is alkoxy substituted with an imaging moiety. In some embodiments, $R^4$ is alkoxyalkyl substituted with an imaging moiety. In some embodiments, $R^4$ is alkoxymethyl substituted with an imaging moiety. In some embodiments, $R^4$ is alkoxyethyl substituted with an imaging moiety. In some embodiments, $R^4$ is alkoxypropyl substituted with an imaging moiety. In certain embodiments, the imaging moiety is $^{18}$F.

In some embodiments, $R^4$ is selected from the group consisting of:

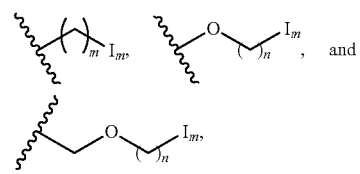

wherein m is an integer between 1 and 6, inclusive; and $I_m$ is an imaging moiety. In some embodiments, $R^4$ is selected from the group consisting of:

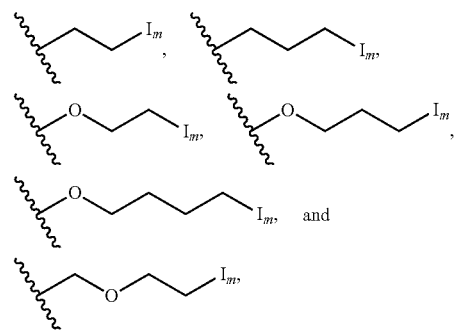

wherein $I_m$ is an imaging moiety. In some embodiments, $R^4$ is selected from the group consisting of:

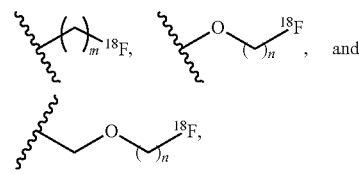

wherein m or n is an integer between 1 and 6, inclusive. In some embodiments, $R^4$ is selected from the group consisting of:

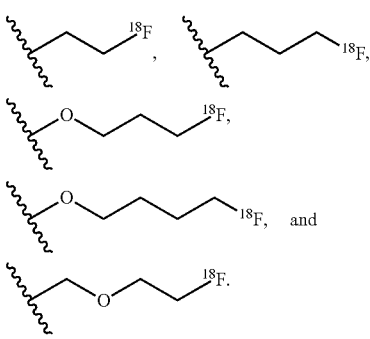

In some embodiments, $R^4$ is:

wherein m is an integer between 1 and 6, inclusive; and $I_m$ is an imaging moiety. In some embodiments, $R^4$ is:

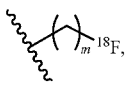

wherein m is an integer between 1 and 6, inclusive. In some embodiments, $R^4$ is:

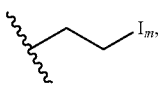

wherein $I_m$ is an imaging moiety. In some embodiments, $R^4$ is:

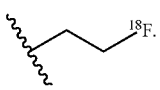

In some embodiments, $R^4$ is:

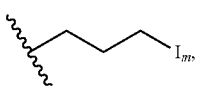

wherein $I_m$ is an imaging moiety. In some embodiments, $R^4$ is:

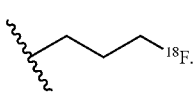

In some cases, $R^4$ is $-(CH_2)_4I_m$, $-(CH_2)_5I_m$, $-(CH_2)_6I_m$, $-(CH_2)_7I_m$, $-(CH_2)_8I_m$, $-(CH_2)_9I_m$, or $-(CH_2)_{10}I_m$. In some cases, $R^4$ is $-(CH_2)_4{}^{18}F$, $-(CH_2)_6{}^{18}F$, $-(CH_2)_7{}^{18}F$, $-(CH_2)_8{}^{18}F$, $-(CH_2)_9{}^{18}F_5$, or $-(CH_2)_{10}{}^{18}F$. In some embodiments, $R^4$ is:

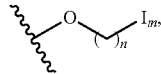

wherein n is an integer between 1 and 6, inclusive; and $I_m$ is an imaging moiety. In some embodiments, $R^4$ is:

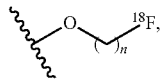

wherein n is an integer between 1 and 6, inclusive. In some embodiments, $R^4$ is:

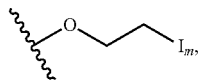

wherein $I_m$ is an imaging moiety. In some embodiments, $R^4$ is:

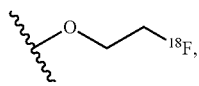

In some embodiments, $R^4$ is:

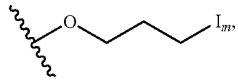

wherein $I_m$ is an imaging moiety. In some embodiments, $R^4$ is:

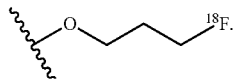

In some embodiments, $R^4$ is:

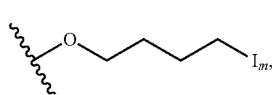

wherein $I_m$ is an imaging moiety. In some embodiments, $R^4$ is:

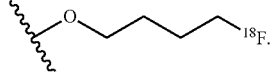

In some cases, R⁴ is —O(CH₂)₅I$_m$, —O(CH₂)₆I$_m$, —O(CH₂)₇I$_m$, —O(CH₂)₈I$_m$, —O(CH₂)₉I$_m$, or —O(CH₂)₁₀I$_m$. In some cases, R⁴ is —O(CH₂)₅¹⁸F, —O(CH₂)₆¹⁸F, —O(CH₂)₇¹⁸F, —O(CH₂)₈¹⁸F, —O(CH₂)₉¹⁸F, or —O(CH₂)₁₀¹⁸F. In some embodiments, R⁴ is:

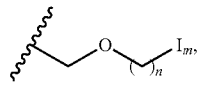

wherein n is an integer between 1 and 6, inclusive; and I$_m$ is an imaging moiety. In some embodiments, R⁴ is:

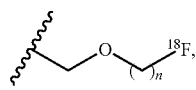

wherein n is an integer between 1 and 6, inclusive. In some embodiments, R⁴ is:

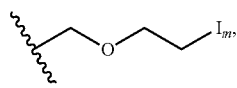

wherein I$_m$ is an imaging moiety. In some embodiments, R⁴ is:

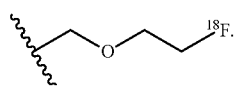

In some cases, R⁴ is —CH₂O(CH₂)₃I$_m$, —CH₂O(CH₂)₄I$_m$, —CH₂O(CH₂)₅I$_m$, —CH₂O(CH₂)₆I$_m$, —CH₂O(CH₂)₇I$_m$, —CH₂O(CH₂)₈I$_m$, —CH₂O(CH₂)₉I$_m$, or —CH₂O(CH₂)₁₀I$_m$. In some cases, R⁴ is —CH₂O(CH₂)₃¹⁸F, —CH₂O(CH₂)₄¹⁸F, —CH₂O(CH₂)₅¹⁸F, —CH₂O(CH₂)₆¹⁸F, —CH₂O(CH₂)₇¹⁸F, —CH₂O(CH₂)₈¹⁸F, —CH₂O(CH₂)₉¹⁸F, or —CH₂O(CH₂)₁₀¹⁸F.

In the above embodiments wherein R⁴ is described in connection with a compound of Formula (IV), the compound of Formula (III) may comprise any suitable R³ as described herein, for example, in connection with a compound of Formula (IIa) or (IV), and/or any L and/or R¹ group as described herein, for example, in connection with a compound of Formula (Ia)-(Id).

The following description of R¹ groups may be used in connection with a compound of Formula (IV), or as noted herein. In some embodiments, R¹ is selected from the group consisting of:

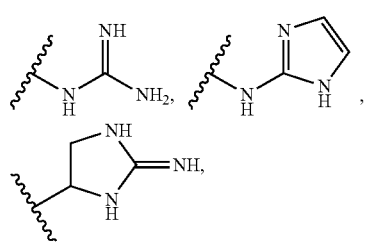

-continued

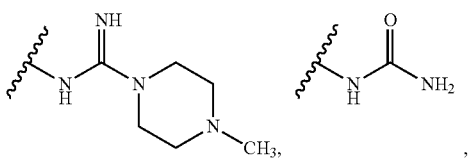

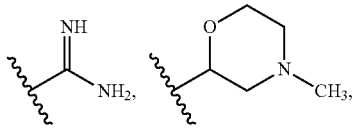

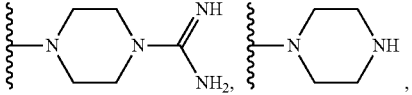

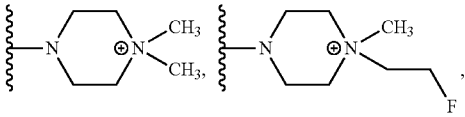

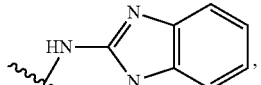

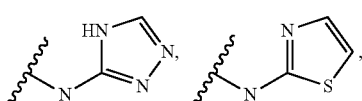

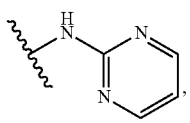

—NH₂, —NHCH₃, —NHCH₂CH₃, and —NHCH₂CH₂CH₃. In some embodiments, R¹ is:

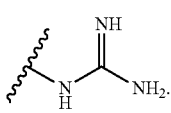

In some embodiments, R¹ is:

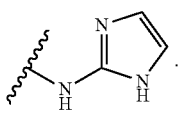 [SMILES: *Nc1ncc[nH]1]

In some embodiments, R¹ is:

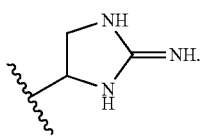 [SMILES: *C1CNC(=N)N1]

In some embodiments, R¹ is:

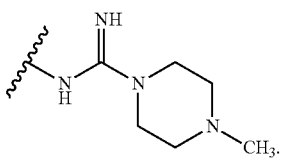

In some embodiments, R¹ is:

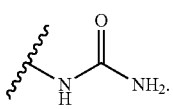

In some embodiments, R¹ is:

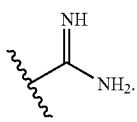

In some embodiments, R¹ is:

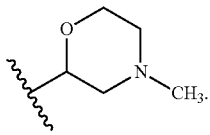

In some embodiments, R¹ is:

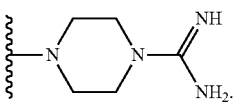

In some embodiments, R¹ is:

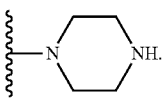

In some embodiments, R¹ is:

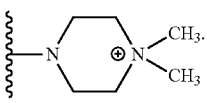

In some embodiments, R¹ is:

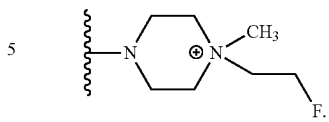

In some embodiments, R¹ is:

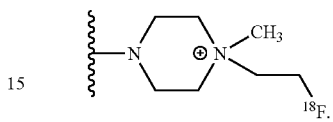

In some embodiments, R¹ is:

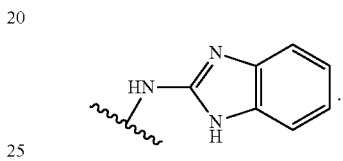

In some embodiments, R¹ is:

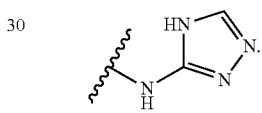

In some embodiments, R¹ is:

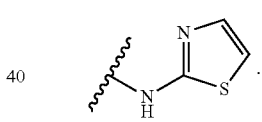

In some embodiments, R¹ is:

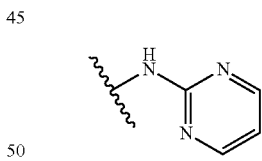

In some embodiments, R¹ is —NH$_2$, —NHCH$_3$, —NHCH$_2$CH$_3$, or —NHCH$_2$CH$_2$CH$_3$. In some embodiments, R³ is hydrogen, fluoro, bromo, chloro, iodo, trifluoromethyl, methoxy, hydroxyl, or —CN; and R⁴ is alkyl substituted with an imaging moiety, alkoxy substituted with an imaging moiety, or alkoxyalkyl substituted with an imaging moiety.

In the above embodiments wherein R¹ is described in connection with a compound of Formula (IV), the compound of Formula (III) may comprise any suitable R³ and/or R⁴ as described herein, for example, in connection with a compound of Formula (IIa) or (IV), and/or any L group as described herein, for example, in connection with a compound of Formula (Ia)-(Id).

As noted above, for a compound of Formula (IV), any suitable combination of R¹, R³, R⁴, R⁵, and L groups may be used as described herein. For example, wherein $R^1$ is as described in connection with a compound of Formula (IV) or (Ia)-(Id), $R^3$ and/or $R^4$ is as described in connection with a compound of Formula (IIa) or (IV), and/or L is as described in connection with a compound of Formula (Ia)-(Id).

In some embodiments, for a compound of Formula (IV), L is —$CH_2$—, and $R^1$ is:

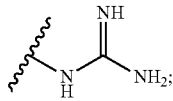

$R^3$ is halogen; and $R^4$ is alkoxyalkyl substituted with an imaging moiety.

In some embodiments, a compound is provided comprising Formula (Va)-(Vd):

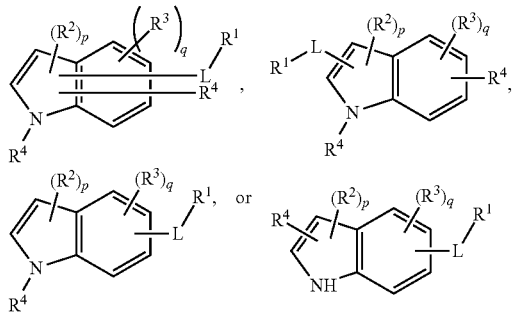

wherein

L is a bond; substituted or unsubstituted, cyclic or acyclic alkylene; substituted or unsubstituted, cyclic or acyclic alkenylene; substituted or unsubstituted, cyclic or acyclic alkynylene; or substituted or unsubstituted, cyclic or acyclic heteroaliphatic;

$R^1$ is a substituted or unsubstituted nitrogen-containing moiety;

$R^2$ is hydrogen, halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, —$OR^{41}$, —$N(R^{42})_2$, —$SR^{41}$, —$C(=O)R^{41}$, —$C(=O)OR^{41}$, —$C(=O)SR^{41}$, —$C(=O)N(R^{42})_2$, —$OC(=O)R^{41}$, —$OC(=O)OR^{41}$, —$OC(=O)SR^{41}$, —$OC(=O)N(R^{42})_2$, —$NR^{42}C(=O)R^{42}$, —$NR^{42}C(=O)OR^{41}$, —$NR^{42}C(=O)SR^{41}$, —$NR^{42}C(=O)N(R^{42})_2$, —$SC(=O)R^{41}$, —$SC(=O)OR^{41}$, —$SC(=O)SR^{41}$, —$SC(=O)N(R^{42})_2$, —$C(=NR^{42})R^{41}$, —$C(=NR^{42})OR^{41}$, —$C(=NR^{42})SR^{41}$, —$C(=NR^{42})N(R^{42})_2$, —$OC(=NR^{42})R^{41}$, —$OC(=NR^{42})OR^{41}$, —$OC(=NR^{42})SR^{41}$, —$OC(=NR^{42})N(R^{42})_2$, —$NR^{42}C(=NR^{42})R^{42}$, —$NR^{42}C(=NR^{42})OR^{41}$, —$NR^{42}C(=NR^{42})SR^{41}$, —$NR^{42}C(=NR^{42})N(R^{42})_2$, —$SC(=NR^{42})R^{41}$, —$SC(=NR^{42})OR^{41}$, —$SC(=NR^{42})SR^{41}$, —$SC(=NR^{42})N(R^{42})_2$, —$C(=S)R^{41}$, —$C(=S)OR^{41}$, —$C(=S)SR^{41}$, —$C(=S)N(R^{42})_2$, —$OC(=S)R^{41}$, —$OC(=S)OR^{41}$, —$OC(=S)SR^{41}$, —$OC(=S)N(R^{42})_2$, —$NR^{42}C(=S)R^{42}$, —$NR^{42}C(=S)OR^{41}$, —$NR^{42}C(=S)SR^{41}$, —$NR^{42}C(=S)N(R^{42})_2$, —$SC(=S)R^{41}$, —$SC(=S)OR^{41}$, —$SC(=S)SR^{41}$, —$SC(=S)N(R^{42})_2$, —$S(=O)R^{41}$, —$SO_2R^{41}$, —$NR^{42}SO_2R^{41}$, —$SO_2N(R^{42})_2$, —$CN$, —$SCN$, or —$NO_2$;

$R^3$ is hydrogen, halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, —$OR^{41}$, —$N(R^{42})_2$, —$SR^{41}$, —$C(=O)R^{41}$, —$C(=O)OR^{41}$, —$C(=O)SR^{41}$, —$C(=O)N(R^{42})_2$, —$OC(=O)R^{41}$, —$OC(=O)OR^{41}$, —$OC(=O)SR^{41}$, —$OC(=O)N(R^{42})_2$, —$NR^{42}C(=O)R^{42}$, —$NR^{42}C(=O)OR^{41}$, —$NR^{42}C(=O)SR^{41}$, —$NR^{42}C(=O)N(R^{42})_2$, —$SC(=O)R^{41}$, —$SC(=O)OR^{41}$, —$SC(=O)SR^{41}$, —$SC(=O)N(R^{42})_2$, —$C(=NR^{42})R^{41}$, —$C(=NR^{42})OR^{41}$, —$C(=NR^{42})SR^{41}$, —$C(=NR^{42})N(R^{42})_2$, —$OC(=NR^{42})R^{41}$, —$OC(=NR^{42})OR^{41}$, —$OC(=NR^{42})SR^{41}$, —$OC(=NR^{42})N(R^{42})_2$, —$NR^{42}C(=NR^{42})R^{42}$, —$NR^{42}C(=NR^{42})OR^{41}$, —$NR^{42}C(=NR^{42})SR^{41}$, —$NR^{42}C(=NR^{42})N(R^{42})_2$, —$SC(=NR^{42})R^{41}$, —$SC(=NR^{42})OR^{41}$, —$SC(=NR^{42})SR^{41}$, —$SC(=NR^{42})N(R^{42})_2$, —$C(=S)R^{41}$, —$C(=S)OR^{41}$, —$C(=S)SR^{41}$, —$C(=S)N(R^{42})_2$, —$OC(=S)R^{41}$, —$OC(=S)OR^{41}$, —$OC(=S)SR^{41}$, —$OC(=S)N(R^{42})_2$, —$NR^{42}C(=S)R^{42}$, —$NR^{42}C(=S)OR^{41}$, —$NR^{42}C(=S)SR^{41}$, —$NR^{42}C(=S)N(R^{42})_2$, —$SC(=S)R^{41}$, —$SC(=S)OR^{41}$, —$SC(=S)SR^{41}$, —$SC(=S)N(R^{42})_2$, —$S(=O)R^{41}$, —$SO_2R^{41}$, —$NR^{42}SO_2R^{41}$, —$SO_2N(R^{42})_2$, —$CN$, —$SCN$, or —$NO_2$;

each occurrence of $R^4$ is independently hydrogen, halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, —$OR^{41}$, —$N(R^{42})_2$, —$SR^{41}$, —$C(=O)R^{41}$, —$C(=O)OR^{41}$, —$C(=O)SR^{41}$, —$C(=O)N(R^{42})_2$, —$OC(=O)R^{41}$, —$OC(=O)OR^{41}$, —$OC(=O)SR^{41}$, —$OC(=O)N(R^{42})_2$, —$NR^{42}C(=O)R^{42}$, —$NR^{42}C(=O)OR^{41}$, —$NR^{42}C(=O)SR^{41}$, —$NR^{42}C(=O)N(R^{42})_2$, —$SC(=O)R^{41}$, —$SC(=O)OR^{41}$, —$SC(=O)SR^{41}$, —$SC(=O)N(R^{42})_2$, —$C(=NR^{42})R^{41}$, —$C(=NR^{42})OR^{41}$, —$C(=NR^{42})SR^{41}$, —$C(=NR^{42})N(R^{42})_2$, —$OC(=NR^{42})R^{41}$, —$OC(=NR^{42})OR^{41}$, —$OC(=NR^{42})SR^{41}$, —$OC(=NR^{42})N(R^{42})_2$, —$NR^{42}C(=NR^{42})R^{42}$, —$NR^{42}C(=NR^{42})OR^{41}$, —$NR^{42}C(=NR^{42})SR^{41}$, —$NR^{42}C(=NR^{42})N(R^{42})_2$, —$SC(=NR^{42})R^{41}$, —$SC(=NR^{42})OR^{41}$, —$SC(=NR^{42})SR^{41}$, —$SC(=NR^{42})N(R^{42})_2$, —$C(=S)R^{41}$, —$C(=S)OR^{41}$, —$C(=S)SR^{41}$, —$C(=S)N(R^{42})_2$, —$OC(=S)R^{41}$, —$OC(=S)OR^{41}$, —$OC(=S)SR^{41}$, —$OC(=S)N(R^{42})_2$, —$NR^{42}C(=S)R^{42}$, —$NR^{42}C(=S)OR^{41}$, —$NR^{42}C(=S)SR^{41}$, —$NR^{42}C(=S)N(R^{42})_2$, —$SC(=S)R^{41}$, —$SC(=S)OR^{41}$, —$SC(=S)SR^{41}$, —$SC(=S)N(R^{42})_2$, —$S(=O)R^{41}$, —$SO_2R^{41}$, —$NR^{42}SO_2R^{41}$, —$SO_2N(R^{42})_2$, —$CN$, —$SCN$, or —$NO_2$;

each occurrence of $R^{41}$ is independently hydrogen, optionally substituted alkyl, optionally substituted alkenyl, optionally substituted alkynyl, optionally substituted carbocyclyl, optionally substituted heterocyclyl, optionally substituted aryl, or optionally substituted heteroaryl; and each occurrence of $R^{42}$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, or an amino protecting group, or two $R^{42}$ groups are joined to form an optionally substituted heterocyclic ring;

p is 0, 1, or 2; and r is 0, 1, 2, 3, or 4;

at least one $R^4$ is substituted with an imaging moiety selected from the group consisting of $^{18}F$, $^{76}Br$, $^{124}I$, and $^{131}I$; or is associated with an imaging moiety selected from the group consisting of $^{64}Cu$, $^{89}Zr$, $^{99m}Tc$, and $^{111}In$ through a chelator; or is an imaging moiety selected from the group consisting of $^{18}$F, $^{76}$Br, $^{124}$I, and $^{131}$I; or a salt thereof.

In some embodiments, a compound is provided comprising Formula (Va)-(Vd):

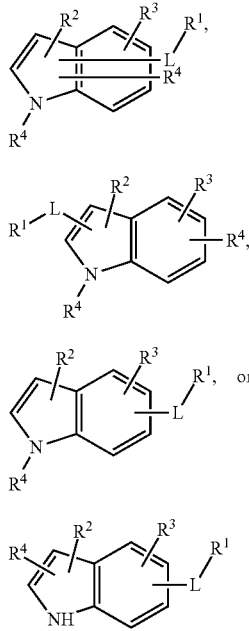

wherein

L is a bond; substituted or unsubstituted, cyclic or acyclic alkylene; substituted or unsubstituted, cyclic or acyclic alkenylene; substituted or unsubstituted, cyclic or acyclic alkynylene; or substituted or unsubstituted, cyclic or acyclic heteroaliphatic;

$R^1$ is a substituted or unsubstituted nitrogen-containing moiety;

$R^2$ is hydrogen, halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, —OR$^{A1}$, —N(R$^{A2}$)$_2$, —SR$^{A1}$, —C(=O)R$^{A1}$, —C(=O)OR$^{A1}$, —C(=O)SR$^{A1}$, —C(=O)N(R$^{A2}$)$_2$, —OC(=O)R$^{A1}$, —OC(=O)OR$^{A1}$, —OC(=O)SR$^{A1}$, —OC(=O)N(R$^{A2}$)$_2$, —NR$^{A2}$C(=O)R$^{A2}$, —NR$^{A2}$C(=O)OR$^{A1}$, —NR$^{A2}$C(=O)SR$^{A1}$, —NR$^{A2}$C(=O)N(R$^{A2}$)$_2$, —SC(=O)R$^{A1}$, —SC(=O)OR$^{A1}$, —SC(=O)SR$^{A1}$, —SC(=O)N(R$^{A2}$)$_2$, —C(=NR$^{A2}$)R$^{A1}$, —C(=NR$^{A2}$)OR$^{A1}$, —C(=NR$^{A2}$)SR$^{A1}$, —C(=NR$^{A2}$)N(R$^{A2}$)$_2$, —OC(=NR$^{A2}$)R$^{A1}$, —OC(=NR$^{A2}$)OR$^{A1}$, —OC(=NR$^{A2}$)SR$^{A1}$, —OC(=NR$^{A2}$)N(R$^{A2}$)$_2$, —NR$^{A2}$C(=NR$^{A2}$)R$^{A2}$, —NR$^{A2}$C(=NR$^{A2}$)OR$^{A1}$, —NR$^{A2}$C(=NR$^{A2}$)SR$^{A1}$, —NR$^{A2}$C(=NR$^{A2}$)N(R$^{A2}$)$_2$, —SC(=NR$^{A2}$)R$^{A1}$, —SC(=NR$^{A2}$)OR$^{A1}$, —SC(=NR$^{A2}$)SR$^{A1}$, —SC(=NR$^{A2}$)N(R$^{A2}$)$_2$, —C(=S)R$^{A1}$, —C(=S)OR$^{A1}$, —C(=S)SR$^{A1}$, —C(=S)N(R$^{A2}$)$_2$, —OC(=S)R$^{A1}$, —OC(=S)OR$^{A1}$, —OC(=S)SR$^{A1}$, —OC(=S)N(R$^{A2}$)$_2$, —NR$^{A2}$C(=S)R$^{A2}$, —NR$^{A2}$C(=S)OR$^{A1}$, —NR$^{A2}$C(=S)SR$^{A1}$, —NR$^{A2}$C(=S)N(R$^{A2}$)$_2$, —SC(=S)R$^{A1}$, —SC(=S)OR$^{A1}$, —SC(=S)SR$^{A1}$, —SC(=S)N(R$^{A2}$)$_2$, —S(=O)R$^{A1}$, —SO$_2$R$^{A1}$, —NR$^{A2}$SO$_2$R$^{A1}$, —SO$_2$N(R$^{A2}$)$_2$, —CN, —SCN, or —NO$_2$;

$R^3$ is hydrogen, halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, —OR$^{A1}$, —N(R$^{A2}$)$_2$, —SR$^{A1}$, —C(=O)R$^{A1}$, —C(=O)OR$^{A1}$, —C(=O)SR$^{A1}$, —C(=O)N(R$^{A2}$)$_2$, —OC(=O)R$^{A1}$, —OC(=O)OR$^{A1}$, —OC(=O)SR$^{A1}$, —OC(=O)N(R$^{A2}$)$_2$, —NR$^{A2}$C(=O)R$^{A2}$, —NR$^{A2}$C(=O)OR$^{A1}$, —NR$^{A2}$C(=O)SR$^{A1}$, —NR$^{A2}$C(=O)N(R$^{A2}$)$_2$, —SC(=O)R$^{A1}$, —SC(=O)OR$^{A1}$, —SC(=O)SR$^{A1}$, —SC(=O)N(R$^{A2}$)$_2$, —C(=NR$^{A2}$)R$^{A1}$, —C(=NR$^{A2}$)OR$^{A1}$, —C(=NR$^{A2}$)SR$^{A1}$, —C(=NR$^{A2}$)N(R$^{A2}$)$_2$, —OC(=NR$^{A2}$)R$^{A1}$, —OC(=NR$^{A2}$)OR$^{A1}$, —OC(=NR$^{A2}$)SR$^{A1}$, —OC(=NR$^{A2}$)N(R$^{A2}$)$_2$, —NR$^{A2}$C(=NR$^{A2}$)R$^{A2}$, —NR$^{A2}$C(=NR$^{A2}$)OR$^{A1}$, —NR$^{A2}$C(=NR$^{A2}$)SR$^{A1}$, —NR$^{A2}$C(=NR$^{A2}$)N(R$^{A2}$)$_2$, —SC(=NR$^{A2}$)R$^{A1}$, —SC(=NR$^{A2}$)OR$^{A1}$, —SC(=NR$^{A2}$)SR$^{A1}$, —SC(=NR$^{A2}$)N(R$^{A2}$)$_2$, —C(=S)R$^{A1}$, —C(=S)OR$^{A1}$, —C(=S)SR$^{A1}$, —C(=S)N(R$^{A2}$)$_2$, —OC(=S)R$^{A1}$, —OC(=S)OR$^{A1}$, —OC(=S)SR$^{A1}$, —OC(=S)N(R$^{A2}$)$_2$, —NR$^{A2}$C(=S)R$^{A2}$, —NR$^{A2}$C(=S)OR$^{A1}$, —NR$^{A2}$C(=S)SR$^{A1}$, —NR$^{A2}$C(=S)N(R$^{A2}$)$_2$, —SC(=S)R$^{A1}$, —SC(=S)OR$^{A1}$, —SC(=S)SR$^{A1}$, —SC(=S)N(R$^{A2}$)$_2$, —S(=O)R$^{A1}$, —SO$_2$R$^{A1}$, —NR$^{A2}$SO$_2$R$^{A1}$, —SO$_2$N(R$^{A2}$)$_2$, —CN, —SCN, or —NO$_2$;

each occurrence of $R^4$ is independently hydrogen, halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, —OR$^{A1}$, —N(R$^{A2}$)$_2$, —SR$^{A1}$, —C(=O)R$^{A1}$, —C(=O)OR$^{A1}$, —C(=O)SR$^{A1}$, —C(=O)N(R$^{A2}$)$_2$, —OC(=O)R$^{A1}$, —OC(=O)OR$^{A1}$, —OC(=O)SR$^{A1}$, —OC(=O)N(R$^{A2}$)$_2$, —NR$^{A2}$C(=O)R$^{A2}$, —NR$^{A2}$C(=O)OR$^{A1}$, —NR$^{A2}$C(=O)SR$^{A1}$, —NR$^{A2}$C(=O)N(R$^{A2}$)$_2$, —SC(=O)R$^{A1}$, —SC(=O)OR$^{A1}$, —SC(=O)SR$^{A1}$, —SC(=O)N(R$^{A2}$)$_2$, —C(=NR$^{A2}$)R$^{A1}$, —C(=NR$^{A2}$)OR$^{A1}$, —C(=NR$^{A2}$)SR$^{A1}$, —C(=NR$^{A2}$)N(R$^{A2}$)$_2$, —OC(=NR$^{A2}$)R$^{A1}$, —OC(=NR$^{A2}$)OR$^{A1}$, —OC(=NR$^{A2}$)N(R$^{A2}$)$_2$, —NR$^{A2}$C(=NR$^{A2}$)R$^{A2}$, —NR$^{A2}$C(=NR$^{A2}$)OR$^{A1}$, —NR$^{A2}$C(=NR$^{A2}$)SR$^{A1}$, —NR$^{A2}$C(=NR$^{A2}$)N(R$^{A2}$)$_2$, —SC(=NR$^{A2}$)R$^{A1}$, —SC(=NR$^{A2}$)OR$^{A1}$, —SC(=NR$^{A2}$)SR$^{A1}$, —SC(=NR$^{A2}$)N(R$^{A2}$)$_2$, —C(=S)R$^{A1}$, —C(=S)OR$^{A1}$, —C(=S)SR$^{A1}$, —C(=S)N(R$^{A2}$)$_2$, —OC(=S)R$^{A1}$, —OC(=S)OR$^{A1}$, —OC(=S)SR$^{A1}$, —OC(=S)N(R$^{A2}$)$_2$, —NR$^{A2}$C(=S)R$^{A2}$, —NR$^{A2}$C(=S)OR$^{A1}$, —NR$^{A2}$C(=S)SR$^{A1}$, —NR$^{A2}$C(=S)N(R$^{A2}$)$_2$, —SC(=S)R$^{A1}$, —SC(=S)OR$^{A1}$, —SC(=S)SR$^{A1}$, —SC(=S)N(R$^{A2}$)$_2$, —S(=O)R$^{A1}$, —SO$_2$R$^{A1}$, —NR$^{A2}$SO$_2$R$^{A1}$, —SO$_2$N(R$^{A2}$)$_2$, —CN, —SCN, or —NO$_2$;

each occurrence of $R^{A1}$ is independently hydrogen, optionally substituted alkyl, optionally substituted alkenyl, optionally substituted alkynyl, optionally substituted carbocyclyl, optionally substituted heterocyclyl, optionally substituted aryl, or optionally substituted heteroaryl; and each occurrence of $R^{A2}$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, or an amino protecting group, or two $R^{A2}$ groups are joined to form an optionally substituted heterocyclic ring;

at least one $R^4$ is substituted with an imaging moiety selected from the group consisting of $^{18}$F, $^{76}$Br, $^{124}$I, and $^{131}$I; or is associated with an imaging moiety selected from the group consisting of $^{64}$Cu, $^{89}$Zr, $^{99m}$Tc, and $^{111}$In through a chelator; or is an imaging moiety selected from the group consisting of $^{18}$F, $^{76}$Br, $^{124}$I, and $^{131}$I; or a salt thereof.

For a compound of Formula (Va)-(Vd), any suitable combination of $R^1$, $R^2$, $R^3$, $R^4$, and L groups may be used as described herein. For example, wherein $R^1$ is as described in connection with a compound of Formula (IV) or (Ia)-(Id), $R^3$ and/or $R^4$ is as described in connection with a compound of Formula (IIa) or (IV), and/or L is as described in connection with a compound of Formula (Ia)-(Id). In certain embodiments, the imaging moiety is $^{18}$F. In certain embodiments, the imaging moiety is $^{76}$Br. In certain embodiments, the imaging moiety is $^{124}$I. In certain embodiments, the imaging moiety is $^{131}$I. In some cases, the imaging moiety is not $^{131}$I. In some cases, the imaging moiety is $^{18}$F, $^{76}$Br, or $^{124}$I. In some cases, the imaging moiety is $^{18}$F or $^{76}$Br.

In some cases, a compound of Formula (Va)-(Vd) comprises the structure:

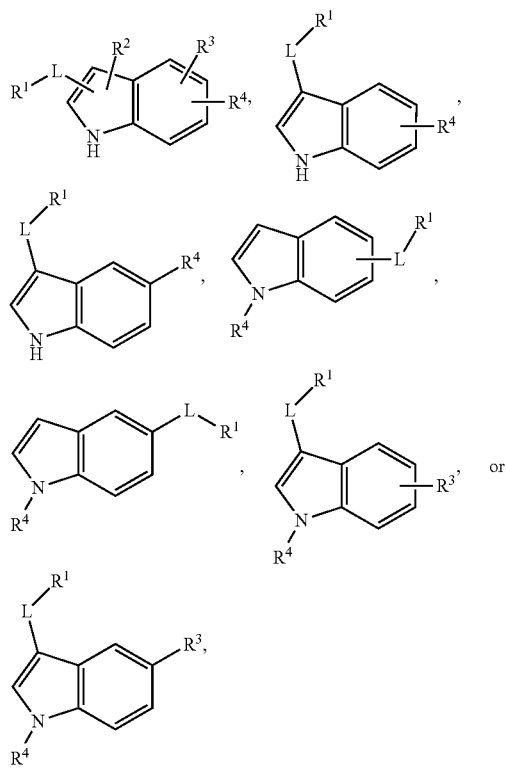

wherein $R^1$, $R^2$, $R^3$, $R^4$, and L are as described herein. For example, wherein $R^1$ is as described in connection with a compound of Formula (IV) or (Ia)-(Id), $R^3$ and/or $R^4$ is as described in connection with a compound of Formula (IIa) or (IV), and/or L is as described in connection with a compound of Formula (Ia)-(Id). In some cases, a compound of Formula (Va)-(Vd) comprises the structure:

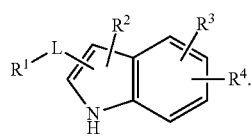

In some cases, a compound of Formula (Va)-(Vd) comprises the structure:

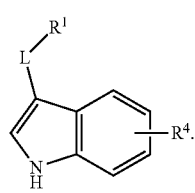

In some cases, a compound of Formula (Va)-(Vd) comprises the structure:

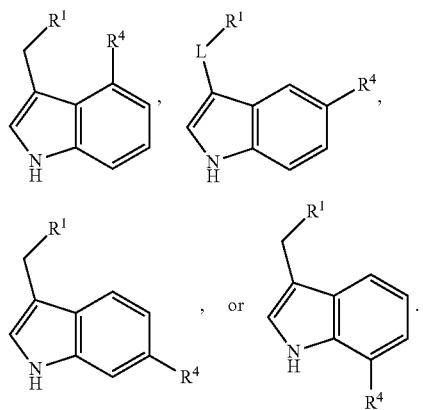

In some cases, a compound of Formula (Va)-(Vd) comprises the structure:

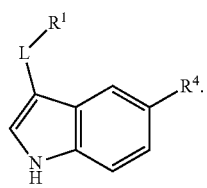

In some cases, a compound of Formula (Va)-(Vd) comprises the structure:

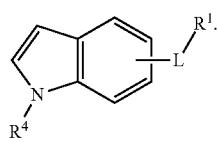

In some cases, a compound of Formula (Va)-(Vd) comprises the structure:

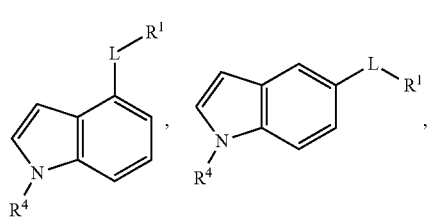

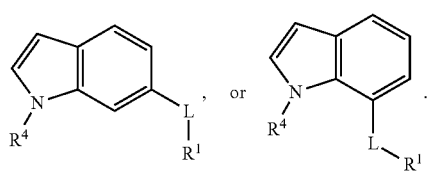

In some cases, a compound of Formula (Va)-(Vd) comprises the structure:

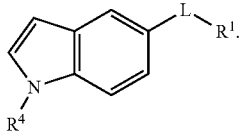

In some cases, a compound of Formula (Va)-(Vd) comprises the structure:

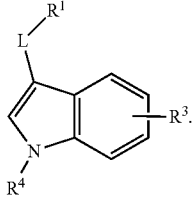

In some cases, a compound of Formula (Va)-(Vd) comprises the structure:

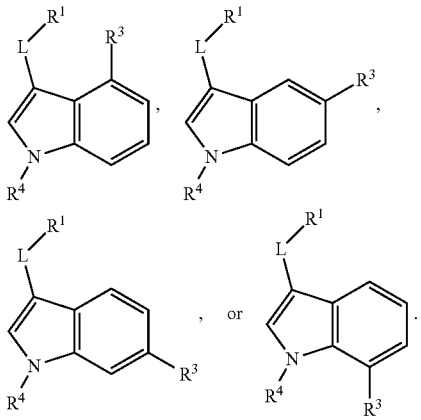

In some cases, a compound of Formula (Va)-(Vd) comprises the structure:

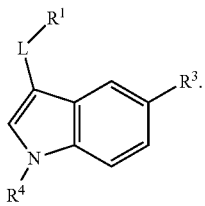

In some embodiments, a compound is provided comprising Formula (VI):

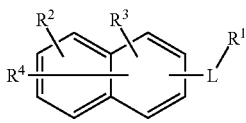

(VI)

wherein

L is a bond; substituted or unsubstituted, cyclic or acyclic alkylene; substituted or unsubstituted, cyclic or acyclic alkenylene; substituted or unsubstituted, cyclic or acyclic alkynylene; or substituted or unsubstituted, cyclic or acyclic heteroaliphatic;

$R^1$ is a substituted or unsubstituted nitrogen-containing moiety;

$R^2$ is hydrogen, halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, —$OR^{41}$, —$N(R^{42})_2$, —$SR^{41}$, —$C(=O)R^{41}$, —$C(=O)OR^{41}$, —$C(=O)SR^{41}$, —$C(=O)N(R^{42})_2$, —$OC(=O)R^{41}$, —$OC(=O)OR^{41}$, —$OC(=O)SR^{41}$, —$OC(=O)N(R^{42})_2$, —$NR^{42}C(=O)R^{42}$, —$NR^{42}C(=O)OR^{41}$, —$NR^{42}C(=O)SR^{41}$, —$NR^{42}C(=O)N(R^{42})_2$, —$SC(=O)R^{41}$, —$SC(=O)OR^{41}$, —$SC(=O)SR^{41}$, —$SC(=O)N(R^{42})_2$, —$C(=NR^{42})R^{41}$, —$C(=NR^{42})OR^{41}$, —$C(=NR^{42})SR^{41}$, —$C(=NR^{42})N(R^{42})_2$, —$OC(=NR^{42})R^{41}$, —$OC(=NR^{42})OR^{41}$, —$OC(=NR^{42})SR^{41}$, —$OC(=NR^{42})N(R^{42})_2$, —$NR^{42}C(=NR^{42})R^{42}$, —$NR^{42}C(=NR^{42})OR^{41}$, —$NR^{42}C(=NR^{42})SR^{41}$, —$NR^{42}C(=NR^{42})N(R^{42})_2$, —$SC(=NR^{42})R^{41}$, —$SC(=NR^{42})OR^{41}$, —$SC(=NR^{42})SR^{41}$, —$SC(=NR^{42})N(R^{42})_2$, —$C(=S)R^{41}$, —$C(=S)OR^{41}$, —$C(=S)SR^{41}$, —$C(=S)N(R^{42})_2$, —$OC(=S)R^{41}$, —$OC(=S)OR^{41}$, —$OC(=S)SR^{41}$, —$OC(=S)N(R^{42})_2$, —$NR^{42}C(=S)R^{42}$, —$NR^{42}C(=S)OR^{41}$, —$NR^{42}C(=S)SR^{41}$, —$NR^{42}C(=S)N(R^{42})_2$, —$SC(=S)R^{41}$, —$SC(=S)OR^{41}$, —$SC(=S)SR^{41}$, —$SC(=S)N(R^{42})_2$, —$S(=O)R^{41}$, —$SO_2R^{41}$, —$NR^{42}SO_2R^{41}$, —$SO_2N(R^{42})_2$, —CN, —SCN, or —$NO_2$;

$R^3$ is hydrogen, halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, —$OR^{41}$, —$N(R^{42})_2$, —$SR^{41}$, —$C(=O)R^{41}$, —$C(=O)OR^{41}$, —$C(=O)SR^{41}$, —$C(=O)N(R^{42})_2$, —$OC(=O)R^{41}$, —$OC(=O)OR^{41}$, —$OC(=O)SR^{41}$, —$OC(=O)N(R^{42})_2$, —$NR^{42}C(=O)R^{42}$, —$NR^{42}C(=O)OR^{41}$, —$NR^{42}C(=O)SR^{41}$, —$NR^{42}C(=O)N(R^{42})_2$, —$SC(=O)R^{41}$, —$SC(=O)OR^{41}$, —$SC(=O)SR^{41}$, —$SC(=O)N(R^{42})_2$, —$C(=NR^{42})R^{41}$, —$C(=NR^{42})OR^{41}$, —$C(=NR^{42})SR^{41}$, —$C(=NR^{42})N(R^{42})_2$, —$OC(=NR^{42})R^{41}$, —$OC(=NR^{42})OR^{41}$, —$OC(=NR^{42})SR^{41}$, —$OC(=NR^{42})N(R^{42})_2$, —$NR^{42}C(=NR^{42})R^{42}$, —$NR^{42}C(=NR^{42})OR^{41}$, —$NR^{42}C(=NR^{42})SR^{41}$, —$NR^{42}C(=NR^{42})N(R^{42})_2$, —$SC(=NR^{42})R^{41}$, —$SC(=NR^{42})OR^{41}$, —$SC(=NR^{42})SR^{41}$, —$SC(=NR^{42})N(R^{42})_2$, —$C(=S)R^{41}$, —$C(=S)OR^{41}$, —$C(=S)SR^{41}$, —$C(=S)N(R^{42})_2$, —$OC(=S)R^{41}$, —$OC(=S)OR^{41}$, —$OC(=S)SR^{41}$, —$OC(=S)N(R^{42})_2$, —$NR^{42}C(=S)R^{42}$, —$NR^{42}C(=S)OR^{41}$, —$NR^{42}C(=S)SR^{41}$, —$NR^{42}C(=S)N(R^{42})_2$, —$SC(=S)R^{41}$, —$SC(=S)OR^{41}$, —$SC(=S)SR^{41}$, —$SC(=S)N(R^{42})_2$, —$S(=O)R^{41}$, —$SO_2R^{41}$, —$NR^{42}SO_2R^{41}$, —$SO_2N(R^{42})_2$, —CN, —SCN, or —$NO_2$;

$R^4$ is hydrogen, halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, —$OR^{41}$, —$N(R^{42})_2$, —$SR^{41}$, —$C(=O)R^{41}$, —$C(=O)OR^{41}$, —$C(=O)SR^{41}$, —$C(=O)N(R^{42})_2$, —$OC(=O)R^{41}$, —$OC(=O)OR^{41}$, —$OC(=O)SR^{41}$, —$OC(=O)N(R^{42})_2$, —$NR^{42}C(=O)R^{42}$, —$NR^{42}C(=O)OR^{41}$, —$NR^{42}C(=O)SR^{41}$, —$NR^{42}C(=O)N(R^{42})_2$, —$SC(=O)R^{41}$, —$SC(=O)OR^{41}$, —$SC(=O)SR^{41}$, —$SC(=O)N(R^{42})_2$, —$C(=NR^{42})R^{41}$, —$C(=NR^{42})OR^{41}$, —$C(=NR^{42})SR^{41}$, —$C(=NR^{42})N(R^{42})_2$, —$OC(=NR^{42})R^{41}$, —$OC(=NR^{42})OR^{41}$, —$OC(=NR^{42})SR^{41}$, —$OC(=NR^{42})N(R^{42})_2$, —$NR^{42}C(=NR^{42})R^{42}$, —$NR^{42}C$ (=NR$^{A2}$)OR$^{A1}$, —NR$^{A2}$C(=NR$^{A2}$)SR$^{A1}$, —NR$^{A2}$C(=NR$^{A2}$)N(R$^{A2}$)$_2$, —SC(=NR$^{A2}$)R$^{A1}$, —SC(=NR$^{A2}$)OR$^{A1}$, —SC(=NR$^{A2}$)SR$^{A1}$, —SC(=NR$^{A2}$)N(R$^{A2}$)$_2$, —C(=S)R$^{A1}$, —C(=S)OR$^{A1}$, —C(=S)SR$^{A1}$, —C(=S)N(R$^{A2}$)$_2$, —OC(=S)R$^{A1}$, —OC(=S)OR$^{A1}$, —OC(=S)SR$^{A1}$, —OC(=S)N(R$^{A2}$)$_2$, —NR$^{A2}$C(=S)R$^{A2}$, —NR$^{A2}$C(=S)OR$^{A1}$, —NR$^{A2}$C(=S)SR$^{A1}$, —NR$^{A2}$C(=S)N(R$^{A2}$)$_2$, —SC(=S)R$^{A1}$, —SC(=S)OR$^{A1}$, —SC(=S)SR$^{A1}$, —SC(=S)N(R$^{A2}$)$_2$, —S(=O)R$^{A1}$, —SO$_2$R$^{A1}$, —NR$^{A2}$SO$_2$R$^{A1}$, —SO$_2$N(R$^{A2}$)$_2$, —CN, —SCN, or —NO$_2$;

R$^4$ is substituted with an imaging moiety selected from the group consisting of $^{18}$F, $^{76}$Br, $^{124}$I, and $^{131}$I; or is associated with an imaging moiety selected from the group consisting of $^{64}$Cu, $^{89}$Zr, $^{99m}$Tc, and $^{111}$In through a chelator; or is an imaging moiety selected from the group consisting of $^{18}$F, $^{76}$Br, $^{124}$I, and $^{131}$I;

each occurrence of R$^{A1}$ is independently hydrogen, optionally substituted alkyl, optionally substituted alkenyl, optionally substituted alkynyl, optionally substituted carbocyclyl, optionally substituted heterocyclyl, optionally substituted aryl, or optionally substituted heteroaryl; and each occurrence of R$^{A2}$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, or an amino protecting group, or two R$^{A2}$ groups are joined to form an optionally substituted heterocyclic ring; or a salt thereof.

For a compound of Formula (VI), any suitable combination of R$^1$, R$^2$, R$^3$, R$^4$, and L groups may be used as described herein. For example, wherein R$^1$ is as described in connection with a compound of Formula (IV) or (Ia)-(Id), R$^3$ and/or R$^4$ is as described in connection with a compound of Formula (IIa) or (IV), and/or L is as described in connection with a compound of Formula (Ia)-(Id). In some cases, R$^2$ is halogen. In certain embodiments, the imaging moiety is $^{18}$F. In certain embodiments, the imaging moiety is $^{76}$Br. In certain embodiments, the imaging moiety is $^{124}$I. In certain embodiments, the imaging moiety is $^{131}$I. In some cases, the imaging moiety is not $^{131}$I. In some cases, the imaging moiety is $^{18}$F, $^{76}$Br, or $^{124}$I. In some cases, the imaging moiety is $^{18}$F or $^{76}$Br.

In some embodiments, a compound of Formula (VI) comprises the structure:

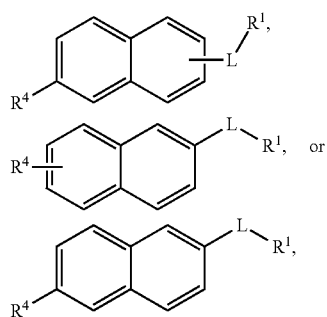

wherein R$^1$, R$^4$, and L are as described herein. For example, wherein R$^1$ is as described in connection with a compound of Formula (IV) or (Ia)-(Id), R$^4$ is as described in connection with a compound of Formula (IIa) or (IV), and/or L is as described in connection with a compound of Formula (Ia)-(Id). In some embodiments, a compound of Formula (VI) has the structure:

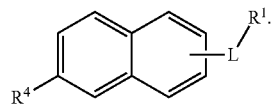

In some embodiments, a compound of Formula (VI) comprises the structure:

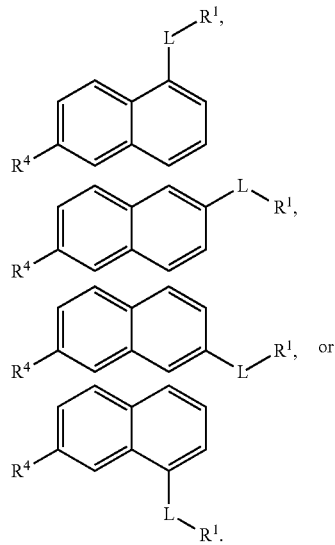

In some embodiments, a compound of Formula (VI) comprises the structure:

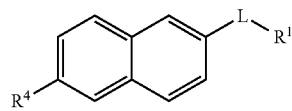

In some embodiments, a compound of Formula (VI) comprises the structure:

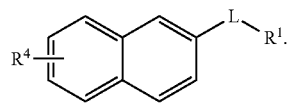

In some embodiments, a compound of Formula (VI) comprises the structure:

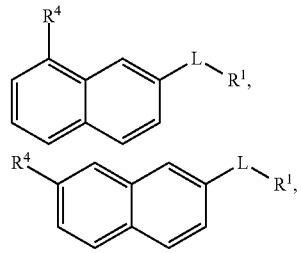

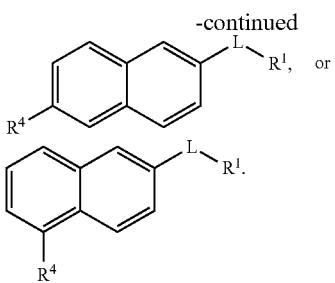

In some embodiments, a compound is provided comprising the formula:

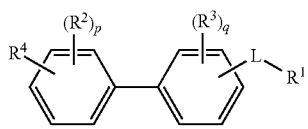

wherein

L is a bond; substituted or unsubstituted, cyclic or acyclic alkylene; substituted or unsubstituted, cyclic or acyclic alkenylene; substituted or unsubstituted, cyclic or acyclic alkynylene; or substituted or unsubstituted, cyclic or acyclic heteroaliphatic;

$R^1$ is a substituted or unsubstituted nitrogen-containing moiety;

$R^2$ is hydrogen, halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, —$OR^{A1}$, —$N(R^{A2})_2$, —$SR^{A1}$, —$C(=O)R^{A1}$, —$C(=O)OR^{A1}$, —$C(=O)SR^{A1}$, —$C(=O)N(R^{A2})_2$, —$OC(=O)R^{A1}$, —$OC(=O)OR^{A1}$, —$OC(=O)SR^{A1}$, —$OC(=O)N(R^{A2})_2$, —$NR^{A2}C(=O)R^{A2}$, —$NR^{A2}C(=O)OR^{A1}$, —$NR^{A2}C(=O)SR^{A1}$, —$NR^{A2}C(=O)N(R^{A2})_2$, —$SC(=O)R^{A1}$, —$SC(=O)OR^{A1}$, —$SC(=O)SR^{A1}$, —$SC(=O)N(R^{A2})_2$, —$C(=NR^{A2})R^{A1}$, —$C(=NR^{A2})OR^{A1}$, —$C(=NR^{A2})SR^{A1}$, —$C(=NR^{A2})N(R^{A2})_2$, —$OC(=NR^{A2})R^{A1}$, —$OC(=NR^{A2})OR^{A1}$, —$OC(=NR^{A2})SR^{A1}$, —$OC(=NR^{A2})N(R^{A2})_2$, —$NR^{A2}C(=NR^{A2})R^{A2}$, —$NR^{A2}C(=NR^{A2})OR^{A1}$, —$NR^{A2}C(=NR^{A2})SR^{A1}$, —$NR^{A2}C(=NR^{A2})N(R^{A2})_2$, —$SC(=NR^{A2})R^{A1}$, —$SC(=NR^{A2})OR^{A1}$, —$SC(=NR^{A2})SR^{A1}$, —$SC(=NR^{A2})N(R^{A2})_2$, —$C(=S)R^{A1}$, —$C(=S)OR^{A1}$, —$C(=S)SR^{A1}$, —$C(=S)N(R^{A2})_2$, —$OC(=S)R^{A1}$, —$OC(=S)OR^{A1}$, —$OC(=S)SR^{A1}$, —$OC(=S)N(R^{A2})_2$, —$NR^{A2}C(=S)R^{A2}$, —$NR^{A2}C(=S)OR^{A1}$, —$NR^{A2}C(=S)SR^{A1}$, —$NR^{A2}C(=S)N(R^{A2})_2$, —$SC(=S)R^{A1}$, —$SC(=S)OR^{A1}$, —$SC(=S)SR^{A1}$, —$SC(=S)N(R^{A2})_2$, —$S(=O)R^{A1}$, —$SO_2R^{A1}$, —$NR^{A2}SO_2R^{A1}$, —$SO_2N(R^{A2})_2$, —CN, —SCN, or —$NO_2$;

$R^3$ is hydrogen, halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, —$OR^{A1}$, —$N(R^{A2})_2$, —$SR^{A1}$, —$C(=O)R^{A1}$, —$C(=O)OR^{A1}$, —$C(=O)SR^{A1}$, —$C(=O)N(R^{A2})_2$, —$OC(=O)R^{A1}$, —$OC(=O)OR^{A1}$, —$OC(=O)SR^{A1}$, —$OC(=O)N(R^{A2})_2$, —$NR^{A2}C(=O)R^{A2}$, —$NR^{A2}C(=O)OR^{A1}$, —$NR^{A2}C(=O)SR^{A1}$, —$NR^{A2}C(=O)N(R^{A2})_2$, —$SC(=O)R^{A1}$, —$SC(=O)OR^{A1}$, —$SC(=O)SR^{A1}$, —$SC(=O)N(R^{A2})_2$, —$C(=NR^{A2})R^{A1}$, —$C(=NR^{A2})OR^{A1}$, —$C(=NR^{A2})SR^{A1}$, —$C(=NR^{A2})N(R^{A2})_2$, —$OC(=NR^{A2})R^{A1}$, —$OC(=NR^{A2})OR^{A1}$, —$OC(=NR^{A2})SR^{A1}$, —$OC(=NR^{A2})N(R^{A2})_2$, —$NR^{A2}C(=NR^{A2})R^{A2}$, —$NR^{A2}C(=NR^{A2})OR^{A1}$, —$NR^{A2}C(=NR^{A2})SR^{A1}$, —$NR^{A2}C(=NR^{A2})N(R^{A2})_2$, —$SC(=NR^{A2})R^{A1}$, —$SC(=NR^{A2})OR^{A1}$, —$SC(=NR^{A2})SR^{A1}$, —$SC(=NR^{A2})N(R^{A2})_2$, —$C(=S)R^{A1}$, —$C(=S)OR^{A1}$, —$C(=S)SR^{A1}$, —$C(=S)N(R^{A2})_2$, —$OC(=S)R^{A1}$, —$OC(=S)OR^{A1}$, —$OC(=S)SR^{A1}$, —$OC(=S)N(R^{A2})_2$, —$NR^{A2}C(=S)R^{A2}$, —$NR^{A2}C(=S)OR^{A1}$, —$NR^{A2}C(=S)SR^{A1}$, —$NR^{A2}C(=S)N(R^{A2})_2$, —$SC(=S)R^{A1}$, —$SC(=S)OR^{A1}$, —$SC(=S)SR^{A1}$, —$SC(=S)N(R^{A2})_2$, —$S(=O)R^{A1}$, —$SO_2R^{A1}$, —$NR^{A2}SO_2R^{A1}$, —$SO_2N(R^{A2})_2$, —CN, —SCN, or —$NO_2$;

$R^4$ is hydrogen, halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, —$OR^{A1}$, —$N(R^{A2})_2$, —$SR^{A1}$, —$C(=O)R^{A1}$, —$C(=O)OR^{A1}$, —$C(=O)SR^{A1}$, —$C(=O)N(R^{A2})_2$, —$OC(=O)R^{A1}$, —$OC(=O)OR^{A1}$, —$OC(=O)SR^{A1}$, —$OC(=O)N(R^{A2})_2$, —$NR^{A2}C(=O)R^{A2}$, —$NR^{A2}C(=O)OR^{A1}$, —$NR^{A2}C(=O)SR^{A1}$, —$NR^{A2}C(=O)N(R^{A2})_2$, —$SC(=O)R^{A1}$, —$SC(=O)OR^{A1}$, —$SC(=O)SR^{A1}$, —$SC(=O)N(R^{A2})_2$, —$C(=NR^{A2})R^{A1}$, —$C(=NR^{A2})OR^{A1}$, —$C(=NR^{A2})SR^{A1}$, —$C(=NR^{A2})N(R^{A2})_2$, —$OC(=NR^{A2})R^{A1}$, —$OC(=NR^{A2})OR^{A1}$, —$OC(=NR^{A2})SR^{A1}$, —$OC(=NR^{A2})N(R^{A2})_2$, —$NR^{A2}C(=NR^{A2})R^{A2}$, —$NR^{A2}C(=NR^{A2})OR^{A1}$, —$NR^{A2}C(=NR^{A2})SR^{A1}$, —$NR^{A2}C(=NR^{A2})N(R^{A2})_2$, —$SC(=NR^{A2})R^{A1}$, —$SC(=NR^{A2})OR^{A1}$, —$SC(=NR^{A2})SR^{A1}$, —$SC(=NR^{A2})N(R^{A2})_2$, —$C(=S)R^{A1}$, —$C(=S)OR^{A1}$, —$C(=S)SR^{A1}$, —$C(=S)N(R^{A2})_2$, —$OC(=S)R^{A1}$, —$OC(=S)OR^{A1}$, —$OC(=S)SR^{A1}$, —$OC(=S)N(R^{A2})_2$, —$NR^{A2}C(=S)R^{A2}$, —$NR^{A2}C(=S)OR^{A1}$, —$NR^{A2}C(=S)SR^{A1}$, —$NR^{A2}C(=S)N(R^{A2})_2$, —$SC(=S)R^{A1}$, —$SC(=S)OR^{A1}$, —$SC(=S)SR^{A1}$, —$SC(=S)N(R^{A2})_2$, —$S(=O)R^{A1}$, —$SO_2R^{A1}$, —$NR^{A2}SO_2R^{A1}$, —$SO_2N(R^{A2})_2$, —CN, —SCN, or —$NO_2$;

wherein $R^4$ is substituted with an imaging moiety selected from the group consisting of $^{18}$F, $^{76}$Br, $^{124}$I, and $^{131}$I; or is associated with an imaging moiety selected from the group consisting of $^{64}$Cu, $^{89}$Zr, $^{99m}$Tc, and $^{111}$In through a chelator; or is an imaging moiety selected from the group consisting of $^{18}$F, $^{76}$Br, $^{124}$I, and $^{131}$I;

wherein p and q are independently 0, 1, 2, 3, or 4.

each occurrence of $R^{A1}$ is independently hydrogen, optionally substituted alkyl, optionally substituted alkenyl, optionally substituted alkynyl, optionally substituted carbocyclyl, optionally substituted heterocyclyl, optionally substituted aryl, or optionally substituted heteroaryl; and each occurrence of $R^{A2}$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, or an amino protecting group, or two $R^{A2}$ groups are joined to form an optionally substituted heterocyclic ring; or a salt thereof.

In some embodiments, a compound is provided comprising Formula (VII):

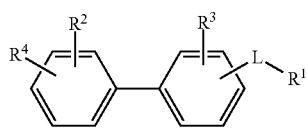

(VII)

wherein

L is a bond; substituted or unsubstituted, cyclic or acyclic alkylene; substituted or unsubstituted, cyclic or acyclic alkenylene; substituted or unsubstituted, cyclic or acyclic alkynylene; or substituted or unsubstituted, cyclic or acyclic heteroaliphatic;

$R^1$ is a substituted or unsubstituted nitrogen-containing moiety;

$R^2$ is hydrogen, halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, $-OR^{A1}$, $-N(R^{A2})_2$, $-SR^{A1}$, $-C(=O)R^{A1}$, $-C(=O)OR^{A1}$, $-C(=O)SR^{A1}$, $-C(=O)N(R^{A2})_2$, $-OC(=O)R^{A1}$, $-OC(=O)OR^{A1}$, $-OC(=O)SR^{A1}$, $-OC(=O)N(R^{A2})_2$, $-NR^{A2}C(=O)R^{A2}$, $-NR^{A2}C(=O)OR^{A1}$, $-NR^{A2}C(=O)SR^{A1}$, $-NR^{A2}C(=O)N(R^{A2})_2$, $-SC(=O)R^{A1}$, $-SC(=O)OR^{A1}$, $-SC(=O)SR^{A1}$, $-SC(=O)N(R^{A2})_2$, $-C(=NR^{A2})R^{A1}$, $-C(=NR^{A2})OR^{A1}$, $-C(=NR^{A2})SR^{A1}$, $-C(=NR^{A2})N(R^{A2})_2$, $-OC(=NR^{A2})R^{A1}$, $-OC(=NR^{A2})OR^{A1}$, $-OC(=NR^{A2})SR^{A1}$, $-OC(=NR^{A2})N(R^{A2})_2$, $-NR^{A2}C(=NR^{A2})R^{A2}$, $-NR^{A2}C(=NR^{A2})OR^{A1}$, $-NR^{A2}C(=NR^{A2})SR^{A1}$, $-NR^{A2}C(=NR^{A2})N(R^{A2})_2$, $-SC(=NR^{A2})R^{A1}$, $-SC(=NR^{A2})OR^{A1}$, $-SC(=NR^{A2})SR^{A1}$, $-SC(=NR^{A2})N(R^{A2})_2$, $-C(=S)R^{A1}$, $-C(=S)OR^{A1}$, $-C(=S)SR^{A1}$, $-C(=S)N(R^{A2})_2$, $-OC(=S)R^{A1}$, $-OC(=S)OR^{A1}$, $-OC(=S)SR^{A1}$, $-OC(=S)N(R^{A2})_2$, $-NR^{A2}C(=S)R^{A2}$, $-NR^{A2}C(=S)OR^{A1}$, $-NR^{A2}C(=S)SR^{A1}$, $-NR^{A2}C(=S)N(R^{A2})_2$, $-SC(=S)R^{A1}$, $-SC(=S)OR^{A1}$, $-SC(=S)SR^{A1}$, $-SC(=S)N(R^{A2})_2$, $-S(=O)R^{A1}$, $-SO_2R^{A1}$, $-NR^{A2}SO_2R^{A1}$, $-SO_2N(R^{A2})_2$, $-CN$, $-SCN$, or $-NO_2$;

$R^3$ is hydrogen, halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, $-OR^{A1}$, $-N(R^{A2})_2$, $-SR^{A1}$, $-C(=O)R^{A1}$, $-C(=O)OR^{A1}$, $-C(=O)SR^{A1}$, $-C(=O)N(R^{A2})_2$, $-OC(=O)R^{A1}$, $-OC(=O)OR^{A1}$, $-OC(=O)SR^{A1}$, $-OC(=O)N(R^{A2})_2$, $-NR^{A2}C(=O)R^{A2}$, $-NR^{A2}C(=O)OR^{A1}$, $-NR^{A2}C(=O)SR^{A1}$, $-NR^{A2}C(=O)N(R^{A2})_2$, $-SC(=O)R^{A1}$, $-SC(=O)OR^{A1}$, $-SC(=O)SR^{A1}$, $-SC(=O)N(R^{A2})_2$, $-C(=NR^{A2})R^{A1}$, $-C(=NR^{A2})OR^{A1}$, $-C(=NR^{A2})SR^{A1}$, $-C(=NR^{A2})N(R^{A2})_2$, $-OC(=NR^{A2})R^{A1}$, $-OC(=NR^{A2})OR^{A1}$, $-OC(=NR^{A2})SR^{A1}$, $-OC(=NR^{A2})N(R^{A2})_2$, $-NR^{A2}C(=NR^{A2})R^{A2}$, $-NR^{A2}C(=NR^{A2})OR^{A1}$, $-NR^{A2}C(=NR^{A2})SR^{A1}$, $-NR^{A2}C(=NR^{A2})N(R^{A2})_2$, $-SC(=NR^{A2})R^{A1}$, $-SC(=NR^{A2})OR^{A1}$, $-SC(=NR^{A2})SR^{A1}$, $-SC(=NR^{A2})N(R^{A2})_2$, $-C(=S)R^{A1}$, $-C(=S)OR^{A1}$, $-C(=S)SR^{A1}$, $-C(=S)N(R^{A2})_2$, $-OC(=S)R^{A1}$, $-OC(=S)OR^{A1}$, $-OC(=S)SR^{A1}$, $-OC(=S)N(R^{A2})_2$, $-NR^{A2}C(=S)R^{A2}$, $-NR^{A2}C(=S)OR^{A1}$, $-NR^{A2}C(=S)SR^{A1}$, $-NR^{A2}C(=S)N(R^{A2})_2$, $-SC(=S)R^{A1}$, $-SC(=S)OR^{A1}$, $-SC(=S)SR^{A1}$, $-SC(=S)N(R^{A2})_2$, $-S(=O)R^{A1}$, $-SO_2R^{A1}$, $-NR^{A2}SO_2R^{A1}$, $-SO_2N(R^{A2})_2$, $-CN$, $-SCN$, or $-NO_2$;

$R^4$ is hydrogen, halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, $-OR^{A1}$, $-N(R^{A2})_2$, $-SR^{A1}$, $-C(=O)R^{A1}$, $-C(=O)OR^{A1}$, $-C(=O)SR^{A1}$, $-C(=O)N(R^{A2})_2$, $-OC(=O)R^{A1}$, $-OC(=O)OR^{A1}$, $-OC(=O)SR^{A1}$, $-OC(=O)N(R^{A2})_2$, $-NR^{A2}C(=O)R^{A2}$, $-NR^{A2}C(=O)OR^{A1}$, $-NR^{A2}C(=O)SR^{A1}$, $-NR^{A2}C(=O)N(R^{A2})_2$, $-SC(=O)R^{A1}$, $-SC(=O)OR^{A1}$, $-SC(=O)SR^{A1}$, $-SC(=O)N(R^{A2})_2$, $-C(=NR^{A2})R^{A1}$, $-C(=NR^{A2})OR^{A1}$, $-C(=NR^{A2})SR^{A1}$, $-C(=NR^{A2})N(R^{A2})_2$, $-OC(=NR^{A2})R^{A1}$, $-OC(=NR^{A2})OR^{A1}$, $-OC(=NR^{A2})SR^{A1}$, $-OC(=NR^{A2})N(R^{A2})_2$, $-NR^{A2}C(=NR^{A2})R^{A2}$, $-NR^{A2}C(=NR^{A2})OR^{A1}$, $-NR^{A2}C(=NR^{A2})SR^{A1}$, $-NR^{A2}C(=NR^{A2})N(R^{A2})_2$, $-SC(=NR^{A2})R^{A1}$, $-SC(=NR^{A2})OR^{A1}$, $-SC(=NR^{A2})SR^{A1}$, $-SC(=NR^{A2})N(R^{A2})_2$, $-C(=S)R^{A1}$, $-C(=S)OR^{A1}$, $-C(=S)SR^{A1}$, $-C(=S)N(R^{A2})_2$, $-OC(=S)R^{A1}$, $-OC(=S)OR^{A1}$, $-OC(=S)SR^{A1}$, $-OC(=S)N(R^{A2})_2$, $-NR^{A2}C(=S)R^{A2}$, $-NR^{A2}C(=S)OR^{A1}$, $-NR^{A2}C(=S)SR^{A1}$, $-NR^{A2}C(=S)N(R^{A2})_2$, $-SC(=S)R^{A1}$, $-SC(=S)OR^{A1}$, $-SC(=S)SR^{A1}$, $-SC(=S)N(R^{A2})_2$, $-S(=O)R^{A1}$, $-SO_2R^{A1}$, $-NR^{A2}SO_2R^{A1}$, $-SO_2N(R^{A2})_2$, $-CN$, $-SCN$, or $-NO_2$;

wherein $R^4$ is substituted with an imaging moiety selected from the group consisting of $^{18}F$, $^{76}Br$, $^{124}I$, and $^{131}I$; or is associated with an imaging moiety selected from the group consisting of $^{64}Cu$, $^{89}Zr$, $^{99m}Tc$, and $^{111}In$ through a chelator; or is an imaging moiety selected from the group consisting of $^{18}F$, $^{76}Br$, $^{124}I$, and $^{131}I$;

each occurrence of $R^{A1}$ is independently hydrogen, optionally substituted alkyl, optionally substituted alkenyl, optionally substituted alkynyl, optionally substituted carbocyclyl, optionally substituted heterocyclyl, optionally substituted aryl, or optionally substituted heteroaryl; and each occurrence of $R^{A2}$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, or an amino protecting group, or two $R^{A2}$ groups are joined to form an optionally substituted heterocyclic ring; or a salt thereof.

For a compound of Formula (VII), any suitable combination of $R^1$, $R^2$, $R^3$, $R^4$, and L groups may be used as described herein. For example, wherein $R^1$ is as described in connection with a compound of Formula (IV) or (Ia)-(Id), $R^3$ and/or $R^4$ is as described in connection with a compound of Formula (IIa) or (IV), and/or L is as described in connection with a compound of Formula (Ia)-(Id). In certain embodiments, the imaging moiety is $^{18}F$. In certain embodiments, the imaging moiety is $^{76}Br$. In certain embodiments, the imaging moiety is $^{124}I$. In certain embodiments, the imaging moiety is $^{131}I$. In some cases, the imaging moiety is not $^{131}I$. In some cases, the imaging moiety is $^{18}F$, $^{76}Br$, or $^{124}I$. In some cases, the imaging moiety is $^{18}F$ or $^{76}Br$.

In some embodiments, a compound of Formula (VII) comprises the structure:

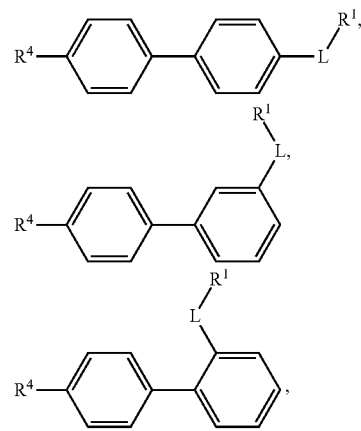

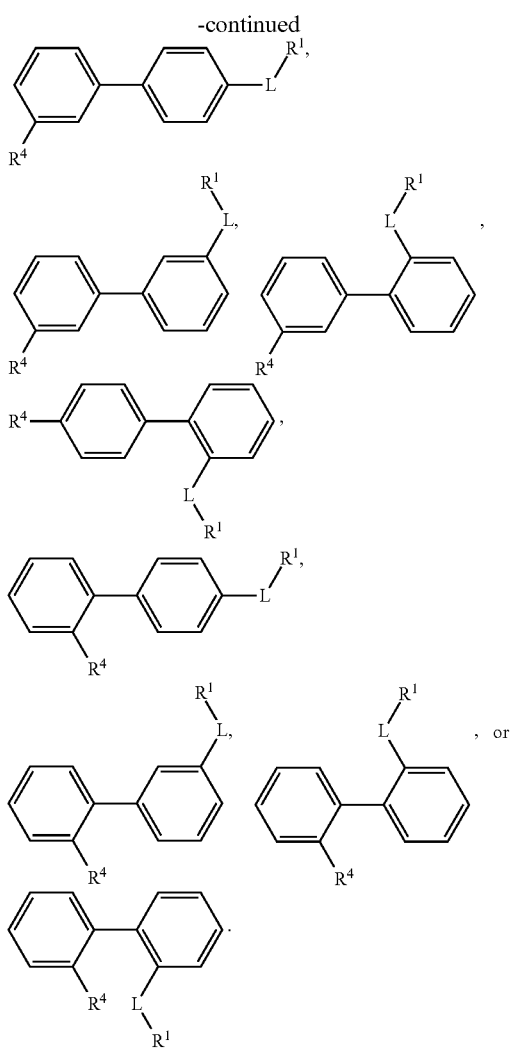

wherein R¹, R⁴, and L are as described herein. For example, wherein R¹ is as described in connection with a compound of Formula (IV) or (Ia)-(Id), R⁴ is as described in connection with a compound of Formula (IIa) or (IV), and/or L is as described in connection with a compound of Formula (Ia)-(Id). The above compounds may optionally be substituted with R² and/or R³ (e.g., as described for Formula (VII)).

In some embodiments, a compound of Formula (VII) comprises the structure:

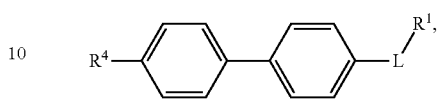

wherein $R^1$, $R^4$, and L are as described herein. For example, wherein $R^1$ is as described in connection with a compound of Formula (IV) or (Ia)-(Id), $R^4$ is as described in connection with a compound of Formula (IIa) or (IV), and/or L is as described in connection with a compound of Formula (Ia)-(Id).

In some embodiments, one or more of L, $R^1$, $R^2$, $R^3$, $R^4$, $R^5$, and $R^6$ of a compound of Formula (Ia)-(Id), (IIa)-(IIb), (III), (IV), (Va)-(Vd), (VI), or (VII) are selected from Table A. In certain embodiments, L or $R^1$ of a compound of Formula (Ia), (Ib), (Ic), or (Id) is selected from Table A. In certain embodiments, L and $R^1$ of a compound of Formula (Ia), (Ib), (Ic), or (Id) are selected from Table A. In some embodiments, one of L, $R^1$, $R^2$, $R^3$, $R^4$, $R^5$, and $R^6$ of a compound of Formula (IIa) or (IIb) is selected from Table A. In certain embodiments, two, three, four, five, six, or all of L, $R^1$, $R^2$, $R^3$, $R^4$, $R^5$, and $R^6$ of a compound of Formula (IIa) or (IIb) are selected from Table A. In some embodiments, one of L, $R^1$, $R^3$, and $R^4$ of a compound of Formula (III) is selected from Table A. In certain embodiments, two, three, or all of L, $R^1$, $R^3$, and $R^4$ of a compound of Formula (III) are selected from Table A. In some embodiments, one of L, $R^1$, $R^3$, $R^4$, and $R^5$ of a compound of Formula (IV) is selected from Table A. In certain embodiments, two, three, four, or all of L, $R^1$, $R^3$, $R^4$, and $R^5$ of a compound of Formula (IV) are selected from Table A. In some embodiments, one of L, $R^1$, $R^2$, $R^3$, and $R^4$ of a compound of Formula (Va), (Vb), (Vc), (Vd), (VI), or (VII) is selected from Table A. In certain embodiments, two, three, four, or all of L, $R^1$, $R^2$, $R^3$, and $R^4$ of a compound of Formula (Va), (Vb), (Vc), (Vd), (VI), or (VII) are selected from Table A.

TABLE A

| L | $R^1$ | $R^2$ | $R^3$ | $R^4$ | $R^5$ | $R^6$ |
|---|---|---|---|---|---|---|
| bond | —NH₂ | —H | —H | —H | —H | —H |
| —CH₂— | —NHCH₃ | | —Br | —OCH₂CH₂F | —Br | —F |
| —CH₂CH₂— | —NHCH₂CH₃ | | —CF₃ | —OCH₂CH₂¹⁸F | —CF₃ | |
| —CH₂CH₂CH₂— | —NHCH₂CH₂CH₃ | | —O(CH₂)₂F | —OCH₂CH₂Im | —O(CH₂)₂F | |
| —(CH₂)₄— | 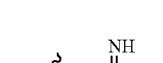 | | —O(CH₂)₂¹⁸F | —¹⁸F | —O(CH₂)₂¹⁸F | |
| —CH(CH₃)— | 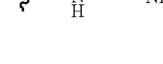 | | —O(CH₂)₂Im | —Im | —O(CH₂)₂Im | |

TABLE A-continued
| L | R¹ | R² | R³ | R⁴ | R⁵ | R⁶ |
|---|---|---|---|---|---|---|
| —CH₂O— | 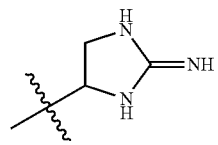 [SMILES: *C1CNC(=N)N1] | | —OH | —CH₂¹⁸F | —OH | |
| —CH₂CH₂O— | 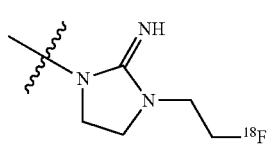 [SMILES: *N1CCN(CC[18F])C1=N] | | —Cl | —CH₂Im | —Cl | |
| —(CH₂)₃O— | 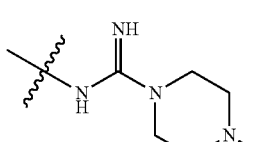 | | —I | —CH₂O(CH₂)₄¹⁸F | —I | |
| —OCH₂— | 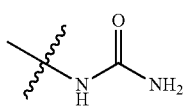 | | —CH₃ | —CH₂O(CH₂)₄Im | —CH₃ | |
| —OCH₂CH₂— | 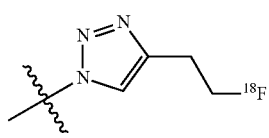 [SMILES: *n1cc(CC[18F])nn1] | | —CN | —CH₂CH₂¹⁸F | —CN | |
| —O(CH₂)₃— | 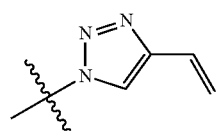 [SMILES: *n1cc(C=C)nn1] | | —OCH₃ | —CH₂CH₂Im | —OCH₃ | |
| 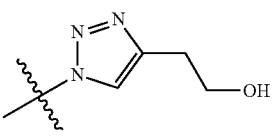 [SMILES: *n1cc(CCO)nn1] | 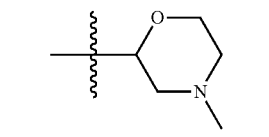 [SMILES: *C1CN(C)CCO1] | | | —CH₂CH₃ | | |
| 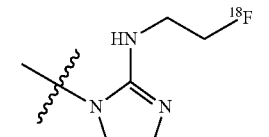 | 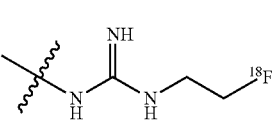 [SMILES: *NC(=N)NCC[18F]] | | | —CH₂CH₂CH₂¹⁸F | | |
| 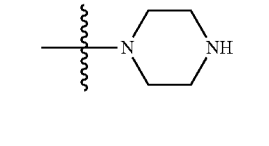 [SMILES: *N1CCNCC1] |  | | | —CH₂CH₂CH₂Im | | |
| —CH(CH₃)CH₂— |  | | | —OH | | |
| —CH₂CH(CH₃)— |  | | | —Br | | |

US 9,550,000 B2
TABLE A-continued
| L | R¹ | R² | R³ | R⁴ | R⁵ | R⁶ |
|---|----|----|----|----|----|----|
| —CH=CH— | 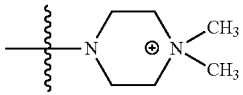 | | | —O(CH$_2$)$_3$$^{18}$F | | |
| 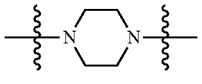 | 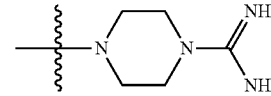 | | | —O(CH$_2$)$_3$IM | | |
| —CH=N— | 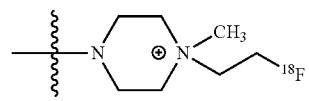 | | | —(CH$_2$)$_4$$^{18}$F | | |
| —NHCH$_2$CH$_2$— | 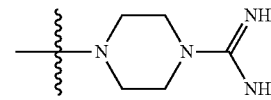 | | | —(CH$_2$)$_4$IM | | |
| | 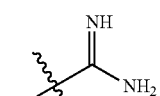 | | | —O(CH$_2$)$_4$$^{18}$F | | |
| | 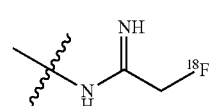 | | | —O(CH$_2$)$_4$Im | | |
| | 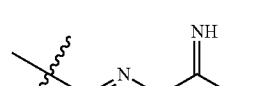 | | | 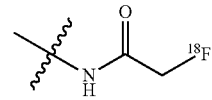 [SMILES: *NC(=O)C[18F]] | | |
| | 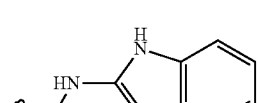 | | | 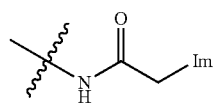 | | |
| | 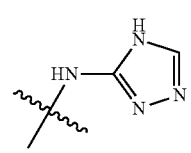 | | | 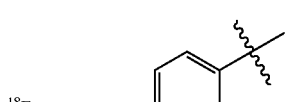 | | |
| | 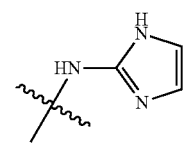 | | | 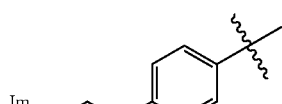 | | |
| | 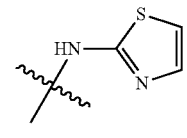 | | —OCH$_2$$^{18}$F | | | |
| | 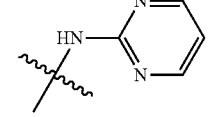 | | —OCH$_2$Im | | | |

TABLE A-continued

| L | R¹ | R² | R³ | R⁴ | R⁵ | R⁶ |
|---|----|----|----|----|----|----|

TABLE A-continued

| L | R¹ | R² | R³ | R⁴ | R⁵ | R⁶ |
|---|----|----|----|----|----|----|

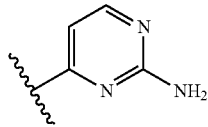

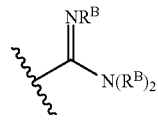

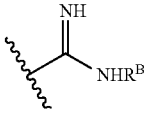

In some cases, a compound is provided of comprising the formula:

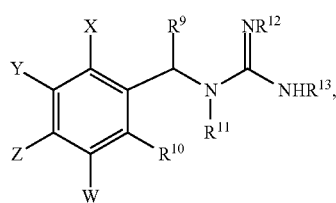

wherein

R⁹ and R¹⁰ are independently selected from the group consisting of H, —OR¹¹, F, Cl, Br, I, —CF₃, alkyl(C₁-C₄), and imaging moiety (I$_m$);

R¹¹, R¹² and R¹³ are selected from the group consisting of H, alkyl, and aryl; and W and X are independently selected from the group consisting of H, —OR₄, —N(R¹¹)₂, F, Cl, Br, —CF₃, I, aryl, and heteroaryl;

wherein A) Y and Z are independently selected from the group consisting of —CH—, —CH₂—, —O—, —N—, —NR¹¹—, and —CH=CH— when a linking group Q between Y and Z is present or absent, wherein Q is selected from the group consisting of —CH—, —CH₂—, —CR¹¹—, —N—, —NH—, —NR¹¹—, —O—, and —S—; or B) Y and Z are independently selected from the group consisting of H, —OR₄, —N(R¹¹)₂, F, Cl, Br, —CF₃, I$_m$, aryl, and heteroaryl when linking group Q is absent;

wherein I$_m$ is selected from the group consisting of ¹⁸F, ⁷⁶Br, ¹²⁴I, and ¹³¹I, and is present in either W—Z or R⁹-R¹³; or a salt thereof, provided the compound is not of the formula:

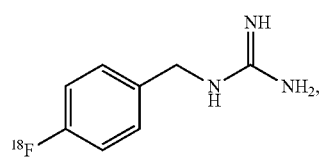

-continued

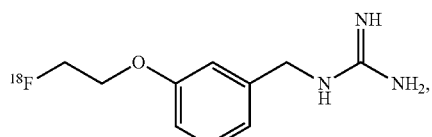

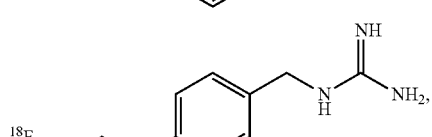

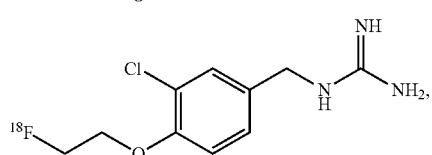

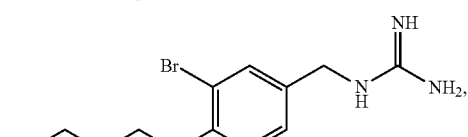

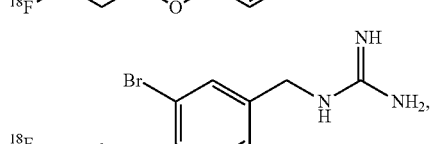

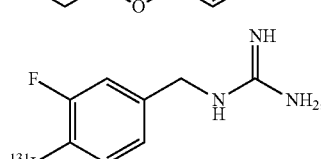

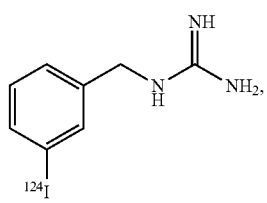

-continued

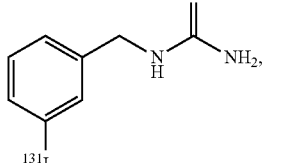

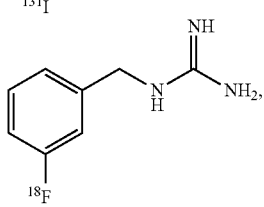

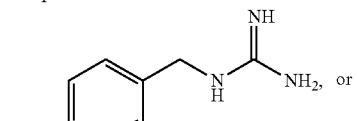

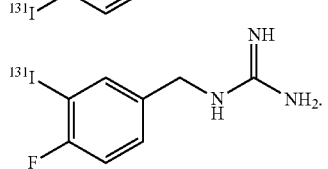

In some cases, a compound is provided comprising the formula:

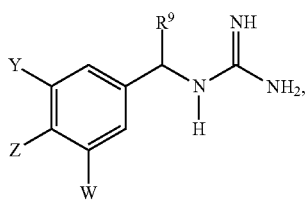

wherein $R^9$ is independently selected from the group consisting of H, —$CF_3$, and alkyl($C_1$-$C_4$);

W, Y and Z are independently selected from the group consisting of H, —$OR^{11}$, $N(R^{11})_2$, F, Cl, Br, —$CF_3$, $I_m$, aryl and heteroaryl; and $R^{11}$ is selected from the group consisting of H, alkyl, and aryl;

wherein $I_m$ is selected from the group consisting of $^{18}F$, $^{76}Br$, $^{124}I$, and $^{131}I$, and is present in either W, Y, Z, $R^9$, or $R^{11}$; or a salt thereof;

provided the compound is not of the formula:

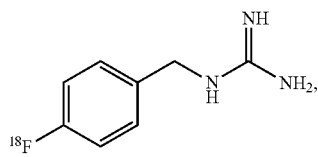

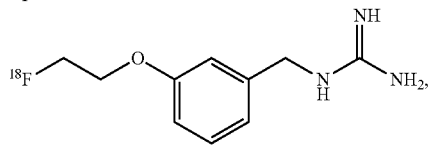

-continued

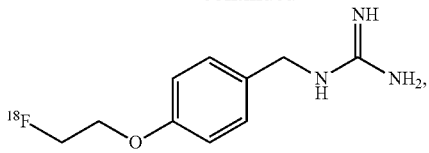

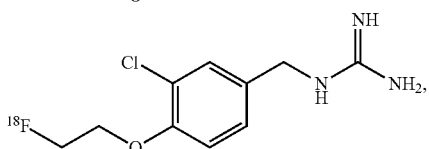

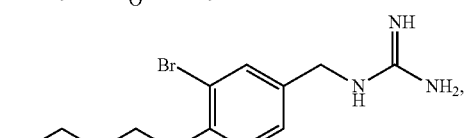

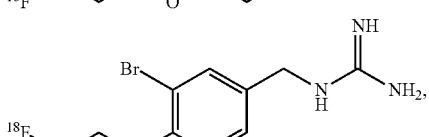

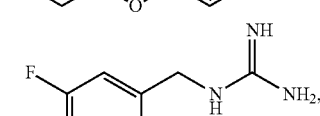

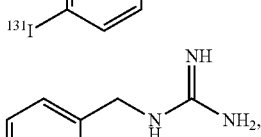

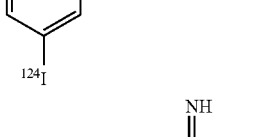

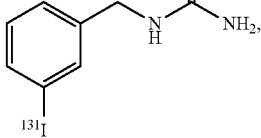

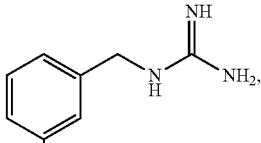

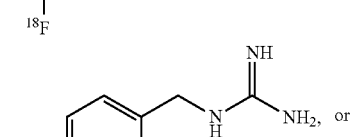

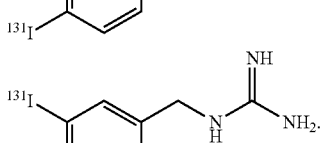

In some cases, a compound is provided comprising the formula:

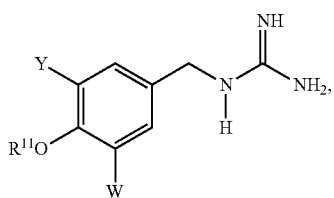
wherein W and Y are independently selected from the group consisting of H, —OR[11], F, Cl, Br, —CF$_3$, and I$_m$; and R[11] is alkyl,
wherein Im is selected from the group consisting of $^{18}$F, $^{76}$Br, $^{124}$I, and $^{131}$I, and is present in either W, Y, or R[11]; or a salt thereof;
provided the compound is not of the formula:
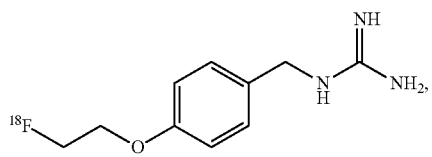
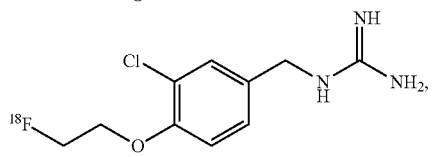
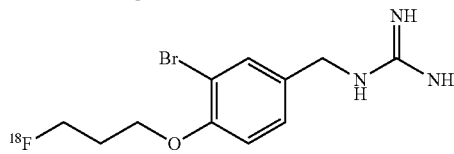, or
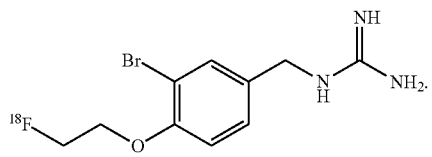.
In some embodiments, a compound comprises the formula:
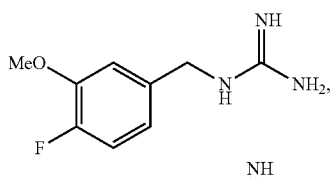
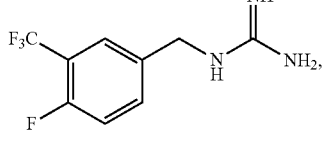
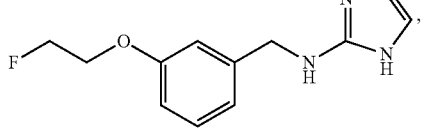
-continued
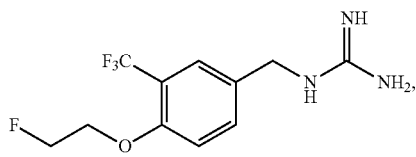
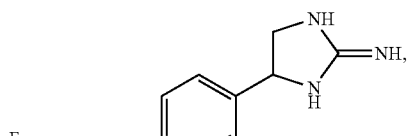
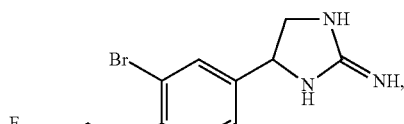
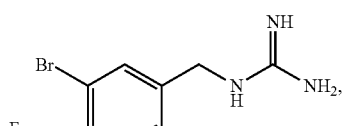,
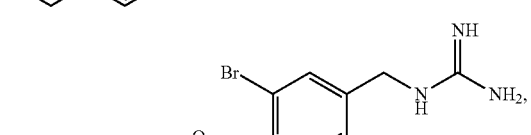
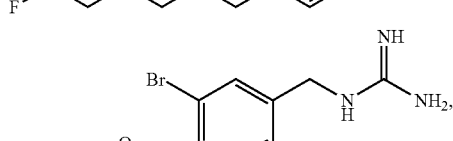
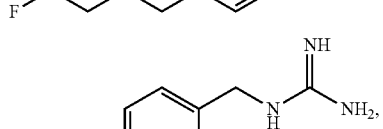,
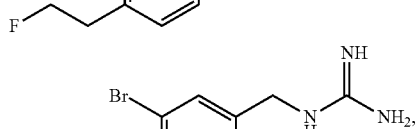,
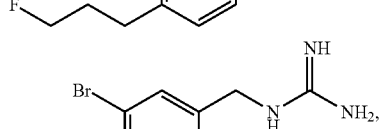,
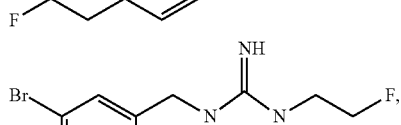,
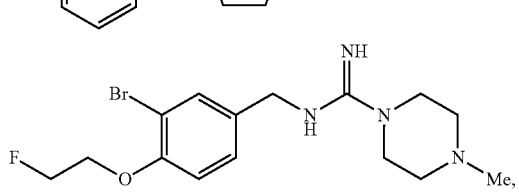

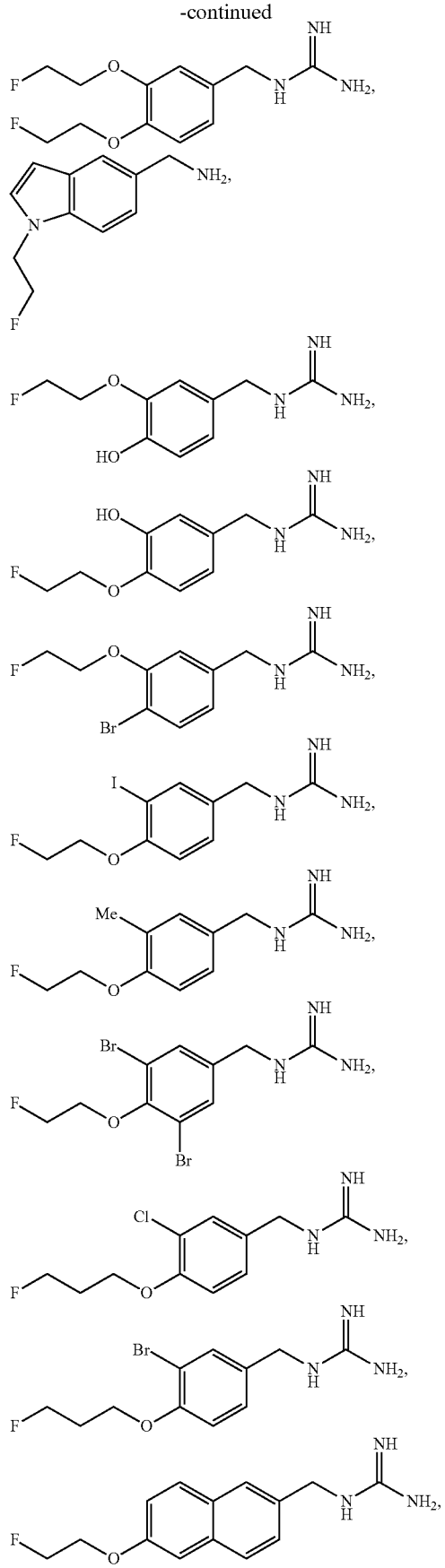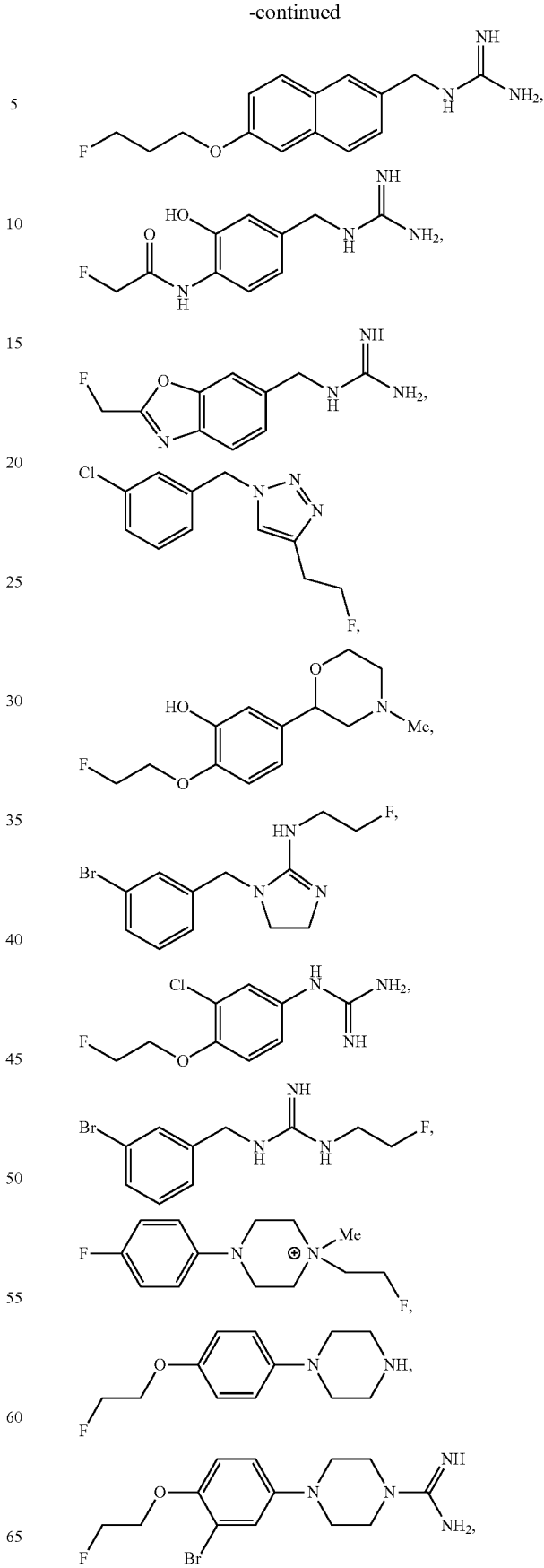

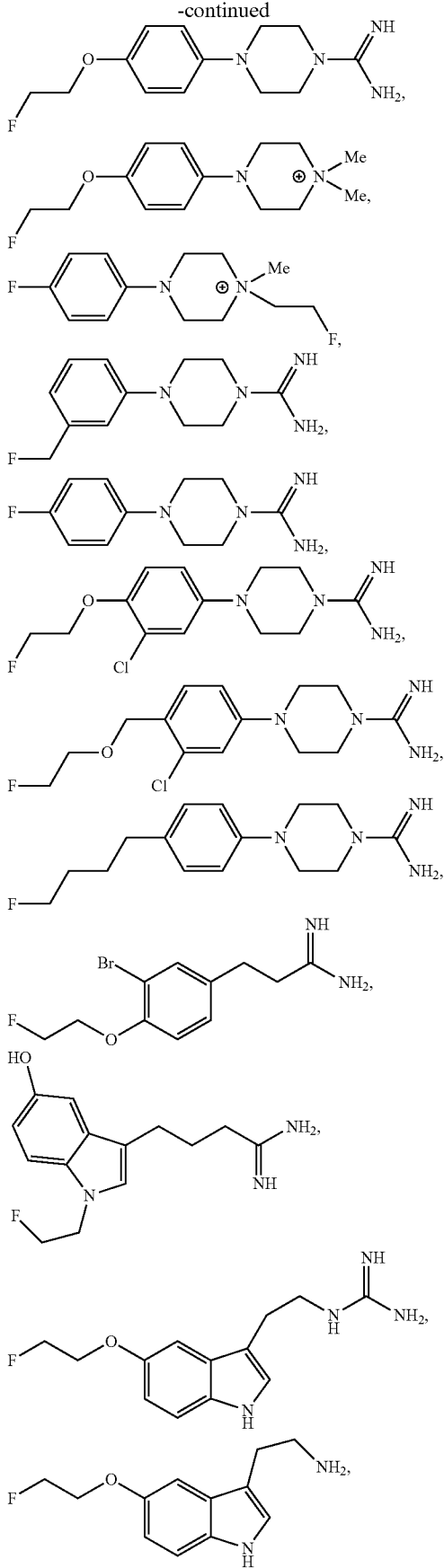
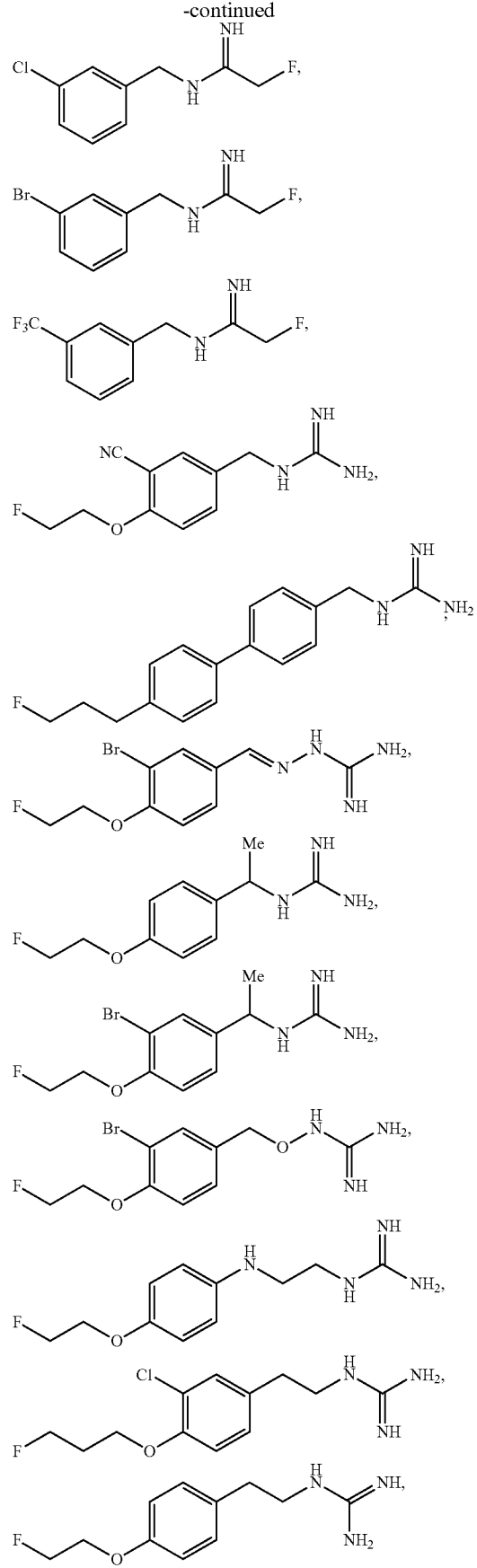

-continued
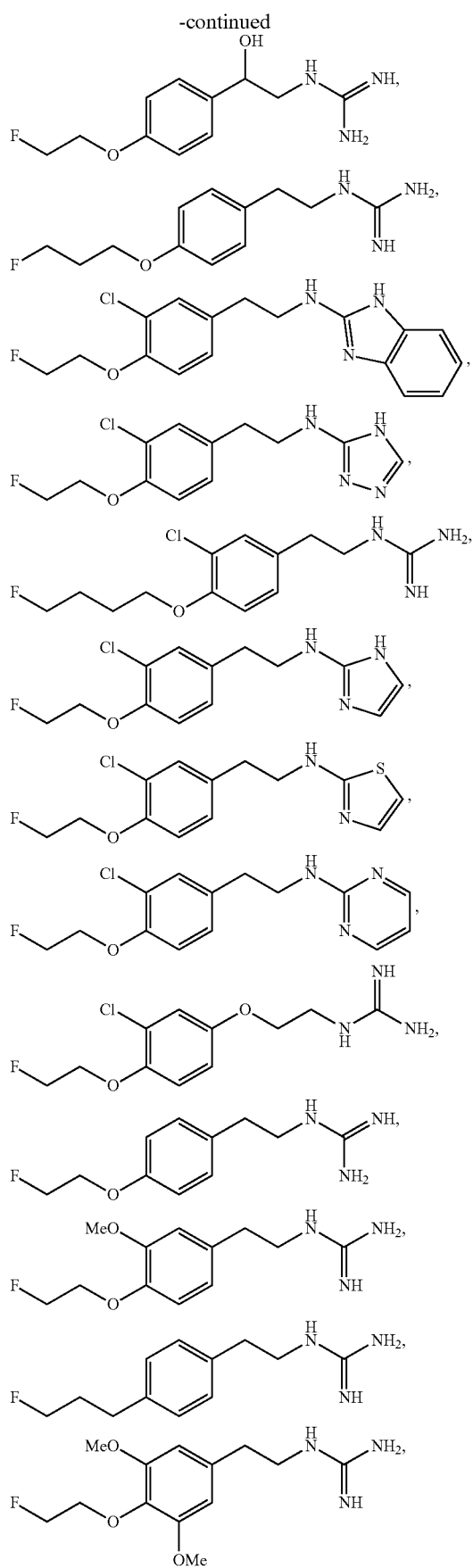
-continued
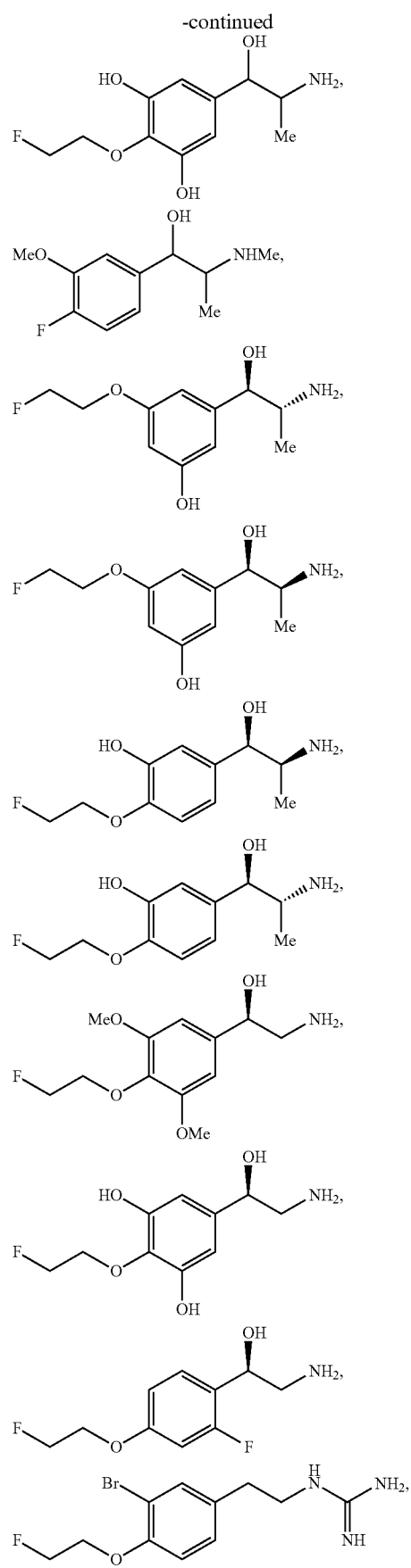

125

-continued

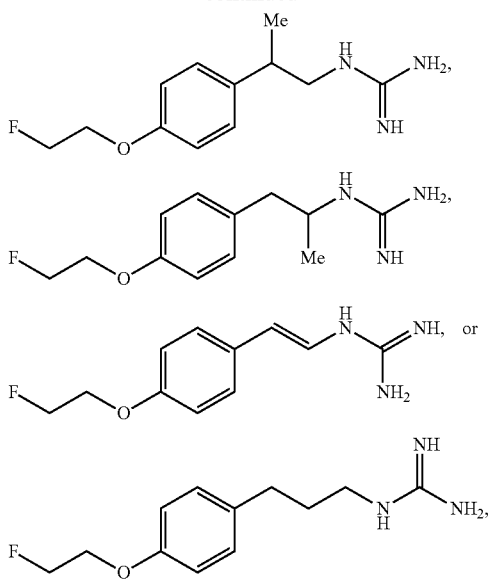

or a salt thereof, wherein each fluorine may optionally be enriched with $^{18}$F and/or each Br may be optionally enriched with $^{76}$Br. In some embodiments, only one $I_m$ is present in the compound.

In some embodiments, a compound of the invention is not:

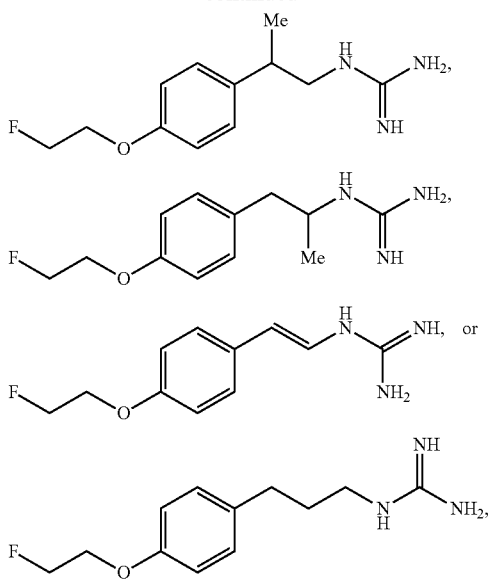

126

-continued

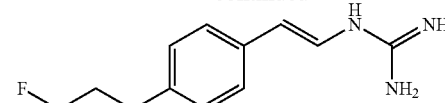

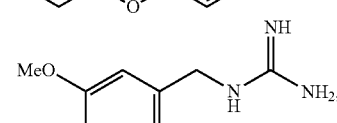

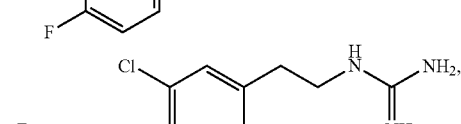

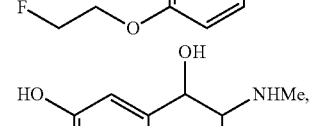

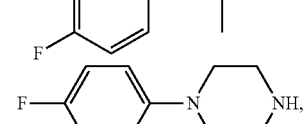

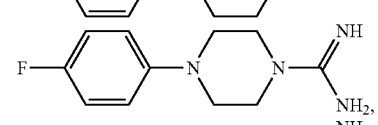

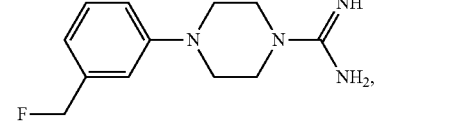

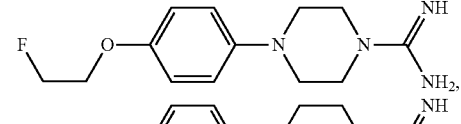

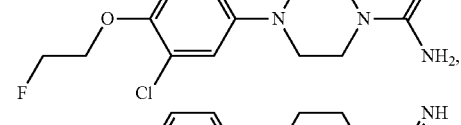

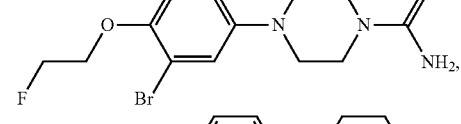

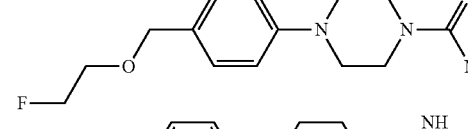

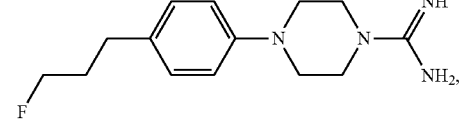

wherein each fluorine may optionally be enriched in $^{18}$F, and/or each Br may be optionally enriched with $^{76}$Br.

As used herein, the term "imaging agent" refers to any chemical compound that includes an imaging moiety. An "imaging moiety" refers to an atom or group of atoms that is capable of producing a detectable signal itself, or upon exposure to an external source of energy (e.g., electromagnetic radiation, ultrasound, and the like). Non-limiting examples of imaging moieties include $^{11}$C, $^{13}$N, $^{18}$F, $^{76}$Br, $^{123}$I, $^{124}$I, $^{125}$I, $^{131}$I, $^{99m}$Tc, $^{95}$Tc, $^{111}$In, $^{62}$Cu, $^{64}$Cu, $^{67}$Ga, and $^{68}$Ga. In some embodiments, the imaging moiety is selected from the group consisting of $^{18}$F, $^{76}$Br, $^{124}$I, $^{131}$I, $^{64}$Cu, $^{89}$Zr, $^{99m}$Tc, and $^{111}$In. In certain embodiments, the imaging moiety is directly associated (i.e., through a covalent bond) with a compound as described herein (e.g., in the case of $^{18}$F, $^{76}$Br, $^{124}$I, or $^{131}$I). In other embodiments, the imaging moiety is associated with the compound through a chelator (e.g., in the case of $^{64}$Cu, $^{89}$Zr, $^{99m}$TC, and $^{111}$In). Chelators are described in more detail herein. In certain embodiments, the imaging moiety is associated with the compound through non-covalent interactions (e.g., electrostatic interactions). In certain embodiments, the imaging moiety is $^{18}$F. In certain embodiments, the imaging moiety is $^{76}$Br. In certain embodiments, the imaging moiety is $^{124}$I. In certain embodiments, the imaging moiety is $^{131}$I. In some cases, the imaging moiety is not $^{131}$I. In some cases, the imaging moiety is $^{18}$F, $^{76}$Br, or $^{124}$I. In some cases, the imaging moiety is $^{18}$F or $^{76}$Br. In some cases, an imaging agent comprises a single imaging moiety. In some cases, an imaging agent comprises more than one imaging moiety (e.g., two imaging moieties).

Imaging agents allow for the detection, imaging, and/or monitoring of the presence and/or progression of a condition, pathological disorder, and/or disease. Typically, the imaging agent may be administered to a subject in order to provide information relating to at least a portion of the subject (e.g., human). In some cases, an imaging agent may be used to highlight a specific area of a subject, rendering organs, blood vessels, tissues, and/or other portions more detectable and more clearly imaged. By increasing the detectability and/or image quality of the area being studied, the presence and extent of disease and/or injury can be determined.

In some embodiments, an imaging agent or composition thereof is enriched with an isotope such as a radioisotope. In such a case, the imaging agent or composition thereof may be referred to as being "isotopically enriched." An "isotopically enriched" composition refers to a composition comprising a percentage of one or more isotopes of an element that is more than the percentage of that isotope that occurs naturally. For example, a composition that is isotopically enriched with a fluoride species may be "isotopically enriched" with fluorine-18 ($^{18}$F). Thus, with regard to a plurality of compounds, when a particular atomic position is designated as $^{18}$F, it is to be understood that the abundance (or frequency) of $^{18}$F at that position (in the plurality) is greater than the natural abundance (or frequency) of $^{18}$F, which is essentially zero.

In some embodiments, an atom designated as being enriched may have a minimum isotopic enrichment factor of about 0.001% (i.e., about 1 out of $10^5$ atoms is an enriched atom), 0.002%, 0.003%, 0.004%, 0.005%, 0.006%, 0.007%, 0.008%, 0.009%, 0.01%, about 0.05%, about 0.1%, about 0.2%, about 0.3%, about 0.4%, about 0.5%, about 0.75%, about 1%, about 2%, about 3%, about 4%, about 5%, about 10%, about 15%, about 20%, about 30%, about 40%, about 50%, about 60%, about 70%, about 80%, about 90%, about 95%, or greater. The minimum isotopic enrichment factor, in some instances, may range from about 0.001% to about 1%. For example, in embodiments wherein the imaging moiety is fluorine, a fluorine designated as $^{18}$F may have a minimum isotopic enrichment factor of about 0.001% (i.e., about 1 out of $10^5$ fluorine species is $^{18}$F), 0.002%, 0.003%, 0.004%, 0.005%, 0.006%, 0.007%, 0.008%, 0.009%, 0.01%, about 0.05%, about 0.1%, about 0.2%, about 0.3%, about 0.4%, about 0.5%, about 0.75%, about 1%, about 2%, about 3%, about 4%, about 5%, about 10%, about 15%, about 20%, about 30%, about 40%, about 50%, about 60%, about 70%, about 80%, about 90%, about 95%, or greater. The isotopic enrichment of the compounds provided herein can be determined using conventional analytical methods known to one of ordinary skill in the art, including mass spectrometry and HPLC.

In some embodiments, compositions, methods, uses, and systems described herein include or use compounds of Formula (Ia)-(Id), (IIa)-(IIb), (III), (IV), (Va)-(Vd), (VI), or (VII). In some embodiments, the present invention relates to methods of imaging, including methods of imaging a subject that includes administering a composition that includes an imaging agent to the subject by injection, infusion, or any other known method, and imaging a region of interest of the subject. Regions of interest may include, but are not limited to, the heart, a portion of the heart, cardiovascular system, cardiac vessels, pancreas, adrenal glands, salivary glands, thymus, or other organs with high sympathetic innervation or high imaging agent uptake. Regions of interest may also include tumors. In certain embodiments, the imaging agent is used as a radiotracer for mapping the cardiac nerve terminal in vivo using positron emission tomography (PET) or other imaging techniques. An event of interest can be imaged and detected and/or other information may be determined using methods and/or systems of the disclosure.

The imaging agents as described herein may act as norepinephrine transporter ligands that target or bind NET. In some embodiments, the methods comprise detecting NET, including determining NET levels, in a subject, wherein determining may comprise determining the level, density, function, and/or localization of NET in a subject. In certain embodiments, without wishing to be bound by a particular theory, the imaging agent binds to norepinephrine transporters (NET) allowing for imaging of cardiac sympathetic innervation or activity. Accordingly, in some aspects, methods for assessing cardiac sympathetic innervation and/or myocardial sympathetic function are provided.

B. Chelators

In some cases, an imaging moiety may be associated with a compound as described herein via association with a chelator (e.g., in embodiments where the imaging moiety is $^{64}$Cu, $^{89}$Zr, $^{99m}$Tc, or $^{111}$In). The term chelator is given its ordinary meaning in the art and generally refers to a chemical moiety capable of complexing an imaging moiety (e.g., a metal ion and/or radionuclide), wherein the complex is stable under physiological conditions. For example, generally, the imaging moiety remains complexed with the chelator in vivo. In some embodiments, the chelator is the moiety or group on a compound that binds to an imaging moiety through one or more donor atoms and/or groups. The chelator may be any chelator known in the art for complexing a medically useful metal ion or radionuclide. In some embodiments, the chelator comprises one, two, three, four, five, six, seven, eight, nine, or ten donor atoms and/or groups. In embodiments where the chelator comprises more than one donor atom and/or group, the donor atoms/groups may be the same or different. Non-limiting examples of donor atoms/groups include —OH, —O⁻, —COOR', —COO⁻, —N(R')$_2$, —SR', —OPO$_3$⁻, or —OPO$_3$R', wherein each R' can be the same or different and is hydrogen, alkyl, alkenyl, alkynyl, cycloalkyl, alkylaryl, alkylcarbonyl, aryl, arylalkyl, alkylarylalkyl, alkoxy, alkoxyalkyl, alkoxycarbonyl, heteroalkyl, heterocyclyl, heterocyclylalkyl, each optionally substituted. In some cases, the chelator may be a macrocycle. Non-limiting examples of chelators are described in International PCT Publication No. WO2011/005322 and U.S. Pat. No. 6,511,648, each of which is incorporated herein by reference. In some embodiments, the chelator comprises diaminodithiol, mercaptoacetyltriglycine, monoaminomonoamide, picolylamine monoacetic acid, 1,4,7,10-tetraazacyclododecane-1,4,7,10-tetraacetic acid, bis(thiosemicarbazone), propyleneamine oxime, ethylenediaminetetraacetic acid, and diethylenetriaminepentaacetic acid.

In some cases, an imaging moiety associated with a chelator may be further associated with one or more ancillary or co-ligands. "Ancillary" or "co-ligands" may be ligands which serve to complete the coordination sphere of the imaging moiety together with the chelator. In some embodiments, the imaging moiety coordination sphere may comprise one or more bonding atoms and/or groups form the chelators or bonding units and optionally, one or more ancillary and/or co-ligands. Ancillary or co-ligands useful in the preparation of radiopharmaceuticals and in diagnostic kits useful for the preparation of said radiopharmaceuticals may be comprised of one or more oxygen, nitrogen, carbon, sulfur, phosphorus, arsenic, selenium, and tellurium donor atoms.

C. Imaging Agent Precursors

In another aspect of the invention, imaging agent precursors useful in the preparation of imaging agents as described herein are provided. In certain embodiments, an imaging agent precursor as described herein comprises a leaving group (e.g., a sulfonate, halide) that can be replaced with a nucleophile in a substitution reaction. The imaging agent precursor may also include functional groups that are optionally protected. Earlier precursors in the synthesis of imaging agents as described herein are also encompassed by the present invention. In some embodiments, an imaging agent precursor has a structure as described above for a compound of Formula (Ia)-(Id), (IIa)-(IIb), (III), (IV), (Va)-(Vd), (VI), or (VII), except that the substituent which includes the imaging moiety instead includes a leaving group or a chelator group which is not yet associated with an imaging moiety.

In certain embodiments, a compound (e.g., an imaging agent precursor) for preparing an imaging agent is provided comprising Formula (VIII):

$$R^{O'}\text{—Ar-L—}R^1 \quad \text{(VIII)}$$

wherein

Ar is substituted or unsubstituted, monocyclic or bicyclic aryl or substituted or unsubstituted, monocyclic or bicyclic heteroaryl;

L is a bond; substituted or unsubstituted, cyclic or acyclic alkylene; substituted or unsubstituted, cyclic or acyclic alkenylene; substituted or unsubstituted, cyclic or acyclic alkynylene; or substituted or unsubstituted, cyclic or acyclic heteroaliphatic;

$R^{O'}$ is halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, —$OR^{41}$, —$N(R^{42})_2$, —$N(R^{42})_3^+$, —$SR^{41}$, —$C(=O)R^{41}$, —$C(=O)OR^{41}$, —$C(=O)SR^{41}$, —$C(=O)N(R^{42})_2$, —$OC(=O)R^{41}$, —$OC(=O)OR^{41}$, —$OC(=O)SR^{41}$, —$OC(=O)N(R^{42})_2$, —$NR^{42}C(=O)R^{41}$, —$NR^{42}C(=O)OR^{41}$, —$NR^{42}C(=O)SR^{41}$, —$NR^{42}C(=O)N(R^{42})_2$, —$SC(=O)R^{41}$, —$SC(=O)OR^{41}$, —$SC(=O)SR^{41}$, —$SC(=O)N(R^{42})_2$, —$C(=NR^{42})R^{41}$, —$C(=NR^{42})OR^{41}$, —$C(=NR^{42})SR^{41}$, —$C(=NR^{42})N(R^{42})_2$, —$OC(=NR^{42})R^{41}$, —$OC(=NR^{42})OR^{41}$, —$OC(=NR^{42})SR^{41}$, —$OC(=NR^{42})N(R^{42})_2$, —$NR^{42}C(=NR^{42})R^{42}$, —$NR^{42}C(=NR^{42})OR^{41}$, —$NR^{42}C(=NR^{42})SR^{41}$, —$NR^{42}C(=NR^{42})N(R^{42})_2$, —$SC(=NR^{42})R^{41}$, —$SC(=NR^{42})OR^{41}$, —$SC(=NR^{42})SR^{41}$, —$SC(=NR^{42})N(R^{42})_2$, —$C(=S)R^{41}$, —$C(=S)OR^{41}$, —$C(=S)SR^{41}$, —$C(=S)N(R^{42})_2$, —$OC(=S)R^{41}$, —$OC(=S)OR^{41}$, —$OC(=S)SR^{41}$, —$OC(=S)N(R^{42})_2$, —$NR^{42}C(=S)R^{42}$, —$NR^{42}C(=S)OR^{41}$, —$NR^{42}C(=S)SR^{41}$, —$NR^{42}C(=S)N(R^{42})_2$, —$SC(=S)R^{41}$, —$SC(=S)OR^{41}$, —$SC(=S)SR^{41}$, —$SC(=S)N(R^{42})_2$, —$S(=O)R^{41}$, —$SO_2R^{41}$, —$OSO_2R^{41}$, —$Si(R^{41})_3$, —$Sn(R^{41})_3$, —$B(OR^{41})_2$, —$NR^{42}SO_2R^{41}$, —$NO_2$, —$SO_2N(R^{42})_2$, —CN, —SCN, or —$NO_2$; or $R^{O'}$ is substituted with a leaving group or is a leaving group; and $R^1$ is a substituted or unsubstituted nitrogen-containing moiety;

each occurrence of $R^{41}$ is independently hydrogen, optionally substituted alkyl, optionally substituted alkenyl, optionally substituted alkynyl, optionally substituted carbocyclyl, optionally substituted heterocyclyl, optionally substituted aryl, or optionally substituted heteroaryl; and each occurrence of $R^{42}$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, or an amino protecting group, or two $R^{42}$ groups are joined to form an optionally substituted heterocyclic ring; or a salt thereof. In some embodiments, a compound of Formula (VIII) is not of the formula:

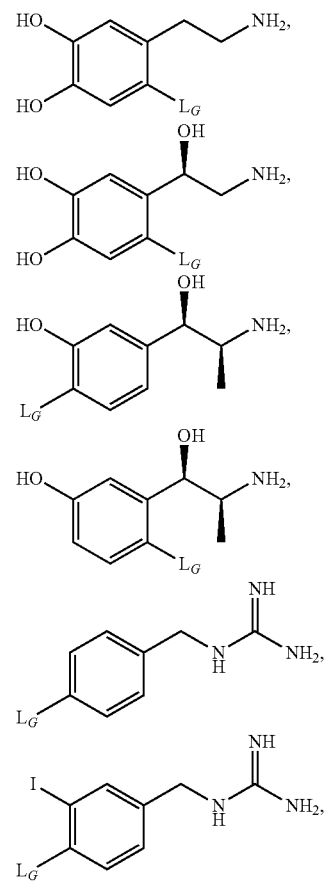

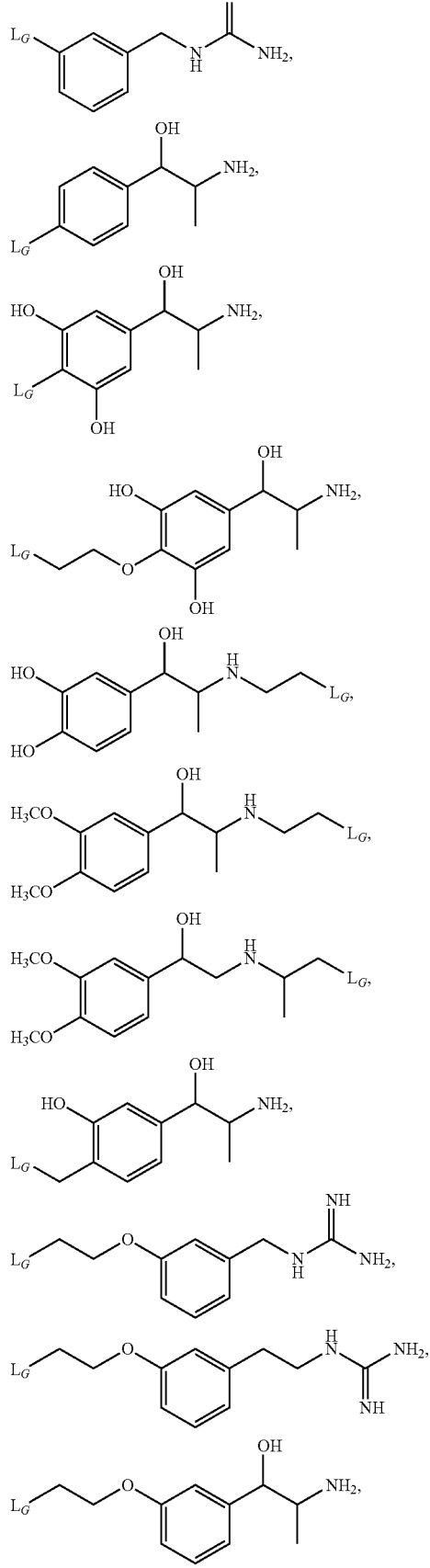
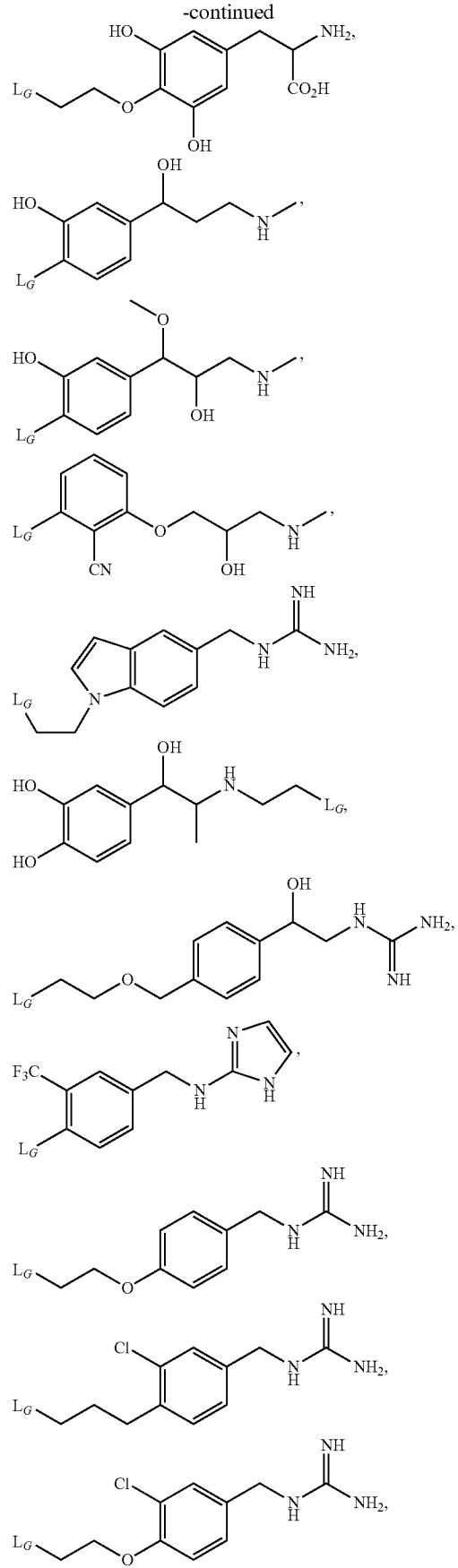

133
-continued
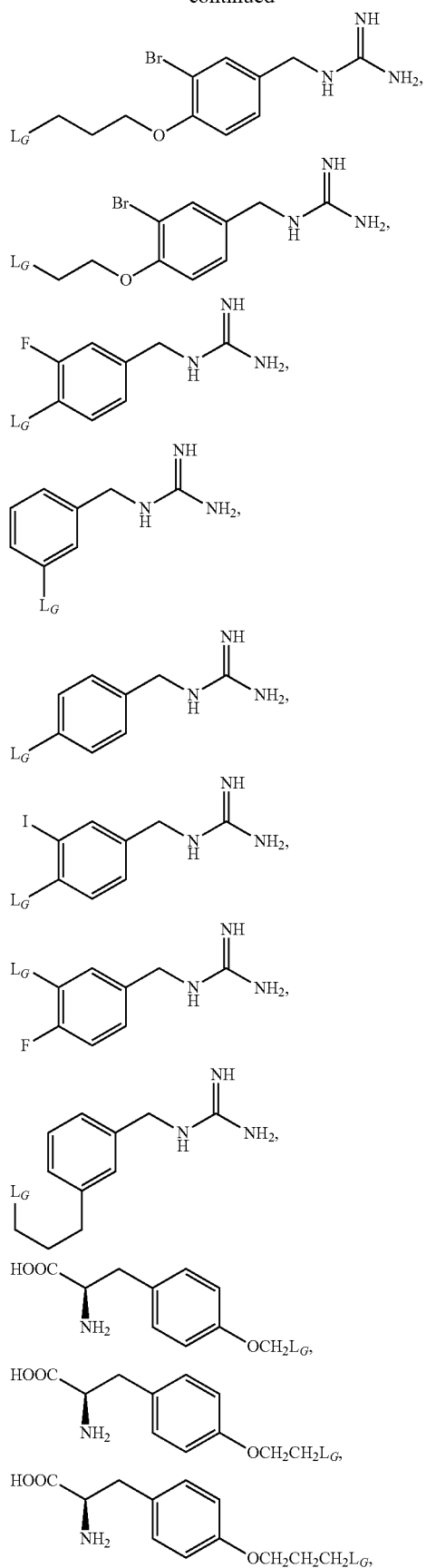
134
-continued
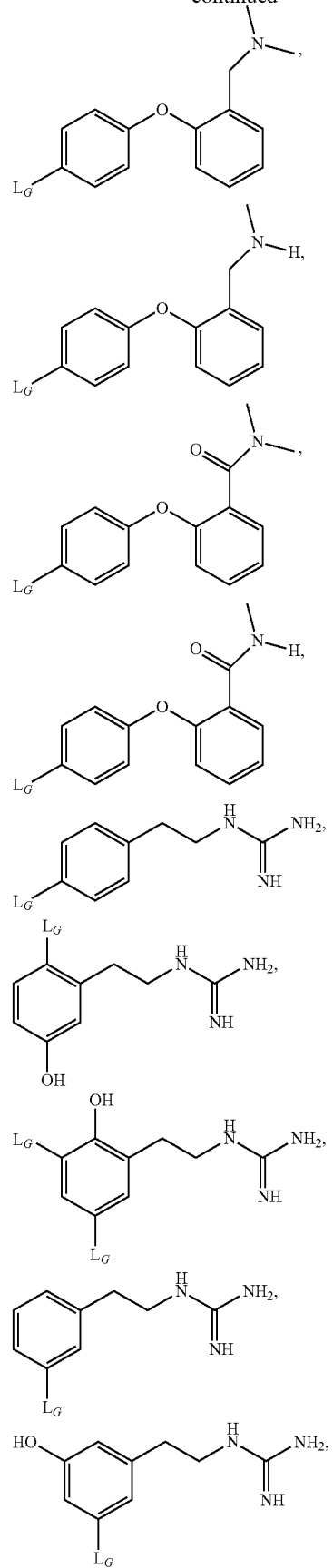

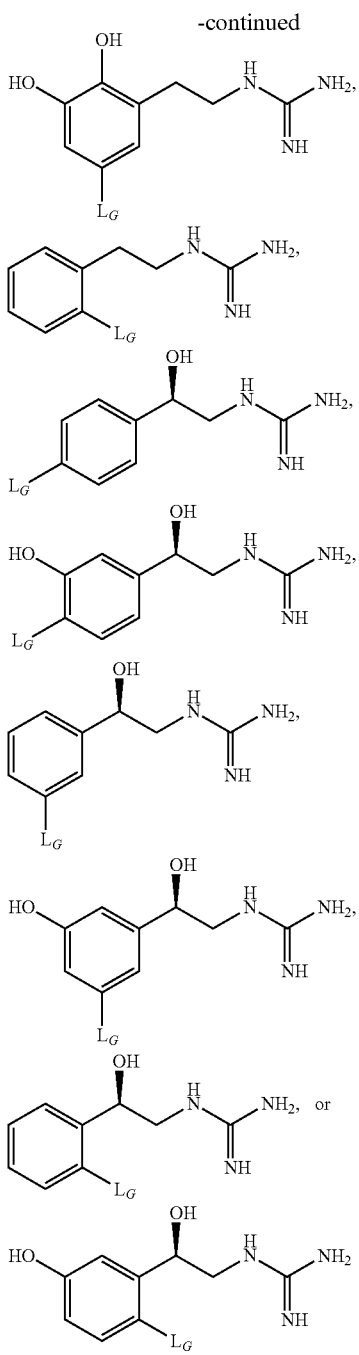

wherein $L_G$ is a leaving group.

In some embodiments, Ar, L, and/or $R^1$ may be as described herein, for example, as described for a compound of Formula (Ia).

As used herein, the term "leaving group" is given its ordinary meaning in the art of synthetic organic chemistry and refers to an atom or a group capable of being displaced by a nucleophile. Examples of suitable leaving groups include, but are not limited to, halides (such as chloride, bromide, or iodide), alkoxycarbonyloxy, aryloxycarbonyloxy, alkanesulfonyloxy, arenesulfonyloxy, alkyl-carbonyloxy (e.g., acetoxy), arylcarbonyloxy, aryloxy, methoxy, N,O-dimethylhydroxylamino, pixyl, and haloformates. In some cases, the leaving group is a sulfonic acid ester, such as toluenesulfonate (tosylate, Ts), methanesulfonate (mesylate, Ms), p-bromobenzenesulfonyl (brosylate, Bs), or trifluoromethanesulfonate (triflate, Tf). In some cases, the leaving group is a brosylate, such as p-bromobenzenesulfonyl. In some cases, the leaving group is a nosylate, such as 2-nitrobenzenesulfonyl. In some embodiments, the leaving group is a sulfonate-containing group. In some embodiments, the leaving group is a tosylate group. The leaving group may also be a phosphineoxide (e.g., formed during a Mitsunobu reaction) or an internal leaving group such as an epoxide or cyclic sulfate.

In some embodiments, the leaving group is a sulfonate leaving group. In some embodiments, $R^{O'}$ is selected from the group consisting of alkoxy substituted with a leaving group, alkyl substituted with a leaving group, and $R^{O'}$ is alkoxyalkyl (e.g., alkoxymethyl) substituted with a leaving group. In some embodiments, $R^{O'}$ is —OCH$_2$L$_G$, —OCH$_2$CH$_2$L$_G$, —OCH$_2$CH$_2$CH$_2$L$_G$, or OCH$_2$CH$_2$CH$_2$CH$_2$L$_G$. In certain embodiments, $R^{O'}$ is —CH$_2$L$_G$, —CH$_2$CH$_2$L$_G$, —CH$_2$CH$_2$CH$_2$L$_G$, or —CH$_2$CH$_2$CH$_2$CH$_2$L$_G$. In certain embodiments, $R^{O'}$ is —CH$_2$OCH$_2$L$_G$, —CH$_2$OCH$_2$CH$_2$L$_G$, —CH$_2$OCH$_2$CH$_2$CH$_2$L$_G$, or —CH$_2$OCH$_2$CH$_2$CH$_2$CH$_2$L$_G$. In certain embodiments, $R^{O'}$ is:

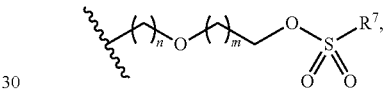

wherein n is an integer between 0 and 6, inclusive; m is an integer between 0 and 6, inclusive; and $R^7$ is substituted or unsubstituted, cyclic or acyclic alkyl; substituted or unsubstituted, cyclic or acyclic alkenyl; substituted or unsubstituted, cyclic or acyclic alkenyl; substituted or unsubstituted, cyclic or acyclic heteroaliphatic; substituted or unsubstituted aryl; substituted or unsubstituted heteroaryl, substituted or unsubstituted arylalkyl; or substituted or unsubstituted heteroarylalkyl.

In some embodiments, $R^{O'}$ is alkoxy substituted with a leaving group. In some embodiments, $R^{O'}$ is —OCH$_2$L$_G$, —OCH$_2$CH$_2$L$_G$, —OCH$_2$CH$_2$CH$_2$L$_G$, or —OCH$_2$CH$_2$CH$_2$CH$_2$L$_G$.

In some embodiments, $R^{O'}$ is alkyl substituted with a leaving group. In some embodiments, $R^{O'}$ is —CH$_2$L$_G$, —CH$_2$CH$_2$L$_G$, —CH$_2$CH$_2$CH$_2$L$_G$, or —CH$_2$CH$_2$CH$_2$CH$_2$L$_G$.

In some embodiments, $R^{O'}$ is alkoxyalkyl substituted with a leaving group. In some embodiments, $R^{O'}$ is of the formula:

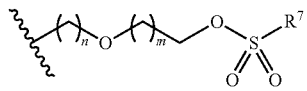

wherein n is an integer between 0 and 6, inclusive; m is an integer between 0 and 6, inclusive; and $R^7$ is substituted or unsubstituted, cyclic or acyclic alkyl; substituted or unsubstituted, cyclic or acyclic alkenyl; substituted or unsubstituted, cyclic or acyclic alkenyl; substituted or unsubstituted, cyclic or acyclic heteroaliphatic; substituted or unsubstituted aryl; substituted or unsubstituted heteroaryl, substituted or unsubstituted arylalkyl; or substituted or unsubstituted heteroarylalkyl. In some embodiments, $R^7$ is substituted or unsubstituted $C_1$-$C_6$ alkyl. In some embodiments, $R^7$ is methyl. In some embodiments, $R^7$ is $CF_3$. In some embodiments, $R^7$ is substituted or unsubstituted aryl. In some embodiments, $R^7$ is substituted or unsubstituted phenyl. In some embodiments, $R^7$ is:

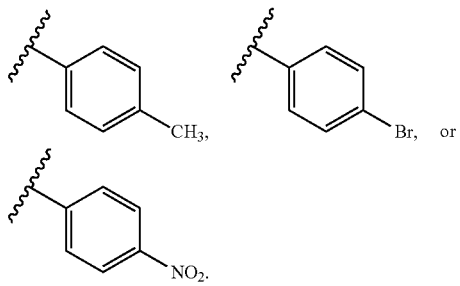

In some embodiments, $R^{0'}$ is alkoxymethyl substituted with a leaving group. In some embodiments, $R^{0'}$ is —$CH_2OCH_2L_G$, —$CH_2OCH_2CH_2L_G$, —$CH_2OCH_2CH_2CH_2L_G$, or —$CH_2OCH_2CH_2CH_2CH_2L_G$.

In certain embodiments, a compound (e.g., an imaging agent precursor) for preparing an imaging agent is provided comprising Formula (IX):

$$R^0—Ar-L—R^{1'} \qquad (IX)$$

wherein

Ar is substituted or unsubstituted, monocyclic or bicyclic aryl or substituted or unsubstituted, monocyclic or bicyclic heteroaryl;

L is a bond; substituted or unsubstituted, cyclic or acyclic alkylene; substituted or unsubstituted, cyclic or acyclic alkenylene; substituted or unsubstituted, cyclic or acyclic alkynylene; or substituted or unsubstituted, cyclic or acyclic heteroaliphatic;

$R^0$ is halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, —$OR^{A1}$, —$N(R^{A2})_2$, —$SR^{A1}$, —$C(=O)R^{A1}$, —$C(=O)OR^{A1}$, —$C(=O)SR^{A1}$, —$C(=O)N(R^{A2})_2$, —$OC(=O)R^{A1}$, —$OC(=O)OR^{A1}$, —$OC(=O)SR^{A1}$, —$OC(=O)N(R^{A2})_2$, —$NR^{A2}C(=O)R^{A2}$, —$NR^{A2}C(=O)OR^{A1}$, —$NR^{A2}C(=O)SR^{A1}$, —$NR^{A2}C(=O)N(R^{A2})_2$, —$SC(=O)R^{A1}$, —$SC(=O)OR^{A1}$, —$SC(=O)SR^{A1}$, —$SC(=O)N(R^{A2})_2$, —$C(=NR^{A2})R^{A1}$, —$C(=NR^{A2})OR^{A1}$, —$C(=NR^{A2})SR^{A1}$, —$C(=NR^{A2})N(R^{A2})_2$, —$OC(=NR^{A2})R^{A1}$, —$OC(=NR^{A2})OR^{A1}$, —$OC(=NR^{A2})SR^{A1}$, —$OC(=NR^{A2})N(R^{A2})_2$, —$NR^{A2}C(=NR^{A2})R^{A2}$, —$NR^{A2}C(=NR^{A2})OR^{A1}$, —$NR^{A2}C(=NR^{A2})SR^{A1}$, —$NR^{A2}C(=NR^{A2})N(R^{A2})_2$, —$SC(=NR^{A2})R^{A1}$, —$SC(=NR^{A2})OR^{A1}$, —$SC(=NR^{A2})SR^{A1}$, —$SC(=NR^{A2})N(R^{A2})_2$, —$C(=S)R^{A1}$, —$C(=S)OR^{A1}$, —$C(=S)SR^{A1}$, —$C(=S)N(R^{A2})_2$, —$OC(=S)R^{A1}$, —$OC(=S)OR^{A1}$, —$OC(=S)SR^{A1}$, —$OC(=S)N(R^{A2})_2$, —$NR^{A2}C(=S)R^{A2}$, —$NR^{A2}C(=S)OR^{A1}$, —$NR^{A2}C(=S)SR^{A1}$, —$NR^{A2}C(=S)N(R^{A2})_2$, —$SC(=S)R^{A1}$, —$SC(=S)OR^{A1}$, —$SC(=S)SR^{A1}$, —$SC(=S)N(R^{A2})_2$, —$S(=O)R^{A1}$, —$SO_2R^{A1}$, —$NR^{A2}SO_2R^{A1}$, —$SO_2N(R^{A2})_2$, —$CN$, —$SCN$, or —$NO_2$; and $R^{1'}$ is a substituted or unsubstituted nitrogen-containing moiety, and $R^{1'}$ substituted with a leaving group;

each occurrence of $R^{A1}$ is independently hydrogen, optionally substituted alkyl, optionally substituted alkenyl, optionally substituted alkynyl, optionally substituted carbocyclyl, optionally substituted heterocyclyl, optionally substituted aryl, or optionally substituted heteroaryl; and each occurrence of $R^{A2}$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, or an amino protecting group, or two $R^{A2}$ groups are joined to form an optionally substituted heterocyclic ring; or a salt thereof.

In some embodiments, Ar, L, and/or $R^0$ for a compound of Formula (IX) is as described for a compound of Formula (Ia).

In some embodiments, for a compound of Formula (IX), $R^1$ is —$N(R^A)_2$, heteroaryl, heterocyclic, —$C(=NH)NH_2$, —$NHC(=NH)NH_2$, —$NR^AC(=NR^A)N(R^A)_2$; —$NHC(=NH)NHR^A$, or —$NHC(=NH)N(R^A)_2$, wherein each occurrence of $R^A$ is independently hydrogen, halogen, substituted or unsubstituted alkyl, substituted or unsubstituted alkenyl, substituted or unsubstituted alkynyl, substituted or unsubstituted carbocyclyl, substituted unsubstituted heterocyclyl, substituted or unsubstituted aryl, or substituted or unsubstituted heteroaryl, or two $R^A$ groups may be joined to form an optional substituted heterocyclic ring, provided $R^{1'}$ comprises at least one leaving group. In some embodiments, $R^1$ is a non-aromatic, cyclic, substituted or unsubstituted nitrogen-containing moiety comprising at least one leaving group. In some embodiments, $R^1$ is selected from the group consisting of —$NHC(=NH)NH_2$, —$NH_2$, —$NHR^A$ (wherein $R^A$ is as defined herein), —$NHCH_3$, —$NHCH_2CH_3$, —$NHCH_2CH_2CH_3$,

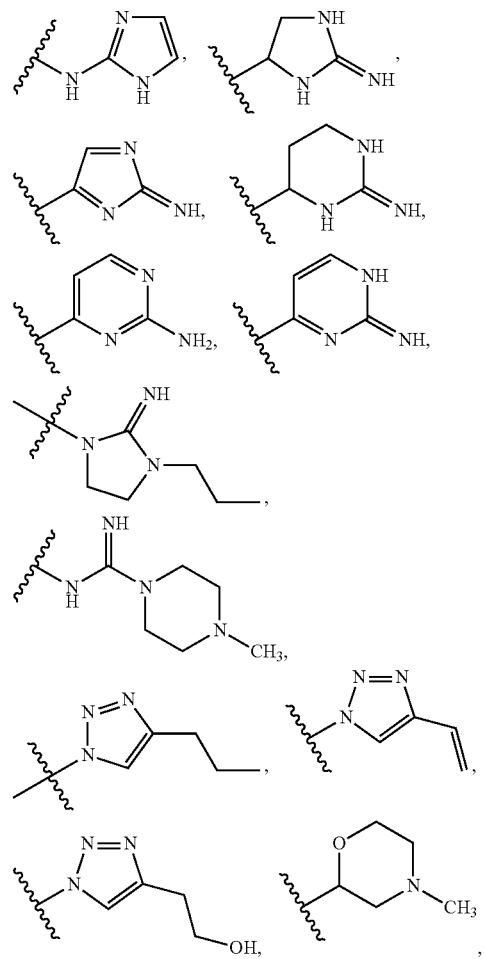

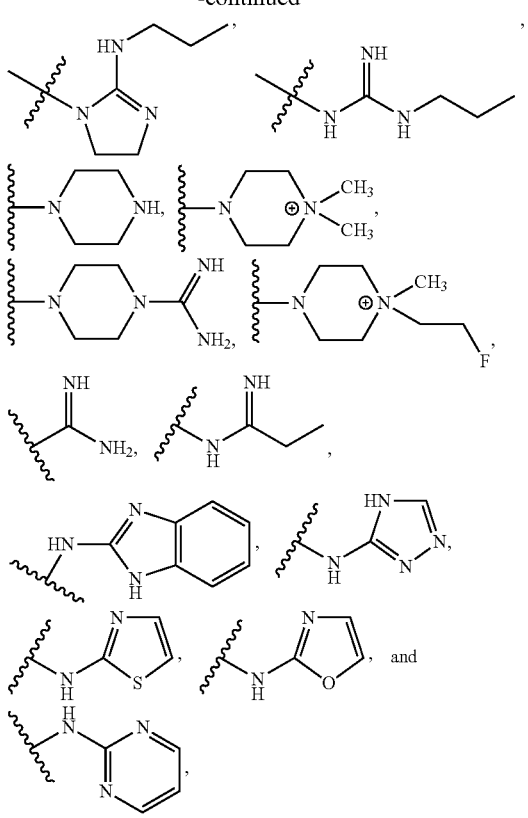

each substituted with at least one leaving group, and optionally other substituents.

In certain embodiments, a compound is provided comprising Formula (X):

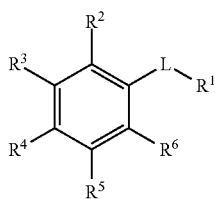

wherein

L is a bond; substituted or unsubstituted, cyclic or acyclic alkylene; substituted or unsubstituted, cyclic or acyclic alkenylene; substituted or unsubstituted, cyclic or acyclic alkynylene; or substituted or unsubstituted, cyclic or acyclic heteroaliphatic;

$R^1$ is a substituted or unsubstituted nitrogen-containing moiety;

each of $R^2$-$R^6$ is independently hydrogen, halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, —$OR^{41}$, —$N(R^{42})_2$, —$SR^{41}$, —$C(=O)R^{41}$, —$C(=O)OR^{41}$, —$C(=O)SR^{41}$, —$C(=O)N(R^{42})_2$, —$OC(=O)R^{41}$, —$OC(=O)OR^{41}$, —$OC(=O)SR^{41}$, —$OC(=O)N(R^{42})_2$, —$NR^{42}C(=O)R^{42}$, —$NR^{42}C(=O)OR^{41}$, —$NR^{42}C(=O)SR^{41}$, —$NR^{42}C(=O)N(R^{42})_2$, —$SC(=O)R^{41}$, —$SC(=O)$
$OR^{41}$, —$SC(=O)SR^{41}$, —$SC(=O)N(R^{42})_2$, —$C(=NR^{42})R^{41}$, —$C(=NR^{42})OR^{41}$, —$C(=NR^{42})SR^{41}$, —$C(=NR^{42})N(R^{42})_2$, —$OC(=NR^{42})R^{41}$, —$OC(=NR^{42})OR^{41}$, —$OC(=NR^{42})R^{41}$, —$OC(=NR^{42})N(R^{42})_2$, —$NR^{42}C(=NR^{42})R^{42}$, —$NR^{42}C(=NR^{42})OR^{41}$, —$NR^{42}C(=NR^{42})SR^{41}$, —$NR^{42}C(=NR^{42})N(R^{42})_2$, —$SC(=NR^{42})R^{41}$, —$SC(=NR^{42})OR^{41}$, —$SC(=NR^{42})SR^{41}$, —$SC(=NR^{42})N(R^{42})_2$, —$C(=S)R^{41}$, —$C(=S)OR^{41}$, —$C(=S)SR^{41}$, —$C(=S)N(R^{42})_2$, —$OC(=S)R^{41}$, —$OC(=S)OR^{41}$, —$OC(=S)SR^{41}$, —$OC(=S)N(R^{42})_2$, —$NR^{42}C(=S)R^{42}$, —$NR^{42}C(=S)OR^{41}$, —$NR^{42}C(=S)SR^{41}$, —$NR^{42}C(=S)N(R^{42})_2$, —$SC(=S)R^{41}$, —$SC(=S)OR^{41}$, —$SC(=S)SR^{41}$, —$SC(=S)N(R^{42})_2$, —$S(=O)R^{41}$, —$SO_2R^{41}$, —$NR^{42}SO_2R^{41}$, —$SO_2N(R^{42})_2$, —CN, —SCN, or —$NO_2$; or any two adjacent $R^2$-$R^6$ are joined to form an optionally substituted or unsubstituted carbocyclic, heterocyclic, aryl, or heteroaryl ring; and each occurrence of $R^{41}$ is independently hydrogen, optionally substituted alkyl, optionally substituted alkenyl, optionally substituted alkynyl, optionally substituted carbocyclyl, optionally substituted heterocyclyl, optionally substituted aryl, or optionally substituted heteroaryl; and each occurrence of $R^{42}$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, or an amino protecting group, or two $R^{42}$ groups are joined to form an optionally substituted heterocyclic ring; and wherein at least one of $R^1$-$R^6$ is substituted with a leaving group.

For example, in some embodiments for a compound of Formula (X), $R^4$ can be substituted with a leaving group, and is represented as $R^{4'}$, wherein $R^{4'}$ is selected from the group consisting of hydrogen, halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, —$OR^{41}$, —$N(R^{42})_2$, —$SR^{41}$, —$C(=O)R^{41}$, —$C(=O)OR^{41}$, —$C(=O)SR^{41}$, —$C(=O)N(R^{42})_2$, —$OC(=O)R^{41}$, —$OC(=O)OR^{41}$, —$OC(=O)SR^{41}$, —$OC(=O)N(R^{42})_2$, —$NR^{42}C(=O)R^{42}$, —$NR^{42}C(=O)OR^{41}$, —$NR^{42}C(=O)SR^{41}$, —$NR^{42}C(=O)N(R^{42})_2$, —$SC(=O)R^{41}$, —$SC(=O)OR^{41}$, —$SC(=O)SR^{41}$, —$SC(=O)N(R^{42})_2$, —$C(=NR^{42})R^{41}$, —$C(=NR^{42})OR^{41}$, —$C(=NR^{42})SR^{41}$, —$C(=NR^{42})N(R^{42})_2$, —$OC(=NR^{42})R^{41}$, —$OC(=NR^{42})OR^{41}$, —$OC(=NR^{42})SR^{41}$, —$OC(=NR^{42})N(R^{42})_2$, —$NR^{42}C(=NR^{42})R^{42}$, —$NR^{42}C(=NR^{42})OR^{41}$, —$NR^{42}C(=NR^{42})SR^{41}$, —$NR^{42}C(=NR^{42})N(R^{42})_2$, —$SC(=NR^{42})OR^{41}$, —$SC(=NR)SR^{41}$, —$SC(=NR^{42})N(R^{42})_2$, —$C(=S)R^{41}$, —$C(=S)OR^{41}$, —$C(=S)SR^{41}$, —$C(=S)N(R^{42})_2$, —$OC(=S)R^{41}$, —$OC(=S)OR^{41}$, —$OC(=S)SR^{41}$, —$OC(=S)N(R^{42})_2$, —$NR^{42}C(=S)R^{42}$, —$NR^{42}C(=S)OR^{41}$, —$NR^{42}C(=S)SR^{41}$, —$NR^{42}C(=S)N(R^{42})_2$, —$SC(=S)R^{41}$, —$SC(=S)OR^{41}$, —$SC(=S)SR^{41}$, —$SC(=S)N(R^{42})_2$, —$S(=O)R^{41}$, —$SO_2R^{41}$, —$NR^{42}SO_2R^{41}$, —$SO_2N(R^{42})_2$, —CN, —SCN, or —$NO_2$, each substituted with a leaving group. In some cases, $R^{4'}$ is selected from the group consisting of $C_{1-6}$alkyl, alkoxy, or alkoxyalkyl, each substituted with a leaving group. In some cases, $R^{4'}$ is alkoxymethyl substituted with a leaving group. In some cases, $R^{4'}$ is selected from the group consisting of —$CH_2L_G$, —$CH_2CH_2L_G$, —$CH_2CH_2CH_2L_G$, —$CH_2CH_2CH_2CH_2L_G$, —$OCH_2L_G$, —$OCH_2CH_2L_G$, —$OCH_2CH_2CH_2L_G$, —$OCH_2CH_2CH_2CH_2L_G$, —$CH_2OCH_2L_G$, —CH$_2$OCH$_2$CH$_2$L$_G$, —CH$_2$OCH$_2$CH$_2$CH$_2$L$_G$, or —CH$_2$OCH$_2$CH$_2$CH$_2$CH$_2$L$_G$, wherein L$_G$ is a leaving group.

In some embodiments, R$^{4'}$ is alkyl substituted with a leaving group. In some embodiments, R$^4$ is C$_{1-6}$alkyl substituted with a leaving group. In some embodiments, R$^4$ is —CH$_2$L$_G$, —CH$_2$CH$_2$L$_G$, —CH$_2$CH$_2$CH$_2$L$_G$, or —CH$_2$CH$_2$CH$_2$CHL$_G$. In some embodiments, R$^4$ is alkoxy substituted with a leaving group. In some embodiments, R$^{4'}$ is —OCH$_2$L$_G$, —OCH$_2$CH$_2$L$_G$, —OCH$_2$CH$_2$CH$_2$L$_G$, or —OCH$_2$CH$_2$CH$_2$CH$_2$L$_G$.

In some embodiments, R$^{4'}$ is alkoxyalkyl substituted with a leaving group. In some embodiments, R$^{4'}$ is of the formula:

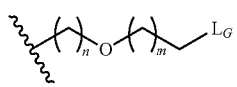

wherein n is an integer between 0 and 6, inclusive; and m is an integer between 0 and 6, inclusive. In some embodiments, R$^{4'}$ is alkoxymethyl substituted with a leaving group. In some embodiments, R$^{4'}$ is —CH$_2$OCH$_2$L$_G$, —CH$_2$OCH$_2$CH$_2$L$_G$, —CH$_2$OCH$_2$CH$_2$CH$_2$L$_G$, or —CH$_2$OCH$_2$CH$_2$CH$_2$CH$_2$L$_G$.

In some embodiments, the leaving group is a sulfonate leaving group. In some embodiments, R$^{4'}$ is

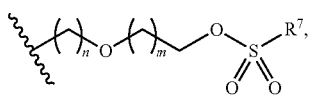

wherein n is an integer between 0 and 6, inclusive; m is an integer between 0 and 6, inclusive; and R$^7$ is substituted or unsubstituted, cyclic or acyclic alkyl; substituted or unsubstituted, cyclic or acyclic alkenyl; substituted or unsubstituted, cyclic or acyclic alkenyl; substituted or unsubstituted, cyclic or acyclic heteroaliphatic; substituted or unsubstituted aryl; substituted or unsubstituted heteroaryl, substituted or unsubstituted arylalkyl; or substituted or unsubstituted heteroarylalkyl. In some embodiments, R$^7$ is substituted or unsubstituted C$_1$-C$_6$ alkyl. In some embodiments, R$^7$ is methyl. In some embodiments, R$^7$ is CF$_3$. In some embodiments, R$^7$ is substituted or unsubstituted aryl. In some embodiments, R$^7$ is substituted or unsubstituted phenyl. In some embodiments, R$^7$ is:

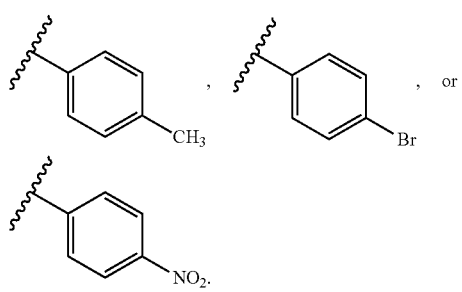

Furthermore, each of the R$^{4'}$ groups described herein in connection with a compound of Formula (X) may be combined with any suitable R$^1$ and/or L group described above, for example, in connection with a compound of Formula (Ia).

In some embodiments, R$^3$ is substituted with a leaving group, and can therein be represented as R$^{3'}$, wherein R$^{3'}$ may be any R$^{4'}$ group as described herein in connection with a compound of Formula (IX).

In some embodiments, a compound of Formula (X) comprises Formula (XI):

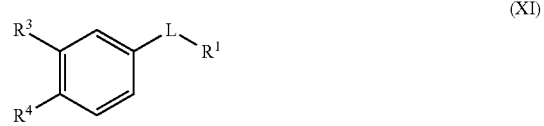

wherein

L is a bond; substituted or unsubstituted alkylene; substituted or unsubstituted alkenylene; or substituted or unsubstituted heteroalkylene;

R$^1$ is a substituted or unsubstituted nitrogen-containing moiety;

R$^3$ is hydrogen, halogen, optionally substituted alkyl, —OR$^{41}$, —N(R$^{42}$)$_2$, —C(=O)R$^{41}$, —C(=O)N(R$^{42}$)$_2$, —NR$^{42}$C(=O)R$^{41}$, or —CN;

R$^4$ is hydrogen, halogen, optionally substituted alkyl, —OR$^{41}$, —N(R$^{42}$)$_2$, —C(=O)R$^{41}$, —C(=O)N(R$^{42}$)$_2$, —NR$^{42}$C(=O)R$^{41}$, or —CN;

each occurrence of R$^{41}$ is independently hydrogen, or optionally substituted alkyl; and each occurrence of R$^{42}$ is independently hydrogen or optionally substituted alkyl, or two R$^{42}$ groups are joined to form an optionally substituted heterocyclic ring; and wherein at least one of R$^3$ and R$^4$ is substituted with an leaving group; or a salt thereof.

The compound of Formula (XI) may comprise any suitable R$^3$ and/or R$^4$ group(s) as described herein in connection with a compound of Formula (X), provided at least one of R$^3$ and R$^4$ is substituted with a leaving group (i.e., thereby being R$^{3'}$ or R$^{4'}$), and/or any L and/or R$^1$ group as described herein, for example, in connection with a compound of Formula (Ia).

In some embodiments, a compound of Formula (XI) comprises the structure:

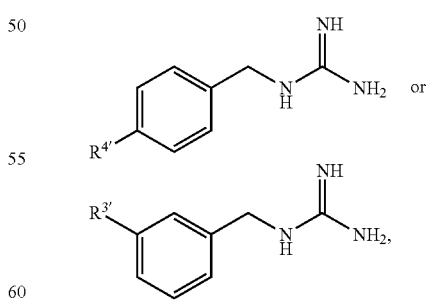

or salt thereof, wherein R$^{4'}$ and R$^{3'}$ may be any suitable R$^{4'}$ and R$^{3'}$ as described herein in connection with a compound of Formula (X) (e.g., is substituted with a leaving group). In some embodiments, a compound of Formula (XI) comprises the structure:

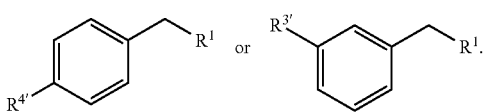

$R^1$ may be any suitable $R^1$ as described in connection with a compound of Formula (Ia); $R^{3'}$ and $R^{4'}$ may be any suitable $R^{3'}$ and $R^{4'}$ as described herein in connection with a compound of Formula (X). In some embodiments, a compound of Formula (X) comprises the structure:

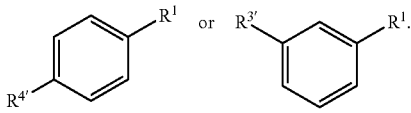

$R^1$ may be any suitable $R^1$ as described in connection with a compound of Formula (Ia); $R^{3'}$ and $R^{4'}$ may be any suitable $R^{3'}$ and $R^{4'}$ as described above in connection with a compound of Formula (X).

In some embodiments, a compound of Formula (X) comprises Formula (XII):

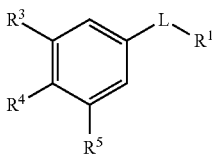

(XII)

wherein

L is a bond; substituted or unsubstituted alkylene; substituted or unsubstituted alkenylene; or substituted or unsubstituted heteroalkylene;

$R^1$ is a substituted or unsubstituted nitrogen-containing moiety;

$R^3$ is halogen, optionally substituted alkyl, —$OR^{41}$, —$N(R^{42})_2$, —$C(=O)R^{41}$, —$C(=O)N(R^{42})_2$, —$NR^{42}C(=O)R^{41}$, or —CN;

$R^4$ is hydrogen, halogen, optionally substituted alkyl, —$OR^{41}$, —$N(R^{42})_2$, —$C(=O)R^{41}$, —$C(=O)N(R^{42})_2$, —$NR^{42}C(=O)R^{41}$, or —CN;

$R^5$ is halogen, optionally substituted alkyl, —$OR^{41}$, —$N(R^{42})_2$, —$C(=O)R^{41}$, —$C(=O)N(R^{42})_2$, —$NR^{42}C(=O)R^{41}$, or —CN;

each occurrence of $R^{41}$ is independently hydrogen, or optionally substituted alkyl; and each occurrence of $R^{42}$ is independently hydrogen or optionally substituted alkyl, or two $R^{42}$ groups are joined to form an optionally substituted heterocyclic ring; and one or more of $R^3$ and $R^4$ is substituted with a leaving group; or a salt thereof.

The compound of Formula (XII) may comprise any suitable $R^3$ and/or $R^4$ as described herein, for example, in connection with a compound of Formula (X), provided at least one of $R^3$ or $R^4$ is substituted with a leaving group (i.e., thereby being $R^{3'}$ or $R^{4'}$). For a compound of Formula (XII), any suitable combination of $R^1$, $R^5$, and L groups may be used as described herein. For example, wherein $R^1$ is as described in connection with a compound of Formula (IV) or (Ia), and/or L is as described in connection with a compound of Formula (Ia).

In some embodiments, compound is provided comprising Formula (XIIIa)-(XIIId):

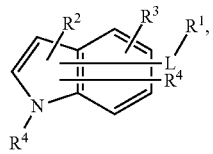

(XIIIa)

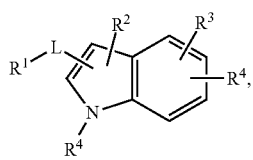

(XIIIb)

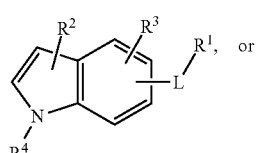

(XIIIc)

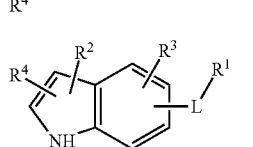

(XIIId)

wherein

L is a bond; substituted or unsubstituted, cyclic or acyclic alkylene; substituted or unsubstituted, cyclic or acyclic alkenylene; substituted or unsubstituted, cyclic or acyclic alkynylene; or substituted or unsubstituted, cyclic or acyclic heteroaliphatic;

$R^1$ is a substituted or unsubstituted nitrogen-containing moiety;

$R^2$ is hydrogen, halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, —$OR^{41}$, —$N(R^{42})_2$, —$SR^{41}$, —$C(=O)R^{41}$, —$C(=O)OR^{41}$, —$C(=O)SR^{41}$, —$C(=O)N(R^{42})_2$, —$OC(=O)R^{41}$, —$OC(=O)OR^{41}$, —$OC(=O)SR^{41}$, —$OC(=O)N(R^{42})_2$, —$NR^{42}C(=O)R^{42}$, —$NR^{42}C(=O)OR^{41}$, —$NR^{42}C(=O)SR^{41}$, —$NR^{42}C(=O)N(R^{42})_2$, —$SC(=O)R^{41}$, —$SC(=O)OR^{41}$, —$SC(=O)SR^{41}$, —$SC(=O)N(R^{42})_2$, —$C(=NR^{42})R^{41}$, —$C(=NR^{42})OR^{41}$, —$C(=NR^{42})SR^{41}$, —$C(=NR^{42})N(R^{42})_2$, —$OC(=NR^{42})R^{41}$, —$OC(=NR^{42})OR^{41}$, —$OC(=NR^{42})SR^{41}$, —$OC(=NR^{42})N(R^{42})_2$, —$NR^{42}C(=NR^{42})R^{42}$, —$NR^{42}C(=NR^{42})OR^{41}$, —$NR^{42}C(=NR^{42})SR^{41}$, —$NR^{42}C(=NR^{42})N(R^{42})_2$, —$SC(=NR^{42})R^{41}$, —$SC(=NR^{42})OR^{41}$, —$SC(=NR^{42})SR^{41}$, —$SC(=NR^{42})N(R^{42})_2$, —$C(=S)R^{41}$, —$C(=S)OR^{41}$, —$C(=S)SR^{41}$, —$C(=S)N(R^{42})_2$, —$OC(=S)R^{41}$, —$OC(=S)OR^{41}$, —$OC(=S)SR^{41}$, —$OC(=S)N(R^{42})_2$, —$NR^{42}C(=S)R^{42}$, —$NR^{42}C(=S)OR^{41}$, —$NR^{42}C(=S)SR^{41}$, —$NR^{42}C(=S)N(R^{42})_2$, —$SC(=S)R^{41}$, —$SC(=S)OR^{41}$, —$SC(=S)SR^{41}$, —$SC(=S)N(R^{42})_2$, —$S(=O)R^{41}$, —$SO_2R^{41}$, —$NR^{42}SO_2R^{41}$, —$SO_2N(R^{42})_2$, —CN, —SCN, or —$NO_2$;

$R^3$ is hydrogen, halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, —OR$^{41}$, —N(R$^{42}$)$_2$, —SR$^{41}$, —C(=O)R$^{41}$, —C(=O)OR$^{41}$, —C(=O)SR$^{41}$, —C(=O)N(R$^{42}$)$_2$, —OC(=O)R$^{41}$, —OC(=O)OR$^{41}$, —OC(=O)SR$^{41}$, —OC(=O)N(R$^{42}$)$_2$, —NR$^{42}$C(=O)R$^{42}$, —NR$^{42}$C(=O)OR$^{41}$, —NR$^{42}$C(=O)SR$^{41}$, —NR$^{42}$C(=O)N(R$^{42}$)$_2$, —SC(=O)R$^{41}$, —SC(=O)OR$^{41}$, —SC(=O)SR$^{41}$, —SC(=O)N(R$^{42}$)$_2$, —C(=NR$^{42}$)R$^{41}$, —C(=NR$^{42}$)OR$^{41}$, —C(=NR$^{42}$)SR$^{41}$, —C(=NR$^{42}$)N(R$^{42}$)$_2$, —OC(=NR$^{42}$)R$^{41}$, —OC(=NR$^{42}$)OR$^{41}$, —OC(=NR$^{42}$)SR$^{41}$, —OC(=NR$^{42}$)N(R$^{42}$)$_2$, —NR$^{42}$C(=NR$^{42}$)R$^{42}$, —NR$^{42}$C(=NR$^{42}$)OR$^{41}$, —NR$^{42}$C(=NR$^{42}$)SR$^{41}$, —NR$^{42}$C(=NR$^{42}$)N(R$^{42}$)$_2$, —SC(=NR$^{42}$)R$^{41}$, —SC(=NR$^{42}$)OR$^{41}$, —SC(=NR$^{42}$)SR$^{41}$, —SC(=NR$^{42}$)N(R$^{42}$)$_2$, —C(=S)R$^{41}$, —C(=S)OR$^{41}$, —C(=S)SR$^{41}$, —C(=S)N(R$^{42}$)$_2$, —OC(=S)R$^{41}$, —OC(=S)OR$^{41}$, —OC(=S)SR$^{41}$, —OC(=S)N(R$^{42}$)$_2$, —NR$^{42}$C(=S)R$^{42}$, —NR$^{42}$C(=S)OR$^{41}$, —NR$^{42}$C(=S)SR$^{41}$, —NR$^{42}$C(=S)N(R$^{42}$)$_2$, —SC(=S)R$^{41}$, —SC(=S)OR$^{41}$, —SC(=S)SR$^{41}$, —SC(=S)N(R$^{42}$)$_2$, —S(=O)R$^{41}$, —SO$_2$R$^{41}$, —NR$^{42}$SO$_2$R$^{41}$, —SO$_2$N(R$^{42}$)$_2$, —CN, —SCN, or —NO$_2$;

each occurrence of R$^4$ is independently hydrogen, halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, —OR$^{41}$, —N(R$^{42}$)$_2$, —SR$^{41}$, —C(=O)R$^{41}$, —C(=O)OR$^{41}$, —C(=O)SR$^{41}$, —C(=O)N(R$^{42}$)$_2$, —OC(=O)R$^{41}$, —OC(=O)OR$^{41}$, —OC(=O)SR$^{41}$, —OC(=O)N(R$^{42}$)$_2$, —NR$^{42}$C(=O)R$^{42}$, —NR$^{42}$C(=O)OR$^{41}$, —NR$^{42}$C(=O)SR$^{41}$, —NR$^{42}$C(=O)N(R$^{42}$)$_2$, —SC(=O)R$^{41}$, —SC(=O)OR$^{41}$, —SC(=O)SR$^{41}$, —SC(=O)N(R$^{42}$)$_2$, —C(=NR$^{42}$)R$^{41}$, —C(=NR$^{42}$)OR$^{41}$, —C(=NR$^{42}$)SR$^{41}$, —C(=NR$^{42}$)N(R$^{42}$)$_2$, —OC(=NR$^{42}$)R$^{41}$, —OC(=NR$^{42}$)OR$^{41}$, —OC(=NR$^{42}$)SR$^{41}$, —OC(=NR$^{42}$)N(R$^{42}$)$_2$, —NR$^{42}$C(=NR$^{42}$)R$^{42}$, —NR$^{42}$C(=NR$^{42}$)OR$^{41}$, —NR$^{42}$C(=NR$^{42}$)SR$^{41}$, —NR$^{42}$C(=NR$^{42}$)N(R$^{42}$)$_2$, —SC(=NR$^{42}$)R$^{41}$, —SC(=NR$^{42}$)OR$^{41}$, —SC(=NR$^{42}$)SR$^{41}$, —SC(=NR$^{42}$)N(R$^{42}$)$_2$, —C(=S)R$^{41}$, —C(=S)OR$^{41}$, —C(=S)SR$^{41}$, —C(=S)N(R$^{42}$)$_2$, —OC(=S)R$^{41}$, —OC(=S)OR$^{41}$, —OC(=S)SR$^{41}$, —OC(=S)N(R$^{42}$)$_2$, —NR$^{42}$C(=S)R$^{42}$, —NR$^{42}$C(=S)OR$^{41}$, —NR$^{42}$C(=S)SR$^{41}$, —NR$^{42}$C(=S)N(R$^{42}$)$_2$, —SC(=S)R$^{41}$, —SC(=S)OR$^{41}$, —SC(=S)SR$^{41}$, —SC(=S)N(R$^{42}$)$_2$, —S(=O)R$^{41}$, —SO$_2$R$^{41}$, —NR$^{42}$SO$_2$R$^{41}$, —SO$_2$N(R$^{42}$)$_2$, —CN, —SCN, or —NO$_2$;

each occurrence of R$^{41}$ is independently hydrogen, optionally substituted alkyl, optionally substituted alkenyl, optionally substituted alkynyl, optionally substituted carbocyclyl, optionally substituted heterocyclyl, optionally substituted aryl, or optionally substituted heteroaryl; and each occurrence of R$^{42}$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, or an amino protecting group, or two R$^{42}$ groups are joined to form an optionally substituted heterocyclic ring;

provided at least one R$^4$ is substituted with a leaving group; or a salt thereof.

For a compound of Formula (XIIIa)-(XIIId), any suitable combination of R$^1$, R$^2$, R$^3$, R$^4$, and L groups may be used as described herein, provided at least one R$^4$ group is substituted with a leaving group (e.g., and thus is R$^{4'}$).

In some cases, a compound of Formula (XIIIa)-(XIIId) comprises the structure:

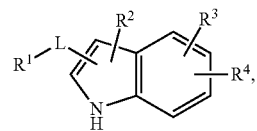

wherein R$^1$, R$^2$, R$^3$, R$^4$, and L are as described herein, provided at least one R$^4$ is R$^{4'}$. For example, wherein R$^1$ is as described in connection with a compound of Formula (IV) or (Ia)-(Id), R$^3$ and/or R$^4$ is as described in connection with a compound of Formula (IIa) or (IV), and/or L is as described in connection with a compound of Formula (Ia), provided at least one R$^4$ is substituted with a leaving group (and thus is R$^{4'}$). In some cases, compound of Formula (XIIIa)-(XIIId) comprises the structure:

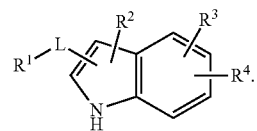

In some cases, a compound of Formula (XIIIa)-(XIIId) comprises the structure:

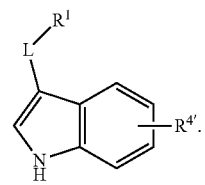

In some cases, a compound of Formula (XIIIa)-(XIIId) comprises the structure:

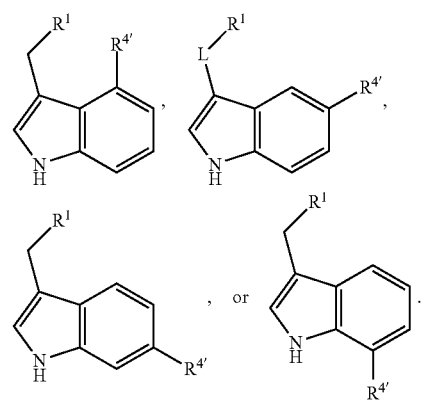

In some cases, a compound of Formula (XIIIa)-(XIIId) comprises the structure:

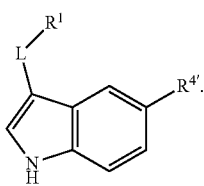

In some cases, a compound of Formula (XIIIa)-(XIIId) comprises the structure:

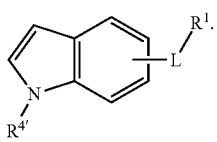

In some cases, a compound of Formula (XIIIa)-(XIIId) comprises the structure:

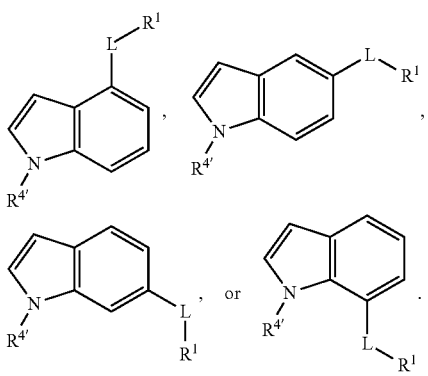

In some cases, a compound of Formula (XIIIa)-(XIIId) comprises the structure:

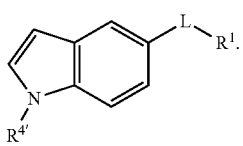

In some cases, a compound of Formula (XIIIa)-(XIIId) comprises the structure:

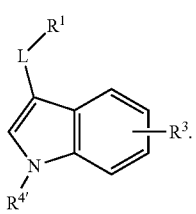

In some cases, a compound of Formula (XIIIa)-(XIIId) comprises the structure:

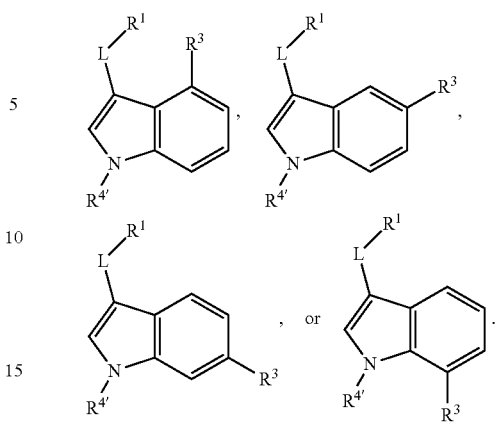

In some cases, a compound of Formula (XIIIa)-(XIIId) comprises the structure:

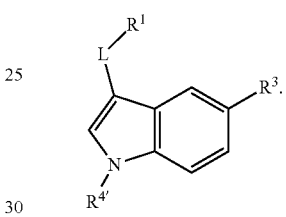

In some embodiments, a compound is provided comprising Formula (XIV):

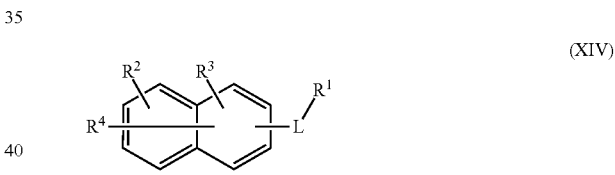

(XIV)

wherein

L is a bond; substituted or unsubstituted, cyclic or acyclic alkylene; substituted or unsubstituted, cyclic or acyclic alkenylene; substituted or unsubstituted, cyclic or acyclic alkynylene; or substituted or unsubstituted, cyclic or acyclic heteroaliphatic;

$R^1$ is a substituted or unsubstituted nitrogen-containing moiety;

$R^2$ is hydrogen, halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, —$OR^{41}$, —$N(R^{42})_2$, —$SR^{41}$, —$C(=O)R^{41}$, —$C(=O)OR^{41}$, —$C(=O)SR^{41}$, —$C(=O)N(R^{42})_2$, —$OC(=O)R^{41}$, —$OC(=O)OR^{41}$, —$OC(=O)SR^{41}$, —$OC(=O)N(R^{42})_2$, —$NR^{42}C(=O)R^{42}$, —$NR^{42}C(=O)OR^{41}$, —$NR^{42}C(=O)SR^{41}$, —$NR^{42}C(=O)N(R^{42})_2$, —$SC(=O)R^{41}$, —$SC(=O)OR^{41}$, —$SC(=O)SR^{41}$, —$SC(=O)N(R^{42})_2$, —$C(=NR^{42})R^{41}$, —$C(=NR^{42})OR^{41}$, —$C(=NR^{42})SR^{41}$, —$C(=NR^{42})N(R^{42})_2$, —$OC(=NR^{42})R^{41}$, —$OC(=NR^{42})OR^{41}$, —$OC(=NR^{42})SR^{41}$, —$OC(=NR^{42})N(R^{42})_2$, —$NR^{42}C(=NR^{42})R^{42}$, —$NR^{42}C(=NR^{42})OR^{41}$, —$NR^{42}C(=NR^{42})SR^{41}$, —$NR^{42}C(=NR^{42})N(R^{42})_2$—$SC(=NR^{42})R^{41}$, —$SC(=NR^{42})OR^{41}$, —$SC(=NR^{42})SR^{41}$, —$SC(=NR^{42})N(R^{42})_2$, —$C(=S)$ R$^{41}$, —C(=S)OR$^{41}$, —C(=S)SR$^{41}$, —C(=S)N(R$^{42}$)$_2$, —OC(=S)R$^{41}$, —OC(=S)OR$^{41}$, —OC(=S)SR$^{41}$, —OC(=S)N(R$^{42}$)$_2$, —NR$^{42}$C(=S)R$^{42}$, —NR$^{42}$C(=S)OR$^{41}$, —NR$^{42}$C(=S)SR$^{41}$, —NR$^{42}$C(=S)N(R$^{42}$)$_2$, —SC(=S) R$^{41}$, —SC(=S)OR$^{41}$, —SC(=S)SR$^{41}$, —SC(=S)N (R$^{42}$)$_2$, —S(=O)R$^{41}$, —SO$_2$R$^{41}$, —NR$^{42}$SO$_2$R$^{41}$, —SO$_2$N (R$^{42}$)$_2$, —CN, —SCN, or —NO$_2$;

R$^3$ is hydrogen, halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, —OR$^{41}$, —N(R$^{42}$)$_2$, —SR$^{41}$, —C(=O)R$^{41}$, —C(=O)OR$^{41}$, —C(=O)SR$^{41}$, —C(=O) N(R$^{42}$)$_2$, —OC(=O)R$^{41}$, —OC(=O)OR$^{41}$, —OC(=O) SR$^{41}$, —OC(=O)N(R$^{42}$)$_2$, —NR$^{42}$C(=O)R$^{42}$, —NR$^{42}$C (=O)OR$^{41}$, —NR$^{42}$C(=O)SR$^{41}$, —NR$^{42}$C(=O)N(R$^{42}$)$_2$, —SC(=O)R$^{41}$, —SC(=O)OR$^{41}$, —SC(=O)SR$^{41}$, —SC (=O)N(R$^{42}$)$_2$, —C(=NR$^{42}$)R$^{41}$, —C(=NR$^{42}$)OR$^{41}$, —C(=NR$^{42}$)SR$^{41}$, —C(=NR$^{42}$)N(R$^{42}$)$_2$, —OC(=NR$^{42}$) R$^{41}$, —OC(=NR$^{42}$)OR$^{41}$, —OC(=NR$^{42}$)SR$^{41}$, —OC (=NR$^{42}$)N(R$^{42}$)$_2$, —NR$^{42}$C(=NR$^{42}$)R$^{42}$, —NR$^{42}$C (=NR$^{42}$)OR$^{41}$, —NR$^{42}$C(=NR$^{42}$)SR$^{41}$, —NR$^{42}$C (=NR$^{42}$)N(R$^{42}$)$_2$, —SC(=NR$^{42}$)R$^{41}$, —SC(=NR$^{42}$) OR$^{41}$, —SC(=NR$^{42}$)SR$^{41}$, —SC(=NR$^{42}$)N(R$^{42}$)$_2$, —C(=S)R$^{41}$, —C(=S)OR$^{41}$, —C(=S)SR$^{41}$, —C(=S)N (R$^{42}$)$_2$, —OC(=S)R$^{41}$, —OC(=S)OR$^{41}$, —OC(=S)SR$^{41}$, —OC(=S)N(R$^{42}$)$_2$, —NR$^{42}$C(=S)R$^{42}$, —NR$^{42}$C(=S) OR$^{41}$, —NR$^{42}$C(=S)SR$^{41}$, —NR$^{42}$C(=S)N(R$^{42}$)$_2$, —SC (=S)R$^{41}$, —SC(=S)OR$^{41}$, —SC(=S)SR$^{41}$, —SC(=S)N (R$^{42}$)$_2$, —S(=O)R$^{41}$, —SO$_2$R$^{41}$, —NR$^{42}$SO$_2$R$^{41}$, —SO$_2$N (R$^{42}$)$_2$, —CN, —SCN, or —NO$_2$;

R$^4$ is hydrogen, halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, —OR$^{41}$, —N(R$^{42}$)$_2$, —SR$^{41}$, —C(=O)R$^{41}$, —C(=O)OR$^{41}$, —C(=O)SR$^{41}$, —C(=O) N(R$^{42}$)$_2$, —OC(=O)R$^{41}$, —OC(=O)OR$^{41}$, —OC(=O) SR$^{41}$, —OC(=O)N(R$^{42}$)$_2$, —NR$^{42}$C(=O)R$^{42}$, —NR$^{42}$C (=O)OR$^{41}$, —NR$^{42}$C(=O)SR$^{41}$, —NR$^{42}$C(=O)N(R$^{42}$)$_2$, —SC(=O)R$^{41}$, —SC(=O)OR$^{41}$, —SC(=O)SR$^{41}$, —SC (=O)N(R$^{42}$)$_2$, —C(=NR$^{42}$)R$^{41}$, —C(=NR$^{42}$)OR$^{41}$, —C(=NR$^{42}$)SR$^{41}$, —C(=NR$^{42}$)N(R$^{42}$)$_2$, —OC(=NR$^{42}$) R$^{41}$, —OC(=NR$^{42}$)OR$^{41}$, —OC(=NR$^{42}$)SR$^{41}$, —OC (=NR$^{42}$)N(R$^{42}$)$_2$, —NR$^{42}$C(=NR$^{42}$)R$^{42}$, —NR$^{42}$C (=NR$^{42}$)OR$^{41}$, —NR$^{42}$C(=NR$^{42}$)SR$^{41}$, —NR$^{42}$C (=NR$^{42}$)N(R$^{42}$)$_2$, —SC(=NR$^{42}$)R$^{41}$, —SC(=NR$^{42}$) OR$^{41}$, —SC(=NR$^{42}$)SR$^{41}$, —SC(=NR$^{42}$)N(R$^{42}$)$_2$, —C(=S)R$^{41}$, —C(=S)OR$^{41}$, —C(=S)SR$^{41}$, —C(=S)N (R$^{42}$)$_2$, —OC(=S)R$^{41}$, —OC(=S)OR$^{41}$, —OC(=S)SR$^{41}$, —OC(=S)N(R$^{42}$)$_2$, —NR$^{42}$C(=S)R$^{42}$, —NR$^{42}$C(=S) OR$^{41}$, —NR$^{42}$C(=S)SR$^{41}$, —NR$^{42}$C(=S)N(R$^{42}$)$_2$, —SC (=S)R$^{41}$, —SC(=S)OR$^{41}$, —SC(=S)SR$^{41}$, —SC(=S)N (R$^{42}$)$_2$, —S(=O)R$^{41}$, —SO$_2$R$^{41}$, —NR$^{42}$SO$_2$R$^{41}$, —SO$_2$N (R$^{42}$)$_2$, —CN, —SCN, or —NO$_2$;

provided at least one R$^4$ is substituted with a leaving group;

each occurrence of R$^{41}$ is independently hydrogen, optionally substituted alkyl, optionally substituted alkenyl, optionally substituted alkynyl, optionally substituted carbocyclyl, optionally substituted heterocyclyl, optionally substituted aryl, or optionally substituted heteroaryl; and each occurrence of R$^{42}$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, or an amino protecting group, or two R$^{42}$ groups are joined to form an optionally substituted heterocyclic ring; or a salt thereof.

For a compound of Formula (XIV), any suitable combination of R$^1$, R$^2$, R$^3$, R$^4$, and L groups may be used as described herein, provided at least one R$^4$ is substituted with a leaving group, so that it is R$^{4'}$. For example, wherein R$^1$ is as described in connection with a compound of Formula (IV) or (Ia), R$^3$ and/or R$^4$ is as described in connection with a compound of Formula (IIa) or (IV), and/or L is as described in connection with a compound of Formula (Ia), provided at least one R$^4$ is substituted with a leaving group.

In some embodiments, a compound of Formula (XIV) comprises the structure:

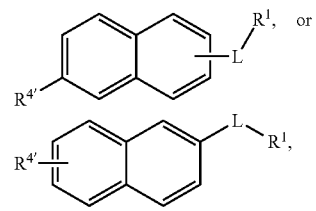

wherein R$^1$, R$^{4'}$, and L are as described herein. For example, wherein R$^1$ is as described in connection with a compound of Formula (IV) or (Ia), R$^{4'}$ is as described in connection with a compound of Formula (VIII), and/or L is as described in connection with a compound of Formula (Ia). In some embodiments, a compound of Formula (XIV) comprises the structure:

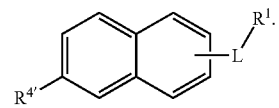

In some embodiments, imaging agent precursor comprises Formula (XV):

(XV)

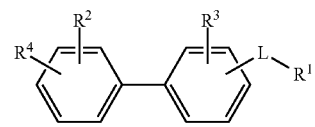

wherein

L is a bond; substituted or unsubstituted, cyclic or acyclic alkylene; substituted or unsubstituted, cyclic or acyclic alkenylene; substituted or unsubstituted, cyclic or acyclic alkynylene; or substituted or unsubstituted, cyclic or acyclic heteroaliphatic;

R$^1$ is a substituted or unsubstituted nitrogen-containing moiety;

R$^2$ is hydrogen, halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, —OR$^{41}$, —N(R$^{42}$)$_2$, —SR$^{41}$, —C(=O)R$^{41}$, —C(=O)OR$^{41}$, —C(=O)SR$^{41}$, —C(=O) N(R$^{42}$)$_2$, —OC(=O)R$^{41}$, —OC(=O)OR$^{41}$, —OC(=O) SR$^{41}$, —OC(=O)N(R$^{42}$)$_2$, —NR$^{42}$C(=O)R$^{42}$, —NR$^{42}$C (=O)OR$^{41}$, —NR$^{42}$C(=O)SR$^{41}$, —NR$^{42}$C(=O)N(R$^{42}$)$_2$, —SC(=O)R$^{A1}$, —SC(=O)OR$^{A1}$, —SC(=O)SR$^{A1}$, —SC(=O)N(R$^{A2}$)$_2$, —C(=NR$^{A2}$)R$^{A1}$, —C(=NR$^{A2}$)OR$^{A1}$, —C(=NR$^{A2}$)SR$^{A1}$, —C(=NR$^{A2}$)N(R$^{A2}$)$_2$, —OC(=NR$^{A2}$)R$^{A1}$, —OC(=NR$^{A2}$)OR$^{A1}$, —OC(=NR$^{A2}$)SR$^{A1}$, —OC(=NR$^{A2}$)N(R$^{A2}$)$_2$, —NR$^{A2}$C(=NR$^{A2}$)R$^{A2}$, —NR$^{A2}$C(=NR$^{A2}$)OR$^{A1}$, —NR$^{A2}$C(=NR$^{A2}$)SR$^{A1}$, —NR$^{A2}$C(=NR$^{A2}$)N(R$^{A2}$)$_2$, —SC(=NR$^{A2}$)R$^{A1}$, —SC(=NR$^{A2}$)OR$^{A1}$, —SC(=NR$^{A2}$)SR$^{A1}$, —SC(=NR$^{A2}$)N(R$^{A2}$)$_2$, —C(=S)R$^{A1}$, —C(=S)OR$^{A1}$, —C(=S)SR$^{A1}$, —C(=S)N(R$^{A2}$)$_2$, —OC(=S)R$^{A1}$, —OC(=S)OR$^{A1}$, —OC(=S)SR$^{A1}$, —OC(=S)N(R$^{A2}$)$_2$, —NR$^{A2}$C(=S)R$^{A2}$, —NR$^{A2}$C(=S)OR$^{A1}$, —NR$^{A2}$C(=S)SR$^{A1}$, —NR$^{A2}$C(=S)N(R$^{A2}$)$_2$, —SC(=S)R$^{A1}$, —SC(=S)OR$^{A1}$, —SC(=S)SR$^{A1}$, —SC(=S)N(R$^{A2}$)$_2$, —S(=O)R$^{A1}$, —SO$_2$R$^{A1}$, —NR$^{A2}$SO$_2$R$^{A1}$, —SO$_2$N(R$^{A2}$)$_2$, —CN, —SCN, or —NO$_2$;

R$^3$ is hydrogen, halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, —OR$^{A1}$, —N(R$^{A2}$)$_2$, —SR$^{A1}$, —C(=O)R$^{A1}$, —C(=O)OR$^{A1}$, —C(=O)SR$^{A1}$, —C(=O)N(R$^{A2}$)$_2$, —OC(=O)R$^{A1}$, —OC(=O)OR$^{A1}$, —OC(=O)SR$^{A1}$, —OC(=O)N(R$^{A2}$)$_2$, —NR$^{A2}$C(=O)R$^{A2}$, —NR$^{A2}$C(=O)OR$^{A1}$, —NR$^{A2}$C(=O)SR$^{A1}$, —NR$^{A2}$C(=O)N(R$^{A2}$)$_2$, —SC(=O)R$^{A1}$, —SC(=O)OR$^{A1}$, —SC(=O)SR$^{A1}$, —SC(=O)N(R$^{A2}$)$_2$, —C(=NR$^{A2}$)R$^{A1}$, —C(=NR$^{A2}$)OR$^{A1}$, —C(=NR$^{A2}$)SR$^{A1}$, —C(=NR$^{A2}$)N(R$^{A2}$)$_2$, —OC(=NR$^{A2}$)R$^{A1}$, —OC(=NR$^{A2}$)OR$^{A1}$, —OC(=NR$^{A2}$)SR$^{A1}$, —OC(=NR$^{A2}$)N(R$^{A2}$)$_2$, —NR$^{A2}$C(=NR$^{A2}$)R$^{A2}$, —NR$^{A2}$C(=NR$^{A2}$)OR$^{A1}$, —NR$^{A2}$C(=NR$^{A2}$)SR$^{A1}$, —NR$^{A2}$C(=NR$^{A2}$)N(R$^{A2}$)$_2$, —SC(=NR$^{A2}$)R$^{A1}$, —SC(=NR$^{A2}$)OR$^{A1}$, —SC(=NR$^{A2}$)SR$^{A1}$, —SC(=NR$^{A2}$)N(R$^{A2}$)$_2$, —C(=S)R$^{A1}$, —C(=S)OR$^{A1}$, —C(=S)SR$^{A1}$, —C(=S)N(R$^{A2}$)$_2$, —OC(=S)R$^{A1}$, —OC(=S)OR$^{A1}$, —OC(=S)SR$^{A1}$, —OC(=S)N(R$^{A2}$)$_2$, —NR$^{A2}$C(=S)R$^{A2}$, —NR$^{A2}$C(=S)OR$^{A1}$, —NR$^{A2}$C(=S)SR$^{A1}$, —NR$^{A2}$C(=S)N(R$^{A2}$)$_2$, —SC(=S)R$^{A1}$, —SC(=S)OR$^{A1}$, —SC(=S)SR$^{A1}$, —SC(=S)N(R$^{A2}$)$_2$, —S(=O)R$^{A1}$, —SO$_2$R$^{A1}$, —NR$^{A2}$SO$_2$R$^{A1}$, —SO$_2$N(R$^{A2}$)$_2$, —CN, —SCN, or —NO$_2$;

R$^4$ is hydrogen, halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, —OR$^{A1}$, —N(R$^{A2}$)$_2$, —SR$^{A1}$, —C(=O)R$^{A1}$, —C(=O)OR$^{A1}$, —C(=O)SR$^{A1}$, —C(=O)N(R$^{A2}$)$_2$, —OC(=O)R$^{A1}$, —OC(=O)OR$^{A1}$, —OC(=O)SR$^{A1}$, —OC(=O)N(R$^{A2}$)$_2$, —NR$^{A2}$C(=O)R$^{A2}$, —NR$^{A2}$C(=O)OR$^{A1}$, —NR$^{A2}$C(=O)SR$^{A1}$, —NR$^{A2}$C(=O)N(R$^{A2}$)$_2$, —SC(=O)R$^{A1}$, —SC(=O)OR$^{A1}$, —SC(=O)SR$^{A1}$, —SC(=O)N(R$^{A2}$)$_2$, —C(=NR$^{A2}$)R$^{A1}$, —C(=NR$^{A2}$)OR$^{A1}$, —C(=NR$^{A2}$)SR$^{A1}$, —C(=NR$^{A2}$)N(R$^{A2}$)$_2$, —OC(=NR$^{A2}$)R$^{A1}$, —OC(=NR$^{A2}$)OR$^{A1}$, —OC(=NR$^{A2}$)SR$^{A1}$, —OC(=NR$^{A2}$)N(R$^{A2}$)$_2$, —NR$^{A2}$C(=NR$^{A2}$)R$^{A2}$, —NR$^{A2}$C(=NR$^{A2}$)OR$^{A1}$, —NR$^{A2}$C(=NR$^{A2}$)SR$^{A1}$, —NR$^{A2}$C(=NR$^{A2}$)N(R$^{A2}$)$_2$, —SC(=NR$^{A2}$)R$^{A1}$, —SC(=NR$^{A2}$)OR$^{A1}$, —SC(=NR$^{A2}$)SR$^{A1}$, —SC(=NR$^{A2}$)N(R$^{A2}$)$_2$, —C(=S)R$^{A1}$, —C(=S)OR$^{A1}$, —C(=S)SR$^{A1}$, —C(=S)N(R$^{A2}$)$_2$, —OC(=S)R$^{A1}$, —OC(=S)OR$^{A1}$, —OC(=S)SR$^{A1}$, —OC(=S)N(R$^{A2}$)$_2$, —NR$^{A2}$C(=S)R$^{A2}$, —NR$^{A2}$C(=S)OR$^{A1}$, —NR$^{A2}$C(=S)SR$^{A1}$, —NR$^{A2}$C(=S)N(R$^{A2}$)$_2$, —SC(=S)R$^{A1}$, —SC(=S)OR$^{A1}$, —SC(=S)SR$^{A1}$, —SC(=S)N(R$^{A2}$)$_2$, —S(=O)R$^{A1}$, —SO$_2$R$^{A1}$, —NR$^{A2}$SO$_2$R$^{A1}$, —SO$_2$N(R$^{A2}$)$_2$, —CN, —SCN, or —NO$_2$;

provided at least one R$^4$ is substituted with a leaving group;

each occurrence of R$^{A1}$ is independently hydrogen, optionally substituted alkyl, optionally substituted alkenyl, optionally substituted alkynyl, optionally substituted carbocyclyl, optionally substituted heterocyclyl, optionally substituted aryl, or optionally substituted heteroaryl; and each occurrence of R$^{A2}$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, or an amino protecting group, or two R$^{A2}$ groups are joined to form an optionally substituted heterocyclic ring; or a salt thereof.

For a compound of Formula (XV), any suitable combination of R$^1$, R$^2$, R$^3$, R$^4$, and L groups may be used as described herein provided at least one R$^4$ is substituted with a leaving group (and thus is R$^{4'}$). For example, wherein R$^1$ is as described in connection with a compound of Formula (IV) or (Ia), R$^3$ and/or R$^4$ is as described in connection with a compound of Formula (IIa) or (IV), and/or L is as described in connection with a compound of Formula (Ia), provided at least one R$^4$ is substituted with a leaving group (and thus is R$^{4'}$).

In some embodiments, a compound of Formula (XV) comprises the structure:

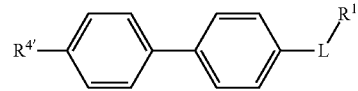

wherein R$^1$, R$^{4'}$, and L are as described herein.

D. Salts

As described herein, the imaging agents and precursors described herein may be salts. In some cases, the salt may be a pharmaceutically acceptable salt. Those of ordinary skill in the art will be aware of suitable counter anions for forming a salt of the imaging agents and imaging agent precursors described herein. In addition, those of ordinary skill in the art will be aware that the counter anion X$^\ominus$ may have a charge of greater than (−1) (e.g., (−2), (−3)), and in such embodiments, each counter anion X Θ may be associated with more than one molecule of a compound. In some embodiments, the counter ion is halide, phosphate, hydrogen phosphate, dihydrogen phosphate, hydrogen sulfate, sulfate, trifluoroacetate, toluenesulfonate, acetate, formate, citrate, ascorbate, mesylate (methanesulfonate), triflate (trifluoromethanesulfonate), tartrate, lactate, or benzoate. Additional non-limiting examples of suitable counter anions include the conjugate base of inorganic acids (e.g., chloride, bromide, iodide, fluoride, nitrate, sulfate, phosphate) or from the conjugate base of organic acids (e.g., carboxylate, acetate, benzoate, tartrate, adipate, lactate, formate, maleate, glutamate, ascorbate, citrate, gluconate, oxalate, succinate, pamoate, salicylate, isethionate, succinamate, mono-diglycollate, di-isobutyrate, glucoheptonate). Still yet other non-limiting examples of salts include adipate, alginate, aminosalicylate, anhydromethylenecitrate, arecoline, aspartate, bisulfate, camphorate, digluconate, dihydrobromide, disuccinate, glycerophosphate, hemisulfate, fluoride, iodide, methylenebis(salicylate), napadisylate, oxalate, pectinate, persulfate, phenylethylbarbiturate, picrate, propionate, thiocyanate, tosylate, undecanoate, acetate, benzenesulfonate, benzoate, bicarbonate, bitartrate, bromide, calcium edentate, camyslate, carbonate, chloride, citrate, dihydrochloride, edentate, edisylate, estolate, esylate, fumarate, gluceptate, gluconate, glutamate, glycollylarsanilate, hexylresorcinate, hydrabamine, bromide, chloride, hydroxynaphthoate, iodide, isethionate, lactate, lactobionate, malate, maleate, mandelate, mesylate, mucate, napsylate, nitrate, pamoate (embonate), pantothenate, phosphate/diphosphate, polygalacturonate, salicylate, stearate, subacetate, succinate, sulfate, tannate, tartrate, teoclate, and triethiodide (see Berge et al., *Journal of Pharmaceutical Sciences,* 66(1), 1977, 1-19).

E. Methods of Synthesizing an Imaging Agent

In other aspects, methods are provided for synthesizing imaging agents. The methods described herein may be used for the synthesis of a variety of imaging agents as described herein from imaging agent precursors as described herein. Generally, an imaging agent may be synthesized by reacting an imaging agent precursor with a reactant comprising the imaging moiety. In some cases, the reaction involves the formation of a covalent bond between the imaging agent precursor and the imaging moiety of the reactant. In other cases, however, the reaction involves non-covalent association of an imaging moiety with an imaging agent precursor (e.g., via chelation). The following sections provide a number of non-limiting embodiments for forming an imaging agent from an imaging agent precursor. Those of ordinary skill in the art will be aware of other suitable methods and techniques for forming an imaging agent from an imaging agent precursor. In addition, other steps which may be conducted in connection with the synthesis of an imaging agent (e.g., formulation, purification) are also described.

E1. General Reaction Conditions

The synthetic methods described herein may be carried out in any suitable solvent, including, but are not limited to, non-halogenated hydrocarbon solvents (e.g., pentane, hexane, heptane, cyclohexane), halogenated hydrocarbon solvents (e.g., dichloromethane, chloroform, fluorobenzene, trifluoromethylbenzene), aromatic hydrocarbon solvents (e.g., toluene, benzene, xylene), ester solvents (e.g., ethyl acetate), ether solvents (e.g., tetrahydrofuran, dioxane, diethyl ether, dimethoxyethane.), and alcohol solvents (e.g., ethanol, methanol, propanol, isopropanol, tert-butanol). In certain embodiments, a protic solvent is used. In other embodiments, an aprotic solvent is used. Non-limiting examples of solvents useful include acetone, acetic acid, formic acid, dimethyl sulfoxide, dimethyl formamide, acetonitrile, p-cresol, glycol, petroleum ether, carbon tetrachloride, hexamethyl-phosphoric triamide, triethylamine, picoline, and pyridine.

The methods may be carried out at any suitable temperature. In some cases, the method is carried out at about room temperature (e.g., about 20° C., between about 20° C. and about 25° C., about 25° C., or the like). In some cases, however, the method is carried out at a temperature below or above room temperature, for example, at about −78° C. at about −70° C., about −50° C., about −30° C., about −10° C., about −0° C., about 10° C., about 30° C., about 40° C., about 50° C., about 60° C., about 70° C., about 80° C., about 90° C., about 100° C., about 120° C., about 140° C., or the like. In some embodiments, the method is carried out at temperatures above room temperature, for example, between about 25° C. and about 120° C., or between about 25° C. and about 100° C., or between about 40° C. and about 120° C., or between about 80° C. and about 120° C. The temperature may be maintained by reflux of the solution. In some cases, the method is carried out at temperatures between about −78° C. and about 25° C., or between about 0° C. and about 25° C.

The methods described herein may be carried out at any suitable pH, for example, equal to or less than about 13, equal to or less than about 12, equal to or less than about 11, equal to or less than about 10, equal to or less than about 9, equal to or less than about 8, equal to or less than about 7, or equal to or less than about 6. In some cases, the pH may be greater than or equal to 1, greater than or equal to 2, greater than or equal to 3, greater than or equal to 4, greater than or equal to 5, greater than or equal to 6, greater than or equal to 7, or greater than or equal to 8. In some cases, the pH may be between about 2 and about 12, or between about 3 and about 11, or between about 4 and about 10, or between about 5 and about 9, or between about 6 and about 8, or about 7.

The percent yield of a product may be greater than about 60%, greater than about 70%, greater than about 75%, greater than about 80%, greater than about 85%, greater than about 90%, greater than about 92%, greater than about 95%, greater than about 96%, greater than about 97%, greater than about 98%, greater than about 99%, or greater.

E2. Halogenation

In some embodiments, an imaging agent is formed by reacting an imaging agent precursor with an imaging moiety. In certain embodiments, an imaging agent precursor comprises at least one leaving group that is susceptible to being displaced by an imaging moiety, such as, for example, a halogen (e.g., $^{18}$F, $^{76}$Br, $^{124}$I, $^{131}$I). Thus, in certain embodiments, the methods described herein involve reacting an imaging agent precursor comprising a leaving group with a source of an imaging moiety.

In some embodiments, an imaging moiety displaces a leaving group on a provided imaging agent precursor via a substitution reaction, such as an $S_N2$ or $S_N1$ reaction, thereby producing an imaging agent. In certain embodiments, a substitution reaction is a one-step procedure which does not require a subsequent deprotection step. That is, the substitution step is performed on a fully deprotected imaging agent precursor. In certain embodiments, a substitution reaction provided by the present invention produces a fluorinated imaging agent (e.g., an imaging agent comprising $^{18}$F).

In some embodiments, a provided imaging agent is synthesized via an aryl halogenation reaction (e.g., aryl fluorination, aryl bromination, aryl iodination). Many techniques for synthesizing aryl halides are known in the art. For example, in certain embodiments, an imaging agent comprising an $^{124}$I, $^{131}$I, or $^{76}$Br imaging moiety is synthesized via a Sandmeyer reaction from a aryl diazonium imaging agent precursor, with or without the use of copper(I) catalysis (see, for example, Beletskaya et al., *Synthesis,* 2007, 2534-2538; Hubbard et al., *J. Org. Chem.,* 2008, 73, 316-319; Filimonov et al., *Org. Lett.,* 2008, 10, 3961-3964; Krasnokutskaya et al., *Synthesis,* 2007, 81-84). In other embodiments, an imaging agent comprising a $^{18}$F imaging moiety is synthesized via a related Balz-Schiemann reaction from a diazonium imaging agent precursor. In certain embodiments, an imaging agent comprising an $^{124}$I, or $^{131}$I imaging moiety is synthesized via an "aromatic Finkelstein" reaction from an aryl bromide imaging agent precursor (see, for example, A. Klapars, S. L. Buchwald, *J. Am. Chem. Soc.,* 2002, 124, 14844-14845). In other embodiments, an imaging agent comprising an $^{124}$I, $^{131}$I, or $^{76}$Br imaging moiety is synthesized by allowing a boronic acid or ester imaging agent precursor to react with the appropriate N-halosuccinimide reagent (Thiebes et al., *Synlett,* 1998, 141-142) or copper bromide reagent (see, for example, Murphy et al., *J. Am. Chem. Soc.,* 2007, 129, 15434-15435; Thompson et al.,

*Synthesis*, 2005, 547-550). In some embodiments, an imaging agent comprising a $^{76}$Br imaging moiety is synthesized via an organotrifluoroborate imaging agent precursor (see, for example, G. W. Kabalka, A. R. Mereddy, *Organometallics*, 2004, 23, 4519-4521). One of ordinary skill in the art will appreciate that there are many other conditions under which activated or deactivated arenes may be halogenated (see, for example, Kraszkiewicz et al., *Synthesis*, 2006, 1195-1199; Ganguly et al., *Synthesis*, 2010, 1467-1472; Iskra et al., *Synthesis*, 2004, 1869-1873; Castanet et al., *Tetrahedron Lett.*, 2002, 43, 5047-5048; Prakash et al., *J. Am. Chem. Soc.*, 2004, 126, 15570-15776; Lulinski et al., *Synthesis*, 2004, 441-445; Ganguly et al., *Synthesis*, 2005, 1103-1108; Rajesh et al., *Org. Chem.*, 2007, 72, 5867-5869; Kumar et al., *Synthesis*, 2010, 1629-1632; Zhou et al., *Synthesis*, 2011, 207-209; Menzel et al., *J. Org. Chem.*, 2006, 71, 2188-2191), and such a reaction may be employed in certain embodiments to synthesize imaging agents described herein. One of ordinary skill in the art will also appreciate that many of the aryl halogenation reactions described herein will also be effective for generating a haloalkene- or haloalkyne-containing imaging agent, as well as haloheteroaryl-containing imaging agents.

In some embodiments, an imaging agent comprising a $^{18}$F imaging moiety is synthesized via an aryl fluorination. See, for example, Furuya et al., *Synthesis*, 2010(11): 1804-1821 (2010), for an informative review of aryl fluorination reactions. For example, in certain embodiments, an imaging agent comprising a $^{18}$F imaging moiety is synthesized via an nucleophilic fluorination reaction. Examples of nucleophilic fluorination reactions include, but are not limited to, the Halex process (Adams et al., *Chem Soc Rev* 1999; 28:225; Horwitz et al., *J. Org. Chem.* 1961; 26:3392; Barlin et al., *J. Chem. Soc., Perkin Trans* 1 1972:1269; Pike et al., *J. Chem. Soc., Chem Commun* 1995:2215; Shah et al., *J. Chem. Soc., Perkin Trans* 1 1998:2043; Ermert et al., *J Labelled Compd Radiopharm* 2004; 47:429), fluorodenitration (Adams et al., *Chem Soc Rev* 1999; 28:225; Adams et al., *J. Fluorine Chem* 1998; 92:127), displacement of ammonium with fluoride (Angelini et al., *J. Fluorine Chem* 1985; 27:177), and fluorination of diaryliodonium salts (Zhdankin et al., *Chem Rev* 2008; 108:5299; Beringer et al., *J. Am. Chem. Soc* 1953; 75:2708; Ross et al., *J. Am. Chem. Soc* 2007; 129:8018). Trialkylammonium fluoride reagents may also be employed in nucleophilic fluorination reactions (Sun et al., *Angew. Chem., Int. Ed* 2006; 45:2720; Grushin et al., *Organometallics* 2008; 27:4825). In certain embodiments, a nucleophilic fluorination reaction is Palladium catalyzed (see, for example, Grushin et al., *Organometallics* 2008; 27:4825; Watson et al., *Science* 2009; 325:1661). In other embodiments, an imaging agent comprising a $^{18}$F imaging moiety is synthesized via an electrophilic fluorination reaction. Examples of electrophilic fluorination reactions include, but are not limited to, fluorination of aryl Grignards reagents (Anbarasan P, Neumann H, Beller M. *Angew Chem, Int Ed.* 2010; 49:2219), fluorination of arylmagnesium reagents (Yamada S, Gavryushin A, Knochel P. *Angew Chem, Int Ed.* 2010; 49:2215), fluorination of organometallic reagents such as arylzinc halides, arylsilanes, arylstannanes, arylgermaniums, or arylboronic acids (Bryce et al., *J. Chem. Soc, Chem Commun* 1986:1623; Tius et al., Synth Commun 1992; 22:1461; Cazorla et al., *Tetrahedron Lett* 2009; 50:3936), fluorination of arylsilanes (Lothian et al., *Synlett* 1993:753), and fluorodestannylation reactions (Lothian et al., *Synlett* 1993:753; Namavari et al., *Appl Radiat Isot* 1992; 43:989.). In some embodiments, an electrophilic fluorination reaction employs stoichiometric or catalytic palladium (see, for example, Furuya et al., *Angew Chem, Int Ed* 2008; 47:5993) or silver (see, for example, Furuya et al., *J. Am. Chem Soc* 2009; 131:1662; Furuya et al., *Org Lett* 2009; 11:2860).

In some embodiments, a method of synthesizing an imaging agent described herein involves the use of one or more reagents (e.g., salts, catalysts) that facilitate a chemical reaction (e.g., a substitution reaction). In certain embodiments, a choice of salt form allows for fluorination of an unprotected imaging agent precursor. Without wishing to be bound by a particular theory, the counter anion may interact with the guanidine functional group or other nitrogen-containing group preventing it from interfering with the fluorination reaction and/or preventing side reactions. In certain embodiments, the salt is a mesylate (i.e., methanesulfonate), phosphate, sulfate, acetate, formate, benzoate, trifluoroacetate, or tosylate salt.

In some embodiments, multiple substitution reactions may occur through multiple leaving groups during synthesis of an imaging agent from an imaging agent precursor. The methods described herein exhibit improved yields may allow for the synthesis of imaging agents, including imaging agents comprising a radioisotope (e.g., $^{18}$F). The imaging agents may be useful as sensors, diagnostic tools, and the like. Synthetic methods for preparing an imaging agent have also been designed to use an automated synthesis system to prepare and purify imaging agents that are enriched with a radioisotope.

E3. Fluorination

It should be understood, that while the following section focuses on fluorination reactions, this is by no means limiting, and the teaching of this section may be applied to other halogenation reactions.

In some embodiments, an imaging moiety displaces a leaving group on a provided imaging agent precursor via a substitution reaction, such as an $S_N2$ or $S_N1$ reaction, thereby producing an imaging agent. In certain embodiments, a substitution reaction is a one-step procedure which does not require a subsequent deprotection step. That is, the substitution step is performed on a fully deprotected imaging agent precursor. In certain embodiments, a substitution reaction provided by the present invention produces a fluorinated imaging agent (e.g., an imaging agent comprising $^{18}$F).

In some embodiments, a method for synthesizing an imaging agent comprises contacting an imaging agent precursor of the invention (e.g., a compound of Formula (VIII)) with a fluoride species resulting in the fluoride species replacing the leaving group of the precursor to produce an imaging agent (e.g., a compound of Formula (Ia)) comprising the fluorine species).

In some embodiments, an inventive method employs a reaction described herein, such as in the description of halogenation reactions above. For example, in certain embodiments, a compound of Formula (VIII) is transformed to a compound of Formula (Ia) using a nucleophilic substitution reaction, an electrophilic substitution reaction, or an organometallic reaction as described herein.

In certain embodiments, a method according to the invention involves a nucleophilic fluorination reaction. It will be understood that the discussion of nucleophilic fluorination is exemplary of the methods described herein and is not limiting. In certain embodiments, an imaging agent precursor comprising a leaving group is reacted in the presence of a fluoride species, whereby $S_N2$ or $S_N1$ displacement of the leaving group by the fluoride species produces an imaging agent. In some embodiments, a fluoride species is isotopically enriched with $^{18}$F.

Those of ordinary skill in the art will be aware of suitable conditions for fluorinating a compound. For example, see International Patent Application No. PCT/US2011/024109, filed Feb. 8, 2011, published as International Patent Publication No. WO/2011/097649, by Cesati et al., incorporated herein by reference. In some cases, a compound of Formula (VIII), or a salt, free base, or combination thereof, is exposed to a source of fluorine, optionally enriched with an isotope of fluorine (e.g., enriched with $^{18}$F). In some cases, the source of fluorine is a fluoride salt (e.g., KF, NaF, tetralkylammonium fluoride).

The following provides a specific non-limiting example of a method of the present invention, comprising reaction an imaging agent precursor with a fluoride species to form an imaging agent. In desired, at least a portion of the imaging agent may optionally be deprotected (e.g., a guanidine functional group) and/or purified prior to use. In certain embodiments, the present invention provides a method comprising reacting a compound of Formula (VIII):

$$R^{O'}\text{—Ar-L—}R^{1} \qquad (VIII)$$

wherein

Ar is substituted or unsubstituted, monocyclic or bicyclic aryl or substituted or unsubstituted, monocyclic or bicyclic heteroaryl;

L is a bond; substituted or unsubstituted, cyclic or acyclic alkylene; substituted or unsubstituted, cyclic or acyclic alkenylene; substituted or unsubstituted, cyclic or acyclic alkynylene; or substituted or unsubstituted, cyclic or acyclic heteroaliphatic;

$R^{O'}$ is halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, —OR$^{A1}$, —N(R$^{A2}$)$_2$, —SR$^{A1}$, —C(=O)R$^{A1}$, —C(=O)OR$^{A1}$, —C(=O)SR$^{A1}$, —C(=O)N(R$^{A2}$)$_2$, —OC(=O)R$^{A1}$, —OC(=O)OR$^{A1}$, —OC(=O)SR$^{A1}$, —OC(=O)N(R$^{A2}$)$_2$, —NR$^{A2}$C(=O)R$^{A2}$, —NR$^{A2}$C(=O)OR$^{A1}$, —NR$^{A2}$C(=O)SR$^{A1}$, —NR$^{A2}$C(=O)N(R$^{A2}$)$_2$, —SC(=O)R$^{A1}$, —SC(=O)OR$^{A1}$, —SC(=O)SR$^{A1}$, —SC(=O)N(R$^{A2}$)$_2$, —C(=NR$^{A2}$)R$^{A1}$, —C(=NR$^{A2}$)OR$^{A1}$, —C(=NR$^{A2}$)SR$^{A1}$, —C(=NR$^{A2}$)N(R$^{A2}$)$_2$, —OC(=NR$^{A2}$)R$^{A1}$, —OC(=NR$^{A2}$)OR$^{A1}$, —OC(=NR$^{A2}$)SR$^{A1}$, —OC(=NR$^{A2}$)N(R$^{A2}$)$_2$, —NR$^{A2}$C(=NR$^{A2}$)R$^{A2}$, —NR$^{A2}$C(=NR$^{A2}$)OR$^{A1}$, —NR$^{A2}$C(=NR$^{A2}$)SR$^{A1}$, —NR$^{A2}$C(=NR$^{A2}$)N(R$^{A2}$)$_2$, —SC(=NR$^{A2}$)R$^{A1}$, —SC(=NR$^{A2}$)OR$^{A1}$, —SC(=NR$^{A2}$)SR$^{A1}$, —SC(=NR$^{A2}$)N(R$^{A2}$)$_2$, —C(=S)R$^{A1}$, —C(=S)OR$^{A1}$, —C(=S)SR$^{A1}$, —C(=S)N(R$^{A2}$)$_2$, —OC(=S)R$^{A1}$, —OC(=S)OR$^{A1}$, —OC(=S)SR$^{A1}$, —OC(=S)N(R$^{A2}$)$_2$, —NR$^{A2}$C(=S)R$^{A2}$, —NR$^{A2}$C(=S)OR$^{A1}$, —NR$^{A2}$C(=S)SR$^{A1}$, —NR$^{A2}$C(=S)N(R$^{A2}$)$_2$, —SC(=S)R$^{A1}$, —SC(=S)OR$^{A1}$, —SC(=S)SR$^{A1}$, —SC(=S)N(R$^{A2}$)$_2$, —S(=O)R$^{A1}$, —SO$_2$R$^{A1}$, —NR$^{A2}$SO$_2$R$^{A1}$, —SO$_2$N(R$^{A2}$)$_2$, —CN, —SCN, or —NO$_2$; and R$^0$ is substituted with a leaving group L$_G$ or is a leaving group L$_G$;

$R^1$ is a substituted or unsubstituted nitrogen-containing moiety;

each occurrence of $R^{A1}$ is independently hydrogen, optionally substituted alkyl, optionally substituted alkenyl, optionally substituted alkynyl, optionally substituted carbocyclyl, optionally substituted heterocyclyl, optionally substituted aryl, or optionally substituted heteroaryl; and each occurrence of $R^{A2}$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, or an amino protecting group, or two R$^{A2}$ groups are joined to form an optionally substituted heterocyclic ring; or a salt, free base, or combination thereof; with a fluorinating reagent under suitable conditions to form a compound of Formula (Ia):

$$R^{O}\text{—Ar-L—}R^{1} \qquad (Ia)$$

$R^O$ is halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, —OR$^{A1}$, —N(R$^{A2}$)$_2$, —SR$^{A1}$, —C(=O)R$^{A1}$, —C(=O)OR$^{A1}$, —C(=O)SR$^{A1}$, —C(=O)N(R$^{A2}$)$_2$, —OC(=O)R$^{A1}$, —OC(=O)OR$^{A1}$, —OC(=O)SR$^{A1}$, —OC(=O)N(R$^{A2}$)$_2$, —NR$^{A2}$C(=O)R$^{A2}$, —NR$^{A2}$C(=O)OR$^{A1}$, —NR$^{A2}$C(=O)SR$^{A1}$, —NR$^{A2}$C(=O)N(R$^{A2}$)$_2$, —SC(=O)R$^{A1}$, —SC(=O)OR$^{A1}$, —SC(=O)SR$^{A1}$, —SC(=O)N(R$^{A2}$)$_2$, —C(=NR$^{A2}$)R$^{A1}$, —C(=NR$^{A2}$)OR$^{A1}$, —C(=NR$^{A2}$)SR$^{A1}$, —C(=NR$^{A2}$)N(R$^{A2}$)$_2$, —OC(=NR$^{A2}$)R$^{A1}$, —OC(=NR$^{A2}$)OR$^{A1}$, —OC(=NR$^{A2}$)SR$^{A1}$, —OC(=NR$^{A2}$)N(R$^{A2}$)$_2$, —NR$^{A2}$C(=NR$^{A2}$)R$^{A2}$, —NR$^{A2}$C(=NR$^{A2}$)OR$^{A1}$, —NR$^{A2}$C(=NR$^{A2}$)SR$^{A1}$, —NR$^{A2}$C(=NR$^{A2}$)N(R$^{A2}$)$_2$, —SC(=NR$^{A2}$)R$^{A1}$, —SC(=NR$^{A2}$)OR$^{A1}$, —SC(=NR$^{A2}$)SR$^{A1}$, —SC(=NR$^{A2}$)N(R$^{A2}$)$_2$, —C(=S)R$^{A1}$, —C(=S)OR$^{A1}$, —C(=S)SR$^{A1}$, —C(=S)N(R$^{A2}$)$_2$, —OC(=S)R$^{A1}$, —OC(=S)OR$^{A1}$, —OC(=S)SR$^{A1}$, —OC(=S)N(R$^{A2}$)$_2$, —NR$^{A2}$C(=S)R$^{A2}$, —NR$^{A2}$C(=S)OR$^{A1}$, —NR$^{A2}$C(=S)SR$^{A1}$, —NR$^{A2}$C(=S)N(R$^{A2}$)$_2$, —SC(=S)R$^{A1}$, —SC(=S)OR$^{A1}$, —SC(=S)SR$^{A1}$, —SC(=S)N(R$^{A2}$)$_2$, —S(=O)R$^{A1}$, —SO$_2$R$^{A1}$, —NR$^{A2}$SO$_2$R$^{A1}$, —SO$_2$N(R$^{A2}$)$_2$, —CN, —SCN, or —NO$_2$; and R$^0$ is substituted with a fluorine.

As described herein, $R^{O'}$ of formula (VIII) comprises a leaving group. In some embodiments, a leaving group according to the present invention is a sulfonate leaving group. In some embodiments, $R^{O'}$ is alkoxy substituted with a leaving group. In certain embodiments, $R^{O'}$ is —OCH$_2$L$_G$, —OCH$_2$CH$_2$L$_G$, —OCH$_2$CH$_2$CH$_2$L$_G$, or —OCH$_2$CH$_2$CH$_2$CH$_2$L$_G$. In some embodiments, $R^{O'}$ is alkyl substituted with a leaving group. In certain embodiments, $R^{O'}$ is —CH$_2$L$_G$, —CH$_2$CH$_2$L$_G$, —CH$_2$CH$_2$CH$_2$L$_G$, or —CH$_2$CH$_2$CH$_2$CH$_2$L$_G$. In some embodiments, $R^{O'}$ is alkoxyalkyl substituted with a leaving group.

In some embodiments, a method according to the present invention employs a compound of Formula (VIII) wherein $R^{O'}$ is of the formula:

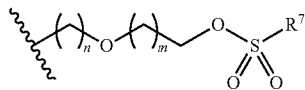

wherein n is an integer between 0 and 6, inclusive; m is an integer between 0 and 6, inclusive; and $R^7$ is substituted or unsubstituted, cyclic or acyclic alkyl; substituted or unsubstituted, cyclic or acyclic alkenyl; substituted or unsubstituted, cyclic or acyclic alkenyl; substituted or unsubstituted, cyclic or acyclic heteroaliphatic; substituted or unsubstituted aryl; substituted or unsubstituted heteroaryl, substituted or unsubstituted arylalkyl; or substituted or unsubstituted heteroarylalkyl.

In some embodiments, $R^7$ is substituted or unsubstituted C$_1$-C$_6$ alkyl. In certain embodiments, $R^7$ is methyl. In certain other embodiments, $R^7$ is CF$_3$. In some embodiments, R$_7$ is substituted or unsubstituted aryl. In certain embodiments, $R^7$ is substituted or unsubstituted phenyl. In certain embodiments, $R^7$ is p-tolyl. In some embodiments, $R^{O'}$ is alkoxymethyl substituted with a leaving group. In certain embodiments, $R^{O''}$ is —CH$_2$OCH$_2$L$_G$, —CH$_2$OCH$_2$CH$_2$L$_G$, —CH$_2$OCH$_2$CH$_2$CH$_2$L$_G$, or —CH$_2$OCH$_2$CH$_2$CH$_2$CH$_2$L$_G$.

In some embodiments, a provided compound of Formula (VIII) for use in synthetic methods of the present invention is as described in embodiments herein. In some embodiments, a provided compound of Formula (Ia) for use in synthetic methods of the present invention is as described in embodiments herein, such as a provided compound of Formula (Ib), (Ic), (Id), (IIa)-(IIb), (III), (IV), (Va)-(Vd), (VI), or (VII) and embodiments thereof described herein.

As described above, in certain embodiments, a compound of Formula (VIII) is allowed to react with a fluorinating reagent under suitable conditions to form a compound of Formula (Ia). In some embodiments, a fluorinating agent for use in a provided method is a source of fluoride. In certain embodiments, a fluorinating agent for use in a provided method is NaF or KF. In certain embodiments, a fluorinating agent for use in a provided method is isotopically enriched with $^{18}$F. In certain embodiments, suitable conditions for a fluorination reaction according to the present invention comprise the presence of an ammonium salt or a bicarbonate salt.

The fluorine source may comprise or be associated with or may be used in connection with another reagent. In some embodiments, an additional reagent may be capable of enhancing the reactivity of the fluorine species or otherwise facilitating conversion of the precursor to the imaging agent. For example, in certain embodiments, an additional reagent is used in combination with a multidentate ligand, such as a crown ether or a cryptand that is capable of chelating a metal ion. In certain embodiments, a multidentate ligand is, for example, 4,7,13,16,21,24-hexaoxa-1,10-diazabicyclo[8.8.8]-hexacosane (i.e., Kryptofix® 222). In certain embodiments, when KF is a fluorine source, cryptands having a high affinity for potassium are useful as they chelate potassium and thereby increase the reactivity of the fluoride ion. In some embodiments, cryptands having an affinity for potassium near that of Kryptofix® 222 (e.g., 75%, 80%, 85%, 90%, 95%, or more of the Kryptofix® 222's affinity for potassium) are used. The reaction conditions may comprise one or more solvents.

In some embodiments, the fluorination occurs in the presence of K$_2$CO$_3$ and Kryptofix® 222 (or any another cryptand having affinity for the cation of interest, including for example potassium, near that of Kryptofix® 222) in MeCN (acetonitrile) alone or in combination with t-BuOH, as the solvent. In some embodiments, the molar ratio of K$_2$CO$_3$ to imaging agent precursor ranges from about 0.5:1 to about 5:1, for example 0.5:1 to 1:1. In some embodiments, the molar ratio is about 0.66:1.

In some embodiments, fluorination occurs in the presence of tetraalkylammonium carbonate or tetraalkylammonium bicarbonate in MeCN as the solvent. In some embodiments, the molar ratio of tetraalkylammonium carbonate or bicarbonate to imaging agent precursor is 5:1. In some embodiments, the molar ratio ranges from about 7:1 to about 3:1, or from about 6:1 to about 4:1, or about 5.5:1 to about 4.5:1. In some embodiments, the tetraalkylammonium cation may be tetraethylammonium or tetrabutylammonium but it is not so limited.

In certain embodiments, the synthetic methods described herein involve a single-step preparation of imaging agents of the invention (e.g., compounds of Formula (Ia)-(Id), (IIa)-(IIb), (III), (IV), (Va)-(Vd), (VI), or (VII), or a salt, free base, or combination thereof). In certain embodiments, a single-step method involves fluorination of a completely or partially deprotected precursor in the presence of, for example, K$_2$CO$_3$/Kryptofix® 222 (or other suitable alternatives to Kryptofix® 222) or tetraalkylammonium carbonate or bicarbonate, in MeCN alone or in an MeCN mixture (such as an MeCN and t-BuOH mixture). In certain embodiments, single-step preparation methods are particularly suitable when particular salt forms of the imaging agent precursors of the invention are used, such as halide, acetate, formate, citric, ascorbate, trifluoroacetate, toluenesulfonate, benzoate, acetate, phosphate, sulfate, tosylate, and mesylate.

In some embodiments, an imaging agent precursor comprises a protected nitrogen functional group (e.g., a protected guanidine functional group) which may or may not be deprotected prior to, or in some instances after, fluorination. For example, a guanidine functional group may or may not be deprotected prior to fluorination. In some embodiments, an imaging agent precursor comprising a protected guanidine functional group is fluorinated, optionally followed by deprotection. In other embodiments, an imaging agent precursor comprising a protected guanidine functional group is deprotected (e.g., according to the methods described herein), followed by fluorination. As described herein, in certain embodiments, a fluorine source is isotopically enriched with $^{18}$F.

In some embodiments, one or more reagents is used in a reaction mixture comprising an imaging agent precursor and a fluoride species. A "reagent," also referred to as an "additive," is used herein to mean any chemical compound added to a reaction mixture. A reagent may be consumed or not consumed during the reaction. A reagent may be a stoichiometric or catalytic reagent. Exemplary reagents include catalysts, salts, oxidants, reductants, chelating agents, bases, acids, metals, phase transfer reagents, and others as would be appreciated by one of skill in the art.

A reagent may, in some embodiments, facilitate reaction between an imaging agent precursor and a fluoride species and/or may aid in stabilizing a resultant imaging agent. For example, in certain embodiments, a fluoride species may have relatively low reactivity (e.g., nucleophilicity), and addition of certain reagents may enhance the reactivity of the fluoride species. As an illustrative embodiment, a fluorine species may be a negatively charged fluoride ion (e.g., an isotopically enriched $^{18}$F ion), and a reagent may be used to bind to any positively charged counter ions present within the reaction mixture, thereby enhancing the reactivity of the fluoride ion. An example of such a reagent is a cryptand such as, but not limited to, Kryptofix (e.g., Kryptofix®-222). In some embodiments, a reagent decreases the rate of undesired side reactions, as described below.

In some embodiments, a reagent may be combined with a fluoride species prior to its contact with an imaging agent precursor. For example, in certain embodiments, a solution comprising a fluoride species and a reagent is prepared, and the solution is added to an imaging agent precursor. In other embodiments, a solid comprising a fluoride species and a reagent is prepared, and the solid is contacted with an imaging agent precursor in solution. In certain embodiments, a fluoride species is adsorbed onto a solid support (e.g., an anion exchange column), and a solution comprising the reagent is used to elute the fluoride species from the solid support. The eluted solution is then contacted with the imaging agent precursor, or is concentrated to produce a solid, which is then contacted with the imaging agent precursor in solution.

In some embodiments, a provided reagent is a bicarbonate salt. As used herein, the term "bicarbonate salt" refers to a salt comprising a bicarbonate or hydrogen carbonate ion ($HCO_3^-$ ion). In some embodiments, a bicarbonate salt is a metal bicarbonate, such as sodium bicarbonate, calcium bicarbonate, potassium bicarbonate, and magnesium bicarbonate. In certain embodiments, a bicarbonate salt is potassium bicarbonate ($KHCO_3$). In some embodiments, a bicarbonate salt comprises a non-metal counter ion, such as ammonium bicarbonate. For example, a bicarbonate salt may be a tetraalkylammonium bicarbonate salt having the formula, $R_4NHCO_3$, wherein R is alkyl. In some embodiments, R may be lower alkyl, such as methyl, ethyl, propyl, butyl, pentyl, hexyl, or the like. In certain embodiments, the ammonium salt is $Et_4NHCO_3$. In other embodiments, the salt is $Me_4NHCO_3$, $i$-$Pr_4NHCO_3$, $n$-$Pr_4NHCO_3$, $n$-$Bu_4NHCO_3$, $i$-$Bu_4NHCO_3$, or $t$-$Bu_4NHCO_3$.

In some embodiments, a provided reagent is a carbonate salt. As used herein, the term "carbonate salt" refers to a salt comprising a carbonate ion ($CO_3^{-2}$ ion). In some embodiments, a carbonate salt is a metal carbonate, such as sodium carbonate, calcium carbonate, potassium carbonate, and magnesium carbonate. In certain embodiments, a carbonate salt is potassium carbonate ($K_2CO_3$). In some embodiments, a carbonate salt comprises a non-metal counter ion, such as ammonium carbonate. For example, a carbonate salt may be a tetraalkylammonium carbonate salt having the formula, $(R_4N)_2CO_3$, wherein R is alkyl. In some embodiments, R may be a lower alkyl, such as methyl, ethyl, propyl, butyl, pentyl, hexyl, or the like. In certain embodiments, the ammonium salt is $(Et_4N)_2CO_3$. In other embodiments, the salt is $(Me_4N)_2CO_3$, $(i$-$Pr_4N)_2CO_3$, $(n$-$Pr_4N)_2CO_3$, $(n$-$Bu_4N)_2CO_3$, $(i$-$Bu_4N)_2CO_3$, or $(t$-$Bu_4N)_2CO_3$.

Without wishing to be bound by any particular theory, use of bicarbonate, carbonate, and/or ammonium salts may aid in decreasing the rate of competing reactions such as hydrolysis during nucleophilic fluorination of an imaging agent precursor.

In some embodiments, a reagent is a salt comprising a cation that forms a weakly coordinating salt with a fluoride species. As used herein, a "cation that forms a weakly coordinating salt with a fluoride species" refers to a cation that renders a fluoride species reactive in the context of a fluorination reaction. For example, a cation may not strongly bind to the fluoride species, allowing the fluoride species to act as a nucleophile during a nucleophilic fluorination reaction. Those of ordinary skill the art would be able to select an appropriate cation that would be suitable as a weakly coordinating counter ion for a fluoride species. For example, a cation may be have a relatively large atomic radius and/or may be a weak Lewis base. In some cases, a cation may be selected to be lipophilic. In some cases, a cation may comprise one or more alkyl groups. Examples of weakly coordinating cations include cesium ions, ammonium ions, weakly coordinating salts of hexamethylpiperidindium, $S(NMe_2)_3$, $P(NMe_2)_4$, tetraalkylphosphonium salts, tetraarylphosphonium salts, (e.g. tetraphenylphosphonium), hexakis(dimethylamino)diphosphazenium, and tris(dimethylamino)sulfonium.

In some embodiments, a provided reagent is an ammonium salt, i.e., a salt comprising a substituted or unsubstituted ammonium ion. In some embodiments, an ammonium ion is a weakly coordinating cation. In some embodiments, an ammonium salt has the formula, $R_4NX$, where each R can be the same or different and is alkyl, heteroalkyl, aryl, heteroaryl, or heterocyclic, each optionally substituted, and X is a negatively charged counter ion. In some cases, R is alkyl, heteroalkyl, aryl, heteroaryl, or heterocyclic, each optionally substituted. In some embodiments, ammonium salt may include a range of negatively charged counter ions, including halides, carbonates, and bicarbonates. Examples of ammonium salts include, but are not limited to, ammonium bicarbonate salts, ammonium hydroxide salts, ammonium acetate salts, ammonium lactate salts, ammonium trifluoroacetate salts, ammonium methanesulfonate salts, ammonium p-toluenesulfonate salts, ammonium nitrate salts, ammonium halide salts (e.g., ammonium iodide salts), and ammonium bisulfate salts.

In one set of embodiments, an ammonium salt is a tetraalkylammonium salt, such as a tetraalkylammonium bicarbonate salt. For example, an ammonium salt may have the formula, $R_4NHCO_3$, wherein each R is independently alkyl. In some cases, R is optionally substituted. In some embodiments, the alkyl group is a lower $C_1$-$C_6$ alkyl group. In some embodiments, an tetraalkylammonium salt is a basic tetraalkylammonium salt.

In some embodiments, a salt (e.g., bicarbonate salt and/or ammonium salt) may be utilized in the reaction such that the molar ratio of the salt to the imaging agent precursor is less than or equal to about 10:1, or less than or equal to about 9:1, or less than or equal to about 8:1, or less than or equal to about 7:1 or less than or equal to about 6:1, or less than or equal to about 5:1, or less than or equal to about 4:1, or less than or equal to about 3:1, or less than or equal to about 2:1, or less than or equal to about 1:1. In some cases, the molar ratio of the salt to the imaging agent precursor is between about 3:1 and about 8:1, or between about 4:1 and about 7:1, or between about 5:1 and about 7:1, or between about 5:1 and about 8:1.

In some embodiments, a reagent is used in combination with a species capable of enhancing the reactivity of the fluoride species or otherwise facilitating conversion of the imaging agent precursor to the imaging agent. For example, a species may be a compound capable of chelating one or more ions (e.g., metal ions) that may be present within the reaction mixture. Without wishing to be bound by theory, a species may be used to chelate a counter ion to a fluoride species, such as a potassium ion, thereby increasing the reactivity (e.g., nucleophilicity) of the fluoride species. In certain embodiments, a reagent is used in combination with a multidentate ligand, such as a crown ether or a cryptand that is capable of chelating a metal ion. The multidentate ligand (e.g., cryptand) may be selected based on the metal ion to be chelated. A multidentate ligand may be, for example, 4,7,13,16,21,24-hexaoxa-1,10-diazabicyclo[8.8.8]-hexacosane (e.g., Kryptofix® 222). Other cryptands will be known to those of ordinary skill in the art.

Some embodiments involve use of a carbonate salt in combination with 4,7,13,16,21,24-hexaoxa-1,10-diazabicyclo[8.8.8]-hexacosane. In a specific embodiment, potassium carbonate is used in combination with 4,7,13,16,21,24-hexaoxa-1,10-diazabicyclo[8.8.8]-hexacosane.

In another set of embodiments, it may be advantageous to utilize the methods described herein in the absence of a cryptand. The term "cryptand" is given its ordinary meaning in the art and refers to a bi- or a polycyclic multidentate ligand for a cation. For example, inventive methods may be carried out using an ammonium salt, in the absence of a cryptand (e.g., 4,7,13,16,21,24-hexaoxa-1,10-diazabicyclo[8.8.8]-hexacosane). In some embodiments, cryptands may increase the pH of the reaction solution, which in the presence of another reagent (e.g. carbonate salt) may adversely affect the yield and/or purity of the fluorination reaction. Accordingly, in certain embodiments, carrying out the fluorination reaction, in the absence of a cryptand, and optionally in the presence of another reagent (e.g., ammonium and/or bicarbonate salt) may increase the yield and/or purity of the reaction, as described herein.

In another set of embodiments, a method according to the present invention is performed in the absence of a carbonate salt.

As will be understood by one of ordinary skill in the art, during fluorination (or other halogenation reactions), any associated anionic species (e.g., in instances where the starting material is a salt) may be exchanged. That is, in certain embodiments, the starting material may be provided as a first salt (e.g., trifluoroacetate, chloride), and the isolated product (e.g., the fluorinated product) may be isolated as a second, different salt (e.g., formate, ascorbate, citrate, or trifluoroacetate). In some embodiments, following formation of a salt, a counter anion may be exchanged in an additional step. For example, an HCl salt of a compound may be exposed to a suitable reagent (e.g., AgOAc or AgOBz) such that the compound forms the corresponding salt of the reagent (e.g., acetate salt or benzoate salt, respectively). As another example, a TFA salt of a compound may be exposed to a suitable reagent (e.g., phosphoric acid or methanesulfonic acid) such that the compound forms the corresponding salt of the reagent (e.g., phosphate salt or methanesulfonate salt, respectively). The intermediate salt (e.g., trifluoroacetate salt or chloride salt in the above-examples) may or may not be isolated prior to exposure to the reagent.

Those of ordinary skill in the art will be able to select and/or determine an appropriate set of reaction conditions (e.g., concentration, temperature, pressure, reaction time, solvents) suitable for use in a particular application. In some embodiments, an imaging agent may be further processed using one or more purification techniques, and may optionally be combined with additional components, such as a stabilizing agent.

In some embodiments, an imaging agent is formed as a salt (e.g., a pharmaceutically acceptable salt). Pharmaceutically acceptable excipients and other aspects of pharmaceutically acceptable compositions are described herein.

Those of ordinary skill in the art would be able to select a source of a fluoride species suitable for use in the methods described herein. The term "fluoride species" as used herein refers to a fluoride atom or group of atoms comprising at least one fluoride atom, wherein the fluoride atom is capable of reacting with another compound (e.g., an imaging agent precursor). In some embodiments, an isotopically-enriched $^{18}F$ species may be produced by the nuclear reaction $^{18}O$ (p,n)$^{18}F$ from proton bombardment of [$^{18}O$]H$_2$O in a cyclotron. In certain embodiments, a method may involve treating a solution of the $^{18}F$ species to remove any impurities, such as unreacted [$^{18}O$]H$_2$O. For example, a solution of the $^{18}F$ species may be filtered through an anion exchange column, where the $^{18}F$ species is retained on the cationic resin matrix while the [$^{18}O$]H$_2$O is eluted. The $^{18}F$ species is then removed by washing the anion exchange column with various mixtures of solvents and optional reagents (e.g., salt), forming an $^{18}F$-containing solution. In some embodiments, an anion exchange column is washed with an aqueous solution of a salt, such as K$_2$CO$_3$ or Et$_4$NHCO$_3$. In other embodiments, a column is washed (e.g., with aqueous K$_2$CO$_3$), and the resulting solution diluted (e.g., with MeCN) and/or concentrated (e.g., to dryness using elevated temperature and/or reduced pressure). Anhydrous [$^{18}F$]KF and/or [$^{18}F$]Et$_4$NF may be obtained and reacted with a compound or a salt thereof.

In some embodiments, a $^{18}F$-containing solution is combined with additional components prior to reaction with an imaging agent precursor. For example, one or more solvents may be added to dilute a $^{18}F$-containing solution to a desired concentration. In certain embodiments, a $^{18}F$-containing solution is diluted with acetonitrile (MeCN). In certain embodiments, a $^{18}F$-containing solution is diluted with acetonitrile (MeCN) and t-BuOH.

In some embodiments, a $^{18}F$-containing solution may be concentrated to dryness by exposure to elevated temperature and/or reduced pressure to form an anhydrous $^{18}F$-containing solid. In some embodiments, a $^{18}F$-containing solid may further comprise one or more reagents (e.g., salts). The chemical composition of a $^{18}F$-containing solid may depend on the number and kind of reagents used in preparation of the $^{18}F$-containing solution. For example, a solution of potassium carbonate may be used to elute a $^{18}F$ species from the anion exchange column, thereby resulting in an $^{18}F$-containing solid comprising [$^{18}F$]KF. In another example, a solution of tetraethylammonium bicarbonate is used to elute a $^{18}F$ species from the anion exchange column, thereby resulting in an $^{18}F$-containing solid comprising [$^{18}F$]Et$_4$NF.

In some embodiments, a solution comprising a $^{18}F$ species is heated to a temperature ranging from room temperature to about 200° C. For example, a solution comprising a [$^{18}F$]-fluoride may be heated to elevated temperatures to encourage evaporation of the solvent (e.g., to about 110° C.). In some embodiments, a solution is heated to a temperature ranging from about 90-120° C. or from about 100-150° C. In some embodiments, a solution is heated to about 75° C., about 85° C., about 95° C., about 105° C., about 115° C., about 125° C., or greater. In some embodiments, a solution is placed under a reduced pressure of about 100 mm Hg, about 125 mm Hg, about 150 mm Hg, about 175 mm Hg, about 200 mm Hg, about 225 mm Hg, about 250 mm Hg, about 275 mm Hg, about 300 mm Hg, about 325 mm Hg, about 350 mm Hg, about 375 mm Hg, about 400 mm Hg, or greater. In some embodiments, a solution is placed under a reduced pressure of about 100 mbar, about 125 mbar, about 150 mbar, about 175 mbar, about 200 mbar, about 225 mbar, about 250 mbar, about 275 mbar, about 280 mbar, about 300 mbar, about 325 mbar, about 350 mbar, about 375 mbar, about 400 mbar, about 450 mbar, about 500 mbar, or greater. Those of ordinary skill in the art would be able to select and/or determine conditions suitable for a particular process. In some embodiments, a solution is concentrated to dryness at about 150 mm Hg and about 115° C. In some embodiments, a solution is concentrated to dryness at about 375 mm Hg and about 115° C. In some embodiments, a solution is concentrated to dryness at about 400 mbar and about 110-150° C. In some embodiments, a solution is concentrated to dryness at about 280 mbar and about 95-115° C.

In certain embodiments, a fluoride species and/or a reagent, if present, is then contacted with an imaging agent precursor under conditions that result in conversion of the imaging agent precursor to the imaging agent product via nucleophilic fluorination. Those of ordinary skill in the art would be able to select conditions suitable for use in a particular reaction. For example, in certain embodiments, the ratio of fluoride species to imaging agent precursor may be selected to be about 1:10,000 or more, about 1:5000 or more, about 1:3000 or more, about 1:2000 or more, about 1:1000 or more, about 1:500 or more, about 1:100 or more, about 1:50 or more, about 1:10 or more, about 1:5 or more, or, in some cases, about 1:1 or more. In some embodiments, a fluoride species may be present at about 10 mol %, or about 5 mol %, or about 3 mol %, or about 2 mol %, or about 1 mol % or about 0.5 mol %, or about 0.1 mol %, or about 0.05 mol %, or about 0.01 mol % relative to the amount of imaging agent precursor. In some embodiments, a fluoride species is isotopically enriched with $^{18}$F. For example, in some embodiments, the ratio of $^{18}$F species to imaging agent precursor may be selected to be about 1:1,000,000 or more, or about 1:500,000 or more, or about 1:250,000 or more, or about 1:100,000 or more, or about 1:50,000 or more, or about 1:25,000 or more, or about 1:10,000 or more, about 1:5000 or more, about 1:3000 or more, about 1:2000 or more, about 1:1000 or more, about 1:500 or more, about 1:100 or more, about 1:50 or more, about 1:10 or more, about 1:5 or more, or, in some cases, about 1:1 or more.

In some embodiments, a nucleophilic fluorination reaction is carried out in the presence of one or more solvents, for example, an organic solvent, a non-organic solvent (e.g., an aqueous solvent), or a combination thereof. In some embodiments, the solvent is a polar solvent or a non-polar solvent. In some embodiments, the solvent is an aqueous solution, such as water. In some embodiments, the solvent comprises at least about 0.001% water, at least about 0.01% water, at least about 0.1% water, at least about 1% water, at least about 5%, at least about 10%, at least about 20% water, at least about 30% water, at least about 40% water, at least about 50% water, or greater. In some embodiments, the solvent may comprise between about 0.1% and about 100% water, about 1% to about 90%, about 1% to about 70%, about 1% to about 50%, or about 10% to about 50%. In some embodiments, the solvent comprises no more than about 10% water, about 5% water, about 4% water, about 3% water, about 2% water, about 1% water, or about 0.5% water. In some embodiments, the solvent comprises between about 0.01% water and about 5% water, or between about 0.01% water and about 2% water, or between about 0.1% water and about 0.2% water.

Other examples of solvents useful in the methods include, but are not limited to, non-halogenated hydrocarbon solvents (e.g., pentane, hexane, heptane, cyclohexane), halogenated hydrocarbon solvents (e.g., dichloromethane, chloroform, fluorobenzene, trifluoromethylbenzene), aromatic hydrocarbon solvents (e.g., toluene, benzene, xylene), ester solvents (e.g., ethyl acetate), ether solvents (e.g., tetrahydrofuran, dioxane, diethyl ether, dimethoxyethane), and alcohol solvents (e.g., ethanol, methanol, propanol, isopropanol, tert-butanol). Other non-limiting examples of solvents include acetone, acetic acid, formic acid, dimethyl sulfoxide, dimethyl formamide, acetonitrile, p-cresol, glycol, petroleum ether, carbon tetrachloride, hexamethyl-phosphoric triamide, triethylamine, picoline, and pyridine. In some embodiments, a provided reaction is carried out in a polar solvent, such as acetonitrile. In some embodiments, a solvent may be selected so as to reduce and/or minimize the formation of side products. In certain embodiments, a fluorination reaction is carried out in MeCN as solvent. In certain embodiments, a fluorination reaction is carried out in t-BuOH as solvent. In certain embodiments, a fluorination reaction is carried out in a mixture of MeCN and t-BuOH as solvent. In certain embodiments, a fluorination reaction is carried out in DMF as solvent. In certain embodiments, a fluorination reaction is carried out in DMSO as solvent. In certain embodiments, a fluorination reaction is carried out in THF as solvent.

In certain embodiments, an anhydrous $^{18}$F-containing solid, optionally comprising a reagent, may be contacted with a solution of an imaging agent precursor (e.g., a tosylate precursor), and the resulting solution is heated to an elevated temperature for a select period of time. A solution may be, for example, an acetonitrile solution. In other embodiments, a solution of an $^{18}$F species and reagent, if present, is contacted with a solid imaging agent precursor or a solution of an imaging agent precursor.

Some embodiments involve contacting an imaging agent precursor with a fluoride species in a solution having a pH below about 13, below about 12, or below about 11. In some cases, a solution has a pH between about 8 and about 9, or between about 8 and about 10, or between about 7 and about 8. In certain embodiments, a pH range for the fluorination reaction is greater than about 6, or greater than about 7, or between and including 7-13, between and including 6-12, between and including 7-12, between and including 8-12, between and including 9-12, and between and including 10-12.

In some cases, a solution comprising a $^{18}$F species, imaging agent precursor, and, optionally, reagent, is heated to an elevated temperature for a period of time. For example, a solution may be heated to about 50° C., about 60° C., about 70° C., about 80° C., about 90° C., about 100° C., about 110° C., about 120° C., about 150° C., about 170° C., about 200° C., about 225° C., about 250° C., or greater, for a period of about 5 minutes or less, about 10 minutes or less, about 20 minutes or less, about 30 minutes or less. It should be understood that other temperatures and reaction times may be used. In some embodiments, upon completion of the reaction, the reaction mixture is cooled (e.g., to room temperature) and optionally diluted with a solvent, such as water, or mixtures of solvents, such as water/acetonitrile. In some embodiments, a reaction mixture is heated to elevated temperatures to encourage evaporation of the solvent (e.g., to about 95° C.). In some embodiments, a solution is heated to a temperature ranging from about 55-125° C. In some cases, a solution is heated to about 65° C., about 75° C., about 85° C., about 95° C., about 105° C., about 115° C., or greater. In some cases, a solution is placed under a reduced pressure of about 100 mm Hg, about 125 mm Hg, about 150 mm Hg, about 175 mm Hg, about 200 mm Hg, about 225 mm Hg, about 250 mm Hg, about 275 mm Hg, about 300 mm Hg, about 325 mm Hg, about 350 mm Hg, about 375 mm Hg, about 400 mm Hg, or greater. In some cases, a solution is placed under a reduced pressure of about 100 mbar, about 125 mbar, about 150 mbar, about 175 mbar, about 200 mbar, about 225 mbar, about 250 mbar, about 275 mbar, about 280 mbar, about 300 mbar, about 325 mbar, about 350 mbar, about 375 mbar, about 400 mbar, about 450 mbar, about 500 mbar, or greater. Those of ordinary skill in the art would be able to select and/or determine conditions suitable for a particular process. In some embodiments, a solution is concentrated to dryness under a flow of inert gas at about 95° C.

In some embodiments, upon completion of a fluorination reaction, the resulting imaging agent is optionally subjected to one or more purification steps. In some embodiments, an imaging agent may be reconstituted in a solvent prior to purification (e.g., by chromatography such as HPLC). In some cases, an imaging agent is dissolved in water, acetonitrile, or combinations thereof. In some embodiments, following formation of a solution comprising an imaging agent and a solvent and prior to purification (e.g., by HPLC), the solution is heated. In a particular embodiment, an imaging agent is reconstituted in a water/acetonitrile mixture and heated (e.g., to a temperature of about 90-100° C.) for about 1 minute, about 3 minutes, about 5 minutes, about 10 minutes, about 20 minutes, about 30 minutes, or more. Following heating of the mixture, the solution may be optionally cooled prior to purification.

E4. Metal Chelation

In some embodiments, an imaging agent according to the present invention does not contain a covalent-bound imaging moiety. In some embodiments, a provided imaging agent comprises a chelator associated with an imaging moiety (e.g., $^{64}$Cu, $^{89}$Zr, $^{99m}$Tc, or $^{111}$In). In some embodiments, a provided imaging agent is formed via association of a chelator with an imaging moiety. For example, in some embodiments, formation of a compound of Formula (Ia) comprises associating the $R^0$ group comprising a chelator with an imaging moiety. Conditions for effecting association of an imaging moiety with a chelator will depend on the type of chelator being used and are well known in the art.

E5. Deprotection

In some embodiments, an imaging agent precursor and/or an imaging agent is deprotected. For example, in embodiments wherein the imaging agent precursor and/or imaging agent comprises a protected nitrogen functional group (e.g., a protected guanidine), the protected nitrogen functional group may be deprotected.

Those of ordinary skill in the art will be aware of suitable conditions for deprotecting a protected nitrogen functional group (e.g., a protected guanidine). The protecting groups may be remove prior to, simultaneously, and/or subsequent formation of an imaging agent from an imaging agent precursor. In some cases, the deprotection occurs following formation of the imaging agent.

In some embodiments, suitable conditions comprise exposing a compound comprising a protected nitrogen functional group (e.g., guanidine) to an acid. An acid may be added neat or in a solution (e.g., such that the acid is at a concentration of about 0.1 M, about 0.2 M, about 0.3 M, about 0.4 M, about 0.5 M, about 0.75 M, or about 1.0 M). In certain embodiments, a nitrogen-protecting group is t-butyloxycarbonyl, and an acid used for deprotection is trifluoroacetic acid. In certain embodiments, following deprotection, a provided compound is a salt (e.g., a trifluoroacetate salt).

In some embodiments, suitable conditions for deprotection comprise acidic conditions. In certain embodiments, an acid is provided at a ratio of about 2:1, about 1:1, about 1:2, about 1:3, or about 1:4 compound:acid. In certain embodiments, the pH range for deprotection of imaging agent precursors such as compounds of Formula (VIII) (or alternatively of protected fluorinated imaging agents of the invention) may be equal to or less than about 4, including equal to or less than about 3, equal to or less than about 2, and equal to or less than about 1.

In certain embodiments, deprotection conditions may comprise one or more solvents. Non-limiting examples of solvents are provided herein. A deprotection reaction may be carried out at any suitable temperature, and in certain embodiments, a deprotection reaction is carried out at room temperature or above room temperature. The product of a deprotection reaction may be analyzed, isolated, and/or purified using techniques known to those of ordinary skill in the art (e.g., column chromatography, HPLC, NMR, MS, IR, UV/Vis). In some embodiments, the product of a deprotection reaction is isolated as a salt (e.g., via filtration, crystallization). In certain embodiments, the salt is an ascorbate salt. In certain embodiments, the salt is a formate salt. In some embodiments, the salt is a citrate salt. In some embodiments, the salt is a trifluoroacetate salt.

E6. Purification and Formulation

In some cases, the synthesis, purification, and/or formulation of an imaging agent is performed using an automated reaction system optionally comprising a cassette, wherein the cassette comprises a synthesis module, a purification module, and/or a formulation module. Automated reaction systems and cassettes are described herein.

Purification and isolation may be performed using methods known to those skilled in the art, including separation techniques like chromatography, or combinations of various separation techniques known in the art, for example, extractions, distillation, and crystallization. In one embodiment, high performance liquid chromatography (HPLC) is used with a solvent, or mixture of solvents, as the eluent, to recover the product. In some cases, the eluent includes a mixture of water and acetonitrile, such as a 20:80 water:acetonitrile mixture. The content of water in the eluent may vary from, for example, about 1% to about 30%. In some cases, HPLC purification may be performed using a C18 column. The product may be analyzed (e.g., by HPLC) to determine yield (e.g., radiochemical yield) and/or radiochemical purity. The radiochemical purity may be greater than about 50%, about 60%, about 70%, about 80%, about 90%, about 95%, about 97%, about 98%, about 99%, or more. The percent yield of a product may be greater than 10%, greater than 20%, greater than 30%, greater than 40%, greater than 50%, greater than about 60%, greater than about 70%, greater than about 75%, greater than about 80%, greater than about 85%, greater than about 90%, greater than about 92%, greater than about 95%, greater than about 96%, greater than about 97%, greater than about 98%, greater than about 99%, or greater. In some embodiments, the radiochemical yield ranges from 15-50%.

The product may be further processed using additional purification techniques, such as filtration. In some cases, the imaging agent is purified using HPLC, to produce a solution of HPLC mobile phase and the imaging agent. The HPLC mobile phase may be subsequently exchanged for a solution of ascorbic acid or a salt thereof, and ethanol solution, by filtration through a C-18 resin (e.g., C18 Sep-Pak® cartridge). In some embodiments, the solution of the HPLC mobile phase and the imaging agent is filtered through a C-18 resin, where the imaging agent remains on the resin and the other components, such as acetonitrile and/or other solvents or components, are removed via elution. The C-18 resin may be further washed with a solution of ascorbic acid or a salt thereof, and the filtrate discarded. To recover the purified imaging agent, the C-18 resin is washed with a solvent, such as ethanol, and the resulting solution is optionally further diluted with an ascorbic acid solution or a salt thereof, as described herein.

Optionally, the recovered product is combined with one or more stabilizing agents, such as ascorbic acid or a salt thereof. For example, a solution comprising the purified imaging agent may be further diluted with a solution of ascorbic acid or a salt thereof. As described herein, a formulation may be prepared via an automated reaction system comprising a cassette.

In some cases, a solution comprising the imaging agent product may be sterile filtered (e.g., using a 13 mm diameter, Millipore, Millex PVDF 0.22 μm sterilizing filter) into a sterile product vial. The sterile product vial may be a commercially available, pre-sterilized unit that is not opened during the production process, as any imaging agents (or other components) may be aseptically inserted through the septum prior to use. Those of ordinary skill in the art would be able to select suitable vials and production components, including commercially available, pre-sterilized units comprising a 0.22 μm pore size membrane venting filter and quality control sampling syringes.

Following aseptic filtration, individual doses may be filled in syringes, labeled, and shipped to a clinical site. Dosing administration techniques, kits, cassettes, methods and systems (e.g., automated reaction systems) for synthesis of the imaging agent, and testing procedures are described herein. In some embodiments, the product is dispensed into a 3 or 5 mL syringe and labeled for distribution. Labels may be prepared at a radiopharmacy and applied to a syringe shield and shipping container. Additional labels may be provided in the shipping container for inclusion in clinical site records.

F. Uses of Imaging Agents

In another aspect, the present invention provides methods of imaging, including methods of imaging a subject that includes administering a composition or formulation that includes an imaging agent as described herein to the subject by injection, infusion, or any other method of administration, and imaging a region of interest of the subject. Regions of interest may include, but are not limited to, the heart, a portion of the heart, the cardiovascular system, cardiac vessels, blood vessels (e.g., arteries and/or veins), brain, pancreas, adrenal glands, other organs, and tumors.

In some embodiments, methods of this disclosure include (a) administering to a subject a composition that includes an imaging agent as described herein, and (b) acquiring at least one image of at least a portion of the subject. In some cases, the step of acquiring employs positron emission tomography (PET) for visualizing the distribution of the imaging agent within at least a portion of the subject. As will be understood by those of ordinary skill in the art, imaging using methods of this disclosure may include full body imaging of a subject, or imaging of a specific body region, organ, or tissue of the subject that is of interest. For example, if a subject is known to have, or is suspected of having myocardial ischemia, methods of this disclosure may be used to image the heart of the subject. In some embodiments, imaging may be limited to the heart or may include the heart and its associated vasculature.

In some embodiments, imaging agents as described herein are used to monitor and/or assess certain aspects of the sympathetic nervous system (SNS). The SNS plays a role in normal cardiac regulation and/or the pathogenesis of heart failure development and/or progression. Generally, following myocardial insult (e.g., myocardial infarction, valve regurgitation, hypertension), compensatory activation of the SNS is induced to help maintain sufficient cardiac output. Sustained elevation of the cardiac SNS can cause elevated cardiac norepinephrine (NE) release, down regulation of the beta1 adrenergic receptor, and/or down regulation of the NE transporter (NET), which can result in spillover of NE. Elevated levels of NE can be attributed to cardiac myocyte hypertrophy, fibroblast activation, collagen deposition, and/or myocyte apoptosis, which can result in ventricle remodeling and/or susceptibility to arrhythmia.

In some embodiments, assessment of the changes and/or the presence of a neurotransmitter in a subject, and certain parameters relating to the neurotransmitter provides feedback relating to cardiac events. For example, assessment of NET in a subject can be used to provide feedback relating to cardiac events and/or cardiac exposure to NE. In some cases, the neurotransmitter is a monoamine other than NE.

In some embodiments, the neurotransmitter is NE. Utilizing an imaging agent that targets NET permits imaging of the location, concentration, density, and/or distribution of NETs and also can be used to detect changes in NETs over time, for example, by acquiring a first NET image in a subject or region of a subject; obtaining a subsequent NET image of the subject or the region of the subject and comparing the first and subsequent images. Differences between the images can provide information on the change in NET status in the subject or region of the subject. Changes in a NET parameter (e.g., location, density, concentration, and/or distribution) over time may be assessed and correlated with disease onset, progression, and/or regression. In some embodiments, a method comprises administering a dose of a pharmaceutically acceptable composition to a subject, and acquiring at least one image of a portion of the subject, wherein the image allows for the assessment and/or detection of NET in the subject. In some cases, the detection comprises detection of the level (e.g., concentration) of NET, detection of the density of NET, detection of NET function, and/or detection of the localization of NET.

In some embodiments, changes in NET (e.g., density, localization, concentration, function) may be used to assess the presence and/or absence of a condition, disease, and/or disorder. For example, in some cases, changes in NET may be used to assess cardiac sympathetic innervation and/or myocardial sympathetic function in a subject. For example, an increase or decrease in NET concentration in a portion of the subject (e.g., heart) may indicate the cardiac sympathetic innervation in that portion of the subject. In some cases, subjects with impaired NET functions are correlated with heart failure and/or rapid myocardial reorganization.

In some embodiments, an imaging agent that targets NET may also be used to observe, estimate, and/or quantify localized blood flow to tissue. More specifically, there may be instances in which the level of imaging agent (or radioactivity) observed in the myocardium, is decreased compared to normal or below threshold. There may be various causes of this decreased signal, one of which may be reduced blood flow to and through the myocardium. In order to determine the cause, the subject may be imaged using a different imaging agent and/or a different imaging modality suitable for detecting blood flow. Comparison of images obtained using the different methods can reveal whether the decrease or absence of signal from the imaging agent that targets NET is attributable to blood flow rather than to a difference in NET level, activity and the like. In other embodiments of the invention, the myocardium may be imaged serially, for example immediately after administration of the imaging agent, in order to observe movement of the imaging agent into the heart. Such serial images should yield information about blood flow through the heart. Later images are also obtained as these reveal a more steady state of blood flow into and out of the heart as well as blood retention in the heart. In this way, alterations in global, local, or regional blood flow may be distinguished from local or regional changes in NET density, localization, concentration, and function as described above.

In some embodiments, an imaging agent that targets NET is used to assess the ability of a therapeutic agent and/or treatment to modify NET. For example, images acquired from a subject administered an imaging agent before therapeutic treatment can be compared to images acquired from the same subject after therapeutic treatment of the subject to determine if the treatment has affected the location, concentration, and/or density of NET for the subject. Similarly, images at different times and/or before and after treatment can be used to detect changes in NET in a subject over time and/or with treatment.

In some aspects, global images (e.g., global NET images) are acquired, and in other aspects of the invention, regional images (e.g., regional NET images) are acquired following administration of an imaging agent that targets NET, wherein a global image is an image of all or substantially all of an organ (e.g., heart, kidney, pancreas), and a regional image is an image of only a portion of an organ. Images can be acquired using an image collection system such as a PET system, a SPECT system, or any other suitable imaging system.

In some embodiments, images may be acquired over a single time interval, and in other embodiments, they may be acquired as a series of images of the same or different acquisition durations beginning either at the time of administration or at a later time.

In some embodiments, the imaging agents may be used to image cardiac innervation. In some embodiments, agents for imaging cardiac innervation may be utilized in the assessment of heart failure. In certain embodiments, the methods comprise an assessment of heart failure progression in a subject, wherein the assessment may include determination of the effectiveness of a treatment regimen. In some cases, the treatment regimen may include a beta blocker. In other cases, the treatment may require implantation of a pacemaker or implantable cardioverter-defibrillator (ICD). In certain embodiments, agents for imaging cardiac innervation may be useful in the prediction of a time course for heart failure disease progression.

In some embodiments, methods of diagnosing or assisting in diagnosing a disease or condition, assessing efficacy of a treatment of a disease or condition, or imaging of a subject with a known or suspected cardiovascular disease or condition changing sympathetic innervations are provided. A cardiovascular disease can be any disease of the heart or other organ or tissue supplied by the vascular system. The vascular system includes coronary arteries, and all peripheral arteries supplying the peripheral vascular system and the brain, as well as veins, arterioles, venules, and capillaries. In cases, cardiac innervation may be examined, as abnormalities in cardiac innervation have been implicated in the pathophysiology of many heart diseases, including sudden cardiac death, congestive heart failure, diabetic autonomic neuropathy, myocardial ischemia, and cardiac arrhythmias. Other non-limiting examples of cardiovascular diseases of the heart include diseases such as coronary artery disease, myocardial infarction, myocardial ischemia, angina pectoris, congestive heart failure, cardiomyopathy (congenital or acquired), arrhythmia, or valvular heart disease. In some embodiments, the methods disclosed herein are useful for monitoring and measuring cardiac innervation. For example, a method described herein can determine the presence or absence of cardiac innervation. Conditions of the heart may include damage, not brought on by disease but resulting from injury e.g., traumatic injury, surgical injury. Methods described herein can be used in some embodiments to determine global or regional changes in cardiac sympathetic innervation.

In some cases, a subject whom an imaging agent as described herein may be administered may have signs or symptoms suggestive of a disease or condition associated with abnormalities in cardiac innervation. In some cases, use of the imaging agent can be used to diagnose early or pre-disease conditions that indicate that a subject is at increased risk of a disease. Imaging methods described herein may be used to detect cardiac innervation in subjects already diagnosed as having a disease or condition associated with abnormalities in cardiac innervation, or in subjects that have no history or diagnosis of such a disease or condition. In other instances, the methods may be used to obtain measurements that provide a diagnosis or aid in providing a diagnosis of a disease or condition associated with abnormalities in cardiac innervation. In some instances, a subject may be already undergoing drug therapy for a disease or condition associated with abnormalities in cardiac innervation, while in other instances a subject may be without present therapy for a disease or condition associated with abnormalities in cardiac innervation. In some embodiments, the method may be used to assess efficacy of a treatment for a disease or condition. For example, the heart can be visualized using contrast/imaging agents described herein before, during, and/or after treatment of a condition affecting the heart of a subject. Such visualization may be used to assess a disease or condition, and aid in selection of a treatment regimen, e.g. therapy, surgery, medications, for the subject.

In some embodiments, an imaging agent as described herein is employed for determining the presence or absence of a tumor in a subject. In some embodiments, the tumor is a NET-expressing tumor. In some embodiments, an imaging agent of the invention is employed for determining the response to therapy of a tumor in a subject. Methods for determining the presence of a tumor and/or for determining the response to therapy of a tumor in a subject can follow the same or similar methods as described for methods of imaging a subject.

Regional denervated myocardium may exhibit comparable effective refractory period (ERP) to normal innervated area but increased sensitivity to NE induced ERP shortening, or increased ERP but similar sensitivity to NE induced ERP shortening. In addition, heterogeneity of sympathetic innervation may render the heart abnormal electrophysiologically and may increase sensitivity to drugs which interact with cardiac ion channel conductance, such as antiarrhythmic drugs. In some cases, the presence of cardiac denervation in a subject may increase the subject's sensitivity and/or cardiac risk to antiarrhythmic agent treatments that induce electrophysiological changes. In some embodiments, an imaging agent as described herein may be used to determine whether a subject has an enhanced cardiac risk to an antiarrhythmic agent treatment, including, for example, antiarrhythmic agents that induce electrophysiological changes. For example, in some embodiments, the images obtained from a subject using an imaging agent as described herein may be used to aid in the selection of an antiarrhythmic agent and/or may be used to determine an appropriate dose and/or adjustment of a dose (e.g., increase or decrease) of an antiarrhythmic agent for administration to the subject by determining the presence, absence, and/or extent of cardiac denervation. If cardiac denervation is present, an antiarrhythmic agent which does not induce electrophysiological changes may be administered and/or the dose of an antiarrhythmic agent which is known to induce electrophysiological changes may be reduced. In some embodiments, the electrophysiological change comprise QT prolongation. In some embodiments, a reduced dose of an antiarrhythmic agent may be determined via a dose titration, wherein the subject is monitored during and/or following administration of the drug to determine or assess the presence of electrophysiological changes depending on the dose of the antiarrhythmic agent.

Antiarrhythmic agents that induce electrophysiological changes in the heart include, for example, agents known to block ion channels (e.g., calcium-, sodium-, or potassium-channels). Non-limiting examples of such agents include, but are not limited to, dofetilide, ibutilide, amiodarone, sotalol, and dronedarone. The invention contemplates the use of reduced doses of these agents in some instances including for example where cardiac denervation exists.

Antiarrhythmic agents that do not induce electrophysiological changes in the heart and/or that induce minimal, electrophysiological changes in the heart include, for example, some beta-blockers. Non-limiting of such agents include, but are not limited to, opranolol, esmolol, timolol, metoprolol, atenolol, and bisoprolol. The invention contemplates the use of these agents in some instances including for example where cardiac denervation exists.

Other non-limiting examples of antiarrhythmic agent include quinidine, procainamide, disopyramide, lidocaine, phenyloin, mexiletine, tocamide, flecamide, propafenone, moricizine, verapamil, diltiazem, adenosine, digoxin, and magnesium sulfate. The invention contemplates the use of reduced doses of these agents in some instances including for example where cardiac denervation exists.

In some embodiments, an imaging agent as described herein may be used to determine a subject's cardiac risk associated with innervation dysfunction.

In some embodiments, an imaging agent as described herein is used as an imaging agent in combination with positron emission tomography (PET) or with other imaging methods including, but not limited to, single photon emission computed tomography (SPECT) imaging. In some cases, PET imaging may be used in cardiac sympathetic neuronal imaging in a subject following administration of the imaging agent to the subject. For example, the imaging agent may be administered to a subject and imaged in the subject using PET. As will be known to those of ordinary skill in the art, PET is a non-invasive technique that allows serial images and measurements to be obtained in a single subject over a time period. PET imaging used may be carried out using known systems, methods, and/or devices. In some embodiments, PET imaging is conducted using a cardiac imaging system. A cardiac imaging system may include PET imaging functionality; and a control unit configured to drive the imaging functionality to perform a PET imaging procedure on a portion of the subject of interest before, during, and/or after administration of the imaging agent to the subject. In some cases, the control unit is configured to drive the imaging functionality to perform a PET imaging procedure. The control unit may comprise a computer system and/or software. In such a case, the computer system may be programmed or configured to execute the required methods for acquiring and/or analyzing the images. Further, the system may include a data storage device that is readable by a machine, embodying a set of instructions executable by the machine to perform the required methods of acquiring and/or analyzing the images.

Imaging systems (e.g., cardiac imaging systems) and components thereof will be known to those of ordinary skill in the art. Many imaging systems and components (e.g., cameras, software for analyzing the images) are known and commercially available, for example, a Siemens Biograph-64 scanner or other scanner suitable for imaging. In some embodiments, image data is acquired in list mode, and such list data may be used to create static, dynamic, or gated images. An appropriate period of time for acquiring images can be determined by one of ordinary skill in the art, and may vary depending on the cardiac imaging system, the imaging agent (e.g., amount administered, composition of the imaging agent, subject parameters, area of interest). As used herein, a "period of acquiring images" or an "image acquisition period" may be a period of time for obtaining a single continuous image, and/or may be a period during which one or more individual discrete images are obtained. Thus, a period of image acquisition can be a period during which one or more images of one or more regions of a subject are acquired.

The term "list mode," as used herein, is given its ordinary meaning in the art. With respect to PET, list mode is a form in which the data that is used to create a PET image can be initially collected. In list mode, each of or a portion of coincidence events (i.e., each of a portion of detected photon pairs) generates an entry in a list of events. Each entry includes various information including, but not limited to, which detectors were involved, the energy of the photons detected, the time of detection, and/or whether there was a cardiac gating mark. The information can be converted into one or more images by the process of rebinning and/or histogramming, in which all or a portion of the events for each pair of detectors is summed, followed by the resulting set of projections (e.g., in the form of a sinogram wherein for each slice, each horizontal line in the sinogram represents the projections for coincidences at a given angle). List mode may be contrasted with "histogram mode" in which the summations are completed during acquisition so that the only raw data is the sinogram. In some embodiments, histogram mode may be employed.

In embodiments where more than one type of imaging agent is administered to a subject, a second imaging agent may be administered to the subject, followed by acquisition of at least one second image. The second imaging agent may be administered to the subject after any suitable period of time has elapsed following administration of the first imaging agent and/or acquisition of the at least one first image. In some cases, the time between administration of the first imaging agent and the second imaging agent is about between about 1 minute and about 48 hours, or between about 1 hour and about 48 hours, or between about 1 minute and about 24 hours, or between about 1 hour and 24 hours, or between about 10 minutes and about 12 hours, or between about 30 minutes and about 8 hours, or between about 30 minutes and about 6 hours, or between 30 minutes and about 3 hours, or between about 30 minutes and about 2 hours, or between about 1 hour and about 6 hours. In some cases, the time between administration of the first imaging agent and the second imaging agent is at least about or about 1 minute, at least about or about 5 minutes, at least about or about 10 minutes, at least about or about 15 minutes, at least about or about 20 minutes, at least about or about 30 minutes, at least about or about 45 minutes, at least about or about 60 minutes, at least about or about 90 minutes, at least about or about 2 hours, at least about or about 3 hours, at least about or about 4 hours, at least about or about 5 hours, at least about or about 6 hours, at least about or about 8 hours, at least about or about 10 hours, at least about or about 12 hours, at least about or about 18 hours, at least about or about 24 hours, or greater.

Those of ordinary skill in the art will be aware of suitable periods of time for acquiring an image. In some embodiments, a period of image acquisition after administration of an imaging agent to a subject may be between about 0 seconds and about 60 minutes, between about 1 minute and about 30 minutes, between about 5 minutes and about 20 minutes, or at least about 1 minute, at least about 3 minutes, at least about 5 minutes, at least about 6 minutes, at least about 7 minutes, at least about 8 minutes, at least about 9 minutes, at least about 10 minutes, at least about 15 minutes, at least about 20 minutes, at least about 30 minutes, at least about 45 minutes, at least about 60 minutes, at least about 90 minutes, at least about 2 hours, at least about 3 hours, at least about 4 hours, at least about 5 hours, or greater. In some embodiments, a period of image acquisition may begin prior to administration of the imaging agent to a subject. For example, a period of image acquisition may begin more than about 10 minutes, about 5 minutes, about 4, minutes, about 3 minutes, about 2 minutes, about 1 minute, or about 0 minutes prior to administration of the imaging agent to the subject. In some embodiments, imaging may be continuous over the imaging period of time, or images may be acquired at intervals such as in periodic or gated imaging.

In some embodiments, an imaging agent as described herein is provided in ethanol/ascorbic acid. In some embodiments, an imaging agent as described herein is provided as a composition comprising ethanol, ascorbic acid or a salt thereof (e.g., as sodium ascorbate), and water. In some cases, the composition comprises less than or about 20 weight % ethanol, less than or about 15 weight % ethanol, less than or about 10 weight % ethanol, less than or about 8 weight % ethanol, less than or about 6 weight % ethanol, less than or about 5 weight % ethanol, less than or about 4 weight % ethanol, less than or about 3 weight % ethanol, or less ethanol. In some cases, the composition comprises less than or about 100 mg/mL, less than or about 75 mg/mL, less than or about 60 mg/mL, less than or about 50 mg/mL, less than or about 40 mg/mL, less than or about 30 mg/mL, less than or about 20 mg/mL, less than or about 10 mg/mL, or less ascorbic acid or a salt thereof (e.g., sodium ascorbate) in water. A non-limiting, exemplary formulation of an imaging agent includes about 5 weight % ethanol and about 50 mg/ml ascorbic acid. As will be understood by those of ordinary skill in the art, in the presence of ascorbic acid, at least a portion of the imaging may be present as the ascorbate salt of the imaging agent.

Additional components of a composition comprising an imaging agent as described herein may be selected depending on the mode of administration to the subject. Various modes of administration will be known to one of ordinary skill in the art which effectively deliver the pharmacological agents as described herein to a desired tissue, cell, organ, or bodily fluid. In some embodiments, an imaging agent as described herein is administered intravenously (e.g., intravenous bolus injection) using methods known to those of ordinary skill in the art. As used herein, a dose that is "administered to a subject" means an amount of the imaging agent that enters the body of the subject.

In some embodiments, the volume of the administered imaging agent may be between 0 and about 3 mL, between about 3 mL and about 5 mL, or between about 5 mL and about 10 mL.

In some embodiments, due to factors such as partial retention of imaging agent in a syringe, tubing, needles, or other equipment used to administer the imaging agent to a subject, the amount of an imaging agent that is measured or determined to be in the a syringe or other equipment prepared for administration may be more than the amount in the dose that is administered to the subject. In some embodiments, an injection of an imaging agent is followed by a flushing injection of normal saline into the subject, using the same tubing, needle, port, etc., used for administration of the imaging agent.

Flushing may be performed immediately following administration of the imaging agent, or up to about 1 min, about 2 min, about 3 min, about 5 min, or more after the administration. In some embodiments, flushing may be performed between 0 and 10 seconds, between 10 seconds and 25 seconds, or between 25 seconds and 60 seconds.

The volume of saline or other agent for flushing may be up to about 5 ml, about 6 ml, about 7 ml, about 8 ml, about 9 ml, about 10 ml, about 15 ml, about 20 ml, or more. As will be understood by those of ordinary skill in the art, in embodiments where the imaging agent is administered using a syringe or other container, the true amount of imaging agent administered to the subject may be corrected for any imaging agent that remains in the container. For example, the amount of radioactivity remaining in the container, and tubing and needle or delivery instrument that carried the imaging agent from the container and into the subject can be determined after the imaging agent has been administered to the subject and the difference between the starting amount of radioactivity and the amount remaining after administration indicates the amount that was delivered into the subject. In some cases, the container or injection device (e.g., catheter, syringe) may be rinsed with a solution (e.g., saline solution) following administration of the imaging agent.

A composition of an imaging agent as described herein for injection may be prepared in an injection syringe. Imaging agents may be prepared by a radiopharmacy (e.g., using the methods described herein) and/or a PET manufacturing center and provided to a health-care professional for administration. A dose of the imaging agent may be diluted with saline (e.g., as described herein), if needed to obtain a practical dose volume. For example, if the activity concentration of the imaging agent is so high that only about 0.1 mL is needed for an appropriate dose for a subject, the solution can be diluted, e.g., with sterile saline, so the syringe contains about 0.5 ml to about 6 ml or more ml of the imaging agent solution for administration. In some embodiments, an injection volume for the imaging agent is between about 0.5 and about 5 ml, about 1 and about 4 ml, about 2 and about 3 ml, at least about 0.5 ml, about 1 ml, about 2 ml, about 3 ml, about 4 ml, about 5 ml, about 6 ml, about 7 ml, about 8 ml, about 9 ml, about 10 ml, or more. Those of skill in the art will recognize how to dilute an imaging agent to produce a sufficient dose volume for administration. In some aspects, an imaging agent is provided in a container such as a vial, bottle, or syringe, and may be transferred, as necessary, into a suitable container, such as a syringe for administration.

Components of a composition comprising an imaging agent as described herein may be selected depending on the mode of administration to the subject. Various modes of administration that effectively deliver imaging agents as described herein to a desired tissue, cell, organ, or bodily fluid will be known to one of ordinary skill in the art. In some embodiments, the imaging agent is administered intravenously (e.g., intravenous bolus injection) using methods known to those of ordinary skill in the art.

The useful dosage of the imaging agent to be administered and the particular mode of administration will vary depending upon such factors as age, weight, and particular region to be imaged, as well as the particular imaging agent used, the diagnostic use contemplated, and the form of the formulation, for example, suspension, emulsion, microsphere, liposome, or the like, as described herein, and as will be readily apparent to those skilled in the art.

Based on dosing studies, the desirable maximum dose administered to a subject may be based on determining the amount of imaging agent(s) as described herein, which limits the radiation dose to about 5 rem to the critical organ (e.g., urinary bladder) and/or about 1 rem effective dose (ED) or lower, as will be understood by those of ordinary skill in the art. In embodiments where more than one imaging agent is administered to the subject, the desirable maximum dose administered to a subject may be based on determining the amounts of the first imaging agent and/or the second imaging agent, which limits the total radiation dose to about 5 rem to the critical organ (e.g., urinary bladder) and/or about 1 rem effective dose (ED) or lower. In some embodiments, a desirable dose of imaging agent(s) may be less than or equal to about 50 mCi, less than or equal to about 40 mCi, less than or equal to about 30 mCi, less than or equal to about 20 mCi, less than or equal to about 15 mCi, less than or equal to about 14 mCi, less than or equal to about 13 mCi, less than or equal to about 12 mCi, less than or equal to about 11 mCi, or less than or equal to about 10 mCi over a period of time of up to about 10 minutes, about 30 minutes, about 1 hour, about 2 hours, about 6 hours, about 12 hours, about 24 hours, or about 48 hours. In some embodiments, the dose of each imaging agent administered per session or day is about 1 mCi, about 2 mCi, about 3 mCi, about 4 mCi, about 5 mCi, about 6 mCi, about 7 mCi, about 8 mCi, about 9 mCi, about 10 mCi, about 11 mCi, about 12 mCi, about 13 mCi, about 14 mCi, or any range therein.

In some embodiments, studies may also be performed using an agent specialized for tissue blood flow using methods known to those familiar with the art. The images from these studies may then be used to distinguish abnormalities seen in images due to changes in NET from those due to alterations of global, regional or local blood flow.

G. Methods for Assessing Perfusion and Innervation Mismatch

In some embodiments, methods and compositions for assessing perfusion and innervation mismatch in a portion of a subject, for example, a human subject, are provided. In some embodiments, the methods and compositions may be employed for assessing perfusion and innervation mismatch in a subject following a tissue insult. In some embodiments, the tissue insult is a cardiac insult, for example, a myocardial infarction. In some embodiments, the portion of the subject being assessed for perfusion/innervation mismatch is the heart or a portion of the heart. Other regions of interest may include, but are not limited to, the cardiovascular system, cardiac vessels, blood vessels (e.g., arteries and/or veins), brain, pancreas, adrenal glands, other organs, and tumors.

In some embodiments, a method comprises administering to a subject a first imaging agent and acquiring at least one first image of a portion of the subject. A second imaging agent is then administered to the subject and at least one second image of the same portion of the subject is acquired. In some embodiments, the first imaging agent is employed to image perfusion (e.g., cardiac perfusion), and the second imaging agent is employed to image innervation (e.g., cardiac innervation). In other embodiments, the first imaging agent is employed to image innervation and the second imaging agent is employed to image perfusion. The region of mismatch of perfusion and innervation is based at least in part on the first image and the second image. Imaging agents which may be used to image innervation or perfusion will be known to those of ordinary skill in the art and are described herein (e.g., see Sections G1 and G2).

In some embodiments, the regional mismatch of perfusion and innervation in a portion of a subject may be determined by determining the difference in uptake of the first imaging agent versus uptake of the second imaging agent in a portion of the subject (e.g., the heart). As a non-limiting example, the first imaging agent may be an imaging agent which is employed for imaging perfusion (e.g., cardiac perfusion). Accordingly, the areas in the at least one first image which indicate uptake of the first imaging agent are areas in which there is perfusion. The second imaging agent may be an imaging agent which is employed for imaging innervation (e.g., cardiac innervation). The areas in the at least one second image which indicate uptake of the second imaging agent are the areas in which there is innervation. The difference in the areas of uptake between the first image and the second image are areas in which there is perfusion (e.g., as indicated by uptake of the first imaging agent) but in which there is decreased or no innervation (e.g., as indicated by lack of or decreased uptake of the second imaging agent).

Generally, the mismatch is the observed difference in the level of innervation and the level of perfusion in a portion of the subject. The mismatch between innervation and perfusion areas, as determined in accordance with the invention, may be expressed or quantified using any suitable technique. In some embodiments, the difference between uptake of the first imaging agent and the uptake of the second imaging agent may be expressed as a percent of defect size in a portion of the subject. For example, in embodiments where the portion of the subject is a the heart or a portion of the heart, the difference between uptake of the first imaging agent and the uptake of the second imaging agent may be expressed as the percent defect size in the left ventricle (LV). In some cases, the difference between the uptake of the first imaging agent and the second imaging agent may be expressed as a ratio. In some embodiments, the mismatch may be determined and/or quantified using polar maps of the images. In some embodiments, the defect areas for perfusion and/or innervation may be defined as those regions in which perfusion and/or innervation is less than 50% of the maximum value of perfusion and/or innervation in a portion of a subject. In some embodiments, the mismatch may be determined by subtracting the perfusion defect from the innervation defect or otherwise quantifying the difference between the perfusion and innervation areas. In some embodiments, the mismatch may be determined using software (e.g., MunichHeart™; see, for example, Nekolla et al., *Eur J Nucl Med* 1998; 25(9):1313-21; Haas et al., *J Am Coll Cardiol* 1997; 30(7):1693-700; Nekolla et al., *J Nucl Med* 1999; 40(5):5P; Hattori, et al., *Europ. J. Nucl. Med.* 2001; 28:221-229; Klein et al., *Circulation* 105: 162-167 (2002); Ibrahim et al., *J. Am. Coll. Cardiol.* 2000; 6; 39(5):864-70).

Those of ordinary skill in the art may be aware of suitable methods and techniques for imaging a subject, for example, a human subject In some embodiments, methods of imaging comprise (a) administering to a subject a composition that includes an imaging agent, and (b) acquiring at least one image of at least a portion of the subject. In some cases, the step of acquiring an image employs positron emission tomography (PET) for visualizing the distribution of the imaging agent within at least a portion of the subject. As will be understood by those of ordinary skill in the art, imaging methods may include full body imaging of a subject, or imaging of a specific body region, organ, or tissue of the subject that is of interest. For example, if a subject is known to have, or is suspected of having a cardiac insult (e.g., myocardial infarction), the methods of this disclosure may be used to image the heart of the subject. In some embodiments, imaging may be limited to the heart or may include the heart and its associated vasculature. Regions of interest may include, but are not limited to, the heart, a portion of the heart, the cardiovascular system, cardiac vessels, blood vessels (e.g., arteries and/or veins), brain, pancreas, adrenal glands, other organs, tumors, and other vascularized soft tissues. A particular region of interest is the heart or a portion of the heart.

In some embodiments, the mismatch is determined in a subject following a tissue insult. In such embodiments, the portion of the subject being imaged may be the portion of the subject that sustained the tissue insult and/or that was affected by the tissue insult. In some embodiments, the tissue insult is an insult which results in denervation of the tissue. In some embodiments, the tissue insult is an insult which results in a perfusion defect and/or denervation of the tissue. In some embodiments, the tissue insult is an insult which results in a perfusion defect and denervation of the tissue. In some embodiments, the tissue insult is a cardiac insult. In some embodiments, the cardiac insult is a myocardial infarction, congestive heart failure, diabetic autonomic neuropathy, myocardial ischemia, and cardiac arrhythmias. Those of ordinary skill in the art will be aware of other tissues which may have an innervation defect including, for example, sympathetically innervated tissues. In some cases, the tissue is a tissue which expresses NET. Non-limiting examples of tissues which express NET include pancreas, adrenal glands, thyroid, and tumors (e.g., neuroendocrine tumors, pheochromocytoma tumors). Non-limiting examples of tissue insults include diseases which affect the tissue (e.g., autoimmune disease (e.g., Graves disease), diabetes, hyperthyroidism, hypothyroidism, acute pancreatitis, etc.), a tumor in the tissue, and/or trauma of the tissue (e.g., blunt force trauma, iatrogenic injury). It should be understood, that while much of the following discussion focuses on the heart or a portion of the heart and/or a tissue insult comprising a cardiac insult (e.g., myocardial infarction), this is by no means limiting, and the invention contemplates imaging and assessing mismatch in other tissues and regions of the body, and those of ordinary skill in the art will be able to apply the teachings herein to other tissues and/or tissue insults.

The mismatch between innervation and perfusion may be determined at any suitable time. In some embodiments, the mismatch is determined at a single time point following a tissue insult (e.g., myocardial infarction). In some cases, the mismatch is determined at a time point near to the time at which the tissue insult occurred. Without wishing to be bound by theory, determining the mismatch at a time point close to the time at which the tissue insult occurred may provide a better indication of the treatment and/or diagnosis for the subject as the tissue may reinnervate over time. In some cases, the difference in the mismatch is determined within about 6 months, about 5 months, about 4 months, about 3 months, about 2 months, about 1 month, about 4 weeks, about 3 weeks, about 2 weeks, about 1 week, about 7 days, about 6 days, about 5 days, about 4 days, about 3 days, about 2 days, about 1 days, about 24 hours, about 20 hours, about 18 hours, about 16 hours, about 14 hours, about 12 hours, about 10 hours, about 8 hours, about 6 hours, about 5 hours, about 4 hours, about 3 hours, about 2 hours, about 1 hour, about 50 minutes, about 40 minutes, about 30 minutes, about 20 minutes, about 10 minutes, about 5 minutes, about 4 minutes, about 3 minutes, about 2 minutes, or about 1 minute of the tissue insult. In some cases, the mismatch is determined within 4 weeks of the tissue insult. In some cases, the mismatch is determined within between about 1 week and about 6 months, between about 1 week and about 5 months, between about 1 week and about 4 months, between about 1 week and about 3 months, between about 1 week and about 2 months, between about 1 week and about 1 month, between about 1 week and about 4 weeks, between about 2 weeks and about 2 months, between about 2 weeks and about 6 weeks, or between about 2 weeks and about 4 weeks of the tissue insult.

In other embodiments, the mismatch may be determined at multiple time points following a tissue insult (e.g., myocardial infarction). In some cases, the change in the mismatch over time may be useful in determining a course of treatment and/or a diagnosis following a tissue insult. In some cases, the change or lack of change in mismatch over time may indicate the effectiveness or lack of effectiveness, respectively, of a course of treatment being administered to the subject. For example, a decrease in the region of mismatch over time may indicate reinnervation of the tissue, and thus, may indicate that the course of treatment may be effective. As another example, a lack of change in the region of mismatch over time may indicate lack of reinnervation of the tissue and thus, the course of treatment that the subject is undergoing is not effective and/or another course of treatment may be warranted and/or the treatment should be continued. The region of mismatch may be determined 2 times, 3 times, 4 times, 5 times, 6 times, 8 times, 10 times, or 12 times within about 4 weeks, about 2 months, about 3 months, about 4 months, about 5 months, about 6 months, about 7 months, about 8 months, about 9 months, about 10 months, about 11 months, about 1 year, about 2 years, about 3 years, about 4 years, or about 5 years following the tissue insult (e.g., myocardial infarction). The mismatch may be monitored at regular frequency or irregular frequency.

In some embodiments, methods of diagnosing or assisting in diagnosing a disease or condition, assessing efficacy of a treatment of a disease or condition, or imaging of a subject with a known or suspected cardiovascular disease or condition changing sympathetic innervations are provided. A cardiovascular disease can be any disease of the heart or other organ or tissue supplied by the vascular system. The vascular system includes coronary arteries, and all peripheral arteries supplying the peripheral vascular system, as well as veins, arterioles, venules, and capillaries. In cases where cardiac innervation and cardiac perfusion are examined, differences in cardiac innervation and perfusion may be implicated in the pathophysiology of many heart diseases, including sudden cardiac death, congestive heart failure, diabetic autonomic neuropathy, myocardial ischemia, and cardiac arrhythmias. In some embodiments, the methods disclosed herein are useful for monitoring and measuring mismatch between cardiac innervation and perfusion. Methods described herein can be used in some embodiments to determine global or regional changes in differences between cardiac innervation and perfusion.

In some cases, a subject whom an imaging agent as described herein is administered has signs or symptoms suggestive of a disease or condition associated with a mismatch in innervation and perfusion. Imaging methods described herein may be used to detect innervation and/or perfusion in subjects already diagnosed as having a disease or condition associated with a mismatch in innervation and perfusion, or in subjects that have no history or diagnosis of such a disease or condition. In other instances, the methods is used to obtain measurements that provide a diagnosis or aid in providing a diagnosis of a disease or condition associated with a mismatch in innervation and perfusion. In some instances, a subject is already undergoing drug therapy for a disease or condition associated with a mismatch in innervation and perfusion, while in other instances a subject is without present therapy for a disease or condition associated with a mismatch in innervation and perfusion. In some embodiments, the method is used to assess efficacy of a treatment for a disease or condition. For example, the heart can be visualized using contrast/imaging agents described herein before, during, and/or after treatment of a condition affecting the heart of a subject. Such visualization may be used to assess a disease or condition and aid in selection of a treatment regimen, e.g. therapy, surgery, or medication, for the subject.

In some embodiments, an imaging agent as described herein is used as an imaging agent in combination with positron emission tomography (PET) or with other imaging methods including, but not limited to, single photon emission computed tomography (SPECT) imaging. In some cases, PET imaging is used in innervation and/or perfusion imaging in a subject following administration of an imaging agent to the subject. For example, the imaging agent may be administered to a subject and imaged in the subject using PET. As will be known to those of ordinary skill in the art, PET is a non-invasive technique that allows serial images and measurements to be obtained in a single subject over a time period. PET imaging used may be carried out using known systems, methods, and/or devices, as described herein. In some embodiments, PET imaging is conducted using a cardiac imaging system. A cardiac imaging system may include PET imaging functionality; and a control unit configured to drive the imaging functionality to perform a PET imaging procedure on a portion of the subject of interest before, during, and/or after administration of the imaging agent to the subject. In some cases, the control unit is configured to drive the imaging functionality to perform a PET imaging procedure. The control unit may comprise a computer system and/or software. In such a case, the computer system may be programmed or configured to execute the required methods for acquiring and/or analyzing the images. Further, the system may include a data storage device that is readable by a machine, embodying a set of instructions executable by the machine to perform the required methods of acquiring and/or analyzing the images.

G1. Perfusion Imaging Agents

Some embodiments of the present invention comprise an imaging agent for imaging perfusion (e.g., cardiac perfusion). Those of ordinary skill in the art will be aware of imaging agents which are capable of imaging perfusion.

In some embodiments, an imaging agent for imaging perfusion (e.g., cardiac perfusion) may be a Complex-1 inhibitor. Complex 1 ("MC-1") is a membrane-bound protein complex of 46 dissimilar subunits. This enzyme complex is one of three energy-transducing complexes that constitute the respiratory chain in mammalian mitochondria. This NADH-ubiquinone oxidoreductase is the point of entry for the majority of electrons that traverse the respiratory chain, eventually resulting in the reduction of oxygen to water (Q. Rev. Biophys. 1992, 25, 253-324). Mitochondria are membrane-enclosed organelles distributed through the cytosol of most eukaryotic cells. Mitochondria are especially concentrated in myocardial tissue. Examples of inhibitors of MC-1 include deguelin, piericidin A, ubicidin-3, rolliniastatin-1, rolliniastatin-2 (bullatacin), capsaicin, pyridaben, fenpyroximate, amytal, MPP+, quinolines, and quinolones (BBA 1998, 1364, 222-235). Studies have shown that interrupting the normal function of mitochondria could advantageously concentrate certain compounds in the mitochondria, and hence in the mitochondria-rich myocardial tissue. Compounds that include an imaging moiety (e.g., $^{18}$F) can be useful in determining such a build-up of compounds and may be useful for imaging perfusion. Accordingly, in some embodiments, an imaging agent for imaging perfusion (e.g., cardiac perfusion) binds to the mitochondrial Complex I of the electron transport chain with high affinity (e.g., the imaging agent may exhibit selective uptake to the heart due to the high density of mitochondria in the myocardium).

In some embodiments, an imaging agent for imaging perfusion comprises the formula:

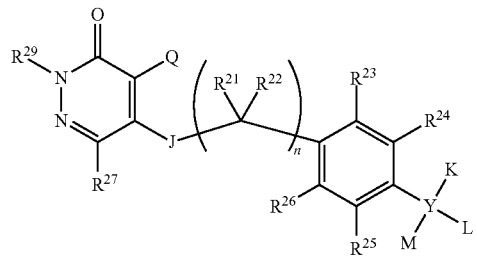

wherein:

J is selected from the group consisting of N($R^{28}$), S, O, C(=O), C(=O)O, NHCH$_2$CH$_2$O, a bond, and C(=O)N($R^{27}$);

when present, K is selected from the group consisting of hydrogen, alkoxyalkyl optionally substituted with an imaging moiety, alkyloxy optionally substituted with an imaging moiety, aryl optionally substituted with an imaging moiety, $C_1$-$C_6$ alkyl optionally substituted with an imaging moiety, heteroaryl optionally substituted with an imaging moiety, and an imaging moiety;

when present, L is selected from the group consisting of hydrogen, alkoxyalkyl optionally substituted with an imaging moiety, alkyloxy optionally substituted with an imaging moiety, aryl optionally substituted with an imaging moiety, $C_1$-$C_6$ alkyl optionally substituted with an imaging moiety, heteroaryl optionally substituted with an imaging moiety, and an imaging moiety;

M is selected from the group consisting of hydrogen, alkoxyalkyl optionally substituted with an imaging moiety, alkyloxy optionally substituted with an imaging moiety, aryl optionally substituted with an imaging moiety, $C_1$-$C_6$ alkyl optionally substituted with an imaging moiety, heteroaryl optionally substituted with an imaging moiety, and an imaging moiety; or L and M, together with the atom to which they are attached, may form a three-, four-, five-, or six-membered carbocyclic ring;

Q is halo or haloalkyl;

n is 0, 1, 2, or 3;

$R^{21}$, $R^{22}$, $R^{27}$, and $R^{28}$ are independently selected from hydrogen, $C_1$-$C_6$ alkyl optionally substituted with an imaging moiety, and an imaging moiety;

$R^{23}$, $R^{24}$, $R^{25}$, and $R^{26}$ are independently selected from hydrogen, halogen, hydroxyl, alkyloxy, $C_1$-$C_6$ alkyl optionally substituted with an imaging moiety, and an imaging moiety;

$R^{29}$ is $C_1$-$C_6$ alkyl optionally substituted with an imaging moiety; and Y is selected from the group consisting of a bond, carbon, and oxygen; provided that when Y is a bond, K and L are absent, and M is selected from the group consisting of aryl optionally substituted with an imaging moiety and heteroaryl optionally substituted with an imaging moiety; and provided that when Y is oxygen, K and L are absent, and M is selected from hydrogen, alkoxyalkyl optionally substituted with an imaging moiety, aryl optionally substituted with an imaging moiety, $C_1$-$C_6$ alkyl optionally substituted with an imaging moiety, and heteroaryl optionally substituted with an imaging moiety;

provided that at least one imaging moiety is present in the compound. In some embodiments, the imaging moiety is $^{18}$F.

In some cases, J is selected from $N(R^{27})$, S, O, C(=O), C(=O)O, $NHCH_2CH_2O$, a bond, or $C(=O)N(R^{27})$. In some cases when present, K is selected from hydrogen, alkoxyalkyl optionally substituted with an imaging moiety, alkyloxy optionally substituted with an imaging moiety, aryl optionally substituted with an imaging moiety, $C_1$-$C_6$ alkyl optionally substituted with an imaging moiety, heteroaryl optionally substituted with an imaging moiety, and an imaging moiety. In some cases, when present, L is selected from hydrogen, alkoxyalkyl optionally substituted with an imaging moiety, alkyloxy optionally substituted with an imaging moiety, aryl optionally substituted with an imaging moiety, $C_1$-$C_6$ alkyl optionally substituted with an imaging moiety, heteroaryl optionally substituted with an imaging moiety, and an imaging moiety. In some cases, M is selected from hydrogen, alkoxyalkyl optionally substituted with an imaging moiety, alkyloxy optionally substituted with an imaging moiety, aryl optionally substituted with an imaging moiety, $C_1$-$C_6$ alkyl optionally substituted with an imaging moiety, heteroaryl optionally substituted with an imaging moiety, and an imaging moiety. In some cases, L and M, together with the atom to which they are attached, form a three- or four-membered carbocyclic ring. In some cases Q is halo or haloalkyl. In some cases, n is 0, 1, 2, or 3. In some cases, $R^{21}$, $R^{22}$, $R^{23}$, $R^{24}$, $R^{25}$, $R^{26}$, and $R^{27}$ are independently selected from hydrogen, $C_1$-$C_6$ alkyl optionally substituted with an imaging moiety, and an imaging moiety. In some cases $R^{29}$ is $C_1$-$C_6$ alkyl optionally substituted with an imaging moiety. In some cases, Y is selected from a bond, carbon, and oxygen; provided that when Y is a bond, K and L are absent and M is selected from aryl and heteroaryl; and provided that when Y is oxygen, K and L are absent and M is selected from hydrogen, alkoxyalkyl optionally substituted with an imaging moiety, aryl, $C_1$-$C_6$ alkyl optionally substituted with an imaging moiety, and heteroaryl.

In some cases, J is O. In some cases $R^{29}$ is methyl, ethyl, n-propyl, i-propyl, n-butyl, i-butyl, or t-butyl, each may be optionally substituted with an imaging moiety. In certain embodiment, $R^{29}$ is t-butyl. In some cases, Q is chloro. In some cases, all of $R^{21}$, $R^{22}$, $R^{23}$, $R^{24}$, $R^{25}$, $R^{26}$, and $R^{27}$ are hydrogen. In some cases, Y is carbon, K and L are hydrogen, and M is alkoxyalkyl optionally substituted with an imaging moiety, alkyloxy optionally substituted with an imaging moiety, aryl optionally substituted with an imaging moiety, $C_1$-$C_6$ alkyl optionally substituted with an imaging moiety, heteroaryl optionally substituted with an imaging moiety, or an imaging moiety. In some cases, Y is carbon, K and L are hydrogen, and M is alkyloxy optionally substituted with an imaging moiety.

In some embodiments, an imaging agent for imaging perfusion comprises the formula:

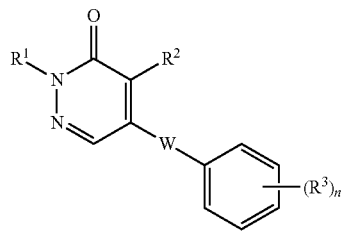

wherein:
W is alkyl or heteroalkyl, optionally substituted;
$R^1$ is alkyl, optionally substituted;
$R^2$ is hydrogen or halide;
each $R^3$ can be the same or different and is alkyl optionally substituted with an imaging moiety or heteroalkyl optionally substituted with an imaging moiety; and
n is 1, 2, 3, 4, or 5.

In some embodiments, the imaging agent for imaging perfusion (e.g., cardiac perfusion) comprises the structure:

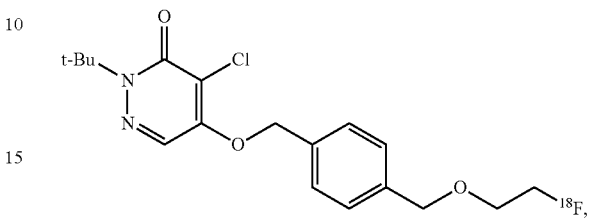

or a pharmaceutically acceptable salt thereof, hereinafter referred to as "Imaging Agent-2."

Those of ordinary skill in the art will be aware of other suitable imaging agents for imaging perfusion (e.g., cardiac perfusion). For example, suitable imaging agents for imaging perfusion include, but are not limited to, thallium-201, technetium-99m sestamibi, technetium-99m tetrofosmin, rubidium-82 chloride, oxygen-15 water, and nitrogen-13 ammonia. In some embodiments, an imaging agent for imaging perfusion is as described in International Patent Publication No. WO 2005/079391, published Sep. 1, 2005, to Casebier et al.; International Patent Publication No. WO 2005/105159, published Nov. 10, 2005, to Radeke et al., International Patent Publication No. WO 2011/097649, published Aug. 11, 2011, to Cesati et al.; each of which is incorporated herein by reference.

G2. Innervation Imaging Agents

Some embodiments of the present invention comprise an imaging agent for imaging innervation (e.g., innervation of the heart). Those of ordinary skill in the art will be aware of imaging agents which are capable of imaging innervation.

In some embodiments, an imaging agent for imaging innervation may be an agent, which is used to monitor and/or assess certain aspects of the sympathetic nervous system (SNS). The SNS plays a role in normal cardiac regulation and/or the pathogenesis of heart failure development and/or progression. Generally, following myocardial insult (e.g., myocardial infarction, valve regurgitation, hypertension), compensatory activation of the SNS is induced to help maintain sufficient cardiac output. Sustained elevation of the cardiac SNS can cause elevated cardiac norepinephrine (NE) release, down-regulation of the beta1 adrenergic receptor, and/or down-regulation of the NE transporter (NET), which can result in spillover of NE. Elevated levels of NE can be attributed to cardiac myocyte hypertrophy, fibroblast activation, collagen deposition, and/or myocyte apoptosis, which can result in ventricle remodeling and/or susceptibility to arrhythmia.

In some embodiments, the imaging agents for imaging innervation as described herein may act as norepinephrine transporter ligands that target or bind NET. In some embodiments, the methods comprise detecting NET, including determining NET levels, in a subject, wherein the determining may comprise determining the level, density, function, and/or localization of NET in a subject or portion thereof. In certain embodiments, without wishing to be bound by a particular theory, the imaging agent binds to norepinephrine transporters (NET) allowing for imaging of innervation (e.g., cardiac sympathetic innervation) or NET activity.

In some embodiments, agents for imaging cardiac innervation may be utilized in the assessment of heart failure. In certain embodiments, the methods comprise an assessment of heart failure progression in a subject, wherein the assessment may include determination of the effectiveness of a treatment regimen. In some cases, the treatment regimen may include a beta blocker. In other cases, the treatment may require implantation of a pacemaker or implantable cardioverter-defibrillator (ICD). In certain embodiments, agents for imaging cardiac innervation may be useful in the prediction of a time course for heart failure disease progression.

In some aspects, global images (e.g., global NET images) are acquired, and in other aspects, regional images (e.g., regional NET images) are acquired following administration of an imaging agent that targets NET, wherein a global image is an image of all or substantially all of an organ (e.g., heart, kidney, pancreas), and a regional image is an image of only a portion of an organ. In some cases, changes in NET may be used to assess cardiac sympathetic innervation and/or myocardial sympathetic function in a subject.

Utilizing an imaging agent that targets NET permits imaging of the location, concentration, density, and/or distribution of NETs and also can be used to detect changes in NET location, concentration, density and/or distribution over time, for example, by acquiring a first NET image in a subject or region of a subject; obtaining a subsequent NET image of the subject or the region of the subject, and comparing the first and subsequent images. Differences between the images can provide information on the change in NET status in the subject or region of the subject. Changes in a NET parameter (e.g., location, density, concentration, and/or distribution) over time may be assessed and correlated with disease onset, progression, and/or regression. In some cases, the detection comprises detection of the level (e.g., concentration) of NET, detection of the density of NET, detection of NET function, and/or detection of the localization of NET.

In some embodiments, the imaging agent employed for imaging innervation comprises the structure:

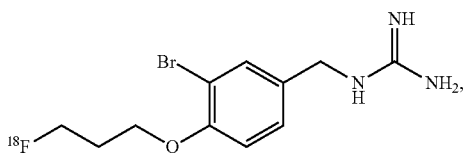 [SMILES: N=C(N)NCc1ccc(OCCC[18F])c(Br)c1]

or a pharmaceutically acceptable salt thereof, hereinafter referred to as "Imaging Agent-1." In some embodiments, Imaging Agent-1 is provided as a formate or ascorbate salt.

In some embodiments, a compound for imaging innervation is provided comprising Formula (Ia):

$$R^0\text{—Ar-L—}R^1 \qquad \text{(Ia)}$$

wherein

Ar is substituted or unsubstituted, monocyclic or bicyclic aryl; or substituted or unsubstituted, monocyclic or bicyclic heteroaryl;

L is a bond; substituted or unsubstituted, cyclic or acyclic alkylene; substituted or unsubstituted, cyclic or acyclic alkenylene; substituted or unsubstituted, cyclic or acyclic alkynylene; or substituted or unsubstituted, cyclic or acyclic heteroaliphatic;

$R^1$ is a substituted or unsubstituted nitrogen-containing moiety; and $R^0$ is halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, —OR$^{A1}$, —N(R$^{A2}$)$_2$, —SR$^{A1}$, —C(=O)R$^{A1}$, —C(=O)OR$^{A1}$, —C(=O)SR$^{A1}$, —C(=O)N(R$^{A2}$)$_2$, —OC(=O)R$^{A1}$, —OC(=O)OR$^{A1}$, —OC(=O)SR$^{A1}$, —OC(=O)N(R$^{A2}$)$_2$, —NR$^{A2}$C(=O)R$^{A2}$, —NR$^{A2}$C(=O)OR$^{A1}$, —NR$^{A2}$C(=O)SR$^{A1}$, —NR$^{A2}$C(=O)N(R$^{A2}$)$_2$, —SC(=O)R$^{A1}$, —SC(=O)OR$^{A1}$, —SC(=O)SR$^{A1}$, —SC(=O)N(R$^{A2}$)$_2$, —C(=NR$^{A2}$)R$^{A1}$, —C(=NR$^{A2}$)OR$^{A1}$, —C(=NR$^{A2}$)SR$^{A1}$, —C(=NR$^{A2}$)N(R$^{A2}$)$_2$, —OC(=NR$^{A2}$)R$^{A1}$, —OC(=NR$^{A2}$)OR$^{A1}$, —OC(=NR$^{A2}$)SR$^{A1}$, —OC(=NR$^{A2}$)N(R$^{A2}$)$_2$, —NR$^{A2}$C(=NR$^{A2}$)R$^{A2}$, —NR$^{A2}$C(=NR$^{A2}$)OR$^{A1}$, —NR$^{A2}$C(=NR$^{A2}$)SR$^{A1}$, —NR$^{A2}$C(=NR$^{A2}$)N(R$^{A2}$)$_2$, —SC(=NR$^{A2}$)R$^{A1}$, —SC(=NR$^{A2}$)OR$^{A1}$, —SC(=NR$^{A2}$)SR$^{A1}$, —SC(=NR$^{A2}$)N(R$^{A2}$)$_2$, —C(=S)R$^{A1}$, —C(=S)OR$^{A1}$, —C(=S)SR$^{A1}$, —C(=S)N(R$^{A2}$)$_2$, —OC(=S)R$^{A1}$, —OC(=S)OR$^{A1}$, —OC(=S)SR$^{A1}$, —OC(=S)N(R$^{A2}$)$_2$, —NR$^{A2}$C(=S)R$^{A2}$, —NR$^{A2}$C(=S)OR$^{A1}$, —NR$^{A2}$C(=S)SR$^{A1}$, —NR$^{A2}$C(=S)N(R$^{A2}$)$_2$, —SC(=S)R$^{A1}$, —SC(=S)OR$^{A1}$, —SC(=S)SR$^{A1}$, —SC(=S)N(R$^{A2}$)$_2$, —S(=O)R$^{A1}$, —SO$_2$R$^{A1}$, —NR$^{A2}$SO$_2$R$^{A1}$, —SO$_2$N(R$^{A2}$)$_2$, —CN, —SCN, or —NO$_2$;

each occurrence of R$^{A1}$ is independently hydrogen, optionally substituted alkyl, optionally substituted alkenyl, optionally substituted alkynyl, optionally substituted carbocyclyl, optionally substituted heterocyclyl, optionally substituted aryl, or optionally substituted heteroaryl; and each occurrence of R$^{A2}$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, or an amino protecting group, or two R$^{A2}$ groups are joined to form an optionally substituted heterocyclic ring; and $R^0$ or $R^1$ is substituted with an imaging moiety selected from the group consisting of $^{18}$F, $^{76}$Br, $^{124}$I, and $^{131}$I, or is associated with an imaging moiety selected from the group consisting of 64Cu, $^{89}$Zr, $^{99m}$Tc, and $^{111}$In through a chelator, or is an imaging moiety selected from the group consisting of $^{18}$F, $^{76}$Br, $^{124}$I, and $^{131}$I; or a salt thereof.

In some embodiments, the agent for imaging innervation comprises a compound as described above in Section A entitled "Imaging Agents." In some embodiments, the agent for imaging innervation is of the formula:

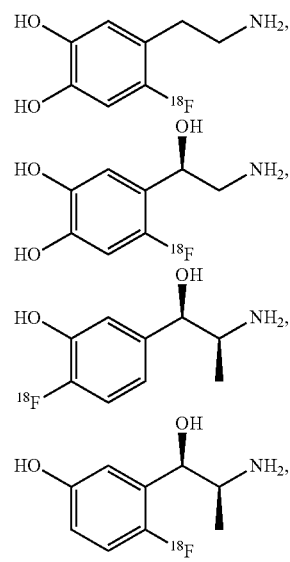

-continued
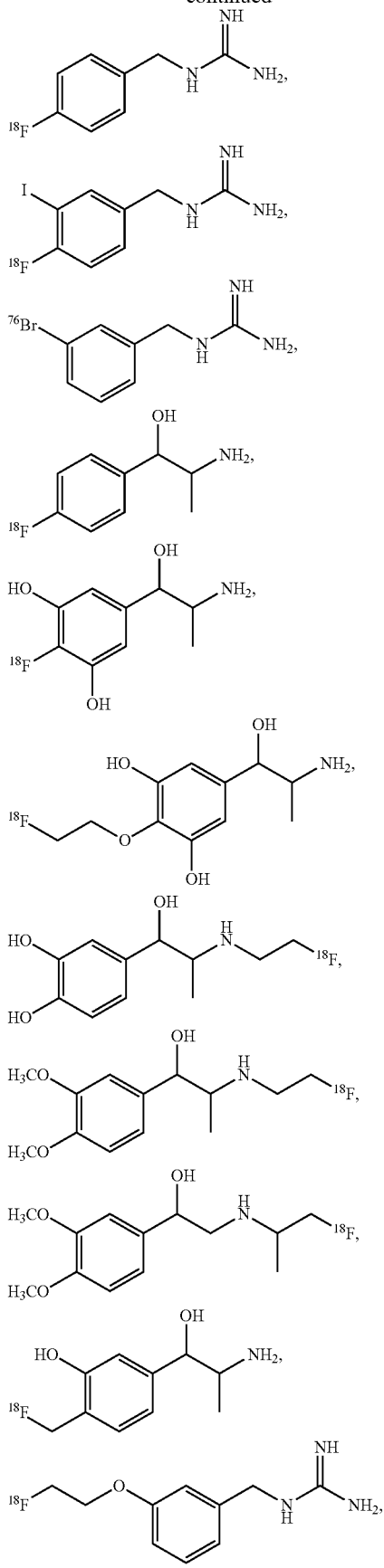
-continued
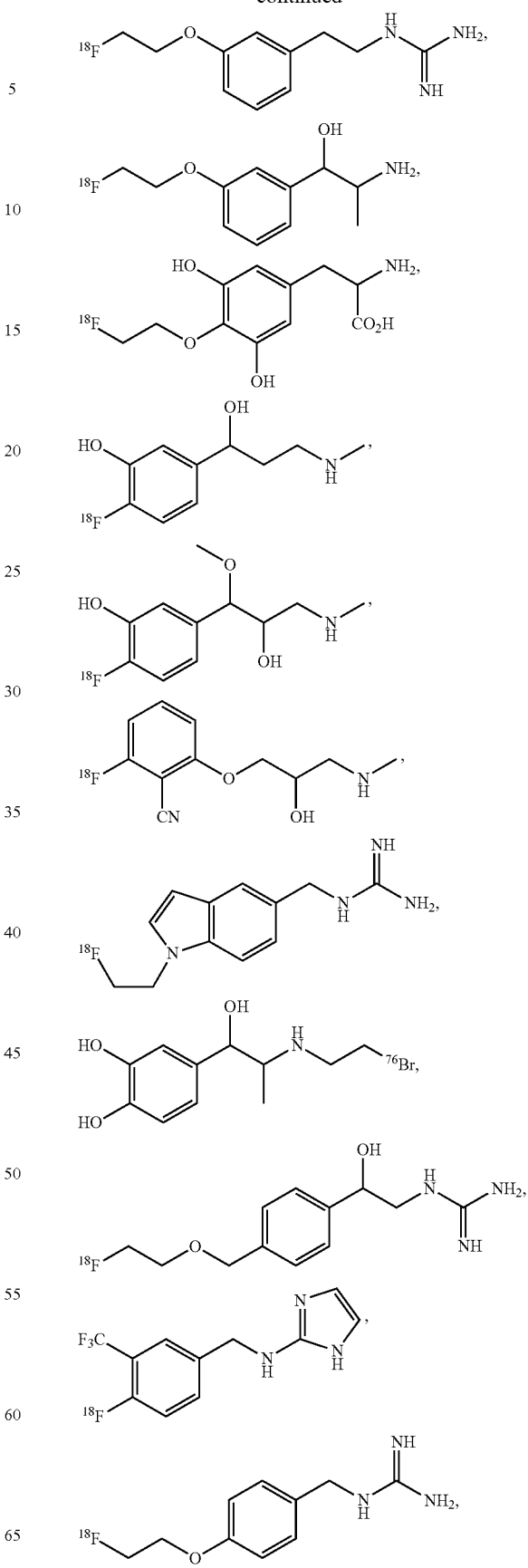

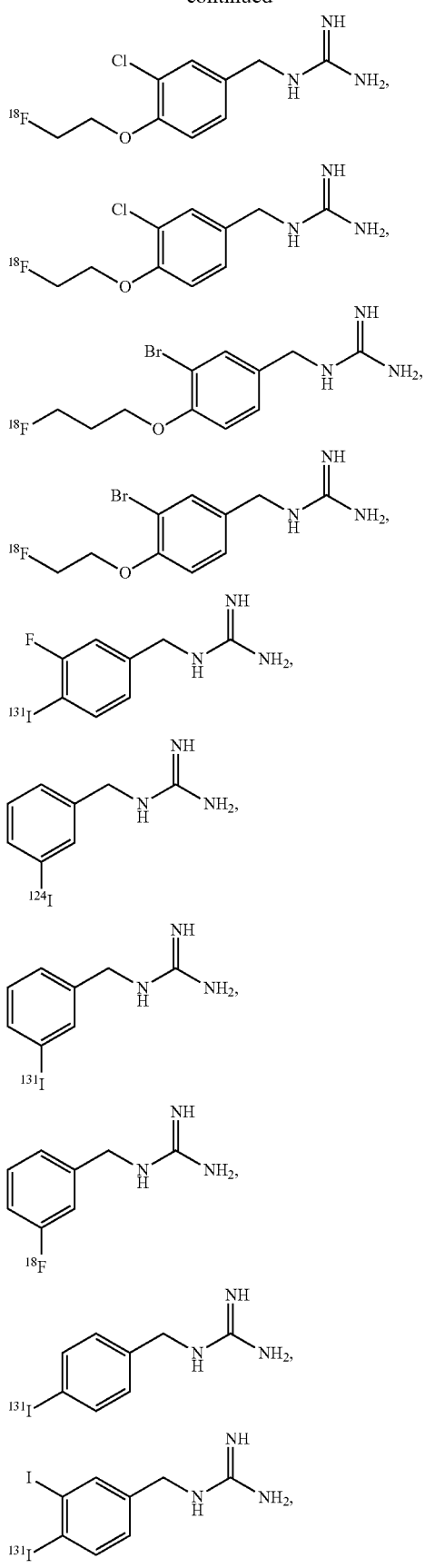
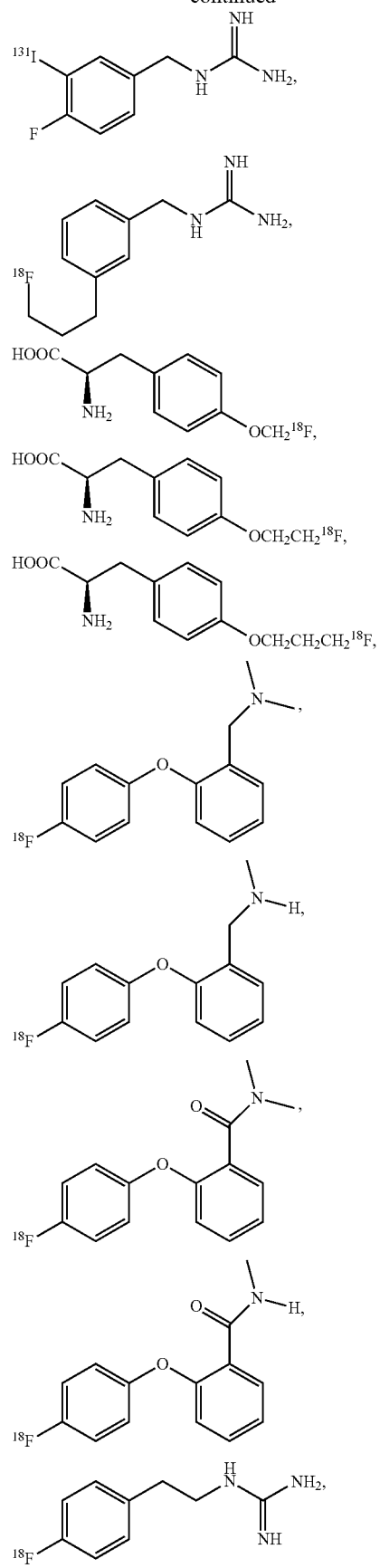

191
-continued
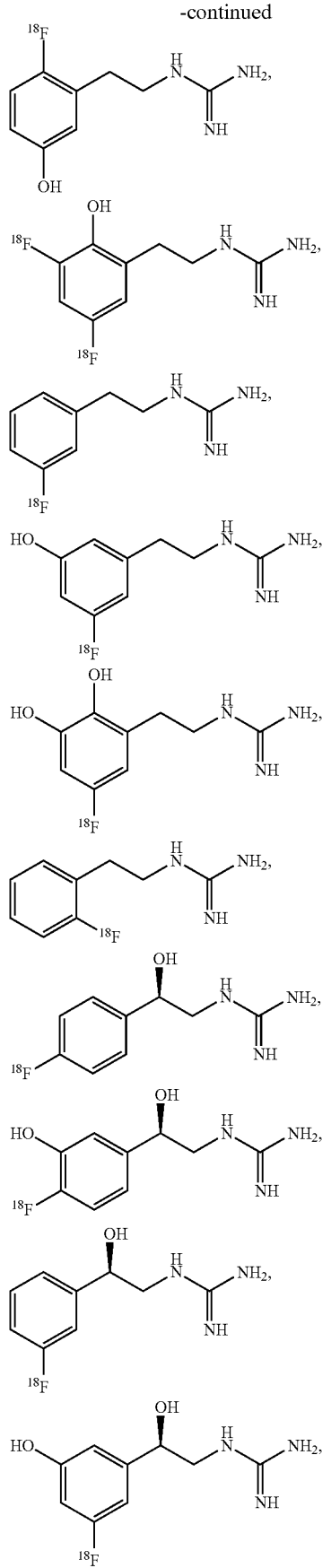
192
-continued
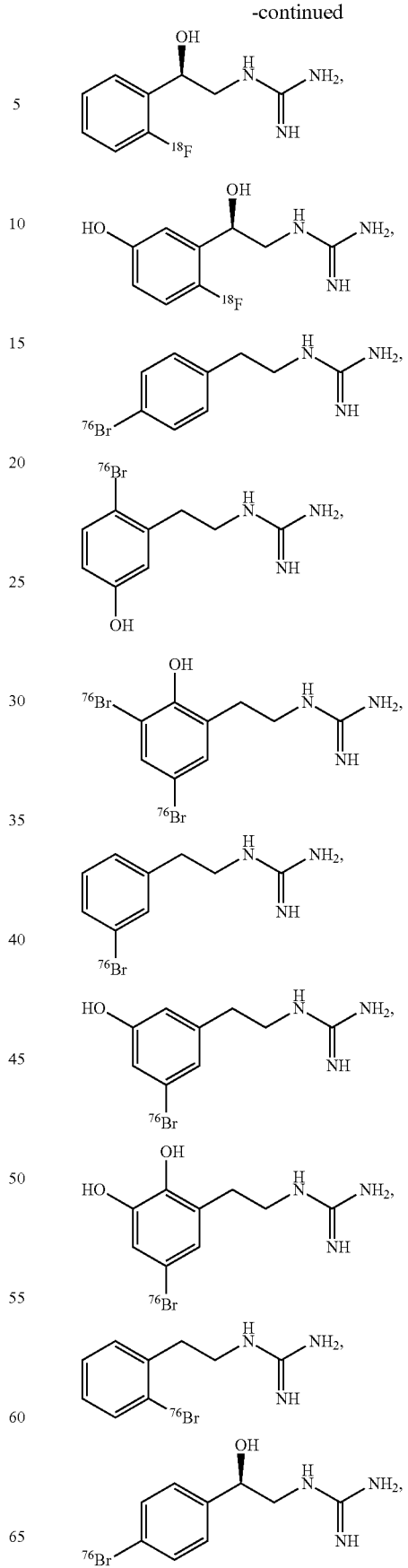

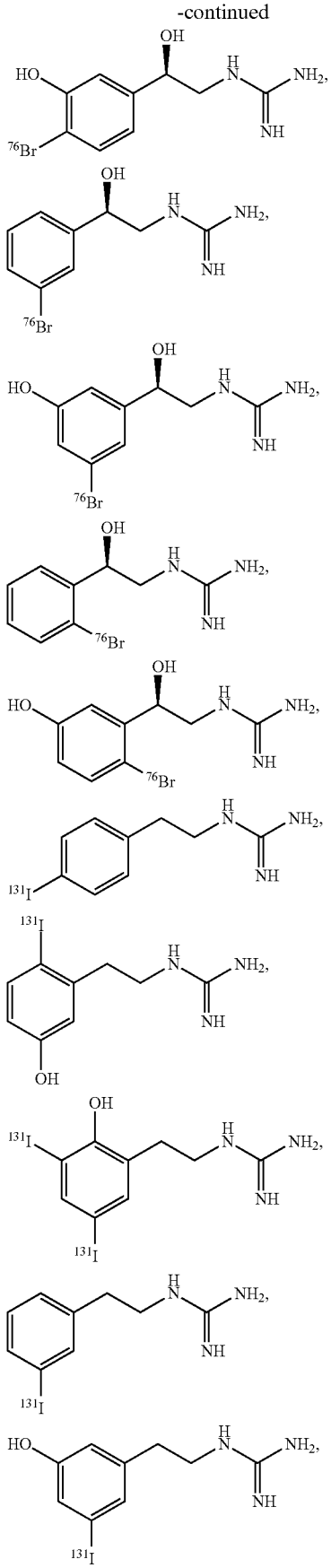
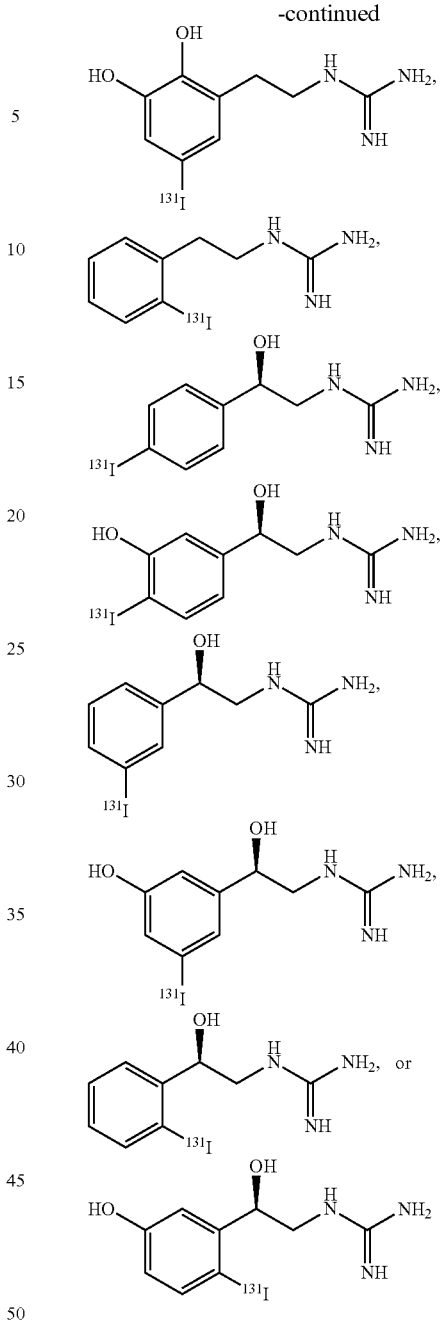

or a pharmaceutically acceptable salt thereof.

Those of ordinary skill in the art will be aware of other suitable imaging agents for imaging innervation (e.g., cardiac innervation). For example, other suitable imaging agents for imaging innervation include, but are not limited to, $^{123}$I-meta-iodobenzylguanidine (MIBG), $^{11}$C-meta-hydroxyephedrine (HED) and $^{11}$C-epinephrine. See, for example, Bengel F M, Schwaiger M. Assessment of cardiac sympathetic neuronal function using PET imaging. *J Nucl Cardiol.* 2004; 11(5):603-16; Henneman M M, Bengel F M, van der Wall E E, Knuuti J, Bax J J. Cardiac neuronal imaging: application in the evaluation of cardiac disease. *J Nucl Cardiol.* 2008; 15(3):442-55; Travin M I. Cardiac neuronal imaging at the edge of clinical application. *Cardiol Clin.* 2009; 27(2):311-27; and Carrio I. Cardiac neurotransmission imaging. *J Nucl Med.* 2001; 42(7):1062-76, incorporated by reference herein. In some embodiments, an imaging agent for imaging perfusion is as described in International Patent Publication No. WO 2008/083056, published Jul. 10, 2008, to Purohit et al., incorporated herein by reference.

H. Exemplary Cassettes and Reaction Systems

In some embodiments, systems, methods, kits, and cassettes are provided for the synthesis of an imaging agent as described herein. In some embodiments, an imaging agent may be prepared using an automated reaction system comprising a disposable or single use cassette. The cassette may comprise all the non-radioactive reagents, solvents, tubing, valves, reaction vessels, and other apparatus and/or components necessary to carry out the preparation of a given batch of imaging agent. The cassette allows the reaction system to have the flexibility to make a variety of different imaging agents with minimal risk of cross-contamination, by simply changing the cassette. By the term "cassette" is meant a piece of apparatus designed to fit removably and interchangeably onto automated reaction systems, in such a way that mechanical movement of moving parts of the automated reaction system controls the operation of the cassette from outside the cassette, i.e., externally. In certain embodiments, a cassette comprises a linear arrangement of valves, each linked to a port where various reagents, cartridges, syringes, and/or vials can be attached, by either needle puncture of a septum-sealed vial, or by gas-tight, marrying joints. Each valve may have a male-female joint which interfaces with a corresponding moving arm of the automated synthesizer. External rotation of the arm can control the opening or closing of the valve when the cassette is attached to the automated reaction system. Additional moving parts of the automated reaction system are designed to clip onto syringe plunger tips, and thus raise or depress syringe barrels. An automated reaction system may further include a controller and one or more controllable valves in electrical communication with the controller. An automated reaction system may also include additional vessels, valves, sensors, heaters, pressurizing elements, etc., in electrical communication with the controller. An automated reaction system may be operated by a controller using suitable software for control of valve openings and closings, heating, cooling, pressure levels, fluid movement, flow rate, etc. The automated reaction system may optionally include a computer operating system, software, controls, etc., or other component. In addition, the automated reaction system may comprise a mount for the cassette.

Examples of automated reaction systems (e.g., a nucleophilic reaction system), include, but are not limited to, the Explora GN or RN synthesis system (Siemens Medical Solutions USA, Inc.), GE-Tracerlab-MX synthesis system (GE Healthcare), Eckert & Zeigler Modular-Lab Synthesis system, etc., which are commonly available at PET manufacturing facilities.

I. Noise Filtering Optimization

The invention also relates, in part, to methods for optimizing noise filtering parameters for PET myocardial imaging. The invention provides a methodology for obtaining optimal noise filtering parameters for any 2D or 3D camera (or scanner as the terms are used interchangeably) used to obtain PET images. The invention also provides optimal noise filtering parameters to be applied to imaging data. These parameters may be used in an imaging data algorithm which may be performed manually or electronically (e.g., via software).

In accordance with the invention, it has been found that a cardiac phantom simulation using known patient myocardial standardized uptake values (SUVs) is an effective method to determine the optimal noise filter parameter set that can produce high-quality diagnostic images. This has been exemplified, as described in the Examples, from the use of imaging data obtained with PET myocardial perfusion Imaging Agent-2.

One method comprises obtaining 3D perfusion imaging data from a cardiac phantom having a defect, applying a series of smoothing filters to the data, and selecting the filter that provides less than 5% defect contrast degradation. The smoothing filter is typically a weighted Gaussian function defined by full width half maximum (FWHM) values. It was found in accordance with the invention that a Gaussian filter set at FWHM of 8 mm was optimal for 3D myocardial perfusion images acquired at rest and after either pharmacological stress or exercise induced stress. As shown in Table B of Example 2, a filter set at FWHM of 8 mm achieves the desired defect contrast degradation of less than 5% and a near maximal signal to noise ratio (SNR). At FWHM less than 8 mm the SNR decreases for each of these data sets and at FWHM more than 8 mm the defect contrast degradation is above the desired 5%. The cardiac phantom may have a defect of 45+/−15°, 45+/−10°, 45+/−5°, 45+/−1°, or simply 45°.

Another method comprises obtaining 2D gated imaging data from a cardiac phantom having a defect, applying a series of smoothing filters to the data, and selecting the filter that provides more than 90% left ventricular volume (LVV) accuracy. The smoothing filter is typically a weighted Gaussian function defined by FWHM values. It was found in accordance with the invention that a Gaussian filter of FWHM of 15 mm was optimal for 2D gated images acquired at rest, and a Gaussian filter of FWHM of 12 mm was optimal for 2D gated images acquired after pharmacological and exercise-induced stress. As shown in Table B, a filter set at FWHM less than or greater than 15 mm achieved LVV accuracy ranging from 50-78% as compared to the FWHM 15 mm filter which achieved 93% LVV accuracy, for images obtained at rest. A filter set at FWHM of 12 mm or 15 mm achieved LVV accuracies of about 93% and 91% for images obtained after pharmacological and exercise-induced stress, while FWHM less than 12 mm or greater than 15 mm achieved suboptimal LVV accuracies ranging from 65-84%.

Thus, the invention provides a method comprising obtaining 3D perfusion images from a patient and applying to such images a FWHM of 8 mm. The invention also provides obtaining 2D gated images from a patient at rest, after pharmacological stress and after exercised-induced stress and applying to such images a FWHM of 15 mm, 12 or 15 mm, and 12 or 15 mm, respectively.

It is to be understood that the foregoing methods can be used when acquiring myocardial perfusion images using a variety of myocardial perfusion imaging agents as described herein. In important embodiments, the myocardial perfusion imaging agent includes $^{18}$F as an imaging moiety, e.g., Imaging Agent—2.]

J. Pharmaceutical Compositions

The imaging agents described herein may be combined with one or more pharmaceutically acceptable excipients to form a pharmaceutical composition that is suitable for administration to a subject, including a human. As would be appreciated by one of skill in this art, the excipients may be chosen, for example, based on the route of administration as described below, the imaging agent being delivered, time course of delivery of the agent, and/or the health/condition of the subject. The pharmaceutical composition may be a solid or liquid.

Pharmaceutical compositions of the present invention and for use in accordance with the present invention may include a pharmaceutically acceptable excipient or carrier. As used herein, the term "pharmaceutically acceptable excipient" or "pharmaceutically acceptable carrier" means a non-toxic, inert solid, semi-solid or liquid filler, diluent, encapsulating material or formulation auxiliary of any type. Some examples of materials which can serve as pharmaceutically acceptable carriers are sugars such as lactose, glucose, and sucrose; starches such as corn starch and potato starch; cellulose and its derivatives such as sodium carboxymethyl cellulose, ethyl cellulose, and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols such as propylene glycol; esters such as ethyl oleate and ethyl laurate; agar; detergents such as Tween 80; buffering agents such as magnesium hydroxide and aluminum hydroxide; alginic acid; pyrogen-free water; isotonic saline; Ringer's solution; ethyl alcohol; and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

Pharmaceutically acceptable excipients include any and all solvents, diluents or other liquid vehicles, dispersion or suspension aids, surface active agents, isotonic agents, thickening or emulsifying agents, preservatives, solid binders, lubricants and the like, as suited to the particular dosage form desired. General considerations in formulation and/or manufacture of pharmaceutical compositions agents can be found, for example, in *Remington's Pharmaceutical Sciences*, Sixteenth Edition, E. W. Martin (Mack Publishing Co., Easton, Pa., 1980), and *Remington: The Science and Practice of Pharmacy*, 21st Edition (Lippincott Williams & Wilkins, 2005).

Pharmaceutical compositions described herein can be prepared by any method known in the art of pharmacology. In general, such preparatory methods include the steps of bringing the compound of the present invention (the "active ingredient") into association with a carrier and/or one or more other accessory ingredients, and then, if necessary and/or desirable, shaping and/or packaging the product into a desired single- or multi-dose unit.

Pharmaceutical compositions can be prepared, packaged, and/or sold in bulk, as a single unit dose, and/or as a plurality of single unit doses. As used herein, a "unit dose" is discrete amount of the pharmaceutical composition comprising a predetermined amount of the active ingredient. The amount of the active ingredient is generally equal to the dosage of the active ingredient which would be administered to a subject and/or a convenient fraction of such a dosage such as, for example, one-half or one-third of such a dosage.

Relative amounts of the active ingredient, the pharmaceutically acceptable excipient, and/or any additional ingredients in a pharmaceutical composition of the invention will vary, depending upon the identity, size, and/or condition of the subject treated and further depending upon the route by which the composition is to be administered. By way of example, the composition may comprise between 0.1% and 100% (w/w) active ingredient.

Pharmaceutically acceptable excipients used in the manufacture of provided pharmaceutical compositions include inert diluents, dispersing and/or granulating agents, surface active agents and/or emulsifiers, disintegrating agents, binding agents, preservatives, buffering agents, lubricating agents, and/or oils. Excipients such as cocoa butter and suppository waxes, coloring agents, coating agents, sweetening, flavoring, and perfuming agents may also be present in the composition.

Exemplary diluents include calcium carbonate, sodium carbonate, calcium phosphate, dicalcium phosphate, calcium sulfate, calcium hydrogen phosphate, sodium phosphate lactose, sucrose, cellulose, microcrystalline cellulose, kaolin, mannitol, sorbitol, inositol, sodium chloride, dry starch, cornstarch, powdered sugar, and combinations thereof.

Exemplary preservatives include antioxidants, chelating agents, antimicrobial preservatives, antifungal preservatives, alcohol preservatives, acidic preservatives, and other preservatives.

Exemplary antioxidants include alpha tocopherol, ascorbic acid, acorbyl palmitate, butylated hydroxyanisole, butylated hydroxytoluene, monothioglycerol, potassium metabisulfite, propionic acid, propyl gallate, sodium ascorbate, sodium bisulfite, sodium iodide, sodium metabisulfite, sodium nitrite, sodium sulfite, and sodium thiosulfate.

Exemplary chelating agents include ethylenediaminetetraacetic acid (EDTA) and salts and hydrates thereof (e.g., sodium edetate, disodium edetate, trisodium edetate, calcium disodium edetate, dipotassium edetate, and the like), citric acid and salts and hydrates thereof (e.g., citric acid monohydrate), fumaric acid and salts and hydrates thereof, malic acid and salts and hydrates thereof, phosphoric acid and salts and hydrates thereof, and tartaric acid and salts and hydrates thereof. Exemplary antimicrobial preservatives include benzalkonium chloride, benzethonium chloride, benzyl alcohol, bronopol, cetrimide, cetylpyridinium chloride, chlorhexidine, chlorobutanol, chlorocresol, chloroxylenol, cresol, ethyl alcohol, glycerin, hexetidine, imidurea, phenol, phenoxyethanol, phenylethyl alcohol, phenylmercuric nitrate, propylene glycol, and thimerosal.

Exemplary antifungal preservatives include butyl paraben, methyl paraben, ethyl paraben, propyl paraben, benzoic acid, hydroxybenzoic acid, potassium benzoate, potassium sorbate, sodium benzoate, sodium propionate, and sorbic acid.

Exemplary alcohol preservatives include ethanol, polyethylene glycol, phenol, phenolic compounds, bisphenol, chlorobutanol, hydroxybenzoate, and phenylethyl alcohol.

Exemplary acidic preservatives include vitamin A, vitamin C, vitamin E, beta-carotene, citric acid, acetic acid, dehydroacetic acid, ascorbic acid, sorbic acid, and phytic acid.

Other preservatives include tocopherol, tocopherol acetate, deteroxime mesylate, cetrimide, butylated hydroxyanisol (BHA), butylated hydroxytoluened (BHT), ethylenediamine, sodium lauryl sulfate (SLS), sodium lauryl ether sulfate (SLES), sodium bisulfite, sodium metabisulfite, potassium sulfite, potassium metabisulfite, Glydant Plus, Phenonip, methylparaben, Germall 115, Germaben II, Neolone, Kathon, and Euxyl. In certain embodiments, the preservative is an anti-oxidant. In other embodiments, the preservative is a chelating agent.

Exemplary buffering agents include citrate buffer solutions, acetate buffer solutions, phosphate buffer solutions, ammonium chloride, calcium carbonate, calcium chloride, calcium citrate, calcium glubionate, calcium gluceptate, calcium gluconate, D-gluconic acid, calcium glycerophosphate, calcium lactate, propanoic acid, calcium levulinate, pentanoic acid, dibasic calcium phosphate, phosphoric acid, tribasic calcium phosphate, calcium hydroxide phosphate, potassium acetate, potassium chloride, potassium gluconate, potassium mixtures, dibasic potassium phosphate, monobasic potassium phosphate, potassium phosphate mixtures, sodium acetate, sodium bicarbonate, sodium chloride, sodium citrate, sodium lactate, dibasic sodium phosphate, monobasic sodium phosphate, sodium phosphate mixtures, tromethamine, magnesium hydroxide, aluminum hydroxide, alginic acid, pyrogen free water, isotonic saline, Ringer's solution, ethyl alcohol, etc., and combinations thereof.

Liquid dosage forms for oral and parenteral administration include pharmaceutically acceptable emulsions, microemulsions, solutions, suspensions, syrups and elixirs. In addition to the active ingredients, the liquid dosage forms may comprise inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (e.g., cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can include adjuvants such as wetting agents, emulsifying and suspending agents, sweetening, flavoring, and perfuming agents. In certain embodiments for parenteral administration, the conjugates of the invention are mixed with solubilizing agents such as Cremophor, alcohols, oils, modified oils, glycols, polysorbates, cyclodextrins, polymers, and combinations thereof.

Injectable preparations, for example, sterile injectable aqueous or oleaginous suspensions can be formulated according to the known art using suitable dispersing or wetting agents and suspending agents. The sterile injectable preparation can be a sterile injectable solution, suspension or emulsion in a nontoxic parenterally acceptable diluent or solvent, for example, as a solution in 1,3-butanediol. Among the acceptable vehicles and solvents that can be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

Suitable devices for use in delivering intradermal pharmaceutical compositions described herein include short needle devices such as those described in U.S. Pat. Nos. 4,886,499; 5,190,521; 5,328,483; 5,527,288; 4,270,537; 5,015,235; 5,141,496; and 5,417,662. Intradermal compositions can be administered by devices which limit the effective penetration length of a needle into the skin, such as those described in PCT publication WO 99/34850 and functional equivalents thereof. Jet injection devices which deliver liquid vaccines to the dermis via a liquid jet injector and/or via a needle which pierces the stratum corneum and produces a jet which reaches the dermis are suitable. Jet injection devices are described, for example, in U.S. Pat. Nos. 5,480,381; 5,599,302; 5,334,144; 5,993,412; 5,649,912; 5,569,189; 5,704,911; 5,383,851; 5,893,397; 5,466,220; 5,339,163; 5,312,335; 5,503,627; 5,064,413; 5,520,639; 4,596,556; 4,790,824; 4,941,880; 4,940,460; and PCT publications WO 97/37705 and WO 97/13537. Ballistic powder/particle delivery devices which use compressed gas to accelerate vaccine in powder form through the outer layers of the skin to the dermis are suitable. Alternatively or additionally, conventional syringes can be used in the classical Mantoux method of intradermal administration.

Although the descriptions of pharmaceutical compositions provided herein are principally directed to pharmaceutical compositions which are suitable for administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and/or perform such modification with ordinary experimentation.

The pharmaceutical compositions of this invention can be administered to humans and/or to other animals parenterally (e.g., by intravenous, intramuscular, subcutaneous, or intraperitoneal injection). The mode of administration will vary depending on the intended use, as is well known in the art.

K. Kits

Systems, methods, kits, and/or cassettes are provided comprising an imaging agent or an imaging agent precursor (or a first imaging agent and a second imaging agent) as described herein or a composition thereof and/or for preparation of an imaging agent. In some embodiments, a kits comprises an imaging agent for imaging perfusion and an imaging agent for imaging innervation (e.g., as described in Sections G1 and G2). In some embodiments, kits for the administration of an imaging agent are provided. In some cases, the composition provided with the kit may be used for or in the preparation of an imaging agent for detecting, imaging, and/or monitoring a disorder or condition. Kits of the invention may include, for example, a container comprising an imaging agent or an imaging agent precursor and instructions for use. Kits may comprise a sterile, non-pyrogenic, formulation comprising a predetermined amount of an imaging agent or an imaging agent precursor, and optionally other components. A container that may be used in conjunction with an imaging agent for example, to deliver and/or administer the imaging agent to a subject, may be a syringe, bottle, vial, or tube. Instructions in a kit of the invention may relate to methods for synthesizing an imaging agent or an imaging agent precursor, methods of diluting the imaging agent or the imaging agent precursor, methods of administering the imaging agent to a subject for diagnostic imaging, or other instructions for use. An imaging agent or an imaging agent precursor may be provided in a kit and additional preparations before use may optionally include diluting the imaging agent or imaging agent precursor to a usable concentration.

In some cases, a kit can also include one or more vials containing a diluent for preparing an imaging agent composition for administration to a subject (e.g., a human). A diluent vial may contain a diluent such as physiological saline or water for diluting the imaging agent. For example, the imaging agent may be packaged in a kit in a ready-toinject formulation, or may require some reconstitution or dilution whereby a final composition/formulation for injection or infusion is prepared.

Instructions in a kit of the invention may also include instructions for administering the imaging agent to a subject and may include information on dosing, timing, stress induction, etc. For example, a kit may include an imaging agent or imaging agent precursor as described herein along with instructions describing the intended application and the proper administration of the agent to a subject. As used herein, "instructions" can define a component of instruction and/or promotion, and typically involve written instructions on or associated with packaging of the invention. Instructions also can include any oral or electronic instructions provided in any manner such that a user will clearly recognize that the instructions are to be associated with the kit, for example, audiovisual (e.g., videotape, DVD), internet, and/or web-based communications. The written instructions may be in a form prescribed by a governmental agency regulating the manufacture, use or sale of pharmaceuticals products, which instructions can also reflect approval by the agency of manufacture, use; or sale for human administration. In some cases, the instructions can include instructions for mixing a particular amount of the diluent with a particular amount of a concentrated solution of the imaging agent or a solid preparation of the imaging agent, whereby a final formulation for injection or infusion is prepared for example, such that the resulting solution is at a suitable concentration for administration to a subject (e.g., at a concentration as described herein). A kit may include a whole treatment regimen of the inventive compound.

The kit may contain any one or more of the components described herein in one or more containers. As an example, in one embodiment, the kit may include instructions for mixing one or more components of the kit and/or isolating and mixing a sample and applying to a subject. The kit may include a container housing an agent described herein (e.g., an imaging agent precursor or an imaging agent). The agent may be in the form of a liquid, gel, or solid (e.g., powder). The agent may be prepared sterilely, packaged in a syringe, and shipped refrigerated. Alternatively it may be housed in a vial or other container for storage. A second container may have other agents prepared sterilely. Alternatively, the kit may include an agent premixed and shipped in a syringe, vial, tube, or other container. The kit may have one or more or all of the components required to administer the agents to a subject, such as a syringe or i.v. needle tubing and bag.

It also will be understood that containers containing the components of a kit of the invention, whether the container is a bottle, a vial (e.g., with a septum), an ampoule, an infusion bag, or the like, can include additional indicia such as conventional markings that change color when the preparation has been autoclaved or otherwise sterilized. A kit of the invention may further include other components, such as syringes, labels, vials, tubing, catheters, needles, ports, and the like. In some aspect of the invention, a kit may include a single syringe containing the imaging agent of the invention sufficient for administration and in some aspects of the invention a kit may include more than one syringe.

Buffers useful in the preparation of imaging agents and kits include, for example, phosphate, citrate, sulfosalicylate, and acetate buffers. A more complete list can be found in the United States Pharmacopoeia. Lyophilization aids useful in the preparation of imaging agents and kits include, for example, mannitol, lactose, sorbitol, dextran, FICOLL® polymer, and polyvinylpyrrolidine (PVP). Stabilization aids useful in the preparation of imaging agents and kits include, for example, ascorbic acid, cysteine, monothioglycerol, sodium bisulfite, sodium metabisulfite, gentisic acid, and inositol. Solubilization aids useful in the preparation of imaging agents and kits include, for example, ethanol, glycerin, polyethylene glycol, propylene glycol, polyoxyethylene sorbitan monooleate, sorbitan monoloeate, polysorbates, poly(oxyethylene)-poly(oxypropylene)-poly(oxyethylene) block copolymers (e.g., Pluronics®) and lecithin. In certain embodiments, the solubilizing aids are polyethylene glycol, cyclodextrins, and Pluronics. Bacteriostats useful in the preparation of imaging agents and kits include, for example, benzyl alcohol, benzalkonium chloride, chlorbutanol, and methyl, propyl, or butyl paraben.

L. Definitions

For convenience, certain terms employed in the specification, examples, and appended claims are listed here.

Definitions of specific functional groups and chemical terms are described in more detail below. For purposes of this invention, the chemical elements are identified in accordance with the Periodic Table of the Elements, CAS version, *Handbook of Chemistry and Physics*, 75$^{th}$ Ed., inside cover, and specific functional groups are generally defined as described therein. Additionally, general principles of organic chemistry, as well as specific functional moieties and reactivity, are described in *Organic Chemistry*, Thomas Sorrell, University Science Books, Sausalito: 1999, the entire contents of which are incorporated herein by reference.

Certain compounds of the present invention may exist in particular geometric or stereoisomeric forms. The present invention contemplates all such compounds, including cis- and trans-isomers, R- and S-enantiomers, diastereomers, (D)-isomers, (L)-isomers, the racemic mixtures thereof, and other mixtures thereof, as falling within the scope of the invention. Additional asymmetric carbon atoms may be present in a substituent such as an alkyl group. All such isomers, as well as mixtures thereof, are intended to be included in this invention.

Isomeric mixtures containing any of a variety of isomer ratios may be utilized in accordance with the present invention. For example, where only two isomers are combined, mixtures containing 50:50, 60:40, 70:30, 80:20, 90:10, 95:5, 96:4, 97:3, 98:2, 99:1, or 100:0 isomer ratios are all contemplated by the present invention. Those of ordinary skill in the art will readily appreciate that analogous ratios are contemplated for more complex isomer mixtures.

If, for instance, a particular enantiomer of a compound of the present invention is desired, it may be prepared by asymmetric synthesis, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts are formed with an appropriate optically-active acid or base, followed by resolution of the diastereomers thus formed by fractional crystallization or chromatographic means well known in the art, and subsequent recovery of the pure enantiomers.

The term "aliphatic," as used herein, includes both saturated and unsaturated, nonaromatic, straight chain (i.e., unbranched), branched, acyclic, and cyclic (i.e., carbocyclic) hydrocarbons, which are optionally substituted with one or more functional groups. As will be appreciated by one of ordinary skill in the art, "aliphatic" is intended herein to include, but is not limited to, alkyl, alkenyl, alkynyl, cycloalkyl, cycloalkenyl, and cycloalkynyl moieties. Thus, as used herein, the term "alkyl" includes straight, branched and cyclic alkyl groups. An analogous convention applies to other generic terms such as "alkenyl", "alkynyl", and the like. Furthermore, as used herein, the terms "alkyl", "alkenyl", "alkynyl", and the like encompass both substituted and unsubstituted groups. In certain embodiments, as used herein, "aliphatic" is used to indicate those aliphatic groups (cyclic, acyclic, substituted, unsubstituted, branched or unbranched) having 1-20 carbon atoms. Aliphatic group substituents include, but are not limited to, any of the substituents described herein, that result in the formation of a stable moiety (e.g., aliphatic, alkyl, alkenyl, alkynyl, heteroaliphatic, heterocyclic, aryl, heteroaryl, acyl, oxo, imino, thiooxo, cyano, isocyano, amino, azido, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted).

As used herein, the term "alkyl" is given its ordinary meaning in the art and refers to the radical of saturated aliphatic groups, including straight-chain alkyl groups, branched-chain alkyl groups, cycloalkyl (alicyclic) groups, alkyl substituted cycloalkyl groups, and cycloalkyl substituted alkyl groups. In some cases, the alkyl group may be a lower alkyl group, i.e., an alkyl group having 1 to 10 carbon atoms (e.g., methyl, ethyl, propyl, butyl, pentyl, hexyl, heptyl, octyl, nonyl, or decyl). In some embodiments, a straight chain or branched chain alkyl may have 30 or fewer carbon atoms in its backbone, and, in some cases, 20 or fewer. In some embodiments, a straight chain or branched chain alkyl may have 12 or fewer carbon atoms in its backbone (e.g., $C_1$-$C_{12}$ for straight chain, $C_3$-$C_{12}$ for branched chain), 6 or fewer, or 4 or fewer. Likewise, cycloalkyls may have from 3-10 carbon atoms in their ring structure, or 5, 6 or 7 carbons in the ring structure. Examples of alkyl groups include, but are not limited to, methyl, ethyl, propyl, isopropyl, cyclopropyl, butyl, isobutyl, t-butyl, cyclobutyl, hexyl, and cyclohexyl.

The term "alkylene" as used herein refers to a bivalent alkyl group. An "alkylene" group is a polymethylene group, i.e., —$(CH_2)_z$—, wherein z is a positive integer, e.g., from 1 to 20, from 1 to 10, from 1 to 6, from 1 to 4, from 1 to 3, from 1 to 2, or from 2 to 3. A substituted alkylene chain is a polymethylene group in which one or more methylene hydrogen atoms are replaced with a substituent. Suitable substituents include those described herein for a substituted aliphatic group.

Generally, the suffix "-ene" is used to describe a bivalent group. Thus, any of the terms defined herein can be modified with the suffix "-ene" to describe a bivalent version of that moiety. For example, a bivalent carbocycle is "carbocyclylene", a bivalent aryl ring is "arylene", a bivalent benzene ring is "phenylene", a bivalent heterocycle is "heterocyclylene", a bivalent heteroaryl ring is "heteroarylene", a bivalent alkyl chain is "alkylene", a bivalent alkenyl chain is "alkenylene", a bivalent alkynyl chain is "alkynylene", a bivalent heteroalkyl chain is "heteroalkylene", a bivalent heteroalkenyl chain is "heteroalkenylene", a bivalent heteroalkynyl chain is "heteroalkynylene", and so forth.

The terms "alkenyl" and "alkynyl" are given their ordinary meaning in the art and refer to unsaturated aliphatic groups analogous in length and possible substitution to the alkyls described above, but that contain at least one double or triple bond respectively.

In certain embodiments, the alkyl, alkenyl and alkynyl groups employed in the invention contain 1-20 aliphatic carbon atoms. In certain other embodiments, the alkyl, alkenyl, and alkynyl groups employed in the invention contain 1-10 aliphatic carbon atoms. In yet other embodiments, the alkyl, alkenyl, and alkynyl groups employed in the invention contain 1-8 aliphatic carbon atoms. In still other embodiments, the alkyl, alkenyl, and alkynyl groups employed in the invention contain 1-6 aliphatic carbon atoms. In yet other embodiments, the alkyl, alkenyl, and alkynyl groups employed in the invention contain 1-4 carbon atoms. Illustrative aliphatic groups thus include, but are not limited to, for example, methyl, ethyl, n-propyl, isopropyl, allyl, n-butyl, sec-butyl, isobutyl, t-butyl, n-pentyl, sec-pentyl, isopentyl, t-pentyl, n-hexyl, sec-hexyl, moieties and the like, which again, may bear one or more substituents. Alkenyl groups include, but are not limited to, for example, ethenyl, propenyl, butenyl, 1-methyl-2-buten-1-yl, and the like. Representative alkynyl groups include, but are not limited to, ethynyl, 2-propynyl (propargyl), 1-propynyl and the like.

The term "cycloalkyl," as used herein, refers specifically to groups having three to ten, preferably three to seven carbon atoms. Suitable cycloalkyls include, but are not limited to cyclopropyl, cyclobutyl, cyclopentyl, cyclohexyl, cycloheptyl and the like, which, as in the case of other aliphatic, heteroaliphatic, or heterocyclic moieties, may optionally be substituted with substituents including, but not limited to aliphatic; heteroaliphatic; aryl; heteroaryl; arylalkyl; heteroarylalkyl; alkoxy; aryloxy; heteroalkoxy; heteroaryloxy; alkylthio; arylthio; heteroalkylthio; heteroarylthio; —F; —Cl; —Br; —I; —OH; —$NO_2$; —CN; —$CF_3$; —$CH_2CF_3$; —$CHCl_2$; —$CH_2OH$; —$CH_2CH_2OH$; —$CH_2NH_2$; —$CH_2SO_2CH_3$; —$C(O)R_x$; —$CO_2(R_x)$; —$CON(R_x)_2$; —$OC(O)R_x$; —$OCO_2R_x$; —$OCON(R_x)_2$; —$N(R_x)_2$; —$S(O)_2R_x$; —$NR_x(CO)R_x$, wherein each occurrence of $R_x$ independently includes, but is not limited to, aliphatic, heteroaliphatic, aryl, heteroaryl, arylalkyl, or heteroarylalkyl, wherein any of the aliphatic, heteroaliphatic, arylalkyl, or heteroarylalkyl substituents described above and herein may be substituted or unsubstituted, branched or unbranched, cyclic or acyclic, and wherein any of the aryl or heteroaryl substituents described above and herein may be substituted or unsubstituted. Additional examples of generally applicable substitutents are illustrated by the specific embodiments shown in the Examples that are described herein.

The term "heteroaliphatic," as used herein, refers to an aliphatic moiety, as defined herein, which includes both saturated and unsaturated, nonaromatic, straight chain (i.e., unbranched), branched, acyclic, cyclic (i.e., heterocyclic), or polycyclic hydrocarbons, which are optionally substituted with one or more functional groups, and that contain one or more oxygen, sulfur, nitrogen, phosphorus, or silicon atoms, e.g., in place of carbon atoms. In certain embodiments, heteroaliphatic moieties are substituted by independent replacement of one or more of the hydrogen atoms thereon with one or more substituents. As will be appreciated by one of ordinary skill in the art, "heteroaliphatic" is intended herein to include, but is not limited to, heteroalkyl, heteroalkenyl, heteroalkynyl, heterocycloalkyl, heterocycloalkenyl, and heterocycloalkynyl moieties. Thus, the term "heteroaliphatic" includes the terms "heteroalkyl," "heteroalkenyl", "heteroalkynyl", and the like. Furthermore, as used herein, the terms "heteroalkyl", "heteroalkenyl", "heteroalkynyl", and the like encompass both substituted and unsubstituted groups. In certain embodiments, as used herein, "heteroaliphatic" is used to indicate those heteroaliphatic groups (cyclic, acyclic, substituted, unsubstituted, branched or unbranched) having 1-20 carbon atoms. Heteroaliphatic group substituents include, but are not limited to, any of the substituents described herein, that result in the formation of a stable moiety (e.g., aliphatic, alkyl, alkenyl, alkynyl, heteroaliphatic, heterocyclic, aryl, heteroaryl, acyl, sulfinyl, sulfonyl, oxo, imino, thiooxo, cyano, isocyano, amino, azido, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted).

The term "heteroalkyl" is given its ordinary meaning in the art and refers to an alkyl group as described herein in which one or more carbon atoms is replaced by a heteroatom. Suitable heteroatoms include oxygen, sulfur, nitrogen, phosphorus, and the like. Examples of heteroalkyl groups include, but are not limited to, alkoxy, amino, thioester, poly(ethylene glycol), and alkyl-substituted amino.

The terms "heteroalkenyl" and "heteroalkynyl" are given their ordinary meaning in the art and refer to unsaturated aliphatic groups analogous in length and possible substitution to the heteroalkyls described above, but that contain at least one double or triple bond respectively.

Some examples of substituents of the above-described aliphatic (and other) moieties of compounds of the invention include, but are not limited to aliphatic; heteroaliphatic; aryl; heteroaryl; alkylaryl; alkylheteroaryl; alkoxy; aryloxy; heteroalkoxy; heteroaryloxy; alkylthio; arylthio; heteroalkylthio; heteroarylthio; F; Cl; Br; I; —OH; —NO$_2$; —CN; —CF$_3$; —CHF$_2$; —CH$_2$F; —CH$_2$CF$_3$; —CHCl$_2$; —CH$_2$OH; —CH$_2$CH$_2$OH; —CH$_2$NH$_2$; —CH$_2$SO$_2$CH$_3$; —C(O)R$_x$; —OC$_2$(R$_x$); —CON(R$_x$)$_2$; —OC(O)R$_x$; —OCO$_2$R$_x$; —OCON(R$_x$)$_2$; —N(R$_x$)$_2$; —S(O)$_2$R$_x$; —NR$_x$(CO)R$_x$ wherein each occurrence of R$_x$ independently includes, but is not limited to, aliphatic, alycyclic, heteroaliphatic, heterocyclic, aryl, heteroaryl, alkylaryl, or alkylheteroaryl, wherein any of the aliphatic, heteroaliphatic, alkylaryl, or alkylheteroaryl substituents described above and herein may be substituted or unsubstituted, branched or unbranched, cyclic or acyclic, and wherein any of the aryl or heteroaryl substituents described above and herein may be substituted or unsubstituted. Additional examples of generally applicable substituents are illustrated by the specific embodiments shown in the Examples that are described herein.

The term "aryl" is given its ordinary meaning in the art and refers to aromatic carbocyclic groups, optionally substituted, having a single ring (e.g., phenyl), multiple rings (e.g., biphenyl), or multiple fused rings in which at least one is aromatic (e.g., 1,2,3,4-tetrahydronaphthyl, naphthyl, anthryl, or phenanthryl). That is, at least one ring may have a conjugated pi electron system, while other, adjoining rings can be cycloalkyls, cycloalkenyls, cycloalkynyls, aryls and/or heterocyclyls. The aryl group may be optionally substituted, as described herein. Substituents include, but are not limited to, any of the previously mentioned substitutents, i.e., the substituents recited for aliphatic moieties, or for other moieties as disclosed herein, resulting in the formation of a stable compound. In some cases, an aryl group is a stable mono- or polycyclic unsaturated moiety having preferably 3-14 carbon atoms, each of which may be substituted or unsubstituted. "Carbocyclic aryl groups" refer to aryl groups wherein the ring atoms on the aromatic ring are carbon atoms. Carbocyclic aryl groups include monocyclic carbocyclic aryl groups and polycyclic or fused compounds (e.g., two or more adjacent ring atoms are common to two adjoining rings) such as naphthyl groups.

The terms "heteroaryl" is given its ordinary meaning in the art and refers to aryl groups comprising at least one heteroatom as a ring atom. A "heteroaryl" is a stable heterocyclic or polyheterocyclic unsaturated moiety having preferably 3-14 carbon atoms, each of which may be substituted or unsubstituted. Substituents include, but are not limited to, any of the previously mentioned substitutents, i.e., the substituents recited for aliphatic moieties, or for other moieties as disclosed herein, resulting in the formation of a stable compound. In some cases, a heteroaryl is a cyclic aromatic radical having from five to ten ring atoms of which one ring atom is selected from S, O, and N; zero, one, or two ring atoms are additional heteroatoms independently selected from S, O, and N; and the remaining ring atoms are carbon, the radical being joined to the rest of the molecule via any of the ring atoms, such as, for example, pyridyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, and the like.

It will also be appreciated that aryl and heteroaryl moieties, as defined herein may be attached via an alkyl or heteroalkyl moiety and thus also include (alkyl)aryl, -(heteroalkyl)aryl, -(heteroalkyl)heteroaryl, and (heteroalkyl)heteroaryl moieties. Thus, as used herein, the phrases "aryl or heteroaryl moieties" and "aryl, heteroaryl, (alkyl)aryl, -(heteroalkyl)aryl, -(heteroalkyl)heteroaryl, and -(heteroalkyl) heteroaryl" are interchangeable. Substituents include, but are not limited to, any of the previously mentioned substituents, i.e., the substituents recited for aliphatic moieties, or for other moieties as disclosed herein, resulting in the formation of a stable compound.

It will be appreciated that aryl and heteroaryl groups (including bicyclic aryl groups) can be unsubstituted or substituted, wherein substitution includes replacement of one or more of the hydrogen atoms thereon independently with any one or more of the following moieties including, but not limited to: aliphatic; alicyclic; heteroaliphatic; heterocyclic; aromatic; heteroaromatic; aryl; heteroaryl; alkylaryl; heteroalkylaryl; alkylheteroaryl; heteroalkylheteroaryl; alkoxy; aryloxy; heteroalkoxy; heteroaryloxy; alkylthio; arylthio; heteroalkylthio; heteroarylthio; F; Cl; Br; I; —OH; —NO$_2$; —CN; —CF$_3$; —CH$_2$F; —CHF$_2$; —CH$_2$CF$_3$; —CHCl$_2$; —CH$_2$OH; —CH$_2$CH$_2$OH; —CH$_2$NH$_2$; —CH$_2$SO$_2$CH$_3$; —C(O)R$_x$; —CO$_2$(R$_x$); —CON(R$_x$)$_2$; —OC(O)R$_x$; —OCO$_2$R$_x$; —OCON(R$_x$)$_2$; —N(R$_x$)$_2$; —S(O)R$_x$; —S(O)$_2$R$_x$; —NR$_x$(CO)R$_x$ wherein each occurrence of R$_x$ independently includes, but is not limited to, aliphatic, alicyclic, heteroaliphatic, heterocyclic, aromatic, heteroaromatic, aryl, heteroaryl, alkylaryl, alkylheteroaryl, heteroalkylaryl or heteroalkylheteroaryl, wherein any of the aliphatic, alicyclic, heteroaliphatic, heterocyclic, alkylaryl, or alkylheteroaryl substituents described above and herein may be substituted or unsubstituted, branched or unbranched, saturated or unsaturated, and wherein any of the aromatic, heteroaromatic, aryl, heteroaryl, -(alkyl)aryl or -(alkyl)heteroaryl substituents described above and herein may be substituted or unsubstituted. Additionally, it will be appreciated, that any two adjacent groups taken together may represent a 4, 5, 6, or 7-membered substituted or unsubstituted alicyclic or heterocyclic moiety. Additional examples of generally applicable substituents are illustrated by the specific embodiments described herein.

The term "heterocycle" is given its ordinary meaning in the art and refers to refer to cyclic groups containing at least one heteroatom as a ring atom, in some cases, 1 to 3 heteroatoms as ring atoms, with the remainder of the ring atoms being carbon atoms. Suitable heteroatoms include oxygen, sulfur, nitrogen, phosphorus, and the like. In some cases, the heterocycle may be 3- to 10-membered ring structures or 3- to 7-membered rings, whose ring structures include one to four heteroatoms.

The term "heterocycle" may include heteroaryl groups, saturated heterocycles (e.g., cycloheteroalkyl) groups, or combinations thereof. The heterocycle may be a saturated molecule, or may comprise one or more double bonds. In some cases, the heterocycle is a nitrogen heterocycle, wherein at least one ring comprises at least one nitrogen ring atom. The heterocycles may be fused to other rings to form a polycyclic heterocycle. The heterocycle may also be fused to a spirocyclic group. In some cases, the heterocycle may be attached to a compound via a nitrogen or a carbon atom in the ring.

Heterocycles include, for example, thiophene, benzothiophene, thianthrene, furan, tetrahydrofuran, pyran, isobenzofuran, chromene, xanthene, phenoxathiin, pyrrole, dihydropyrrole, pyrrolidine, imidazole, pyrazole, pyrazine, isothiazole, isoxazole, pyridine, pyrazine, pyrimidine, pyridazine, indolizine, isoindole, indole, indazole, purine, quinolizine, isoquinoline, quinoline, phthalazine, naphthyridine, quinoxaline, quinazoline, cinnoline, pteridine, carbazole, carboline, triazole, tetrazole, oxazole, isoxazole, thiazole, isothiazole, phenanthridine, acridine, pyrimidine, phenanthroline, phenazine, phenarsazine, phenothiazine, furazan, phenoxazine, pyrrolidine, oxolane, thiolane, oxazole, oxazine, piperidine, homopiperidine (hexamethyleneimine), piperazine (e.g., N-methyl piperazine), morpholine, lactones, lactams such as azetidinones and pyrrolidinones, sultams, sultones, other saturated and/or unsaturated derivatives thereof, and the like. The heterocyclic ring can be optionally substituted at one or more positions with such substituents as described herein. In some cases, the heterocycle may be bonded to a compound via a heteroatom ring atom (e.g., nitrogen). In some cases, the heterocycle may be bonded to a compound via a carbon ring atom. In some cases, the heterocycle is pyridine, imidazole, pyrazine, pyrimidine, pyridazine, acridine, acridin-9-amine, bipyridine, naphthyridine, quinoline, benzoquinoline, benzoisoquinoline, phenanthridine-1,9-diamine, or the like.

The terms "halo" and "halogen" as used herein refer to an atom selected from the group consisting of fluorine, chlorine, bromine, and iodine.

The term "haloalkyl" denotes an alkyl group, as defined above, having one, two, or three halogen atoms attached thereto and is exemplified by such groups as chloromethyl, bromoethyl, trifluoromethyl, and the like.

The term "amino," as used herein, refers to a primary ($-NH_2$), secondary ($-NHR_x$), tertiary ($-NR_xR_y$), or quaternary ($-N^+R_xR_yR_z$) amine, where $R_x$, $R_y$, and $R_z$ are independently an aliphatic, alicyclic, heteroaliphatic, heterocyclic, aryl, or heteroaryl moiety, as defined herein. Examples of amino groups include, but are not limited to, methylamino, dimethylamino, ethylamino, diethylamino, methylethylamino, iso-propylamino, piperidino, trimethylamino, and propylamino.

The term "alkyne" is given its ordinary meaning in the art and refers to branched or unbranched unsaturated hydrocarbon groups containing at least one triple bond. Non-limiting examples of alkynes include acetylene, propyne, 1-butyne, 2-butyne, and the like. The alkyne group may be substituted and/or have one or more hydrogen atoms replaced with a functional group, such as a hydroxyl, halogen, alkoxy, and/or aryl group.

The term "alkoxy" (or "alkyloxy"), or "thioalkyl" as used herein refers to an alkyl group, as previously defined, attached to the parent molecular moiety through an oxygen atom or through a sulfur atom. In certain embodiments, the alkyl group contains 1-20 aliphatic carbon atoms. In certain other embodiments, the alkyl group contains 1-10 aliphatic carbon atoms. In yet other embodiments, the alkyl, alkenyl, and alkynyl groups employed in the invention contain 1-8 aliphatic carbon atoms. In still other embodiments, the alkyl group contains 1-6 aliphatic carbon atoms. In yet other embodiments, the alkyl group contains 1-4 aliphatic carbon atoms. Examples of alkoxy, include but are not limited to, methoxy, ethoxy, propoxy, isopropoxy, n-butoxy, t-butoxy, neopentoxy and n-hexoxy. Examples of thioalkyl include, but are not limited to, methylthio, ethylthio, propylthio, isopropylthio, n-butylthio, and the like.

The term "aryloxy" refers to the group, $-O$-aryl.

The term "acyloxy" refers to the group, $-O$-acyl.

The term "alkoxyalkyl" refers to an alkyl group substituted with at least one alkoxy group (e.g., one, two, three, or more, alkoxy groups). For example, an alkoxyalkyl group may be $-(C_{1-6}$-alkyl$)-O-(C_{1-6}$-alkyl), optionally substituted. In some cases, the alkoxyalkyl group may be optionally substituted with another alkyoxyalkyl group (e.g., $-(C_{1-6}$-alkyl$)-O-(C_{1-6}$-alkyl$)-O-(C_{1-6}$-alkyl), optionally substituted.

It will be appreciated that the above groups and/or compounds, as described herein, may be optionally substituted with any number of substituents or functional moieties. That is, any of the above groups may be optionally substituted. As used herein, the term "substituted" is contemplated to include all permissible substituents of organic compounds, "permissible" being in the context of the chemical rules of valence known to those of ordinary skill in the art. In general, the term "substituted" whether preceeded by the term "optionally" or not, and substituents contained in formulas of this invention, refer to the replacement of hydrogen radicals in a given structure with the radical of a specified substituent. When more than one position in any given structure may be substituted with more than one substituent selected from a specified group, the substituent may be either the same or different at every position. It will be understood that "substituted" also includes that the substitution results in a stable compound, e.g., which does not spontaneously undergo transformation such as by rearrangement, cyclization, elimination, etc. In some cases, "substituted" may generally refer to replacement of a hydrogen with a substituent as described herein. However, "substituted," as used herein, does not encompass replacement and/or alteration of a key functional group by which a molecule is identified, e.g., such that the "substituted" functional group becomes, through substitution, a different functional group. For example, a "substituted phenyl group" must still comprise the phenyl moiety and cannot be modified by substitution, in this definition, to become, e.g., a pyridine ring. In a broad aspect, the permissible substituents include acyclic and cyclic, branched and unbranched, carbocyclic and heterocyclic, aromatic and nonaromatic substituents of organic compounds. Illustrative substituents include, for example, those described herein. The permissible substituents can be one or more and the same or different for appropriate organic compounds. For purposes of this invention, the heteroatoms such as nitrogen may have hydrogen substituents and/or any permissible substituents of organic compounds described herein which satisfy the valencies of the heteroatoms. Furthermore, this invention is not intended to be limited in any manner by the permissible substituents of organic compounds. Combinations of substituents and variables envisioned by this invention are preferably those that result in the formation of stable compounds useful for the formation of an imaging agent or an imaging agent precursor. The term "stable," as used herein, preferably refers to compounds which possess stability sufficient to allow manufacture and which maintain the integrity of the compound for a sufficient period of time to be detected and preferably for a sufficient period of time to be useful for the purposes detailed herein.

Examples of substituents include, but are not limited to, halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, $-CF_3$, $-CN$, aryl, aryloxy, perhaloalkoxy, aralkoxy, heteroaryl, heteroaryloxy, heteroarylalkyl, heteroaralkoxy, azido, amino, halide, alkylthio, oxo, acylalkyl, carboxy esters, -carboxamido, acyloxy, aminoalkyl, alkylaminoaryl, alkylaryl, alkylaminoalkyl, alkoxyaryl, arylamino, aralkylamino, alkylsulfonyl, -carboxamidoalkylaryl, -carboxamidoaryl, hydroxyalkyl, haloalkyl, alkylaminoalkylcarboxy-, aminocarboxamidoalkyl-, cyano, alkoxyalkyl, perhaloalkyl, arylalkyloxyalkyl, and the like. In some embodiments, a substituent may also be an imaging moiety (e.g., 18F) or a group for associating an imaging moiety (e.g., a chelator).

Nitrogen-protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference. For example, nitrogen protecting groups include, but are not limited to, carbamates (including methyl, ethyl and substituted ethyl carbamates (e.g. Troc), to name a few), amides, cyclic imide derivatives, N-alkyl and N-aryl amines, imine derivatives, and enamine derivatives, to name a few. In some embodiments, the nitrogen-protecting group is carbobenzyloxy (Cbz), p-methoxybenzyl carbonyl (MeOZ), t-butyloxycarbonyl (Boc), 9-fluorenylmethyloxycarbonyl (Fmoc), acetyl (Ac), benzoyl (Bz), benzyl (Bn), p-methoxybenzyl (PMB), 3,4-dimethoxybenzyl (DMPM), p-methoxyphenyl (PMP), or p-toluenesulfonyloxy (Ts).

Nitrogen-protecting groups such as amide groups include, but are not limited to, formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, p-phenylbenzamide, o-nitrophenylacetamide, o-nitrophenoxyacetamide, acetoacetamide, (N'-dithiobenzyloxyacylamino)acetamide, 3-(p-hydroxyphenyl)propanamide, 3-(o-nitrophenyl)propanamide, 2-methyl-2-(o-nitrophenoxy) propanamide, 2-methyl-2-(o-phenylazophenoxy) propanamide, 4-chlorobutanamide, 3-methyl-3-nitrobutanamide, o-nitrocinnamide, N-acetylmethionine derivative, o-nitrobenzamide, and o-(benzoyloxymethyl)benzamide.

Nitrogen-protecting groups such as carbamate groups include, but are not limited to, methyl carbamate, ethyl carbamante, 9-fluorenylmethyl carbamate (Fmoc), 9-(2-sulfo)fluorenylmethyl carbamate, 9-(2,7-dibromo)fluoroenylmethyl carbamate, 2,7-di-t-butyl-[9-(10,10-dioxo-10,10,10,10-tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-adamantyl)-1-methylethyl carbamate (Adpoc), 1,1-dimethyl-2-haloethyl carbamate, 1,1-dimethyl-2,2-dibromoethyl carbamate (DBtBOC), 1,1-dimethyl-2,2,2-trichloroethyl carbamate (TCBOC), 1-methyl-1-(4-biphenylyl)ethyl carbamate (Bpoc), 1-(3,5-di-t-butylphenyl)-1-methylethyl carbamate (t-Bumeoc), 2-(2'- and 4'-pyridyl)ethyl carbamate (Pyoc), 2-(N,N-dicyclohexylcarboxamido)ethyl carbamate, t-butyl carbamate (BOC), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitrobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl)ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, m-chloro-p-acyloxybenzyl carbamate, p-(dihydroxyboryl)benzyl carbamate, 5-benzisoxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl(o-nitrophenyl)methyl carbamate, t-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxyacylvinyl carbamate, o-(N,N-dimethylcarboxamido)benzyl carbamate, 1,1-dimethyl-3-(N,N-dimethylcarboxamido)propyl carbamate, 1,1-dimethylpropynyl carbamate, di(2-pyridyl)methyl carbamate, 2-furanylmethyl carbamate, 2-iodoethyl carbamate, isobornyl carbamate, isobutyl carbamate, isonicotinyl carbamate, p-(p'-methoxyphenylazo)benzyl carbamate, 1-methylcyclobutyl carbamate, 1-methylcyclohexyl carbamate, 1-methyl-1-cyclopropylmethyl carbamate, 1-methyl-1-(3,5-dimethoxyphenyl)ethyl carbamate, 1-methyl-1-(p-phenylazophenyl)ethyl carbamate, 1-methyl-1-phenylethyl carbamate, 1-methyl-1-(4-pyridyl)ethyl carbamate, phenyl carbamate, p-(phenylazo)benzyl carbamate, 2,4,6-tri-t-butylphenyl carbamate, 4-(trimethylammonium) benzyl carbamate, and 2,4,6-trimethylbenzyl carbamate.

Nitrogen-protecting groups such as sulfonamide groups include, but are not limited to, p-toluenesulfonamide (Ts), benzenesulfonamide, 2,3,6,-trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), β-trimethylsilylethanesulfonamide (SES), 9-anthracenesulfonamide, 4-(4',8'-dimethoxynaphthylmethyl)benzenesulfonamide (DNMBS), benzylsulfonamide, trifluoromethylsulfonamide, and phenacylsulfonamide.

Other nitrogen-protecting groups include, but are not limited to, phenothiazinyl-(10)-acyl derivative, N'-p-toluenesulfonylaminoacyl derivative, N'-phenylaminothioacyl derivative, N-benzoylphenylalanyl derivative, N-acetylmethionine derivative, 4,5-diphenyl-3-oxazolin-2-one, N-phthalimide, N-dithiasuccinimide (Dts), N-2,3-diphenylmaleimide, N-2,5-dimethylpyrrole, N-1,1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridone, N-methylamine, N-allylamine, N-[2-(trimethylsilyl)ethoxy]methylamine (SEM), N-3-acetoxypropylamine, N-(1-isopropyl-4-nitro-2-oxo-3-pyroolin-3-yl)amine, quaternary ammonium salts, N-benzylamine, N-di(4-methoxyphenyl)methylamine, N-5-dibenzosuberylamine, N-triphenylmethylamine (Tr), N-[(4-methoxyphenyl)diphenylmethyl]amine (MMTr), N-9-phenylfluorenylamine (PhF), N-2,7-dichloro-9-fluorenylmethyleneamine, N-ferrocenylmethylamino (Fcm), N-2-picolylamino N'-oxide, N-1,1-dimethylthiomethyleneamine, N-benzylideneamine, N-p-methoxybenzylideneamine, N-diphenylmethyleneamine, N-[(2-pyridyl)mesityl]methyleneamine, N—(N',N'-dimethylaminomethylene)amine, N,N'-isopropylidenediamine, N-p-nitrobenzylideneamine, N-salicylideneamine, N-5-chlorosalicylideneamine, N-(5-chloro-2-hydroxyphenyl)phenylmethyleneamine, N-cyclohexylideneamine, N-(5,5-dimethyl-3-oxo-1-cyclohexenyl)amine, N-borane derivative, N-diphenylborinic acid derivative, N-[phenyl(pentaacylchromium- or tungsten)acyl]amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfenamide, 2-nitro-4-methoxybenzenesulfenamide, triphenylmethylsulfenamide, and 3-nitropyridinesulfenamide (Npys).

As used herein, the term "determining" generally refers to the analysis of a species or signal, for example, quantitatively or qualitatively, and/or the detection of the presence or absence of the species or signals.

The term "diagnostic imaging," as used herein, refers to a procedure used to detect an imaging agent.

The term "diagnosis" as used herein encompasses identification, confirmation, and/or characterization of a condition, a disease, and/or a disorder.

A "diagnostic kit" or "kit" comprises a collection of components, termed the formulation, in one or more vials which are used by the practicing end user in a clinical or pharmacy setting to synthesize diagnostic radiopharmaceuticals. For example, the kit may be used by the practicing end user in a clinical or pharmacy setting to synthesize and/or use diagnostic radiopharmaceuticals. In some embodiments, the kit may provide all the requisite components to synthesize and use the diagnostic pharmaceutical except those that are commonly available to the practicing end user, such as water or saline for injection and/or the radioisotope (e.g., $^{18}F$). equipment for processing the kit during the synthesis and manipulation of the radiopharmaceutical, if required, equipment necessary for administering the radiopharmaceutical to the subject such as syringes, shielding, imaging equipment, and the like. In some embodiments, imaging agents may be provided to the end user in their final form in a formulation contained typically in one vial or syringe, as either a lyophilized solid or an aqueous solution.

As used herein, a "portion of a subject" refers to a particular region of a subject, location of the subject. For example, a portion of a subject may be the brain, heart, vasculature, cardiac vessels, tumor, etc., of a subject.

As used herein a "session" of testing may be a single testing protocol that a subject undergoes.

As used herein, the term "subject" refers to a human or non-human mammal or animal. Non-human mammals include livestock animals, companion animals, laboratory animals, and non-human primates. Non-human subjects also specifically include, without limitation, horses, cows, pigs, goats, dogs, cats, mice, rats, guinea pigs, gerbils, hamsters, mink, and rabbits. In some embodiments of the invention, a subject is referred to as a "patient." In some embodiments, a patient or subject may be under the care of a physician or other health care worker, including, but not limited to, someone who has consulted with, received advice from or received a prescription or other recommendation from a physician or other health care worker.

The term "perfusion" is given its ordinary meaning in the art and refers to the flow of blood to a muscle or a tissue. The term "cardiac perfusion" refers to the flow of blood to the heart. The term "innervation" is given its ordinary meaning in the art and refers to the supply of nervous energy or of nerve stimulus sent to a portion of a subject. The term "cardiac innervation" refers to the supply of nervous energy or of nerve stimulus sent to the heart of a subject.

Any of the compounds described herein may be in a variety of forms, such as, but not limited to, salts, solvates, hydrates, tautomers, and isomers.

In certain embodiments, the imaging agent is a pharmaceutically acceptable salt of the imaging agent. The term "pharmaceutically acceptable salt" as used herein refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, Berge et al., describe pharmaceutically acceptable salts in detail in *J. Pharmaceutical Sciences,* 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and $N^+(C_{1-4}alkyl)_4$ salts. Representative alkali or alkaline earth metal salts include sodium, lithium, potassium, calcium, magnesium, and the like. Further pharmaceutically acceptable salts include, when appropriate, non-toxic ammonium, quaternary ammonium, and amine cations formed using counter ions such as halide, hydroxide, carboxylate, sulfate, phosphate, nitrate, loweralkyl sulfonate and aryl sulfonate.

In certain embodiments, the compound is in the form of a hydrate or solvate. The term "hydrate" as used herein refers to a compound noncovalently associated with one or more molecules of water. Likewise, the term "solvate" refers to a compound noncovalently associated with one or more molecules of an organic solvent.

In certain embodiments, the compound described herein may exist in various tautomeric forms. The term "tautomer" as used herein includes two or more interconvertible compounds resulting from at least one formal migration of a hydrogen atom and at least one change in valency (e.g., a single bond to a double bond, a triple bond to a single bond, or vice versa). The exact ratio of the tautomers depends on several factors, including temperature, solvent, and pH. Tautomerizations (i.e., the reaction providing a tautomeric pair) may be catalyzed by acid or base. Exemplary tautomerizations include keto-to-enol; amide-to-imide; lactam-to-lactim; enamine-to-imine; and enamine-to-(a different) enamine tautomerizations.

In certain embodiments, the compounds described herein may exist in various isomeric forms. The term "isomer" as used herein includes any and all geometric isomers and stereoisomers (e.g., enantiomers, diasteromers, etc.). For example, "isomer" includes cis- and trans-isomers, E- and Z-isomers, R- and S-enantiomers, diastereomers, (D)-isomers, (L)-isomers, racemic mixtures thereof, and other mixtures thereof, as falling within the scope of the invention. For instance, an isomer/enantiomer may, in some embodiments, be provided substantially free of the corresponding enantiomer, and may also be referred to as "optically enriched." "Optically-enriched," as used herein, means that the compound is made up of a significantly greater proportion of one enantiomer. In certain embodiments the compound of the present invention is made up of at least about 90% by weight of a preferred enantiomer. In other embodiments the compound is made up of at least about 95%, 98%, or 99% by weight of a preferred enantiomer. Preferred enantiomers may be isolated from racemic mixtures by any method known to those skilled in the art, including chiral high pressure liquid chromatography (HPLC) and the formation and crystallization of chiral salts or prepared by asymmetric syntheses. See, for example, Jacques, et al., *Enantiomers, Racemates and Resolutions* (Wiley Interscience, New York, 1981); Wilen, S. H., et al., *Tetrahedron* 33:2725 (1977); Eliel, E. L. *Stereochemistry of Carbon Compounds* (McGraw-Hill, NY, 1962); Wilen, S. H. *Tables of Resolving Agents and Optical Resolutions* p. 268 (E. L. Eliel, Ed., Univ. of Notre Dame Press, Notre Dame, Ind. 1972).

These and other aspects of the present invention will be further appreciated upon consideration of the following Examples, which are intended to illustrate certain particular embodiments of the invention but are not intended to limit its scope, as defined by the claims.

EXAMPLES

The following examples related to the compounds shown in FIG. 1 or salts thereof. For example, Example 1 provides the synthesis of the compound of Example 1 shown in FIG. 1.

Example 1

4-(4-(2-fluoroethoxy)phenyl)imidazolidin-2-imine

Part 1A—Preparation of tert-butyl [(Z)-[(tert-butoxycarbonyl)amino]{[2-hydroxy-2-(4-hydroxyphenyl)ethyl]amino}methylidene]carbamate

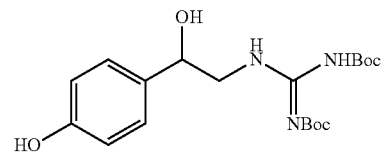

4-(2-Amino-1-hydroxyethyl)phenol hydrochloride (0.493 g, 2.6 mmol), was dissolved in dry DMF (10.0 mL) then successively treated with N,N-diisopropylethylamine (645 µL, 3.6 mmol) and N,N'-di-Boc-1H-pyrazole-1-carboxamidine (1.15 g, 3.7 mmol), and the resulting solution stirred 1 h at ambient temperature. All volatiles were then removed in vacuo and the residue dissolved in EtOAc with transfer to a separatory funnel. The EtOAc solution was exhaustively washed with dilute aqueous solutions of $KHSO_4$ and $Na_2CO_3$ then dried over $Na_2SO_4$, filtered and concentrated in vacuo. Purification by chromatography on silica using a step gradient from 7:3 hexanes/EtOAc to 1:1 hexanes/EtOAc afforded the title compound as a white solid (0.837 g, 2.12 mmol; 81.4%).

Part 1B—Preparation of tert-butyl [(Z)-[(tert-butoxycarbonyl)amino] ({2-[4-(2-fluoroethoxy)phenyl]-2-hydroxyethyl}amino)methylidene]carbamate

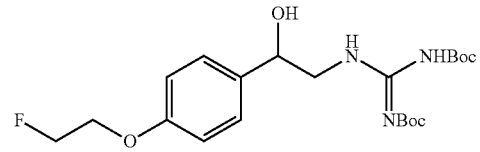

The product of Part 1A (0.312 g, 0.790 mmol) was dissolved in dry DMSO (2.00 mL) then successively treated with $K_2CO_3$ (0.164 g, 1.19 mmol), KI (1.16 mg, 0.007 mmol) and 1-bromo-2-fluoroethane (89.0 µL, 1.19 mmol) at ambient temperature. The resulting suspension was warmed to 50° C. and maintained 3 h. After cooling to ambient temperature, the solution was partitioned between EtOAc and H₂O (15 mL each) with transfer to a separatory funnel. The layers separated and the EtOAc layer washed with saturated aqueous NaCl, dried over Na₂SO₄, filtered and concentrated in vacuo. Purification by chromatography on silica using 9:1 hexanes/EtOAc afforded the title compound as a white solid (0.178 g, 0.403 mmol; 51.0%).

Part 1C—Preparation of 4-(4-(2-fluoroethoxy)phenyl)imidazolidin-2-imine, hydrochloric acid salt

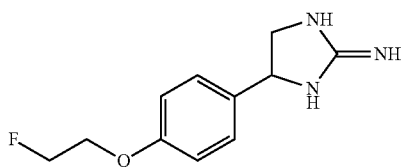 [SMILES: N=C1NCC(c2ccc(OCCF)cc2)N1]

The product of Part 1B (88.3 mg, 0.20 mmol) was dissolved in a solution of Et₃SiH/H₂O/CF₃CO₂H (0.5:0.5/19 v/v/v; 2.0 mL) at ambient temperature then warmed to 55° C. and maintained 10 min. The resulting solution was cooled, concentrated in vacuo then directly purified by HPLC on a Phenomenex Luna C18 column (21.2×250 mm) using a 0.8%/min gradient from 0-20% MeCN containing 0.1% HCO₂H and 10% H₂O at 20 mL/min. The main product peak eluting at 17 min was collected, pooled then lyophilized to a hygroscopic white powder. The solids were re-dissolved in 0.5 N HCl and lyophilized to afford the title compound as a white powder (14.2 mg, 0.055 mmol; 27.3%).

Part 1D—Preparation of Preparation of [¹⁸F]Fluoride

[¹⁸F]Fluoride was produced by proton bombardment of [¹⁸O]H₂O in a cyclotron; the nuclear chemical transformation is shown below and may be summarized as ¹⁸O(p,n)¹⁸F. For purposes of the bombardment, the chemical form of the ¹⁸O is H₂¹⁸O. The chemical form of the resulting ¹⁸F is fluoride ion.

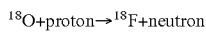

According to established industry procedures, [¹⁸O]H₂O (2-3 mL) housed within a tantalum target body using Havar® foil, was bombarded with 11 MeV protons (nominal energy); where the proton threshold energy for the reaction is 2.57 MeV and the energy of maximum cross section is 5 MeV. Target volume, bombardment time and proton energy each may be adjusted to manage the quantity of [¹⁸F]fluoride produced.

Part 1E—Preparation of 2-[¹⁸F]fluoroethyl 4-methylbenzenesulfonate

An MP1 anion exchange cartridge containing 1,000 mCi of [¹⁸F]NaF (produced according to the general procedure described in Part 1D) was eluted with 0.20% aqueous K₂CO₃ (1.0 mL), using an automated liquid handling system, into a 25 mL conical-bottomed silanized flask. All volatiles were removed by applying a gentle stream of warm Ar and applied vacuum. The contents of the flask were reconstituted with 0.5 mL of MeCN, and concentrated again using warm Ar and applied vacuum (azeotropic evaporation). A separate 5 mL conical-bottomed Wheaton™ vial was used to prepared a solution of 4,7,13,16,21,24-hexaoxa-1,10-diazabicyclo[8.8.8]hexacosane (22.5 mg) and ethylene di-(p-toluenesulfonate) (3.8 mg) in MeCN (1.0 mL). The constituents of the vial were transferred to the 25 mL flask containing [¹⁸F]KF then positioned inside a microwave cavity (model 520 Resonance Instruments, Skokie, Ill.) and irradiated for 3 min at 75 watts. After cooling, the contents of the microwave reaction vial were filtered through an anion exchange resin to remove residual fluoride ion, collected in a 5 mL conical-bottomed Wheaton™ reaction vial and used without further purification in the subsequent reaction.

Part 1F—Preparation of 4-{4-[2-(¹⁸F)fluoroethoxy] phenyl}imidazolidin-2-imine, formic acid salt

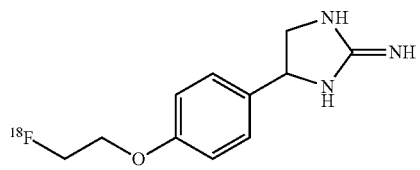 [SMILES: N=C1NCC(c2ccc(OCC[18F])cc2)N1]

The product of Part 1E was transferred to a 5 mL conical-bottomed Wheaton™ reaction vial containing the product of Part 1A (4.0 mg), K₂CO₃ (10.9 mg) and anhydrous DMSO (400 µL). The resulting mixture was heated at 80° C. for 30 min then cooled to ambient temperature then transferred to a clean 25 mL pear-shaped flask and diluted with H₂O (18.5 mL). The contents of the pear shaped flask were passed through a Sep Pak™ C18 cartridge and the cartridge was rinsed with H₂O (5.0 mL). The desired product was eluted from the cartridge with MeCN (3.0 mL) into a 5 mL conical-bottomed Wheaton™ vial. All volatiles were removed, and the residue treated with a solution of trifluoroacetic acid in CH₂Cl₂ (1:1 v/v, 2.0 mL). The resulting solution was warmed to 50° C., maintained 15 min then cooled to ambient temperature and concentrated to dryness. Purification by HPLC on a Phenomenex Luna C18(2) column (10×250 mm, 5 micron particle size, 100 Angstrom pore size) using a 5.0%/min gradient of 0-100% MeCN containing 0.1% HCO₂H acid at a flow rate of 2.0 mL/min. The title compound was collected, all volatiles removed, and the residue reconstituted with 10% aqueous ethanol solution for biological experiments.

Example 2

4-(3-bromo-4-(2-fluoroethoxy)phenyl)imidazolidin-2-imine, hydrochloric acid salt

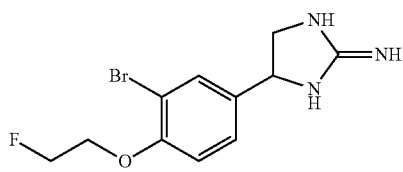 [SMILES: N=C1NCC(c2ccc(OCCF)c(Br)c2)N1]

Part 2A—Preparation of tert-butyl [(Z)-[(tert-butoxycarbonyl)amino]{[2-hydroxy-2-(3-bromo-4-hydroxyphenyl)ethyl]amino}methylidene]carbamate

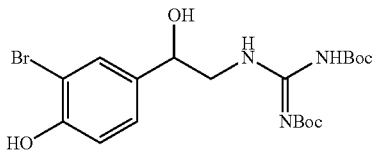

The product of Part 1A (1.75 g, 4.43 mmol), was dissolved $H_2O$/MeCN (3:2 v/v, 75.0 mL) then successively treated with $NaBrO_3$ (0.735 g, 4.87 mmol) and $NaHSO_3$ (0.507 g, 4.87 mmol) and the resulting solution stirred 40 min at ambient temperature. Additional $NaBrO_3$ (1.13 g, 7.5 mmol) and $NaHSO_3$ (0.780 g, 7.5 mmol) and the resulting solution stirred 3 h. Excess $NaBrO_3$ was then consumed by the addition of $Na_2S_2O_3$ (2.1 g, 13.3 mmol). After 30 min, the MeCN was removed in vacuo and the aqueous solution washed with $CH_2Cl_2$. The $CH_2Cl_2$ was further washed with saturated aqueous NaCl, then dried over $Na_2SO_4$, filtered and concentrated in vacuo. The residue was purified by chromatography on silica using a hexanes/EtOAc gradient to afford the title compound as a white solid (0.635 g, 1.34 mmol; 30.2%).

Part 2B—Preparation of tert-butyl [(Z)-[(tert-butoxycarbonyl)amino]({2-[3-bromo-4-(2-fluoroethoxy)phenyl]-2-hydroxyethyl}amino)methylidene]carbamate

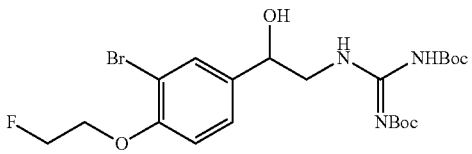

The product of Part 2A (0.306 g, 0.645 mmol) was dissolved in dry DMSO (3.00 mL) then successively treated with $K_2CO_3$ (0.134 g, 0.968 mmol), KI (single crystal) and 1-bromo-2-fluoroethane (48 μL, 0.645 mmol) at ambient temperature. The resulting suspension was warmed to 50° C. and maintained 1.5 h. After cooling to ambient temperature, the solution was partitioned between EtOAc and $H_2O$ with transfer to a reparatory funnel. The layers separated and the EtOAc layer washed with $H_2O$ followed by saturated aqueous NaCl then dried over $Na_2SO_4$, filtered and concentrated in vacuo. Purification by chromatography on silica using a hexanes/EtOAc gradient afforded the title compound as a white solid (0.218 g, 0.419 mmol; 64.9%).

Part 2C—Preparation of 4-(3-bromo-4-(2-fluoroethoxy)phenyl)imidazolidin-2-imine, hydrochloric acid salt

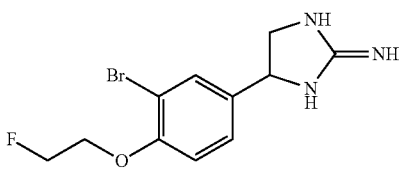 [SMILES: N=C1NCC(c2ccc(OCCF)c(Br)c2)N1]

The product of Part 2B (90.0 mg, 0.173 mmol) was dissolved in aqueous $CF_3CO_2H$ (1:40 v/v; 2.0 mL) at ambient temperature then warmed to 55° C. and maintained 15 min. The resulting solution was cooled, concentrated in vacuo then directly purified by HPLC on a Phenomenex Luna C18 column (21.2×250 mm) using a 0.6%/min gradient from 5-23% MeCN containing 0.1% $HCO_2H$ and 10% $H_2O$ at 20 mL/min. The main product peak eluting at 2 min was collected, pooled then lyophilized to a hygroscopic white powder. The solids were re-dissolved in 0.5 N HCl and lyophilized to afford the title compound as a white powder (18.6 mg, 0.055 mmol; 31.7%).

Part 2D—Preparation of 4-{4-[2-($^{18}$F)fluoroethoxy]phenyl}imidazolidin-2-imine, formic acid salt

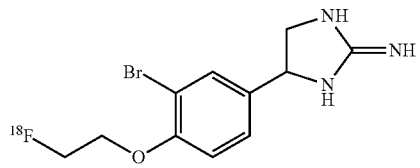 [SMILES: N=C1NCC(c2ccc(OCC[18F])c(Br)c2)N1]

The product of Part 1E was transferred to a 5 mL conical-bottomed Wheaton™ reaction vial containing the product of Part 2A (4.0 mg), $K_2CO_3$ (10.9 mg) and anhydrous DMSO (400 μL). The resulting mixture was heated at 80° C. for 30 min then cooled to ambient temperature then transferred to a clean 25 mL pear-shaped flask and diluted with $H_2O$ (18.5 mL). The contents of the pear shaped flask were passed through a Sep Pak™ C18 cartridge and the cartridge was rinsed with $H_2O$ (5.0 mL). The desired product was eluted from the cartridge with MeCN (3.0 mL) into a 5 mL conical-bottomed Wheaton™ vial. All volatiles were removed, and the residue treated with a solution of trifluoroacetic acid in $CH_2Cl_2$ (1:1 v/v, 2.0 mL). The resulting solution was warmed to 50° C., maintained 15 min then cooled to ambient temperature and concentrated to dryness. Purification by HPLC on a Phenomenex Luna C18(2) column (10×250 mm, 5 micron particle size, 100 Angstrom pore size) using a 5.0%/min gradient of 0-100% EtOH containing 0.1% $HCO_2H$ acid at a flow rate of 2.0 mL/min. The title compound was collected, all volatiles removed, and the residue reconstituted with 10% aqueous ethanol solution for biological experiments.

Example 3

1-(3-bromo-4-(fluoromethyl)benzyl)guanidine

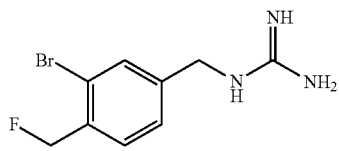 [SMILES: N=C(N)NCc1ccc(CF)c(Br)c1]

Part 3A—Preparation of 3-bromo-4-(dibromomethyl)benzonitrile

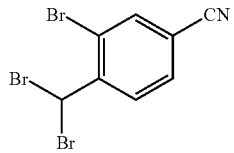

A solution of 3-bromo-4-methyl-benzonitrile (5.00 g, 25.5 mmol) was dissolved in $CCl_4$ (170 mL) and successively treated with NBS (18.2 g, 102 mmol) and benzoyl peroxide (0618 g, 2.55 mmol) at ambient temperature. The resulting solution was warmed to reflux, maintained 48 h then cooled to ambient temperature and filtered through a sintered glass funnel of medium porosity. The filtrate was concentrated, and the crude orange solid thus obtained purified by chromatography on silica using 49:1 hexanes/EtOAc to afford the title compound as a white solid (8.80 g, 24.9 mmol; 97.5%).

Part 3B—Preparation of 3-bromo-4-formylbenzonitrile

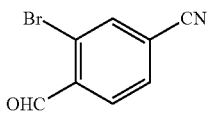 [SMILES: N#Cc1ccc(C=O)c(Br)c1]

A solution of the product of Part 3A (8.80 g, 24.9 mmol) was dissolved in wet DMSO (83 mL) at ambient temperature then warmed to 120° C. and maintained 6 h. After cooling to ambient temperature, the resulting solution was diluted with H$_2$O with transfer to a separatory funnel then washed EtOAc. The EtOAc solution was separated, washed with H$_2$O and saturated aqueous NaCl then dried over Na$_2$SO$_4$, filtered and concentrated in vacuo to a yellow solid. Subsequent purification by chromatography on silica using 20:1 hexanes/EtOAc afforded the title compound as a white solid (3.10 g, 14.8 mmol; 59.3%).

Part 3C—Preparation of 3-bromo-4-(hydroxymethyl)benzonitrile

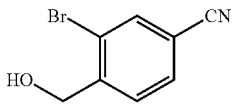

A solution of the product of Part 3B (3.10 g, 14.7 mmol) was dissolved MeOH (74 mL) at ambient temperature then cooled to 0° C. using an ice bath. NaBH$_4$ (0.279 g, 7.38 mmol) was then added in one portion and the resulting solution maintained 40 min at 0° C. Dilute aqueous HCl was added to consume excess NaBH$_4$ then all volatiles removed in vacuo. The residue was redissolved in EtOAc with transfer to a separatory funnel, successively washed with 5% aqueous citric acid and H$_2$O, then dried over Na$_2$SO$_4$, filtered and concentrated in vacuo. Purification by chromatography on silica using a step gradient from 9:1 hexanes/EtOAc to 1:1 hexanes/EtOAc afforded the title compound as a white solid (1.90 g, 8.96 mmol; 60.7%).

Part 3D—Preparation of [4-(aminomethyl)-2-bromophenyl]methanol

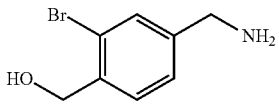 [SMILES: NCc1ccc(CO)c(Br)c1]

LiAlH$_4$ (34.0 mmol; 34.0 mL of a 1.0 M solution in THF) was cooled to 0° C. using an ice bath then treated with MeOH (102 mmol; 26.4 mL of a 3.86 M solution in THF) dropwise over 5 min. The product of Part 3C (0.900 g, 4.24 mmol) was then added and the resulting solution warmed slowly to ambient temperature as the ice bath melted. After 16 h total reaction time, the solution was diluted with H$_2$O (9.0 mL) and the resulting suspension filtered through a sintered glass funnel of medium porosity. The solids were exhaustively washed with H$_2$O and Et$_2$O then transferred to a reparatory funnel and split. The aqueous layer was further washed with Et$_2$O and EtOAc and the combined organic layers dried over Na$_2$SO$_4$, filtered and concentrated in vacuo to a yellow solid (0.591 g), which was used without further purification in the subsequent reaction.

Part 3E—Preparation of tert-but-2-yl [(Z)-{[3-bromo-4-(hydroxymethyl)benzyl]-amino}{[(tert-but-2-yloxy)carbonyl]amino}methylidene]carbamate

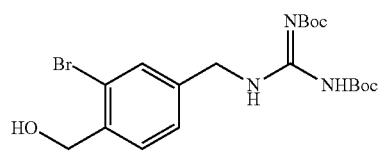

A solution of the product of Part 3D (0.585 g, 2.71 mmol) was dissolved MeCN (9.00 mL) at ambient temperature then treated with N,N'-di-Boc-1H-pyrazole-1-carboxamidine (1.00 g, 3.25 mmol) in one portion at ambient temperature. After 30 min, all volatiles were removed in vacuo and the residue purified by chromatography on silica using 5:1 hexanes/EtOAc to afford the title compound as a white foam (0.860 g, 1.88 mmol; 69.2%).

Part 3F—Preparation of 1-[3-bromo-4-(fluoromethyl)benzyl]guanidine, trifluoroacetic acid salt

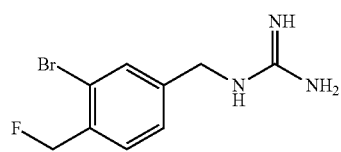 [SMILES: N=C(N)NCc1ccc(CF)c(Br)c1]

Deoxo-Fluor® (0.240 mmol; 103 µL of a 50% solution in THF) was diluted with CH$_2$Cl$_2$ (137 µL) then cooled to −78° C. and treated with a solution of the product of Part 3E (0.218 mmol; 218 µL of a 1.0 M solution in CH$_2$Cl$_2$) dropwise over 5 min. After 2 h, additional Deoxo-Fluor® (0.044 mmol; 19 µL) was added, the resulting solution stirred 1 h at −78° C. then treated with saturated aqueous NaHCO$_3$ (273 µL) before warming to ambient temperature. The layers were then separated and the aqueous layer washed with CH$_2$Cl$_2$ (2×164 µL). The combined organic layers were dried over Na$_2$SO$_4$, filtered, concentrated in vacuo then redissolved in dioxane (200 µL) and treated with concentrated HCl (600 µL) at ambient temperature. After 1 h, all volatiles were removed and the residue purified by HPLC on a Phenomenex Luna C18 column (21.2×250 mm) using a 2%/min gradient from 0-60% MeCN containing 0.1% CF$_3$CO$_2$H and 10% H$_2$O at 20 mL/min. The main product peak was collected, pooled and lyophilized to a white solid (14 mg, 37 mmol; 17%).

221

Part 3G—Preparation of tert-but-2-yl [(Z)-{[3-bromo-4-(bromomethyl)benzyl]-amino}{[(tert-but-2-yl oxy)carbonyl]amino}methylidene]carbamate

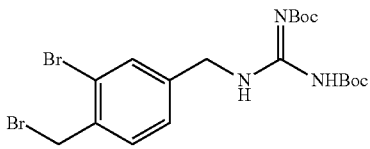

A solution of the product of Part 3E (75.0 mg, 0.164 mmol) was dissolved dry $CH_2Cl_2$ (2.00 mL) then successively treated with $CBr_4$ (109 mg, 0.327 mmol) and $PPh_3$ (85.8 mg, 0.327 mmol) at ambient temperature; within 2 h, complete conversion to the expected product was observed. All volatiles were then removed in vacuo and the residue purified by chromatography on silica using hexanes/EtOAc to afford the title compound as a white solid that was used without further purification in the subsequent fluorination reaction.

Part 3H—Preparation of 1-{3-bromo-4-[[$^{18}$F]fluoromethyl]benzyl}guanidine, formic acid salt

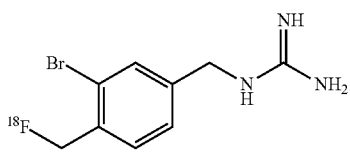 [SMILES: N=C(N)NCc1ccc(C[18F])c(Br)c1]

An MP1 anion exchange cartridge containing 1,000 mCi of [$^{18}$F]NaF (produced according to the general procedure described in Part 1D) was eluted with 0.20% aqueous $K_2CO_3$ (1.0 mL), using an automated liquid handling system, into a 25 mL conical-bottomed silanized flask. All volatiles were removed by applying a gentle stream of warm Ar and applied vacuum. The contents of the flask were reconstituted with 0.5 mL of MeCN, and concentrated again using warm Ar and applied vacuum (azeotropic evaporation). The residue was treated with a solution of 4,7,13,16,21,24-hexaoxa-1,10-diazabicyclo[8.8.8]hexacosane (19.7 mg) in MeCN (0.90 mL) then transferred to a solution of the product of Part 3G (3.8 mg) in dry MeCN (0.40 mL). The resulting solution was heated to 49° C., maintained 45 min then cooled to ambient temperature and concentrated. The residue thus obtained was redissolved in $CH_2Cl_2$ (0.40 mL) then treated with $CF_3CO_2H$ (1.00 mL) at ambient temperature. After 30 min, all volatiles were removed and the residue purified by HPLC on a Phenomenex Luna C18(2) column (250×10 mm, 5 micron particle size, 100 Angstrom pore size) using a 5.0%/min gradient of 0-100% MeCN containing 0.1% $HCO_2H$ acid at a flow rate of 2.0 mL/min. The title compound was collected, all volatiles removed, and the residue reconstituted with 10% aqueous ethanol solution for biological experiments.

222

Example 4

1-(3-bromo-4-((2-fluoro ethoxy)methyl)benzyl) guanidine

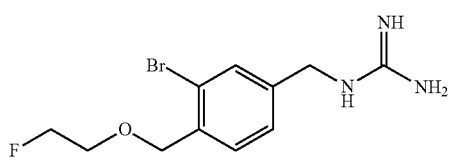 [SMILES: N=C(N)NCc1ccc(COCCF)c(Br)c1]

Part 4A—Preparation of 1-{3-bromo-4-[(2-fluoroethoxy)methyl]benzyl}guanidine, trifluoroacetic acid salt

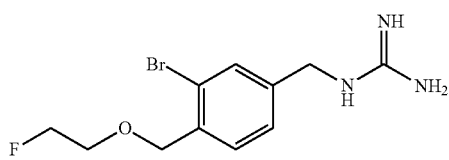 [SMILES: N=C(N)NCc1ccc(COCCF)c(Br)c1]

The product of Part 3E (0.100 g, 0.218 mmol) was dissolved in wet DMSO (2.20 mL) then treated with powdered NaOH (17.0 mg, 0.436 mmol) at ambient temperature. After 30 min, 2-fluoroethyl 4-methylbenzenesulfonate (48.0 mg, 0.218 mmol) was added in one portion and the resulting solution warmed to 75° C. and maintained 80 min. After cooling to ambient temperature, the solution was diluted with $H_2O$, with transfer to a reparatory funnel then exhaustively washed with EtOAc. The combined EtOAc washes were further washed with 5% aqueous citric acid then dired over Na2SO4, filtered and concentrated in vacuo. The crude residue was redissolved in dioxane (200 μL) then treated with concentrated HCl (600 μL) at ambient temperature. After 1 h, all volatiles were removed and the residue purified by HPLC on a Phenomenex Luna C18 column (21.2×250 mm) using a 2%/min gradient from 0-30% MeCN containing 0.1% $CF_3CO_2H$ and 10% $H_2O$ at 20 mL/min. The main product peak was collected, pooled and lyophilized to a white solid (10.7 mg, 25.6 μmol; 11.7%).

Part 4B—Preparation of 1-{3-bromo-4-[(2-[$^{18}$F] fluoroethoxy)methyl]benzyl}guanidine, trifluoroacetic acid salt

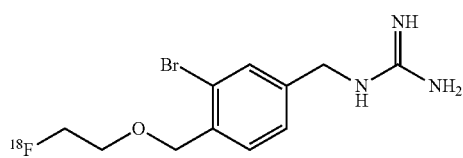 [SMILES: N=C(N)NCc1ccc(COCC[18F])c(Br)c1]

The product of Part 1E was transferred to a 5 mL conical-bottomed Wheaton™ reaction vial containing the product of Part 3E (4.0 mg), KOH (1.6 mg) and anhydrous DMSO (400 mL). The resulting mixture was heated at 80° C. for 45 min, cooled to ambient temperature, concentrated in vacuo then treated with $CF_3CO_2H$ (1.00 mL) and warmed to 50° C. After 15 min, the resulting mixture was cooled to ambient temperature, concentrated to dryness then purified by HPLC on a Phenomenex Luna C18(2) column (10×250 mm, 5 micron particle size, 100 Angstrom pore size) using a 5.0%/min gradient of 0-100% MeCN containing 0.1% HCO$_2$H acid at a flow rate of 2.0 mL/min. The title compound was collected, all volatiles removed, and the residue reconstituted with 10% aqueous ethanol solution for biological experiments.

Example 5

1-[4-(2-fluoroethyl)benzyl]guanidine

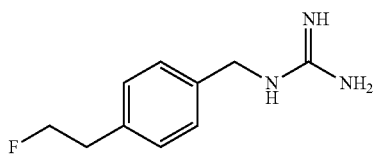 [SMILES: N=C(N)NCc1ccc(CCF)cc1]

Part 5A—Preparation of
4-(2-fluoroethyl)benzonitrile

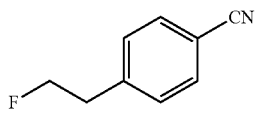

Deoxo-Fluor® (0.843 g, 3.81 mmol) was dissolved in CH$_2$Cl$_2$ (0.50 mL) then cooled to −78° C. and treated with a solution of 4-(2-hydroxyethyl)benzonitrile (3.47 mmol; 1.50 mL of a 2.31 M solution in CH$_2$Cl$_2$) dropwise over 5 min. The resulting mixture warmed slowly to ambient temperature as the cooling bath evaporated overnight. Saturated aqueous NaHCO$_3$ (50 mL) was then added with transfer to a reparatory funnel and the layers separated. The aqueous layer washed with CH$_2$Cl$_2$ (3×25 mL) and the combined organic layers dried over MgSO$_4$, filtered and concentrated in vacuo. Subsequent purification by chromatography on silica using 4:1 hexanes/EtOAc afforded the title compound as a pale yellow oil (0.305 g, 2.04 mmol; 59.0%).

Part 5B—Preparation of
1-[4-(2-fluoroethyl)phenyl]methenamine

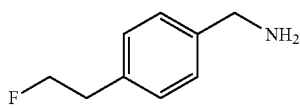 [SMILES: NCc1ccc(CCF)cc1]

The product of Part 5A (0.210 g, 1.41 mmol) was dissolved in MeOH (13.0 mL) then successively treated with concentrated HCl (1.00 mL) and Pd/C (0.141 mmol; 10 mol %) at ambient temperature. The headspace of the reaction vessel was sparged with 1 atm H$_2$ then maintained 2 h. Upon complete reduction, the headspace was sparged with dry N$_2$ and the catalyst removed by filtration through Celite. The filter cake was exhaustively washed with MeOH and the combined filtrates concentrated in vacuo to a white powder. The crude material was used without further purification in the subsequent reaction.

Part 5C—Preparation of
4-(2-fluoroethyl)benzylguanidine, trifluoroacetic
acid salt

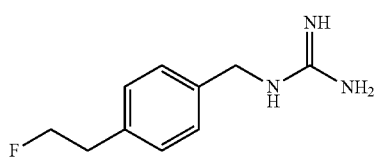 [SMILES: N=C(N)NCc1ccc(CCF)cc1]

The product of Part 5B (0.150 g, 0.791 mmol) was dissolved in MeCN (4.00 mL) and successively treated with N,N-diisopropylethylamine (152 mL, 0.867 mmol) and 1H-pyrazole-1-carboximidamide (0.128 g, 0.870 mmol) at ambient temperature. After 1 h, all volatiles were removed in vacuo and the residue purified by HPLC on a Phenomenex Luna C18 column (21.2×250 mm) using 1%/min gradient from 2-32% MeCN containing 0.1% CF$_3$CO$_2$H and 10% H$_2$O at 20 mL/min. The main product peak was collected, pooled and lyophilized to a white solid (0.189 g, 0.484 mmol; 61.2%).

Part 5D—Preparation of
2-[4-(aminomethyl)phenyl]ethanol

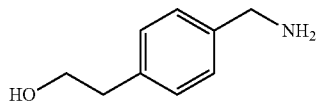 [SMILES: NCc1ccc(CCO)cc1]

4-(2-Hydroxyethyl)benzonitrile (0.402 g, 2.73 mmol) was dissolved in MeOH (10.0 mL) then successively treated with concentrated HCl (0.50 mL) and Pd/C (0.145 mmol; 5 mol %) at ambient temperature. The headspace of the reaction vessel was sparged with 1 atm H$_2$ then maintained 16 h. Upon complete reduction, the headspace was sparged with dry N$_2$ and the catalyst removed by filtration through Celite. The filter cake was exhaustively washed with MeOH and the combined filtrates concentrated in vacuo to a white powder. The crude material was used without further purification in the subsequent reaction.

Part 5E—Preparation of tert-butyl [(Z)-[(tert-butoxycarbonyl)amino]{[4-(2-hydroxyethyl)benzyl]amino}methylidene]carbamate

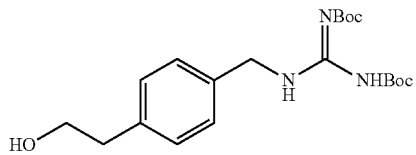

The product of Part 5D (0.553 g, 2.95 mmol) was dissolved in MeCN (5.00 mL) and successively treated with N,N-diisopropylethylamine (513 μL, 2.95 mmol) and N,N'-di-Boc-1H-pyrazole-1-carboxamidine (0.915 g, 2.95 mmol) at ambient temperature. After 2 h, all volatiles were removed in vacuo and the residue redissolved in CH₂Cl₂ (15 mL) with transfer to a separatory funnel. The CH₂Cl₂ solution was successively washed with 10% aqueous citric acid, H₂O and saturated aqueous NaCl (1×15 mL each) then dried over Na₂SO₄, filtered and concentrated in vacuo. Subsequent purification by chromatography on silica, using a hexanes/EtOAc gradient from 0-100% EtOAc over 17 min, afforded the title compound as a white solid (0.777 g, 1.97 mmol; 67.0%).

Part 5F—Preparation of 2-{4-[(N',N"-bis(tert-butoxycarbonyl)carbamimidamido)methyl]-phenyl}ethyl 4-methylbenzenesulfonate

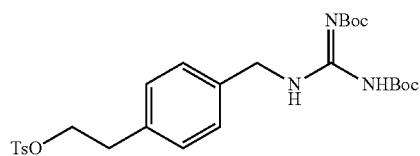

The product of Part 5E (0.363 g, 0.918 mmol) was dissolved in CH₂Cl₂ (4.00 mL) and successively treated with p-toluenesulfonyl chloride (0.264 g, 1.38 mmol) and pyridine (164 μL, 2.03 mmol) at 0° C. After 16 h, the resulting solution was diluted with CH₂Cl₂ (10 mL) with transfer to a separatory funnel. The CH₂Cl₂ solution was successively washed with 5% aqueous NaHCO₃, H₂O and saturated aqueous NaCl (1×15 mL each) then dried over Na₂SO₄, filtered and concentrated in vacuo. Subsequent purification by chromatography on silica, using a hexanes/EtOAc gradient from 0-100% EtOAc over 17 min, afforded the title compound as a white solid (0.393 g, 0.717 mmol; 77.8%).

Part 5G—Preparation of 1-{4-[2-[$^{18}$F]fluoroethyl]benzyl}guanidine, formic acid salt

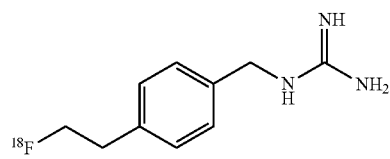 [SMILES: N=C(N)NCc1ccc(CC[18F])cc1]

An MP1 anion exchange cartridge containing 1,000 mCi of [$^{18}$F]NaF (produced according to the general procedure described in Part 1D) was eluted with 0.20% aqueous K₂CO₃ (1.0 mL), using an automated liquid handling system, into a 25 mL conical-bottomed silanized flask. All volatiles were removed by applying a gentle stream of warm Ar and applied vacuum. The contents of the flask were reconstituted with 0.5 mL of MeCN, and concentrated again using warm Ar and applied vacuum (azeotropic evaporation). The residue was treated with a solution of 4,7,13,16,21,24-hexaoxa-1,10-diazabicyclo[8.8.8]hexacosane (20.5 mg) in MeCN (0.90 mL) then transferred to a solution of the product of Part 5F (3.97 mg) in dry MeCN (0.40 mL). The resulting solution was heated to 60° C., maintained 45 min then cooled to ambient temperature and concentrated. The residue thus obtained was redissolved in CF₃CO₂H (1.00 mL), stirred 15 min at 4o ° C. then cooled and concentrated. Subsequent purification by HPLC on a Phenomenex Luna C18(2) column (250×10 mm, 5 micron particle size, 100 Angstrom pore size) using a 5.0%/min gradient of 0-100% MeCN containing 0.1% HCO₂H acid at a flow rate of 2.0 mL/min. The title compound was collected, all volatiles removed, and the residue reconstituted with 10% aqueous ethanol solution for biological experiments.

Example 8

1-(3-bromo-4-(2-fluoro ethyl)benzyl)guanidine

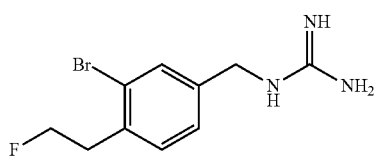 [SMILES: N=C(N)NCc1ccc(CCF)c(Br)c1]

Part 8A—Preparation of 3-bromo-4-(2-hydroxyethyl)benzonitrile

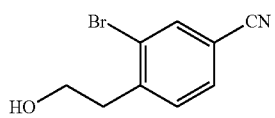 [SMILES: N#Cc1ccc(CCO)c(Br)c1]

4-(2-Hydroxyethyl)benzonitrile (1.22 g, 8.29 mmol) was dissolved in H₂O/H₂SO₄ (1:1 v/v, 8.00 mL) then treated with NBS (1.48 g, 8.32 mmol) in one portion at ambient temperature. The reaction vessel was then covered with aluminum foil and maintained 48 h. The resulting solution was transferred to a reparatory funnel, neutralized with 10% aqueous NaOH then washed with EtOAc (3×20 mL). The combined EtOAc washes were dried over Na₂SO₄, filtered and concentrated in vacuo. Subsequent purification by chromatography on silica using 3:1 hexanes/EtOAc afforded the title compound as a pale yellow oil (0.285 g, 1.26 mmol; 15.2%).

Part 8B—Preparation of 3-bromo-4-(2-fluoroethyl)benzonitrile

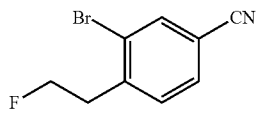 [SMILES: N#Cc1ccc(CCF)c(Br)c1]

Deoxo-Fluor® (0.291 g, 1.32 mmol) was dissolved in CH₂Cl₂ (2.00 mL) then cooled to −78° C. and treated with a solution of the product of Part 8A (0.270 g, 1.19 mmol) dropwise over 5 min. The resulting mixture warmed slowly to ambient temperature as the cooling bath evaporated overnight. Saturated aqueous NaHCO₃ (50 mL) was then added with transfer to a reparatory funnel and the layers separated. The aqueous layer washed with CH₂Cl₂ (3×25 mL) and the combined organic layers dried over MgSO₄, filtered and concentrated in vacuo. Subsequent purification by chromatography on silica using 3:1 hexanes/EtOAc afforded the title compound as a pale yellow oil (0.115 g, 0.504 mmol; 42.2%).

Part 8C—Preparation of
1-[3-bromo-4-(2-fluoroethyl)phenyl]methenamine

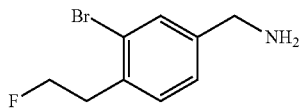 [SMILES: NCc1ccc(CCF)c(Br)c1]

LiAlH$_4$ (3.79 mmol; 3.79 mL of a 1.0 M solution in THF) was cooled to 0° C. using an ice bath then treated with MeOH (461 µL, 11.4 mmol) dropwise over 5 min.

The product of Part 8B (0.482 mmol; 3.00 mL of a 0.16 M solution in THF) was then added and the resulting solution warmed slowly to ambient temperature as the ice bath melted. After 6 h, excess LiAlH$_4$ was consumed by the careful addition of H$_2$O (0.50 mL). The resulting white suspension was successively treated with 15% aqueous NaOH (0.50 mL) and H$_2$O (1.50 mL) and stirred for 15 min to a fine white slurry. The resulting mixture was filtered through a pad of Celite and concentrated in vacuo. The crude material thus obtained was purified by chromatography on silica using 4:1 CH$_2$Cl$_2$/MeOH to afford the title compound as a pale yellow oil (11.0 mg, 0.047 mmol; 9.8%).

Part 8D—Preparation of
1-[3-bromo-4-(2-fluoroethyl)benzyl]guanidine,
trifluoroacetic acid salt

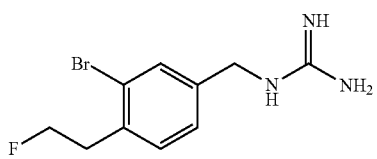 [SMILES: N=C(N)NCc1ccc(CCF)c(Br)c1]

The product of Part 8C (11.0 mg, 0.047 mmol) was dissolved in MeCN (2.00 mL) and successively treated with N,N-diisopropylethylamine (18.2 µL, 0.104 mmol) and 1H-pyrazole-1-carboximidamide (15.3 mg, 0.104 mmol) at ambient temperature. After 2 h, all volatiles were removed in vacuo and the residue purified by HPLC on a Phenomenex Luna C18 column (21.2×250 mm) using 1%/min gradient from 10-40% MeCN containing 0.1% CF$_3$CO$_2$H and 10% H$_2$O at 20 mL/min. The main product peak was collected, pooled and lyophilized to a white solid.

Part 8E—Preparation of
2-[4-(aminomethyl)-2-bromophenyl]ethanol

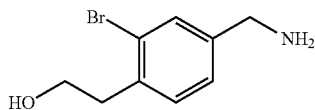 [SMILES: NCc1ccc(CCO)c(Br)c1]

LiAlH$_4$ (8.85 mmol; 8.85 mL of a 1.0 M solution in THF) was cooled to 0° C. using an ice bath then treated with MeOH (1.08 mL, 26.4 mmol) dropwise over 5 min. The product of Part 8A (1.11 mmol; 1.00 mL of a 1.11 M solution in THF) was then added and the resulting solution warmed slowly to ambient temperature as the ice bath melted. After 4.5 h, excess LiAlH$_4$ was consumed by the careful addition of H$_2$O (0.335 mL). The resulting white suspension was successively treated with 15% aqueous NaOH (0.335 mL) and H$_2$O (1.01 mL) and stirred for 15 min to a fine white slurry. The resulting mixture was filtered through a pad of Celite and the filter cake exhaustively washed with THF and MeOH (3×0.5 mL each). The combined filtrate was concentrated in vacuo to a pale yellow oil that was used without further purification in the subsequent reaction.

Part 8F—Preparation of tert-butyl [(Z)-[(tert-butoxycarbonyl)amino]{[3-bromo-4-(2-hydroxyethyl)benzyl]amino}methylidene]carbamate

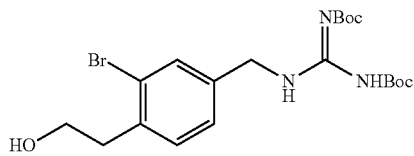

The product of Part 8E (0.162 g, 0.704 mmol) was dissolved in MeCN (1.00 mL) and successively treated with N,N-diisopropylethylamine (123 µL, 0.705 mmol) and N,N'-di-Boc-1H-pyrazole-1-carboxamidine (0.219 g, 0.705 mmol) at ambient temperature. After 0.5 h, all volatiles were removed in vacuo and the residue redissolved in CH$_2$Cl$_2$ (15 mL) with transfer to a separatory funnel. The CH$_2$Cl$_2$ solution was successively washed with 10% aqueous citric acid, H$_2$O and saturated aqueous NaCl (1×15 mL each) then dried over Na$_2$SO$_4$, filtered and concentrated in vacuo. Subsequent purification by chromatography on silica, using a hexanes/EtOAc gradient from 0-100% EtOAc over 17 min, afforded the title compound as a colorless oil (0.235 g, 0.497 mmol; 70.7%).

Part 8G—Preparation of 2-{3-bromo-4-[(N',N"-bis(tert-butoxycarbonyl)carbamimid-amido)methyl]phenyl}ethyl 4-methylbenzenesulfonate

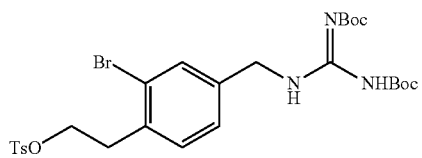

The product of Part 8F (0.220 g, 0.465 mmol) was dissolved in CH$_2$Cl$_2$ (2.00 mL) and successively treated with p-toluenesulfonyl chloride (0.133 g, 0.698 mmol) and pyridine (83 µL, 1.03 mmol) at 0° C. After 5 h, the resulting solution was diluted with CH$_2$Cl$_2$ (10 mL) with transfer to a separatory funnel. The CH$_2$Cl$_2$ solution was successively washed with 5% aqueous NaHCO$_3$, H$_2$O and saturated aqueous NaCl (1×15 mL each) then dried over Na$_2$SO$_4$, filtered and concentrated in vacuo. Subsequent purification by chromatography on silica, using a hexanes/EtOAc gradient from 0-100% EtOAc over 17 min, afforded the title compound as a white solid (0.183 g, 0.292 mmol; 62.7%).

Part 8H—Preparation of 1-{4-[3-bromo-2-[$^{18}$F] fluoroethyl]benzyl}guanidine, formic acid salt

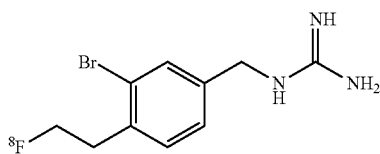

An MP1 anion exchange cartridge containing 1,000 mCi of [$^{18}$F]NaF (produced according to the general procedure described in Part 1D) was eluted with 0.20% aqueous K$_2$CO$_3$ (1.0 mL), using an automated liquid handling system, into a 25 mL conical-bottomed silanized flask. All volatiles were removed by applying a gentle stream of warm Ar and applied vacuum. The contents of the flask were reconstituted with 0.5 mL of MeCN, and concentrated again using warm Ar and applied vacuum (azeotropic evaporation). The residue was treated with a solution of 4,7,13,16,21,24-hexaoxa-1,10-diazabicyclo[8.8.8]hexacosane (21.7 mg) in MeCN (0.90 mL) then transferred to a solution of the product of Part 8G (5.00 mg) in dry DMSO (0.50 mL). The resulting solution was heated to 80° C., maintained 30 min then cooled to ambient temperature and concentrated. The residue thus obtained was redissolved in CF$_3$CO$_2$H (1.00 mL), stirred 15 min at 40° C. then cooled and concentrated. Subsequent purification by HPLC on a Phenomenex Luna C18(2) column (250×10 mm, 5 micron particle size, 100 Angstrom pore size) using a 5.0%/min gradient of 0-100% MeCN containing 0.1% HCO$_2$H acid at a flow rate of 2.0 mL/min. The title compound was collected at 14 min, all volatiles removed, and the residue reconstituted with 10% aqueous ethanol solution for biological experiments.

Example 11

1-((6-(2-fluoro ethoxy)naphthalen-2-yl)methyl) guanidine

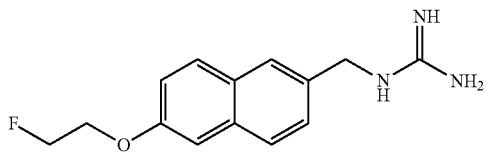 [SMILES: N=C(N)NCc1ccc2cc(OCCF)ccc2c1]

Part 11A—Preparation of 6-(2-fluoroethoxy)naphthalene-2-carbonitrile

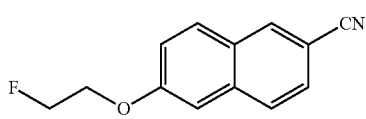 [SMILES: N#Cc1ccc2cc(OCCF)ccc2c1]

6-Hydroxynaphthalene-2-carbonitrile (2.00 g, 11.8 mmol) was dissolved in DMSO (36.0 mL) and successively treated with 1-bromo-2-fluoroethane (1.32 mL, 17.7 mmol) and K$_2$CO$_3$ (4.90 g, 35.5 mmol) at ambient temperature. The resulting suspension was stirred 16 h then filtered through a scintered glass funnel of medium porosity and treated with EtOAc (150 mL). The EtOAc solution was transferred to a separatory funnel where it was successively washed with H$_2$O (200 mL), 5 N NaOH (50 mL) and saturated aqueous NaCl then dried over MgSO$_4$, filtered and concentrated in vacuo to a pale yellow solid that was used without further purification in the subsequent reaction.

Part 11B—Preparation of 1-[6-(2-fluoroethoxy)naphthalen-2-yl]methanamine

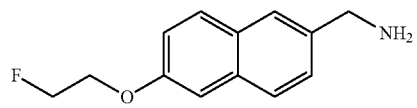 [SMILES: NCc1ccc2cc(OCCF)ccc2c1]

The product of Part 11A (0.750 g, 3.49 mmol) was dissolved in Et$_2$O/THF (1:1 v/v, 24.0 mL), cooled to 0° C. and treated with LiAlH$_4$ (0.463 g, 12.2 mmol) portionwise over 5 min. After 3 h, excess LiAlH$_4$ was consumed by the careful addition of H$_2$O (0.463 mL). The resulting white suspension was successively treated with 15% aqueous NaOH (0.463 mL) and H$_2$O (1.39 mL) and stirred for 15 min to a fine white slurry. The resulting mixture was filtered through a pad of Celite and the filtrate concentrated in vacuo to a pale yellow solid that was used without further purification in the subsequent reaction.

Part 11C—Preparation of tert-butyl [(Z)-[(tert-butoxycarbonyl)amino]{[6-(2-fluoroethoxy)naphthalen-2-yl]amino}methylidene]carbamate

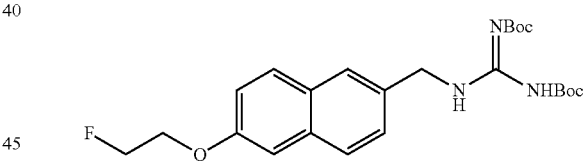

The product of Part 11B (0.500 g, 2.28 mmol) was dissolved in MeOH (25.0 mL) and successively treated with N,N'-di-Boc-1H-pyrazole-1-carboxamidine (0.849 g, 2.74 mmol) at ambient temperature. After 2 h, all volatiles were removed in vacuo and the residue purified by chromatography on silica to afford the title compound as a white solid.

Part 11D—Preparation of 1-{[6-(2-fluoroethoxy) naphthalen-2-yl]methyl}guanidine, hydrochloric acid salt

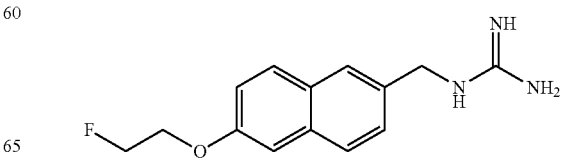

The product of Part 11C (75.0 mg, 0.163 mmol) was dissolved in dioxane (1.00 mL) then treated with concentrated HCl (1.50 mL) at ambient temperature. After 3 h, all volatiles were removed in vacuo, the residue redissolved in H₂O/MeCN (1:1 v/v) then lyophilized to a pale yellow solid (48.0 mg, 0.161 mmol; >98%).

Part 11E—Preparation of methyl 6-((tert-butyldimethylsilyl)oxy)naphthalene-2-carboxylate

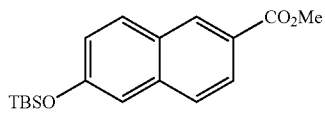 [SMILES: COC(=O)c1ccc2cc(O[Si](C)(C)C(C)(C)C)ccc2c1]

Methyl 6-hydroxynaphthalene-2-carboxylate (1.00 g, 4.95 mmol) was dissolved in DMF (20.0 mL) and successively treated with tert-butyldimethylsilyl chloride (1.11 mL, 7.42 mmol) and imidazole (0.673 g, 9.89 mmol) at ambient temperature. After 16 h, the solution was partitioned between EtOAc and H₂O with transfer to a reparatory funnel. The layers separated and the EtOAc layer washed with H₂O (210 mL) and saturated aqueous NaCl (300 mL) then dried over MgSO₄, filtered and concentrated in vacuo to a white solid that was used without further purification in the subsequent reaction.

Part 11F—Preparation of (6-((tert-butyldimethylsilyl)oxy)naphthalen-2-yl)methanol

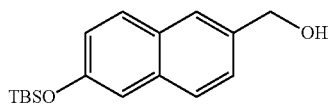 [SMILES: CC(C)(C)[Si](C)(C)Oc1ccc2cc(CO)ccc2c1]

The product of Part 11E (0.500 g, 1.58 mmol) was dissolved in Et₂O (5.00 mL), cooled to 0° C. and treated with LiAlH₄ (0.180 g, 4.74 mmol) portionwise over 5 min. After 10 min, excess LiAlH₄ was consumed by the careful addition of H₂O. The resulting white suspension was successively treated with 15% aqueous NaOH and H₂O and stirred for 15 min to a fine white slurry. The resulting mixture was filtered through a pad of Celite and the filtrate concentrated in vacuo to a white solid that was used without further purification in the subsequent reaction.

Part 11G—Preparation of tert-butoxy [(E)-amino{(tert-butoxycarbonyl){[(((6-tert-butyldimethylsilyl)oxy)naphthalen-2-yl)methyl]amino}methylidene]carbamate

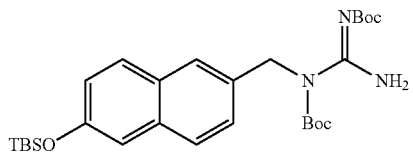

The product of Part 11F (0.250 g, 0.870 mmol) was dissolved in THF (5.00 mL), successively treated with 1,3-bis(tert-butoxycarbonyl)guanidine (0.451 g, 1.74 mmol) and PPh₃ (0.456 g, 1.74 mmol) then cooled to 0° C. DIAD (336 µL, 1.74 mmol) was then added dropwise over 5 min at the ice bath removed. After 4 h, all volatiles were removed and the residue directly purified by chromatography on silica using 4:1 hexanes/Et₂O to afford the title compound as a white solid (0.451 mg, 0.851 mmol; 97.9%).

Part 11H—Preparation of tert-butoxy [(E)-amino{(tert-butoxycarbonyl)[(6-hydroxynaphthalen-2-yl)methyl]amino}methylidene]carbamate

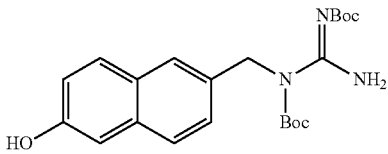

The product of Part 11G (0.100 g, 0.189 mmol) was dissolved in THF (0.50 mL) then treated with tetrabutylammonium fluoride (0.567 mmol; 0.567 mL of a 1.0 M solution in THF) at ambient temperature. After 2 h, all volatiles were removed and the residue purified by chromatography on silica using 4:1 hexanes/EtOAc to afford the title compound as a white solid (45.0 mg, 0.108 mmol; 57.3%).

Part 11I—Preparation of 1-{[6-(2-[¹⁸F]fluoroethoxy)naphthalen-2-yl]methyl}guanidine, formic acid salt

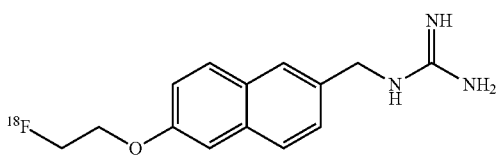 [SMILES: N=C(N)NCc1ccc2cc(OCC[18F])ccc2c1]

The product of Part 1E was transferred to a 5 mL conical-bottomed Wheaton™ reaction vial containing the product of Part 11H (4.2 mg), K₂CO₃ (3.6 mg) and anhydrous DMSO (400 µL). The resulting mixture was heated at 80° C. for 45 min then cooled to ambient temperature, treated with CF₃CO₂H (1.00 mL) and warmed to 50° C. After 15 min, the resulting mixture was cooled to ambient temperature, concentrated to dryness then purified by HPLC on a Phenomenex Luna C18(2) column (10×250 mm, 5 micron particle size, 100 Angstrom pore size) using a 5.0%/min gradient of 0-100% MeCN containing 0.1% HCO₂H acid at a flow rate of 2.0 mL/min. The title compound was collected, all volatiles removed, and the residue reconstituted with 10% aqueous ethanol solution for biological experiments.

Example 12

1-((6-(3-fluoropropoxy)naphthalen-2-yl)methyl)guanidine

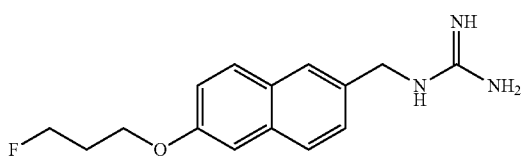 [SMILES: N=C(N)NCc1ccc2cc(OCCCF)ccc2c1]

Part 12A—Preparation of tert-butoxy [(E)-amino{(tert-butoxycarbonyl){[(6-(3-fluoropropoxy)naphthalen-2-yl)methyl]amino}methylidene]carbamate

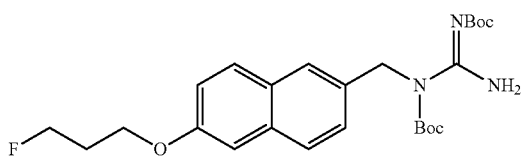

The product of Part 11H (75.0 mg, 0.181 mmol) was dissolved in dry DMF (3.00 mL), successively treated with 3-fluoropropyl 4-methylbenzenesulfonate (62.8 mg, 0.271 mmol) and $K_2CO_3$ (99.7 mg, 0.772 mmol) then warmed to 50° C. and maintained 48 h. All volatiles were removed, and the residue purified by preparative TLC using 4:1 pentane/EtOAc for development, to afford the title compound as a white powder (36.0 mg, 0.076 mmol; 41.9%).

Part 12B—Preparation of 1-{[6-(2-fluoropropoxy)naphthalen-2-yl]methyl}guanidine, trifluoroacetic acid salt

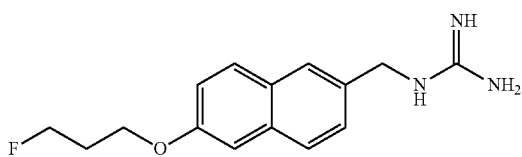 [SMILES: N=C(N)NCc1ccc2cc(OCCCF)ccc2c1]

The product of Part 12A (36.0 mg, 0.076 mmol) was dissolved in dioxane (1.00 mL) then treated with concentrated HCl (1.00 mL) at ambient temperature. After 45 min all volatiles were removed in vacuo, the residue redissolved in $H_2O$/MeCN (1:1 v/v, 2.0 mL) then directly purified by HPLC on a Phenomenex Luna C18 column (21.2×250 mm) using a 3%/min gradient from 0-90% MeCN containing 0.1% $CF_3CO_2H$ and 10% $H_2O$ at 20 mL/min to afford the title compound as a white powder (18.0 mg, 0.046 mmol; 61.0%).

Part 12C—Preparation of 2-[$^{18}$F]fluoropropyl 4-methylbenzenesulfonate

An MP1 anion exchange cartridge containing 1,000 mCi of [$^{18}$F]NaF (produced according to the general procedure described in Part 1D) was eluted with 0.20% aqueous $K_2CO_3$ (1.0 mL), using an automated liquid handling system, into a 25 mL conical-bottomed silanized flask. All volatiles were removed by applying a gentle stream of warm Ar and applied vacuum. The contents of the flask were reconstituted with 0.5 mL of MeCN, and concentrated again using warm Ar and applied vacuum (azeotropic evaporation). A separate 5 mL conical-bottomed Wheaton™ vial was used to prepared a solution of 4,7,13,16,21,24-hexaoxa-1,10-diazabicyclo[8.8.8]hexacosane (19.3 mg) and propylene di-(p-toluenesulfonate) (4.0 mg) in MeCN (1.0 mL). The constituents of the vial were transferred to the 25 mL flask containing [$^{18}$F]KF then positioned inside a microwave cavity (model 520 Resonance Instruments, Skokie, Ill.) and irradiated for 3 min at 75 watts. After cooling, the contents of the microwave reaction vial were filtered through an anion exchange resin to remove residual fluoride ion, collected in a 5 mL conical-bottomed Wheaton™ reaction vial and used without further purification in the subsequent reaction.

Part 12D—Preparation of 1-{[6-(2-[$^{18}$F]fluoropropoxy)naphthalen-2-yl]methyl}guanidine, formic acid salt

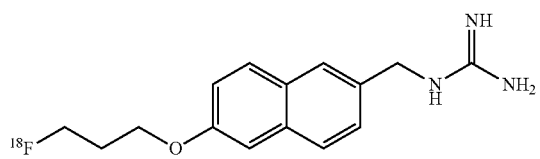 [SMILES: N=C(N)NCc1ccc2cc(OCCC[18F])ccc2c1]

The product of Part 12C was transferred to a 5 mL conical-bottomed Wheaton™ reaction vial containing the product of Part 11H (4.0 mg), $K_2CO_3$ (2.8 mg) and anhydrous DMSO (400 μL). The resulting mixture was heated at 80° C. for 30 min then cooled to ambient temperature, treated with $CF_3CO_2H$ (1.00 mL) and warmed to 50° C. After 15 min, the resulting mixture was cooled to ambient temperature, concentrated to dryness then purified by HPLC on a Phenomenex Luna C18(2) column (10×250 mm, 5 micron particle size, 100 Angstrom pore size) using a 5.0%/min gradient of 0-100% MeCN containing 0.1% $HCO_2H$ acid at a flow rate of 2.0 mL/min. The title compound was collected, all volatiles removed, and the residue reconstituted with 10% aqueous ethanol solution for biological experiments.

Example 21

1-(2-(5-(2-fluoroethoxy)-1H-indol-3-yl)ethyl)guanidine

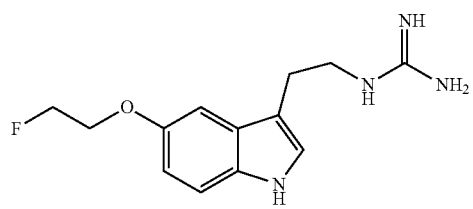 [SMILES: N=C(N)NCCc1c[nH]c2ccc(OCCF)cc12]

Part 21A—Preparation of tert-butyl [(Z)-[(tert-butoxycarbonyl)amino]{[2-(5-hydroxy-1H-indol-3-yl)ethyl]amino}methylidene]carbamate

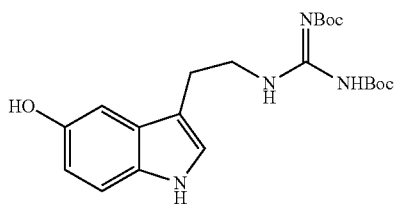

Serotonin hydrochloride (2.00 g, 11.3 mmol) was dissolved in MeCN (38.0 mL) and successively treated with N,N-diisopropylethylamine (1.98 mL, 11.3 mmol) and N,N'-di-Boc-1H-pyrazole-1-carboxamidine (4.20 g, 13.6 mmol) at ambient temperature. After 30 min, the resulting suspension was filtered though a scintered glass funnel of medium porosity, the filtrate diluted with $H_2O$ then transferred to a reparatory funnel and washed with EtOAc. The combined washes were further treated with $H_2O$ and saturated aqueous NaCl then dried over $Na_2SO_4$, filtered and concentrated in vacuo. Subsequent purification by chromatography on silica using a step gradient from 3:1 hexanes/EtOAc to 1:1 hexanes/EtOAc afforded the title compound as a white solid (2.90 g, 6.93 mmol; 61.0%).

Part 21B—Preparation of tert-butyl [(Z)-[(tert-butoxycarbonyl)amino]{[2-(5-(3-fluoroethoxy)-1H-indol-3-yl)ethyl]amino}methylidene]carbamate

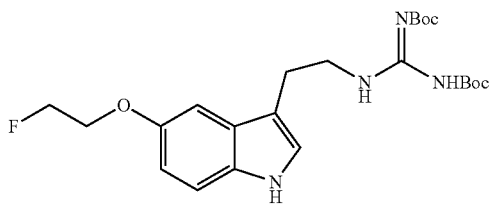

The product of Part 21A (0.400 g, 0.956 mmol) was dissolved in DMF (38.0 mL) and successively treated with $Cs_2CO_3$ (1.60 g, 4.78 mmol) and 1-bromo-2-fluoroethane (178 μL, 2.39 mmol) at ambient temperature. The resulting suspension was warmed to 70° C., maintained 1 h then cooled to ambient temperature and partitioned between EtOAc and $H_2O$. The layers separated and the EtOAc layer further washed with saturated aqueous NaCl, dried over $Na_2SO_4$, filtered and concentrated in vacuo. Subsequent purification by chromatography on silica, using a hexanes/EtOAc gradient from 0-100% EtOAc over 15 min, afforded the title compound as a white solid (0.176 g, 0.379 mmol; 39.6%).

Part 21C—Preparation of 1-(2-(5-(2-fluoroethoxy)-1H-indol-3-yl)ethyl)guanidine, trifluoroacetic acid salt

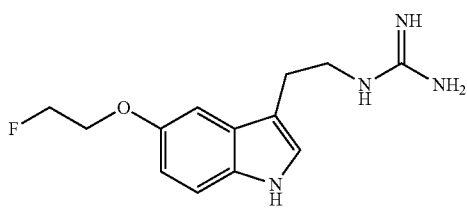 [SMILES: N=C(N)NCCc1c[nH]c2ccc(OCCF)cc12]

The product of Part 21B (0.100 g, 0.215 mmol) was dissolved in dioxane (1.00 mL) and treated with concentrated HCl (3.00 mL) at ambient temperature. After 30 min, all volatiles were removed in vacuo and the residue directly purified by HPLC on a Phenomenex Luna C18 column (21.2×250 mm) using an 8.3%/min gradient from 0-100% MeCN containing 0.1% $CF_3CO_2H$ and 10% $H_2O$ at 20 mL/min. The main product peak was collected, pooled and lyophilized to a white solid. NOTE: an accurate yield could not be obtained due to the extreme hydroscopicity of the selected salt form.

Part D—Preparation of 1-(2-(5-(2-[$^{18}$F]fluoroethoxy)-1H-indol-3-yl)ethyl)guanidine, formic acid salt

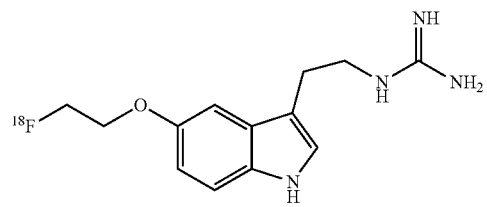 [SMILES: N=C(N)NCCc1c[nH]c2ccc(OCC[18F])cc12]

The product of Part 1E was transferred to a 5 mL conical-bottomed Wheaton™ reaction vial containing the product of Part 21A (3.3 mg), $Cs_2CO_3$ (13.1 mg) and anhydrous DMF (400 μL). The resulting mixture was heated at 80° C. for 45 min then cooled to ambient temperature and concentrated in vacuo. The residue was treated with $CF_3CO_2H$ (1.00 mL) then warmed to 40° C. and maintained 20 min. The resulting mixture was cooled to ambient temperature, concentrated to dryness then purified by HPLC on a Phenomenex Luna C18(2) column (10×250 mm, 5 micron particle size, 100 Angstrom pore size) using a 5.0%/min gradient of 0-100% MeCN containing 0.1% $HCO_2H$ acid at a flow rate of 2.0 mL/min. The title compound was collected, all volatiles removed, and the residue reconstituted with 10% aqueous ethanol solution for biological experiments.

Example 33

1-(4-(3-fluoropropyl)phenethyl)guanidine

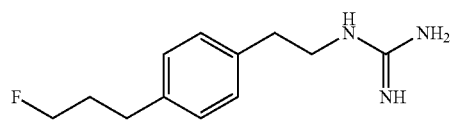 [SMILES: N=C(N)NCCc1ccc(CCCF)cc1]

Part 33A—Preparation of [4-(3-hydroxyprop-1-yn-1-yl)phenyl]acetonitrile

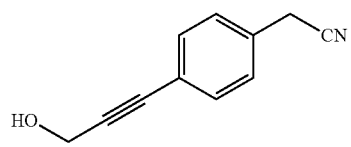 [SMILES: N#CCc1ccc(C#CCO)cc1]

(4-Iodophenyl)acetonitrile (1.00 g, 4.12 mmol), $PPh_3$ (11.0 mg, 0.041 mmol) and propargyl alcohol (243 μL, 4.12 mmol) were dissolved in N,N-diethylamine (14.0 mL) then treated with 8.0 mg CuI (0.041 mmol; 1.0 mol %) and 11.0 mg PdCl$_2$ (0.041 mmol; 1.0 mol %) at ambient temperature. After 48 h, all volatiles were removed in vacuo and the residue purified by chromatography on silica using a hexanes/EtOAc gradient from 0-100% EtOAc over 18 min to afford the title compound as an orange solid (0.453 g, 2.65 mmol; 64.3%).

Part 33B—Preparation of 3-[4-(2-aminoethyl)phenyl]propan-1-ol, hydrochloric acid salt

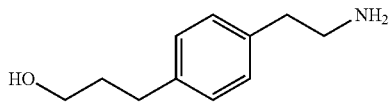 [SMILES: NCCc1ccc(CCCO)cc1]

The product of Part 33A (0.386 g, 2.26 mmol) was dissolved in EtOH (22.0 mL) then successively treated with concentrated HCl (3.00 mL) and Pd/C (0.363 mmol; 16 mol %) at ambient temperature. The headspace of the reaction vessel was sparged with 50 psi H$_2$ then maintained 16 h. Upon complete reduction, the headspace was sparged with dry N$_2$ and the catalyst removed by filtration through Celite. The filter cake was exhaustively washed with EtOH and the combined filtrates concentrated in vacuo to an orange solid (0.420 g). The crude material was used without further purification in the subsequent reaction.

Part 33C—Preparation of tert-butoxy {(Z)-({2-[4-(3-hydroxypropyl)phenyl]ethyl}amino)[(tert-butoxycarbonyl)amino]methylidene}carbamate

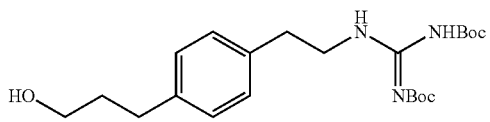

The product of Part 33B (2.26 mmol theoretical) was dissolved in MeCN (1.00 mL) and successively treated with N,N-diisopropylethylamine (816 µL, 4.69 mmol) and N,N'-di-Boc-1H-pyrazole-1-carboxamidine (0.831 g, 2.68 mmol) at ambient temperature. After 45 min, the solution was diluted with H$_2$O with transfer to a separatory funnel then washed with EtOAc. The combined EtOAc washes were further washed with H$_2$O and saturated aqueous NaCl then dried over Na$_2$SO$_4$, filtered and concentrated in vacuo. Subsequent purification by chromatography on silica, using a hexanes/EtOAc gradient from 0-100% EtOAc over 18 min, afforded the title compound as a pale yellow solid (0.288 g, 0.683 mmol; 30.3%).

Part 33D—Preparation of tert-butoxy {(Z)-({2-[4-(3-fluoropropyl)phenyl]ethyl}amino) [(tert-butoxycarbonyl)amino]methylidene}carbamate

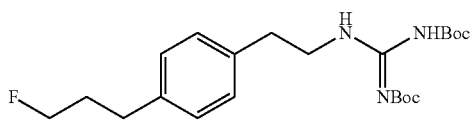

Deoxo-Fluor® (115 µL, 0.521 mmol) was diluted with CH$_2$Cl$_2$ (57 µL) then cooled to 0° C. and treated with a solution of the product of Part 33C (0.474 mmol; 100 µL of 4.74 M solution in CH$_2$Cl$_2$) dropwise over 2 min. The resulting mixture warmed slowly to ambient temperature as the cooling bath evaporated overnight. All volatiles were removed in vacuo and the residue directly purified by chromatography on silica using a hexanes/EtOAc gradient from 0-100% EtOAc over 18 min to afford the title compound as a white solid (24.5 mg, 0.0578 mmol; 12.2%).

Part 33E—Preparation of 1-(4-(3-fluoropropyl)phenethyl)guanidine, trifluoroacetic acid salt

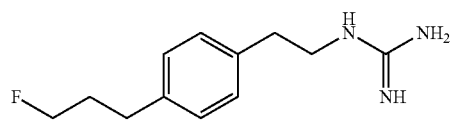 [SMILES: N=C(N)NCCc1ccc(CCCF)cc1]

The product of Part 33D (20.0 mg, 0.047 mmol) was dissolved in dioxane (1.00 mL) then treated with concentrated HCl (3.00 mL) at ambient temperature. After 30 min all volatiles were removed in vacuo, the residue redissolved in H$_2$O/MeCN (1:1 v/v, 2.0 mL) then directly purified by HPLC on a Phenomenex Luna C18 column (21.2×250 mm) using a 7.1%/min gradient from 0-100% MeCN containing 0.1% CF$_3$CO$_2$H and 10% H$_2$O at 20 mL/min to afford the title compound as a white powder (16.0 mg, 0.047 mmol; >98%).

Part 33F—Preparation of 3-{-4-[2-(N',N"-bis(tert-butoxycarbonyl)carbamimidamido)ethyl]phenyl}propyl 4-methylbenzenesulfonate

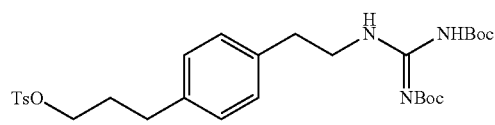

The product of Part 33C (20.0 mg, 0.047 mmol) was dissolved in CH$_2$Cl$_2$ (336 mL) and successively treated with p-toluenesulfonyl chloride (13.0 mg, 0.071 mmol) and pyridine (38 µL, 0.470 mmol) at 0° C. After 16 h, the resulting solution was diluted with CH$_2$Cl$_2$, with transfer to a reparatory funnel then successively washed with 5% aqueous CuSO$_4$, H$_2$O and saturated aqueous NaCl. After drying over Na$_2$SO$_4$, the solution was filtered and concentrated in vacuo then purified by chromatography on silica, using a hexanes/EtOAc gradient from 0-100% EtOAc over 18 min, to afford the title compound as a colorless oil (5.0 mg, 8.7 µmol; 18.3%).

Part 33G—Preparation of 1-(4-(3-[$^{18}$F]fluoropropyl)phenethyl)guanidine, formic acid salt

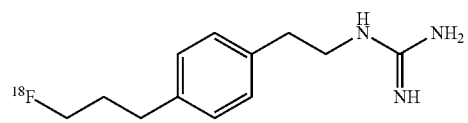 [SMILES: N=C(N)NCCc1ccc(CCC[18F])cc1]

An MP1 anion exchange cartridge containing 1,000 mCi of [$^{18}$F]NaF (produced according to the general procedure described in Part 1D) was eluted with 0.20% aqueous $K_2CO_3$ (1.0 mL), using an automated liquid handling system, into a 25 mL conical-bottomed silanized flask. All volatiles were removed by applying a gentle stream of warm Ar and applied vacuum. The contents of the flask were reconstituted with 0.5 mL of MeCN, and concentrated again using warm Ar and applied vacuum (azeotropic evaporation). The residue was treated with a solution of 4,7,13,16,21,24-hexaoxa-1,10-diazabicyclo[8.8.8]hexacosane (20.0 mg) in MeCN (0.90 mL) then transferred to a solution of the product of Part 33F (4.4 mg) in dry MeCN (0.40 mL). The constituents of the vial were then positioned inside a microwave cavity (model 520 Resonance Instruments, Skokie, Ill.) and irradiated for 3 min at 100 watts. The resulting solution was cooled, treated with $CF_3CO_2H$ (1.00 mL) and the microwave heating cycle repeated. After cooling, all volatiles were removed and the residue purified by HPLC on a Phenomenex Luna C18(2) column (250×10 mm, 5 micron particle size, 100 Angstrom pore size) using a 5.0%/min gradient of 0-100% MeCN containing 0.1% $HCO_2H$ acid at a flow rate of 2.0 mL/min. The title compound was collected, all volatiles removed, and the residue reconstituted with 10% aqueous ethanol solution for biological experiments.

Example 35

In-Vitro Assays

Part 35A Norepinephrine Transporter Binding Assay

Individual inhibitors were dissolved in incubation buffer (50 mM Tris-HCl, 10% sucrose, pH 7.4) at appropriate dilutions. The inhibitor solutions were added to the wells of a microtiter plate (40 µL/well) in triplicate. Each well of test agent (and appropriate control wells) was treated with a mixture of MDCK cell membrane preparation (22.4 µg of membrane) expressing human norepinephrine transporter (Bmax=3.7 pmol norepinephrine transporter/mg protein), and [$^3$H]desipramine (2 nM, 64.8 Ci/mmol) in a total volume of 0.2 mL. The resulting mixtures were incubated for 2 h on ice.

A 96 well GF/C filter plate was presoaked with coating buffer (0.5% polyvinylpyrrolidine and 0.1% Tween 20) for 2 h at room temperature, then washed with incubation buffer (6×0.2 mL). The competition reactions were transferred to the coated plate and filtered. The filter plate was washed (6×0.2 mL) with ice cold wash buffer (50 mM Tris-HCl, 0.9% NaCl, pH 7.4) then dried overnight and treated with 25 µL scintillation fluid for analysis on a plate reader (Microbeta TriLux 1450 LSC and Luminescence counter, Perkin Elmer, Shelton Conn.).

Part 35B Cell—Preparation

Rat pheochromocytoma cell line (PC-12) were purchased from the American Type Culture Collection (ATCC) then cultured in collagen-coated flasks (BD Bio Coat Collagen Type 1, BD Biosciences) using a growth media composed of F-12 K media, 2 mM L-glutamine, 15% horse serum, 2.5% fetal bovine serum (FBS) and 1% penicillin-streptomycin.

Part 35C—PC-12 Binding Assay

Prepared PC-12 cells were seeded into 6-well plates at a density of 1×10$^6$ cells/well with 2 mL of growth media and maintained 24 h at 37° C. under a 5% $CO_2$ atmosphere. The media was exchanged and each well treated with 0.1 µCi test agent, with or without 1 µM desipramine. The resulting mixture was incubated for 60 min at 37° C. and 5% $CO_2$ then centrifuged at 500×g for 3 min and washed with PBS buffer. Radioactivity associated with the cells was then measured, and total uptake determined in the wells without desipramine; nonspecific uptake was measured in the associated wells containing desipramine. The specific NET mediated cell uptake is calculated as percent total uptake minus percent nonspecific uptake.

TABLE 1

In-vitro association data

| Example | NET Affinity (µM) | PC-12 (% bound) Control | PC-12 (% bound) Block |
|---|---|---|---|
| 1 | 7.27 | 3.1 | 0.30 |
| 2 | 11.19 | 3.20 | 0.60 |
| 3 | 7.35 | 32.76 | 2.36 |
| 4 | 5.41 | 1.00 | 0.50 |
| 5 | 18.73 | 1.00 | 0.90 |
| 6 | 7.91 | 2.40 | 0.70 |
| 7 | 10.04 | 1.40 | 0.70 |
| 8 | 17.37 | 1.30 | 0.60 |
| 9 | 3.07 | 3.90 | 3.30 |
| 10 | >73.5 | — | — |
| 11 | 0.12 | 23.90 | 2.70 |
| 12 | 0.14 | 5.30 | 0.50 |
| 13 | >73.5 | — | — |
| 14 | >73.5 | — | — |
| 15 | 32.11 | — | — |
| 16 | >73.5 | — | — |
| 17 | 59.19 | — | — |
| 18 | >73.5 | — | — |
| 19 | 70.71 | — | — |
| 20 | 2.06 | 0.10 | 0.10 |
| 21 | 1.19 | 0.10 | 0.10 |
| 22 | 18.97 | 0.00 | 0.00 |
| 23 | 6.42 | 1.40 | 0.50 |
| 24 | 4.86 | 2.10 | 0.90 |
| 25 | >73.5 | — | — |
| 26 | >73.5 | — | — |
| 27 | 1.55 | — | — |
| 28 | 7.89 | 0.10 | 0.10 |
| 29 | 10.30 | 12.20 | 2.20 |
| 30 | 2.01 | — | — |
| 31 | 12.96 | — | — |
| 32 | 115.20 | — | — |
| 33 | 3.95 | 2.30 | 1.50 |
| 34 | 4.10 | — | — |

Example 36

In Vivo Tissue Distribution Assays

Part 36A Animal—Preparation

Male Sprague Dawley rats (300-500 g, Taconic), and male New Zealand rabbits (3-4 kg, Covance) were used in accordance with our Institutional Animal Care and Use Committee. Rats were anesthetized with sodium pentobarbital (50 mg/kg, i.p.) and the left femoral vein cannulated with PESO tubing for drug injection. Rabbits were pre-sedated with acepromazine (0.75 mg/kg i.m.) then anesthetized with ketamine (40 mg/kg, i.m.) and xylazine (8 mg/kg, i.m); the marginal ear vein was cannulated for drug injection. Additional doses of anesthetics were given as needed.

Part 36B—Tissue Distribution in Rats and Rabbits

After preparation, each animal received a bolus injection of the test agent via the venous catheter. Rats and rabbits were euthanized after the injection and samples of the blood, heart, lung, liver, spleen, kidney, femur and muscle were collected. All samples were weighed and counted for radioactivity (Wallac Wizard 1480, PerkinElmer Life and Analytical Sciences, Shelton, Conn.); net radioactivity administered in each animal was determined by subtracting the residual activity in both the syringe and venous catheter. Tissue uptake of each agent was determined as a percentage of the injected dose per gram tissue (% ID/g).

TABLE 2

In-vivo rat biodistribution data

| Example | Rat (% ID/g) | | | |
|---|---|---|---|---|
| | Heart | Lung | Liver | Blood |
| 1 | 1.03 | 0.24 | 0.15 | 0.18 |
| 2 | 1.33 | 0.94 | 0.25 | 0.19 |
| 3 | 0.71 ± 0.24 | 1.12 ± 0.29 | 0.15 ± 0.03 | 0.35 ± 0.15 |
| 4 | 1.04 ± 0.95 | 0.34 ± 0.18 | 0.37 ± 0.24 | 0.13 ± 0.02 |
| 5 | 1.23 | 0.59 | 0.26 | 0.69 |
| 7 | 1.60 ± 0.13 | 0.80 ± 0.09 | 0.30 ± 0.12 | 0.11 ± 0.02 |
| 8 | 1.61 | 0.94 | 0.27 | 0.21 |
| 11 | 1.74 ± 0.27 | 2.71 ± 0.51 | 0.61 ± 0.40 | 0.51 ± 0.11 |
| 12 | 1.93 ± 0.11 | 2.09 ± 0.08 | 0.18 ± 0.01 | 0.37 ± 0.05 |
| 21 | 0.35 | 0.38 | 1.01 | 0.41 |
| 33 | 1.94 ± 0.16 | 0.66 ± 0.11 | 0.21 ± 0.04 | 0.10 ± 0.01 |

TABLE 3

In-vivo rabbit biodistribution data

| Example | Rabbit (% ID/g) | | | |
|---|---|---|---|---|
| | Heart | Lung | Liver | Blood |
| 3 | 0.29 | 0.39 | 0.02 | 0.01 |
| 4 | 0.025 | 0.031 | 0.012 | 0.014 |
| 7 | 0.066 | 0.078 | 0.021 | 0.013 |
| 11 | 0.39 ± 0.02 | 0.39 ± 0.11 | 0.02 ± 0.00 | 0.04 ± 0.01 |
| 12 | 0.29 ± 0.09 | 0.28 ± 0.17 | 0.02 ± 0.01 | 0.04 ± 0.02 |

Example 37

PET Imaging

Part 37A—Image Acquisition

Cardiac PET imaging was performed in anesthetized rats and rabbits prepared according to Part 36A. The animal was appropriately positioned in a microPET camera (Focus220, CTI Molecular Imaging, Inc. Knoxville, Tenn.) for cardiac imaging and the test agent injected using the venous catheter. Complete acquisition required 120 min.

Part 37B—Image Reconstruction and Analysis

Acquired images were reconstructed in a matrix of 256× 256 pixels with 95 transverse slices, using the filtered back projection algorithm, and decay corrected (microPET Manager and ASIPro, CTI Molecular Imaging, Inc. Knoxville, Tenn.); pixel size was 0.47 mm and slice thickness was 0.80 mm. Images were reoriented to the cardiac axis and serial tomographic image frames generated for every 10 min interval from 5 to 125 minutes. FIGS. 2 through 8 represent images derived using compounds described herein. FIGS. 2 through 8 represent images derived using compounds described herein (e.g., wherein FIG. 2 relates to a compound from Example 1, FIG. 3 relates to a compound from Example 2, etc.).

Example 38

Introduction

Heart failure (HF) has been associated with increased sympathetic tone and noradrenaline (NA; also referred to herein as NE) release, and decreased neuronal NA transporter (NAT; also referred herein as NET) function and NA concentration in the failing heart (Rundqvist et al., Circulation. 1997; 95(1):169-75; Bohm et al., J Am Coll Cardiol. 1995; 25(1):146-53; Liang et al., J Clin Invest. 1989; 84(4): 1267-75). The reduced cardiac NA concentration due primarily to the impaired NAT function is usually referred to as cardiac sympathetic denervation, even though the sympathetic activation is elevated with increased NA spillover (Esler, J Appl Physiol. 2010; 108(2):227-37). Cardiac sympathetic neuronal function can be assessed by nuclear imaging. Indeed, global cardiac sympathetic denervation associated with reduced NAT function has been detected by cardiac imaging with a radiolabeled substrate for NAT, such as $^{123}$I-meta-iodobenzylguanidine (MIBG), $^{11}$C-meta-hydroxyephedrine (HED) and $^{11}$C-epinephrine (Bengel et al., J Nucl Cardiol. 2004; 11(5):603-16; Henneman et al., J Nucl Cardiol. 2008; 15(3): 442-55; Travin, Cardiol Clin. 2009; 27(2):311-27; Carrio, J Nucl Med. 2001; 42(7):1062-76). The imaging findings provided robust values in prediction of cardiac events in HF patients (Jacobson et al., J Am Coll Cardiol. 2010; 55(20):2212-21; Pietila et al., Eur J Nucl Med. 2001; 28(3):373-6). Additionally, incidence of ventricular arrhythmia and subsequent sudden cardiac death has also been linked to regional cardiac sympathetic dysfunction (Podrid et al., Circulation. 1990; 82(2 Suppl):I103-I113; Chen et al., J Cardiovasc Electrophysiol. 2007; 18(1):123-7). Regional cardiac sympathetic denervation (RCSD) or innervation heterogeneity identified by cardiac imaging with $^{123}$I-MIBG, $^{11}$C-HED or $^{11}$C-epinephrine has shown a strong association with enhanced probability of ventricular arrhythmia both in animals and humans (Dae et al., Circulation. 1997; 96(4):1337-42; Mitrani et al., J Am Coll Cardiol. 1993; 22(5):1344-53; Sasano et al., J Am Coll Cardiol. 2008; 51(23):2266-75; Stevens et al., Circulation. 1998; 98(10):961-8) and a correlation with arrhythmia induced implantable cardioverter defibrillator activation or cardiac death in HF patients (Boogers et al., J Am Coll Cardiol. 2010; 55(24):2769-77). However, the image quality of $^{123}$I-MIBG is suboptimal with low energy single-photon emission computed tomography (SPECT) imaging and, in some patients, results in undetected regional defects (Matsunari et al., Circ Cardiovasc Imaging. 2010; 3(5):595-603). Positron emission tomography (PET) imaging with $^{11}$C-HED has demonstrated superiority to $^{123}$I-MIBG in image quality and detection of regional abnormalities (Matsunari et al., Circ Cardiovasc Imaging. 2010; 3(5):595-603). However, the short half-life of $^{11}$C isotope limits its broad clinical application.

Imaging Agent-1 has recently been studied, wherein Imaging Agent-1 comprises the structure:

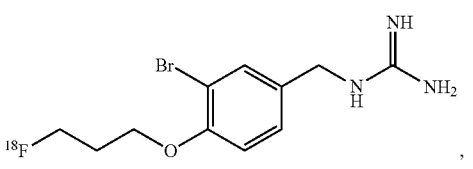 [SMILES: N=C(N)NCc1ccc(OCCC[18F])c(Br)c1]

or a pharmaceutically acceptable salt thereof. Imaging Agent-1 it is a benzylguanidine analog and was designed as a NAT substrate for evaluation of cardiac neuronal function. However, Imaging Agent-1 is radiolabeled with $^{18}$F allowing PET imaging and regional radiopharmacy production. Imaging with Imaging Agent-1 showed clear detection of global cardiac denervation (Yu et al., Circ Cardiovasc Imaging. 2011; 4(4):435-43). In this study, the Imaging Agent-1 imaging profile was further characterized for NAT association in-vitro by comparison with NE, the natural NAT substrate, and MIBG. Given the importance of regional cardiac denervation in HF stratification, Imaging Agent-1 imaging cardiac denervation and heart uptake kinetics in dynamic imaging were assessed in a rabbit model of RCSD. In addition, RCSD increases the risk of cardiac arrhythmia and treatments with antiarrhythmic drugs, such as dofetilide, may be used in patients with cardiac denervation. Dofetilide is a class III antiarrhythmic agent that selectively blocks the rapid component of the delayed rectifier outward potassium current (Lenz et al., *Pharmacotherapy.* 2000; 20(7):776-86). It is generally well tolerated in patients, but torsade de pointes (TdP) may occur following the drug induced prolongation of QTc interval. Thus, dofetilide induced changes in QTc interval and TdP were investigated in control and RCSD rabbits to determine the potential role of Imaging Agent-1 imaging cardiac sympathetic denervation in antiarrhythmic drug treatment.

Materials and Methods

Cell Uptake Comparison and Competition:

Imaging Agent-1 cell uptake in comparison with $^3$H-NA and $^{123}$I-MIBG was assayed in human neuroblastoma cells (SK-N-SH, ATCC) with expression of NAT (Buck et al., *Cancer Res.* 1985; 45(12 Pt 1):6366-70). Cells were prepared in 6-well plates at a density of $1\times10^6$ cells/well in 2 mL media. Imaging Agent-1, $^3$H-NA or $^{123}$I-MIBG at 3.7 kBq was added to each well with or without desipramine (1 µM), a selective NAT inhibitor. In assay with NA, pargyline (10 µM) was included to inhibit monoamine oxidase activity. Following incubation for 60 minutes at 37° C., cells were washed twice with ice-cold phosphate-buffered saline, trypsinized and centrifuged at 1000 g for 3 minutes to collect cell pellet. Radioactivity associated with the cells was measured with a γ-(Wallac Wizard 1480, PerkinElmer) or β-counter (Microbeta TriLux 1450 LSC, PerkinElmer). Each assay was performed in triplicate and the uptake was expressed as a percent of total radioactivity added to the well.

For the competitive inhibition assay, Imaging Agent-1 at 3.7 kBq was incubated in SK-N-SH cells with various concentrations (0.1, 1, 10, or 100 µM) of non-radioactive NA, MIBG or $^{19}$F-Imaging Agent-1 (self) at 37° C. for 60 minutes. Similarly, following the incubation, Imaging Agent-1 cell uptake was determined. The $IC_{50}$ value of each agent was determined using GraphPad software (v5).

Development of Regional Cardiac Sympathetic Denervation in Rabbits:

Animal study protocol was approved by the Institutional Animal Care and Use Committee. Male New Zealand rabbits (2.5-3.5 kg, Harlan) were maintained in the AAALAC-accredited Animal Care Facility and acclimated for 7 days. The thoracotomy procedure was similar to the method described previously (Yu et al., *J Nucl Cardiol.* 2010; 17(4):631-6). Briefly, the rabbit was anesthetized with ketamine (40 mg/kg, im) and xylazine (9 mg/kg, im) and placed in a supine position. Under aseptic conditions, a mid-sternotomy was performed carefully to avoid injury of parietal pleura. The pericardial sac was exposed and incised to reveal the left ventricular (LV) wall. Phenol (89% carbolic acid, Sigma) or saline (sham-control group) was applied on the surface of the LV lateral wall with a cotton-tipped applicator. The chest was then closed and the animal allowed to recover.

Cardiac PET Imaging:

Cardiac PET imaging was performed in both sham control and phenol induced RCSD rabbits at 2 and 12 weeks after surgery. Rabbits were anesthetized and maintained with isoflurane (0.5-2.5%) using a face mask, and positioned in a microPET camera (Focus220, CTI Molecular Imaging, Inc). Approximately 55.5 MBq of Imaging Agent-2, having the structure:

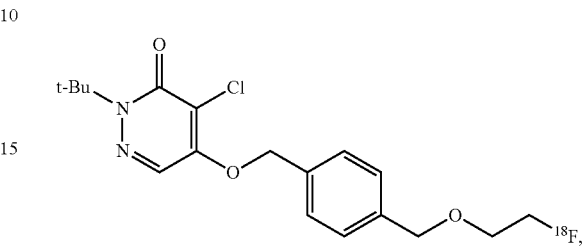

which is a myocardial perfusion imaging agent (Yu et al., *Semin Nucl Med.* 2011; 41(4):305-13; Yu et al., *J Nucl Cardiol.* 2007; 14(6):789-98; Nekolla et al., *Circulation.* 2009; 119(17):2333-42), was injected via a catheter in the marginal ear vein and the heart was imaged for 60 minutes. Imaging Agent-1 and Imaging Agent-2 imaging in each rabbit was performed in a two-day interval.

Image Reconstruction and Analysis:

Following the acquisition, images were reconstructed in a matrix of 256×256 pixels with 95 transverse slices using the OSEM2D algorithm and decay corrected (microPET Manager and ASIPro, CTI Molecular Imaging, Inc). The pixel size was 0.47 mm and the slice thickness was 0.80 mm. Serial tomographic cardiac images were framed in 2×5-, 2×10-, 3×30-, 1×60-, 1×120-, 1×300- and 5×600-second and reoriented based on cardiac axis. Time activity curves (TAC) were generated from these sequential images. The maximal radioactivity in the myocardium was determined from the images acquired at 20-30 minutes using Amide software (Amide's a Medical Image Data Examiner, v1.0.1). The normal LV areas of sympathetic innervation and perfusion (non-defect areas) detected by Imaging Agent-1 and Imaging Agent-2 imaging, respectively, were defined as regions with radioactivity ≥50% of the maximal activity. The 50% cutoff was selected based on published studies (Matsunari et al., *J Nucl Med.* 2001; 42(10):1579-85; Sherif et al., *Circ Cardiovasc Imaging.* 2009; 2(2):77-84; Simoes et al., *Eur Heart J.* 2004; 25(7):551-7). In addition, polar map images were generated from reconstructed cardiac short-axis images using QPS 2008 software (Cedars-Sinai Medical Center).

Assessment of Cardiac Regional Denervation on Dofetilide Treatment:

Dofetilide is an antiarrhythmic drug used clinically and known to cause QTc prolongation and possible TdP. The role of cardiac denervation in dofetilide induced changes in QTc interval, premature ventricular contraction (PVC) and TdP was assessed in sham control and RCSD rabbits at 3 weeks after surgery. Rabbits were anesthetized with ketamine (40 mg/kg, im) and xylazine (9 mg/kg, im), and dofetilide (1 and 4 µg/kg/min, Haorui Pharma-Chem Inc. Edison, N.J.) was infused for 10 minutes via a catheter in the marginal ear vein. Electrocardiogram (ECG) in lead II configuration was recorded with Ponemah system (v4.3, Data Science International) before and during the drug infusion. Heart rate (HR) and QT interval were derived from ECG waveforms. The QT interval was corrected by Fridericia method ($QT_{cf}=QT/RR^{1/3}$).

Radiopharmaceutical Agents:

Imaging Agent-1 and Imaging Agent-2 were radiosynthesized as previously described (Yu et al., *Circ Cardiovasc Imaging*. 2011; 4(4):435-43; Yu et al., *J Nucl Cardiol*. 2007; 14(6):789-98). The radiochemical purity of each imaging agent was consistently >99% and specific activity was >148000 GBq/mmol. Both agents were formulated in 5% ethanol (v/v) and 50 mg/ml ascorbic acid in water for injection.

Data Analysis:

Values are expressed as mean±SD. Comparisons were performed after data passed normality and variance homogeneity tests with or without simple data transformation using SigmaPlot software (v12). One-way ANOVA was used in comparison of cell uptake of radioactive agents and the non-defect LV volume detected by cardiac imaging, while two-way repeated measures ANOVA was used in analyzing changes in $QT_{cf}$ interval between control and denervated rabbits at various time points. The post hoc comparisons were performed with the Bonferroni test. Dofetilide induced frequencies of PVC and TdP between control and denervated rabbits were compared by Fisher Exact Test. $p<0.05$ was considered statistically significant.

Figure 9:
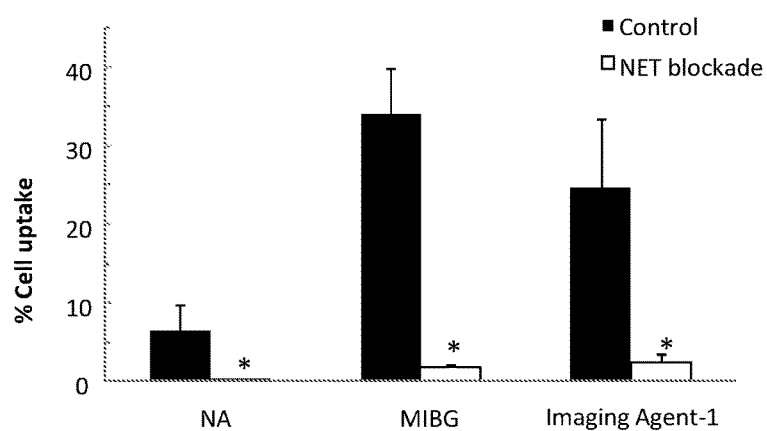
FIG. 9 shows a plot of percent cell uptakes for non-limiting examples of imaging agents.

Results:

Comparison of Imaging Agent-1 NAT Association with NA and MIBG:

As shown in FIG. 9, Imaging Agent-1 uptake in SK-N-SH cells was 24.6±9% (n=50), comparable to $^{123}$I-MIBG and higher than $^{3}$H-NA (n=8/each). Blockade of NAT with desipramine achieved ≥90% inhibition of cell uptake for Imaging Agent-1 (90±3%), $^{123}$I-MIBG (94±2%) and $^{3}$H-NA (97±2%).

FIG. 9 shows Imaging Agent-1 uptake (n=50) in comparison with $^{3}$H-noradrenaline (NA, n=8) and $^{123}$I-MIBG (n=8) in SK-N-SH cells with and without desipramine to block noradrenaline transporter (NAT). Similarly, NAT blockade inhibited over 90% cell uptake of Imaging Agent-1, NE and MIBG. * indicates p<0.05 vs. control. In competitive inhibition assay (FIG. 10), non-radioactive NA, MIBG and self (n=4/each) inhibited Imaging Agent-1 cell uptake in a concentration-dependent fashion. The $IC_{50}$ values were 1.09, 0.21 and 0.90 µM for NA, MIBG and $^{19}$F-Imaging Agent-1, respectively.

Figure 10:
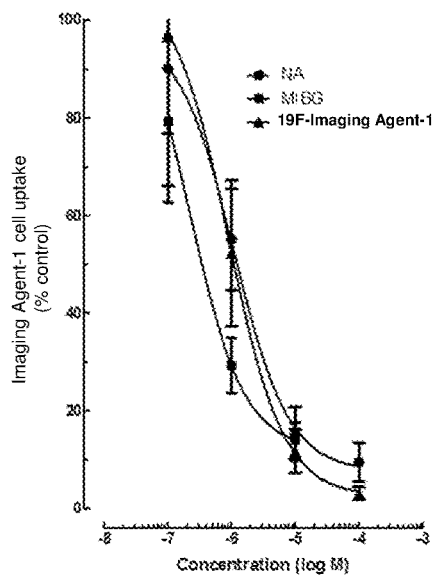
FIG. 10 shows dose-response curves of a non-limiting imaging agent in non-limiting cell lines.

FIG. 10 shows dose-response curves of Imaging Agent-1 uptake in SK-N-SH cells in the presence of increasing concentrations of non-radioactive compounds: noradrenaline (NA, n=4), MIBG (n=4, concentration at 100 µM was not tested) or $^{19}$F—Imaging Agent-1 (n=4). Results are expressed as percent of control Imaging Agent-1 uptake at each concentration of the compound. NA, MIBG and $^{19}$F—Imaging Agent-1 inhibited Imaging Agent-1 cell uptake concentration-dependently with $IC_{50}$ values in a 0.2-1.1 µM range.

Assessment of Cardiac Denervation by Imaging with Imaging Agent-1 and Imaging Agent-2:

Cardiac sympathetic innervation and myocardial perfusion were assessed by imaging with Imaging Agent-1 and Imaging Agent-2, respectively. In control rabbits (n=3-5, FIG. 11), the images of both agents showed well delineated myocardium with homogeneous activity distribution. The radioactivity in adjacent organs, like the blood, liver and lung, was low. In cardiac phenol denervated rabbits (n=8-14, FIG. 12), Imaging Agent-2 imaging showed well perfused myocardium, similar to that in the control. In contrast, in the same rabbit, cardiac neuronal imaging with Imaging Agent-1 revealed denervated regions in the LV wall. The denervated area was observed in the views of both cardiac short- and long-axis and polar map. Additionally, the denervated area reduced in Imaging Agent-1 images from 2 to 12 weeks after phenol denervation.

Figure 11:
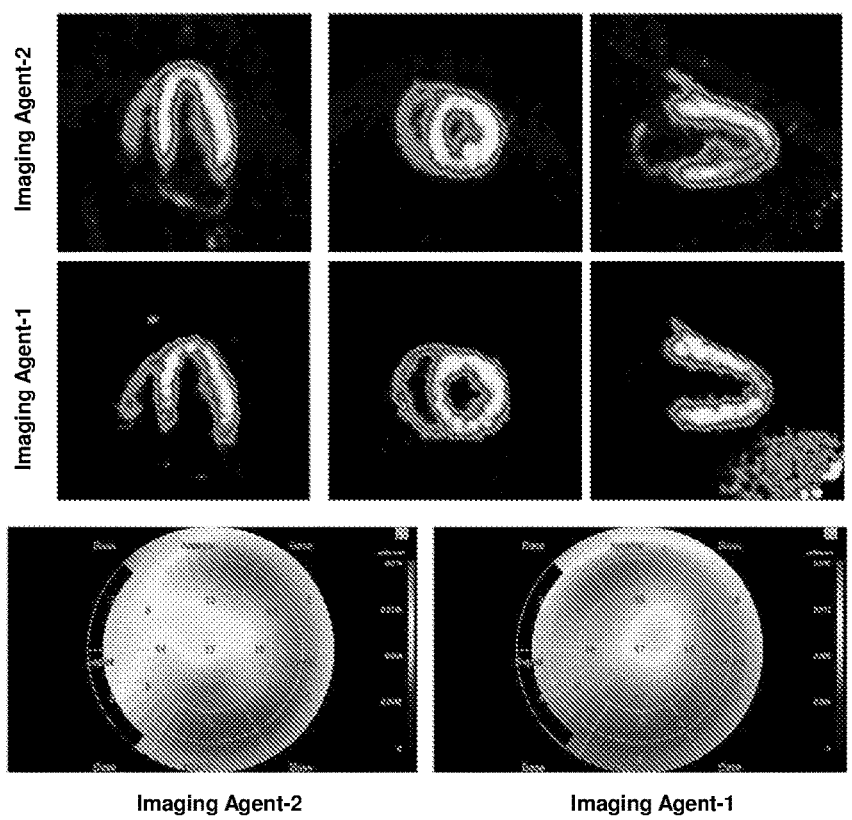
FIGS. 11 and 12 shows representative cardiac images and polar maps of a non-limiting imaging agent and a myocardial perfusion imaging agent.
Figure 12:
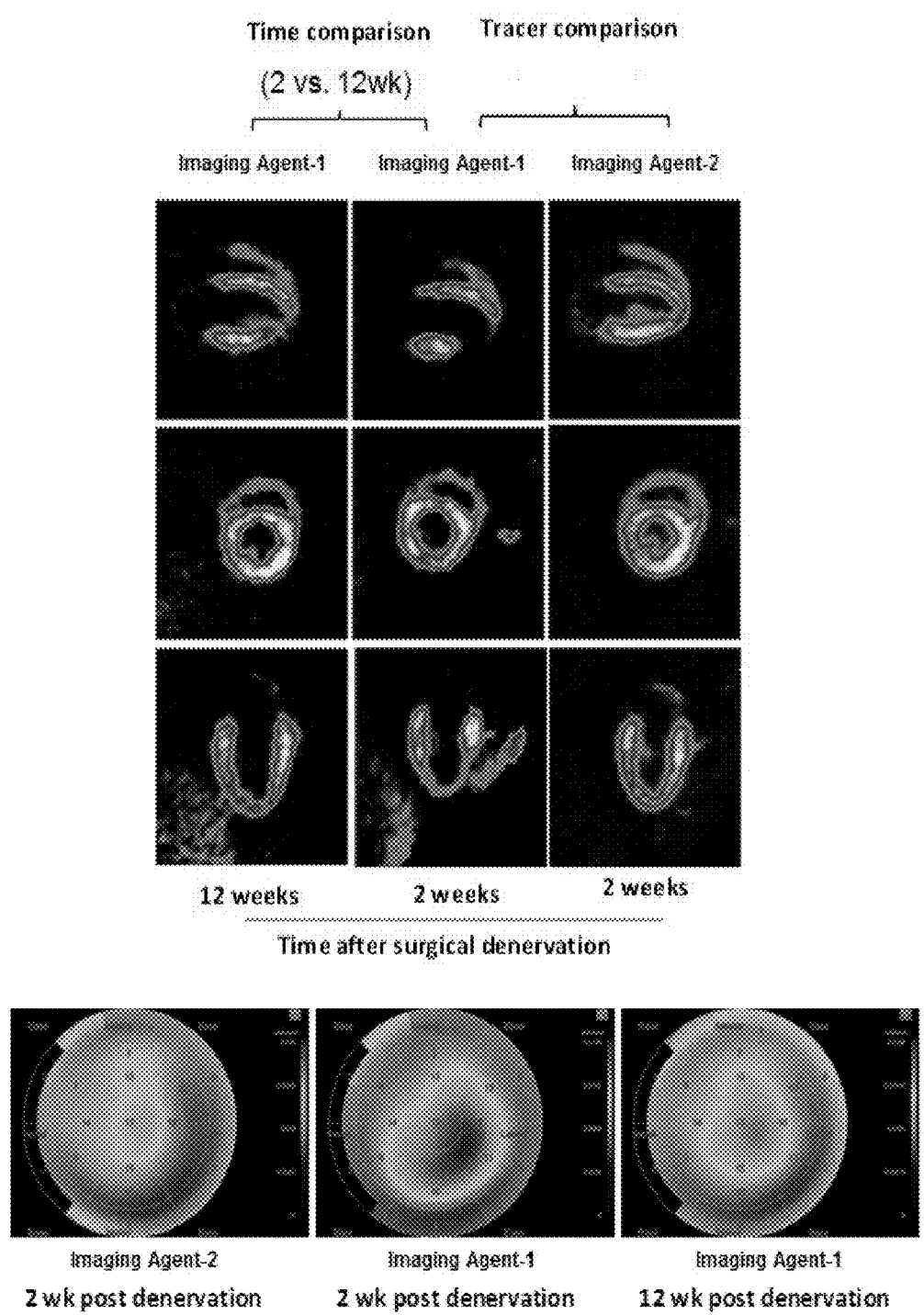

FIG. 11 shows representative cardiac images and polar maps of Imaging Agent-1 and Imaging Agent-2, a PET myocardial perfusion imaging agent, from a control rabbit (same rabbit imaged 2 times). The images were acquired at 20-30 min after injection. The myocardium was clearly delineated with homogeneous activity distribution in the left ventricle. Radioactivity levels in the adjacent organs were low. FIG. 12 shows representative cardiac images and polar maps of Imaging Agent-1 and Imaging Agent-2, a PET myocardial perfusion imaging agent, from a regional cardiac denervated rabbit (same rabbit imaged 3 times). The images were acquired at 20-30 min after injection. The regional denervation was detected by Imaging Agent-1 imaging at 2 weeks after phenol denervation and the defect was not due to reduced perfusion (normal Imaging Agent-2 images). The denervated area observed in Imaging Agent-1 images was reduced from 2 to 12 weeks post denervation, indicating re-innervation in the previous denervated area.

As shown in the injected dose corrected TACs (FIG. 13A-FIG. 13C), radioactivity in the blood cleared similarly for Imaging Agent-1 and Imaging Agent-2 in control rabbits: reaching a peak immediately after iv administration, then decreasing rapidly with time. In the heart, the activity levels for Imaging Agent-1 exhibited a quick washout after the initial peak and then plateaued (FIG. 13B). This differed from Imaging Agent-2 (FIG. 13A), where the plateau was reached without marked washout following the initial activity peak in the heart. However, a small and slow decrease in Imaging Agent-2 levels was observed between 5 to 25 minutes in the rabbit heart. Radioactivity levels in the liver cleared rapidly after injection of both imaging agents. In RCSD rabbits (FIG. 13C), Imaging Agent-1 was delivered to the denervated region initially and then washed out to a plateau, lower than that in the innervated region.

Figure 13A:
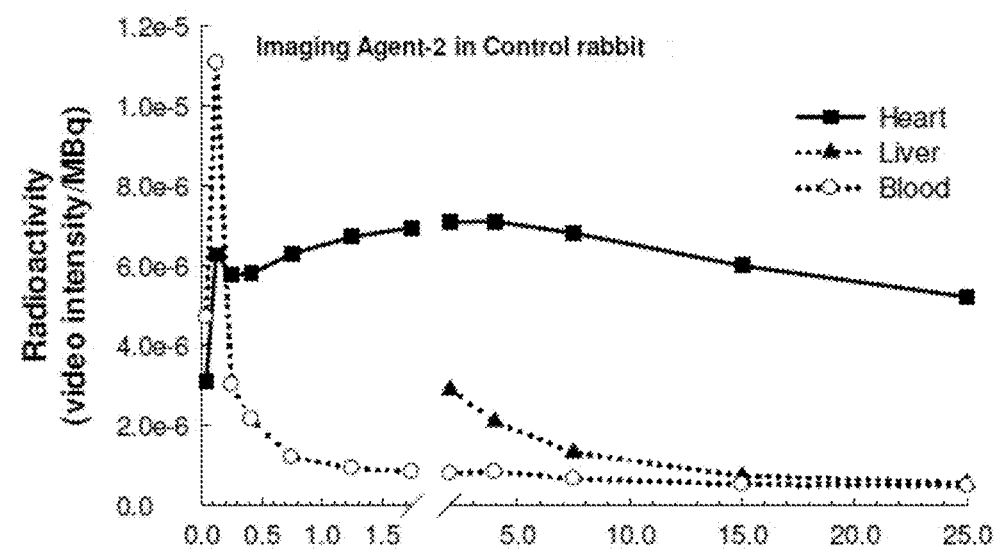
FIG. 13A-FIG. 13C shows representative time-activity curves derived from a non-limiting imaging agent and a myocardial perfusion imaging agent.
Figure 13B:
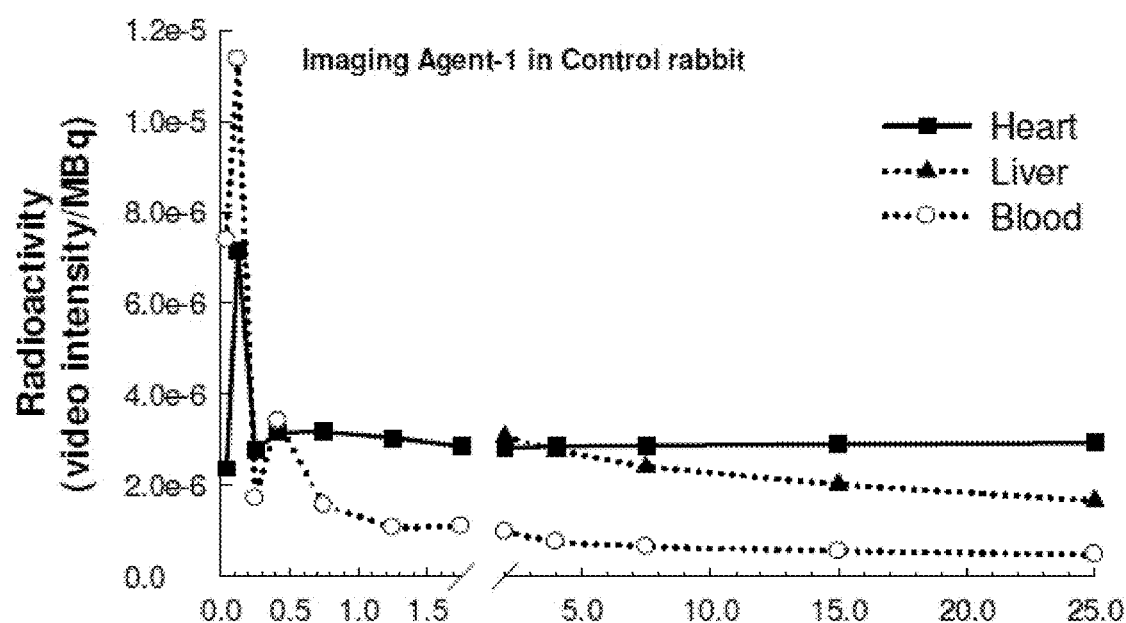
Figure 13C:
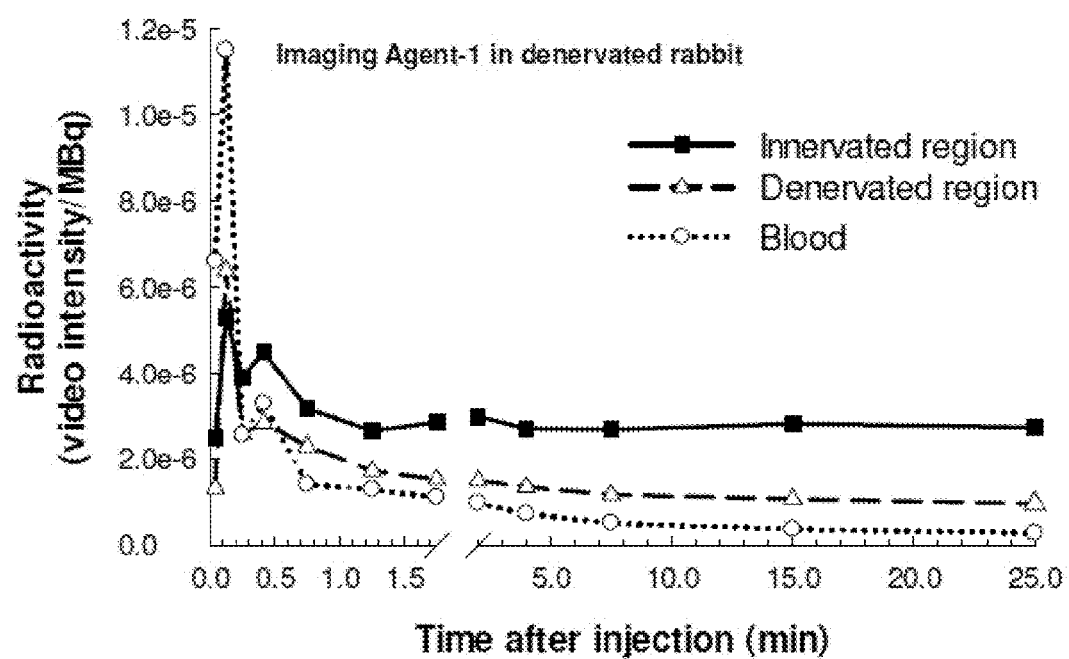

FIG. 13A-FIG. 13C shows representative time-activity curves (TAC) derived from Imaging Agent-2 and Imaging Agent-1 images in the same control rabbit (FIG. 13A and FIG. 13B) as shown in FIG. 11, and from Imaging Agent-1 images in the denervated rabbit (FIG. 13C) as shown in FIG. 12. Regions of interest were selected from the anterior wall of the LV (heart), liver and LV chamber (blood) in the control rabbit, and from the non-defect area of the LV anterior wall (innervated region) and the defect area (denervated region). TACs were expressed as video intensity unit corrected by injected dose (MBq). For visual simplicity, only TACs of the heart and blood were shown in the first 2 minutes. Unlike Imaging Agent-2 which reached an uptake plateau phase immediately after injection, Imaging Agent-1 washed quickly from the heart initially and them reached a plateau phase.

Figure 14:
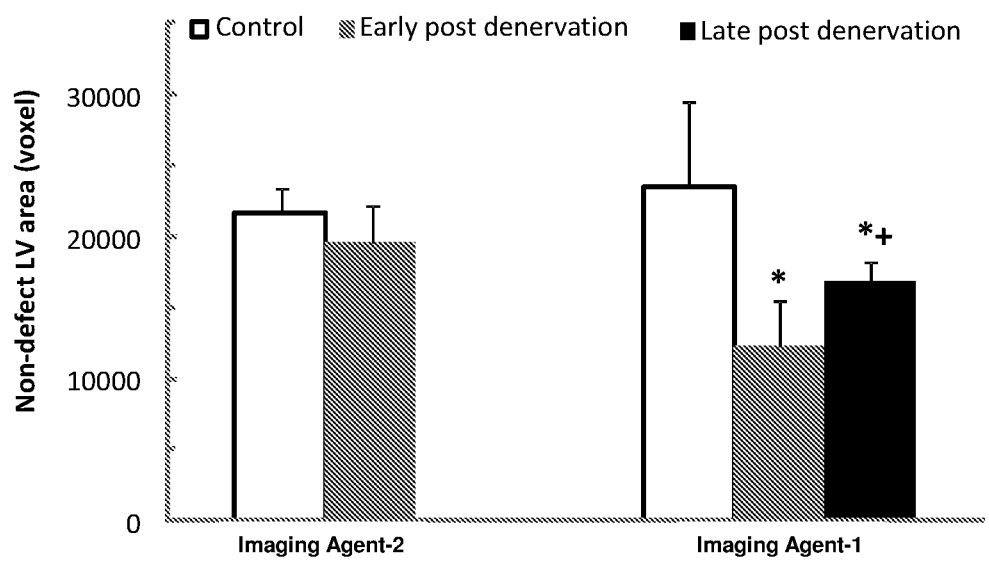
FIG. 14 shows image quantification to assess non-defect left ventricular areas in rabbits at varying time points according to some embodiments.

Comparison of Non-Defect LV Areas Detected by Imaging Agent-1 and Imaging Agent-2:

The innervated and perfused LV areas, which were defined as total LV volume with radioactive intensity ≥50% of the maximal activity in cardiac images of Imaging Agent-1 and Imaging Agent-2, were compared between sham control (n=3-5) and RCSD (n=8-14) rabbits (FIG. 14). The perfused LV region detected by Imaging Agent-2 imaging was 21594±1805 voxels in control rabbits, similar to the perfused area detected in RCSD rabbits. However, Imaging Agent-1 imaging revealed the denervated region in RCSD rabbits, and the innervated area (non-defect area) decreased by 48% compared to the control at 2 weeks (Early) post cardiac phenol denervation. Following the recovery from 2 to 12 weeks (Late), the denervated area recovered partially and the innervated area increased by 37%, significantly larger than that at 2 weeks but still less than in sham control rabbits.

FIG. 14 shows image quantification to assess non-defect left ventricular areas (normal perfused and innervated areas detected by Imaging Agent-2 and Imaging Agent-1 imaging respectively) in rabbits of control (n=3-5), and 2 weeks (Early, n=11-14) and 12 weeks (Late, n=8) post denervation. Regional phenol denervation did not impair myocardial perfusion, but reduced the innervated area detected by Imaging Agent-1 at 2 weeks post denervation. The innervated area increased at 12 weeks, indicating re-innervation. * indicates p<0.05 vs. control and + indicates p<0.05 vs. early time point.

Effect of Regional Cardiac Denervation on Dofetilide Induced ECG Changes:

Changes in ECG induced by iv infusion of dofetilide, an antiarrhythmic drug, were investigated in sham control (n=6) and RCSD (n=8) rabbits at 3 weeks after surgery.

ECG waveform was normal with regular cardiac rhythm (FIG. 15A) and baseline values of HR and $QT_{cf}$ were comparable (Table 4) in the two groups before drug infusion. Intravenous administration of dofetilide induced bradycardia and QT prolongation. Dofetilide induced bradycardia was similar in the two rabbit groups at doses of both 1 and 4 µg/kg/min (FIG. 15B). In contrast, dofetilide at a dose of 4 µg/kg/min increased $QT_{cf}$ interval to a greater extent than at 1 µg/kg/min, and the $QT_{cf}$ prolongation was significantly more severe in RCSD rabbits than the control at both dose levels (FIG. 15C). In addition, dofetilide (4 µg/kg/min) induced PVC and TdP, and the frequency of these events in RCSD rabbits was high, but did not reach statistical significance compared to the sham control (Table 4).

Figure 15A:
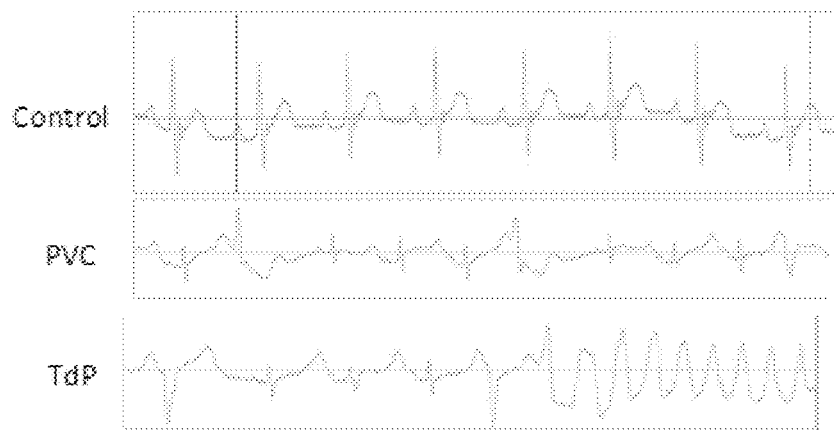
FIG. 15A shows examples of ECG tracings in rabbits before and during dofetilide infusion.
Figure 15B:
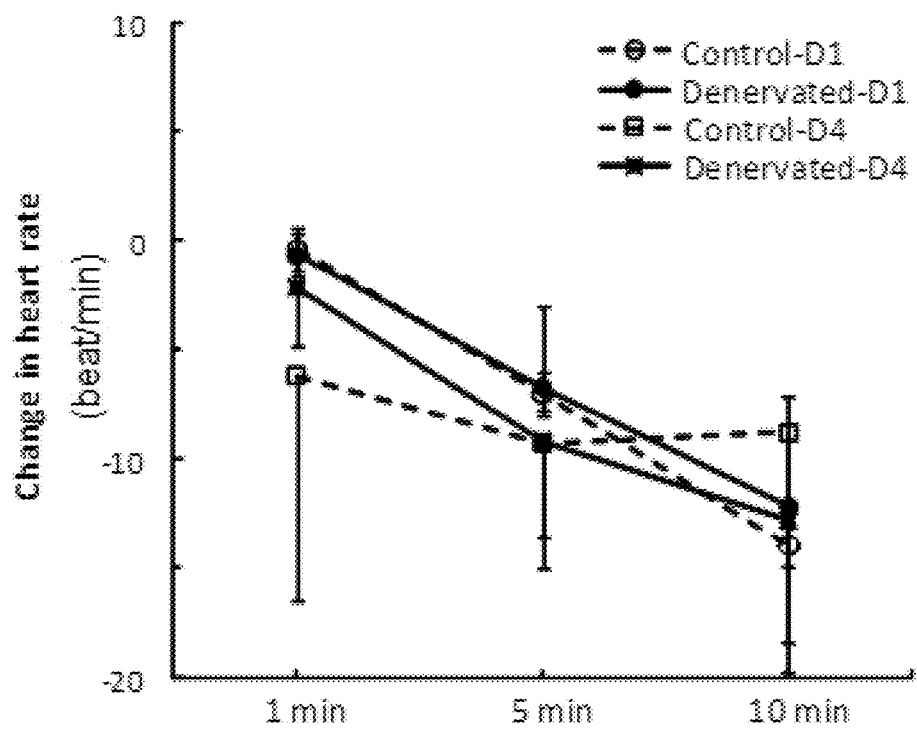
FIG. 15B and FIG. 15C show changes in heart rate (HR) and $QT_{cf}$ interval in rabbits, according to some embodiments.
Figure 15C:
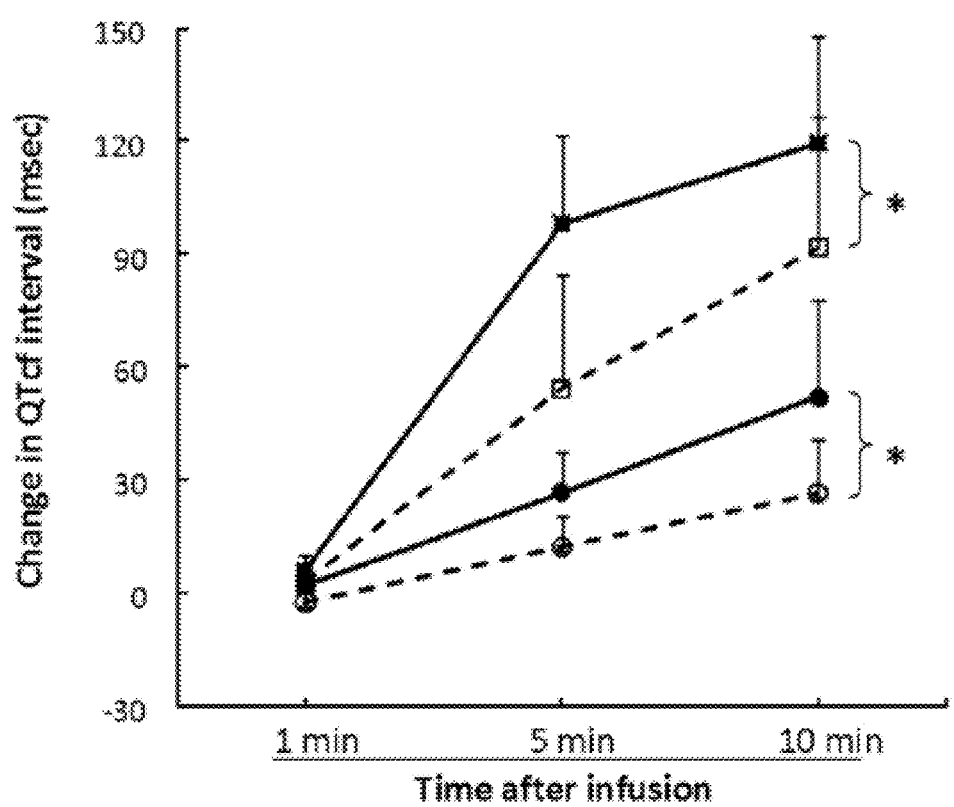

FIG. 15A shows examples of ECG tracings in rabbits before and during dofetilide infusion. Before infusion (Control), ECG was normal with regular rhythm. During the infusion, arrhythmia was observed with premature ventricular contractions (PVC) and torsade de pointes (TdP). FIG. 15B and FIG. 15C show comparison of changes in heart rate (HR) and $QT_{cf}$ interval (corrected by Fridericia method) between sham control (n=6) and regional cardiac denervated (n=8) rabbits iv infused with dofetilide at doses of 1 and 4 µg/kg/min for 10 minutes. Dofetilide infusion induced bradycardia and $QT_{cf}$ prolongation. In contrast to changes in HR (similar between control and denervated groups), dofetilide increased $QT_{cf}$ interval more in denervated than in control rabbits at both doses. Control-D1 and -D4: control rabbits infused with dofetilide at 1 and 4 µg/kg/min; Denervated-D1 and D4: denervated rabbits with dofetilide at 1 and 4 µg/kg/min. * indicates p<0.05.

Discussion:

Increased NA release and reduced neuronal NAT function in the heart are associated with HF. Imaging with a NAT substrate, such as $^{123}$I-MIBG or $^{11}$C-HED, to assess cardiac neuronal function has demonstrated robust values in predication of cardiac events and treatment stratification in HF patients (Carrio, J Nucl Med. 2001; 42(7):1062-76; Jacobson et al., J Am Coll Cardiol. 2010; 55(20):2212-21; Pietila et al., Eur J Nucl Med. 2001; 28(3):373-6; Boogers et al., J Am Coll Cardiol. 2010; 55(24):2769-77). In the present study, the NAT association of Imaging Agent-1, an MIBG analog designed also as a NAT substrate, was investigated in cells with NAT expression. These cells have been used previously for evaluation of MIBG and its analogs (Vaidyanathan et al., J Nucl Med. 1997; 38(2):330-4; Ko et al., Eur J Nucl Med Mol Imaging. 2008; 35(3):554-61). Imaging Agent-1 cell uptake was inhibited by non-radioactive MIBG, NA or self in a concentration-dependent fashion with comparable $IC_{50}$ values in a low µM range, similar to our previously reported $K_m$ values of $^{19}$F—Imaging Agent-1 and NA (Yu et al., Circ Cardiovasc Imaging. 2011; 4(4):435-43). Furthermore, blockade of NAT with desipramine reduced the uptake of all these test agents by more than 90%. These findings suggest that Imaging Agent-1, NA and MIBG share the same transporter, NAT, and possess similar NAT association at least in NAT expressing cells.

Imaging Agent-1 radiolabeled with $^{18}$F is a PET imaging agent. It has demonstrated better uptake ratio of the heart to liver and quicker liver clearance than $^{123}$I-MIBG in rats and nonhuman primates (NHP) (Yu et al., Circ Cardiovasc Imaging. 2011; 4(4):435-43). Consistently in this study, cardiac image quality of Imaging Agent-1 was excellent with low activity in adjacent organs (FIG. 11). Immediately after the initial Imaging Agent-1 heart uptake in rabbits, a quick, transit washout phase was observed and the retention reached a plateau phase (FIG. 13B). This kinetics profile is similar to the observations of Imaging Agent-1 in NHPs (Yu et al., Circ Cardiovasc Imaging. 2011; 4(4):435-43), but seems to differ from $^{11}$C-HED where the cardiac uptake plateaus after the initial uptake (Raffel et al., J Med Chem. 2007; 50(9):2078-88; Munch et al., Circulation. 2000; 101 (5):516-23). This may be due to the uptake kinetics of each imaging agent: integration of various $k_1$, $k_2$ and $k_3$ (rate constants for imaging agent distribution into extracellular space, washout from extracellular space back into the blood and transportation into the neuron via the NAT from the extracellular space, respectively). In a kinetics study comparing phenethylguanidine analogs, Raffel et al suggested that an analog with rate-limited neuronal uptake ($k_3 \ll k_2$, depending more on NAT function) is superior to no rate-limited uptake ($k_3 \gg k_2$, depending more on flow, such as Imaging Agent-2 (Nekolla et al., Circulation. 2009; 119(17): 2333-42) in evaluation of cardiac neuronal function (Raffel et al., J Med Chem. 2007; 50(9):2078-88). The TACs generated in rabbits, together with our previous observation in NHPs (high initial cardiac activity followed by a quick washout), support the notion that Imaging Agent-1 cardiac uptake may be rate limited ($k_3 \ll k_2$), depending more on neuronal function than flow. However, based on the instantaneous MIBG heart extraction fraction measured within 40 seconds after injection and flow increased by infusion of dipyridamole in pigs, Glowniak et al demonstrated that MIBG heart uptake is flow dependent (Glowniak et al., J Nucl Med. 1992; 33(5):716-23). In contrast to Imaging Agent-1 initial rapid washout, myocardial TACs of Imaging Agent-2 showed a rapid uptake to a plateau (FIG. 13A), supporting the findings that Imaging Agent-2 myocardial uptake may depend on changes in flow at a large range of flow rates (Yu et al., J Nucl Cardiol. 2007; 14(6):789-98; Nekolla et al., Circulation. 2009; 119(17):2333-42). A small and slow myocardial Imaging Agent-2 washout was seen from 5 to 25 minutes post injection, which differs from our observations in other species: rats, pigs, NHPs and humans (Yu et al., J Nucl Cardiol. 2007; 14(6):789-98; Nekolla et al., Circulation. 2009; 119(17):2333-42; Sherif et al., Circ Cardiovasc Imaging. 2009; 2(2):77-84; Maddahi et al., J Nucl Med. 2011; 52(9):1490-8). This could be due to species variation.

Moreover, in this study, Imaging Agent-1 imaging demonstrated clear detection of regional sympathetic denervation in the heart. Animal models of sympathetic denervation induced by local phenol application on the myocardial surface have been widely utilized in assessment of regional sympathetic denervation previously (Minardo et al., *Circulation.* 1988; 78(4):1008-19; Rimoldi et al., *Eur J Nucl Med Mol Imaging.* 2007; 34(2):197-205). Imaging with $^{123}$I-MIBG or $^{11}$C-HED detected the denervated area in the heart. This model differs from the coronary ligation induced myocardial infarction model in that there is minimal flow interruption and regional cardiac retention of an imaging agent is little affected by flow. A similar scenario of regional sympathetic denervation is seen clinically in patients with non-ischemic cardiomyopathy, such as diabetes (Scholte et al., *Eur J Nucl Med Mol Imaging.* 2010; 37(9):1698-705). In agreement with $^{123}$I-MIBG and $^{11}$C-HED, Imaging Agent-1 imaging identified the denervated region corresponding to the area that phenol had been applied. The reduced local Imaging Agent-1 uptake was not the consequence of myocardial perfusion interruption as Imaging Agent-2 imaging showed normal uptake in the denervated area (FIG. 12). Additionally, myocardial TACs in the RCSD rabbit (FIG. 13c) also confirmed that Imaging Agent-1 was initially delivered by blood to the denervated region, similar to the innervated area, and then quickly cleared from that region to a lower level consistent with reduced NAT function (low $k_3$) associated with the denervation. Cardiac imaging detection of regional sympathetic neuronal dysfunction has been suggested to predict ventricular tachycardia, arrhythmia and increased risk of cardiac death (Dae et al., *Circulation.* 1997; 96(4):1337-42; Mitrani et al., J Am Coll Cardiol. 1993; 22(5):1344-53; Sasano et al., *J Am Coll Cardiol.* 2008; 51(23):2266-75; Stevens et al., *Circulation.* 1998; 98(10): 961-8; Boogers et al., *J Am Coll Cardiol.* 2010; 55(24): 2769-77; Minardo et al., *Circulation.* 1988; 78(4):1008-19; Calkins et al., *Circulation.* 1993; 88(1):172-9). However, clinical assessment of cardiac neuronal function is not performed routinely. One of the possible reasons may be associated with the lack of an ideal neuronal imaging agent for tomographic imaging. Cardiac PET neuronal imaging has been shown to be superior to SPECT in image quality and identification of neuronal abnormalities (Matsunari et al., *Circ Cardiovasc Imaging.* 2010; 3(5):595-603). Imaging Agent-1 PET imaging showed high image quality and allowed quantification of regional sympathetic innervation/denervation. The innervated region increased over time following phenol denervation in the heart (FIGS. 12 and 14), consistent with reinnervation occurring over time (Odaka et al., *J Nucl Med.* 2001; 42(7):1011-6).

Regional denervated myocardium has been suggested to exhibit comparable effective refractory period (ERP) to normal innervated area but increased sensitivity to NA induced ERP shortening (Minardo et al., *Circulation.* 1988; 78(4):1008-19) or increased ERP but similar sensitivity to NA induced ERP shortening (Calkins et al., *Circulation.* 1993; 88(1):172-9). Regardless of the different findings, heterogeneity of sympathetic innervation may render the heart abnormal electrophysiologically and increase sensitivity to drugs which interact with cardiac ion channel conductance, such as antiarrhythmic drugs (Nattel, *J Cardiovasc Electrophysiol.* 1999; 10(2):272-82). In this study, we observed a marked increase in QTc prolongation in regional cardiac denervated rabbits during dofetilide infusion, even though the baseline values of HR and QTc interval were comparable to the sham control. The dose of dofetilide used in this study is in a range of clinical doses (500 μg twice a day with >90% bioavailability in humans, Package Insert). Dofetilide is known to increases ERP (Lenz et al., *Pharmacotherapy.* 2000; 20(7):776-86) and this action seems to be potentiated by regional denervation or innervation heterogeneity. Similarly, in humans, an antiarrhythmic drug (ibutilide) induced QT prolongation, not changes in HR, was exaggerated when the autonomic system was impaired (Smith et al., *J Cardiovasc Electrophysiol.* 2007; 18(9):960-4). These findings suggested that denervation in the heart enhances cardiac risk to some antiarrhythmic drug treatments, and this risk associated with innervation dysfunction can potentially be assessed by Imaging Agent-1 imaging.

Conclusion:

Imaging Agent-1 was designed as an $^{18}$F labeled NAT substrate for cardiac sympathetic neuronal imaging. It exhibits high association with NAT and its neuronal uptake may be NAT mediated. Cardiac imaging demonstrates high image quality with homogeneous heart uptake and rapid blood and liver clearance in controls, and clear detection and quantification of regional denervated areas in cardiac denervated animals. Since cardiac denervation increased the sensitivity to dofetilide induced electrophysiological changes, Imaging Agent-1 cardiac imaging may provide a means to identify patients with enhanced risk to dofetilide-like antiarrhythmic agents.

TABLE 4

Control values and dofetilide induced events in control and regional cardiac denervated rabbits

|  | Control value (Before dofetilide infusion) | | Dofetilide induced events (4 μg/kg/min iv infusion) | |
| --- | --- | --- | --- | --- |
|  | HR (beat/min) | QT$_{cf}$ (msec) | PVC | TdP |
| Sham (n = 6) | 158 ± 10 | 236 ± 5 | 3 (50%) | 1 (17%) |
| Denervated (n = 8) | 169 ± 7 | 246 ± 8 | 5 (63%) | 2 (25%) |

HR: heart rate, QT$_{cf}$: QT interval corrected by Fridericia method, PVC: premature ventricular contraction, TdP: torsade de pointes.

Example 39

The following example describes studies completed on rabbits to assess cardiac perfusion and innervation mismatch following myocardial infarction. The imaging agent employed for determining innervation was Imaging Agent-1 or a salt thereof. The imaging agent employed for imaging cardiac perfusion was Imaging Agent-2.

In this example, the rabbit model of myocardial infarction (MI) comprises a surgical 30-min left coronary temporary occlusion followed by reperfusion. The rabbits recovered from the surgery.

For cardiac PET imaging with Imaging Agent-1 and Imaging Agent-2, the imaging was performed in a 2-day interval. The MI rabbits were assessed at 4, 13, and 46 weeks post ischemia-reperfusion injury. The innervation defect (e.g., denervation) was determined from the Imaging Agent-1 images whereas that of the perfusion defect was determined from the Imaging Agent-2 images. The images were analyzed using the MunichHeart™ software package. The defect area is defined as a percentage of left ventricle (% LV) area with radioactivity levels <50% of the maximum radioactivity in the LV.

Figure 16A:
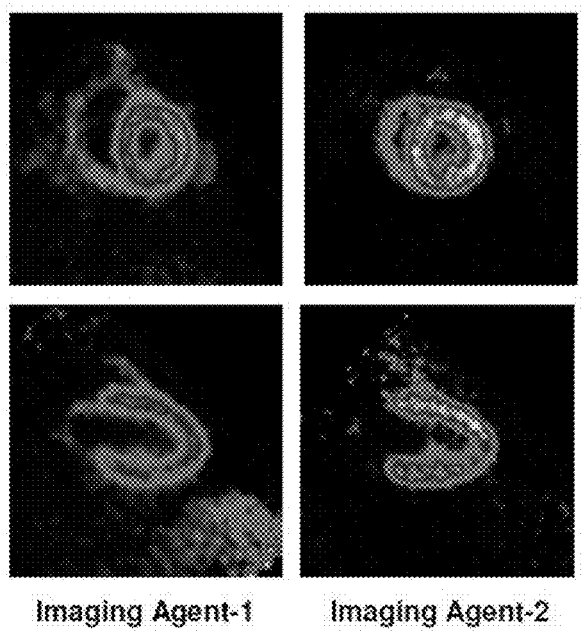
FIG. 16A-FIG. 16C show images obtained using either Imaging Agent-1 or Imaging Agent-2, for a control rabbit, a rabbit having global denervation, and a rabbit having regional denervation.
Figure 16B:
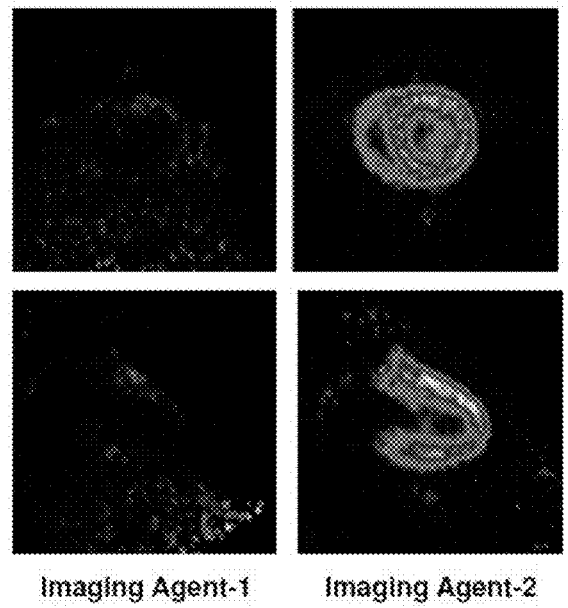
Figure 16C:
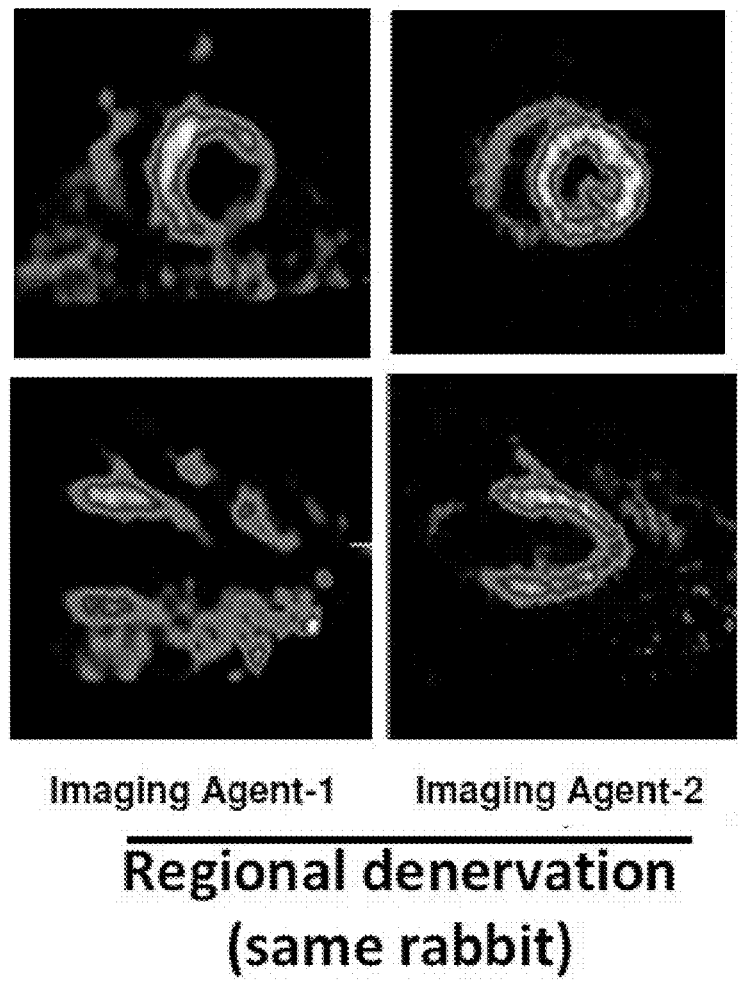

FIG. 16A shows images of a heart of a control rabbit using both Imaging Agent-1 and Imaging Agent-2. As can be observed in the images, the areas of uptake in the heart of the imaging agents are approximately equal for both agents. In contrast, FIGS. 16B and 16C shows images of a heart of rabbits having global denervation and regional denervation, respectively. As can be observed in the images, the areas of uptake of Imaging Agent-1 in the heart is less than the areas of uptake of Imaging Agent-2, indicating a mismatch between innervation and perfusion.

Figure 17:
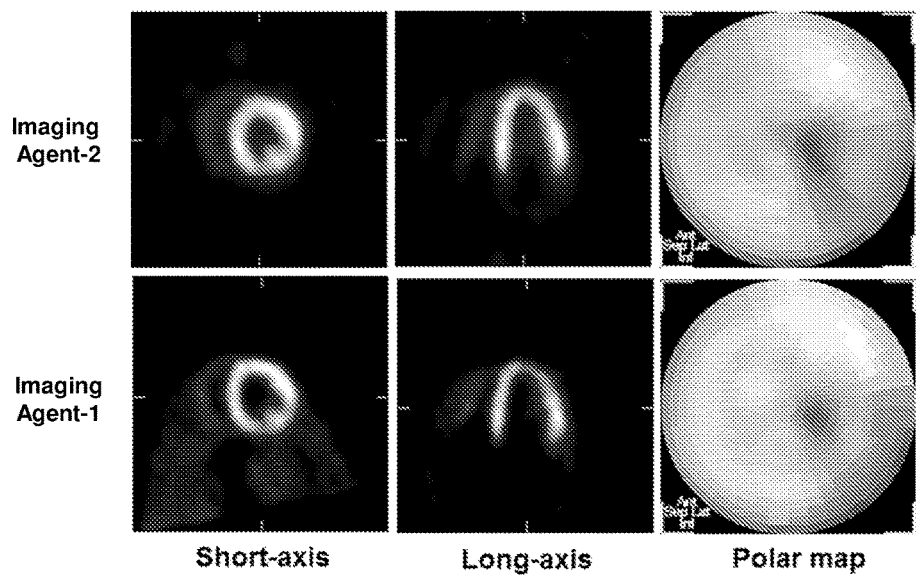
FIG. 17 shows images obtained using either Imaging Agent-1 or Imaging Agent-2, and corresponding polar maps for a control rabbit.
Figure 18A:
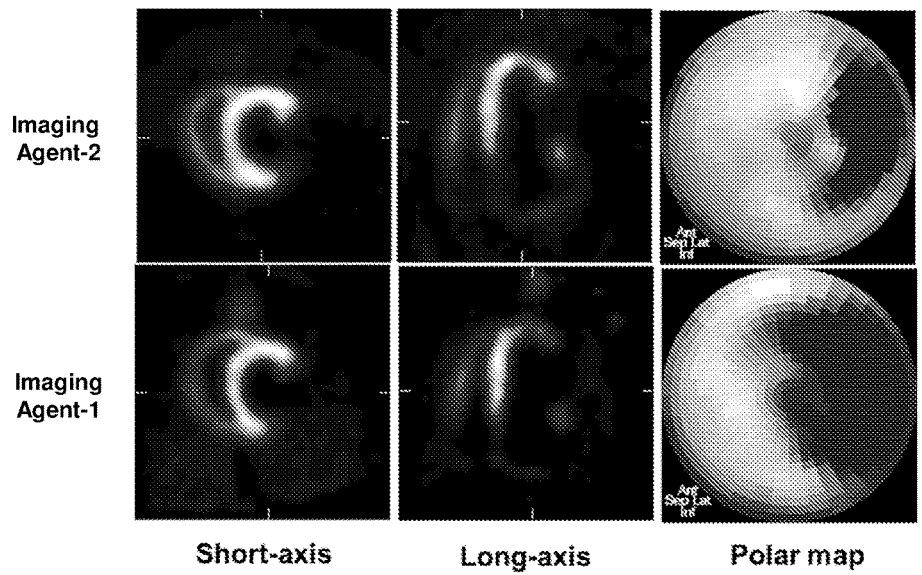
FIG. 18A-FIG. 18C show images obtained using either Imaging Agent-1 or Imaging Agent-2, and corresponding polar maps for a rabbit having regional denervation at 4 weeks, 13 weeks, and 46 weeks post-surgery.
Figure 18B:
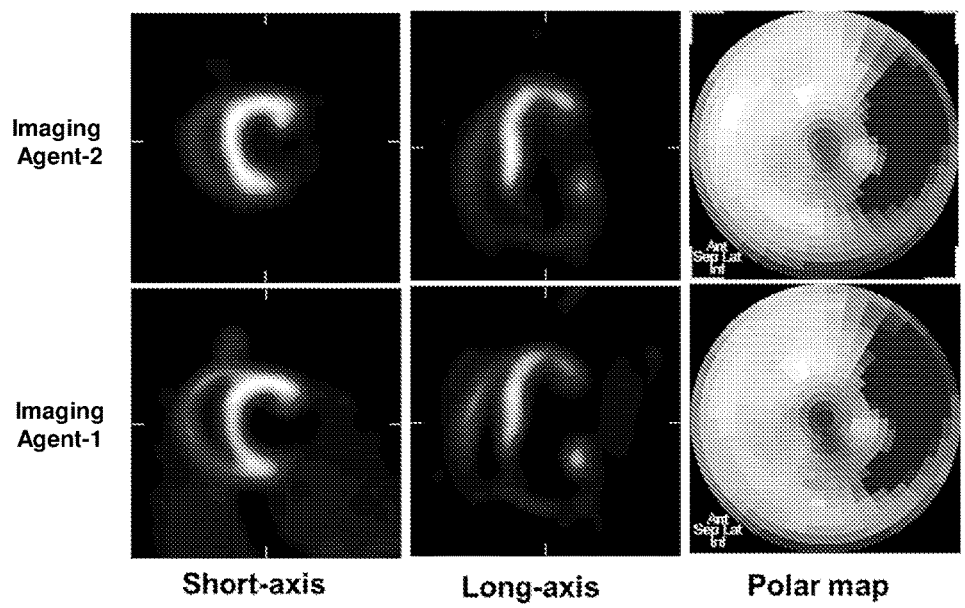
Figure 18C:
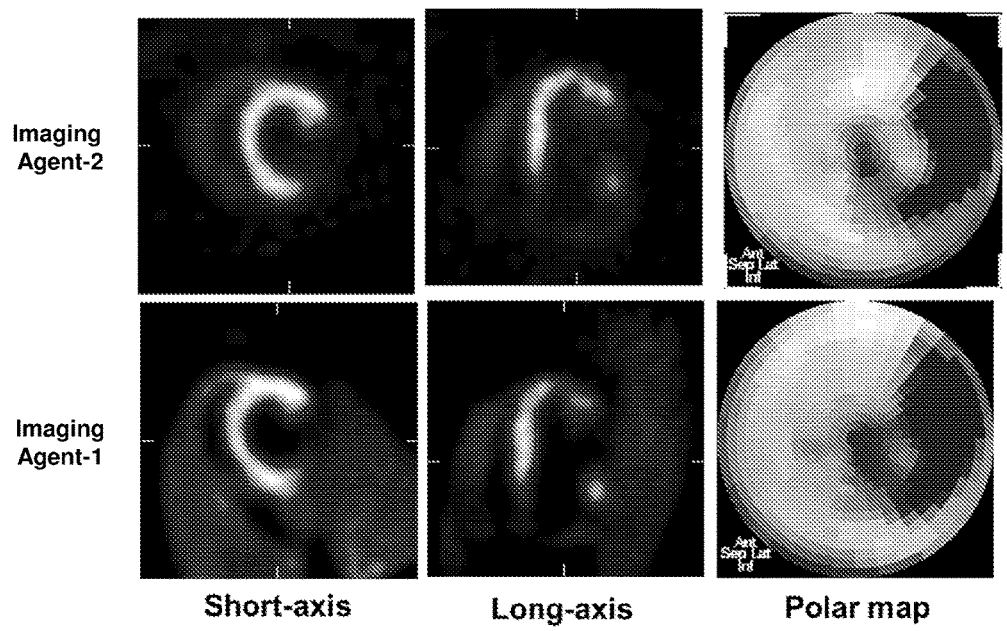
Figure 18D:
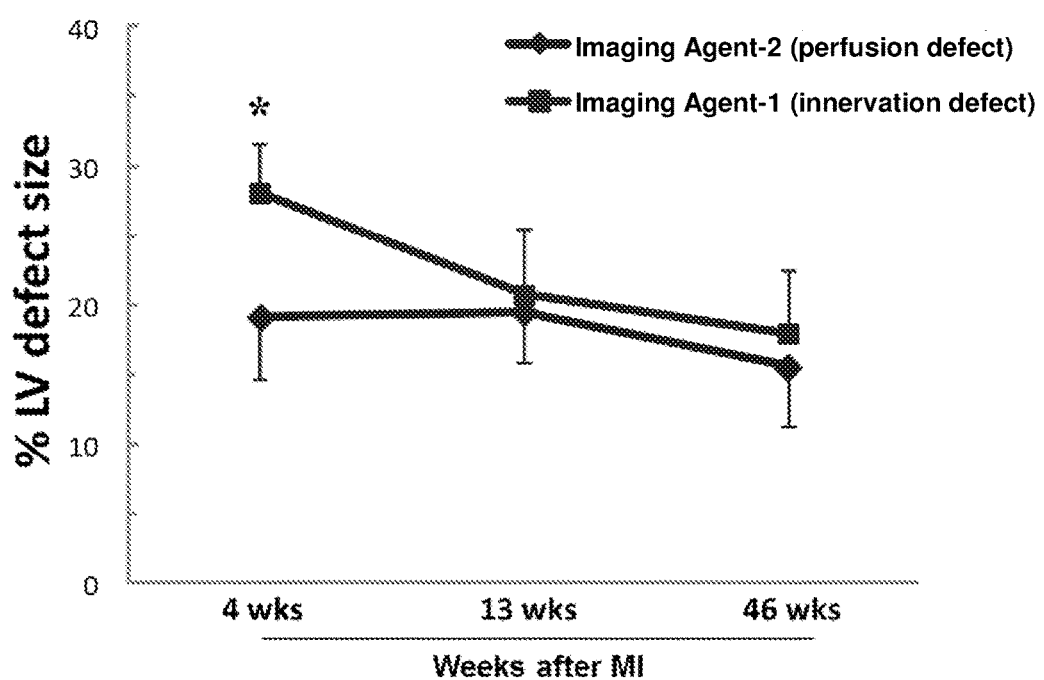
FIG. 18D shows a plot of the % LV defect versus time for the images shown in FIG. 18A-FIG. 18C.

FIG. 17 shows images of a heart of a control rabbit using both Imaging Agent-1 and Imaging Agent-2, as well as the corresponding polar maps. As can be observed in the images and the polar maps, the areas of uptake in the heart of the imaging agents is approximately equal for both agents. FIG. 18A-FIG. 18C show images of a heart of a rabbit 4, 13, and 46 weeks following the ischemia-reperfusion injury using both Imaging Agent-1 and Imaging Agent-2, as well as their corresponding polar maps. As can be observed in the images and the polar maps, the areas of uptake of Imaging Agent-1 in the heart is less than the areas of uptake of Imaging Agent-2, indicating a mismatch between innervation and perfusion. The mismatch decreased with time, indicating reinnervation. FIG. 18D shows a plot of the % LV defect versus time for the images shown in FIG. 18A-FIG. 18C. Accordingly, it may be beneficial to evaluate the mismatch at an early time point following acute MI.

Example 40

In imaging, noise filtration (NF) is preferred so that noise does not negatively impact diagnostic information contained in the image. NF with optimized filter parameters (OFP) may minimize count-related uncertainty while preserving diagnostic information. A method is described using a cardiac phantom to determine the OFP for the Phase 3 study of Imaging Agent-2 injection.

Based on Standardized Uptake Values (SUVs) in normal patient myocardium, a cardiac phantom fitted with a 45° defect insert was loaded with 12.3 uCi/ml in the myocardium and 3.1 uCi/ml in the defect to simulate a 70 kg patient injected with midpoint doses for imaging at rest of 2.75 mCi, during pharmacological stress of 6.25 mCi, and during exercise stress of 9.25 mCi. A GE Discovery ST PET/CT was then employed to scan the phantom in both 3D and 2D modes. Multiple PET image data sets were first reconstructed from the listmode rebinning to generate realistic 3D perfusion images (3D-PI) and 2D ECG-gated images (2D-G1), then filtered with a 3D Gaussian filter (FWHM=4-20 mm). Defect contrast (DC) was then calculated to determine OFP for 3D-PI with <5% DC degradation. Left ventricular volume (LVV) was quantified with the QGS cardiac tool to determine OFP for 2D-G1 while maintaining >90% accuracy of LVV. The signal-to-noise (SNR), as the mean/SD in normal myocardium was assessed with respect to the degree of filtering. Finally, in order to test OFP adequacy in a clinical setting, 10 patient images generated on a GE Discovery ST PET/CT were processed with the appropriate OFP value then visually assessed using an image quality score (IQS) (excellent=3, good=2, fair=1, poor=0). The imaging parameters applied are set forth in Table 5 and the results presented in Table 6.

TABLE 5

| Imaging Parameters | | | |
|---|---|---|---|
| | Rest | Pharmacological | Exercise |
| Normal Myocardial SUV from Phase II | 4.8 | 11.1 | 6.7 |
| Mean Phase III Dose (mCi) | 2.75 (2.5-3.0) | 6.25 (6.0-6.5) | 9.25 (9.0-9.5) |
| Assumed Patient Weight (kg) | 70 | 70 | 70 |
| F18 Activity Concentration in Myocardial Wall (uCi/ml) | 0.184 | 0.984 | 0.880 |
| Defect Severity | 75% | 75% | 75% |
| Imaging Duration for 3D Perfusion (sec) | 600 | 600 | 600 |
| Imaging Duration for 2D Gated (sec) | 600 | 600 | 600 |

TABLE 6

| | Results | | | | | | | | | | | | | |
|---|---|---|---|---|---|---|---|---|---|---|---|---|---|---|
| | FWHM (mm), DC Degradation (%), SNR | | | | | | | FWHM (mm), LVV Accuracy (%) | | | | | | |
| Rest | 4, | 6, | 8, | 10, | 12, | 15, | 20, | 4, 50 | 6, 55 | 8, 65 | 10, | 12, | 15, | 20, |
| | 1.6, | 3.1, | 4.9, | 7.8, | 11.7, | 19.1, | 33.2, | | | | 70 | 78.3 | 93.3 | 65.2 |
| | 7.25 | 7.8 | 8.0 | 8.2 | 8.2 | 8.0 | 7.5 | | | | | | | |
| Pharm | 4, | 6, | 8, | 10, | 12, | 15, | 20, | 4, | 6, | 8, | 10, | 12, | 15, | 20, |
| | 3.1, | 3.1, | 4.4, | 7.1, | 11.1, | 18.8, | 33.0 | 66.7 | 71.7 | 76.7 | 83.3 | 93.3 | 91.7 | 74.3 |
| | 8.1 | 8.3 | 8.5 | 8.8 | 8.7 | 8.4 | 7.6 | | | | | | | |
| Exercise | 4, | 6, | 8, | 10, | 12, | 15, | 20, | 4, | 6, | 8, | 10, | 12, | 15, | 20, |
| | 0.4, | 2.7, | 3.2, | 7.2, | 12.2, | 21.1, | 35.7, | 65.1 | 72.2 | 77.1 | 84.2 | 92.7 | 91.2 | 72.5 |
| | 8.1 | 8.3 | 8.5 | 8.7 | 8.6 | 8.3 | 7.6 | | | | | | | |

Using preferred SNR and DC degradation (<5%) settings, the optimal filter parameters (OFP) for rest, and pharmacological and exercise induced stress 3D perfusion imaging, were found to be FWHM=8.0 mm, while the OFP for rest and pharmacological and exercise inducedstress 2D gated imaging were found to be 15.0 mm and 12.0 mm, respectively. The mean IQS for the 3D erfusion images were 2.6±0.7 while that for the 2D gated images were 2.2±0.6 (data not shown).

A cardiac phantom simulation using known patient myocardial SUVs is an effective method to determine an optimal noise filter parameter set that can produce high-quality diagnostic images when using an Imaging Agent-2 injection.

TERMS AND EQUIVALENTS

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present invention.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified unless clearly indicated to the contrary. Thus, as a non-limiting example, a reference to "A and/or B," when used in conjunction with open-ended language such as "comprising" can refer, in one embodiment, to A without B (optionally including elements other than B); in another embodiment, to B without A (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed:

1. A method of determining perfusion and innervation mismatch in a portion of a human subject, comprising:
   administering to the subject a first imaging agent and acquiring at least one first image of a portion of the subject, wherein the first imaging agent is employed to image perfusion;
   administering to the subject a second imaging agent and acquiring at least one second image of the portion of the subject, wherein the second imaging agent is employed to image innervation; and
   determining regional mismatch of innervation and perfusion areas in the portion of the subject based at least in part on the at least one first image and the at least one second image, wherein the first imaging agent has the structure:

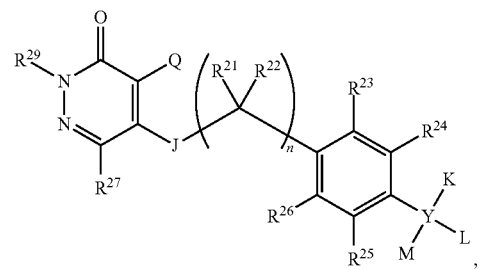

wherein
   J is selected from the group consisting of $N(R^{28})$, S, O, $C(=O)$, $C(=O)O$, $NHCH_2CH_2O$, a bond, and $C(=O)N(R^{27})$;
   when present, K is selected from the group consisting of hydrogen, alkoxyalkyl optionally substituted with an imaging moiety, alkyloxy optionally substituted with an imaging moiety, aryl optionally substituted with an imaging moiety, $C_1$-$C_6$ alkyl optionally substituted with an imaging moiety, heteroaryl optionally substituted with an imaging moiety, and an imaging moiety;

when present, L is selected from the group consisting of hydrogen, alkoxyalkyl optionally substituted with an imaging moiety, alkyloxy optionally substituted with an imaging moiety, aryl optionally substituted with an imaging moiety, $C_1$-$C_6$ alkyl optionally substituted with an imaging moiety, heteroaryl optionally substituted with an imaging moiety, and an imaging moiety;

M is selected from the group consisting of hydrogen, alkoxyalkyl optionally substituted with an imaging moiety, alkyloxy optionally substituted with an imaging moiety, aryl optionally substituted with an imaging moiety, $C_1$-$C_6$ alkyl optionally substituted with an imaging moiety, heteroaryl optionally substituted with an imaging moiety, and an imaging moiety; or L and M, together with the atom to which they are attached, may form a three- or four-membered carbocyclic ring;

Q is halo or haloalkyl;

n is 0, 1, 2, or 3;

$R^{21}$, $R^{22}$, $R^{27}$, and $R^{28}$ are independently selected from hydrogen, $C_1$-$C_6$ alkyl optionally substituted with an imaging moiety, and an imaging moiety;

$R^{23}$, $R^{24}$, $R^{25}$, and $R^{26}$ are independently selected from hydrogen, halogen, hydroxyl, alkyloxy, $C_1$-$C_6$ alkyl optionally substituted with an imaging moiety, and an imaging moiety; $R^{29}$ is $C_1$-$C_6$ alkyl optionally substituted with an imaging moiety; and Y is selected from the group consisting of a bond, carbon, and oxygen; provided that when Y is a bond, K and L are absent, and M is selected from the group consisting of aryl optionally substituted with an imaging moiety and heteroaryl optionally substituted with an imaging moiety; and provided that when Y is oxygen, K and L are absent, and M is selected from hydrogen, alkoxyalkyl optionally substituted with an imaging moiety, aryl optionally substituted with an imaging moiety, $C_1$-$C_6$ alkyl optionally substituted with an imaging moiety, and heteroaryl optionally substituted with an imaging moiety;

provided that at least one imaging moiety is present, or a salt thereof.

2. The method of claim 1, wherein the first imaging agent has the structure:

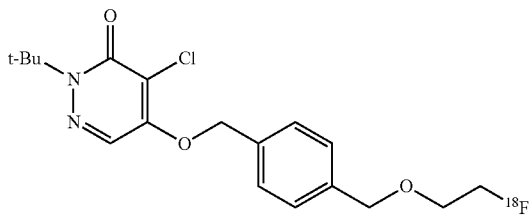 [SMILES: CC(C)(C)n1ncc(OCc2ccc(COCC[18F])cc2)c(Cl)c1=O]

or a pharmaceutically acceptable salt thereof.

3. The method of claim 2, wherein the second imaging agent has the structure:

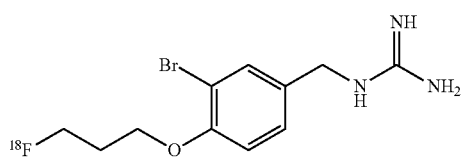 [SMILES: N=C(N)NCc1ccc(OCCC[18F])c(Br)c1]

or a pharmaceutically acceptable salt thereof.

4. The method of claim 1, wherein the second imaging agent is of the formula:

$$R^0—Ar-L-R^1$$

wherein

Ar is substituted or unsubstituted, monocyclic or bicyclic aryl or substituted or unsubstituted, monocyclic or bicyclic heteroaryl;

L is a bond; substituted or unsubstituted, cyclic or acyclic alkylene; substituted or unsubstituted, cyclic or acyclic alkenylene; substituted or unsubstituted, cyclic or acyclic alkynylene; or substituted or unsubstituted, cyclic or acyclic heteroaliphatic;

$R^1$ is a substituted or unsubstituted nitrogen-containing moiety; and $R^0$ is halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, —$OR^{41}$, —$N(R^{42})_2$, —$SR^{41}$, —$C(=O)R^{41}$, —$C(=O)OR^{41}$, —$C(=O)SR^{41}$, —$C(=O)N(R^{42})_2$, —$OC(=O)R^{41}$, —$OC(=O)OR^{41}$, —$OC(=O)SR^{41}$, —$OC(=O)N(R^{42})_2$, —$NR^{42}C(=O)R^{42}$, —$NR^{42}C(=O)OR^{41}$, —$NR^{42}C(=O)SR^{41}$, —$NR^{42}C(=O)N(R^{42})_2$, —$SC(=O)R^{41}$, —$SC(=O)OR^{41}$, —$SC(=O)SR^{41}$, —$SC(=O)N(R^{42})_2$, —$C(=NR^{42})R^{41}$, —$C(=NR)OR^{41}$, —$C(=NR^{42})SR^{41}$, —$C(=NR^{42})N(R^{42})_2$, —$OC(=NR^{42})R^{41}$, —$OC(=NR^{42})OR^{41}$, —$OC(=NR^{42})SR^{41}$, —$OC(=NR^{42})N(R^{42})_2$, —$NR^{42}C(=NR^{42})R^{42}$, —$NR^{42}C(=NR)OR^{41}$, —$NR^{42}C(=NR^{42})SR^{41}$, —$NR^{42}C(=NR^{42})N(R^{42})_2$, —$SC(=NR^{42})R^{41}$, —$SC(=NR^{41})OR^{41}$, —$SC(=NR^{42})SR^{41}$, —$SC(=NR^{42})N(R^{42})_2$, —$C(=S)R^{41}$, —$C(=S)OR^{41}$, —$C(=S)SR^{41}$, —$C(=S)N(R^{42})_2$, —$OC(=S)R^{41}$, —$OC(=S)OR^{41}$, —$OC(=S)SR^{41}$, —$OC(=S)N(R^{42})_2$, —$NR^{42}C(=S)R^{42}$, —$NR^{42}C(=S)OR^{41}$, —$NR^{42}C(=S)SR^{41}$, —$NR^{42}C(=S)N(R^{42})_2$, —$SC(=S)R^{41}$, —$SC(=S)OR^{41}$, —$SC(=S)SR^{41}$, —$SC(=S)N(R^{42})_2$, —$S(=O)R^{41}$, —$SO_2R^{41}$, —$NR^{42}SO_2R^{41}$, —$SO_2N(R^{42})_2$, —CN, —SCN, or —$NO_2$;

each occurrence of $R^{41}$ is independently hydrogen, optionally substituted alkyl, optionally substituted alkenyl, optionally substituted alkynyl, optionally substituted carbocyclyl, optionally substituted heterocyclyl, optionally substituted aryl, or optionally substituted heteroaryl; and each occurrence of $R^{42}$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, or an amino protecting group, or two $R^{42}$ groups are joined to form an optionally substituted heterocyclic ring; and $R^0$ or $R^1$ is substituted with an imaging moiety selected from the group consisting of $^{18}F$, $^{76}Br$, $^{124}I$, and $^{131}I$, or is associated with an imaging moiety selected from the group consisting of $^{64}Cu$, $^{89}Zr$, $^{99m}Tc$, and $^{111}In$ through a chelator, or is an imaging moiety selected from the group consisting of $^{18}F$, $^{76}Br$, $^{124}I$, and $^{131}I$;

or a salt thereof.

5. The method of claim 1, wherein the second imaging agent is of the formula of the formula:

$$R^0—Ar-L-R^1$$

wherein

Ar is substituted or unsubstituted, monocyclic or bicyclic aryl or substituted or unsubstituted, monocyclic or bicyclic heteroaryl;

L is a bond; substituted or unsubstituted, cyclic or acyclic alkylene; substituted or unsubstituted, cyclic or acyclic alkenylene; substituted or unsubstituted, cyclic or acyclic alkynylene; or substituted or unsubstituted, cyclic or acyclic heteroaliphatic;

$R^1$ is a substituted or unsubstituted nitrogen-containing moiety; and $R^0$ is halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, $-OR^{41}$, $-N(R^{42})_2$, $-SR^{41}$, $-C(=O)R^{41}$, $-C(=O)OR^{41}$, $-C(=O)SR^{41}$, $-C(=O)N(R^{42})_2$, $-OC(=O)R^{41}$, $-OC(=O)OR^{41}$, $-OC(=O)SR^{41}$, $-OC(=O)N(R^{42})_2$, $-NR^{42}C(=O)R^{42}$, $-NR^{42}C(=O)OR^{41}$, $-NR^{42}C(=O)SR^{41}$, $-NR^{42}C(=O)N(R^{42})_2$, $-SC(=O)R^{41}$, $-SC(=O)OR^{41}$, $-SC(=O)SR^{41}$, $-SC(=O)N(R^{42})_2$, $-C(=NR^{42})R^{41}$, $-C(=NR^{42})OR^{41}$, $-C(=NR^{42})SR^{41}$, $-C(=NR^{42})N(R^{42})_2$, $-OC(=NR^{42})R^{41}$, $-OC(=NR^{42})OR^{41}$, $-OC(=NR^{42})SR^{41}$, $-OC(=NR^{42})N(R^{42})_2$, $-NR^{42}C(=NR^{42})R^{42}$, $-NR^{42}C(=NR^{42})OR^{41}$, $-NR^{42}C(=NR^{42})SR^{41}$, $-NR^{42}C(=NR^{42})N(R^{42})_2$, $-SC(=NR^{42})R^{41}$, $-SC(=NR^{42})OR^{41}$, $-SC(=NR^{42})SR^{41}$, $-SC(=NR^{42})N(R^{42})_2$, $-C(=S)R^{41}$, $-C(=S)OR^{41}$, $-C(=S)SR^{41}$, $-C(=S)N(R^{42})_2$, $-OC(=S)R^{41}$, $-OC(=S)OR^{41}$, $-OC(=S)SR^{41}$, $-OC(=S)N(R^{42})_2$, $-NR^{42}C(=S)R^{42}$, $-NR^{42}C(=S)OR^{41}$, $-NR^{42}C(=S)SR^{41}$, $-NR^{42}C(=S)N(R^{42})_2$, $-SC(=S)R^{41}$, $-SC(=S)OR^{41}$, $-SC(=S)SR^{41}$, $-SC(=S)N(R^{42})_2$, $-S(=O)R^{41}$, $-SO_2R^{41}$, $-NR^{42}SO_2R^{41}$, $-SO_2N(R^{42})_2$, $-CN$, $-SCN$, or $-NO_2$;

each occurrence of $R^{41}$ is independently hydrogen, optionally substituted alkyl, optionally substituted alkenyl, optionally substituted alkynyl, optionally substituted carbocyclyl, optionally substituted heterocyclyl, optionally substituted aryl, or optionally substituted heteroaryl; and each occurrence of $R^{42}$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, or an amino protecting group, or two $R^{42}$ groups are joined to form an optionally substituted heterocyclic ring; and $R^0$ or $R^1$ is substituted with an imaging moiety selected from the group consisting of $^{18}F$, $^{76}Br$, and $^{124}I$, or is associated with an imaging moiety selected from the group consisting of $^{64}Cu$, $^{89}Zr$, $^{99m}Tc$, and $^{111}In$ through a chelator, or is an imaging moiety selected from the group consisting of $^{18}F$, $^{76}Br$, and $^{124}I$;

or a salt thereof;

provided that when Ar is phenyl, when L is $-CH_2-$, when $R^1$ is

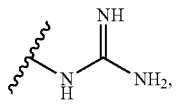

and when $R^0$ is an imaging moiety selected from the group consisting of $^{18}F$, $^{76}Br$, and $^{124}I$, then Ar is substituted.

6. The method of claim 1, wherein the second imaging agent is of the formula:

$R^0$-Ar-L-$R^1$ wherein

Ar is substituted or unsubstituted, monocyclic or bicyclic aryl or substituted or unsubstituted, monocyclic or bicyclic heteroaryl;

L is a bond; substituted or unsubstituted, cyclic or acyclic alkylene; substituted or unsubstituted, cyclic or acyclic alkenylene; substituted or unsubstituted, cyclic or acyclic alkynylene; or substituted or unsubstituted, cyclic or acyclic heteroaliphatic;

$R^1$ is a substituted or unsubstituted nitrogen-containing moiety; and $R^0$ is halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, $-OR^{41}$, $-N(R^{42})_2$, $-SR^{41}$, $-C(=O)R^{41}$, $-C(=O)OR^{41}$, $-C(=O)SR^{41}$, $-C(=O)N(R^{42})_2$, $-OC(=O)R^{41}$, $-OC(=O)OR^{41}$, $-OC(=O)SR^{41}$, $-OC(=O)N(R^{42})_2$, $-NR^{42}C(=O)R^{42}$, $-NR^{42}C(=O)OR^{41}$, $-NR^{42}C(=O)SR^{41}$, $-NR^{42}C(=O)N(R^{42})_2$, $-SC(=O)R^{41}$, $-SC(=O)OR^{41}$, $-SC(=O)SR^{41}$, $-SC(=O)N(R^{42})_2$, $-C(=NR^{42})R^{41}$, $-C(=NR^{42})OR^{41}$, $-C(=NR^{42})SR^{41}$, $-C(=NR^{42})N(R^{42})_2$, $-OC(=NR^{42})R^{41}$, $-OC(=NR^{42})OR^{41}$, $-OC(=NR^{42})SR^{41}$, $-OC(=NR^{42})N(R^{42})_2$, $-NR^{42}C(=NR^{42})R^{42}$, $-NR^{42}C(=NR^{42})OR^{41}$, $-NR^{42}C(=NR^{42})SR^{41}$, $-NR^{42}C(=NR^{42})N(R^{42})_2$, $-SC(=NR^{42})R^{41}$, $-SC(=NR^{42})OR^{41}$, $-SC(=NR^{42})SR^{41}$, $-SC(=NR^{42})N(R^{42})_2$, $-C(=S)R^{41}$, $-C(=S)OR^{41}$, $-C(=S)SR^{41}$, $-C(=S)N(R^{42})_2$, $-OC(=S)R^{41}$, $-OC(=S)OR^{41}$, $-OC(=S)SR^{41}$, $-OC(=S)N(R^{42})_2$, $-NR^{42}C(=S)R^{42}$, $-NR^{42}C(=S)OR^{41}$, $-NR^{42}C(=S)SR^{41}$, $-NR^{42}C(=S)N(R^{42})_2$, $-SC(=S)R^{41}$, $-SC(=S)OR^{41}$, $-SC(=S)SR^{41}$, $-SC(=S)N(R^{42})_2$, $-S(=O)R^{41}$, $-SO_2R^{41}$, $-NR^{42}SO_2R^{41}$, $-SO_2N(R^{42})_2$, $-CN$, $-SCN$, or $-NO_2$;

each occurrence of $R^{41}$ is independently hydrogen, optionally substituted alkyl, optionally substituted alkenyl, optionally substituted alkynyl, optionally substituted carbocyclyl, optionally substituted heterocyclyl, optionally substituted aryl, or optionally substituted heteroaryl; and each occurrence of $R^{42}$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, or an amino protecting group, or two $R^{42}$ groups are joined to form an optionally substituted heterocyclic ring; and $R^0$ or $R^1$ is substituted with an imaging moiety selected from the group consisting of $^{18}F$, $^{76}Br$, and $^{124}I$, or is associated with an imaging moiety selected from the group consisting of $^{64}Cu$, $^{89}Zr$, $^{99m}Tc$, and $^{111}In$ through a chelator, or is an imaging moiety selected from the group consisting of $^{18}F$, $^{76}Br$, and $^{124}I$;

or a salt thereof;

provided that when Ar is phenyl, $R^0$ is not $^{18}F$;

further provided that when Ar is phenyl, when L is $-CH_2-$, when $R^1$ is

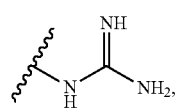

and when $R^0$ is an imaging moiety selected from the group consisting of $^{76}Br$ and $^{124}I$, then Ar is substituted.

7. The method of claim 1, wherein the second imaging agent is of the formula:

$R^0$-Ar-L-$R^1$ wherein
- Ar is substituted or unsubstituted, monocyclic or bicyclic aryl or substituted or unsubstituted, monocyclic or bicyclic heteroaryl;
- L is a bond; substituted or unsubstituted, cyclic or acyclic alkylene; substituted or unsubstituted, cyclic or acyclic alkenylene; substituted or unsubstituted, cyclic or acyclic alkynylene; or substituted or unsubstituted, cyclic or acyclic heteroaliphatic;
- $R^1$ is a substituted or unsubstituted nitrogen-containing moiety; and
- $R^0$ is halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, $-OR^{41}$, $-N(R^{42})_2$, $-SR^{41}$, $-C(=O)R^{41}$, $-C(=O)OR^{41}$, $-C(=O)SR^{41}$, $-C(=O)N(R^{42})_2$, $-OC(=O)R^{41}$, $-OC(=O)OR^{41}$, $-OC(=O)SR^{41}$, $-OC(=O)N(R^{42})_2$, $-NR^{42}C(=O)R^{42}$, $-NR^{42}C(=O)OR^{41}$, $-NR^{42}C(=O)SR^{41}$, $-NR^{42}C(=O)N(R^{42})_2$, $-SC(=O)R^{41}$, $-SC(=O)OR^{41}$, $-SC(=O)SR^{41}$, $-SC(=O)N(R^{42})_2$, $-C(=NR^{42})R^{41}$, $-C(=NR^{42})OR^{41}$, $-C(=NR^{42})SR^{41}$, $-C(=NR^{42})N(R^{42})_2$, $-OC(=NR^{42})R^{41}$, $-OC(=NR^{42})OR^{41}$, $-OC(=NR^{42})SR^{41}$, $-OC(=NR^{42})N(R^{42})_2$, $-NR^{42}C(=NR^{42})R^{42}$, $-NR^{42}C(=NR^{42})OR^{41}$, $-NR^{42}C(=NR^{42})SR^{41}$, $-NR^{42}C(=NR^{42})N(R^{42})_2$, $-SC(=NR^{42})R^{41}$, $-SC(=NR^{42})OR^{41}$, $-SC(=NR^{42})SR^{41}$, $-SC(=NR^{42})N(R^{42})_2$, $-C(=S)R^{41}$, $-C(=S)OR^{41}$, $-C(=S)SR^{41}$, $-C(=S)N(R^{42})_2$, $-OC(=S)R^{41}$, $-OC(=S)OR^{41}$, $-OC(=S)SR^{41}$, $-OC(=S)N(R^{42})_2$, $-NR^{42}C(=S)R^{42}$, $-NR^{42}C(=S)OR^{41}$, $-NR^{42}C(=S)SR^{41}$, $-NR^{42}C(=S)N(R^{42})_2$, $-SC(=S)R^{41}$, $-SC(=S)OR^{41}$, $-SC(=S)SR^{41}$, $-SC(=S)N(R^{42})_2$, $-S(=O)R^{41}$, $-SO_2R^{41}$, $-NR^{42}SO_2R^{41}$, $-SO_2N(R^{42})_2$, $-CN$, $-SCN$, or $-NO_2$;
  - each occurrence of $R^{41}$ is independently hydrogen, optionally substituted alkyl, optionally substituted alkenyl, optionally substituted alkynyl, optionally substituted carbocyclyl, optionally substituted heterocyclyl, optionally substituted aryl, or optionally substituted heteroaryl; and each occurrence of $R^{42}$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, or an amino protecting group, or two $R^{42}$ groups are joined to form an optionally substituted heterocyclic ring; and
- $R^0$ or $R^1$ is substituted with an imaging moiety selected from the group consisting of $^{18}F$, $^{76}Br$ and $^{124}I$, or is associated with an imaging moiety selected from the group consisting of $^{64}Cu$, $^{89}Zr$, $^{99m}Tc$, and $^{111}In$ through a chelator, or is an imaging moiety selected from the group consisting of $^{18}F$, $^{76}Br$, and $^{124}I$;
- or a salt thereof;
- provided that when Ar is phenyl, $R^0$ is not $^{18}F$,
- further provided that when Ar is phenyl, when L is $-CH_2-$, when $R^1$ is

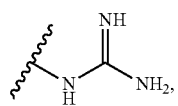

and when $R^0$ is an imaging moiety selected from the group consisting of $^{76}Br$ and $^{124}I$, then Ar is substituted;
- further provided that when Ar is phenyl, then Ar is not substituted with OH.

8. The method of claim 1, wherein the perfusion is cardiac perfusion and/or the innervation is cardiac innervation.

9. The method of claim 1, wherein the method is performed following a tissue insult.

10. The method of claim 9, wherein the tissue insult is an insult which is known or suspected to result in denervation.

11. The method of claim 9, wherein the tissue insult is an insult which is known or suspected to result in innervation and perfusion defects.

12. The method of claim 9, wherein the tissue insult is a cardiac insult.

13. The method of claim 9, wherein the cardiac insult is a myocardial infarction.

14. The method of claim 1, wherein the portion of the subject is a portion of the heart.

15. The method of claim 1, wherein the mismatch is determined at a single time point following the tissue insult.

16. The method of claim 1, wherein the mismatch is determined at more than one time point following the tissue insult.

17. The method of claim 3, wherein the perfusion is cardiac perfusion and/or the innervation is cardiac innervation.

18. The method of claim 3, wherein the method is performed following a tissue insult.

19. The method of claim 18, wherein the tissue insult is an insult which is known or suspected to result in denervation.

20. The method of claim 18, wherein the tissue insult is an insult which is known or suspected to result in innervation and perfusion defects.

21. The method of claim 18, wherein the tissue insult is a cardiac insult.

22. The method of claim 18, wherein the cardiac insult is a myocardial infarction.

23. The method of claim 3, wherein the portion of the subject is a portion of the heart.

24. The method of claim 3, wherein the mismatch is determined at a single time point following the tissue insult.

25. The method of claim 3, wherein the mismatch is determined at more than one time point following the tissue insult.

26. The method of claim 1, wherein for the first imaging agent, the at least one imaging moiety is $^{18}F$.

27. The method of claim 26, wherein the second imaging agent comprises an imaging moiety, wherein the imaging moiety is $^{18}F$.

28. The method of claim 4, wherein for the second imaging agent, the imaging moiety is $^{18}F$, and wherein for the first imaging agent, the at least one imaging moiety is $^{18}F$.

29. The method of claim 1, wherein the second imaging agent comprises an imaging moiety, wherein the imaging moiety is $^{18}F$.

* * * * *

UNITED STATES PATENT AND TRADEMARK OFFICE
CERTIFICATE OF CORRECTION

PATENT NO. : 9,550,000 B2
APPLICATION NO. : 14/343627
DATED : January 24, 2017
INVENTOR(S) : Simon P. Robinson et al.

It is certified that error appears in the above-identified patent and that said Letters Patent is hereby corrected as shown below:

In the Claim 4, at Column 256, Line 26, please replace:
"$R^{A1}, -C(=NR)OR^{A1}, -C(=NR^{A2})SR^{A1}, -C(=NR^{A2})N$"
With:
"$R^{A1}, -C(=NR^{A2})OR^{A1}, -C(=NR^{A2})SR^{A1}, -C(=NR^{A2})N$"

In the Claim 4, at Column 256, Line 29, please replace:
"$(=NR^{A2})R^{A2}, -NR^{A2}C(=NR)OR^{A1}, -NR^{A2}C(=NR^{A2})$"
With:
"$(=NR^{A2})R^{A2}, -NR^{A2}C(=NR^{A2})OR^{A1}, -NR^{A2}C(=NR^{A2})$"

In the Claim 4, at Column 256, Line 31, please replace:
"$-SC(=NR^{A1})OR^{A1}, -SC(=NR^{A2})SR^{A1}, -SC(=NR^{A2})$"
With:
"$-SC(=NR^{A2})OR^{A1}, -SC(=NR^{A2})SR^{A1}, -SC(=NR^{A2})$"

Signed and Sealed this
Twenty-first Day of November, 2017

Joseph Matal
*Performing the Functions and Duties of the
Under Secretary of Commerce for Intellectual Property and
Director of the United States Patent and Trademark Office*